(12) United States Patent
Reed et al.

(10) Patent No.: US 12,257,299 B2
(45) Date of Patent: Mar. 25, 2025

(54) SARS-COV-2 RNA VACCINE COMPOSITIONS AND METHODS OF USE

(71) Applicant: HDT Bio Corp., Seattle, WA (US)

(72) Inventors: Steven Gregory Reed, Bellevue, WA (US); Darrick Albert Carter, Seattle, WA (US); Amit Praful Khandhar, Issaquah, WA (US); Jacob Freeman Archer, Seattle, WA (US); Lars Peter Aksel Berglund, Seattle, WA (US); Jesse Erasmus, Port Orchard, WA (US); Bryan Berube, Issaquah, WA (US); Malcolm S. Duthie, Sammamish, WA (US)

(73) Assignee: HDT Bio Corp., Seattle, WA (US)

(*) Notice: Subject to any disclaimer, the term of this patent is extended or adjusted under 35 U.S.C. 154(b) by 0 days.

(21) Appl. No.: 18/612,698

(22) Filed: Mar. 21, 2024

(65) Prior Publication Data

US 2024/0261393 A1 Aug. 8, 2024

Related U.S. Application Data

(63) Continuation of application No. PCT/US2022/013513, filed on Jan. 24, 2022.

(60) Provisional application No. 63/297,397, filed on Jan. 7, 2022, provisional application No. 63/247,169, filed on Sep. 22, 2021.

(51) Int. Cl.
| | |
|---|---|
| A61K 39/215 | (2006.01) |
| A61K 9/107 | (2006.01) |
| A61K 9/16 | (2006.01) |
| A61K 9/19 | (2006.01) |
| A61K 39/00 | (2006.01) |
| A61P 37/04 | (2006.01) |

(52) U.S. Cl.
CPC .......... *A61K 39/215* (2013.01); *A61K 9/1075* (2013.01); *A61K 9/1617* (2013.01); *A61K 9/1623* (2013.01); *A61K 9/19* (2013.01); *A61P 37/04* (2018.01); *A61K 2039/53* (2013.01); *A61K 2039/55505* (2013.01); *A61K 2039/55516* (2013.01)

(58) Field of Classification Search
None
See application file for complete search history.

(56) References Cited

U.S. PATENT DOCUMENTS

| | | | |
|---|---|---|---|
| 7,045,335 B2 | 5/2006 | Smith | |
| 7,425,337 B2 | 9/2008 | Smith | |
| 8,709,441 B2 | 4/2014 | Rayner | |
| 8,734,832 B2 | 5/2014 | O'Hagan et al. | |
| 8,853,179 B2 | 10/2014 | Mauro | |
| 9,295,646 B2 | 3/2016 | Kline | |
| 9,555,136 B2 | 1/2017 | Khandhar et al. | |
| 9,655,845 B2 | 5/2017 | Brito | |
| 10,023,871 B2 | 7/2018 | Rohayem | |
| 10,238,733 B2 | 3/2019 | Brito | |
| 10,307,374 B2 | 6/2019 | Brito | |
| 11,026,890 B2 | 6/2021 | Brito | |
| 11,083,786 B2 | 8/2021 | Kamrud | |
| 11,135,287 B2 | 10/2021 | Brito | |
| 11,141,377 B2 | 10/2021 | Fox | |
| 11,318,213 B2 | 5/2022 | Khandhar | |
| 11,364,310 B2 | 6/2022 | Kamrud | |
| 11,376,335 B2 | 7/2022 | Khandhar | |
| 11,406,699 B2 * | 8/2022 | Kehn-Hall | C07K 14/005 |
| 11,433,142 B2 | 9/2022 | Khandhar | |
| 11,458,209 B2 | 10/2022 | Khandhar | |
| 11,534,497 B2 | 12/2022 | Khandhar | |
| 2006/0128011 A1 | 6/2006 | Zhu | |
| 2009/0252721 A1 | 10/2009 | Buschmann | |
| 2012/0156251 A1 | 6/2012 | Brito | |
| 2013/0195751 A1 | 8/2013 | Hahn | |
| 2013/0202707 A1 | 8/2013 | Ali | |
| 2016/0000886 A1 | 1/2016 | Parker | |
| 2016/0201067 A1 | 7/2016 | Ataullakhanov | |
| 2017/0189368 A1 | 7/2017 | Troiano | |
| 2018/0008694 A1 | 1/2018 | Ciaramella | |
| 2018/0104325 A1 | 4/2018 | Gale, Jr. | |
| 2018/0147298 A1 | 5/2018 | Besin | |
| 2018/0153848 A1 | 6/2018 | Chen | |
| 2018/0207295 A1 | 7/2018 | Fotin-Mleczek | |
| 2019/0015501 A1 | 1/2019 | Ciaramella | |
| 2019/0274968 A1 | 9/2019 | Weissman | |
| 2020/0006973 A1 | 1/2020 | Petersen | |
| 2020/0069599 A1 | 3/2020 | Smith | |
| 2020/0123573 A1 | 4/2020 | Kamrud | |
| 2020/0157571 A1 | 5/2020 | Nakanishi | |

(Continued)

FOREIGN PATENT DOCUMENTS

| | | |
|---|---|---|
| WO | 2001021810 A1 | 3/2001 |
| WO | 2002080982 A2 | 10/2002 |

(Continued)

OTHER PUBLICATIONS

Gerhardt et al. (BioRxiv Feb. 2, 2021, p. 1-10).*
Pin, Elisa, et al. "Identification of a Novel Autoimmune Peptide Epitope of Prostein in Prostate Cancer." Journal of Proteome Research 16.1 (2017): 204-216.
International Search Report issued Jun. 13, 2024 in PCT/US2024/010326.
Agnihothram, S., et al., "Development of a Broadly Accessible Venezuelan Equine Encephalitis Virus Replicon Particle Vaccine Platform" J Virol. May 14, 2018;92(11):e00027-18. doi: 10.1128/JVI.00027-18.
Anderluzzi, G., et al., "Investigating the Impact of Delivery System Design on the Efficacy of Self-Amplifying RNA Vaccines" Vaccines (Basel). May 8, 2020;8(2):212. doi: 10.3390/vaccines8020212.

(Continued)

*Primary Examiner* — Agnieszka Boesen
(74) *Attorney, Agent, or Firm* — Greenberg Traurig, LLP

(57) ABSTRACT

The disclosure provides compositions, methods of treatment, and methods of making and using compositions to deliver a nucleic acid to a subject. Methods of using the compositions as a COVID-19 vaccine for the treatment of a coronavirus infection are also provided.

30 Claims, 15 Drawing Sheets

Specification includes a Sequence Listing.

(56) References Cited

U.S. PATENT DOCUMENTS

| | | |
|---|---|---|
| 2020/0224174 A1 | 7/2020 | Irvine |
| 2020/0230056 A1 | 7/2020 | Fox |
| 2020/0297834 A1 | 9/2020 | Kehn-Hall |
| 2020/0368344 A1 | 11/2020 | Ciaramella |
| 2020/0370052 A1 | 11/2020 | Wilson |
| 2021/0128583 A1 | 5/2021 | Zhang |
| 2021/0283242 A1 | 9/2021 | Hutchins |
| 2021/0290752 A1 | 9/2021 | Sullivan |
| 2021/0290756 A1 | 9/2021 | Sullivan |
| 2021/0330781 A1 | 10/2021 | Kamrud |

FOREIGN PATENT DOCUMENTS

| | | |
|---|---|---|
| WO | 2005107760 | 11/2005 |
| WO | 2007024826 A2 | 3/2007 |
| WO | 2008124647 A2 | 10/2008 |
| WO | 2008153541 A1 | 12/2008 |
| WO | WO2009049083 | 4/2009 |
| WO | 2010141861 A1 | 12/2010 |
| WO | WO 2011/156761 | 12/2011 |
| WO | 2014042780 A1 | 3/2014 |
| WO | 2015103167 A2 | 7/2015 |
| WO | 2017200852 A1 | 11/2017 |
| WO | 2017200957 A1 | 11/2017 |
| WO | 2017205225 A2 | 11/2017 |
| WO | 2017210364 A1 | 12/2017 |
| WO | 2017218704 | 12/2017 |
| WO | 2017218704 A1 | 12/2017 |
| WO | WO2018022957 | 2/2018 |
| WO | 2018/044028 | 3/2018 |
| WO | 2018053294 A1 | 3/2018 |
| WO | WO 2018/147710 | 8/2018 |
| WO | 2018232257 | 12/2018 |
| WO | WO2018232257 | 12/2018 |
| WO | WO 2019/152884 | 8/2019 |
| WO | 2020132279 A1 | 6/2020 |
| WO | 2020/243115 | 12/2020 |
| WO | 2020254804 A1 | 12/2020 |
| WO | 2021021605 A1 | 2/2021 |
| WO | 2021076630 | 4/2021 |
| WO | WO 2021/067480 | 4/2021 |
| WO | WO 2021/072112 | 4/2021 |
| WO | WO 2021/163536 | 8/2021 |
| WO | 2021178886 | 9/2021 |
| WO | 2021178886 A1 | 9/2021 |
| WO | 2021183564 A1 | 9/2021 |
| WO | 2021194672 A1 | 9/2021 |
| WO | WO 2021/194672 | 9/2021 |
| WO | 2021210686 A1 | 10/2021 |
| WO | WO 2022/051022 | 3/2022 |
| WO | 2022136952 A1 | 6/2022 |
| WO | 2023286076 A1 | 1/2023 |
| WO | 2023026301 A1 | 3/2023 |
| WO | 2023049636 A1 | 3/2023 |
| WO | 2023049636 A2 | 3/2023 |
| WO | 2023056202 | 4/2023 |

OTHER PUBLICATIONS

Bazhan, S., et al., "Immunogenicity and Protective Efficacy of Influenza A DNA Vaccines Encoding Artificial Antigens Based on Conservative Hemagglutinin Stem Region and M2 Protein in Mice." Vaccines vol. 8,3 448. Aug. 9, 2020, doi:10.3390/vaccines8030448.

Boettler, T., et al., "SARS-CoV-2 vaccination can elicit a CD8 T-cell dominant hepatitis" J Hepatol. Sep. 2022;77(3):653-659. doi: 10.1016/j.jhep.2022.03.040.

Brito, L.A., et al., "A Cationic Nanoemulsion for the Delivery of Next-Generation RNA Vaccines" Mol Ther. 2014;22(12):2118-2129. doi:10.1038/mt.2014.133.

Chiu, C.Y.H., et al., "Association of antibodies to Plasmodium falciparum reticulocyte binding protein homolog 5 with protection from clinical malaria" Front Microbiol. Jun. 30, 2014;5:314. doi: 10.3389/fmicb.2014.00314.

Deo, S., et al. "Evaluation of self-amplifying mRNA platform for protein expression and genetic stability: Implication for mRNA therapies." Biochemical and Biophysical Research Communications 680 (2023): 108-118.

Dewey, E.C., et al., "Programming of RIG-I Signaling Through Co-Factor Interactions," The Journal of Immunology 96(1 Suppl):203, May 2016, 4 pages.

Du, L., et al., "The Spike Protein of SARS-COV—A Target for Vaccine and Therapeutic Development", Nat Rev Microbiol 7, 226-236 (2009). https://doi.org/10.1038/nrmicro2090.

Duerrwald, R., et al., "Influenza A virus (A/swine/Bueren/5439/2006(H3N2)) segment 4 hemagglutinin (HA) gene, complete cds". Genbank entry (online). National Center for Biotechnology Information. URL: Https://www.ncbi.nlm.nih.gov/nucleotide/MK362039.1J. Jan. 31, 2020; pp. 1-2.

Erasmus, J.A., et al., "A Nanostructured Lipid Carrier for Delivery of a Replicating Viral RNA Provides Single, Low-Dose Protection against Zika", Mol Ther. Oct. 3, 2018;26(10):2507-2522. doi: 10.1016/j.ymthe.2018.07.010. Epub Aug. 2, 2018. PMID: 30078765; PMCID: PMC6171036.

Felgner, Philip L., et al. "Lipofection: a highly efficient, lipid-mediated DNA-transfection procedure." Proceedings of the National Academy of Sciences 84.21 (1987): 7413-7417.

Fleeton, M. N., et al., "Self-Replicative RNA Vaccines Elicit Protection Against Influenza A Virus, Respiratory Syncytial Virus, and a Tickborne Encephalitis Virus", The Journal of Infectious Diseases, vol. 183, Issue 9, May 1, 2001, pp. 1395-1398, https://doi.org/10.1086/319857.

Fox, C.B., "Squalene emulsions for parenteral vaccine and drug delivery" Molecules. Sep. 1, 2009;14(9):3286-312. doi: 10.3390/molecules14093286.

Gao, Y., et al., "Structure of the RNA-dependent RNA polymerase from COVID-19 virus" Science. May 15, 2020;368 (6492):779-782. doi: 10.1126/science.abb7498.

Gehardt, Alana, et al., "A flexible, thermostable nanostructured lipid carrier platform for RNA vaccine delivery" Mol Ther Methods Clin Dev. Jun. 9, 2022;25:205-214. doi: 10.1016/j.omtm.2022.03.009.

Hartmann, G. "Chapter 4: Nucleic Acid Immunity," in F. Alt (ed.), "Advances in Immunology," 133:121-169, 2017.

Hatmal, M.M., et al., "Comprehensive Structural and Molecular Comparison of Spike Proteins of SARS-CoV-2, Sars-CoV and MERS-COV, and Their Interactions with ACE2" Cells Dec. 8, 2020;9(12):2638. doi: 10.3390/cells9122638.

Hawman, D. W et al., "SARS-CoV2 variant-specific replicating RNA vaccines protect from disease and pathology and reduce viral shedding following challenge with heterologous SARS-CoV2 variants of concern" bioRxiv [Preprint]. Dec. 1, 20213:2021.12.10.472134. doi: 10.1101/2021.12.10.472134 bioRxiv 2021.12.10.472134; doi: https://doi.org/10.1101/2021.12.10.472134.

Heinz, F.X., and Stiasny, K., "Distinguishing features of current COVID-19 vaccines: knowns and unknowns of antigen presentation and modes of action" NPJ Vaccines. Aug. 16, 2021;6(1):104. doi: 10.1038/s41541-021-00369-6.

Huang, H.C., et al., "Formulation of novel lipid-coated magnetic nanoparticles as the probe for in vivo imaging" J Biomed Sci. Sep. 21, 2009;16(1):86. doi: 10.1186/1423-0127-16-86.

Huang, Y., et al., "Structural and functional properties of SARS-CoV-2 spike protein: potential antivirus drug development for COVID-19" Acta Pharmacol Sin 41, 1141-1149 (2020). https://doi.org/10.1038/s41401-020-0485-4.

International Search Report issued Jun. 6, 2022 in PCT/US2022/13513.

International Search Report issued Jun. 8, 22 in PCT/US2022/013516.

International Search Report issued Jun. 14, 2022 in PCT/US2022/13508.

International Search Report issued in PCT/US2023/060225 dated Jul. 28, 23.

International Search Report issued Jun. 6, 2022 in PCT/US2022/013513.

International Search Report issued Jun. 8, 2023 in PCT/US2022/076821.

(56) References Cited

OTHER PUBLICATIONS

Kautz, T. F., et al., "Low-fidelity Venezuelan equine encephalitis virus polymerase mutants to improve live-attenuated vaccine safety and efficacy" Virus Evol.: 4(1); pp. 1-14, Mar. 6, 2018;. doi: 10.1093/ve/vey004.
Kimuira, T, et al., "A localizing nanocarrier formulation enables multi-target immune responses to multivalent replicating RNA with limited systemic inflammation", Molecular Therapy (2023), doi: https://doi.org/10.1016/j.ymthe.2023.06.017.
Kwon, S.M., et al., "In vivo time-dependent gene expression of cationic lipid-based emulsion as a stable and biocompatible non-viral gene carrier" J Control Release. May 2, 20082;128(1):89-97. doi: 10.1016/j.jconrel.2008.02.004. Epub Feb. 19, 2008. Erratum in: J Control Release. Nov. 16, 2009;140(1):74.
Li, X-Y., et al., "Tumor Suppressor Activity of RIG-I," Molecular and Cellular Oncology 1(4):e968016, Dec. 2014.
Marcus, M., et al., "Iron oxide nanoparticles for neuronal cell applications: uptake study and magnetic manipulations", J Nanobiotechnology, vol. 14, Issue 37, May 2016, https://doi.org/10.1186/s12951-016-0190-0.
Maruggi, G., et al., "A self-amplifying mRNA SARS-CoV-2 vaccine candidate induces safe and robust protective immunity in preclinical' models" Mol Ther. Jan. 3, 2022:S1525-0016(22)00001-6. doi: 10.1016/j.ymthe.2022.01.001.
Min, J. W., et al., "Hemagglutinin (Influenza A virus (A/Aichi/Feb. 1968(H3N2)]". Genbank entry (online). National Center for Biotechnology Information. Retrieved From The Internet. URL: https://www.ncbi.nlm.nih.gov/protein/AAA43239.1]. Jul. 13, 2006; p. 1.
Pardi, N., et al., "mRNA vaccines—a new era in vaccinology" Nat Rev Drug Discov. Apr. 2018;17(4):261-279. doi: 10.1038/nrd.2017.243. Epub Jan. 12, 2018. PMID: 29326426.
Roeffen, W., et al., "Transmission-blocking activity of antibodies to Plasmodium falciparum GLURP.10C chimeric protein formulated in different adjuvants" Malar J 14, 443 (2015). https://doi.org/10.1186/s12936-015-0972-0.
Safety and Immunogenicity of HDT-301 Targeting a SARS-CoV-2 Variant Spike Protein, Sponsor: HDT Bio, posted Nov. 24, 2021ClinicalTrials.gov Identifier: NCT05132907 found at https://clinicaltrials.gov/ct2/show/record/NCT05132907? term=hdt+bio &draw=2&rank=1 11 pages.
Schoenmaker, L., et al. "mRNA-lipid nanoparticle COVID-19 vaccines: Structure and stability." International journal of pharmaceutics vol. 601 (2021): 120586. doi:10.1016/j.ijpharm.2021.120586.
Shu, B., et al., "Structural basis of viral RNA-dependent RNA polymerase catalysis and translocation", Proc Natl Acad Sci USA; 113(28):E4005-14, Jun. 23, 2016 doi: 10.1073/pnas.1602591113.
Singh, K., et al., "Malaria vaccine candidate based on Duffy-binding protein elicits strain transcending functional antibodies in a Phase I trial" NPJ Vaccines. Sep. 28, 2018;3:48. doi: 10.1038/s41541-018-0083-3.
Starmans, L.W.E., et al., "Iron oxide nanoparticle-micelles (ION-micelles) for sensitive (molecular) magnetic particle imaging and magnetic resonance imaging" PLoS One. 2013;8(2):e57335. doi: 10.1371/journal.pone.0057335. Epub Feb. 20, 2013.
Stokes, A., et al., "Nonclinical safety assessment of repeated administration and biodistribution of a novel rabies self-amplifying mRNA vaccine in rats" Regul Toxicol Pharmacol. Jun. 2020;113:104648. doi: 10.1016/j.yrtph.2020.104648.
Teixeira, T. et al., "Cationic nanoemulsions as nucleic acids delivery systems" Int J Pharm. Dec. 20, 2017;534(1-2):356-367. doi: 10.1016/j.ijpharm.2017.10.030.
Tregoning, J. S., et al., "Formulation, inflammation, and RNA sensing impact the immunogenicity of self-amplifying RNA vaccines" Mol Ther Nucleic Acids. Dec. 5, 2022;31:29-42. doi: 10.1016/j.omtn.2022.11.024.
Tregoning, J.S.. "LION: Taming RNA vaccine inflammation" Mol Ther. Aug. 3, 2023:S1525-0016(23)00386-6. doi: 10.1016/j.ymthe.2023.07.006.
Valdivia, L, et al., Solid Lipid Particles for Lung Metastasis Treatment. Pharmaceutics. 2021;13(1):93. Published Jan. 13, 2021. doi:10.3390/pharmaceutics 13010093.
Voigt, E.A., et al., "A self-amplifying RNA vaccine against COVID-19 with long-term room-temperature stability" npj Vaccines 7, 136 (2022). https://doi.org/10.1038/s41541-022-00549-y.
Walton, T.E., et al., "Experimental infection of horses with an attenuated Venezuelan equine encephalomyelitis vaccine (strain TC-83)" Infect Immun. May 1972;5(5):750-6. doi: 10.1128/iai.5.5.750-756.1972.
Wu, F., et al., "Severe acute respiratory syndrome coronavirus 2 isolate Wuhan-Hu-1, complete genome" GenBank: MN908947.3, VRL Mar. 18, 2020, available at https://www.ncbi.nlm.nih.gov/nuccore/MN908947.
International Search Report issued Jun. 29, 2023 in PCT/US2022/076787.
International Search Report issued Jun. 7, 2023 in PCT/US2022/076304.
"Gennova's mRNA vaccine to come in powder form; will stay stable at 2-8 ° C" Business Standard. Sep. 13, 2021 02:56 IST.
Brinckerhoff, L. H., et al., "Melanoma vaccines" Current Opinion in Oncology: Mar. 2000—vol. 12—Issue 2—p. 163-173.
Brocato, R. L., et al., Protective efficacy of a SARS-COV-2 DNA vaccine in wild-type and immunosuppressed Syrian hamsters. NPJ Vaccines 6, 16 (2021). https://doi.org/10.1038/s41541-020-00279-z.
Brown, C. M., et al. Outbreak of SARS-CoV-2 Infections, Including COVID-19 Vaccine Breakthrough Infections, Associated with Large Public Gatherings—Barnstable County, Massachusetts, Jul. 2021. MMWR Morb Mortal Wkly Rep 2021;70:1059-1062.
Corbett, K. S., et al., "Evaluation of the mRNA-1273 Vaccine against SARS-CoV-2 in Nonhuman Primates" N Engl J Med. Oct. 15, 2020;383(16):1544-1555. doi: 10.1056/NEJMoa2024671.
Corman, V. C., et al., Detection of 2019 novel coronavirus (2019-nCOV) by real-time RT-PCR. Euro Surveill. 2020;25 (3), https://doi.org/10.2807/1560-7917.ES.2020.25.3.2000045.
CustomBiotech Online Development Exchange (CODE), Beyond COVID: The Future of mRNA technology, Webinar held Thursday, Nov. 11, 2021, https://dianews.roche.com/CustomBiotech-Webinar-2021.html.
Edara, V., et al., Infection and Vaccine-Induced Neutralizing-Antibody Responses to the SARS-CoV-2 B.1.617 Variants. N Engl J Med. Aug. 12, 2021;385(7):664-666. doi: 10.1056/NEJMc2107799. Epub Jul. 7, 2021. PMID: 34233096; PMCID: PMC8279090.
Erasmus, J. H., A Nanostructured Lipid Carrier for Delivery of Replicating Viral RNA Provides Single, Low-Dose Protection against Zika, Molecular Therapy, vol. 26, No. 10. pp. 2507-2522.
Erasmus, J. H., et al., "An Alphavirus-derived replicon RNA vaccine induces SARS-CoV-2 neutralizing antibody and T cell responses in mice and nonhuman primates" Science Translational Medicine, Aug. 5, 2020, vol. 12, Issue 555.
Erasmus, J.H. et al., "Single-dose Replicating RNA Vaccine Induces Neutralizing Antibodies Against SARS-CoV-2 in Nonhuman Primates", bioRxiv, 28 pages.
Erasmus, J.H., "An Alphavirus-derived replicon RNA vaccine induces SARS-CoV-2 Neutralizing Antibody and T-cell Responses in Mice and Nonhuman Primates", Science Translational Medicine, vol. 12, No. 555.
Erasmus, J.H., et al., Intramuscular Delivery of Replicon RNA Encoding ZIKV-117 Human Monoclonal Antibody Protects against Zika Virus Infection. Mol Ther—Methods Clin Dev. 2020;18:402-414. PMID: 32695842.
File No. BIO/CT/20/000182, CT No. CT-2/2021 Government of India Directorate General of Health Services Central Drugs Standard Control Organization (Biological Division), Form CT-06 Permission To Conduct Clinical Trial of New Drug or Investigational New Drug, Jan. 25, 2021, 3 pages.
File No. BIO/CT/21/000105, CT No. CT-28/2021 Government of India Directorate General of Health Services Central Drugs Standard Control Organization (Biological Division), Form CT-06 Permission To Conduct Clinical Trial of New Drug or Investigational New Drug, Aug. 22, 2021, 3 pages.

(56) References Cited

OTHER PUBLICATIONS

Fischer, Robert J., et al. "ChAdOx1 nCOV-19 (AZD1222) protects Syrian hamsters against SARS-CoV-2 B.1.351 and B.1.1.7." bioRxiv : the preprint server for biology 2021.03.11.435000. Jun. 30, 2021, doi:10.1101/2021.03.11.435000. Preprint.

Geall, Andrew J., et al. "Nonviral delivery of self-amplifying RNA vaccines." PNAS. Vol 109. No 36, pp. 14604-14609 (2012).

Gilchuk, P., et al., "Integrated pipeline for the accelerated discovery of antiviral antibody therapeutics" Nat Biomed Eng. 2020;4(11):1030-1043. PMID: 32747832.

Hörner , C., et al., A highly immunogenic and effective measles virus-based Th1-biased COVID-19 vaccine, Proceedings of the National Academy of Sciences Dec. 2020, 117 (51) 32657-32666; DOI: 10.1073/pnas.2014468117.

Hou, X., et al., Lipid nanoparticles for mRNA delivery. Nat Rev Mater (2021). https://doi.org/10.1038/s41578-021-00358-0.

International Search Report and Written Opinion for PCT/US2021/019103 issued Sep. 30, 2021.

Jain, T.K., et al., Iron Oxide Nanoparticles for Sustained Delivery of Anticancer Agents, Molecular Pharmaceutics, American Chemical Society, 2 (3), 194-205, 2005.

Kalnin, K.V., et al., Immunogenicity and efficacy of mRNA COVID-19 vaccine MRT5500 in preclinical animal models. npj Vaccines 6, 61 (2021). https://doi.org/10.1038/s41541-021-00324-5.

Kurup, D. et al., Inactivated rabies virus vectored SARS-CoV-2 vaccine prevents disease in a Syrian hamster model, PLOS Pathogens 17(3): e1009383. https://doi.org/10.1371/journal.ppat.1009383.

Li, Q. et al., "A Review of the Structure, Preparation, and Application of NLCs, PNPs and PLNs", Nanomaterials, vol. 7, No. 6, p. 1-25.

Limbach, P A et al. "Summary: the modified nucleosides of RNA." Nucleic acids research vol. 22,12 (1994): 2183-96. doi:10.1093/nar/22.12.2183.

Lopez Bernal, J, et al., Effectiveness of Covid-19 Vaccines against the B.1.617.2 (Delta) Variant. N Engl J Med. Aug. 12, 2021;385(7):585-594. doi: 10.1056/NEJMoa2108891. Epub Jul. 2, 20211. PMID: 34289274; PMCID: PMC8314739.

Machado, B.A.S., et al., The Importance of RNA-Based Vaccines in the Fight against COVID-19: An Overview. Vaccines (Basel). Nov. 17, 2021;9(11):1345. doi: 10.3390/vaccines9111345. PMID: 34835276; PMCID: PMC8623509.

Mckay, P. F., et al., Self-amplifying RNA SARS-CoV-2 lipid nanoparticle vaccine candidate induces high neutralizing antibody titers in mice. Nat Commun. Jul. 9, 2020;11(1):3523. doi: 10.1038/s41467-020-17409-9. PMID: 32647131; PMCID: PMC7347890.

Mercado, N.B., et al., "Single-shot Ad26 vaccine protects against SARS-COV-2 in rhesus macaques" Nature. Oct. 2020;586(7830):583-588. doi: 10.1038/s41586-020-2607-z. Epub Jul. 30, 2020. Erratum in: Nature. Feb. 2021;590(7844):E25. PMID: 32731257; PMCID: PMC7581548.

Meyer, B., et al., Characterising proteolysis during SARS-CoV-2 infection identifies viral cleavage sites and cellular targets with therapeutic potential. Nat Commun. Sep. 21, 2021;12(1):5553. doi: 10.1038/s41467-021-25796-w. PMID: 34548480; PMCID: PMC8455558.

Mohandas, S., et al., Immunogenicity and protective efficacy of BBV152, whole virion inactivated Sars- CoV-2 vaccine candidates in the Syrian hamster model. iScience. Feb. 19, 2021;24(2):102054. doi: 10.1016/j.isci.2021.102054. Epub Jan. 9, 2021. PMID: 33521604; PMCID: PMC7829205.

Planas, D., et al., Reduced sensitivity of SARS-COV-2 variant Delta to antibody neutralization. Nature. Aug. 2021;596(7871):276-280. doi: 10.1038/s41586-021-03777-9. Epub Jul. 8, 2021. PMID: 34237773.

Rauch, S, et al., mRNA-based SARS-CoV-2 vaccine candidate CVnCOV induces high levels of virus-neutralising antibodies and mediates protection in rodents. NPJ Vaccines. Apr. 16, 2021;6(1):57. doi: 10.1038/s41541-021-00311-w. PMID: 33863911; PMCID: PMC8052455.

Sheikh, A, et al., SARS-CoV-2 Delta VOC in Scotland: demographics, risk of hospital admission, and vaccine effectiveness. Lancet. Jun. 26, 2021;397(10293):2461-2462. doi: 10.1016/S0140-6736(21)01358-1. Epub Jun. 14, 2021. PMID: 34139198; PMCID: PMC8201647.

Shen, X, et al., SARS-COV-2 variant B.1.1.7 is susceptible to neutralizing antibodies elicited by ancestral spike vaccines. Cell Host Microbe. Apr. 14, 2021;29(4):529-539.e3. doi: 10.1016/j.chom.2021.03.002. Epub Mar. 5, 2021. PMID: 33705729; PMCID: PMC7934674.

Szurgot, I., et al., DNA-launched RNA replicon vaccines induce potent anti-SARS-CoV-2 immune responses in mice. 2021 Scientific Reports. 11. 10.1038/s41598-021-82498-5.

Van Der Lubbe, J. E. M., et al., Ad26.CoV2.S protects Syrian hamsters against G614 spike variant SARS-CoV-2 and does not enhance respiratory disease. NPJ Vaccines. Mar. 19, 2021;6(1):39. doi: 10.1038/s41541-021-00301-y. PMID: 33741993; PMCID: PMC7979827.

Van Doremalen, N., et al. Immunogenicity of low dose prime-boost vaccination of mRNA vaccine CV07050101 in non-human primates. bioRxiv [Preprint]. Jul. 7, 2021:2021.07.07.451505. doi: 10.1101/2021.07.07.451505. Update in: Viruses. Aug. 19, 2021;13(8): PMID: 34268507; PMCID: PMC8282095.

Van Doremalen, N., et al., ChAdOx1 nCoV-19 vaccine prevents SARS-COV-2 pneumonia in rhesus macaques. Nature. Oct. 2020;586(7830):578-582. doi: 10.1038/s41586-020-2608-y. Epub Jul. 30, 2020. Erratum in: Nature. Feb. 2021;590(7844): E24. PMID: 32731258; PMCID: PMC8436420.

V'kovski, P, et al., "Coronavirus biology and replication: implications for SARS-CoV-2". Nature Reviews. (Mar. 2021). Microbiology. 19 (3): 155-170. doi: 10.1038/s41579-020-00468-6. PMC 7592455. PMID 33116300.

Wang, P., et al., Antibody resistance of SARS-CoV-2 variants B.1.351 and B.1.1.7. Nature. May 2021;593 (7857):130-135. doi: 10.1038/s41586-021-03398-2. Epub Mar. 8, 2021. PMID: 33684923.

Wang, Z., et al., Naturally enhanced neutralizing breadth against SARS-CoV-2 one year after infection. Nature. Jul. 2021;595(7867):426-431. doi: 10.1038/s41586-021-03696-9. Epub Jun. 14, 2021. PMID: 34126625; PMCID: PMC8277577.

Wu, C, et al. "Analysis of therapeutic targets for SARS-CoV-2 and discovery of potential drugs by computational methods," Acta Pharmaceutica Sinica (May 2020). B. 10 (5): 766-788. doi:10.1016/j.apsb.2020.02.008. PMC 7102550. PMID 32292689, the contents of which are hereby incorporated by reference in their entirety.

Yinda, C. K., et al., Prior aerosol infection with lineage A SARS-CoV-2 variant protects hamsters from disease, but not reinfection with B.1.351 SARS-CoV-2 variant. Emerg Microbes Infect. Dec. 2021;10(1):1284-1292. doi: 10.1080/22221751.2021.1943539. PMID: 34120579; PMCID: PMC8238069.

Yu, Jingyou et al. "DNA vaccine protection against SARS-CoV-2 in rhesus macaques." Science (New York, N.Y.) vol. 369,6505 (2020): 806-811. doi:10.1126/science.abc6284.

Zhang, Y., et al., A second functional furin site in the SARS-CoV-2 spike protein. Emerg Microbes Infect. Dec. 3, 2021:1-35. doi: 10.1080/22221751.2021.2014284. Epub ahead of print. PMID: 34856891.

Zhou, D., et al., Evidence of escape of SARS-CoV-2 variant B.1.351 from natural and vaccine-induced sera. Cell. Apr. 29, 2021;184(9):2348-2361.e6. doi: 10.1016/j.cell.2021.02.037. Epub Feb. 23, 2021. PMID: 33730597; PMCID: PMC7901269.

Zost, S.J., et al., Rapid isolation and profiling of a diverse panel of human monoclonal antibodies targeting the SARS-CoV-2 spike protein. Nat Med. 2020;26(9):1422-1427. PMID: 32651581.

\* cited by examiner

SEQ ID NO: 1: A.1 spike

| sp | S1 | S2 | TM | CD |

B.1 spike

| sp | *D614G | TM | CD |

(Native)

SEQ ID NO: 2: A.1 pre-fusion stabilized spike

| sp | S1 | S2 **KV995PP | TM | CD |

B.1 pre-fusion stabilized spike

| sp | *D614G **KV995PP | TM | CD |

SEQ ID NO: 5: B.1.1.7 pre-fusion stabilized spike

| sp | *A570D  *S982A **KV995PP | TM | CD |
| *N501Y *D614G *P681H *T716I |

SEQ ID NO: 4: B.1.351 pre-fusion stabilized spike

| sp | *L18F *D80A *D215G Δ242-244  **KV995PP | TM | CD |
| *R246I *K417N *E484K *N501Y *D614G *A701V |

(Pre-Fusion)

*FIG. 1*

SEQUENCE LISTING

```
Sequence total quantity: 39
SEQ ID NO: 1          moltype = RNA  length = 3846
FEATURE               Location/Qualifiers
source                1..3846
```

```
                    mol_type = other RNA
                    organism = Severe acute respiratory syndrome coronavirus 2
SEQUENCE: 1
atgtttctgc tcacaaccaa acgcactatg tttgttttcc tcgtgctgct ccctttggta    60
agttctcagt gtgtaaacct gacaacacga acccagttgc ctccagctta taccaactca   120
tttactcgcg gagtatatta tcccgataag gtctttagaa gtagcgtgtt gcactctaca   180
caggatctgt tcttgccctt ctttagtaac gttacctggt ttcatgcaat acatgtgagc   240
ggaacaaatg gaacaaaaag atttgacaat ccagtgcttc catttaatga tggggtttac   300
tttgccagta ccgaaaagtc aaacataatc cgggggtgga tctttggaac cactttggac   360
tctaagacac agtctctcct catagtaaac aacgccacca atgttgtcat aaaagtatgc   420
gaatttcagt tttgcaacga tcccttttct ggggtgtatt accataagaa taataaatcc   480
tggatggagt ctgagttccg ggtttatagt agtgctaata attgcacttt cgaatacgtg   540
tcccaaccat tcctcatgga ccttgagggc aaacagggga atttaaaaa cttgcgcgaa   600
tttgtcttta agaatatcga cggatactttt aagatctata gtaaacacac tcctatcaac   660
ctcgttcggg atcttcccca aggctttct gctctcgaac cctcgtaga cttgccaatt   720
gggataaata tcactcgctt tcaaactttg cttccctcc acaggagcta cctgacaccc   780
ggcgactctt cttctggttg gaccgccggc gccgctgcct attatgttgg ttaccttcag   840
ccacgaacat tcttgctcaa gtataacgag aatggcacca ttaccgacgc cgtcgattgt   900
gcattggatc ccttgtctga aacaaaatgt accttgaagt cctttaccgt agagaaaggc   960
atataccaga cttccaactt ccgagttcag cctacagaat ccattgtgag atttcccaac  1020
atcacaaacc tctgcccttt cggtgaagta tttaatgcta cacgcttcgc ttcagtctat  1080
gcctggaata ggaagcgcat atcaaattgc gtggccgatt attcagtcct ctataatagc  1140
gcatccttca gtactttcaa gtgctacggc gtttccccca ccaaactcaa tgatctttgc  1200
ttcaccaacg tctatgctga cagttttgtc atacgaggcg acgaagtacg ccagattgcc  1260
cccgggcaga caggtaaaat tgctgattat aattataaac tcccagatga ctttactgga  1320
tgcgtcatag cctggaattc caacaatctt gattccaagg ttggtggaa ttataattac  1380
ctttatcgac tgttcagaaa gagtaacttg aaaccatttg agagagacat atccaccgag  1440
atttaccagg caggcagtac tccttgtaac ggcgttgagg gatttaactg ctatttttcct  1500
ttgcaatcct atggctttca accaacaaac ggggttggct atcaacccta tcgagtggtt  1560
gtcctgagct ttgaacttt gcacgctccc gccacagtc gcggaccaaa aaagagtaca  1620
aatcttgtca agaataagtg cgtaaatttc aatttcaatg ccttacagg aacaggcgtg  1680
ctgactgagt caaacaagaa gttcctgcca tttcagcagt ttgggcggga tatagcagac  1740
acaactgacg ctgtacgcga tcctcagact ttggagatct ggacatcac tccctgttct  1800
ttcggagggg tatctgtcat caccccccgga actaatacat caaatcaggt cgctgtgttg  1860
taccaagatg tcaactgcac agaagtcccc gttgctatac acgcagacca gctcaccccc  1920
acatggcggg tgtactcaac tggctcaaac gtattccaga ccagagctgg gtgcttgatc  1980
ggtgctgaac acgtaaacaa tagctatgaa tgcgatattc ccatcggtgc cgggatctgc  2040
gctagctatc agacacagac caattcccgc cggcagacga gatctgtagc atcccagtct  2100
attattgcct acactatgtc attgggcgcc gagaatagcg tcgcatattc aaataattct  2160
attgcaatac ccaccaactt cacaatctcc gtaactacaa aatacttcc agtttccatg  2220
acaaagacat cagtggattg tacaatgtat atatgcggag attccacaga atgttcaaat  2280
ttgctcttgc agtacggctc cttctgcacc cagctcaaca gggcccttac aggtattgct  2340
gtcgaacagg acaagaacac acaagaagtc ttcgcccaag tcaaacagat atacaaaact  2400
cctcccataa aggattttgg cggcttcaac tttagtcaga tcctcccaga cccttcaaaa  2460
ccatctaaac gatcatttat tgaagatctg ctgttcaaca aggtcactct tgccgatgct  2520
ggattcatta agcaatacgg tgactgcctt ggtgatattg ctgcccgaga tctgatctgt  2580
gcccagaaat tcaacgggct cactgtactc cctccactgc tcacagacga aatgattgca  2640
cagtacacaa gtgccctgtt ggcaggcaca atcactagcg gctggaccct tggcgcaggt  2700
gcagcactcc aaataccttt tgccatgcag atggcctatc ggtttaatgg gataggcgtg  2760
actcaaaatg tcctctacga aaaccaaaag ttgatagcta accaattcaa ttcagcaatc  2820
gggaagatac aggattcact gtctagtact gctagtgccc ttggtaagct gggcgacgtt  2880
gtcaaccaga atgctcaagc tctgaataca ttggttaagc agctctctag taatttttggg  2940
gccatctctt cagtacttaa tgatatttgt agccgattgg acaaagtgga agctgaagta  3000
cagatcgaca ggctgataac aggccggctc caatccctcc aaacatacgt gacacaacaa  3060
ctcatacgcg cagccgaaat ccgagccagc gctaacctag cagctaccaa cgtcagaa  3120
tgcgttctgg gccagagtaa acgcgtagat ttctgcggga agggtaccaa cctgatgtcc  3180
tttccacaat ctgcacctca cggggtcgtc tttttgcatg taacatatgt acccgcacaa  3240
gagaagaatt ttactaccgc tcctgccatc tgtcatgacg ggaaagctca tttcctcgc  3300
gaaggtgtgt ttgtattctaa tggtacacat tggttttgtca cacagcggaa tttctatgaa  3360
ccccagatca ttacaactgca caacactttt gtttccggaa attgtgacgt ggtcatagga  3420
atcgtaaata acactgtata tgatcccctc caaccagagc tggactcttt taaagaagaa  3480
ctggataaat atttcaagaa ccacacaagt cccgacgtgg accttgggga cataagtggt  3540
attaacgcat ctgtggttaa cattcaaaag gaaatcgaca gactcaacga ggtggccaaa  3600
aacctgaacg aaagcttgat agatctccag gagttgggca agtataagcattaa  3660
tggccatggt acatatggct tggctttatc gctggcctta tcgccatcgt aatggttaca  3720
atcatgctgt gctgcatgac ctcctgctgt ctcttgtttga aagggtgttg ttcttgtggt  3780
agttgttgca gtttgacga agatgattcc gaacctgttc ttaaaggggt aaagcttcac  3840
tataca                                                              3846

SEQ ID NO: 2         moltype = RNA   length = 3846
FEATURE              Location/Qualifiers
source               1..3846
                     mol_type = other RNA
                     organism = Severe acute respiratory syndrome coronavirus 2
SEQUENCE: 2
atgtttctgc tcacaaccaa acgcactatg tttgttttcc tcgtgctgct ccctttggta    60
agttctcagt gtgtaaacct gacaacacga acccagttgc ctccagctta taccaactca   120
tttactcgcg gagtatatta tcccgataag gtctttagaa gtagcgtgtt gcactctaca   180
caggatctgt tcttgccctt ctttagtaac gttacctggt ttcatgcaat acatgtgagc   240
```

```
ggaacaaatg gaacaaaaag atttgacaat ccagtgcttc catttaatga tggggtttac  300
tttgccagta ccgaaaagtc aaacataatc cgggggtgga tctttggaac cactttggac  360
tctaagacac agtctctcct catagtaaac aacgccacca atgttgtcat aaaagtatgc  420
gaatttcagt tttgcaacga tccctttctc ggggtgtatt accataagaa taataaatcc  480
tggatggagt ctgagttccg ggtttatagt agtgctaata attgcacttt cgaatacgtg  540
tcccaaccat tcctcatgga ccttgagggc aaacagggga attttaaaaa cttgcgcgaa  600
tttgtcttta agaatatcga cggatacttt aagatctata gtaaacacac tcctatcaac  660
ctcgttcggg atcttcccca aggcttttct gctctcgaac ccctcgtaga cttgccaatt  720
gggataaata tcactcgctt tcaaactttg cttgccctcc acaggagcta cctgacaccc  780
ggcgactctt cttctggttg gaccgccggc gccgctgcct attatgttgg ttaccttcag  840
ccacgaacat tcttgctcaa gtataacgag aatggcacca ttaccgacgc cgtcgattgt  900
gcattggatc ccttgtctga aacaaaatgt accttgaagt cctttaccgt agagaaaggc  960
atataccaga cttccaactt ccgagttcag cctacagaat ccattgtgag atttcccaac  1020
atcacaaacc tctgcccttt cggtgaagta tttaatgcta cacgcttcgc ttcagtctat  1080
gcctggaata ggaagcgcat atcaaattgc gtggccgatt attcagtcct ctataatagc  1140
gcatccttca gtactttcaa gtgctacggc gtttccccca ccaaactcaa tgatctttgc  1200
ttcaccaacg tctatgctga cagttttgtc atacgaggcg acgaagtacg ccagattgcc  1260
cccgggcaga caggtaaaat tgctgattat aattataaac tcccagatga ctttactgga  1320
tgcgtcatag cctggaattc caacaatctt gattccaagg ttggtgggaa ttataattac  1380
ctttatcgac tgttcagaaa gagtaacttg aaaccatttg agagagacat atccaccgag  1440
atttaccagg caggcagtac tccttgtaac ggcgttgagg gatttaactg ctatttttcct  1500
ttgcaatcct atggctttca accaacaaac ggggttggct atcaacccta tcgagtggtt  1560
gtcctgagct ttgaactttt gcacgctccc gccacagtct gcggaccaaa aaagagtaca  1620
aatcttgtca agaataagtg cgtaaatttc aatttcaatg gccttacagg aacaggcgtg  1680
ctgactgagt caaacaagaa gttcctgcca tttcagcagt ttgggcggga tatagcagac  1740
acaactgacg ctgtacgcga tcctcagact ttggagatct tggacatcac tccctgttct  1800
ttcggagggg tatctgtcat cacccccgga actaatacat caaatcaggt cgctgtgttg  1860
taccaagatg tcaactgcac agaagtcccc gttgctatac acgcagacca gctcaccccc  1920
acatggcggg tgtactcaac tggctcaaac gtattccaga ccagagctgg gtgcttgatc  1980
ggtgctgaac acgtaaacaa tagctatgaa tgcgatattc ccatcggtgc cgggatctgc  2040
gctagctatc agacacagac caattccccc cggcgagcac gatctgtagc atcccagtct  2100
attattgcct acactatgtc attgggcgcc gagaatagcg tcgcatattc aaataattct  2160
attgcaatac ccaccaactt cacaatctcc gtaactacag aaatacttcc agtttccatg  2220
acaaagacat cagtggattg tacaatgtat atatgcggag attccacaga atgttcaaat  2280
ttgctcttgc agtacggctc cttctgcacc cagctcaaca gggcccttac aggtattgct  2340
gtcgaacagg acaagaacac acaagaagtc ttcgcccaag tcaaacagat atacaaaact  2400
cctcccataa aggattttgg cggcttcaac tttagtcaga tcctcccaga cccttcaaaa  2460
ccatctaaac gatcatttat tgaagatctg ctgttcaaca aggtcactct tgccgatgct  2520
ggattcatta agcaatacgg tgactgcctt ggtgatattg ctgcccgaga tctgatctgt  2580
gcccagaaat tcaacgggct cactgtactc cctccactgc tcacagacga aatgattgca  2640
cagtacacaa gtgccctgtt ggcaggcaca atcactagcg gctggacctt tggcgcaggt  2700
gcagcactcc aaataccttt tgccatgcag atggcctatc ggtttaatgg gataggcgtg  2760
actcaaaatg tcctctacga aaaccaaaag ttgatagcta accaattcaa ttcagcaatc  2820
gggaagatac aggattcact gtctagtact gctagtgccc ttggtaagct gcaggacgtt  2880
gtcaaccaga atgctcaagc tctgaataca ttggttaagc agctctctag taattttggg  2940
gccatctctt cagtacttaa tgatattttg agccgattgg acccacccga agctgaagta  3000
cagatcgaca ggctgataac aggccggctc caatccctcc aaacatacgt gacacaacaa  3060
ctcatacgcg cagccgaaat ccgagccagc gctaacctgg cagctaccaa gatgtcagaa  3120
tgcgttctgg gccagagtaa acgcgtagat ttctgcggga aagggtacca cctgatgtcc  3180
tttccacaat ctgcacctca cggggtcgtc tttttgcatg taacatatgt acccgcacaa  3240
gagaagaatt ttactaccgc tcctgccatc tgtcatgacg ggaaagctca ttttcctcgc  3300
gaaggtgtgt ttgtatctaa tggtacacat tggtttgtca cacagcggaa tttctatgaa  3360
ccccagatca ttacaactga caacactttt gtttccggga attgtgacgt ggtcatagga  3420
atcgtaaata acactgtata tgatcccctc caaccagagc tggactcttt taaagaagaa  3480
ctggataaat atttcaagaa ccacacaagt cccgacgtgg accttgggga cataagtggt  3540
attaacgcat ctgtggttaa cattcaaaag gaaatcgaca gactcaacga ggtggccaaa  3600
aacctgaacg aaagcttgat agatctccag gagttgggca agtatgaaca gtacattaaa  3660
tggccatggt acatatggct tggctttatc gctggcctta tcgccatcgt aatggttaca  3720
atcatgctgt gctgcatgac ctcctgctgt tcttgtttga aagggtgttg ttcttgtggt  3780
agttgttgca agtttgacga agatgattcc gaacctgttc ttaaaggggt aaagcttcac  3840
tataca                                                             3846
```

```
SEQ ID NO: 3          moltype = RNA  length = 3846
FEATURE               Location/Qualifiers
source                1..3846
                      mol_type = other RNA
                      organism = Severe acute respiratory syndrome coronavirus 2
SEQUENCE: 3
atgtttctgc tcacaaccaa acgcactatg tttgttttcc tcgtgctgct ccctttggta  60
agttctcagt gtgtaaacct gacaacacga acccagttgc ctccagctta taccaactca  120
tttactcgcg gagtatatta tcccgataag gtctttagaa gtagcgtgtt gcactctaca  180
caggatctgt tcttgccctt ctttagtaac gttacctggt ttcatgcaat acatgtgagc  240
ggaacaaatg gaacaaaaag atttgacaat ccagtgcttc catttaatga tggggtttac  300
tttgccagta ccgaaaagtc aaacataatc cgggggtgga tctttggaac cactttggac  360
tctaagacac agtctctcct catagtaaac aacgccacca atgttgtcat aaaagtatgc  420
gaatttcagt tttgcaacga tccctttctc ggggtgtatt accataagaa taataaatcc  480
tggatggagt ctgagttccg ggtttatagt agtgctaata attgcacttt cgaatacgtg  540
tcccaaccat tcctcatgga ccttgagggc aaacagggga attttaaaaa cttgcgcgaa  600
tttgtcttta agaatatcga cggatacttt aagatctata gtaaacacac tcctatcaac  660
```

```
ctcgttcggg atcttcccca aggcttttct gctctcgaac ccctcgtaga cttgccaatt    720
gggataaata tcactcgctt tcaaactttg cttgccctcc acaggagcta cctgacaccc    780
ggcgactctt cttctggttg daccgccggc gccgctgcct attatgttgg ttaccttcag    840
ccacgaacat tcttgctcaa gtataacgag aatggcacca ttaccgacgc cgtcgattgt    900
gcattggatc ccttgtctga aacaaaatgt accttgaagt cctttaccgt agagaaaggc    960
atataccaga cttccaactt ccgagttcag cctacagaat ccattgtgag atttcccaac   1020
atcacaaacc tctgcccttt cggtgaagta tttaatgcta cacgcttcgc ttcagtctat   1080
gcctggaata ggaagcgcat atcaaattgc gtggccgatt attcagtcct ctataatagc   1140
gcatccttca gtactttcaa gtgctacggc gtttccccca ccaaactcaa tgatctttg    1200
ttcaccaacg tctatgctga cagttttgtc atacgaggcg acgaagtacg ccagattgcc   1260
cccgggcaga caggtaaaat tgctgattat aattataaac tcccagatga ctttactgga   1320
tgcgtcatag cctggaattc caacaatctt gattccaagg ttggtgggaa ttataattac   1380
ctttatcgac tgttcagaaa gagtaacttg aaaccatttg agagagacat atccaccgag   1440
atttaccagg caggcagtac tccttgtaac ggcgttgagg gatttaactg ctattttcct   1500
ttgcaatcct atggctttca accaacaaac ggggttggct atcaaccta tcgagtggtt    1560
gtcctgagct ttgaactttt gcacgctccc gccacagtct gcggaccaaa aaagagtaca   1620
aatcttgtca gaataagtg cgtaaatttc aatttcaatg gccttacagg aacaggcgtg    1680
ctgactgagt caaacaagaa gttcctgcca tttcagcagt ttgggcggga tatagcagac   1740
acaactgacg ctgtacgcga tcctcagact ttggagatct tggacatcac tccctgttct   1800
ttcggagggg tatctgtcat caccccggga actaatacat caaatcaggt cgctgtgttg   1860
taccaagatg tcaactgcac agaagtcccc gttgctatac acgcaggcca gctcacccccc  1920
acatggcgtg tgtactcaac tggctcaaac gtattccaga ccagagctgg gtgcttgatc   1980
ggtgctgaac acgtaaacaa tagctatgaa tgcgatattc ccatcggtgc cgggatctgc   2040
gctagctatc agacacagac caattcccccc ggcgagcac gatctgtagc atcccagtct  2100
attattgcct acactatgtc attgggcgcc gagaatagcc tcgcatattc aaataattct   2160
attgcaatac ccaccaactt cacaatctcc gtaactacaa aaatacttcc agtttccatg   2220
acaaagacat cagtggattg tacaatgtat atatgcggag attccacaga atgttcaaat   2280
ttgctcttgc agtacggctc cttctgcacc cagctcaaca gggcccttac aggtattgct   2340
gtcgaacagg acaagaacac acaagaagtc ttcgcccaag tcaaacgat atacaaaact    2400
cctcccataa aggattttgg cggcttcaac tttagtcaga tcctcccaga ccctcaaaa    2460
ccatctaaac gatcatttat tgaagatctg ctgttcaaca aggtcactct tgccgatgcc   2520
ggattcatta gcaatacgg tgactgcctt ggtgatattg ctgccgaga tctgatctgt    2580
gcccagaaat caacgggct cactgtactc cctccactgc tcacagacga aatgattgca   2640
cagtacacaa gtgccctgtt ggcaggcaca atcactagcg gctggaccttt tggcgcaggt  2700
gcagcactcc aaatacctt tgccatgcag atggcctatc ggttaatgg gataggcgtg    2760
actcaaaatg tcctctacga aaaccaaaag ttgatagcta accaattcaa ttcagcaatc   2820
gggaagatac aggattcact gtctagtact gctagtgccc ttggtaagct gcaggacgtt   2880
gtcaaccaga atgctcaagc tctgaataca ttggttaagc agctcctctag taatttttggg  2940
gccatctctt cagtacttaa tgatatttg agcgattgg acaaagtgga agctgaagta    3000
cagatcgaca ggctgataac aggccggctc caatccctcc aaacatcgt gacacaacaa   3060
ctcatacgcg cagccgaaat ccgagccagc gctaacctgg cagctaccaa gatgtcagaa   3120
tgcgttctgg gccagagtaa acgcgtagat ttctgcggga aagggtacca cctgatgtcc   3180
tttccacaat ctgcacctca cggggtcgtc ttttgcatg taacatatgt acccgcacaa    3240
gagaagaatt ttactaccgc tcctgccatc tgtcatgacg ggaaagctca ttttcctcgc   3300
gaaggtgtgt tgtatctaa tggtacacat tggtttgtca cacagcggaa tttctatgaa   3360
ccccagatca ttacaactga caacactttt gtttccggga attgtgacgt ggtcatagga   3420
atcgtaaata cactgtata tgatcccctc caaccagagc tggactcttt taaagaagaa   3480
ctggataaat atttcaagaa ccacacaagt cccgacgtgg accttgggga cataagtggt   3540
attaacgcat ctgtgttaa cattcaaaag gaaatcgaca gactcaacga ggtgccaaaa   3600
aacctgaacg aaagcttgat agatctccag gagttgggca gtatgaaca gtacattaaa   3660
tggccatggt acatatggct tggctttatc gctggccttca tcgccatgct aatgttaca   3720
atcatgctgt gctgcatgac ctcctgctgt tcttgtttga aagggtgttg ttcttgtggt   3780
agttgttgca gtttgacga agatgattcc gaacctgttc ttaaagggt aaagcttcac    3840
tataca                                                            3846

SEQ ID NO: 4            moltype = RNA    length = 3837
FEATURE                 Location/Qualifiers
source                  1..3837
                        mol_type = other RNA
                        organism = Severe acute respiratory syndrome coronavirus 2
SEQUENCE: 4
atgtttctgc tcacaaccaa acgcactatg tttgttttcc tcgtgctgct ccctttggta     60
agttctcagt gtgtaaactt cacaacacga acccagttgc ctccagctta taccaactca   120
tttactcgcg gagtatatta tcccgataag gtctttagaa gtagcgtgtt gcactcataca  180
caggatctgt tcttgccctt ctttagtaac gttaccggt ttcatgcaat acatgtgagc    240
ggaacaaatg aacaaaaag atttgccaat ccagtgcttc catttaatga tgggttta     300
tttgccagta ccgaaaagtc aaacataatc cggggtgga tctttggaac cactttggac    360
tctaagacac agtctctcct catagtaaac aacgccacca atgttgtcat aaaagtatgc   420
gaatttcagt tttgcaacga tcccttttctc ggggtgtatt accataagaa taataatc    480
tggatggagt ctgagttccg ggtttatagt agtgctaata attgcacttt cgaatacgtg   540
tcccaaccat tcctcatgga ccttgagggc aaacagggga ttttaaaaa cttgcgcgaa   600
tttgtctttta agaatatcga cggatactt aagatctata gtaaacacac tcctatcaac   660
ctcgttcggg gccttcccca aggcttttct gctctcgaac ccctcgtaga cttgccaatt   720
gggataaata tcactcgctt tcaaactttg cacatcgagt cacaggcagt ggcgactctt   780
tcttctggtt ggaccgccgg cgccgctgcc tattatgttg gttaccttca gccacgaaca   840
ttcttgctca gtataacga gaatggcacc attaccgacg ccgtcgattg tgcattggat    900
cccttgtctg aaacaaaatg taccttgaag tcctttaccg tagagaaagg catataccag   960
acttccaact tccgagttca gcctacagaa tccattgtga gatttcccaa catcacaaac  1020
ctctgccctt tcggtgaagt atttaatgct acacgcttcg cttcagtcta tgcctggaat  1080
```

-continued

```
aggaagcgca tatcaaattg cgtggccgat tattcagtcc tctataatag cgcatccttc 1140
agtactttca agtgctacgg cgtttccccc accaaactca atgatctttg cttcaccaac 1200
gtctatgctg acagttttgt catacgaggc gacgaagtac gccagattgc ccccgggcag 1260
acaggtaaca ttgctgatta taattataaa ctcccagatg actttactgg atgcgtcata 1320
gcctggaatt ccaacaatct tgattccaag gttggtggga attataatta cctttatcga 1380
ctgttcagaa agagtaactt gaaaccattt gagagagaca tatccaccga gatttaccag 1440
gcaggcagta ctccttgtaa cggcgttaag ggatttaact gctattttcc tttgcaatcc 1500
tatgctttc aaccaacata cggggttggc tatcaaccct atcgagtggt tgtcctgagc 1560
tttgaacttt tgcacgctcc cgccacagtc tgcggaccaa aaaagagtac aaatcttgtc 1620
aagaataagt gcgtaaattt caatttcaat ggccttacag gaacaggcgt gctgactgag 1680
tcaaacaaga agttcctgcc atttcagcag tttgggcggg atatagcaga cacaactgac 1740
gctgtacgcg atcctcagac tttggagatc ttggacatca ctccctgttc tttcggaggg 1800
gtatctgtca tcaccccggg aactaataca tcaaatcagg tcgctgtgtt gtaccaaggc 1860
gtcaactgca cagaagtccc cgttgctata cacgcagacc agctcacccc cacatggcgg 1920
gtgtactcaa ctggctcaaa cgtattccag accagagctg ggtgcttgat cggtgctgaa 1980
cacgtaaaca atagctatga atgcgatatt cccatcggtg ccgggatctg cgctagctat 2040
cagacacaga ccaattcccc ccggcgagca cgatctgtag catcccagtc tattattgcc 2100
tacactatgt cattgggcgt ggagaatagc gtcgcatatt caaataattc tattgcaata 2160
cccaccaact tcacaatctc cgtaactaca gaaatacttc cagtttccat gacaaagaca 2220
tcagtggatt gtacaatgta tatatgcgga gattccacag aatgttcaaa tttgctcttg 2280
cagtacggct ccttctgcac ccagctcaac agggccctta caggtattgc tgtcgaacag 2340
gacaagaaca cacaagaagt cttcgcccaa gtcaaacaga tatacaaaac tcctcccata 2400
aaggattttg gcggcttcaa ctttagtcag atcctcccag acccttcaaa accatctaaa 2460
cgatcattta ttgaagatct gctgttcaac aaggtcactc ttgccgatgc tggattcatt 2520
aagcaatacg gtgactgcct tggtgatatt gctgcccgag atctgatctg tgcccagaaa 2580
ttcaacgggc tcactgtact ccctccactg ctcacagacg aaatgattgc acagtacaca 2640
agtgccctgt tggcaggcac aatcactagc ggctggacct ttggcgcagg tgcagcactc 2700
caaataccct ttgccatgca gatggcctat cggtttaatg gataggcgt gactcaaaat 2760
gtcctctacg aaaaccaaaa gttgatagct aaccaattca attcagcaat cgggaagata 2820
caggattcac tgtctagtac tgcctagtgcc cttggtaagc tgcaggacgt tgtcaaccag 2880
aatgctcaag ctctgaatac attggttaag cagctctcta gtaattttgg ggccatctct 2940
tcagtactta atgatatttt gagccgattg gacccacccg aagctgaagt acagatcgac 3000
aggctgataa caggccggct ccaatccctc caaacatacg tgacacaaca actcatacgc 3060
gcagccgaaa tccgagccag cgctaacctg gcagctacca agatgtcaga atgcgttctg 3120
ggccagagta aacgcgtaga tttctgcggg aaagggtacc acctgatgtc ctttccacaa 3180
tctgcacctc acggggtcgt cttttttgcat gtaacatatg tacccgcaca agagaagaat 3240
tttactaccg ctcctgccat ctgtcatgac gggaaagctc attttcctcg cgaaggtgtg 3300
tttgtatcta atggtacaca ttggtttgtc acacagcgga atttctatga accccagatc 3360
attacaactg acaacacttt tgtttccggg aattgtgacg tggtcatagg aatcgtaaat 3420
aacactgtat atgatcccct ccaaccagag ctggactctt ttaaagaaga actggataaa 3480
tatttcaaga accacacaag tcccgacgtg gaccttgggg acataagtgg tattaacgca 3540
tctgtggtta acattcaaaa ggaaatcgac agactcaacg aggtggccaa aaacctgaac 3600
gaaagcttga tagatctcca ggagttgggc aagtatgaac agtacattaa atggccatgg 3660
tacatatggc ttggctttat cgctggcctt atcgccatcg taatggttac aatcatgctg 3720
tgctgcatga cctcctgctg ttcttgtttg aaagggtgtt gttcttgtgg tagttgttgc 3780
aagtttgacg aagatgattc cgaacctgtt cttaaagggg taaagcttca ctataca 3837
```

SEQ ID NO: 5         moltype = RNA  length = 3837
FEATURE            Location/Qualifiers
source             1..3837
                    mol_type = other RNA
                    organism = Severe acute respiratory syndrome coronavirus 2
SEQUENCE: 5

```
atgtttctgc tcacaaccaa acgcactatg tttgttttcc tcgtgctgct ccctttggta 60
agttctcagt gtgtaaacct gacaacacga acccagttgc ctccagctta taccaactca 120
tttactcgcg gagtatatta tcccgataag gtctttagaa gtagcgtgtt gcactctaca 180
caggatctgt tcttgccctt cttttagtaac gttacctggt ttcatgcaat aagcggaaca 240
aatgaacaa aaagatttga caatccagtc cttccattta atgatggggt ttactttgcc 300
agtaccgaaa agtcaaacat aatccggggg tggatcttca gaaccacttt ggactctaag 360
acacagtctc tcctcatagt aaacaacgcc accaatgttg tcataaaagt atgcgaattt 420
cagttttgca acgatccctt tctcggggtg taccataaga ataataaatc ctggatggag 480
tctgagttcc gggtttatag tagtgctaat aattgcactt tcgaatacgt gtcccaacca 540
ttcctcatgg accttgaggg caaacagggg aattttaaaa acttgcgcga atttgtcttt 600
aagaatatcg acggatactt taagatctat agtaaacaca ctcctatcaa cctcgttcgg 660
gatcttcccc aaggcttttc tgctctcgaa cccctcgtag acttgccaat gggataaat 720
atcactcgct ttcaaacttt gcttgccctc cacaggagct acctgacacc cggcgactct 780
tcttctggtt ggaccgccgg cgccgctgcc tattatgttg ttaccttca gccacgaaca 840
ttcttgctca agtataacga gaatggcacc attaccgaca ccgtcgattg tgcattggat 900
cccttgtctg aaacaaaatg taccttgaag tccttaccg tagagaaaaga catataccag 960
acttccaact tccgagttca gcctacgaaa tccattgtga gatttcccaa catcacaaac 1020
ctctgccctt tcggtgaagt attttaatgct acacgcttcg cttcagtcta tgcctggaat 1080
aggaagcgca tatcaaattg cgtggccgat tattcagtcc tctataatag cgcatccttc 1140
agtactttca agtgctacgg cgtttccccc accaaactca atgatctttg cttcaccaac 1200
gtctatgctg acagttttgt catacgaggc gacgaagtac gccagattgc ccccgggcag 1260
acaggtaaaa ttgctgatta taattataaa ctcccagatg actttactgg atgcgtcata 1320
gcctggaatt ccaacaatct tgattccaag gttggtggga attataatta cctttatcga 1380
ctgttcagaa agagtaactt gaaaccattt gagagagaca tatccaccga gatttaccag 1440
gcaggcagta ctccttgtaa cggcgttgag ggatttaact gctattttcc tttgcaatcc 1500
tatgctttc aaccaacata cggggttggc tatcaaccct atcgagtggt tgtcctgagc 1560
```

```
tttgaacttt tgcacgctcc cgccacagtc tgcggaccaa aaaagagtac aaatcttgtc  1620
aagaataagt gcgtaaattt caatttcaat ggccttacag gaacaggcgt gctgactgag  1680
tcaaacaaga agttcctgcc atttcagcag tttgggcggg atatagacga cacaactgac  1740
gctgtacgcg atcctcagac tttggagatc ttggacatca ctccctgttc tttcggaggg  1800
gtatctgtca tcacccccgg aactaataca tcaaatcagg tcgctgtgtt gtaccaaggc  1860
gtcaactgca cagaagtccc cgttgctata cacgcagatc agctcacccc cacatggcgg  1920
gtgtactcaa ctggctcaaa cgtattccag accagagctg ggtgcttgat cggtgctgaa  1980
cacgtaaaca atagcctatga atgcgatatt cccatcggtg ccgggatctg cgctagctat  2040
cagacacaga ccaattccca tcggcgagca cgatctgtag catcccagtc tattattgca  2100
tacactatgt cattgggcgc cgagaatagc gtcgcatatt caaataattc tattgcaata  2160
cccatcaact tcacaatctc cgtaactaca gaaatacttc cagtttccat gacaaagaca  2220
tcagtggatt gtacaatgta tatatgcgga gattccacag aatgttcaaa tttgctcttg  2280
cagtacggct ccttctgcac ccagctcaac agggccctta caggtattgc tgtcgaacag  2340
gacaagaaca cacaagaagt cttcgccaa gtcaaacaga tatacaaaac tcctcccata  2400
aaggattttg gcggcttcaa ctttagtcag atcctcccag acccttcaaa accatctaaa  2460
cgatcattta ttgaagatct gctgttcaac aaggtcactc ttgccgatgc tggattcatt  2520
aagcaatacg gtgactgcct tggtgatatt gctgcccgag atctgatctg tgcccagaaa  2580
ttcaacgggc tcactgtact ccctccactg ctcacagacg aaatgattgc acagtacaca  2640
agtgccctgt tggcaggcac aatcactagc ggctggacct ttgcgcagg tgcagcactc  2700
caaatacctt ttgccatgca gatggcctat cggtttaatg ggataggcgt gactcaaaat  2760
gtcctctacg aaaaccaaaa gttgatagct aaccaattca attcagcaat cgggaagata  2820
caggattcac tgtctagtac tgctagtgcc cttggtaagc agtgacagt tgtcaaccag  2880
aatgctcaag ctctgaatac attggttaag cagctctcta gtaattttgg ggccatctct  2940
tcagtactta atgatatttt ggcccgattg gacccacccg aagctgaagt acagatcgac  3000
aggctgataa caggccggct ccaatccctc caaacatacg tgacacaaca actcatacgc  3060
gcagccgaaa tccgagccag cgctaacctg gcagctacca agatgtcaga atgcgtttcg  3120
ggccagagta aacgcgtaga tttctgcggg aaagggtacc acctgatgtc ctttccacaa  3180
tctgcacctc acgggtcgt ctttttgcat gtaacatatg tacccgcaca agagaagaat  3240
tttactaccg ctcctgccat ctgtcatgac gggaaagctc attttcctcg cgaaggtgtg  3300
tttgtatcta atggtacaca ttggtttgtc acacagcgga atttctatga accccagatc  3360
attacaactc acaacacttt tgtttccggg aattgtgacg tggtcatagg aatcgtaaat  3420
aacactgtat atgatcccct caaccagag ctggactctt ttaaagaaga actggataaa  3480
tatttcaaga accacacaag tcccgacgtg gaccttgggg acataagtgg tattaacgca  3540
tctgtggtta acattcaaaa ggaaatcgac agactcaacg aggtggccaa aaacctgaac  3600
gaaagcttga tagatctcca ggagttggc aagtatgaac agtacattaa atggccatgg  3660
tacatatggc ttggctttat cgctggcctt atcgccatcg taatggttac aatcatgctg  3720
tgctgcatga cctcctgctg ttcttgtttg aaagggtgtt gttcttgtgg tagttgttgc  3780
aagtttgacg aagatgattc cgaacctgtt cttaaagggg taaagcttca ctataca     3837
```

```
SEQ ID NO: 6            moltype = RNA   length = 3843
FEATURE                 Location/Qualifiers
source                  1..3843
                        mol_type = other RNA
                        organism = Severe acute respiratory syndrome coronavirus 2
SEQUENCE: 6
atgtttctgc tcacaaccaa acgcactatg tttgttttcc tcgtgctgct ccctttggta   60
agttctcagt gtgtaaacct gagaacacga acccagttgc ctccagctta taccaactca  120
tttactcgcg gagtatatta tcccgataag gtctttagaa gtagcgtgtt gcactctaca  180
caggatctgt tcttgccctt ctttagtaac gttaccggt tcatgcaat acatgtgagc  240
ggaacaaatg gaacaaaaag atttgacaat ccagtgcttc catttaatga tggggtttac  300
tttgccagta tcgaaaagtc aaacataatc cggggtgctc tctttggaac cactttggaa  360
tctaagacac agtctctcct catagtaaac aacgccacca atgttgtcat aaaagtatgc  420
gaatttcagt tttgcaacga tcccttctc gacgtgtatt accataagaa taataaatcc  480
tggatggagt ctgggttta tagtagtgct aataattgca ctttcgaata cgtgtcccaa  540
ccattcctca tggaccttga gggcaaacag gggaattta aaaacttgcg cgaatttgtc  600
tttaagaata tcgacggata cttaagatc tatagtaaac acactcctat caacctcgtt  660
cgggatcttc cccaaggctt ttctgctctc gaacccctcg tagacttgcc aattgggata  720
aatatcactc gctttcaaac tttgcttgcc ctccacagga gctacctgac acccggcgac  780
tcttcttctg gtttgaccgc cggcgccgct gcctattacg ttggttacct tcagccacga  840
acattcttgc tcaagtataa cgagaatggc accattaccg acgcgtcga ttgtgcattg  900
gatcccttgt ctgaaacaaa atgtaccttg aagtcctta ccgtagaaa aggcatatac  960
cagacttcca acttccgagt tcagcctaca gaatccatcg tacgatttcc caacatcaca 1020
aacctctgcc ctttcggtga agtatttaat gctacgcgct tcgcttcagt ctatgcctgg 1080
aataggaagc gcatatcaaa ttgcgtggcc gattattcga tcctctataa tagcgcatcc 1140
ttcagtactt tcaagtgcta cggcgtttcc cccaccaaac tcaatgatct tgcttcacc  1200
aacgtctatg ctgacagttt tgtcatacga ggcgacgaag tacgccagat tgcccccggg 1260
cagacaggta atattgctga ttataattat aaactcccag atgactttac ggatgcgtc  1320
atagcctgga attccaacaa tctagattcc aaggttggtg ggaattataa ttaccgttat 1380
cgactgttca gaaagagtaa tttgaaacca tttgagagag acatatccac cgagatttac 1440
caggcaggca gtaagccttg taacggcgtt gagggattta actgctattt cccttttgcaa 1500
tcctatggct tcaaccaaac aaacgggtt ggctatcaac cctatcgagt ggttgtcctc 1560
agctttgaac ttttgcacgc tcccgccaca gtctgcggac aaaaagag tacaaatctt 1620
gtcaagaata gtgcgtaaa tttcaatttc aatggcctta caggaacagg cgtgctgact 1680
gagtcaaaca agagttcct gccatttcag cagtttgggc gggatatagc agacacactga 1740
gacgctgtac gcgatcctca gactttggag atcttggaca tcactccctg ttcttcgga 1800
gggtatctg tcatcacccc cggaactaat acatcaaatc aggtcgctgt gttgtaccaa 1860
ggtgtcaact gcacagaagt ccccgttgct atacacgcag accagctcac ccccacatgg 1920
cgggtgtact caactggctc aaacgtattc agaccagag ctgggtgctt gatcggtgct 1980
gaacacgtga acaatagcta tgaatgcgat attcccatcg tgccgggat ctgcgctagc 2040
```

```
tatcagacac agaccaattc ccgcaggcgg gctcgctctg tagcatccca gtctattatt    2100
gcctacacta tgtcattggg cgccgagaat agcgtcgcat attcaaataa ttctattgca    2160
atacccacca acttcacaat ctccgtaact acagaaatac ttccagtttc catgacaaag    2220
acatcagtgg attgtacaat gtatatatgc ggagattcca cagaatgttc aaatttgctc    2280
ttgcagtacg gctccttctg cacccagctc aacagggcac ttacaggtat tgctgtcgaa    2340
caggacaaga acacacaaga agtcttcgcc caagtcaaac agatatacaa aactcctccc    2400
ataaaggatt ttggcggctt caactttagt cagatcctcc cagacccttc aaaaccatct    2460
aaacgatcat ttattgaaga tctgctgttc aacaaggtca ctcttgccga tgctggattc    2520
attaagcaat acggtgccg ccttggtgat attgctgccc gagatctgat ctgtgcccat    2580
aaattcaacg ggctcactgt actccctcca ctgctcacag acgaaatgat tgcacagtac    2640
acaagtgccc tgttggcagg cacaatcact agcggctgga cctttggcgc aggtgcagca    2700
ctccaaatac ctttttgccat gcagatggcc tatcggttta tgggataggg cgtgactcaa    2760
aatgtcctct acgaaaacca aaagttgata gctaaccaat tcaattcagc aatcgggaag    2820
atacaggatt cactgtctag tactgctagt gcccttggta agctgcagaa cgttgtcaac    2880
cagaatgctc aagctctgaa tacattggtt aagcagctct ctagtaattt tggggccatc    2940
tcttcagtac ttaatgatat tttgagccga ttggacccac ctgaagctga agtacagatc    3000
gacaggctga taacaggccg gctccaatcc ctccaaacat acgtgacaca caactcata    3060
cgcgcagccg aaatccgagc cagcgctaac ctggcagcta ccaagatgct agaatgcgtt    3120
ctgggccaga gtaaacgcgt agatttctgc gggaaagggt accacctgat gtcctttcca    3180
caatctgcac ctcacggggt cgtcttttg catgtaacat acgtacccgc acaagagaag    3240
aatttttacta ccgctcctgc catctgtcat gacgggaaag ctcattttcc tcgcgaaggt    3300
gtgtttgtat ctaatggtac acattggttt gtcacacagc ggaatttcta tgaacccaaa    3360
atcattacaa ctgacaacac tttttgtccc gggaattgtg acgtggtcat aggaatcgta    3420
aataacactg tatatgatcc cctccaacca gagctggact cttttaaaga gaactggat    3480
aaaatatttca agaaccacac aagtcccgac gtggaccttg gggacataag tggtattaac    3540
gcatctgtgg ttaacattca aaaggaaatc gacagactca acaggtgcc caaaaacctg    3600
aacgaaagct tgatagatct ccaggagttg ggcaagtatg aacagtacat taaatgggcca    3660
tggtacatat ggcttggctt tatcgctggc cttatcgcca tcgtaatggt tacaatcatg    3720
ctgtgctgca tgacctcctg ctgttcttgt ttgaaagggt gttgttcttg tggtagttgt    3780
tgcaagtttg acgaagatga ttccgaacct gttcttaagg gggtaaagct tcactataca    3840
tga                                                                 3843
```

SEQ ID NO: 7          moltype = RNA  length = 3843
FEATURE               Location/Qualifiers
source                1..3843
                      mol_type = other RNA
                      organism = Severe acute respiratory syndrome coronavirus 2
SEQUENCE: 7

```
atgtttctgc tcacaaccaa acgcactatg tttgttttcc tcgtgctgct cccttttggta    60
agttctcagt gtgtaaacct gagaacacga acccagttgc ctccagctta taccaactca    120
tttactcgcg gagtatatta tcccgataag gtctttagaa gtagcgtgtt gcactctaca    180
caggatctgt tcttgccctt ctttagtaac gttacctggt tcatgcaat acatgtgagc    240
ggaacaaatg gaacaaaaag atttgacaat ccagtgctgc catttaatga tggggtttac    300
tttgccagta tcgaaaagtc aaacataatc cggggggtgga tctttggaac cacttttggac    360
tctaagacac agtctctcct catagtaaac aacgccacca atgttgtcat aaaagtatgc    420
gaatttcagt tttgcaacga tcccttttctc gacgtgtatt accataagaa taataaaatcc    480
tggatggagt ctgggggttta tagtagtgct aataattgca cttttcgaata cgtgtcccaa    540
ccattcctca tggaccttga gggcaaacag gggaattttta aaacttgcg cgaatttgtc    600
tttaagaata tcgacggata cttttaagatc tatagtaaac acactcctat caacctcgtt    660
cgggatcttc cccaaggctt ttctgctctc gaaccctcg tagacttgcc aattgggata    720
aatatcactc gcttttcaaac tttgcttgcc ctccacagga gctacctgac acccggctac    780
tcttcttctg gtttgaccgc cggcgccgct gccatatatg ttggttacct tcagccacga    840
acattcttgc tcaagtataa cgagaatggc accattaccg acgccgtcga ttgtgcattg    900
gatcccttgt ctgaaacaaa atgtaccttg aagtccttta ccgtagagaa aggcatatac    960
cagacttcca acttccgagt tcagcctaca gaatccataca tacgatttcc caacatcaca    1020
aacctctgcc ctttcggtga agtatttaat gctacacgct tcgcttcagt ctatgctgga    1080
aataggaagc gcatatcaaa ttgcgtggcc gattatcag tcctctataa tagcgcatcc    1140
ttcagtactt tcaagtgcta cggcgtttcc cccaccaaac tcaatgatct ttgcttcacc    1200
aacgtctatg ctgacagttt tgtcatacga ggcgacgaag tacgccagat tgcccccgag    1260
cagacaggta atattgctga ttataattat aaactcccag atgactttac tggatgcgtc    1320
atagcctgga attccaacaa tctagattcc aaggttggtg ggaattataa ttaccgttat    1380
cgactgttca gaaagagtaa cttgaaacca ttttgagagag acatatccac cgagatttac    1440
caggcaggca gtaagccttg taacggcgtt gagggattta actgctattt tcccttttgcaa    1500
tcctatggct ttcaaccaac aaacgggtt ggctatcaac cctatcggtt cctcc         1560
agctttgaac ttttgcacgc tcccgccaca gtctgcggaca caaaaaagag tacaaatctt    1620
gtcaagaata agtgcgtaaa tttcaatttc aatggcctta caggaacagg cgtgctgact    1680
gagtcaaaca agaatttcct gccatttcag cagtttgggc gggatatagc agacacaact    1740
gacgctgtac gcgatcctca gactttggag atcttggaca tcactccctg ttctttcgga    1800
ggggtatctg tcatcacccc cggaactaat acatcaaatc aggtcgctgt gttgtaccaa    1860
ggtgtcaact gcacagaagt ccccgttgct atacacgcag accagctcac ccccacatgg    1920
cgggtgtact caactggctc aaacgtattc cagaccagag ctgggtgctt gatcggtgct    1980
gaacacgtga acaatagcta tgaatgcgat attcccatcg gtgccgggat ctgcgctagc    2040
tatcagacac agaccaattc ccgcaggcgg gctcgctctg tagcatccca gtctattatt    2100
gcctacacta tgtcattggg cgccgagaat agcgtcgcat attcaaataa ttctattgca    2160
atacccacca acttcacaat ctccgtaact acagaaatac ttccagtttc catgacaaag    2220
acatcagtgg attgtacaat gtatatatgc ggagattcca cagaatgttc aaatttgctc    2280
ttgcagtacg gctccttctg cacccagctc aacagggcac ttacaggtat tgctgtcgaa    2340
caggacaaga acacacaaga agtcttcgcc caagtcaaac agatatacaa aactcctccc    2400
ataaaggatt ttggcggctt caactttagt cagatcctcc cagacccttc aaaaccatct    2460
```

-continued

```
aaacgatcat ttattgaaga tctgctgttc aacaaggtca ctcttgccga tgctggattc    2520
attaagcaat acggtgactg ccttggtgat attgctgccc gagatctgat ctgtgcccag    2580
aaattcaacg ggctcactgt actccctcca ctgctcacag acgaaatgat tgcacagtac    2640
acaagtgccc tgttggcagg cacaatcact agcggctgga cctttggcgc aggtgcagca    2700
ctccaaatac cttttgccat gcagatggcc tatcggttta tgggatagg cgtgactcaa     2760
aatgtcctct acgaaaacca aaagttgata gctaaccaat tcaattcagc aatcgggaag    2820
atacaggatt cactgtctag tactgctagt gcccttggta agctgcagaa cgttgtcaac    2880
cagaatgctc aagctctgaa tacattggtt aagcagctct ctagtaattt tggggccatc    2940
tcttcagtac ttaatgatat tttgagccga ttggacccac ctgaagctga agtacagatc    3000
gacaggctga taacaggccg gctccaatcc ctccaaacat acgtgacaca acaactcata    3060
cgcgcagccg aaatccgagc cagcgctaac ctggcagcta ccaagatgtc agaatgcgtt    3120
ctgggccaga gtaaacgcgt agatttctgc gggaaagggt accactgat gtcctttcca     3180
caatctgcac ctcacggggt cgtcttttg catgtaacat acgtaccgc acaagagaag       3240
aattttacta ccgctcctgc catctgtcat gacgggaaag ctcattttcc tcgcgaaggt    3300
gtgtttgtat ctaatggtac acattggttt gtcacacagc ggaattcta tgaaccccag     3360
atcattacaa ctgacaacac tttttgtttcc gggaattgtg acgtggtcat aggaatcgta   3420
aataacactg tatatgatcc cctccaacca gagctggact cttttaaaga gaactggat     3480
aaatatttca agaaccacac aagtcccgac gtggaccttg gggacataag tggtattaac    3540
gcatctgtgg ttaacattca aaaggaaatc gacagactca acgaggtggc caaaaacctg    3600
aacgaaagct tgatagatct ccaggagttg ggcaagtatg aacagtacat taaatggcca    3660
tggtacatat ggcttggctt tatcgctggc cttatcgcca tcgtaatggt tacaatcatg    3720
ctgtgctgca tgacctcctg ctgttcttgt ttgaaaggt gttgttcttg tggtagttgt     3780
tgcaagtttg acgaagatga ttccgaacct gttcttaagg gggtaaagct tcactataca    3840
tga                                                                  3843

SEQ ID NO: 8         moltype = RNA  length = 3847
FEATURE              Location/Qualifiers
source               1..3847
                     mol_type = other RNA
                     organism = Severe acute respiratory syndrome coronavirus 2
SEQUENCE: 8
cgccaccatg tttctgttga cgaccaagcg aacgatgttc gttttcttgg tgcttttgcc    60
acttgtcagt tccagtgcg tcaatctgac gacacgaaca cagctgcctc ctgcgtacac     120
taacagtttt acgcgaggag tgtattaccc tgacaaagtt ttccgctcta gtgtcctcca    180
tagcacacag gacttgtttc tccccttctt ttccaacgtt acgtggttcc atgtgattag    240
tggaactaac ggtactaaaa gattcgacaa tccagtattg cctttcaacg atgggggtcta  300
tttcgcgtcc atcgagaaat caaatatcat cgcggttgg attttggaa cgacactcga      360
ttcaaagacg caatccctcc ttattgtcaa caacgccact aacgtagtca ttaaggtttg    420
tgagttccag ttttgtaatg atcccttttt tgaccacaag aataacaaga gctgatgga    480
aagcgagttc agagtgtata gctctgcaaa caactgtact tttgaatacg tgagtcaacc    540
tttccttatg gaccttgaag gtaaacaggg taacttttaag aatttgcgcg aatttgtttt   600
caaaaacatt gatggttact ttaaaatcta gtaagcac actcctatca ttgtaagaga      660
gccggaggac cttccacagg gttttagtgc gctcgagccc ctcgttgacc tgcccattgg    720
gatcaacata actcgattcc aaacattgct cgccctttcat cggtcctatc tgactccgg    780
tgactcctct agcggatgga cggcaggtgc cgccgcatac tacgtggggt accttcaacc    840
tcggacattt ttgttgaaat acaatgagaa tggcactata actgacgcgg ttgattgcgc    900
gctcgaccca ttgtccgaaa ctaagtgtac tttgaagtca tttacagtgg agaaaggaat    960
atatcagact agcaatttc gggtacagcc cacggagtc atcgtacggt ttcctaacat      1020
cacgaatctg tgccctttg atgaggtctt taatgcaaca cggttcgcct ccgtctatgc     1080
gtggaataga aagcgcatct caaattgtgt agctgattat tccgtacttt acaacttggc    1140
cccgttcttc acatttaagt gctacggtgt aagccctact aaactgaacg atttgtttt     1200
caccaacgtc tatgcagata gctttgttat tcgaggcgat gaggtacgcc agattgcgcc    1260
tggtcaaacg gtaatatcg ccgactacaa ttataaattg ccagacgatt ttactggttg     1320
tgtcatcgct tggaatagta ataagttgga cagtaaggta tccggcaatt acaactatct    1380
ctaccgattg ttccggaagt ctaacctcaa gccgtttgaa agagacatat ccactgagat    1440
ataccaagca ggcaataaac catgcaacgg agttgctggt ttcaactgct atttcccgtt    1500
gcggtcttat tccttcagac ctacttacgg agtcggacac caaccctaca gggtcgtcgt    1560
tttgagtttt gaattgttgc atgctccagc aaccgtgtgt ggacctaaaa agtccacgaa    1620
tctcgtgaag aataagtgcg taaacttcaa tttcaacggt ctgaaggga ctggtgtatt    1680
gacagaaagc aacaagaagt ttctgccatt ccagcaattt ggtagggata tagcggatac    1740
aactgatgcc gttcgggatc ctcaaacatt ggagatcttg gacatcacac cgtgttcttt    1800
tggggggtgtc tccgttatca caccgggtac aaatacgagc aatcaggttg cggtcctta    1860
ccaaggcgtt aattgtaccg aggttccagt agcaatacac gcggatcaac tcacgccac     1920
atggagggtt tacagtacag gcagtaatgt tttccaaacg agagcgggat gcctcatcgg    1980
ggcagaatac gtaaataatt cttacgaatg cgacatccct attggcgcag gaatttgcgc    2040
aagttaccaa acccagacca agtctcatag gcgggcgcgg tctgttgcaa gccaatctat    2100
aatagcgtac actatgtccc tcggcgcgga gaacagtgtc gcatattcca caactctat    2160
tgcgatacct actaatttca ctattagcgt cacaactgag atccttcccg tcagtatgac    2220
caaaacgtct gtcgactgta tatgtttggc ggcgac agtaccgaat gctctaatct        2280
tttgttgcag tatggttctt tttgcacgca acttaagaga gctttgacgg ggatagctgt    2340
ggaacaagat aaaaacacac aggaggtatt tgcacaagtg aaacagatct ataaactcc     2400
accgatcaag tactttggcg gctttaactt ctccccagatc ttgccgacc cgtcaaacc     2460
aagtaaacgg agttttatag gaccttctct tcaataag gtaacattgg cagacgccgg     2520
cttcattaaa caatacgag attgcttgg agacatcgct gcgcgcact tgatagcaca       2580
acaaaaattt aaaggcttga cggtcctccc tcctttgctc acagacgaga tgatagcaca    2640
atacacttcc gcactgcttg ctggaaccat cacctctggt tggacattcg gtgcgggagc    2700
ggctttgcag attccgtttg cgatgcaaat ggcttatcgg tttaacggca ttggagtaac    2760
acagaatgtg ctctacgaga atcaaaagct tattgcgaat caattcaact ctgcgattgg    2820
caaaattcaa gattcattga gtagcaccgc cagtgctctt ggcaagcttc aggatgtcgt    2880
```

-continued

```
aaaccacaat gcacaagctc tgaatacact ggttaaacaa ttgtccagta aatttgggc  2940
aatctcttca gtgctgaacg acatttttctc aagattggat ccaccccgaag cggaggtaca  3000
gattgaccgc ctgataaccg ggaggttgca aagccttcag acttatgtta cacaacagtt  3060
gattcgggca gcagagataa gagcctcagc aaacctcgca gctacgaaga tgtcagagtg  3120
tgtccttggg caatctaagc gggtagattt ctgcggcaaa ggatatcatt tgatgagctt  3180
tccccaatca gccccacatg gagtagtttt tcttcatgtc acttacgttc cggcgcagga  3240
aaagaacttc accacagcgc cagccatttg tcatgatggg aaggcgcatt cccaagaga   3300
aggtgttttc gtgtctaacg gtacccactg gttcgttacg cagcggaatt tctacgaacc  3360
acagatcatc actaccgaca cacgtttgt ctctggaata tgtgacgttg tcatagggat  3420
agtgaacaat acagtatatg atccacttca gcctgaactt gactcttta aggaggagct  3480
ggacaaatat ttcaaaaatc atacaagccc ggacgtcgat cttggagata tttcaggtat  3540
caacgcaagt gtcgtaaata ttcagaagga gatcgatcga ttgaacgagg ttgcaaaaaa  3600
ccttaatgag agccttatag atcttcaaga gctggggaag tatgaacaat atatcaagtg  3660
gccttggtac atttggctcg ggttcattgc cggacttatc gcgatcgtaa tggtaacaat  3720
catgctctgc tgtatgactt cttgctgttc atgcctcaaa ggttgttgct cctgtgggtc  3780
ttgctgtaaa tttgacgagg atgattctga accagtgctt aaaggcgtga agctccacta  3840
tacctga                                                            3847
```

```
SEQ ID NO: 9            moltype = AA   length = 1280
FEATURE                 Location/Qualifiers
source                  1..1280
                        mol_type = protein
                        organism = Severe acute respiratory syndrome coronavirus 2
SEQUENCE: 9
MFLLTTKRTM FVFLVLLPLV SSQCVNLRTR TQLPPAYTNS FTRGVYYPDK VFRSSVLHST   60
QDLFLPFFSN VTWFHAIHVS GTNGTKRFDN PVLPFNDGVY FASIEKSNII RGWIFGTTLD  120
SKTQSLLIVN NATNVVIKVC EFQFCNDPFL DVYYHKNNKS WMESGVYSSA NNCTFEYVSQ  180
PFLMDLEGKQ GNFKNLREFV FKNIDGYFKI YSKHTPINLV RDLPQGFSAL EPLVDLPIGI  240
NITRFQTLLA LHRSYLTPGD SSSGLTAGAA AYYVGYLQPR TFLLKYNENG TITDAVDCAL  300
DPLSETKCTL KSFTVEKGIY QTSNFRVQPT ESIVRFPNIT NLCPFGEVFN ATRFASVYAW  360
NRKRISNCVA DYSVLYNSAS FSTFKCYGVS PTKLNDLCFT NVYADSFVIR GDEVRQIAPG  420
QTGNIADYNY KLPDDFTGCV IAWNSNNLDS KVGGNYNYRY RLFRKSNLKP FERDISTEIY  480
QAGSKPCNGV EGFNCYFPLQ SYGFQPTNGV GYQPYRVVVL SFELLHAPAT VCGPKKSTNL  540
VKNKCVNFNF NGLTGTGVLT ESNKNFLPFQ QFGRDIADTT DAVRDPQTLE ILDITPCSFG  600
GVSVITPGTN TSNQVAVLYQ GVNCTEVPVA IHADQLTPTW RVYSTGSNVF QTRAGCLIGA  660
EHVNNSYECD IPIGAGICAS YQTQTNSRRR ARSVASQSII AYTMSLGAEN SVAYSNNSIA  720
IPTNFTISVT TEILPVSMTK TSVDCTMYIC GDSTECSNLL LQYGSFCTQL NRALTGIAVE  780
QDKNTQEVFA QVKQIYKTPP IKDFGGFNFS QILPDPSKPS KRSFIEDLLF NKVTLADAGF  840
IKQYGDCLGD IAARDLICAQ KFNGLTVLPP LLTDEMIAQY TSALLAGTIT SGWTFGAGAA  900
LQIPFAMQMA YRFNGIGVTQ NVLYENQKLI ANQFNSAIGK IQDSLSSTAS ALGKLQNVVN  960
QNAQALNTLV KQLSSNFGAI SSVLNDILSR LDPPEAEVQI DRLITGRLQS LQTYVTQQLI 1020
RAAEIRASAN LAATKMSECV LGQSKRVDFC GKGYHLMSFP QSAPHGVVFL HVTYVPAQEK 1080
NFTTAPAICH DGKAHFPREG VFVSNGTHWF VTQRNFYEPQ IITTDNTFVS GNCDVVIGIV 1140
NNTVYDPLQP ELDSFKEELD KYFKNHTSPD VDLGDISGIN ASVVNIQKEI DRLNEVAKNL 1200
NESLIDLQEL GKYEQYIKWP WYIWLGFIAG LIAIVMVTIM LCCMTSCCSC LKGCCSCGSC 1260
CKFDEDDSEP VLKGVKLHYT                                             1280
```

```
SEQ ID NO: 10           moltype = AA   length = 1280
FEATURE                 Location/Qualifiers
source                  1..1280
                        mol_type = protein
                        organism = Severe acute respiratory syndrome coronavirus 2
SEQUENCE: 10
MFLLTTKRTM FVFLVLLPLV SSQCVNLRTR TQLPPAYTNS FTRGVYYPDK VFRSSVLHST   60
QDLFLPFFSN VTWFHAIHVS GTNGTKRFDN PVLPFNDGVY FASIEKSNII RGWIFGTTLD  120
SKTQSLLIVN NATNVVIKVC EFQFCNDPFL DVYYHKNNKS WMESGVYSSA NNCTFEYVSQ  180
PFLMDLEGKQ GNFKNLREFV FKNIDGYFKI YSKHTPINLV RDLPQGFSAL EPLVDLPIGI  240
NITRFQTLLA LHRSYLTPGD SSSGLTAGAA AYYVGYLQPR TFLLKYNENG TITDAVDCAL  300
DPLSETKCTL KSFTVEKGIY QTSNFRVQPT ESIVRFPNIT NLCPFGEVFN ATRFASVYAW  360
NRKRISNCVA DYSVLYNSAS FSTFKCYGVS PTKLNDLCFT NVYADSFVIR GDEVRQIAPG  420
QTGNIADYNY KLPDDFTGCV IAWNSNNLDS KVGGNYNYRY RLFRKSNLKP FERDISTEIY  480
QAGSKPCNGV EGFNCYFPLQ SYGFQPTNGV GYQPYRVVVL SFELLHAPAT VCGPKKSTNL  540
VKNKCVNFNF NGLTGTGVLT ESNKNFLPFQ QFGRDIADTT DAVRDPQTLE ILDITPCSFG  600
GVSVITPGTN TSNQVAVLYQ GVNCTEVPVA IHADQLTPTW RVYSTGSNVF QTRAGCLIGA  660
EHVNNSYECD IPIGAGICAS YQTQTNSRRR ARSVASQSII AYTMSLGAEN SVAYSNNSIA  720
IPTNFTISVT TEILPVSMTK TSVDCTMYIC GDSTECSNLL LQYGSFCTQL NRALTGIAVE  780
QDKNTQEVFA QVKQIYKTPP IKDFGGFNFS QILPDPSKPS KRSFIEDLLF NKVTLADAGF  840
IKQYGDCLGD IAARDLICAQ KFNGLTVLPP LLTDEMIAQY TSALLAGTIT SGWTFGAGAA  900
LQIPFAMQMA YRFNGIGVTQ NVLYENQKLI ANQFNSAIGK IQDSLSSTAS ALGKLQNVVN  960
QNAQALNTLV KQLSSNFGAI SSVLNDILSR LDPPEAEVQI DRLITGRLQS LQTYVTQQLI 1020
RAAEIRASAN LAATKMSECV LGQSKRVDFC GKGYHLMSFP QSAPHGVVFL HVTYVPAQEK 1080
NFTTAPAICH DGKAHFPREG VFVSNGTHWF VTQRNFYEPQ IITTDNTFVS GNCDVVIGIV 1140
NNTVYDPLQP ELDSFKEELD KYFKNHTSPD VDLGDISGIN ASVVNIQKEI DRLNEVAKNL 1200
NESLIDLQEL GKYEQYIKWP WYIWLGFIAG LIAIVMVTIM LCCMTSCCSC LKGCCSCGSC 1260
CKFDEDDSEP VLKGVKLHYT                                             1280
```

```
SEQ ID NO: 11           moltype = AA   length = 1280
FEATURE                 Location/Qualifiers
source                  1..1280
```

```
                        mol_type = protein
                        organism = Severe acute respiratory syndrome coronavirus 2
SEQUENCE: 11
MFLLTTKRTM  FVFLVLLPLV  SSQCVNLRTR  TQLPPAYTNS  FTRGVYYPDK  VFRSSVLHST    60
QDLFLPFFSN  VTWFHAIHVS  GTNGTKRFDN  PVLPFNDGVY  FASIEKSNII  RGWIFGTTLD   120
SKTQSLLIVN  NATNVVIKVC  EFQFCNDPFL  DVYYHKNNKS  WMESGVYSSA  NNCTFEYVSQ   180
PFLMDLEGKQ  GNFKNLREFV  FKNIDGYFKI  YSKHTPINLV  RDLPQGFSAL  EPLVDLPIGI   240
NITRFQTLLA  LHRSYLTPGD  SSSGLTAGAA  AYYVGYLQPR  TFLLKYNENG  TITDAVDCAL   300
DPLSETKCTL  KSFTVEKGIY  QTSNFRVQPT  ESIVRFPNIT  NLCPFGEVFN  ATRFASVYAW   360
NRKRISNCVA  DYSVLYNSAS  FSTFKCYGVS  PTKLNDLCFT  NVYADSFVIR  GDEVRQIAPG   420
QTGNIADYNY  KLPDDFTGCV  IAWNSNNLDS  KVGGNYNYRY  RLFRKSNLKP  FERDISTEIY   480
QAGSKPCNGV  EGFNCYFPLQ  SYGFQPTNGV  GYQPYRVVVL  SFELLHAPAT  VCGPKKSTNL   540
VKNKCVNFNF  NGLTGTGVLT  ESNKNFLPFQ  QFGRDIADTT  DAVRDPQTLE  ILDITPCSFG   600
GVSVITPGTN  TSNQVAVLYQ  GVNCTEVPVA  IHADQLTPTW  RVYSTGSNVF  QTRAGCLIGA   660
EHVNNSYECD  IPIGAGICAS  YQTQTNSRRR  ARSVASQSII  AYTMSLGAEN  SVAYSNNSIA   720
IPTNFTISVT  TEILPVSMTK  TSVDCTMYIC  GDSTECSNLL  LQYGSFCTQL  NRALTGIAVE   780
QDKNTQEVFA  QVKQIYKTPP  IKDFGGFNFS  QILPDPSKPS  KRSFIEDLLF  NKVTLADAGF   840
IKQYGDCLGD  IAARDLICAQ  KFNGLTVLPP  LLTDEMIAQY  TSALLAGTIT  SGWTFGAGAA   900
LQIPFAMQMA  YRFNGIGVTQ  NVLYENQKLI  ANQFNSAIGK  IQDSLSSTAS  ALGKLQNVVN   960
QNAQALNTLV  KQLSSNFGAI  SSVLNDILSR  LDPPEAEVQI  DRLITGRLQS  LQTYVTQQLI  1020
RAAEIRASAN  LAATKMSECV  LGQSKRVDFC  GKGYHLMSFP  QSAPHGVVFL  HVTYVPAQEK  1080
NFTTAPAICH  DGKAHFPREG  VFVSNGTHWF  VTQRNFYEPQ  IITTDNTFVS  GNCDVVIGIV  1140
NNTVYDPLQP  ELDSFKEELD  KYFKNHTSPD  VDLGDISGIN  ASVVNIQKEI  DRLNEVAKNL  1200
NESLIDLQEL  GKYEQYIKWP  WYIWLGFIAG  LIAIVMVTIM  LCCMTSCCSC  LKGCCSCGSC  1260
CKFDEDDSEP  VLKGVKLHYT                                                  1280

SEQ ID NO: 12           moltype = AA  length = 1279
FEATURE                 Location/Qualifiers
source                  1..1279
                        mol_type = protein
                        organism = Severe acute respiratory syndrome coronavirus 2
SEQUENCE: 12
MFLLTTKRTM  FVFLVLLPLV  SSQCVNFTTR  TQLPPAYTNS  FTRGVYYPDK  VFRSSVLHST    60
QDLFLPFFSN  VTWFHAIHVS  GTNGTKRFAN  PVLPFNDGVY  FASTEKSNII  RGWIFGTTLD   120
SKTQSLLIVN  NATNVVIKVC  EFQFCNDPFL  GVYYHKNNKS  WMESEFRVYS  SANNCTFEYV   180
SQPFLMDLEG  KQGNFKNLRE  FVFKNIDGYF  KIYSKHTPIN  LVRGLPQGFS  ALEPLVDLPI   240
GINITRFQTL  HISYLTPGDS  SSGWTAGAAA  YYVGYLQPRT  FLLKYNENGT  ITDAVDCALD   300
PLSETKCTLK  SFTVEKGIYQ  TSNFRVQPTE  SIVRFPNITN  LCPFGEVFNA  TRFASVYAWN   360
RKRISNCVAD  YSVLYNSASF  STFKCYGVSP  TKLNDLCFTN  VYADSFVIRG  DEVRQIAPGQ   420
TGNIADYNYK  LPDDFTGCVI  AWNSNNLDSK  VGGNYNYLYR  LFRKSNLKPF  ERDISTEIYQ   480
AGSTPCNGVE  GFNCYFPLQS  YGFQPTYGVG  YQPYRVVVLS  FELLHAPATV  CGPKKSTNLV   540
KNKCVNFNFN  GLTGTGVLTE  SNKKFLPFQQ  FGRDIADTTD  AVRDPQTLEI  LDITPCSFGG   600
VSVITPGTNT  SNQVAVLYQG  VNCTEVPVAI  HADQLTPTWR  VYSTGSNVFQ  TRAGCLIGAE   660
HVNNSYECDI  PIGAGICASY  QTQTNSPRRA  RSVASQSIIA  YTMSLGVENS  VAYSNNSIAI   720
PTNFTISVTT  EILPVSMTKT  SVDCTMYICG  DSTECSNLLL  QYGSFCTQLN  RALTGIAVEQ   780
DKNTQEVFAQ  VKQIYKTPPI  KDFGGFNFSQ  ILPDPSKPSK  RSFIEDLLFN  KVTLADAGFI   840
KQYGDCLGDI  AARDLICAQK  FNGLTVLPPL  LTDEMIAQYT  SALLAGTITS  GWTFGAGAAL   900
QIPFAMQMAY  RFNGIGVTQN  VLYENQKLIA  NQFNSAIGKI  QDSLSSTASA  LGKLQDVVNQ   960
NAQALNTLVK  QLSSNFGAIS  SVLNDILSRL  DPPEAEVQID  RLITGRLQSL  QTYVTQQLIR  1020
AAEIRASANL  AATKMSECVL  GQSKRVDFCG  KGYHLMSFPQ  SAPHGVVFLH  VTYVPAQEKN  1080
FTTAPAICHD  GKAHFPREGV  FVSNGTHWFV  TQRNFYEPQI  ITTDNTFVSG  NCDVVIGIVN  1140
NTVYDPLQPE  LDSFKEELDK  YFKNHTSPDV  DLGDISGINA  SVVNIQKEID  RLNEVAKNLN  1200
ESLIDLQELG  KYEQYIKWPW  YIWLGFIAGL  IAIVMVTIML  CCMTSCCSCL  KGCCSCGSCC  1260
KFDEDDSEPV  LKGVKLHYT                                                   1279

SEQ ID NO: 13           moltype = AA  length = 1282
FEATURE                 Location/Qualifiers
source                  1..1282
                        mol_type = protein
                        organism = Severe acute respiratory syndrome coronavirus 2
SEQUENCE: 13
MFLLTTKRTM  FVFLVLLPLV  SSQCVNLTTR  TQLPPAYTNS  FTRGVYYPDK  VFRSSVLHST    60
QDLFLPFFSN  VTWFHAIHVS  GTNGTKRFDN  PVLPFNDGVY  FASTEKSNII  RGWIFGTTLD   120
SKTQSLLIVN  NATNVVIKVC  EFQFCNDPFL  GVYYHKNNKS  WMESEFRVYS  SANNCTFEYV   180
SQPFLMDLEG  KQGNFKNLRE  FVFKNIDGYF  KIYSKHTPIN  LVRDLPQGFS  ALEPLVDLPI   240
GINITRFQTL  LALHRSYLTP  GDSSSGWTAG  AAAYYVGYLQ  PRTFLLKYNE  NGTITDAVDC   300
ALDPLSETKC  TLKSFTVEKG  IYQTSNFRVQ  PTESIVRFPN  ITNLCPFGEV  FNATRFASVY   360
AWNRKRISNC  VADYSVLYNS  ASFSTFKCYG  VSPTKLNDLC  FTNVYADSFV  IRGDEVRQIA   420
PGQTGKIADY  NYKLPDDFTG  CVIAWNSNNL  DSKVGGNYNY  LYRLFRKSNL  KPFERDISTE   480
IYQAGSTPCN  GVEGFNCYFP  LQSYGFQPTN  GVGYQPYRVV  VLSFELLHAP  ATVCGPKKST   540
NLVKNKCVNF  NFNGLTGTGV  LTESNKKFLP  FQQFGRDIAD  TTDAVRDPQT  LEILDITPCS   600
FGGVSVITPG  TNTSNQVAVL  YQDVNCTEVP  VAIHAGQLTP  TWRVYSTGSN  VFQTRAGCLI   660
GAEHVNNSYE  CDIPIGAGIC  ASYQTQTNSP  RRARSVASQS  IIAYTMSLGA  ENSVAYSNNS   720
IAIPTNFTIS  VTTEILPVSM  TKTSVDCTMY  ICGDSTECSN  LLLQYGSFCT  QLNRALTGIA   780
VEQDKNTQEV  FAQVKQIYKT  PPIKDFGGFN  FSQILPDPSK  PSKRSFIEDL  LFNKVTLADA   840
GFIKQYGDCL  GDIAARDLIC  AQKFNGLTVL  PPLTDEMIA   QYTSALLAGT  ITSGWTFGAG   900
AALQIPFAMQ  MAYRFNGIGV  TQNVLYENQK  LIANQFNSAI  GKIQDSLSST  ASALGKLQDV   960
VNQNAQALNT  LVKQLSSNFG  AISSVLNDIL  SRLDKVEAEV  QIDRLITGRL  QSLQTYVTQQ  1020
LIRAAEIRAS  ANLAATKMSE  CVLGQSKRVD  FCGKGYHLMS  FPQSAPHGVV  FLHVTYVPAQ  1080
```

```
EKNFTTAPAI CHDGKAHFPR EGVFVSNGTH WFVTQRNFYE PQIITTDNTF VSGNCDVVIG    1140
IVNNTVYDPL QPELDSFKEE LDKYFKNHTS PDVDLGDISG INASVVNIQK EIDRLNEVAK    1200
NLNESLIDLQ ELGKYEQYIK WPWYIWLGFI AGLIAIVMVT IMLCCMTSCC SCLKGCCSCG    1260
SCCKFDEDDS EPVLKGVKLH YT                                             1282

SEQ ID NO: 14           moltype = AA   length = 1282
FEATURE                 Location/Qualifiers
source                  1..1282
                        mol_type = protein
                        organism = Severe acute respiratory syndrome coronavirus 2
SEQUENCE: 14
MFLLTTKRTM FVFLVLLPLV SSQCVNLTTR TQLPPAYTNS FTRGVYYPDK VFRSSVLHST     60
QDLFLPFFSN VTWFHAIHVS GTNGTKRFDN PVLPFNDGVY FASTEKSNII RGWIFGTTLD    120
SKTQSLLIVN NATNVVIKVC EFQFCNDPFL GVYYHKNNKS WMESEFRVYS SANNCTFEYV    180
SQPFLMDLEG KQGNFKNLRE FVFKNIDGYF KIYSKHTPIN LVRDLPQGFS ALEPLVDLPI    240
GINITRFQTL LALHRSYLTP GDSSSGWTAG AAAYYVGYLQ PRTFLLKYNE NGTITDAVDC    300
ALDPLSETKC TLKSFTVEKG IYQTSNFRVQ PTESIVRFPN ITNLCPFGEV FNATRFASVY    360
AWNRKRISNC VADYSVLYNS ASFSTFKCYG VSPTKLNDLC FTNVYADSFV IRGDEVRQIA    420
PGQTGKIADY NYKLPDDFTG CVIAWNSNNL DSKVGGNYNY LYRLFRKSNL KPFERDISTE    480
IYQAGSTPCN GVEGFNCYFP LQSYGFQPTN GVGYQPYRVV VLSFELLHAP ATVCGPKKST    540
NLVKNKCVNF NFNGLTGTGV LTESNKKFLP FQQFGRDIAD TTDAVRDPQT LEILDITPCS    600
FGGVSVITPG TNTSNQVAVL YQDVNCTEVP VAIHADQLTP TWRVYSTGSN VFQTRAGCLI    660
GAEHVNNSYE CDIPIGAGIC ASYQTQTNSP RRARSVASQS IIAYTMSLGA ENSVAYSNNS    720
IAIPTNFTIS VTTEILPVSM TKTSVDCTMY ICGDSTECSN LLLQYGSFCT QLNRALTGIA    780
VEQDKNTQEV FAQVKQIYKT PPIKDFGGFN FSQILPDPSK PSKRSFIEDL LFNKVTLADA    840
GFIKQYGDCL GDIAARDLIC AQKFNGLTVL PPLLTDEMIA QYTSALLAGT ITSGWTFGAG    900
AALQIPFAMQ MAYRFNGIGV TQNVLYENQK LIANQFNSAI GKIQDSLSST ASALGKLQDV    960
VNQNAQALNT LVKQLSSNFG AISSVLNDIL SRLDPPEAEV QIDRLITGRL QSLQTYVTQQ   1020
LIRAAEIRAS ANLAATKMSE CVLGQSKRVD FCGKGYHLMS FPQSAPHGVV FLHVTYVPAQ   1080
EKNFTTAPAI CHDGKAHFPR EGVFVSNGTH WFVTQRNFYE PQIITTDNTF VSGNCDVVIG   1140
IVNNTVYDPL QPELDSFKEE LDKYFKNHTS PDVDLGDISG INASVVNIQK EIDRLNEVAK   1200
NLNESLIDLQ ELGKYEQYIK WPWYIWLGFI AGLIAIVMVT IMLCCMTSCC SCLKGCCSCG   1260
SCCKFDEDDS EPVLKGVKLH YT                                            1282

SEQ ID NO: 15           moltype = AA   length = 1260
FEATURE                 Location/Qualifiers
source                  1..1260
                        mol_type = protein
                        organism = Severe acute respiratory syndrome coronavirus 2
SEQUENCE: 15
MFLLTTKRTM FVFLVLLPLV SSQCVNLTTR TQLPPAYTNS FTRGVYYPDK VFRSSVLHST     60
QDLFLPFFSN VTWFHAIHVS GTNGTKRFDN PVLPFNDGVY FASTEKSNII RGWIFGTTLD    120
SKTQSLLIVN NATNVVIKVC EFQFCNDPFL GVYYHKNNKS WMESEFRVYS SANNCTFEYV    180
SQPFLMDLEG KQGNFKNLRE FVFKNIDGYF KIYSKHTPIN LVRDLPQGFS ALEPLVDLPI    240
GINITRFQTL LALHRSYLTP GDSSSGWTAG AAAYYVGYLQ PRTFLLKYNE NGTITDAVDC    300
ALDPLSETKC TLKSFTVEKG IYQTSNFRVQ PTESIVRFPN ITNLCPFGEV FNATRFASVY    360
AWNRKRISNC VADYSVLYNS ASFSTFKCYG VSPTKLNDLC FTNVYADSFV IRGDEVRQIA    420
PGQTGKIADY NYKLPDDFTG CVIAWNSNNL DSKVGGNYNY LYRLFRKSNL KPFERDISTE    480
IYQAGSTPCN GVEGFNCYFP LQSYGFQPTN GVGYQPYRVV VLSFELLHAP ATVCGPKKST    540
NLVKNKCVNF NFNGLTGTGV LTESNKKFLP FQQFGRDIAD TTDAVRDPQT LEILDITPCS    600
FGGVSVITPG TNTSNQVAVL YQDVNCTEVP VAIHADQLTP TWRVYSTGSN VFQTRAGCLI    660
GAEHVNNSYE CDIPIGAGIC ASYQTQTNSP RRARSVASQS IIAYTMSLGA ENSVAYSNNS    720
IAIPTNFTIS VTTEILPVSM TKTSVDCTMY ICGDSTECSN LLLQYGSFCT QLNRALTGIA    780
VEQDKNTQEV FAQVKQIYKT PPIKDFGGFN FSQILPDPSK PSKRSFIEDL LFNKVTLADA    840
GFIKQYGDCL GDIAARDLIC AQKFNGLTVL PPLLTDEMIA QYTSALLAGT ITSGWTFGAG    900
AALQIPFAMQ MAYRFNGIGV TQNVLYENQK LIANQFNSAI GKIQDSLSST ASALGKLQDV    960
VNQNAQALNT LVKQLSSNFG AISSVLNDIL SRLDKVEAEV QIDRLITGRL QSLQTYVTQQ   1020
LIRAAEIRAS ANLAATKMSE CVLGQSKRVD FCGKGYHLMS FPQSAPHGVV FLHVTYVPAQ   1080
EKNFTTAPAI CHDGKAHFPR EGVFVSNGTH WFVTQRNFYE PQIITTDNTF VSGNCDVVIG   1140
IVNNTVYDPL QPELDSFKEE LDKYFKNHTS PDVDLGDISG INASVVNIQK EIDRLNEVAK   1200
NLNESLIDLQ ELGKYEQYIK WPWYIWLGFI AGLIAIVMVT IMLCCMTSCC SCLKGCCSCG   1260

SEQ ID NO: 16           moltype = AA   length = 1279
FEATURE                 Location/Qualifiers
source                  1..1279
                        mol_type = protein
                        organism = Severe acute respiratory syndrome coronavirus 2
SEQUENCE: 16
MFLLTTKRTM FVFLVLLPLV SSQCVNLTTR TQLPPAYTNS FTRGVYYPDK VFRSSVLHST     60
QDLFLPFFSN VTWFHVISGT NGTKRFDNPV LPFNDGVYFA SIEKSNIIRG WIFGTTLDSK    120
TQSLLIVNNA TNVVIKVCEF QFCNDPFFDH KNNKSWMESE FRVYSSANNC TFEYVSQPFL    180
MDLEGKQGNF KNLREFVFKN IDGYFKIYSK HTPIIVREPE DLPQGFSALE PLVDLPIGIN    240
ITRFQTLLAL HRSYLTPGDS SSGWTAGAAA YYVGYLQPRT FLLKYNENGT ITDAVDCALD    300
PLSETKCTLK SFTVEKGIYQ TSNFRVQPTE SIVRFPNITN LCPFDEVFNA TRFASVYAWN    360
RKRISNCVAD YSVLYNLAPF FTFKCYGVSP TKLNDLCFTN VYADSFVIRG DEVRQIAPGQ    420
TGNIADYNYK LPDDFTGCVI AWNSNKLDSK VGGNYNYLYR LFRKSNLKPF ERDISTEIYQ    480
AGNKPCNGVA GFNCYFPLRS YSFRPTYGVG HQPYRVVVLS FELLHAPATV CGPKKSTNLV    540
KNKCVNFNFN GLKGTGVLTE SNKKFLPFQQ FGRDIADTTD AVRDPQTLEI LDITPCSFGG    600
VSVITPGTNT SNQVAVLYQG VNCTEVPVAI HADQLTPTWR VYSTGSNVFQ TRAGCLIGAE    660
```

```
YVNNSYECDI PIGAGICASY QTQTKSHRRA RSVASQSIIA YTMSLGAENS VAYSNNSIAI     720
PTNFTISVTT EILPVSMTKT SVDCTMYICG DSTECSNLLL QYGSFCTQLK RALTGIAVEQ     780
DKNTQEVFAQ VKQIYKTPPI KYFGGFNFSQ ILPDPSKPSK RSFIEDLLFN KVTLADAGFI     840
KQYGDCLGDI AARDLICAQK FKGLTVLPPL LTDEMIAQYT SALLAGTITS GWTFGAGAAL     900
QIPFAMQMAY RFNGIGVTQN VLYENQKLIA NQFNSAIGKI QDSLSSTASA LGKLQDVVNH     960
NAQALNTLVK QLSSKFGAIS SVLNDIFSRL DPPEAEVQID RLITGRLQSL QTYVTQQLIR    1020
AAEIRASANL AATKMSECVL GQSKRVDFCG KGYHLMSFPQ SAPHGVVFLH VTYVPAQEKN    1080
FTTAPAICHD GKAHFPREGV FVSNGTHWFV TQRNFYEPQI ITTDNTFVSG NCDVVIGIVN    1140
NTVYDPLQPE LDSFKEELDK YFKNHTSPDV DLGDISGINA SVVNIQKEID RLNEVAKNLN    1200
ESLIDLQELG KYEQYIKWPW YIWLGFIAGL IAIVMVTIML CCMTSCCSCL KGCCSCGSCC    1260
KFDEDDSEPV LKGVKLHYT                                                1279

SEQ ID NO: 17            moltype = AA   length = 1273
FEATURE                  Location/Qualifiers
source                   1..1273
                         mol_type = protein
                         organism = Severe acute respiratory syndrome coronavirus 2
SEQUENCE: 17
MFVFLVLLPL VSSQCVNLTT RTQLPPAYTN SFTRGVYYPD KVFRSSVLHS TQDLFLPFFS      60
NVTWFHAIHV SGTNGTKRFD NPVLPFNDGV YFASTEKSNI IRGWIFGTTL DSKTQSLLIV     120
NNATNVVIKV CEFQFCNDPF LGVYYHKNNK SWMESEFRVY SSANNCTFEY VSQPFLMDLE     180
GKQGNFKNLR EFVFKNIDGY FKIYSKHTPI NLVRDLPQGF SALEPLVDLP IGINITRFQT     240
LLALHRSYLT PGDSSSGWTA GAAAYYVGYL QPRTFLLKYN ENGTITDAVD CALDPLSETK     300
CTLKSFTVEK GIYQTSNFRV QPTESIVRFP NITNLCPFGE VFNATRFASV YAWNRKRISN     360
CVADYSVLYN SASFSTFKCY GVSPTKLNDL CFTNVYADSF VIRGDEVRQI APGQTGKIAD     420
YNYKLPDDFT GCVIAWNSNN LDSKVGGNYN YLYRLFRKSN LKPFERDIST EIYQAGSTPC     480
NGVEGFNCYF PLQSYGFQPT NGVGYQPYRV VVLSFELLHA PATVCGPKKS TNLVKNKCVN     540
FNFNGLTGTG VLTESNKKFL PFQQFGRDIA DTTDAVRDPQ TLEILDITPC SFGGVSVITP     600
GTNTSNQVAV LYQDVNCTEV PVAIHADQLT PTWRVYSTGS NVFQTRAGCL IGAEHVNNSY     660
ECDIPIGAGI CASYQTQTNS PRRARSVASQ SIIAYTMSLG AENSVAYSNN SIAIPTNFTI     720
SVTTEILPVS MTKTSVDCTM YICGDSTECS NLLLQYGSFC TQLNRALTGI AVEQDKNTQE     780
VFAQVKQIYK TPPIKDFGGF NFSQILPDPS KPSKRSFIED LLFNKVTLAD AGFIKQYGDC     840
LGDIAARDLI CAQKFNGLTV LPPLLTDEMI AQYTSALLAG TITSGWTFGA GAALQIPFAM     900
QMAYRFNGIG VTQNVLYENQ KLIANQFNSA IGKIQDSLSS TASALGKLQD VVNQNAQALN     960
TLVKQLSSNF GAISSVLNDI LSRLDKVEAE VQIDRLITGR LQSLQTYVTQ QLIRAAEIRA    1020
SANLAATKMS ECVLGQSKRV DFCGKGYHLM SFPQSAPHGV VFLHVTYVPA QEKNFTTAPA    1080
ICHDGKAHFP REGVFVSNGT HWFVTQRNFY EPQIITTDNT FVSGNCDVVI GIVNNTVYDP    1140
LQPELDSFKE ELDKYFKNHT SPDVDLGDIS GINASVVNIQ KEIDRLNEVA KNLNESLIDL    1200
QELGKYEQYI KWPWYIWLGF IAGLIAIVMV TIMLCCMTSC CSCLKGCCSC GSCCKFDEDD    1260
SEPVLKGVKL HYT                                                      1273

SEQ ID NO: 18            moltype = AA   length = 302
FEATURE                  Location/Qualifiers
source                   1..302
                         mol_type = protein
                         organism = Severe acute respiratory syndrome coronavirus 2
SEQUENCE: 18
QNVLYENQKL IANQFNSAIG KIQDSLSSTA SALGKLQDVV NQNAQALNTL VKQLSSNFGA      60
ISSVLNDILS RLDKVEAEVQ IDRLITGRLQ SLQTYVTQQL IRAAEIRASA NLAATKMSEC     120
VLGQSKRVDF CGKGYHLMSF PQSAPHGVVF LHVTYVPAQE KNFTTAPAIC HDGKAHFPRE     180
GVFVSNGTHW FVTQRNFYEP QIITTDNTFV SGNCDVVIGI VNNTVYDPLQ PELDSFKEEL     240
DKYFKNHTSP DVDLGDISGI NASVVNIQKE IDRLNEVAKN LNESLIDLQE LGKYEQYIKW     300
PW                                                                  302

SEQ ID NO: 19            moltype = AA   length = 302
FEATURE                  Location/Qualifiers
source                   1..302
                         mol_type = protein
                         organism = Severe acute respiratory syndrome coronavirus 2
SEQUENCE: 19
QNVLYENQKL IANQFNSAIG KIQDSLSSTA SALGKLQDVV NHNAQALNTL VKQLSSKFGA      60
ISSVLNDIFS RLDPPEAEVQ IDRLITGRLQ SLQTYVTQQL IRAAEIRASA NLAATKMSEC     120
VLGQSKRVDF CGKGYHLMSF PQSAPHGVVF LHVTYVPAQE KNFTTAPAIC HDGKAHFPRE     180
GVFVSNGTHW FVTQRNFYEP QIITTDNTFV SGNCDVVIGI VNNTVYDPLQ PELDSFKEEL     240
DKYFKNHTSP DVDLGDISGI NASVVNIQKE IDRLNEVAKN LNESLIDLQE LGKYEQYIKW     300
PW                                                                  302

SEQ ID NO: 20            moltype = RNA   length = 7561
FEATURE                  Location/Qualifiers
source                   1..7561
                         mol_type = other RNA
                         organism = Venezuelan equine encephalitis virus
SEQUENCE: 20
ataggcgcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
```

```
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggc agttagagtc gcctactgga taggctttga caccacccct tttatgttta    600
agaacttggc tggagcatat ccatcatact ctaccaactg ggccgacgaa accgtgttaa    660
cggctcgtaa catagggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa ggcttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac ctttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctcatttat aagcgcccgg atacccaaac catcatcaaa gtgaacagcg   1380
atttccactc attcgtgctg cccaggatag gcagtaacac attggagatc gggctgagaa   1440
caagaatcag gaaatgttta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccacccctct cgctgaacaa gtcatagtga   1800
taacacactc tggccgaaaaa gggcgttatg ccgtggaacc ataccatggt aaagtagtgg   1860
tgccagaggg acatgcaata cccgtccagg acttttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca cccgtagag acctgtata   2400
ttgacgaagc ttttgcttgt catgcaggta ctctcagagc gctcatagcc attataagac   2460
ctaaaaaggc agtgctctgc ggggatcca aacagtgcgg tttttttaac atgatgtgcc   2520
tgaaagtgca ttttaaccac gagatttgca cacaagtctt ccacaaagc atctctcgcc   2580
gttgcactaa atctgtgact tcggtcgtct caaccttgtt ttacgacaaa aaaatgagaa   2640
cgacgaatcc gaaagagact aagattgtga tgacactac cggcagtgca aaacctaagc   2700
aggacgatct cattctcact tgtttcagag ggtgggtgaa gcagtttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag tacccctggg aattcactgc cacgatagag gagtggcaag   3000
cagagcatga tgccatcatg aggcacatct tggagagacc ggaccctacc gacgtcttcc   3060
agaataaggc aaacgtgtgt tgggccaagg cttttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactgaaa gagtctatga catgaacact ggtacactgg   3420
gcaattatga tccgcgcata aacctagtac ctgtaaacag aagactgcct catgctttag   3480
tcctccacca taatgaacac ccacagagtg acttttcttc attcgtcagc aaatttgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggaccc atataaatac catcactatc   3720
agcagtgtga agaccatgcc attaagctta gcatgttgac caagaaagct tgtctgcatc   3780
tgaatcccgg cggaacctgt gtcagcatag ttatggtta cgctgacagg gccagcgaaa   3840
gcatcattgg tgctatagcg cggcattca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacatttta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgaa   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc tttttccggga   4380
acaaagatcg actaaccaa tcattgaacc atttgctgac agctttagac accactgatg   4440
cagatgtagc catatactgc agggacaaga aatgggaaat gactctcaag gaagcagtga   4500
ctaggagaga agcagtggag gagatatgca tatccgacga ctcttcagtg acagaacctg   4560
atgcagagct ggtgagggtg catccgaaga gttctttggc tggaaggaag gctacagca   4620
caagcgatgt caaaactttc tcatatttgg aagggaccaa gttcaccag gcggccaagg   4680
atatagcaga aattaatgcc atgtggcccg ttgcaacgga ggcaatgag caggtatgca   4740
tgtatatcct cggagaaagc atgagcagta taggtgcaga ttaggtcccgtc gaagagtcga   4800
aagcctccac accacctagc acgctgcctt gcttgtgcat ccatgccatg actcagaaaa   4860
gagtacagcg cctaaaagcc tcacgtccag aacaaattac tgtgtgctca tccttttccat   4920
tgccgaagta tagaatcact ggtgtgcaga agatccaatg ctcccagcct atattgttct   4980
caccgaaagt gcctgcgtat attcatcaa ggaagtatct cgtggaaaca ccaccggtag   5040
acgagactcc ggagccatcg gcagagaacc aatccacaga ggggacaccct gaacaaccac   5100
```

```
cacttataac cgaggatgag accaggacta gaacgcctga gccgatcatc atcgaagagg   5160
aagaagagga tagcataagt ttgctgtcag atgcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggaggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttacccg tcacgcactc    5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag gcatttaca acaaaaatca gtaaggcaaa    5760
cggtgctatc cgaagtggtg ttggagagga ccgaattgga gatttcgtat gccccgcgcc   5820
tcgaccaaga aaaagaagaa ttactacgca agaaattaca gttaaatccc acacctgtca   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagtcga   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta gcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
g                                                                    7561

SEQ ID NO: 21          moltype = AA   length = 51
FEATURE                Location/Qualifiers
source                 1..51
                       mol_type = protein
                       organism = Venezuelan equine encephalitis virus
SEQUENCE: 21
RELPVLDSAA FNVECFKKYA CNNEYWETFK ENPIRLTEEN VVNYITKLKG P            51

SEQ ID NO: 22          moltype = AA   length = 41
FEATURE                Location/Qualifiers
source                 1..41
                       mol_type = protein
                       organism = Venezuelan equine encephalitis virus
SEQUENCE: 22
TQMRELPVLD SAAFNVECFK KYACNNEYWE TFKENPIRLT E                       41

SEQ ID NO: 23          moltype = AA   length = 536
FEATURE                Location/Qualifiers
source                 1..536
                       mol_type = protein
                       organism = Venezuelan equine encephalitis virus
SEQUENCE: 23
MKAITARRIL QGLGHYLKAE GKVECYRTLH PVPLYSSSVN RAFSSPKVAV EACNAMLKEN    60
FPTVASYCII PEYDAYLDMI DGASCCLDTA SFCPAKLRSF PKKHSYLEPT IRSAVPSAIQ   120
NTLQNVLAAA TKRNCNVTQM RELPVLDSAA FNVECFKKYA CNNEYWETFK ENPIRLTEEN   180
VINYITKLKG PKAAALYAKT HNLNMLQDIP MDRFVMDLKR DVKVTPGTKH TEERPKVQVI   240
QAADPLATAY LCGIHRELVR RLNAVLLPNI HTLFDMSAED FDAIIAEHFQ PGDCVLETDI   300
ASFDKSEDDA MALTAMMILE DLGVDAELLT LIEAAFGEIS SIHLPTKTKF KFGAMMKSGM   360
FLTLFVNTVI NIVIASRVLR ERLTGSPCAA FIGDDNIVKG VKSDKLMADR CATWLNMEVK   420
IIDAVVGEKA PYFCGGFILC DSVTGTACRV ADPLKRLFKL GKPLAADDEH DDDRRRALHE   480
ESTRWNRVGI LPELCKAVES RYETVGTSVI VMAMATLASS VKSFSYLRGA PITLYG       536

SEQ ID NO: 24          moltype = RNA  length = 11707
FEATURE                Location/Qualifiers
misc_feature           1..11707
                       note = Description of Artificial Sequence: Synthetic
```

| | polynucleotide | |
|---|---|---|
| source | 1..11707 | |
| | mol_type = other RNA | |
| | organism = synthetic construct | |

SEQUENCE: 24

```
ataggcggcg catgagagaa gcccagacca attacctacc caaaatggag aaagttcacg   60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacgagcc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg 1020
tctcttttcc cgtgtgcacg tatgtgccaa ctacattgtg tgaccaaatg actggctacc 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgccccg 1200
tagtcgccaa ggcatttgct aggtgggcaa aggaatataa ggaagatgaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgaag 1500
acgtacaaga agctaagtgc gcagccgatg aggctaagga ggtgcgtgaa gccgaggagt 1560
tgcgcgcagc tctaccacct ttggcagctg atgttgagga gcccactctg gaggcagacg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacgggg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatgcgtg ccaggatcag 2220
gcaagtcgac catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctccttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcc ttttttttaac atgatgtgcc 2520
tgaaagtgca tttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctatttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactgaaa gagtctatga catgaacact ggtacactgc 3420
gcaattatga tccgcgcata aacctagtac ctgtaaacag aagactgcct catgctttag 3480
tcctccacca taatgaacac cacagagtg actttttctt attcgtcaga aaattgaagg 3540
gcagaactgt cctggtggtc ggggaaaagt tgtccgtccc aggcaaaatg ttgactggt 3600
tgtcagaccg gcctgaggct accttcagag ctcggctgga tttaggcatc ccaggtgatg 3660
tgcccaaata tgacataata tttgttaatg tgaggaccc atataaatac catcactatc 3720
agcagtgtga agaccatgcc attaagctta gcatgttgac caagaaagct tgtctgcatc 3780
tgaatccgg cggaacctgt gtcagcatag gttatggta cgctgacagg gccagcgaaa 3840
gcatcattgg tgctatagcg cggcagttca gttttcccg ggtatgcaaa ccgaaatcct 3900
cacttgaaga gacgaagtt ctgtttgtat tcattgggta cgatcgcaag gcccgtacgc 3960
acaatcctta caagctttca tcaacctga ccaacatttta tacaggttcc agactccacg 4020
aagccggatg tgcacctctca tatcatgtgg tgcgagggga tattgccacg gccaccgaag 4080
gagtgattat aaatgctgct aacagcaaag tcgggggggg tgcggagcga 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
```

```
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgc caaaactttc tcatatttgg aagggaccaa gtttcaccag gcggccaagg    4680
atatagcaga aattaatgcc atgtggcccg ttgcaacgga ggcaatgag caggtatgca     4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tccttttccat  4920
tgccgaagta tagaatcact ggtgtgcaga agatccaatg ctcccagcct atattgttct   4980
caccgaaagt gcctgcgtat attcatccaa ggaagtatct cgtcggaaaca ccaccggtag   5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacacccc ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa tagggtgatc actagagagg agctcgaggc gcttaccccg tcacgcactc    5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag gacatttaca acaaaaatca gtaaggcaaa   5760
cggtgctatc cgaagtggtg ttggagagga ccgaattgga gatttcgtat gcccgcgcc    5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc    6000
tgcatcctgt tccttttgtat tcatctagtg tgaaccgtgc ctttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca    6180
ctgccagttt ttgccctgca aagctgcgca gcttttccaaa gaaacactcc tatttggaac   6240
ccacaataccg atcggcagtg ccttcagcga tccagaacac gctccagaac gtcctggcag   6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca   6540
taccaatgga caggttttgta atggacttaa agagagacgt gaaagtgact ccaggaacaa   6600
aacatactga agaacggccc aaggtacagg tgatccaggc tgccgatccg ctagcaacag    6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatgtcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggcatgact actctagcta gcagtgttaa atcattcagc tacctgagag    7500
gggcccctat aactctctac ggctaacctg aatggactac gacatagtct agtccgccaa    7560
gatgtttctg ctcacaacca aacgcactat gtttgttttc ctcgtgctgc tcccttggt    7620
aagttctcag tgtgtaaacc tgacaacacg aacccagttg cctccagctt ataccaactc    7680
atttactcgc ggagtatatt atcccgataa ggtctttaga agtagcgtgt tgcactctac    7740
acaggatctg ttcttgccct tctttagtaa cgttacctgg tttcatgcaa tacatgtgag    7800
cggaacaaat ggaacaaaaa gatttgacaa tccagtgctt ccatttaatg atgggggtta    7860
ctttgccagt accgaaaagt caaacataat ccgggggtgg atctttggaa ccactttgga    7920
ctctaagaca cagtctctcc tcatagtaaa caacgccacc aatgttgtca taaaagtatg    7980
cgaatttcag ttttgcaacg atccctttct cggggtgtat taccataaga ataataaatc    8040
ctggatggag tctgagttcc gggttatag tagtgctaat aattgcactt tcgaatacgt     8100
gtcccaacca ttcctcatgg accttgaggg caaacagggg aatttaaaa acttgcgcga    8160
atttgtcttt aagaatatcg acggatactt taagatctat agtaaacaca ctcctatcaa    8220
cctcgttcgg gatcttcccc aaggcttttc tgctctcgaa ccctccgtag acttgccaat    8280
tgggataaat atcactcgct ttcaaacttt gcttgccctc cacaggagcc acctgacacc    8340
cggcgactct tcttctggtt ggaccgccgg cgccgctgcc tattatgttg gttaccttca    8400
gccacgaaca ttcttgctca gtataacga gaatggcacc attaccgacg ccgtcgattg     8460
tgcattggat cccttgtctg aaacaaatg taccttgaag tcctttaccg tagagaaagg     8520
catataccag acttccaact tccagttca gcctacagaa tccattgtga gatttcccaa    8580
catcacaaac ctctgccctt tcggtgaagt atttaatgct acacgcttcg cttcagtcta    8640
tgcctggaat aggaagcgca tatcaaattg cgtggccgat tattcagtcc tctataatag    8700
cgcatccttc agtactttca agtgctacgg cgttccccccc accaaactca atgatctttg   8760
cttccaccaac gtctatgctg acagttttgt catacgaggc gacgaagtac gccagattgc    8820
cccggcag acaggtaaaa ttgctgatta taattataaa ctcccagatg acttactgg       8880
atgcgtcata gcctgcgaatt ccaacaatct tgattccaag gttggtggga attataatta   8940
cctttatcga ctgttcagaa agagtaactt gaaaccattt gagagagaca tatccaccga    9000
gatttaccag gcaggcagta ctccttgtaa cggcgttgag ggatttaact gctatttttcc   9060
tttgcaatcc tatggctttc aaccaacaaa cggggttggc tatcaaccct atcgagtggt    9120
tgtcctgagc tttgaacttt tgcacgctcc cgccacagtc tgcggaccaa aaaagagtac    9180
```

```
aaatcttgtc aagaataagt gcgtaaattt caatttcaat ggccttacag gaacaggcgt    9240
gctgactgag tcaaacaaga agttcctgcc atttcagcag tttgggcggg atatagcaga    9300
cacaactgac gctgtacgcg atcctcagac tttggagatc ttggacatca ctccctgttc    9360
tttcggaggg gtatctgtca tcaccccccgg aactaataca tcaaatcagg tcgctgtgtt   9420
gtaccaagat gtcaactgca cagaagtccc cgttgctata cacgcagacc agctcacccc    9480
cacatggcgg gtgtactcaa ctggctcaaa cgtattccag accagagctg ggtgcttgat    9540
cggtgctgaa cacgtaaaca atagctatga atgcgatatt cccatcggtg ccgggatctg    9600
cgctagctat cagacacaga ccaattcccc cggcgagca cgatctgtag catcccagtc     9660
tattattgcc tacactatgt cattgggcgc cgagaatagc gtcgcatatt caaataattc    9720
tattgcaata cccaccaact tcacaatctc cgtaactaca gaaatacttc cagtttccat    9780
gacaaagaca tcagtggatt gtacaatgta tatatgcgga gattccacag aatgttcaaa    9840
tttgctcttg cagtacggct ccttctgcac ccagctcaac agggcccta caggtattgc      9900
tgtcgaacag gacaagaaca cacaagaagt cttcgcccaa gtcaaacaga tatacaaaac    9960
tcctcccata aaggattttg gcggcttcaa ctttagtcag atcctcccag acccttcaaa   10020
accatctaaa cgatcattta ttgaagatct gctgttcaac aaggtcactc ttgccgatgc   10080
tggattcatt aagcaatacg gtgactgcct tggtgatatt gctgcccgag atctgatctg   10140
tgcccagaaa ttcaacgggc tcactgtact ccctccactg ctcacagacg aaatgattgc   10200
acagtacaca agtgccctgt tggcaggcac aatcactagc ggctggacct ttggcgcagg   10260
tgcagcactc caaatacctt ttgccatgca gatggcctat cggtttaatg ggataggcgt   10320
gactcaaaat gtcctctacg aaaaccaaaa gttgatagct aaccaattca attcagcaat   10380
cgggaagata caggattcac tgtctagtac tgctagtgcc cttggtaagc tgcaggacgt   10440
tgtcaaccag aatgctcaag ctctgaatac attggttaag cagctctcta gtaattttgg   10500
ggccatctct tcagtactta atgatatttt gagccgattg gacaaagtgg aagctgaagt   10560
acagatcgac aggctgataa caggccggct ccaatccctc caaacatacg tgacacaaca   10620
actcatacgc gcagccgaaa tccgagccag cgctaacctg gcagctacca agatgtcaga   10680
atgcgttctg ggccagagta aacgcgtaga tttctgcggg aaagggtacc acctgatgtc   10740
ctttccacaa tctgcacctc acggggtcgt cttttttgcat gtaacatatg tacccgcaca   10800
agagaagaat tttactaccg ctcctgccat ctgtcatgac gggaaagctc attttcctcg   10860
cgaaggtgtg tttgtatcta atggtacaca ttggtttgtc acacagcgga atttctatga   10920
accccagatc attacaactg acaacacttt tgtttccggg aattgtgacg tggtcatagg   10980
aatcgtaaat aacactgtat atgatccccct ccaaccagag ctggactctt ttaaagaaga   11040
actggataaa tatttcaaga accacacaag tcccgacgtg gaccttgggg acataagtgg   11100
tattaacgca tctgtggtta acattcaaaa ggaaatcgac agactcaacg aggtggccaa   11160
aaacctgaac gaaagcttga tagatctcca ggagtgggc aagtatgaac agtacattaa    11220
atggccatgg tacatatggc ttggctttat cgctggcctt atcgccatcg taatggttac   11280
aatcatgctg tgctgcatga cctcctgctg ttcttgtttg aaagggtgtt gttcttgtgg   11340
tagttgttgc aagtttgacg aagatgattc cgaacctgtt cttaaagggg taaagcttca   11400
ctatacatga taaccgcggt gtcaaaaacc gcgtggacgt ggttaacatc cctgctggga   11460
ggatcagccg taattattat aattggcttg gtgctggcta ctattgtggc catgtacgtg   11520
ctgaccaacc agaaacataa ttgaatacag cagcaattgg caagctgctt acatagaact   11580
cgcggcgatt ggcatgccgc cttaaaattt ttattttatt ttttcttttc ttttccgaat   11640
cggattttgt ttttaatatt tcaaaaaaaa aaaaaaaaaa aaaaaaaaaa aaaaaaaaaa    11700
aaaaaaa                                                            11707
```

| | | |
|---|---|---|
| SEQ ID NO: 25 | moltype = RNA   length = 11707 | |
| FEATURE | Location/Qualifiers | |
| misc_feature | 1..11707 | |
| | note = Description of Artificial Sequence: Synthetic polynucleotide | |
| source | 1..11707 | |
| | mol_type = other RNA | |
| | organism = synthetic construct | |

SEQUENCE: 25

```
ataggcggcg catgagagaa gcccagacca attacctacc caaatggag aaagttcacg       60
ttgacatcga ggaagacagc ccattcctca gagctttgca gcggagcttc ccgcagtttg    120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagtc ggccgccgtc atgacgcgacc    420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccaccect tttatgttta     600
agaacttggc tggagcatat ccatcatact ctaccaactg ggcgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaaattac acatgtcggt gtgagactat agtagttgc gacgggtacg     900
tcgttaaaag aatagctatc agtccagccc tgtatggaa gccttcaggc tatgctgcta     960
cgatgcaccg cgagggattc ttgtgctgca aagtgacaga cacattgaac ggggagaggg    1020
tctcttttcc cgtgtgcacg tatgtgccag ctacattgtg tgaccaaatg actggcatac    1080
tggcaacaga tgtcagtgcg gacgacgcgc aaaaactgct ggtgggctc aaccagcgta     1140
tagtcgtcaa cggtcgcacc cagagaaaca ccaataccat gaaaaattac ctttgccccg    1200
tagtggccca tgcatttgct agttgggtga aggaataa gaagatgaa                   1260
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggcgt    1560
```

```
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgaagaa 2160
cacgaccagc cgctccttac caagtaccaa ccatagggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg tttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga ataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actaccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg cttttagtgc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgtat ccattaggaa taatcactgg gataactccc  3300
cgtcgcctaa catgtacggg ctgaataaag aagtggtccg tcagctctct gcgcaggtacc 3360
cacaactgcc tcgggcagtt gccactggaa gagtctatga catgaacact ggtacactgg  3420
gcaattatga tccgcgcata aacctagtac ctgtaaacag aagctgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggaccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggcga cgatcgcaag gcccgtacgc  3960
acaatcctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cgggaggtgt gcggagcgg  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaaccaa tcattgaacc atttgctgac agcttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaacttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga gggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacacct ggagggagct agcgtgacca  5340
gcggggcaac gtcagccgag actaactctt acttcgcaaa ggatgggag tttctgccag  5400
gaccggtgcc tgcgcctcga acagtattca ggaaccctcc acatcccgct ccgcgcacaa  5460
gaacaccgtc acttgcaccc agcagggcct gctcgagaac cagcctagtt tccacccgc  5520
caggcgtgaa tagggtgatc actagagagg agctcgaggc gcttacccg tcacgcactc  5580
ctagcaggtc ggtctcgaga accagcctgg tctccaaccc gccaggcgta aatggggtga  5640
ttacaagaga ggagtttgag gcgttcgtag cacaacaaca atgacggttt gatgcgggtg  5700
catacatctt ttcctccgac accggtcaag ggcatttaca acaaaatca gtaaggcaaa  5760
cggtgctatc cgaagtggtg ttggagagga ccgaattgga gatttcgtat gccccgcgcc  5820
tcgaccaaga aaagaagaa ttactacgca agaaattaca gttaaatccc acacctgcta  5880
acagaagcag ataccagtcc aggaaggtgg agaacatgaa agccataaca gctagactga  5940
ttctgcaagg cctagggcat tatttgaagg cagaaggaaa agtggagtgc taccgaaccc  6000
tgcatcctgt tccttttgtat tcatctagtg tgaaccgtgc cttttcaagc cccaaggtcg  6060
cagtggaagc ctgtaacgcc atgttgaaag agaactttcc gactgtgget tcttactgta  6120
ttattccaga gtacgatgcc tatttggaca tggttgacgg agcttcatgc tgcttagaca  6180
ctgccagttt ttgccctgca aagctgcgca gcttccaaa gaaacactcc tatttggaac  6240
ccacaataag atcggcagtg ccttcagcga tccagaacac gctccagaac gtcctggcag  6300
```

```
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctga   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggccccctat aactctctac ggctaacctg aatggactac gacatagtct agtccgccaa   7560
gatgtttctg ctcacaacca aacgcactat gttttgttttc ctcgtgctgc tcccttttggt   7620
aagttctcag tgtgtaaacc tgacaacacg aacccagttg cctccagctt ataccaactc   7680
atttactcgc ggagtatatt atcccgataa ggtcttagaa agtagcgtgt tgcactctac   7740
acaggatctg ttcttgccct tctttagtaa cgttacctgg tttcatgcaa tacatgtgag   7800
cggaacaaat ggaacaaaaa gatttgacaa tccagtgctt ccatttaatg atggggttta   7860
ctttgccagt accgaaaagt caaacataat ccggggtgg atctttggaa ccactttgga   7920
ctctaagaca cagtctctcc tcatagtaaa caacgccacc aatgttgtca taaaagtatg   7980
cgaatttcag ttttgcaacg atcccttttct cggggtgtat taccataaga ataataaatc   8040
ctggatggag tctgagttcc gggtttatag tagtgctaat aattgcactt tcgaatacgt   8100
gtcccaacca ttcctcatgg accttgaggg caaacagggg aatttttaaaa acttgcgcga   8160
atttgtctttt aagaatatcg acggatactt taagatctat agtaaacaca ctcctatcaa   8220
cctgttcgg gatcttcccc aaggcttttc tgctctcgaa cccctcgtag acttgccaat   8280
tgggataaat atcactcgct ttcaaacttt gcttgccctc cacaggagct acctgacacc   8340
cggcgactct tcttctggtt ggaccgccgg cgccgctgcc tattatgttg gttaccttca   8400
gccacgaaca ttcttgctca agtataacga gaatggcacc attaccgacg ccgtcgattg   8460
tgcattggat cccttgtctg aaacaaaatg taccttgaag tcctttaccg tagagaaagg   8520
catataccag acttccaact tccgagttca gcctacagaa tccattgtga gatttcccaa   8580
catcacaaac ctctgcccctt tcggtgaagt atttaatgct aacacgcttcg cttcagtcta   8640
tgcctggaat aggaagcgca tatcaaattg cgtggccgat tattcagtcc tctataatga   8700
cgcatccttc agtactttca agtgctacgg cgttttcccc accaaactca atgatctttg   8760
cttccaccaac gtctatgctg acagttttgt catacgaggc gacgaagtac gccagattgc   8820
ccccggacag acaggtaaaa ttgctgatta taattataaa ctcccagatg acttttactgg   8880
atgcgtcata gcctgaatt ccaacaatct tgattccaag gttggtggga attataatta   8940
cctttatcga ctgttcagaa agagtaactt gaaaccattt gagagagaca tatccaccga   9000
gatttaccag gcaggcagta ctccttgtaa cggcgttgag ggatttaact gctattttcc   9060
tttgtcaatcc tatggctttc aaccaacaaa cggggttgc tatcaaccct atcgagtggt   9120
tgtcctgagc tttgaacttt tgcacgctcc cgccacagtc tgcggaccaa aaaagagtac   9180
aaatcttgtc aagaataagt gcgtaaattt caatttcaat ggcctacag gaacaggcgt   9240
gctgactgag tcaaacaaga agttcctgcc atttcagcag tttgggcggg atatagcaga   9300
cacaactgac gctgtacgcg atcctcagac tttggagatc ttggacatca ctccctgttc   9360
tttcggaggg gtatctgtca tcacccccgg aactaataca tcaaatcagg tcgctgtgtt   9420
gtaccaagat gtcaactgca cagaagtccc cgttgctata cacgcagacc agctcacccc   9480
cacatgcgcg gtgtactcaa ctggctcaaa cgtattccag accagagctg ggtgcttgat   9540
cggtgctgaa cacgtaaaca atagctatga atgcgatatt cccatcggtg ccgggatctg   9600
cgctagctat cagacacaga ccaattcccc ccggcgagca cgatctgtag catcccagtc   9660
tattattgcc tacactatgt cattgggcgc cgagaatagc gtcgcatatt caaataattc   9720
tattgcaata cccaccaact tcacaatctc cgtaactaca gaaatacttc cagttttccat   9780
gacaaagaca tcagtggatt gtacaagta tatatgcgga gattccacag aatgttcaaa   9840
tttgctcttg cagtacggct ccttctgcac ccagctcaac agggccctta caggtattgc   9900
tgtcgaacag gacaagaaca cacaagaagt cttcgcccaa gtcaaacaga tatacaaaac   9960
tcctcccata aaggattttg gcggcttcaa ctttagtcag atcctcccag cccttcaaa   10020
accatctaaa cgatcattta ttgaagatct gctgttcaac aaggtcactc ttgccgatgc   10080
tggattcatt aagcaatacg gtgactgcct tggtgatatt gctgcccgag atcgatctg   10140
tgccagaaaa ttcaacgggc tcactgtact ccctccactg ctcacagacg aaatgattgc   10200
acagtacaca agtgccctgt tggcaggcac aatcactagc ggctggaacct ttggcgcagg   10260
tgcagcactc caaataccct tgccatgca gatggcctat cggtttaatg ggataggcgt   10320
gactcaaaat gtcctctacg aaaaccaaaa gttgatagct aaccaattca attcagcaat   10380
cgggaagata caggattcac tgtctagtac tgctagtgcc cttggtaagc tgcaggacgt   10440
tgtcaaccag aatgctcaag ctctgaatac attggttaag cagctctcta gtaattttgg   10500
ggccatctct tcagtactta atgatatttt gagccgattg gacccacccg aagctgaagt   10560
acagatcgac aggctgataa caggccggct ccaatccctc caaacatacg tgacacaaca   10620
actcatacgc gcagccgaaa tccgagccag cgctaacctg gcagctacca agatgtcaga   10680
atgcgttctg ggccagagta aacgcgtaga tttctgcggg aaagggtacc acctgatgtc   10740
ctttccacaa tctgcacctc acggggtcgt cttttttgcat gtaacatatg taccgcaca   10800
agagaagaat tttactaccg ctcctgccat ctgtcatgac gggaaagctc atttttcctcg   10860
cgaaggtgtg tttgtatcta atggtacaca ttggtttgtc acacagcgga attttctatga   10920
accccagatc attacaactg acaacacttt tgtttccggg aattgtgacg tggtcatagg   10980
aatcgtaaat aacactgtat atgatcccct ccaaccagag ctggactctt ttaaagaaga   11040
```

```
actggataaa tatttcaaga accacacaag tcccgacgtg gaccttgggg acataagtgg     11100
tattaacgca tctgtggtta acattcaaaa ggaaatcgac agactcaacg aggtggccaa     11160
aaacctgaac gaaagcttga tagatctcca ggagttgggc aagtatgaac agtacattaa     11220
atggccatgg tacatatggc ttggctttat cgctggcctt atcgccatcg taatggttac     11280
aatcatgctg tgctgcatga cctcctgctg ttcttgtttg aaagggtgtt gttcttgtgg     11340
tagttgttgc aagtttgacg aagatgattc cgaacctgtt cttaaagggg taaagcttca     11400
ctatacatga taaccgcggt gtcaaaaacc gcgtggacgt ggttaacatc cctgctggga     11460
ggatcagccg taattattat aattggcttg gtgctggcta ctattgtggc catgtacgtg     11520
ctgaccaacc agaaacataa ttgaatacag cagcaattgg caagctgctt acatagaact     11580
cgcggcgatt ggcatgccgc cttaaaattt ttattttatt tttctttttc ttttccgaat     11640
cggattttgt ttttaatatt tcaaaaaaaa aaaaaaaaaa aaaaaaaaaa aaaaaaaaaa     11700
aaaaaaa                                                               11707
```

| SEQ ID NO: 26 | moltype = RNA length = 11707 |
|---|---|
| FEATURE | Location/Qualifiers |
| misc_feature | 1..11707 |
| | note = Description of Artificial Sequence: Synthetic polynucleotide |
| source | 1..11707 |
| | mol_type = other RNA |
| | organism = synthetic construct |

SEQUENCE: 26
```
ataggcggcg catgagagaa gcccagacca attacctacc caaaatggag aaagttcacg       60
ttgacatcga ggaagacagc ccattcctca gagctttgca gcggagcttc ccgcagtttg      120
aggtagaagc caagcaggtc actgataatg accatgctaa tgccagagcg tttccgcatc      180
tggcttcaaa actgatcgaa acggaggtgg acccatccga cacgatccct gacattggaa      240
gtgcgcccgc ccgcagaatg tattctaagc acaagtatca ttgtatctgt ccgatgagat      300
gtgcggaaga tccggacaga ttgtataagt atgcaactaa gctgaagaaa aactgtaagg      360
aaataactga taaggaattg gacaagaaaa tgaaggagct ggccgccgtc atgagcgacc      420
ctgacctgga aactgagact atgtgcctcc acgacgacga gtcgtgtcgc tacgaaggcc      480
aagtcgctgt ttaccaggat gtatacgcgg ttgacgacc gacaagtctc tatccaccaag     540
ccaataaggg agttagagtc gcctactgga taggctttga caccaccect tttatgttta      600
agaacttggc tggagcatat ccatcatact ctaccaactg gccgacgaa accgtgttaa      660
cggctcgtaa cataggccta tgcagctctg acgttatgga gcggtcacgt agagggatgt      720
ccattcttag aaagaagtat ttgaaaccat ccaacaatgt tctattctct gttggctcga      780
ccatctacca cgagaagagg gacttactga ggagctggca cctgccgtct gtatttcact      840
tacgtggcaa gcaaaattac acatgtcggt gtgagactat agttagttgc gacgggtacg      900
tcgttaaaag aatagctatc agtccaggcc tgtatggaa gccttcaggc tatgctgcta      960
cgatgcaccg cgagggattc ttgtgctgca aagtgacaga cacattgaac ggggagaggg     1020
tctctttttcc cgtgtgcacg tatgtgccag ctacattgtg tgaccaaatg actggcatac     1080
tggcaacaga tgtcagtgcg gacgacgcgc aaaaactgct ggttgggctc aaccagcgta     1140
tagtcgtcaa cggtcgcacc cagagaaaca ccaataccat gaaaaattac cttttgcccg     1200
tagtgcccca ggcatttgct aggtgggcaa aggaaataaa ggaagatgaa                 1260
ggccactagg actacgagat agacagttag tcatggggtg ttgttgggct tttagaaggc     1320
acaagataac atctatttat aagcgcccgg ataccaaaac catcatcaaa gtgaacagcg     1380
atttccactc attcgtgctg cccaggatag gcagtaacac attggagatc gggctgagaa     1440
caagaatcag gaaatgtta gaggagcaca aggagccgtc acctctcatt accgccgagg     1500
acgtacaaga agctaagtgc gcagccgatg aggctaagga ggtgcgtgaa gccgaggagt     1560
tgcgcgcagc tctaccacct ttggcagctg atgttgagga gccactctg gaggcagacg     1620
tcgacttgat gttacaagag gctggggccg gctcagtgga gacacctcgt ggcttgataa     1680
aggttaccag ctacgatggc gaggacaaga tcggctctta cgctgtgctt tctccgcagg     1740
ctgtactcaa gagtgaaaaa ttatcttgca tccaccctct cgctgaacaa gtcatagtgg     1800
taacacactc tggccgaaaa gggcgttatg ccgtggaacc ataccatggt aaagtagtgg     1860
tgccagaggc acatgcaata cccgtccagg actttcaagc tctgagtgaa agtgccacca     1920
ttgtgtacaa cgaacgtgaa ttcgtaaaca ggtacctgca ccatattgcc acacatggag     1980
gagcgctgaa cactgatgag gaatattaca aaactgtcaa gcccagcgag cacgacggcg     2040
aatacctgta cgacatcgac aggaaacagt gcgtcaagaa agaactagtc actgggctag     2100
ggctcacagg cgagctggtg gatcctccct tccatgaatt cgcctacgag agtctgaaga     2160
cacgaccagc cgctccttac caagtaccaa catagggg gtatggcgtg caggatcag     2220
gcaagtctgg catcattaaa agcgcagtca caaaaaaga tctagtggtg agcgccaaga     2280
aagaaaactg tgcagaaatt ataagggacg tcaagaaaat gaaagggctg gacgtcaatg     2340
ccagaactgt ggactcagtg ctcttgaatg gatgcaaaca ccccgtagag accctgtata     2400
ttgacgaagc ttttgcttgt catgcaggta ctctcagagc gctcatagcc attataagac     2460
ctaaaaaggc agtgctctgc ggggatccca aacagtgcgg tttttttaac atgatgtgcc     2520
tgaaagtgca ttttaaccac gagatttgca cacaagtctt ccacaaaagc atctctcgcc     2580
gttgcactaa atctgtgact tcggtcgtct caaccttgtt ttacgacaaa aaaatgagaa     2640
cgacgaatcc gaaagagact aagattgtga ttgacactac cggcagtacc aaacctaagc     2700
aggacgatct cattctcact tgtttcagag ggtgggtgaa gcagttgcaa atagattaca     2760
aaggcaacga aataatgacg gcagctgcct ctcaagggct gacccgtaaa ggtgtgtatg     2820
ccgttcggta caagatgaat gaaaatcctc tgtacgcacc cacctcagaa catgtgaacg     2880
tcctactgac ccgcacggag gaccgcatcg tgtggaaaac actagccggc gacccatgga     2940
taaaaacact gactgccaag taccctggga atttcactgc cacgatagag gagtggcaag     3000
cagagcatga tgccatcatg aggcacatct tggagaccc ggaccctacc gacgtcttcc     3060
agaataaggc agtagcgtgt ggcaagtt ctttagtgcg gtgctgaag accgctggca     3120
tagcatgac cactgaacaa tggaacactg tggattattt tgaaacggac aaagctcact     3180
cagcagagat agtattgaac caactatgcg tgaggttctt tggactcgat ctggactccg     3240
gtctatttc tgcacccact gttccgttat ccattaggaa taatcactgg gataactccc     3300
cgtcgcctaa catgtacggg ctgaataaag aagtggtccg tcagctctct cgcaggtacc     3360
cacaactgcc tcgggcagtt gccactggaa gagtctatga catgaacact ggtacactgc     3420
```

```
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgcataata tttgttaatg tgaggaccaa atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggtg tgcggagcgc    4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggcaatgag caggtatgca    4740
tgtatatcct cggagaaagc atgagcagta ttaggtcgaa atgccccgtc gaagagtcgg   4800
aagcctccac accaccctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggaggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgccaaa   5460
gaacaccgtc acttgcaccc agcagggcct gctcgagaac cagccagtt tccacccgc    5520
caggcgtgaa tagggtgatc actagagagg agctcgaggc gcttaccccg tcacgcactc   5580
ctagcaggtc ggtctcgaga accagcctgg tctccaaccc gccaggcgta atagggtga   5640
ttacaagaga ggagtttgag gcgttcgtag cacaacaaca atgacggttt gatgcggtg    5700
catacatctt ttcctccgac accggtcaag gacatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tccttttgtat tcatctagtg tgaaccgtgc ctttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagcgcatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccgc acagcgtgc    7260
gtgtggcaga cccccctaaaa aggctgttta agcttggcaa acctctggca gcagacgatg   7320
aacatgatga tgacaggaga aggggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgtttctg ctcacaacca aacgcactat gtttgttttc ctcgtgctgc tccctttggt   7620
aagttctcag tgtgtaaacc tgacaacacg aacccagttg cctccagctt ataccaactc   7680
atttactcgc ggagtatatt atcccgataa ggtcttaga agtagcgtgt tgcactctac   7740
acaggatctg ttccttgccct tctttagtaa cgttacctgg tttcatgcaa tacatgtgag   7800
cggaacaaat ggaacaaaaa gattgacaa tccagtgctt ccattaatg atgggggtta   7860
ctttgccagt accgaaaagt caaacataat ccggggggtgg atcttgaa ccactttgga    7920
ctctaagaca cagtctctcc tcatagtaaa caacgccacc aatgttgtca taaaagtatg   7980
cgaatttcag ttttgcaacg atcccttcct cggggtgat taccataaga ataataaatc    8040
ctggatggag tctgagttcc gggttatag tagtgctaat aattgcactt tcgaatacgt    8100
gtcccaacca ttcctcatgg accttgaggg caaacagggg aattttaaaa acttgcgcga   8160
```

```
atttgtcttt aagaatatcg acggatactt taagatctat agtaaacaca ctcctatcaa    8220
cctcgttcgg gatcttcccc aaggcttttc tgctctcgaa cccctcgtag acttgccaat    8280
tgggataaat atcactcgct ttcaaacttt gcttgccctc cacaggagct acctgacacc    8340
cggcgactct tcttctggtt ggaccgccgg cgccgctgcc tattatgttg gttaccttca    8400
gccacgaaca ttcttgctca agtataacga gaatggcacc attaccgacg ccgtcgattg    8460
tgcattggat cccttgtctg aaacaaaatg taccttgaag tcctttaccg tagagaaagg    8520
catataccag acttccaact tccgagttca gcctacagaa tccattgtga gatttcccaa    8580
catcacaaac ctctgccctt tcggtgaagt atttaatgct acacgcttcg cttcagtcta    8640
tgcctggaat aggaagcgca tatcaaattg cgtggccgat tattcagtcc tctataatag    8700
cgcatccttc agtactttca agtgctacgg cgtttccccc accaaactca atgatctttg    8760
cttcaccaac gtctatgctg acagtttttgt catacgaggc gacgaagtac gccagattgc    8820
ccccgggcag acaggtaaaa ttgctgatta aattataaa ctcccagatg actttactgg    8880
atgcgtcata gcctggaatt ccaacaatct tgattccaag gttggtggga attataatta    8940
cctttatcga ctgttcagaa agagtaactt gaaaccattt gagagagaaca tatccaccga    9000
gatttaccag gcaggcagta ctccttgtaa cggcgttgag ggatttaact gctattttcc    9060
tttgcaatcc tatggctttc aaccaacaaa cggggttggc tatcaaccct atcgagtggg    9120
tgtcctgagc tttgaacttt tgcacgctcc cgccacagtg tgcggaccaa aaaagagtac    9180
aaatcttgtc aagaataagt gcgtaaattt caatttcaat ggccttacag gacaggcgt    9240
gctgactgag tcaaacaaga agttcctgcc atttcagcag tttgggcggg atatagcaga    9300
cacaactgac gctgtacgcg atcctcagac ttttggagatc ttggacatca ctccctgttc    9360
tttcggaggg gtatctgtca tcaccccgg aactaataca tcaaatcagg tcgctgtgtt    9420
gtaccaagat gtcaactgca cagaagtccc cgttgctata cggcagcc agctcaccc    9480
cacatggcgg gtgtactcaa ctggctcaaa cgtattccag accagagctg ggtgcttgat    9540
cggtgctgaa cacgtaaaca atagcctatga atgcgatatt cccatcggtg ccgggatctg    9600
cgctagctat cagacacaga ccaattcccc ccggcgagca cgatctgtag catcccagtc    9660
tattattgcc tacactatgt cattgggcgc cgagaatgac gtcgcatatt caaataattc    9720
tattgcaata cccaccaact tcacaatctc cgtaactaca gaaatactc cagtttccat    9780
gacaaagaca tcagtggatt gtacaatgta tatgcgga gattccacag aatgttcaaa    9840
tttgctcttg cagtacggct ccttctgcac ccagctcaac agggccctta caggtattgc    9900
tgtcgaacag gacaagaaca cacaagaagt cttcgccaca gtcaaacaga tatacaaaac    9960
tcctcccata aaggattttg gcggcttcaa ctttagtcag atcctcccag acccttcaaa    10020
accatctaaa cgatcattta ttgaagatct gctgttcaac aaggtcactc ttgccgatgc    10080
tggattcatt aagcaatacg gtgactgcct tggtgatatt gctgcccgag atctgatctg    10140
tgcccagaaa ttcaacgggc tcactgtact cctccactg ctcacagacg aaatgattgc    10200
acagtacaca agtgccctgt tggcaggcac aatcactagc ggctggacct ttggcgcagg    10260
tgcagcactc caaatacctt tgccatgca gatggcctat cggtttaatg ggataggcgt    10320
gactcaaaat gtcctctacg aaaaccaaaa gttgatagct aaccaattca attcagcaat    10380
cgggaagata caggattcac tgtctagtac tgctagtgcc cttggtaagc tgcaggacgt    10440
tgtcaaccag aatgctcaag ctctgaatac attggttaag cagctctcta gtaattttgg    10500
ggccatctct tcagtactta atgatattt gagccgattg gacaaagtgg aagctgaagt    10560
acagatcgac aggctgataa caggccggct ccaatccctc caaacatacg tgacacaaca    10620
actcatacgc gcagccgaaa tccgagccag cgctaacctg gcagctacca agatgtcaga    10680
atgcgttctg ggccagagta aacgcgtaga tttctgcggg aaagggtacc acctgatgtc    10740
cttttccacaa tctgcacctc acggggtcgt ctttttgcat gtaacatatg tacccgcaca    10800
agagaagaat tttactaccg ctcctgccat ctgtcatgac gggaaagctc attttcctcg    10860
cgaaggtgtg tttgtatcta atggtacaca ttggtttgtc acacagcgga attctatga    10920
accccagatc attacaactg acaacacttt tgtttccggg aattgtgacg tggtcatagg    10980
aatcgtaaat aacactgtat atgatcccct ccaaccagag ctggactctt ttaaagaaga    11040
actggataaa tatttcaaga accacacaag tcccgacgtg gaccttgggg acataagtgg    11100
tattaacgca tctgtggtta acattcaaaa ggaaatcgac agactcaacg aggtggccaa    11160
aaacctgaac gaaagcttga tagatctcca ggagttgggc aagtatgaac agtacattaa    11220
atggccatgg tacatatggc ttggcttat cgctggcctt atcgccatcg taatggttac    11280
aatcatgctg tgctgcatga cctcctgctg ttcttgtttg aaagggtgtt gttcttgtgg    11340
tagttgttgc aagtttgacg aagatgattc cgaacctgtt cttaagggg taaagcttca    11400
ctatacataag taaccgcggt gtcaaaaacc gcgtggacatc ggttaacatc cctgctggga    11460
ggatcagccg taattattat aattggcttg gtgctggcta ctattgtggc catgtacgtg    11520
ctgaccaacc agaaacataa ttgaatacag cagcaattgg caagctgctt acatagaact    11580
cgcggcgatt ggcatgccgc cttaaaattt tattttatt tttttctttt ttttccgaat    11640
cggattttgt ttttaatatt tcaaaaaaa aaaaaaaaa aaaaaaaa aaaaaaaaa    11700
aaaaaaa                                                              11707

SEQ ID NO: 27         moltype = RNA   length = 11698
FEATURE               Location/Qualifiers
misc_feature          1..11698
                      note = Description of Artificial Sequence: Synthetic
                      polynucleotide
source                1..11698
                      mol_type = other RNA
                      organism = synthetic construct
SEQUENCE: 27
ataggcggcg catgagagaa gcccagacca attacctacc caaatggag aaagttcacg    60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg accatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa actgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
```

```
ccaataaggg agttagagtc gcctactgga taggctttga caccaccect tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacgaa tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg ataccaacac catcatcaaa gtgaacgcg    1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaaca ataccatggt aaagtagtgg   1860
tgccagaggg acatgcaata cccgtccagg acttcaagc tctgagtgaa agtgccacca    1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctcct tccatgaatt cgcctacgac agtctgaaga    2160
cacgaccagc cgctccttac caagtaccaa ccataggggt gtatgcctg ccaggatcag    2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca acagtgcgg ttttttaac atgatgtgcc     2520
tgaaagtgca ttttaaccac gagatttgca cacagtctt ccacaaaagc atctctcgcc    2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaaggggct gacccgtaaa ggtgtgtatg   2820
ccgttcggta caaggtgaat gaaaatcctc tgtacgcacc cacctcagaa catgtgaaga   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg cttttagtgc ggtgctgaag accgctgcca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctatttc tgcaccact gttccgttat ccattaggaa taatcactgg gataactccc     3300
cgtcgcctaa catgtacggg ctgaataaag aagtggtccg tcagctctct cgcaggtacc   3360
cacaactgcc tcgggcagtt gccactggaa gagtctatga catgaacact ggtacactgg   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggaccc atataaatac catcactatc    3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatccta caagctttca tcaaccttga ccaacattta tcaggttcc agactccacg      4020
aagccggatg tgcaccctca tatcatgtgg tgcgagggga ttgccacg gccaccgaag      4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga atgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatga caaacttc tcatatttgg aagggaccaa gtttcaccag ccggccaagg     4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtcccag aacaaattac tgtgtgctca tcttttcat    4920
tagagtagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
```

```
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccacccccgc  5520
caggcgtgaa tagggtgatc actagagagg agctcgaggc gcttacccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaagaaa agtggagtgc taccgaaccc    6000
tgcatcctgt tcctttgtat tcatctagtg tgaaccgtgc cttttcaagc cccaaggtcg   6060
cagtggaagc ctgtaacgcc atgttgaaag agaacttttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa cccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatgcga agcagagtgt tgagagaacg gctaaccgga tcaccatgtg   7080
cagcattcat tggagatgac aatatcgtga aaggagtcaa atcggacaaa ttaatgcag   7140
acaggtgcgc cacctggttg aatatgaag tcaagattat agatgctgtg gtgggcgaga   7200
aagcgccctta tttctgtgga gggttttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
ggcccctat aactctctac ggctaacctg aatggactac gacatagtct agtccgccaa   7560
gatgtttctg ctcacaacca aacgcactat gtttgtttttc ctcgtgctgc tcccttttgg   7620
aagttctcag tgtgtaaact tcacaacacg aacccagttg cctccagctt ataccaactc   7680
atttactcgc ggagtatatt atcccgataa ggtcttaga agtagcgtgt tgcactctac   7740
acaggatctg ttcttgccct tcttttagtaa cgttacctgg tttcatgcaa tacatgtgag   7800
cggaacaaat ggaacaaaaa gattgccaa tccagtgctt ccatttaatg atgggggttta   7860
ctttgccagt accgaaaagt caaacataat ccggggggtgg atctttggaa ccactttgga   7920
ctctaagaca cagtctctcc tcatagtaaa caacgccacc aatgttgtca taaaagtatg   7980
cgaattttcag ttttgcaacg atcccttcct cggggtgtat taccataaga ataataaatc   8040
ctggatggag tctgagttcc gggtttatag tagtgctaat aattgcactt tcgaatacgt   8100
gtcccaacca ttcctcatgg accttgagg caaacagggg aatttttaaaa acttgcgcga   8160
atttgtcttt aagaatatcg acggatactt taagatctat agtaaacaca ctcctatcaa   8220
cctcgttcgg ggccttcccc aaggcttttc tgctctcgaa ccccctcgtag acttgccaat   8280
tggataaat atcactcgct ttcaaacttt gcacatcgac tacctgacac ccggcgactc   8340
ttcttctggt tggaccgccg gcgccgctgc ctattatgtt ggttaccttc agccacgaac   8400
attcttgctc aagtataacg agaatggcac cattaccgac gccgtcgatt gtgcattgga   8460
tccccttgtct gaaacaaaat gtaccttgaa gtcctttacc gtagagaaag gcatatacca   8520
gacttccaac ttccgagttc agcctacaga atccattgtg agatttccca acatcacaaa   8580
cctctgccct ttcggtgaag tatttaatgc tacacgcttc gcttcagtct atgcctggaa   8640
taggaagcgc atatcaaatt gcgtggccga ttattcagtc ctctataata gcgcatcctt   8700
cagtactttc aagtgctacg gcgtttcccc caccaaactc aatgatcttt gcttcaccaa   8760
cgtctatgct gacagttttg tcatacgagg cgacgaagta cgcagattg ccccccgggca   8820
gacaggtaac attgctgatt ataattataa actcccagat gacttactg gatgcgtcat   8880
agcctgaat tccaacaatc ttgattccaa ggttggtggg aattataatt acctttatcg   8940
actgttcaga aagagtaact tgaaaccatt tgagagagac atatccaccg agatttaccca   9000
ggcaggcagt actccttgta acggcgttaa gggatttaac tgctatttttc ctttgcaatc   9060
ctatgctttt caaccaacat acggggttgg ctatcaaccc tatcgagttg ttgtcctgag   9120
ctttgaactt ttgcacgctc ccgccacagt ctgcggacca aaaaagagta caaatcttgt   9180
caagaataag tgcgtaaatt tcaatttcaa tggccttaca ggaacaggcg tgctgactga   9240
gtcaaacaag aagttcctgc catttcagca gtttgggcgg gatatagcag acacaactga   9300
cgctgtacgc gatcctcaga ctttggagat cttggacatc actccctgtt ctttcggagg   9360
ggtatctgtc atcaccccccg gaactaatac atcaaatcag gtcgctgtgt tgtaccaagg   9420
cgtcaactgc acagaagtcc ccgttgctat acacgcagac cagctcaccc ccacatggcg   9480
ggtgtactca actggctcaa acgtattcca gaccagagct gggtgcttga tcggtgctga   9540
acacgtaaac aatagctatg aatgcgatat tcccatcggt gccgggatct gcgctagcta   9600
tcagacacag accaattccc ccggcgagc acgatccgta gcatcccagt ctattattgc   9660
ctacactatg tcattgggcg tggagaatag cgtgcatat tcaaataatt ctattgcaat   9720
acccaccaac ttcacaatct ccgtaactac agaaatactt ccagtttcca tgacaaagac   9780
atcagtggat tgtacaatgt atatatgcgg agattccaca gaatgttcaa atttgctctt   9840
gcagtacggc tccttctgca cccagctcaa cagggcccctt acaggtattg ctgtcgaaca   9900
ggacaagaac acacaagaag tcttcgccca agtcaaacag atatacaaaa ctcctccccat  9960
aaaggatttt ggcggcttca actttagtca gatcctccca gacccttcaa aaccatcaa   10020
```

-continued

```
acgatcattt attgaagatc tgctgttcaa caaggtcact cttgccgatg ctggattcat  10080
taagcaatac ggtgactgcc ttggtgatat tgctgcccga gatctgatct gtgcccagaa  10140
attcaacggg ctcactgtac tccctccact gctcacagac gaaatgattg cacagtacac  10200
aagtgccctg ttggcaggca caatcactag cggctggacc tttggcgcag gtgcagcact  10260
ccaaataccct tttgccatgc agatggccta tcggtttaat gggataggcg tgactcaaaa  10320
tgtcctctac gaaaaccaaa agttgatagc taaccaattc aattcagcaa tcgggaagat  10380
acaggattca ctgtctagta ctgctagtgc ccttggtaag ctgcaggacg ttgtcaacca  10440
gaatgctcaa gctctgaata cattggttaa gcagctctct agtaattttg gggccatctc  10500
ttcagtactt aatgatattt tgagccgatt ggacccaccc gaagctgaag tacagatacg  10560
caggctgata acaggccggc tccaatccct ccaaacatac gtgacacaac aactcatacg  10620
cgcagccgaa atccgagcca gcgctaacct ggcagctacc aagatgtcag aatgcgttct  10680
gggccagagt aaacgcgtag atttctgcgg gaaagggtac cacctgatgt cctttccaca  10740
atctgcacct cacgggtcg tcttttttgca tgtaacatat gtacccgcac aagagaagaa  10800
ttttactacc gctcctgcca tctgtcatga cgggaaagct cattttcctc gcgaaggtgt  10860
gtttgtatct aatggtacac attggttgt cacacagcgg aatttctatg aaccccagat  10920
cattacaact gacaacactt ttgtttccgg gaattgtgac gtggtcatag gaatcgtaaa  10980
taacactgta tatgatcccc tccaaccaga gctggactct tttaaagaag aactggataa  11040
atatttcaag aaccacacaa gtcccgacgt ggaccttggg gacataagtg gtattaacgc  11100
atctgtggtt aacattcaaa aggaaatcga cagactcaac gaggtggcca aaaacctgaa  11160
cgaaagcttg atagatctcc aggagttggg caagtatgaa cagtacatta atgccatg    11220
gtacatatgg cttggcttta tcgctggcct tatcgccatc gtaatggtta caatcatgct  11280
gtgctgcatg acctcctgct gttcttgttt gaaagggtgt tgttcttgtg gtagttgttg  11340
caagtttgac gaagatgatt ccgaacctgt tcttaaaggg gtaaagcttc actatacatg  11400
ataaccgcgg tgtcaaaaac cgcgtggacg tggttaacat ccctgctggg aggatcagcc  11460
gtaattatta taattggctt ggtgctggct actattgtgg ccatgtacgt gctgaccaac  11520
cagaaacata attgaataca gcagcaattg gcaagctgct tacatagaac tcgcggcgat  11580
tggcatgccg ccttaaaatt tttattttat tttttctttt cttttccgaa tcggattttg  11640
ttttaatat ttcaaaaaaa aaaaaaaaaa aaaaaaaaaa aaaaaaaaaa aaaaaaa      11698
```

```
SEQ ID NO: 28          moltype = RNA  length = 11698
FEATURE                Location/Qualifiers
misc_feature           1..11698
                       note = Description of Artificial Sequence: Synthetic
                       polynucleotide
source                 1..11698
                       mol_type = other RNA
                       organism = synthetic construct
SEQUENCE: 28
ataggcggcg catgagagaa gcccagacca attacctacc caaaatggag aaagttcacg   60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattgaa   240
gtgcgcgacc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg acaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacgagc gacaagtctc tatcaccaag  540
ccaataaggg agttagagtc gcctactgga taggctttga caccaccccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg 1020
tctctttttcc cgtgtgcacg tatgtgccaa ctacattgtg tgaccaaatg actggatac  1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggcctactagg actacgagat agacagttag tcatggggtg ttgtttggct tttagaaggc 1320
acaagataac atctatttat aagcgcccgg ataccccaaac catcatcaaa gtgaacagcg 1380
atttccactc attcgtgctg cccaggatag gcagtaacac attggagatc gggctgagaa 1440
caagaatcag gaaatgttta gaggagcaca aggagccgtc acctctcatt accgccgagg 1500
acgtacaaga agctaagtgc gcagccgatg aggctaagga ggtgcgtgaa gtgcgagggt 1560
tgcgcgcagc tctaccacct ttggcagctg atgttgagga gcccactctg gaggcagacg 1620
tcgacttgat gttacaagag gctggggccg gctcagtgga gacaccgtg ggcttgataa  1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggc aaagtagtgg 1860
tgccagaggg acatgcaata cccgtccagg acttttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt gctctacgag agtctgaaaa 2160
cacgaccagc cgctcttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
```

```
ctaaaaaggc agtgctctgc ggggatccca aacagtgcgg ttttttaac atgatgtgcc    2520
tgaaagtgca tttaaccac gagatttgca cacaagtctt ccacaaaagc atctctcgcc    2580
gttgcactaa atctgtgact tcggtcgtct caaccttgtt ttacgacaaa aaatgagaa    2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctatttc tgcacccact gttccgttat ccattaggaa taatcactgg gataactcc    3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagctgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct acccttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgttttat tcatttggga cgatcgcaag gcccgtacgc   3960
acaatcctta caagctttca tcaacccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtg   4500
ctaggagaga agcagtggag gagatatgca tatccgacga ctcttcagtg acagaacctg   4560
atgcagagct ggtgagggtg catccgaaga gttcttggc tggaaggaag ggctacagca   4620
caagcgatgc caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa aggcccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacacccc ggaggagct agcgtgacca   5340
gcgggggcaa gtcagccgag actaactctt acttcgcaaa gagtatggag tttctggcgc   5400
gaccggtgcc tgcgcctcga acagtattca ggaaccctcc acatcccgct ccgcgcacaa   5460
gaaccacgtc acttgcaccc agcagggcct gctcgagaac cagcctagtt tccacccgg   5520
caggcgtgaa tagggtgatc actagagagg agctcgagc gcttaccccg tcacgcactc   5580
ctagcaggtc ggtctcgaga accagcctgg tctccaaccc gccaggcgta aataggtgaa   5640
ttacaagaga ggagtttgag gcgttcgtag cacaacaaca atgacggttt gatgcggtgt   5700
catacatctt ttcctccgac accggtcaag gacatttaca acaaaaatca gtaaggcaaa   5760
cggtgctatc cgaagtggtg ttggagagga ccgaattgga gatttcgtat gcccgcgcc   5820
tcgaccaaga aaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtgagtgc taccgaacga   6000
tgcatcctgt tcctttgtat tcatctagtg tgaaccgtgc cttttcaagc cccaaggtca   6060
cagtggaagc ctgtaacgcc atgttgaaag aagactttcc gactgtggct tcttactgta   6120
ttattccaga gtacgatgcc tatttggaca tggttgacgg agcttcatgc tgcttagaca   6180
ctgccagttt tgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggccttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggttttgta atggacttaa agagagacgt gaaagtgact ccagaacaa   6600
aacatactga agaacggccc aaggtacagg tgatccaggc tgccgatccg ctagcaacag   6660
cgtatctgtg cggaatccac cgagagctgg ttaggagatt aaatgcgtc ctgcttccga   6720
acattcatac actgttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgc   6900
tgacgctgat tgaggcggct ttcggcgaaa tttcatcaat acatttgccc actaaaacta   6960
aatttaaatt cggagccatg atgaaatctg aatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
```

```
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgtttctg ctcacaacca aacgactat gttttgttttc ctcgtgctgc tcccttggt    7620
aagttctcag tgtgtaaacc tgacaacacg aacccagttg cctccagctt ataccaactc   7680
atttactcgc ggagtatatt atcccgataa ggtctttaga agtagcgtgt tgcactctac   7740
acaggatctg ttcttgccct tctttagtaa cgttacctgg tttcatgcaa taagcggaac   7800
aaatggaaca aaaagatttg acaatccagt gcttccattt aatgatgggg tttactttgc   7860
cagtaccgaa aagtcaaaca taatccgggg gtggatcttt ggaaccactt tggactctaa   7920
gacacagtct ctcctcatag taaacaacgc caccaatgtt gtcataaaag tatgcgaatt   7980
tcagttttgc aacgatccct ttctcggggt gtaccataag aataataaat cctggatgga   8040
gtctgagttc cgggtttata gtagtgctaa taattgcact ttcgaatacg tgtcccaacc   8100
attcctcatg gaccttgagg gcaaacaggg gaattttaaa aacttgcgcg aatttgtctt   8160
taagaatatc gacggatact ttaagatcta tagtaaacac actcctatca acctcgttcg   8220
ggatcttccc caaggctttt ctgctctcga accctcgta gacttgccaa ttggataaa    8280
tatcactcgc tttcaaactt tgcttgcct ccacaggagc tacctgacac ccggcgactc     8340
ttcttctggt tggaccgccg gcgccgctgc ctattatgtt ggttaccttc agccacgaac   8400
attcttgctc aagtataacg agaatggcac cattaccgac gccgtcgatt gtgcattgga   8460
tccctgtct gaaacaaaat gtaccttgaa gtccttacc ggtagagaaag gcatataccaa    8520
gacttccaac ttccgagttc agcctacaga atccattgtg agatttccca acatcacaaa   8580
cctctgccct ttcggtgaag tatttaatgc tacacgcttc gcttcagtct atgcctggaa   8640
taggaagcgc atatcaaatt gcgtggccga ttattcagtc ctctataata gcgcatcctt   8700
cagtactttc aagtgctacg gcgttttcccc caccaaactc aatgatcttt gcttcaccaa   8760
cgtctatgct gacagttttg tcatacgagg cgacgaagta cgccagattg cccccgggca   8820
gacaggtaaa attgctgatt ataattataa actcccagat gacttactg gatgcgtcat    8880
agcctggaat tccaacaatc ttgattccaa ggttggtggg aattataatt acctttatcg   8940
actgttcaga aagagtaact tgaaaccatt tgagagagac atatccaccg agatttacca   9000
ggcaggcagt actccttgta acggcgttga gggatttaac tgctattttc ctttgcaatc   9060
ctatggcttt caaccaacat acggggttgg ctataaccc tatcgagtgg ttgtcctgag    9120
ctttgaactt ttgcacgctc ccgccacagt ctgcggacca aaaaagagta caaatcttgt   9180
caagaataag tgcgtaaatt tcaatttcaa tggccttaca ggaacaggcg tgctgactga   9240
gtcaaacaag aagttcctgc catttcagca gtttgggcgg gatatagacg acacaactga   9300
cgctgtacgc gatcctcaga cttttggagat cttggacatc actccctgtt ctttcggagg   9360
ggtatctgtc atcaccccg gaactaatac atcaaatcag gtcgctgtgt tgtaccaagg    9420
cgtcaactgc acagaagtcc ccgttgctat acacgcagat cagctcaccc ccacatggcg   9480
ggtgtactca actggctcaa acgtattcca gaccagagct gggtgcttga tcggtgctga   9540
acacgtaaac aatagctatg aatgcgatat tcccatcggt gccgggatct gcgctagcta   9600
tcagacacag accaattccc atcggcgagc acgatctgta gcatcccagt ctattattgc   9660
ctacactatg tcattgggcg ccgagaatag cgtcgcatat tcaaataatt ctattgcaat   9720
acccatcaac ttcacaatct ccgtaactac agaaatactt ccagtttcca tgcacaaagac   9780
atcagtggat tgtacaatgt atatatgcgg agattccaca gaatgttcaa atttgctctt   9840
gcagtacggc tccttctgca cccagctcaa cagggccctt acaggtattg ctgtcgaaca   9900
ggacaagaac acacaagaag tcttcgccca agtcaaacag atatacaaaa ctcctcccat   9960
aaaggatttt ggcggcttca actttagtca gatcctccca gacccttcaa aaccatctaa  10020
acgatcattt attgaagatc tgctgttcaa caaggtcact cttgccgatg ctggattcat  10080
taagcaaatac ggtgactgcc ttggtgatat tgctgcccga gatctgatct gtcccagaa   10140
attcaacggg ctcactgtac tccctccact gctcacagac gaaatgattg cacagtacac  10200
aagtgccctg ttggcaggca caatcactag cggctggacc tttggcgcag gtgcagcact  10260
ccaaatacct tttgccatgc agatggccta tcggtttaat gggataggcg tgactcaaaa  10320
tgtcctctac gaaaccaaa agttgatagc taaccaattc aattcagcaa tcgggaagat    10380
acaggattca ctgtctagta ctgctagtgc ccttggtaag ctgcaggacg ttgtcaacca  10440
agctcaa gctctgaata cattggttaa gcagctctct agtaattttg gggccatctc      10500
ttcagtactt aatgatattt tggcccgatt ggaccacccc gaagctgaag tacagatcga  10560
caggctgata acaggccggc tccaatccct ccaaacatac gtgacacaac aactcatacg  10620
cgcagccgaa atccgagcca gcgctaacct ggcagctacc aagatgtcag aatgcgttct  10680
gggccagagt aaaacgcgtag atttctgcgg gaaagggtac cacctgatgt cctttccaca  10740
atctgcacct cacggggtcg tcttttttgca tgtaacatat gtacccgcac aagagaagaa  10800
ttttactacc gctcctgcca tctgtcatga cgggaaagct cattttcctc gcgaaggtgt  10860
gtttgtatct aatggtacac attggtttgt cacacagcgg aatttctatg aaccccagat  10920
cattacaact cacaacactt ttgtttccgg gaattgtgac gtggtcatag aatcgtaaa    10980
taacctgta tatgatcccc tccaaccaga gctggactct tttaaagaag aactggataa  11040
atatttcaag aaccacacaa gtcccgacgt ggaccttggg gacataagtg gtattaacgc  11100
atctgtggtt aacattcaaa aggaaatcga cagactcaac gaggtggcca aaaacctgaa  11160
cgaaagcttt atagatctcc aggagttggg caagtatgaa cagtacatta atggccatg    11220
gtacatatgg cttggcttta tcgctggcct tatcgccatc gtaatggtta caatcatgct  11280
gtgctgcatg acctcctgct gttcttgttt gaaagggtgt tgttcttgtg gtagttgttg  11340
caagtttgac gaagatgatt ccgaacctgt tcttaaaggg gtaaagcttc actatacatg  11400
ataaccgcgg tgtcaaaaac cgcgtggacg tggttaacat ccctgctggg aggatcagcc  11460
gtaattatta taattggctt ggtgctggct actattgtgg ccatgtacgt gctgaccaac  11520
cagaaacata attgaataca gcagcaattg gcaagctgct tacatagaac tcgcggcgat  11580
tggcatgccg ccttaaaatt tttattttat tttttcttt ctttccgaa tcggatttg     11640
tttttaatat ttcaaaaaaa aaaaaaaaaa aaaaaaaaaa aaaaaaaaaa aaaaaaaa    11698

SEQ ID NO: 29        moltype = RNA  length = 11701
FEATURE              Location/Qualifiers
misc_feature         1..11701
```

```
                    note = Description of Artificial Sequence: Synthetic
                    polynucleotide
source              1..11701
                    mol_type = other RNA
                    organism = synthetic construct
SEQUENCE: 29
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaaggcg    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gccgtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatggaaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggct gtatgccgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca acagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaatgagaaa   2640
cgacgaatcc gaaagagact aagattgtga tgcacactac cggcagtacc aaacctaagc   2700
aggacgatct cattctcact tgtttcagag gtgggtgaa gcagttgcaa atagattaca   2760
aaggcaacga ataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacgag gaccgcatcg tgtggaaaac actagccgcc gacccatga   2940
taaaaacact gactgccaag tacctgggaa atttcactgc cacgatagag gagtggcaag   3000
cagagcatga tgccatcatg aggcacatct ggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactgaa gagtctatga catgaacact ggtacactgc   3420
gcaattatga tccgcgcata aacctagtac ctgtaaacag aagctgcct catgctttag   3480
tcctccacca taatgaacac ccacagagtg acttttcttc attcgtcagc aaattgaagg   3540
gcagaactgt cctggtggtc gggaaaagt tgtccgtccc aggcaaatg ttgactggt   3600
tgtcagaccg gcctgaggct accttcagag ctcggctgga tttaggcatc ccaggtgatg   3660
tgcccaaata tgacataata tttgttaatg tgaggaccc atataaatac catcactatc   3720
agcagtgtga agaccatgcc attaagctta catgttgac caagaaagct tgtctgcatc   3780
tgaatcccgg cggaacctgt gtcagcatag gttatggtta cgctgacagg gccagcgaaa   3840
gcatcattgg tgctatagcg cggcagttca gtttttcccg ggtatgcaaa ccgaaatcct   3900
cacttgaaga gacggaagtt ctgtttgtat tcattgggta cgatcgcaag gcccgtacgc   3960
acaatccta caagctttca tcaacctga ccaacattta acaggttcc agactccacg   4020
aagccggatg tgcacccgca tatcatgtgg tgcgagggga ttgccaccgaga aga         4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
```

```
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaaggaga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccacccgc    5520
caggcgtgaa tagggtgatc actagagagg agctcgaggc gcttacccg tcacgcactc     5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag atatccagtcc aggaaggtgg agaacatgaa agcataaca gctagacgta   5940
ttctgcaagg cctagggcat atttgaagg cagaagcaaa agtggagtgc taccgaaccc     6000
tgcatcctgt tcctttgtat tcatctagtg tgaaccgtgc ctttcaagc cccaaggtcg     6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg cctcagcga tccagaacac gctccagaac gtcctggcag     6300
ctgccacaaa agaaattgc aatgtcacgc aaatgagaga attgcccgta ttggattcgg      6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgcc actaaaacta    6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtggcgaga    7200
aagcgcctta tttctgtgga gggtttattt tgtgtgactc cgtgaccggc acagcgtgcc    7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaagggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgtttctg ctcacaacca aacgcactat gttttgttttc ctcgtgctgc tccctttggt   7620
aagttcctcag tgtgtaaacc tgagaacacg aacccagttg cctccagctt ataccaactc   7680
atttactcgc ggagtatatt atccgataaa ggtcttaga agtagcgtgt tgcactctac    7740
acaggatctg ttcttgccct tctttagtaa cgttacctgg tttcatgcaa tacatgtgag   7800
cggaacaaat ggaacaaaaa gatttgacaa tccagtgctt ccatttaatg atgggggttta   7860
ctttgccagt atcgaaaagt caaacataat ccggggtgg atctttggaa ccactttgga   7920
ctctaagaca cagtctctcc tcatagtaaa caacgccacc aatgttgtca taaaagtatg   7980
cgaatttcag ttttgcaacg atcccttttct cgacgtgtat taccataaga ataataaatc   8040
ctggatggag tctgggggttt atagtagtgc taataattgc actttcgaat acgtgtccca   8100
accattcctc atggaccttg agggcaaaca ggggaattttt aaaaacttgc gcgaatttgt   8160
ctttaagaat atcgacgat actttaagat ctatagtaaa cactccta tcaaccctgt    8220
tcggatcttt ccccaaggct tttctgctct cgaacccctc gtagacttgc caattgggat   8280
aaatatcact cgctttcaaa cttttgcttgc cctccacagg agctacctga cacccggcga   8340
ctcttcttct ggtttgaccg ccggcgccgc tgccctattat gttggttacc ttcagccacg   8400
aacattcttg ctcaagtata acgagaatgg caccattacc gacgccgtcg attgtgcatt   8460
ggatcccttg tctgaaacaa aatgtaccttt gaagtccttt accgtagaga aaggcatata   8520
ccagacttcc aacttccgag ttcagcctac agaatccatc gtacgatttc caacatcac    8580
aaacctctgc cctttcggtg aagtattaa tgctacacgc ttcgcttcag tctatgcctg   8640
gaataggaag cgcatatcaa attgcgtggc cgattattca gtcctctata atagcgcatc    8700
cttcagtact ttcaagtgct acggcgtttc ccccaccaaa ctcaatgatc tttgcttcac    8760
caacgtctat gctgacagtt ttgtcatacg aggcgacgaa gtgccccga                8820
gcagacaggt aatattgctg attataatta taaactccca gatgactta ctggatgcgt     8880
catagcctgg aattccaaca atctagattc caaggttggt gggaattata attaccgtta   8940
tcgactgttc agaaagagta acttgaaacc atttgagaga gacatatcca ccgagattta   9000
ccaggcaggc agtaagcctt gtaacggcgt tgagggattt aactgctatt ttcctttgca   9060
atcctatggc tttcaaccaa caaacggggt tggctatcaa ccctatcgag tggttgtcct   9120
```

```
cagctttgaa cttttgcacg ctcccgccac agtctgcgga ccaaaaaaga gtacaaatct  9180
tgtcaagaat aagtgcgtaa atttcaattt caatggcctt acaggaacag gcgtgctgac  9240
tgagtcaaac aagaatttcc tgccatttca gcagtttggg cgggatatag cagacacaac  9300
tgacgctgta cgcgatcctc agactttgga gatcttggac atcactccct gttctttcgg  9360
aggggtatct gtcatcaccc ccggaactaa tacatccaat caggtcgctg tgttgtacca  9420
aggtgtcaac tgcacagaag tccccgttgc tatacacgca gaccagctca cccccacatg  9480
gcgggtgtac tcaactggct caaacgtatt ccagaccaga gctgggtgct tgatcggtgc  9540
tgaacacgtg aacaatagct atgaatgcga tattcccatc ggtgccggga tctgcgctag  9600
ctatcagaca cagaccaatt cccgcaggcg ggctcgctct gtagcatccc agtctattat  9660
tgcctacact atgtcattgg gcgccgagaa tagcgtcgca tattcaaata attctattgc  9720
aatacccacc aacttcacaa tctccgtaac tacagaaata cttccagttt ccatgacaaa  9780
gacatcagtg gattgtacaa tgtatatatg cggagattcc acagaatgtt caaatttgct  9840
cttgcagtac ggctccttct gcaccccagct caacagggca cttacaggta ttgctgtcga  9900
acaggacaag aacacacaag aagtcttcgc ccaagtcaaa cagatataca aaactcctcc  9960
cataaaggat tttggcggct tcaacttag tcagatcctc ccagacccct caaaaccatc  10020
taaacgatca tttattgaag atctgctgtt caacaaggtc actcttgccg atgctggatt  10080
cattaagcaa tacggtgact gccttggtga tattgctgcc cgagatctga tctgtgccca  10140
gaaattcaac gggctcactg tactccctcc actgctcaca gacgaaatga ttgcacagta  10200
cacaagtgcc ctgttggcag gcacaatcac tagcggctgg acctttggcg caggtgcagc  10260
actccaaata ccttttgcca tgcagatggc ctatcggttt aatgggatag gcgtgactca  10320
aaatgtcctc tacgaaaacc aaaagttgat agctaaccaa ttcaattcag caatcgggaa  10380
gatacaggat tcactgtcta gtactgctag tgcccttggt aagctgcaga acgttgtcaa  10440
ccagaatgct caagctctga atacattggt taagcagctc tctagtaatt ttggggccat  10500
ctcttcagta cttaatgata ttttgagccg attggaccca cctgaagctg aagtacagat  10560
cgacaggctg ataacaggcc ggctccaatc cctccaaaca tacgtgacac aacaactcat  10620
acgcgcagcc gaaatccgag ccagcgctaa cctggcagct accaagatgt cagaatgcgt  10680
tctgggccag agtaaacgcg tagatttctg cgggaaaggg taccacctga tgtcctttcc  10740
acaatctgca cctcacgggg tcgtcttttt gcatgtaaca tacgtacccg cacaagagaa  10800
gaattttact accgctcctg ccatctgtca tgacgggaaa gctcattttc ctcgcgaagg  10860
tgtgtttgta tctaatggta cacattggtt tgtcacacag cggaatttct atgaacccca  10920
gatcattaca actgacaaca cttttgtttc cgggaattgt gacgtggtca taggaatcgt  10980
aaataacact gtatatgatc ccctccaacc agagctggac tctttaaag aagaactgga  11040
taaatatttc aagaaccaca caagtcccga cgtggacctt ggggacataa gtggtattaa  11100
cgcatctgtg gttaacattc aaaaggaaat cgacagactc aacgaggtgg ccaaaaacct  11160
gaacgaaagc ttgatagatc tccaggagtt gggcaagtat gaacagtaca ttaaatggcc  11220
atggtacata tggcttggct ttatcgctgg ccttatcgcc atcgtaatgg ttacaatcat  11280
gctgtgctgc atgacctcct gctgttcttg tttgaaaggg tgttgttctt gtggtagttg  11340
ttgcaagttt gacgaaatg attccgaacc tgttcttaag ggggtaaagc ttcactatac  11400
atgataaccg cggtgtcaaa aaccgcgtgg acgttgataa catccctgct gggaggatca  11460
gccgtaatta ttataattgg cttggtgctg gctactattg tggccatgta cgtgctgacc  11520
aaccagaaac ataattgaat acagcagcaa ttggcaagct gcttacatag aactcgcggc  11580
gattggcatg ccgccttaaa attttatttt tattttttct tttcttttcc gaatcggatt  11640
ttgtttttaa tatttcaaaa aaaaaaaaaa aaaaaaaaaa aaaaaaaaaa aaaaaaaaaa  11700
a                                                                  11701

SEQ ID NO: 30          moltype = RNA   length = 11703
FEATURE                Location/Qualifiers
misc_feature           1..11703
                       note = Description of Artificial Sequence: Synthetic
                       polynucleotide
source                 1..11703
                       mol_type = other RNA
                       organism = synthetic construct
SEQUENCE: 30
ataggcggcg catgagagaa gcccagacca attacctacc caaaatggag aaagttcacg   60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaagaaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataagg agttagagtc gcctactgga taggctttta caccacccct tttatgttca  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaaggag gacttactga ggagctggca cctgccgtct gtatttcact  840
tacgtggcaa gcaaaattac acatgtcggt gtgagactat agttagttgc gacgggtaca  900
tcgttaaaag aatagctatc agtccaggcc tgtatgggaa gccttcaggc tatgctgcta  960
cgatgcaccg cgagggattc ttgtgctgca aagtgacaga cattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgccca  1200
tagtggccca ggcatttgct aggtgggcaa aggaatataa ggaagatcaa gaagatgaaa  1260
ggccactagg actacgagat agacagttag tcatgggggtt gttgggct ttagaaggc  1320
acaagataac atctatttat aagcgccggg atacccaaac catcatcaaa gtgaacagcg  1380
atttccactc attcgtgctg cccagatag gcagtaacac attggagatc gggctgagaa  1440
caagaatcag gaaaatgtta gaggagcaca aggagccgtc acctctcatt accgccgagg  1500
```

```
acgtacaaga agctaagtgc gcagccgatg aggctaagga ggtgcgtgaa gccgaggagt 1560
tgcgcgcagc tctaccacct ttggcagctg atgttgagga gcccactctg gaggcagacg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtga 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgac agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaca gaaggtg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca acagtgcgg tttttttaac atgatgtgcc 2520
tgaaagtgca ttttaaccac gagatttgca caagtgtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatcc cattctcact tgtttcagag ggtgggtgaa gcagttgcaa atagattaca 2760
aaggcaacga aataatgacg gcagctgcct ctcaaggcgt gaccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga attcactgc cacgatagag gagtggcaag 3000
cagagcatga tgccatcatg aggcacatct tggagagaca ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgcctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagcggatg tgcaccctca tatcatgtgg tgcgagggga tattgccacg gccaccgaaa 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga atgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaacttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccgaaaa 4860
gagtacagcg cctaaaagcc tcacgtcag aacaaattac tgtgtgctca tccttttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaaggga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgaccacca ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt ccacccgc 5520
caggcgtgaa tagggtgatc actagagagg agctcgaggc gcttaccccg tcacgcactc 5580
ctagcaggtc ggtctcgaga accgcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc agaaggtgg agacataaca gctagacgta 5940
ttctgcaagg cctagggcat tatttgaagg cagaaggaaa agtggagtgc taccgaaccc 6000
tgcatctgtt cctttgtatt catccagtgt gaaccgtgcc ttttcaagcc caaggtcgc 6060
agtggaagcc tgtaacgcca tgttgaagaa gaactttccg actgtggctt cttactgtat 6120
tattccagag tacgatgcct atttggacat ggttgacgga gcttcatgct gcttagacac 6180
tgccagtttt tgccctgcaa agctgcgcag cttttccaaag aaacactcct atttggaacc 6240
```

```
cacaatacga tcggcagtgc cttcagcgat ccagaacacg ctccagaacg tcctggcagc   6300
tgccacaaaa agaaattgca atgtcacgca aatgagagaa ttgcccgtat tggattcggc   6360
ggcctttaat gtggaatgct tcaagaaata tgcgtgtaat aatgaatatt gggaaacgtt   6420
taaagaaaac cccatcaggc ttactgaaga aaacgtggta aattcatta ccaaattaaa    6480
aggaccaaaa gctgctgctc ttttttgcgaa gacacataat ttgaatatgt tgcaggacat  6540
accaatggac aggtttgtaa tggacttaaa gagagacgtg aaagtgactc caggaacaaa   6600
acatactgaa gaacggccca aggtacaggt gatccaggct gccgatccgc tagcaacagc   6660
gtatctgtgc ggaatccacc gagagctggt taggagatta aatgcggtcc tgcttccgaa   6720
cattcataca ctgttttgata tgtcggctga agactttgac gctattatag ccgagcactt   6780
ccagcctggg gattgtgttc tggaaactga catcgcgtcg tttgataaaa gtgaggacga   6840
cgccatggct ctgaccgcgt taatgattct ggaagactta ggtgtggacg cagagctgtt   6900
gacgctgatt gaggcggctt tcggcgaaat ttcatcaata catttgccca ctaaaactaa   6960
atttaaattc ggagccatga tgaaatctgg aatgttcctc acactgtttg tgaacacagt   7020
cattaacatt gtaatcgcaa gcagagtgtt gagagaacgg ctaaccggat caccatgtgc   7080
agcattcatt ggagatgaca atatcgtgaa aggagtcaaa tcggacaaat taatggcaga   7140
caggtgcgcc acctggttga atatggaagt caagattata gatgctgtgg tgggcgagaa   7200
agcgccttat ttctgtggag ggtttatttt gtgtgactcc gtgaccggca cagcgtgccg   7260
tgtggcagac cccctaaaaa ggctgtttaa gcttggcaaa cctctggcag cagacgatga   7320
acatgatgat gacaggagaa gggcattgca tgaagagtca acacgctgga accgagtggg   7380
tattctttca gagctgtgca aggcagtaga atcaaggtat gaaaccgtag gaacttccat   7440
catagttatg gccatgacta ctctagctag cagtgttaaa tcattcagct acctgagagg   7500
ggccctata actctctacg gctaacctga atggactacg acatagtcta gtccgccgcc   7560
accatgtttc tgctcacaac caaacgcact atgtttgttt tcctcgtgct gctcccttttg  7620
gtaagttctc agtgtgtaaa cctgagaaca cgaacccagt tgcctccagc ttataccaac   7680
tcatttactc gcggagtata ttatcccgat aaggtctta gaagtagcgt gttgcactct    7740
acacaggatc tgttccttgcc cttctttagt aacgttacct ggtttcatgc aatacatgtc   7800
agcggaacaa atgaacaaa aagatttgac aatccagtgc ttccatttaa tgatggggtt    7860
tactttgcca gtatcgaaaa gtcaaacata tccgggggt ggatctttgg aaccactttg    7920
gactctaaga cacagtctct cctcatagta aacaacgcca ccaatgttgt cataaaagta    7980
tgcgaatttc agttttgcaa cgatcccttt ctcgacgtgt attaccataa gaataataaa   8040
tcctggatgg agtctggggt ttatagtagt gctaataatt gcactttcga atacgtgtcc   8100
caaccattcc tcatggacct tgagggcaaa caggggaatt ttaaaaactt gcgcgaattt   8160
gtctttaaga atatcgacgg atactttaag atctatagta aacacactcc tatcaacctc   8220
gttcgggatc ttccccaagg cttttctgct ctcgaacccc tcgtagactc gccaattggg   8280
ataaatatca ctcgcttttca aactttgctt gccctccaca ggagctacct gacacccgtg   8340
gactcttctt ctggtttgac cgccggcgcc gctgccatt atgttggtta ccttcagcca    8400
cgaacattct tgctcaagta taacgagaat ggcaccatta ccgacgccgt cgattgtgca   8460
ttggatccct tgtctgaaac aaaatgtacc ttgaagtcct ttaccgtaga gaaaggcata   8520
taccagactt ccaacttccg agttcagcct acagaatcca tcgtacgatt tcccaacatc   8580
acaaacctct gcccttttcgg tgaagtattt aatgctacac gcttcgcttc agtctatgcc   8640
tggaatagga agcgcatatc aaattgcgtg gccgattatt cagtcctcta taatagcgca   8700
tccttcagta ctttcaagtg ctacggcgtt tcccccacca aactcaatga tctttgcttc   8760
accaacgtct atgctgacag tttttgtcata cgaggcgacg aagtacgcca gattgcccccc  8820
gggcagacag gtaatattgc tgattataat tataaactcc cagatgactt tactggatgc   8880
gtcatagcct ggaattccaa caatctagat tccaaggttg gtgggaatta taattaccgt   8940
tatcgactgt tcagaaagag taacttgaaa ccatttgaga gagacatatc caccgagatt   9000
taccaggcag gcagtaagcc ttgtaacggc gttgagggat ttaactgcta ttttccttttg   9060
caatcctatg gctttcaacc aacaaacggg gttggctatc aaccctatcg agtggttgtc   9120
ctcagcttttg aacttttgca cgctcccgcc acagtctgcg gaccaaaaaa gagtacaaat   9180
cttgtcaaga ataagtgcgt aaatttcaat ttcaatggcc ttacaggaac aggcgtgctg   9240
actgcgtcaa acaagaattt cctgccattt cagcagtttg ggcgggatat agcagacaca   9300
actgacgctg tacgcgatcc tcagactttg gagatcttgg acatcactcc ctgttctttc   9360
ggaggggtat ctgtcatcac ccccggaact aatacatcaa atcaggtcgc tgtgttgtac   9420
caaggtgtca actgcacaga agtccccgtt gctatacacg cagaccagct caccccccaca  9480
tggcgggtgt actcaactgg ctcaaacgta ttccagacca gagctgggtg cttgatcggt   9540
gctgaaacg tgaacaatag ctatgaatgc gatattccca tcggtgccgg gatctgcgct    9600
agctatcaga cacagaccaa ttcccgcagg cgggctcgct ctgtagcatc ccagtctatt   9660
attgcctaca ctatgtcatt gggcgccgag aatagcgtcg catattcaaa taattctatt   9720
gcaatacccca ccaacttcac aatctccgta actacagaaa tacttccagt ttccatgaca   9780
aagacatcag tggattgtac aatgtatata tgcggagatt ccacagaatg ttcaaatttg   9840
ctcttgcagt acggctcctt ctgcacccag ctcaacaggg cacttacagg tattgctgtc   9900
gaacaggaca agaacacaca agaagtcttc gcccaagtca aacagatata caaaactcct   9960
cccataaagg attttggcgg cttcaacttt agtcagatcc tcccagaccc ttcaaaacca  10020
tctaaacgat catttattga agatctgctg ttcaacaagg tcactcttgc tggatgtgga  10080
ttcattaagc aatacggtga ctgccttggt gatattgctg cccgagatct gatctgtgcc  10140
cagaaattca acgggctcac tgtactccct ccactgctca cagacgaaat gattgcacag  10200
tacacaagtg ccctgttggc aggcacaatc actagcggct ggaccttttgg cgcaggtgca  10260
gcactccaaa tacctttgc catgcagatg gcctatcggt ttaatgggat aggcgtgact   10320
caaaatgtcc tctacgaaaa ccaaaagttg atagctaaac aattcaattc agcaatcggg  10380
aagatacagg attcactgtc tagtactgct agtgcccttg gtaagctgca gaacgttgtc  10440
aaccagaatg ctcaagctct gaatacattg gttaagcagc tctctagtaa ttttggggcc  10500
atctcttcag tacttaatga tattttgagc cgattggacc cacctgaagc tgaagtacag  10560
atcgacaggc tgataacagg ccggctccaa tccctccaaa catacgtgac acaacaatc   10620
atacgcggcc ccgaaatccg agccagcgct aacctggcac tccaagat gtcagaatgc  10680
gttctgggcc agagtaaacg cgtagatttc tgcgggaaag gtaccacct gatgtccttt  10740
ccacaatctg cacctcacgg ggtcgtcttt tgcatgtaa catacgtacc cgcacaagag  10800
aagaatttta ctaccgctcc tgccatcgtc atgacggga aagctcattt tcctcgcgaa   10860
ggtgtgtttg tatctaatgg tacacattgg tttgtcacac agcggaattt ctatgaaccc  10920
cagatcatta caactgacaa cacttttgtt tccgggaatt gtgacgtggt cataggaatc  10980
```

```
gtaaataaca ctgtatatga tccccctccaa ccagagctgg actcttttaa agaagaactg 11040
gataaatatt tcaagaacca cacaagtccc gacgtggacc ttggggacat aagtggtatt 11100
aacgcatctg tggttaacat tcaaaaggaa atcgacagac tcaacgaggt ggccaaaaac 11160
ctgaacgaaa gcttgataga tctccaggag ttgggcaagt atgaacagta cattaaatgg 11220
ccatggtaca tatggcttgg ctttatcgct ggccttatcg ccatcgtaat ggttacaatc 11280
atgctgtgct gcatgacctc ctgctgttct tgtttgaaag ggtgttgttc ttgtggtagt 11340
tgttgcaagt ttgacgaaga tgattccgaa cctgttctta aggggtaaa gcttcactat 11400
acatgataac cgcggtgtca aaaccgcgt ggacgtggtt aacatccctg ctgggaggat 11460
cagccgtaat tattataatt ggcttggtgc tggctactat tgtggccatg tacgtgctga 11520
ccaaccagaa acataattga atacagcagc aattggcaag ctgcttacat agaactcgcg 11580
gcgattggca tgccgcctta aaattttttat tttattttttt cttttctttt ccgaatcgga 11640
ttttgttttt aatatttcaa aaaaaaaaaa aaaaaaaaaa aaaaaaaaaa aaaaaaaaaa 11700
aaa                                                                11703

SEQ ID NO: 31          moltype = RNA   length = 11701
FEATURE                Location/Qualifiers
misc_feature           1..11701
                       note = Description of Artificial Sequence: Synthetic
                       polynucleotide
source                 1..11701
                       mol_type = other RNA
                       organism = synthetic construct
SEQUENCE: 31
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagca ttttcgcatc 180
tggcttcaaa actgatcgaa acggaggtgg acccatccga cacgatcctt gacattgaaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct ggccgccgtc atgagcgacc 420
ctgacctgga aactgagact atgtgcctcc acgacgacga gtcgtgtcgc tacgaaggge 480
aagtcgctgt ttaccaggat gtatacgcgg ttgacggacc gacaagtctc tatcaccaag 540
ccaataaggg agttagagtc gcctactgga taggctttga caccaccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca agtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca caataccat gaaaaattac ctttttgcccg 1200
tagtggccca ggcatttgct aggtgggcaa aggaatataa ggaagatcaa gaagatgaaa 1260
ggccactagg actacgagat agacagttag tcatggggt tgttgggct tttagaaggc 1320
acaagataac atctatttat aagcgcccgg ataccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaggcagacg 1620
tcgacttgat gttacaagag gctggggccg gctcagtgga gacacctgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagagga acatgcaata cccgtccagg actttcagg tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatgcgtg ccaggatcag 2220
gcaagtctgg catcattaaa agcgcagtca ccaaaaaga tctagtggtg agcgccaaga 2280
aagaaaactg tgcagaaatt ataagggacg tcaagaaaat gaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attatagcgc 2460
ctaaaaaggc agtgctctgc ggggatccca acagtgcgg ttttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaatgagaa 2640
cgacgaatcc gaaagagact aagattgtga ttgacactac cggcagtcaa aaacctaagc 2700
aggacgatct cattctcact tgtttcagag gtggggtgaa gcagttgcaa atagattaca 2760
aaggcaacga aataatgacg gcagctgcct ctcaagggct gacccgtaaa ggtgtgtatg 2820
ccgttcggta caagtgaat gaaaatcctc tgtacgcacc cacctcagaa catgtgaacg 2880
tcctactgac ccgcacggag gaccgcatcg tgtggaaaac actagccggc gacccatgga 2940
taaaacact gactgccaag tacccgggaa atttcactgc cacgatagag gagtggcaag 3000
cagagcgta tgccatcatg aggcacatct tgggagaccc gaccctaaga gctcttcca 3060
agaataaggc aaacgtgtgt tgggccaagt cttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcaccact gttccgtat ccattaggaa taatcactgg gataactccc 3300
cgtcgcctaa catgtacggg ctgaataaag aagtggtccg tcagctctct cgcaggtacc 3360
```

```
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catccactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacgaagttt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag acaacctggc cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag aagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga acgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcgggcaaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttacccgg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt agttcatgc   5700
catacatctt ttcctccgac accggtcaag gcatttaca acaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc ccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa agaaattgc aatgtcacgc aaatgagaga attgcccgta ttggattcgg   6360
cggccttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgg   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aggagtcaa atcggacaaa ttaatggcag   7140
acaggtgcgc cacctggttg aatatggaag tcaagattat agatgctgtg gggcgaga   7200
aagcgcctta tttctgtgga gggtttattg tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagta aatcaaggta tgaaaccgta ggaacttcca   7440
tcatagttat ggccatgact actcctagcta gcagtgttaa atcattcagc tacctgagag   7500
gggcccctat aactctctac ggctaacctg aatggactac gacatagtct agtccgccgc   7560
caccatgttt ctgttgacga ccaagcgaac gatgttcgtt tcttggtgc ttttgccact   7620
tgtcagttcc cagtgcgtca atctgacgac acgaacacag ctgcctcctg cgtacactaa   7680
cagttttacg cgaggagtgt attccctgac aaagttttc cgctctagtg tcctccatag   7740
cacacaggac ttgtttctcc ccttcttttc caacgttacg tggttccatg tgattagtag   7800
aactaacggt actaaaagat tcgacaatcc agtattgcct ttcaacgatg ggtctatttt   7860
cgcgtccatc gagaaatcaa atatcattcg cggttggatt tttggaacga cactcgattc   7920
aaaagacgca tccctcctta ttgtcaacaa cgccactaac gtagtcatta ggtttgtga   7980
gttccagttt tgtaatgatc ctttttttga ccacaagaat aacaagagct ggatggaaag   8040
cgagttcaga gtgtatagct ctgcaaacaa ctgtactttt gaatacgtga gtcaaccttt   8100
```

```
cctta tggac cttgaaggta aacagggtaa ctttaagaat ttgcgcgaat ttgttttcaa    8160
aaacattgat ggttactta  aaatctatag taagcacact cctatcattg taagagagcc    8220
ggaggacctt ccacagggtt ttagtgcgct cgagcccctc gttgacctgc ccattgggat    8280
caacataact cgattccaaa cattgctcgc ccttcatcgg tcctatctga ctcccggtga    8340
ctcctctagc ggatggacgg caggtgccgc cgcatactac gtgggtacc  ttcaacctcg    8400
gacatttttg ttgaaatca  atgagaatgg cactataact gacgcggttg attgcgcgct    8460
cgacccattg tccgaaacta agtgtacttt gaagtcattt acagtggaga aaggaatata    8520
tcagactagc aattttcggg tacagcccac ggagtctatc gtacggtttc ctaacatcac    8580
gaatctgtgc cctttgatg  aggtctttaa tgcaacacgg ttcgcctccg tctatgcgtg    8640
gaatagaaag cgcatctcaa attgtgtagc tgattattcc gtactttaca acttggcccc    8700
gttcttcaca tttaagtgct acggtgtaag ccctactaaa ctgaacgatt tgtgtttcac    8760
caacgtctat gcagatagct ttgttattcg aggcgatgag gtacgccaga ttgcgcctgg    8820
tcaaacgggt aatatcgccg actacaatta taaattgcca gacgattta  ctggttgtgt    8880
catcgcttgg aatagtaata agttggacag taaggtatcc ggcaattaca actatctcta    8940
ccgattgttc cggaagtcta acctcaagcc gtttgaaaga gacatatcca ctgagatata    9000
ccaagcaggc aataaaccat gcaacggagt tgctggtttc aactgctatt tcccgttgcg    9060
gtcttattcc ttcagaccta cttacggagt cggacaccaa ccctacaggg tcgtcgtttt    9120
gagttttgaa ttgttgcatg ctccagcaac cgtgtgtgga cctaaaaagt ccacgaatct    9180
cgtgaagaat aagtgcgtaa acttcaattt caacggtctg aaagggactg gtgtattgac    9240
agaaagcaac aagaagtttc tgccattcca gcaatttggt agggatatag cggatacaac    9300
tgatgccgtt cgggatcctc aaacattgga gatcttggac atcacaccgt gttctttgg    9360
gggtgtctcc gttatcacac cgggtacaaa tacgagcaat caggttgcgg tccttacca    9420
aggcgttaat tgtaccgagg ttccagtagc aatacacgcg gatcaactca cgcccacatg    9480
gagggtttac agtacaggca gtaatgtttt ccaaacgaga gcgggatgcc tcatcggggc    9540
agaatacgta aataattctt acgaatgcga catccctatt ggcgcaggaa tttgcgcaag    9600
ttaccaaacc cagaccaagt ctcataggcg ggcgcggtct gttgcaagcc aatctataat    9660
agcgtacact atgtccctcg cgcgggagaa cagtgtcgca tattccaaca actctattgc    9720
gatacctact aatttcacta ttagcgtcac aactgagatc cttcccgtca gtatgaccaa    9780
aacgtctgtc gactgtacta tgtatatttg cggcgacagt accgaatgct ctaatctttt    9840
gttgcagtat ggttctttt  gcacgcaact taagagagct ttgacgggga tagctgtgga    9900
acaagataaa aacacacagg aggtatttgc acaagtgaaa cagatctata aaactccacc    9960
gatcaagtac tttggcggct ttaacttctc ccagatcttg cccgacccgt ctaaaccaag   10020
taaacggagt tttatagagg accttctctt caataaggta acattggcag acgccggctt   10080
cattaaacaa tacggagatt gccttggaga catcgctgcg cgcgacttga tctgcgcaca   10140
aaaatttaaa ggcttgacgg tcctccctcc tttgctcaca gacgagatga tagcacaata   10200
cacttccgca ctgcttgctg gaaccatcac ctctggttgg acattcggtg cgggagcggc   10260
tttgcagatt ccgttttgcga tgcaaatggc ttatcggttt aacggcattg gagtaacaca   10320
gaatgtgctc tacgagaatc aaaagcttat tgcgaatcaa ttcaactctg cgattggcaa   10380
aattcaagat tcattgagta gcaccgccag tgctcttgac aagcttcagg atgtcgtaaa   10440
ccacaatgca caagctctga atacactggt taaacaattg tccagtaaat ttggggcaat   10500
ctcttcagtc ctgaacgaca ttttctcaag attggatcca cccgaagcgg aggtacagat   10560
tgaccgcctg ataaccggga ggttgcaaag ccttcagact tatgttacac aacagttgat   10620
tcgggcagca gagataagag cctcagcaaa cctcgcagct acgaagatgt cagagtgtgt   10680
ccttgggcaa tctaagcggg tagatttctg cggcaaagga tatcatttga tgagcttttcc   10740
ccaatcagcc ccacatggag tagttttct  tcatgtcact tacgttccgg cgcaggaaaa   10800
gaacttcacc acagcgccag ccatttgtca tgatgggaag gcgcatttcc caagagaagg   10860
tgttttcgtg tctaacggta cccactggtt cgttacgcag cggaatttct acgaaccaca   10920
gatcatcact accgcacaac cgtttgtctc tggaaattgt gacgttgtca tagggatagt   10980
gaacaataca gtatatgatc cacttcagcc tgaacttgac tcttttaagg aggagctgga   11040
caaatatttc aaaaatcata caagcccgga cgtcgatctt ggagatattt caggtatcaa   11100
cgcaagtgtc gtaaatattc agaaggagat cgatcgattg aacgaggttg caaaaaacct   11160
taatgagagc cttatagatc ttcaagagct ggggaagtat gaacaatata tcaagtggcc   11220
ttggtacatt tggctcgggt tcattgccgg acttatcgcg atcgtaatgg taacaatcat   11280
gctctgctgt atgacttctt gctgttcatg cctcaaaggt tgttgctcct gtgggtcttg   11340
ctgtaaattt gacgaggatg attctgaacc agtgcttaaa ggcgtgaagc tccactatac   11400
ctgataaccg cggtgtcaaa accgcgtgg  acgtggttaa catccctgct gggaggatca   11460
gccgtaatta ttataattgg cttggtgctg ctactattg  tggccatgta cgtgctgacc   11520
aaccagaaac ataattgaat acagcagcaa ttggcaagct gcttacatag aactcgcggc   11580
gattggcatg ccgccttaaa attttttattt tatttttttct tttcttttcc gaatcggatt   11640
ttgttttaa  tattcaaaa  aaaaaaaaaa aaaaaaaaaa aaaaaaaaaa aaaaaaaaaa   11700
a                                                                  11701

SEQ ID NO: 32      moltype = RNA  length = 7862
FEATURE            Location/Qualifiers
misc_feature       1..7862
                   note = Description of Artificial Sequence: Synthetic
                   polynucleotide
misc_difference    7562
                   note = a, c, g, or u
source             1..7862
                   mol_type = other RNA
                   organism = synthetic construct
SEQUENCE: 32
ataggcggcg catgagagaa gcccagacca attacctacc caaaatggag aaagttcacg      60
ttgacatcga ggaagacagc ccattcctca gagctttgca gcggagcttc cgcagtttg     120
aggtagaagc caagcaggtc actgataatg accatgctaa tgccagagcg ttttcgcatc     180
tggcttcaaa actgatcgaa acggaggtgg acccatccga cacgtccctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
```

```
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccaccct tttatgttta    600
agaacttggc tggagcatat ccatcatact ctaccaactg ggccgacgaa accgtgttaa    660
cggctcgtaa catagccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa ggcttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac ctttttgcccg   1200
tagtggccca ggcattgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctgggggcg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca cccgtagag accctgtata   2400
ttgacgaagc ttttgcttgt catgcaggta ctctcagagc gctcatagcc attataagac   2460
ctaaaaaggc agtgctctgc ggggatcca aacagtgcgg ttttttaac atgatgtgcc   2520
tgaaagtgca ttttaaccac gagatttgca cacaagtctt ccacaaaagc atctctcgcc   2580
gttgcactaa atctgtgact cggtcgtct caaccttgtt ttacgacaaa aaaatgagaa   2640
cgacgaatcc gaaagagact aagattgtga ttgcacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac gcagccgcga caccatgga   2940
taaaaacact gactgccaag taccctggga atttcactgc cacgatagag gagtggcaag   3000
cagagcatga tgccatcatg aggcacatct ggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaactat ggtacactgg   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag ttatggtta cgctgacagg gccagcgaaa   3840
gcatcattgg tgctatagcg cggcagttca agttttcccg ggtatgcaaa ccgaaatcct   3900
cacttgaaga gacgaagttc tgtttgtat tcattggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttcgggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttcttggc tggaaggaag ggctacagca   4620
caagcgatgg caaaactttc tcatatttgg aagggaccaa gttcaccag gcggccaagg   4680
atatagcaga aattaatgcc atgtggcccg ttgcaacgga ggcaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaaattac tgtgtgctca tcctttccat   4920
tgccgaagta tagaatcact ggtgtgcaga agatccaatg ctcccagcct atattgttct   4980
caccgaaagt gcctgcgtat attcatcaa ggaagtatct cgtggaaaca ccaccggtag   5040
acgagactcc ggagccatcg gcagagaacc aatccacaga ggggacacct gaacaaccac   5100
```

-continued

```
cacttataac cgaggatgag accaggacta gaacgcctga gccgatcatc atcgaagagg    5160
aagaagagga tagcataagt ttgctgtcag atgcccgac ccaccaggtg ctgcaagtcg     5220
aggcagacat tcacgggccg ccctctgtat ctagctcatc ctggtccatt cctcatgcat    5280
ccgactttga tgtggacagt ttatccatac ttgacaccct ggaggagct agcgtgacca     5340
gcgggcaac gtcagccgag actaactctt acttcgcaaa gagtatggag tttctggcgc    5400
gaccggtgcc tgcgcctcga acagtattca ggaaccctcc acatcccgct ccgcgcacaa   5460
gaacaccgtc acttgcaccc agcagggcct gctcgagaac cagcctagtt tccacccgc     5520
caggcgtgaa tagggtgatc actagagagg agctcgaggc gcttacccg tcacgcactc     5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta   6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag   6300
ctgccacaaa agaaattgc aatgtcacgc aaatgagaga attgcccgta ttggattcgg     6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact   6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtcgaccgg acagcgtgcc    7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggccctat aactctctac ggctaacctg aatggactac gacatagtct agtccgccaa     7560
gntgataacc gcggtgtcaa aaaccgcgtg gacgtggtta acatccctgc tgggaggatc    7620
agccgtaatt attataattg gcttggtgct ggctactatt agtgccatgt acgtgctgac    7680
caaccagaaa cataattgaa tacagcagca attggcaagc tgcttacata gaactcgcgg    7740
cgattggcat gccgccttaa aattttattt ttattttttc ttttctttc cgaatcggat     7800
tttgttttta atatttcaaa aaaaaaaaaa aaaaaaaaaa aaaaaaaaaa aaaaaaaaaa    7860
aa                                                                   7862
```

SEQ ID NO: 33        moltype = RNA  length = 7862
FEATURE             Location/Qualifiers
misc_feature       1..7862
                       note = Description of Artificial Sequence: Synthetic
                       polynucleotide
misc_difference    7562
                       note = a, c, g, or u
source              1..7862
                       mol_type = other RNA
                       organism = synthetic construct
SEQUENCE: 33

```
ataggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct ggccgccgtc atgagcgacc     420
ctgacctgga aactgagact atgtgcctcc acgacgacga gtcgtgtcgc tacgaagggc     480
aagtcgctgt ttaccaggat gtataacgcgg ttgacggacc gacaagtctc tatcaccaag     540
ccaataaggg agttagagtc gcctactgga taggctttga caccaccccct tttatggtca    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtattcact    840
tacgtggcaa gcaaaattac acatgtcggt gtgactctat agttagttgc gacggtggaa    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac ctttttgccc   1200
```

```
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc cagccgatg aggctaagga ggtgcgtgaa gccgaggagt    1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctcccgcagg  1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcca gcccagccga cacgacgggcg  2040
aatacctgta cgacatcgac aggaaacagt gcgtcaagaa agaactagtc actgggctag   2100
ggctcacagg cgagctggtg gatcctccct tccatgaatt cgcctacgac agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaggc agtgctctgc ggggatccca aacagtgcgg tttttttaac atgatgtgcc    2520
tgaaagtgca ttttaaccac gagatttgca cacaagtctt ccacaaaagc atctctcgcc   2580
gttgcactaa atctgtgact tcggtcgtct caaccttgtt ttacgacaaa aaatgagaa    2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtgaaaac actagccggc gacccatgga   2940
taaaaacact gactgccaag tacccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctatttc tgcacccact gttccgttat ccattaggaa taatcactgg gataactccc    3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg actttttctc attcgtcagc aaattgaagg   3540
gcagaactgt cctggtggtc ggggaaaagt tgtccgtccc aggcaaaatg ttgactggt    3600
tgtcagaccg gcctgaggct accttcagag ctcggctgga tttaggcatc ccaggtgatg   3660
tgcccaaata tgacataata tttgttaatg tgaggaccc atataaatac catcactatc    3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag acaacctgg cggagggtg tgcggagcgc     4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag gctacagca    4620
caagcgatgc caaaacttc tcatatttgg aagggaccaa gtttcaccag gcggccaagg    4680
atatagcaga aattaatgcc atgtggccgg ttgcaacgga ggccaatgag caggtatgca   4740
tgtatatcct cggagaaagc atgagcagta ttaggtcgaa atgcccgtc gaagagtcgg    4800
aagcctccac accacctagc acgctgcctt gcttgtgcat ccatgccatg actccagaaa   4860
gagtacagcg cctaaaagcc tcacgtccag aacaaattac tgtgtgctca tccttttccat  4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggttct agctgacca    5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctgagaac cagcctagtt ccacccccgc    5520
caggcgtgaa tagggtgatc actagagagg agctcgagc gcttacccg tcacgcactc     5580
ctagcaggtc ggtctcgaga accagcctgg tctccaaccc gcaggcgta aataggggtga   5640
ttacaagaga ggagttgag gcgttcgtag cacaacaaca atgacggttt gatgcgggtg    5700
catacatctt ttcctccgac accggtcaag gcatttacta caaaaatca gtaaggcaaa    5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
```

```
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctgcag    6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggttttatt tgtgtgactc cgtgaccggc acagcgtca    7260
gtgtggcaga cccctaaaa aggctgttta agcttggcaa acctctggca gcagacgatg    7320
aacatgatga tgacaggaga agggcattgc atgaagagtc aacacgctgg aaccgagtgg   7380
gtattctttc agagctgtgc aaggcagtag aatcaaggta tgaaccgta ggaacttcca    7440
tcatagttat ggccatgact actctagcta gcagtgttaa atcattcagc tacctgagag   7500
gggcccctat aactctctac ggctaacctg aatggactac gacatagtct agtccgccaa   7560
gntgataacc gcggtgtcaa aaaccgcgtg gacgtggtta acatccctgc tgggaggatc   7620
agccgtaatt attataattg gcttggtgct ggctactatt gtggccatgt acgtgctgac   7680
caaccagaaa cataattgaa tacagcagca attggcaagc tgcttacata gaactcgcgg   7740
cgattggcat gccgccttaa aattttattt ttattttttc ttttcttttc cgaatcggat   7800
tttgttttta atatttcaaa aaaaaaaaaa aaaaaaaaaa aaaaaaaaaa aaaaaaaaaa   7860
aa                                                                  7862

SEQ ID NO: 34          moltype = RNA   length = 7862
FEATURE                Location/Qualifiers
misc_feature           1..7862
                       note = Description of Artificial Sequence: Synthetic
                        polynucleotide
misc_difference        7562
                       note = a, c, g, or u
source                 1..7862
                       mol_type = other RNA
                       organism = synthetic construct
SEQUENCE: 34
ataggcggcg catgagagaa gcccagacca attacctacc caaaatggag aaagttcacg     60
ttgacatcga ggaagacagc ccattcctca gagctttgca ggagcttc ccgcagtttg      120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacgacc gacaagtctc tatcaccaag    540
ccaataaggg agttagagtc gcctactgga taggctttga caccaccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtcc gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttggctc aaccagcgta    1140
tagtcgtcaa cggtcgcacc cagagaaaca ccaataccat gaaaaattac ctttttgccca  1200
tagtggccca ggcattttgct aggtgggcaa aggaatataa ggaagatcaa gaagatgaaa  1260
ggccactagg actacgagat agacagttag tcatggggtt tgttgggct tttagaaggc    1320
acaagataac atctatttat aagcgcccgg ataccacaac catcatcaaa gtgaacagcg    1380
atttccactc attcgtgctg cccaggatag cagtaacac attggagatc ggcgtgaaa     1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct tggcagctg atgttgagga gccactctg gaggcagacg     1620
tcgacttgat gttacaagag gctggggcg gctcagtgga gacaccgtcg gcttgataa     1680
aggttaccag ctacgatggc gaggacaaga tcggctctta cgctgtgctt tctccgcagg   1740
ctgtactcca gagtgaaaaa ttatcttgca tccacccctct cgctgaacaa gtcatagtaa   1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacgcg    2040
```

```
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag    2220
gcaagtctgg catcattaaa agcgcagtca ccaaaaaaga tctagtggtg agcgccaaga   2280
aagaaaactg tgcagaaatt ataagggacg tcaagaaaat gaaaggtcag gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca acagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actaccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg cttttagtgcc ggtgctgaag accgctggca   3120
tagacatgac cactgaacaa tggaacactg tggattattt tgaaacggac aaaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgg   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc ggcaaaatg gttgactggt   3600
tgtcagaccg gcctgaggct accttcagag ctcggctgga tttaggcatc ccaggtgatg   3660
tgcccaaata tgacataata tttgttaatg tgaggaccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggt tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga atgggaaat gactctcaag gaagcagtgg   4500
ctaggagaga agcagtggag gagatatgca tatccgacga ctcttcagtg acagaacctg   4560
atgcagagct ggtgagggtg catccgaaga gttcttttgc tggaaggaag ggctacagca   4620
caagcgatgg caaaacttc tcatatttgg aagggaccaa gttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatcaa ggaagtatct cgtggaaaca ccaccggtag   5040
acgagctcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctgcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgagc gcttaccccg tcacgcactc   5580
ctagcaggtc ggtctcgaga accagcctgg tctccaaccc gccaggcgta aataggtgta   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactaccga agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaagaaa agtggagtgc taccgaaccc   6000
tgcatcctgt tccttgtat tcatctagtg tgaaccgtgc cttttcaagc cccaaggtcg   6060
cagtggaagc ctgtaacgcc atgttgaaag agaacttcc gactgtggct tcttactgta   6120
ttattccaga gtacgatgcc tatttggaca ggttcatgc agcttcagca tgcttagaca   6180
ctgccagttt ttgccctgca agctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggccttta tgtggaatgc ttcaagaaat atgcgtgaa taatgaatat tgggaaacgt   6420
ttaaagaaaa ccccatcagg cttactgaag aaaacgttgt aaattacatt accaaaatta   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
```

```
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gntagtaacc gcggtgtcaa aaaccgcgtg gacgtggtta acatccctgc tgggaggatc   7620
agccgtaatt attataattg gcttggtgct ggctactatt gtggccatgt acgtgctgac   7680
caaccagaaa cataattgaa tacagcagca attggcaagc tgcttacata gaactcgcgg   7740
cgattggcat gccgccttaa aattttttatt ttatttttttc ttttcttttc cgaatcggat   7800
tttgttttta atatttcaaa aaaaaaaaaa aaaaaaaaaa aaaaaaaaaa aaaaaaaaaa   7860
aa                                                                  7862

SEQ ID NO: 35          moltype = RNA  length = 7862
FEATURE                Location/Qualifiers
misc_feature           1..7862
                       note = Description of Artificial Sequence: Synthetic
                       polynucleotide
misc_difference        7562
                       note = a, c, g, or u
source                 1..7862
                       mol_type = other RNA
                       organism = synthetic construct
SEQUENCE: 35
ataggcggcg catgagagaa gcccagacca attacctacc caaatggag aaagttcacg     60
ttgacatcga ggaagacagc ccattcctca gagctttgca gcggagcttc ccgcagtttg    120
aggtagaagc caagcaggtc actgataatg accatgctaa tgccgagacg ttttcgcttg    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagtc ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggcgacgaa accgtgttaa    660
cggctcgtaa cataggccta tgcagtctg acgttatgga cggtcacgt agagggatgt     720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc tgtgctgcaa agtgacagaa cacattgaac ggggagaggg   1020
tctctttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca caataccat gaaaaattac ctttgcccg    1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg ataccaaac catcatcaaa gtgaacagcg   1380
atttccactc attcgtgctg cccaggatag gcagtaacac attggagatc gggctgagaa   1440
caagaatcag gaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctgggggcg gctcagtgga gacaccgcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctcct tccatgaatt cgcctacgag agtctgagaa   2160
cacgaccagc cgctccttac caagtaccaa catagggggt gtatgcgtg ccaggatcag   2220
gcaagtctgt catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttaac atgatgtgcc   2520
tgaaagtgca tttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gaccccgtaaa ggtgtgtatg   2820
ccgttcggta caaggtgaat gaaaatcctc tgtacgcacc caccctcagaa catgtgaacg   2880
```

```
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaaccat ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggaacac atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgttttgtat tcattggaca gctttagac accactgatg 3960
acaatcctta caagctttca tcaacccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgta gaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgaa agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgc caaaacttt tcatattggg aagggaccaa gtttcaccag gcggccaagg 4680
atatagcaga aattaatgcc atgtggcccg ttgcaacgga ggccaatgag caggtatgca 4740
tgtatatcct cggagaaagc atgacgcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtc ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcgggcaac gtcagccgag actaactctt acttcgcaaa gagtatggag tttctggcgc 5400
gaccggtgcc tgcgcctcga acagtattca gaaaccctcc acatcccggc cgcgcacaa 5460
gaacaccgtc acttgcaccc agcagggcct gctcgagaac cagcctagtt ccaccccgc 5520
caggcgtgaa tagggtgatc actagagagg agctcgaggc gcttacccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaatttgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaagcaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaataca gatcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttcgca 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagcatg atgaaatctg cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatgcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctcctgga gcagcagttg 7320
aacatgatga tgacaggaga agggcattgc atgaagagtc aacacgctgg aaccgagtgg 7380
gtattctttc agagctgtgc aaggcagtag aatcaaggta tgaaccgta ggaacttcca 7440
tcatagttat ggccatgact actctagcta gcagtgttaa atcattcagc tacctgagag 7500
gggccccat aactctctac ggctaacctg aatggactac gacatagtct agtccgccaa 7560
gntgataacc gcggtgtcaa aaaccgcgtg gacgtggtta acatccctgc tgggaggatc 7620
```

```
agccgtaatt attataattg gcttggtgct ggctactatt gtggccatgt acgtgctgac    7680
caaccagaaa cataattgaa tacagcagca attggcaagc tgcttacata gaactcgcgg    7740
cgattggcat gccgccttaa aatttttatt ttattttttc ttttcttttc cgaatcggat    7800
tttgttttta atatttcaaa aaaaaaaaaa aaaaaaaaaa aaaaaaaaaa aaaaaaaaaa    7860
aa                                                                   7862

SEQ ID NO: 36          moltype = RNA   length = 7862
FEATURE                Location/Qualifiers
misc_feature           1..7862
                       note = Description of Artificial Sequence: Synthetic
                       polynucleotide
misc_difference        7562
                       note = a, c, g, or u
source                 1..7862
                       mol_type = other RNA
                       organism = synthetic construct
SEQUENCE: 36
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattgaa    240
gtgcgcccgc ccgcagaatg tattctaagc acaagtatca ttgtatctgt gctgatgagt    300
gtgcggaaga tccggacaga ttgtataagt atgcaactaa gctgaagaaa aactgtaagg    360
aaataactga taaggaattg acaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacgagc gacaagtctc tatcaccaag    540
ccaataaggg agttagagtc gcctactgga taggctttga caccaccct tttatgttta    600
agaacttggc tggagcatat ccatcatact ctaccaactg ggcgacgaa accgtgttaa    660
cggctcgtaa cataggccta tgcagctctg acgttatgga gcggtcacgt agagggatgt    720
ccattcttag aaaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagtgc gacgggtacg    900
tcgttaaaag aatagctatc agtccaggcc tgtatgggaa gccttcaggc tatgctgcta    960
cgatgccaccg cgagggattc ttgtgctgca aagtgacaga cacattgaac ggggagaggg   1020
tctcttttcc cgtgtgcacg tatgtgccag ctacattgtg tgaccaaatg actggctac    1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg ataccaaaa catcatcaaa gtgaacagcg   1380
atttccactc attcgtgctg cccaggatag gcagtaacac attggagatc gggctgaaa   1440
caagaatcag gaaaatgtta gaggagcaca aggagccgtc acctctcatt accgccgagg   1500
acgtacaaga agctaagtgc gcagccgatg aggctaagga ggtgctgaa gccgaggagt   1560
tgcgcgcagc tctaccacct ttggcagctg atgttgagga gcccactctg gaggcagacg   1620
tcgacttgat gttacaagag gctggggccg gctcagtgga gacaccgtg gcttgataa   1680
aggttaccag ctacgatggc gaggacaaga tcggctctta cgctgtgctt tctccgcagg   1740
ctgtactcaa gagtgaaaaa ttatcttgca tccaccctct cgtgaacaa gtcatagtga   1800
taacacactc tggccgaaaa gggcgttatg ccgtggaacc ataccatggt aaagtagtg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacgggc   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca caaaaaaga tctagtggtg agcgccaaga   2280
aagaaaactg tgcagaaatt ataagggacg tcaagaaaat gaaagggctg acgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaagc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtca caaccttgtt ttacgacaaa aaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatacg gcagctgcct ctcaagggct gacccgtaaa ggtgtgtatg   2820
ccgttcggta caagggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctcac gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgtat ccattaggaa taatcactgg gataactccc   3300
cgtcgcctaa catgtacggg ctgaataaag aagtggtccg tcagctctct cggcaggtacc   3360
cacaactcc tcgggcagtt gccactgaca gtctatga catgaacact ggtacactgc   3420
gcaattatga tccgcgcata aacctagtac ctgtaaacag aagactgcct catgcttag   3480
tcctccacca taatgaacac ccacagagtg acttttcttc attcgtcagc aaattgaagg   3540
gcagaactgt cctggtggtc gggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
```

```
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacatttt tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaaactt caacaaagtt  4260
cggaggttga aggtgacaaa cagttggcag aggcttatga gtccatcgct aagattgtca  4320
acgataacaa ttacaagtca gtagcgattc cactgttgtc caccggcatc tttccggga   4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttcttggc tggaaggaag ggctacagca  4620
caagcgatgc caaaactttc tcatatttgg aagggaccaa gtttcaccag gcggccaagg  4680
atatagcaga aattaatgcc atgtggcccg ttgcaacgga ggcaatgag caggtatgca  4740
tgtatatcct cggagaaagc atgagcagta ttaggtcgaa agccccgtc gaagagtcgg   4800
aagcctccac accacctagc acgctgcctt gcttgtgcat ccatgccatg actccagaaa  4860
gagtacagcg cctaaaagcc tcacgtccag aacaaattac tgtgtgctca tccttttccat 4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggcg ccctctgtat ctagctcatc ctggtccatt cctcatgcat   5280
ccgactttga tgtggacagt ttatccatac ttgacacccc ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccacccga   5520
caggcgtgaa tagggtgatc actagagagg agctcgagg gcttacccgg tcacgcactc   5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tccttttgtat tcatctagtg tgaaccgtgc cttttcaagc ccaaggtcg   6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttcaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct cttttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatgtcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgca  7260
gtgtggcaga ccccctaaaa aggctgtta gcttggcaa acctctggca gcagcgatg    7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagtttat ggccatgact actctagcta gcagtgttaa atcattcagc tacctgagag  7500
gggcccctat aactctctac ggctaacctg aatggactac gacatagtct agtccgccaa  7560
gntgataacc gcgtgtcaa aaaccgcgtg gacgtggtta acatccctgc tgggaggatc   7620
agccgtaatt attataattg gcttggtgct ggctactatt gtggccatgt acgtgctgac  7680
caaccagaaa cataattgaa tacagcagca attggcaagc tgcttacata gaactcgcgg  7740
cgattggcat gccgccttaa aatttttatt ttattttttc ttttcttttc gaatcggat   7800
tttgttttta atatttcaaa aaaaaaaaaa aaaaaaaaaa aaaaaaaaaa aaaaaaaaaa  7860
aa                                                                 7862

SEQ ID NO: 37          moltype = RNA   length = 11701
FEATURE                Location/Qualifiers
misc_feature           1..11701
                       note = Description of Artificial Sequence: Synthetic
                       polynucleotide
source                 1..11701
                       mol_type = other RNA
                       organism = synthetic construct
```

SEQUENCE: 37

```
ataggcggcg catgagagaa gcccagacca attacctacc caaaatggag aaagttcacg    60
ttgacatcga ggaagacagc ccattcctca gagctttgca gcggagcttc ccgcagtttg   120
aggtagaagc caagcaggtc actgataatg accatgctaa tgccagagcg ttttcgcatc   180
tggcttcaaa actgatcgaa acggaggtgg acccatccga cacgatcctt gacattggaa   240
gtgcgcccgc ccgcagaatg tattctaagc acaagtatca ttgtatctgt ccgatgagat   300
gtgcggaaga tccggacaga ttgtataagt atgcaactaa gctgaagaaa aactgtaagg   360
aaataactga taaggaattg gacaagaaaa tgaaggagct ggccgccgtc atgagcgacc   420
ctgacctgga aactgagact atgtgcctcc acgacgacga gtcgtgtcgc tacgaagggc   480
aagtcgctgt ttaccaggat gtatacgcgg ttgacggacc gacaagtctc tatcaccaag   540
ccaataaggg agttagagtc gcctactgga taggctttga caccacccct tttatgttta   600
agaacttggc tggagcatat ccatcatact ctaccaactg ggccgacgaa accgtgttaa   660
cggctcgtaa cataggccta tgcagctctg acgttatgga gcggtcacgt agagggatgt   720
ccattcttag aaagaagtat ttgaaaccat ccaacaatgt tctattctct gttggctcga   780
ccatctacca cgagaagagg gacttactga ggagctggca cctgccgtct gtatttcact   840
tacgtggcaa gcaaaattac acatgtcggt gtgagactat agttagttgc gacgggtacg   900
tcgttaaaag aatagctatc agtccaggcc tgtatgggaa gccttcaggc tatgctgcta   960
cgatgcaccg cgaggggattc ttgtgctgca aagtgacaga cacattgaac ggggagaggg  1020
tctctttttcc cgtgtgcacg tatgtgccaa ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagttgccca ggcatttgct aggtgggcaa aggaaataaa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgtgg  1500
acgtacaaga agctaagtgc gcagccgatg aggctaagga ggtgcgtgaa gccgaggagt  1560
tgcgcgcagc tctaccacct ttggcagctg atgttgagga gcccactctg gaggcagacg  1620
tcgacttgat gttacaagag gctggggccg gctcagtgga gacacctcgt ggcttgataa  1680
aggttaccag ctacgatggc gaggacaaga tcggctctta cgctgtgctt tctccgcagg  1740
ctgtactcaa gagtgaaaaa ttatcttgca tccaccctct cgctgaacaa gtcatagtag  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacagggag  1980
gagcgctgaa cactgatgaa gaatattaca aaactgtcaa gcccagcgca cacgacggcg  2040
aatacctgta cgacatcgac aggaaacagt gcgtcaagaa agaactagtc actgggctag  2100
ggctcacagg cgagctggtg gatcctcccct tccatgaatt cgcctacgag agtctgagaa  2160
cacgaccagc cgctccttac caagtaccaa ccataggggt gtatgcgtg ccaggatcag   2220
gcaagtctgg catcattaaa agcgcagtca ccaaaaaaga tctagtggtg gcgccaaga   2280
aagaaaactg tgcagaaatt ataagggacg tcaagaaaat gaaagggctg gacgtcaatg  2340
ccagaactgt ggactcagtg ctccttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtgaaaaac actagccggc gacccatgga  2940
taaaaacact gactgccaag tacccctggga atttcactgc cacgatagag gagtggcaga  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg ttgactggt   3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca gttttcccg ggtatgcaaa ccgaaatcct   3900
cacttgaaga cggaagtt ctgtttgtat tcattgggta cgatcgcaag gcccgtacgc    3960
acaatcctta caagctttca tcaaccttga ccaacatttta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaagttt   4260
cggaggttga aggtgacaaa cagttggcag aggcttatga gtccatcgct aagattgtca  4320
acgataacaa ttacaagtca gtagcgattc cactgttgtc cactgtgtt ttctccggga   4380
acaaagatcg actaacccaa tcattgaacc atttgctgac agcttagac caccactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaacttc tcatatttgg aagggaccaa gttccaccag gcggccaagg   4680
```

```
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtcagt aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaaggaga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag gcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc ctttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctgcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagacttga cgctcattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatgcag   7140
acaggtgcgc cacctggttg aatatggaag tcaagattat agatgctgtg gtgggcgaga   7200
aagcgcctta tttctgtgga gggttttattt tgtgtgactc cgtgaccggc acagcgtgc   7260
gtgtggcaga ccccctaaaa aggctgttta gcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggccctat aactctctac ggctaacctg aatggactac gacatagtct agtccgccaa   7560
gatgtttctg ctcacaacca aacgactat gttttgttttc ctcgtgctgc tcccttggt   7620
aagttctcag tgtgtaaacc tgagaacacg aacccagttg cctccagctt ataccaactc   7680
atttactcgc ggagtatatt atcccgataa ggtctttaga agtagcgtgt tgcactcac   7740
acaggatctg ttcttgccct tctttagtaa cgttacctgg tttcatgcaa tacatgtgag   7800
cggaacaaat ggaacaaaaa gatttgacaa tccagtgctt ccatttaatg atgggggttta   7860
ctttgccagt atcgaaaagt caaacataat ccggggtgg atctttggaa ccactttgga   7920
ctctaagaca cagtctctcc tcatagtaaa caacgccacc aatgttgtca taaaagtatg   7980
cgaatttcag ttttgcaacg atcccttttct cgacgtgtat taccataaga ataataaatc   8040
ctggatggag tctggggttt atagtagtgc taataattgc actttcgaat acgtgtccca   8100
accattcctc atggaccttg agggcaaaca ggggaattt aaaaacttgc gcgaatttgt   8160
ctttaagaat atcgacggat actttaagat ctatagtaaa cacactccta tcaacctcgt   8220
tcggatctt cccccaaggct tttctgctct cgaacccctc gtagacttgc caattgggat   8280
aaatatcact cgcttcaaa ctttgcttgc cctccacagg agctacctga cacccggcga   8340
ctcttcttct ggttgaccg ccggcgccgc tgcctattat gttggttacc ttcagccacg   8400
aacattcttg ctcaagtata cgagaatgg accattacc gacgccgtcg attgtgcatt   8460
ggatcccttg tctgaaacaa aatgtacctt gaagtcctct accgtagaga aggcatata   8520
ccagacttcc aacttccgag ttcagcctac agaatccatc gtacgatttc caacatcac   8580
aaacctctgc cctttcggtg aagtatttaa tgctacacgc ttccttcag tctatgcctt   8640
gaataggaag cgcatatcaa aattgcgtgg cgattattca gtcctctata atagcgcatc   8700
cttcagtact ttcaagtgct acggcgtttc ccccaccaaa ctcaatgatc tttgcttcac   8760
caacgtctat gctgacagtt ttgtcatacg aggcgacgaa gtacgccaga ttgccccccga   8820
gcagacaggt aatattgctg attataatta taaactccca gatgacttta ctggatgcgt   8880
catagcctgg aattccaaca atctagattc caaggttggt gggaattata attaccgtta   8940
tcgactgttc agaaagagta acttgaaacc atttgagaga gacatatcca ccgagattta   9000
ccaggcaggc agtaagcctt gtaacggcgt tgagggattt aactgctatt ttcctttgca   9060
atcctatggc tttcaaccaa caaacggggt tggctatcaa ccctatgag tggttgtcct   9120
cagcttgaa cttttgcacg ctcccgccac agtctgcgga ccaaaaaaga gtacaaatct   9180
tgtcaagaat aagtgcgtaa atttcaattt caatggcctt acaggaacag gcgtgctgac   9240
tgagtcaaac aagaatttcc tgccatttca gcagttggg cgggatatag cagacacaac   9300
tgacgctgta cgcgatcctc agactttga gatcttggac atcactccct gttctttcgg   9360
aggggtatct gtcatcacccc ccggaactaa tacatcaaat caggtcgctg tgttgtacca   9420
```

```
aggtgtcaac tgcacagaag tccccgttgc tatacacgca gaccagctca cccccacatg   9480
gcgggtgtac tcaactggct caaacgtatt ccagaccaga gctgggtgct tgatcggtgc   9540
tgaacacgtg aacaatagct atgaatgcga tattcccatc ggtgccggga tctgcgctag   9600
ctatcagaca cagaccaatt cccgcaggcg ggctcgctct gtagcatccc agtctattat   9660
tgcctacact atgtcattgg gcgccgagaa tagcgtccga tattcaaata attctattgc   9720
aatacccacc aacttcacaa tctccgtaac tacagaaata cttccagttt ccatgacaaa   9780
gacatcagtg gattgtacaa tgtatatatg cggagattcc acagaatgtt caaatttgct   9840
cttgcagtac ggctccttct gcacccagct caacagggca cttacaggta ttgctgtcga   9900
acaggacaag aacacacaag aagtcttcgc ccaagtcaaa cagatataca aaactcctcc   9960
cataaaggat tttggcggct tcaactttag tcagatcctc ccagacccctt caaaaccatc  10020
taaacgatca tttattgaag atctgctgtt caacaaggtc actcttgccg atgctggatt  10080
cattaagcaa tacggtgact gccttggtga tattgctgcc cgagatctga tctgtgccca  10140
gaaattcaac gggctcactg tactccctcc actgctcaca gacgaaatga ttgcacagta  10200
cacaagtgcc ctgttggcag gcacaatcac tagcggctgg accttttggcg caggtgcagc  10260
actccaaata cctttttgcca tgcagatggc ctatcggttt aatgggatag gcgtgactca  10320
aaatgtcctc tacgaaaacc aaaagttgat agctaaccaa ttcaattcag caatcgggaa  10380
gatacaggat tcactgtcta gtactgctag tgcccttggt aagctgcaga acgttgtcaa  10440
ccagaatgct caagctctga atacattggt taagcagctc tctagtaatt ttgggggcat  10500
ctcttcagta cttaatgata ttttgagccg attggaccca cctgaagctg aagtacagat  10560
cgacaggctg ataacaggcc ggctccaatc cctccaaaca tacgtgacac aacaactcat  10620
acgcgcagcc gaaatccgag ccagcgctaa cctggcagct accaagatgt cagaatgcgt  10680
tctgggccag agtaaacgcg tagatttcgt cgggaaaggg taccacctga tgtcctttcc  10740
acaatctgca cctcacgggg tcgtcttttt gcatgtaaca tacgtacccg cacaagagaa  10800
gaattttact accgctcctg ccatctgtca tgacgggaaa gctcattttc ctcgcgaagg  10860
tgtgtttgta tctaatggta cacattggtt tgtcacacag cggaatttct atgaaccccca  10920
gatcattaca actgacaaca cttttgtttc cgggaattgt gacgtggtca taggaatgct  10980
aaataacact gtatatgatc ccctccaacc agagctggac tctttttaaag aagaactgga  11040
taaatatttc aagaaccaca caagtcccga cgtggacctt ggggacataa gtggtattaa  11100
cgcatctgtg gttaacattc aaaaggaaat cgacagactc aacgaggtgg ccaaaaacct  11160
gaacgaaagc ttgatagatc tccaggagtt gggcaagtag gaacagtaca ttaaatgcct  11220
atggtacata tggcttggct ttatcgctgg ccttatcgcc atcgtaatgg ttacaatcat  11280
gctgtgctgc atgacctcct gctgttcttg tttgaaaggg tgttgttctt gtggtagttg  11340
ttgcaagttt gacgaagatg attccgaacc tgttcttaag ggggtaaagc ttcactatac  11400
atgataaccg cggtgtcaaa aaccgcgtgg acgtggttca atccctgct gggaggatca  11460
gccgtaatta ttataattgg cttggtgctg gctactattg tggccatgta cgtgctgacc  11520
aaccagaaac ataattgaat acagcagcaa ttggcaagct gcttacatag aactcgcggc  11580
gattggcatg ccgccttaaa attttttattt tatttttttct tttcttttcc gaatcggatt  11640
ttgttttttaa tatttcaaaa aaaaaaaaaa aaaaaaaaaa aaaaaaaaaa aaaaaaaaaa  11700
a                                                                  11701
```

| | | |
|---|---|---|
| SEQ ID NO: 38 | moltype = RNA  length = 7862 | |
| FEATURE | Location/Qualifiers | |
| misc_feature | 1..7862 | |
| | note = Description of Artificial Sequence: Synthetic polynucleotide | |
| misc_difference | 7565 | |
| | note = a, c, g, or u | |
| source | 1..7862 | |
| | mol_type = other RNA | |
| | organism = synthetic construct | |

SEQUENCE: 38
```
ataggcggcg catgagagaa gcccagacca attacctacc caaaatggag aaagttcacg    60
ttgacatcga ggaagacagc ccattcctca gagctttgca gcggagcttc ccgcagtttg   120
aggtagaagc caagcaggtc actgataatg accatgctaa tgccagagcg ttttcgcatc   180
tggcttcaaa actgatcgaa acggaggtgg acccatccga cacgatcctt gacattggaa   240
gtgcgcccgc ccgcagaatg tattctaagc acaagtatcc ttgtatctgt ccgatgagat   300
gtgcggaaga tccggacaga ttgtataagt atgcaactaa gctgaagaaa actgtaaggg   360
aaataactga taaggaattg gacaagaaaa tgaaggagct ggccgccgtc atgagcgacc   420
ctgacctgga aactgagact atgtgcctcc acgacgacga gtcgtgtcgc tacgaagggc   480
aagtcgctgt ttaccaggat gtatacgcgg ttgacgacc gacaagtctc tatccaccaag   540
ccaataaggg agtagagtc gcctactgga taggctttga caccaccccct tttatgttta   600
agaacttggc tggagcatat ccatcatact ctaccaactg ggccgacgaa accgtgttaa   660
cggctcgtaa cataggccta tgcagctctg acgttatgga gcggtcacgt agagggatgt   720
ccattcttag aaagaagtat tgaaaccat ccaacaatgt tctattctct gttgctcgta   780
ccatctacca cgagaagagg gacttactga gagctggcca cctgccgtct gtatttcact   840
tacgtggcaa gcaaaattac acatgtcggt gtgagactat agttagtgc gacgggacg    900
tcgttaaaag aatagctatc agtccaggcc tgtatgggaa gccttcaggc tatgctgcta   960
cgatgcaccg cgagggattc ttgtgctgca aagtgacaga cactgaac ggggagaggg   1020
tctcttttcc cgtgtgcaca tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac ctttttgcccg   1200
tagtggccca ggcatttgct aggtgggcaa aggaatataa ggaagatcaa gaagatgaaa   1260
ggccactagg actacgagat agacagttag tcatgggtgt tgttgggct tttagaaggc   1320
acaagataac atctatttat aagcgcccgg acccaacca catcatcaaa gtgaacagtg   1380
atttccactc attcgtgctg cccaggatg gcagtaacac attggagatc gggctgaaa   1440
caagaatcag gaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gccactctg gaggcagacg   1620
tcgacttgat gttacaagag gctggggccg gctcagtgga gacacctcgt ggcttgataa   1680
```

```
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcgagag gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtgaaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg ttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaggg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatggaagat gactctcaag aagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgcccgtc gaagagtcgg   4800
aagcctccac accaccctagc acgctgcctt gcttgtgcat ccatgccatg actccagaaa   4860
gagtacagcg cctaaaagcc tcacgtcag aacaaattac tgtgtgctca tccttctccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggaggagct agcgtgacca   5340
gcgggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccacccgc   5520
caggcgtgaa tagggtgatc actagagagg agctcgaggc gcttacccg tcacgcactc   5580
ctagcaggtc ggtctcgaga accagcctgg tctccaaccc gccaggcgta aataggtga   5640
ttacaagaga ggagtttgag gcgttcgtag cacaacaaca atgacggttt gatgcggtg   5700
catacatctt ttcctccgac accggtcaag ggcatttaca acaaaaatca gtaaggcaaa   5760
cggtgctatc cgaagtggtg ttggagagga ccgaattgga gatttcgtat gcccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtgaagc ctgtaacgcc atgttgaaag aaactttcc gactagtcga   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
```

```
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccgc   7560
caccntaacc gcggtgtcaa aaaccgcgtg gacgtggtta acatccctgc tgggaggatc   7620
agccgtaatt attataattg gcttggtgct ggctactatt gtggccatgt acgtgctgac   7680
caaccagaaa cataattgaa tacagcagaa attggcaggc tgcttacata gaactcgcgg   7740
cgattggcat gccgccttaa aattttttatt ttattttttc ttttcttttc cgaatcggat   7800
tttgttttta atatttcaaa aaaaaaaaa aaaaaaaaa aaaaaaaaa aaaaaaaaa       7860
aa                                                                    7862

SEQ ID NO: 39          moltype = DNA  length = 6569
FEATURE                Location/Qualifiers
misc_feature           1..6569
                       note = Description of Artificial Sequence: Synthetic
                       polynucleotide
source                 1..6569
                       mol_type = other DNA
                       organism = synthetic construct
SEQUENCE: 39
tcgcgcgttt cggtgatgac ggtgaaaacc tctgacacat gcagctcccg gagacggtca   60
cagcttgtct gtaagcggat gccgggagca gacaagcccg tcaggcgcg tcagcggggtg   120
ttggcggggt tcggggctgg cttaactatg cggcatcaga gcagattgta ctgagagtgc   180
accatagcgc gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaatagggca cttttccattg acgtcaatgg gtggagtatt tacggtaaac   540
tgcccacttg gcagtacatc aagtgtatca tatgccaagt acgccccctta ttgacgtcaa   600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agttttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
tagaagacac cgggaccgat ccagcctccg cggccgggaa cggtgcattg gaacgcggat   1020
tccccgtgcc aagagtgacg taagtaccgc ctatagactc tataggcaca ccctttggc    1080
tcttatgcat gctatactgt ttttggcttg gggcctatac ccccgcttcc ttatgcta     1140
taggtgatgg tatagcttag cctataggtg tgggttattg accattattg accactccc   1200
tattggtgac gatactttcc attactaatc cataacatgg ctctttgcca caactatctc   1260
tattggctat atgccaatac tctgtccttc agagactgac acggactctg tattttttaca   1320
ggatggggtc ccatttatta tttacaaatt cacatataca acaacgccgt ccccgtgcc    1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atgaagact taaggcagcg   1680
gcagaagaag atgcaggcag ctgagttgtt gtattctgat aaggagtcaga ggtaactccc   1740
gttgcggtgc tgttaaccggt ggagggcagt gtagtctgaca cagtactcgt tgctgccgcg   1800
cgcgccacca gacataatag ctgacagact aacagactgt tcctttccat gggtcttttc   1860
tgcagtcacc gtcgtcgaca agcttcctgc atgctgctgc tgctgctgct gctgggcctg   1920
aggctacagc tctcctggg catcatccca gttgaggagg agaacccgga cttctggaac    1980
cgcgaggcag ccgaggccct gcgtgccgcc aagaagctga agcctgcaca gacagccgcc   2040
aagaacctca tcatcttcct gggcgatggg atggggtgt ctacggtgac agctgccagg   2100
atcctaaaag gcagaagaa ggacaaactg gggcctgaga tacccctggc catgaccgcc    2160
ttcccatatg tggctctgtc caagacatac aatgtagaca acatgtgcc agacagtgga   2220
gccacagcca cggcctacct gtgcgggtc aagggcaact tccagaccat ggcttgagt    2280
gcagccgccc gcctttaacca gtgcaacacg acagggtcat cctccgtgatg             2340
aatcgggcca agaaagcagg gaagtcagtg gagtggtaa ccaccacacg agtgcagcac   2400
gcctcgccag ccggcaccta cgcccacacg tgaaccgca actggtactc ggacgccgac   2460
gtgcctgcct cggccgcca ggaggggtgc caggacatcg ctacgcagct catctccaac   2520
atggacattg acgtgatcct aggtggaggc cgaaagtaca tgtttcgcat gggaaccccca   2580
gaccctgagt acccagatga ctacagccaa ggtgggacca gctggacgg gaagaatctg   2640
```

```
gtgcaggaat ggctggcgaa gcgccagggt gcccggtatg tgtggaaccg cactgagctc   2700
atgcaggctt ccctggaccc gtctgtgacc catctcatgg gtctctttga gcctggagac   2760
atgaaatacg agatccaccg agactccaca ctggacccct ccctgatgga gatgacagag   2820
gctgccctgc gcctgctgag caggaacccc cgcggcttct tcctcttcgt ggagggtggt   2880
cgcatcgacc atggtcatca tgaaagcagg gcttaccggg cactgactga gacgatcatg   2940
ttcgacgacg ccattgagag ggcgggccag ctcaccagcg aggaggacac gctgagcctc   3000
gtcactgccg accactccca cgtcttctcc ttcggaggct accccctgcg agggagctcc   3060
atcttcgggc tggcccctgg caaggccggg acaggaagg cctacacggt cctcctatac    3120
ggaaacggtc caggctatgt gctcaaggac ggcgcccggc cggatgttac cgagagcgag   3180
agcgggagcc ccgagtatcg gcagcagtca gcagtgcccc tggacgaaga gacccacgca   3240
ggcgaggacg tggcggtgtt cgcgcgcggc ccgcaggcgc acctggttca cggcgtgcag   3300
gagcagacct tcatagcgca cgtcatggcc ttcgccgcct gcctggagcc ctacaccgcc   3360
tgcgacctgg cgccccccgc cggcaccacc gacgccgacc acccgggtta acccgtggtc   3420
agatccagat ccagatcact tctggctaat aaaagatcag agctctagag atctgtgtgt   3480
tggtttttg tggatctgct gtgccttcta gttgccagcc atctgttgtt tgcccctccc     3540
ccgtgccttc cttgaccctg gaaggtgcca ctcccactgt cctttcctaa taaaatgagg    3600
aaattgcatc gcattgtctg agtaggtgtc attctattct gggggggtggg gtggggcagc   3660
acagcaaggg ggaggattgg gaagacaata gcaggcatgc tggggatgcg gtgggctcta   3720
tgggtaccte tctctctctc tctctctctc tctctctctc tctctctcgg tacctctctc    3780
tctctctctc tctctctctc tctctctctc tctcggtacc aggtgctgaa gaattgaccc    3840
ggttcctcct gggccagaaa gaagcaggca catcccttc tctgtgacac accctgtcca     3900
cgcccctggt tcttagttcc agccccactc ataggacact catagctcag gagggctccg    3960
ccttcaatcc cacccgctaa agtacttgga gcggtcctcc cctccctcat cagcccacca    4020
aaccaaacct agcctccaag agtgggaaga aattaaagca agataggcta ttaagtgcag    4080
agggagagaa aatgcctcca acatgtgagg aagtaatgag agaaatcata gaatttcttc    4140
cgcttcctcg ctcactgact cgctgcgctc ggtcgttcgg ctgcggcgag cggtatcagc    4200
tcactcaaag gcggtaatac ggttatccac agaatcaggg gataacgcag gaaagaacat    4260
gtgagcaaaa ggccagcaaa aggccaggaa ccgtaaaaag gccgcgttgc tggcgttttt    4320
ccataggctc cgcccccctg acgagcatca caaaaatcga cgctcaagtc agaggtggcg    4380
aaacccgaca ggactataaa gataccaggc gtttccccct ggaagctccc tcgtgcgctc    4440
tcctgttccg accctgccgc ttaccggata cctgtccgcc tttctccctt cgggaagcgt    4500
ggcgctttct caatgctcac gctgtaggta tctcagttcg gtgtaggtcg ttcgctccaa    4560
gctgggctgt gtgcacgaac cccccgttca gcccgaccgc tgcgccttat ccggtaacta    4620
tcgtcttgag tccaacccgg taagacacga cttatcgcca ctggcagcag ccactggtaa   4680
caggattagc agagcgaggt atgtaggcgg tgctacagag ttcttgaagt ggtggcctaa    4740
ctacggctac actagaagga cagtatttgg tatctgcgct ctgctgaagc cagttacctt    4800
cggaaaaaga gttggtagct cttgatccgg caaacaaacc accgctggta gcggtggttt    4860
ttttgtttgc aagcagcaga ttacgcgcag aaaaaaagga tctcaagaag atcctttgat    4920
cttttctacg gggtctgacg ctcagtggaa cgaaaactca cgttaaggga ttttggtcat    4980
gagattatca aaaaggatct tcacctagat ccttttaaat taaaaatgaa gttttaaatc    5040
aatctaaagt atatatgagt aaacttggtc tgacagttac caatgcttaa tcagtgaggc    5100
acctatctca gcgatctgtc tatttcgttc atccatagt gcctgactcc ggggggggg      5160
ggcgctgagg tctgcctcgt gaagaaggtg ttgctgactc ataccaggcc tgaatcgccc    5220
catcatccag ccagaaagtg agggagccac ggttgatgag agctttgttg taggtggacc    5280
agttggtgat tttgaacttt tgctttgcca cggaacggtc tgcgttgtcg ggaagatgcg    5340
tgatctgatc cttcaactca gcaaagttc gatttattca acaaagccgc cgtcccgtca     5400
agtcagcgta atgctctgcc agtgttacaa ccaattaacc aattctgatt agaaaaactc    5460
atcgagcatc aaatgaaact gcaatttatt catatcagga ttatcaatac catattttg     5520
aaaaagccg ttctgtaatg aaggagaaaa ctcaccgagg cagttccata ggatggcaag     5580
atcctggtat cggtctgcga ttccgactcg tccaacatca atacaaccta ttaatttccc    5640
ctcgtcaaaa taaggttat caagtgagaa atcaccatga gtgacgactg aatccggtga     5700
gaatggcaaa agcttatgca tttctttcca gacttgttca acaggccagc cattacgctc    5760
gtcatcaaaa tcactcgcat caaccaaacc gttattcatt cgtgattgcg cctgagcgag    5820
acgaaatacg cgatcgctgt taaaaggaca attacaaaca ggaatcgaat gcaaccggcg    5880
caggaacact gccagcgcat caacaatatt ttcacctgaa tcaggatatt cttctaatac    5940
ctggaatgct gttttccgg ggatcgcagt ggtgagtaac catgcatcat caggagtacg     6000
gataaaatgc ttgatggtcg gaagaggcat aaattccgtc agccagttta gtctgaccat    6060
ctcatctgta acatcattgg caacgctacc tttgccatgt ttcagaaaca actctggcgc    6120
atcgggcttc ccatacaatc gatagattgt cgcacctgat tgcccgacat tatcgcgagc    6180
ccatttatac ccatataaat cagcatccat gttggaattt aatcgcggcc tcgagcaaga    6240
cgtttcccgt tgaatatggc tcataacacc ccttgtatta ctgtttatgt aagcagacag   6300
ttttattgtt catgatgata tatttttatc ttgtgcaatg taacatcaga gattttgaga    6360
cacaacgtgg ctttccccccc ccccccatta ttgaagcatt tatcagggtt attgtctcat   6420
gagcggatac atatttgaat gtatttagaa aaataaacaa ataggggttc gcgcacatt     6480
tccccgaaaa gtgccacctg acgtctaaga aaccattatt atcatgacat aacctataa     6540
aaataggcgt atcacgaggc cctttcgtc                                      6569
```

SARS-COV-2 RNA VACCINE COMPOSITIONS AND METHODS OF USE

CROSS-REFERENCE

This application is a continuation of International Application No. PCT/US2022/013513, filed Jan. 24, 2022, which claims the benefit of priority to U.S. Provisional Patent Application No. 63/247,169, filed Sep. 22, 2021, and U.S. Provisional Patent Application No. 63/297,397, filed Jan. 7, 2022, the contents of each of which is incorporated herein by reference in their entirety.

STATEMENT AS TO FEDERALLY SPONSORED RESEARCH

This invention was made with government support under contracts 75N93020C00052 and 75N93019C00037 awarded by the National Institute of Allergy and Infectious Diseases, Division of Microbiology and Infectious Diseases. The government has certain rights in the invention.

SEQUENCE LISTING

The instant application contains a Sequence Listing which has been submitted electronically in xml format and is hereby incorporated by reference in its entirety. Said xml copy, created on Apr. 16, 2024, is named 201953-713301-SL.xml and is 258,048 bytes in size.

BACKGROUND

COVID-19 is an infectious respiratory illness caused by the severe acute respiratory syndrome-corona virus 2 (SARS-CoV-2), which has spread across the world. Commercially available mRNA vaccines provide some protection against COVID-19 disease in individuals infected with SARS-CoV-2, the virus is still highly transmissible and can cause a wide array of symptoms even in vaccinated individuals that become infected. Furthermore, SARS-CoV-2 is known to mutate and the effectiveness of vaccines against current and new variants of SARS-CoV-2 are still being determined. Thus, there is a great need for vaccine compositions that are highly effective against SARS-CoV-2 infections.

BRIEF SUMMARY

Provided herein are compositions, wherein the compositions comprise a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the at least one nucleic acid comprises a sequence at least 85% identical to SEQ ID NOS: 1-8.

Further provided herein are compositions, wherein the compositions comprise a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the nucleic acid comprises a sequence coding a SARS-CoV-2 omicron variant spike protein antigen sequence or functional variant thereof.

Further provided herein are compositions, wherein the compositions comprise a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the nucleic acid comprises a sequence coding a S2 region, optionally a stem helix, of SARS-CoV-2 spike protein antigen sequence or functional variant thereof.

Further provided herein are compositions, wherein the compositions comprise a lipid carrier, wherein the lipid carrier comprises: liquid oil; an inorganic nanoparticle, wherein the inorganic nanoparticle comprises iron oxide present in an amount of about 0.2 mg/ml 12 nm iron oxide; and surfactants, wherein the surfactants comprise a cationic lipid; and at least one nucleic acid, wherein the nucleic acid comprises a sequence coding a SARS-CoV-2 spike protein antigen sequence or functional variant thereof.

Further provided herein are compositions, wherein the compositions comprise a lipid carrier, wherein the lipid carrier is a nanoemulsion comprising: about 30 mg/mL DOTAP chloride; about 37.5 mg/mL squalene; about 37 mg/ml sorbitan monostearate; about 37 mg/ml polysorbate 80; about 10 mM sodium citrate; and about 0.2 mg Fe/ml 12 nm oleic acid-coated iron oxide nanoparticles; and at least one nucleic acid, wherein the at least one nucleic acid comprises a sequence coding a SARS-CoV-2 spike protein antigen sequence or functional variant thereof.

Further provided herein are compositions, wherein the compositions comprise a lipid carrier, wherein the lipid carrier is a nanoemulsion comprising: DOTAP chloride present in an amount of about 0.75 mg; squalene present in an amount of about 0.94 mg; sorbitan monostearate present in an amount of about 0.93 mg; polysorbate 80 present in an amount of about 0.93 mg; citric acid monohydrate present in an amount of about 1.05 mg; oleic acid-coated iron oxide nanoparticles present in an amount of about 0.005 mg; and at least one nucleic acid, wherein the at least one nucleic acid comprises a sequence coding a SARS-CoV-2 spike protein antigen sequence or functional variant thereof.

Further provided herein are compositions, wherein the compositions comprise: a lipid carrier, wherein the lipid carrier is a nanoemulsion comprising a hydrophobic core, one or more inorganic nanoparticles and one or more lipids, and at least one nucleic acid sequence, wherein the nucleic acid sequence comprises a sequence which encodes an antigen, wherein the antigen is a SARS-CoV-2 spike protein.

Further provided herein are vaccines comprising: a lipid carrier, wherein the lipid carrier is a nanoemulsion comprising a hydrophobic core, one or more inorganic nanoparticles and one or more lipids, and at least one nucleic acid sequence, wherein the nucleic acid sequence comprises a sequence which encodes an antigen, wherein the antigen is a SARS-CoV-2 spike protein.

Further provided herein are methods of generating an immune response in a subject, the methods comprising: administering to a subject a composition provided herein thereby generating an immune response to an antigen.

Further provided herein are methods of reducing the severity of a SARS-CoV-2 infection, the methods comprising: administering prior to infection a composition provided herein.

Further provided herein are methods of augmenting an immune response in a subject, the method comprising: administering to a subject the composition provided herein, thereby augmenting an immune response to an antigen.

Further provided herein are methods of treating a coronavirus infection, the method comprising: administering to a subject the composition provided herein, thereby treating the coronavirus infection.

Further provided herein are methods of immunoprotecting a subject, the methods comprise administering to a subject a composition or a vaccine provided herein.

Further provided herein are compositions for immunoprotecting a subject, the compositions comprise: a lipid carrier, wherein the lipid carrier is a nanoemulsion comprising a hydrophobic core, one or more inorganic nanoparticles and one or more lipids, and at least one nucleic acid sequence, wherein the nucleic acid sequence comprises a sequence which encodes an antigen, wherein the antigen is a SARS-CoV-2 spike protein.

Provided herein are dried compositions, the dried compositions comprising: a lipid carrier, wherein the lipid carrier is a nanoemulsion comprising a hydrophobic core, one or more inorganic nanoparticles and one or more lipids, at least one nucleic acid sequence, wherein the nucleic acid sequence comprises a sequence which encodes an antigen, wherein the antigen is a SARS-CoV-2 spike protein, and at least one cryoprotectant.

Further provided herein are methods for preparing a lyophilized composition, the methods comprising: obtaining a lipid carrier, wherein the lipid carrier is a nanoemulsion comprising a hydrophobic core, one or more inorganic nanoparticles and one or more lipids, incorporating at least one nucleic acid into the lipid carrier to form a lipid carrier-nucleic acid complex, adding at least one cryoprotectant to the lipid carrier-nucleic acid complex to form a formulation, and lyophilizing the formulation to form a lyophilized composition.

Further provided herein are methods for preparing a spray-dried composition, the methods comprising: obtaining a lipid carrier, wherein the lipid carrier is a nanoemulsion comprising a hydrophobic core, one or more inorganic nanoparticles and one or more lipids, incorporating at least one nucleic acid into the lipid carrier to form a lipid carrier-nucleic acid complex, adding at least one cryoprotectant to the lipid carrier-nucleic acid complex to form a formulation, and spray drying the formulation to form a spray-dried composition.

Further provided herein are methods for reconstituting a lyophilized composition, the methods comprising: (a) obtaining a lipid carrier, wherein the lipid carrier is a nanoemulsion comprising a hydrophobic core, one or more inorganic nanoparticles, and one or more lipids; (b) incorporating at least one nucleic acid into the said lipid carrier to form a lipid carrier-nucleic acid complex, adding at least one cryoprotectant to the lipid carrier-nucleic acid complex to form a formulation; (c) lyophilizing the formulation to form a lyophilized composition, and reconstituting the lyophilized composition in a suitable diluent.

Further provided herein are methods for reconstituting a spray-dried composition, the methods comprising: (a) obtaining a lipid carrier, wherein the lipid carrier is a nanoemulsion comprising a hydrophobic core, one or more inorganic nanoparticles, and one or more lipids; (b) incorporating at least one nucleic acid into the said lipid carrier to form a lipid carrier-nucleic acid complex; (c) adding at least one cryoprotectant to the lipid carrier-nucleic acid complex to form a formulation; (d) spray drying the formulation to form a spray-dried composition; and (e) reconstituting the spray-dried composition in a suitable diluent.

Further provided herein are compositions for prophylaxis of SARS-CoV-2, wherein the compositions comprise: (a) a sorbitan fatty acid ester; (b) an ethoxylated sorbitan ester; (c) a cationic lipid; (d) an immune stimulant; and (e) at least one RNA molecule.

Further provided herein are compositions for prophylaxis of SARS-CoV-2 wherein the compositions comprise: (a) sorbitan monostearate (e.g., SPAN-60®); (b) polysorbate 80 (e.g., TWEEN-80®); (c) DOTAP; (d) an immune stimulant; and (e) at least one RNA molecule.

Further provided herein are dried compositions comprising: a lipid carrier, wherein the lipid carrier is a nanoemulsion comprising a hydrophobic core, and one or more lipids; at least one nucleic acid that comprises a sequence which encodes a sequence capable of expressing an antigen, optionally wherein the antigen is a SARS-CoV-2 spike protein or a functional variant thereof; and at least one sugar present in amount of (i) at least about 50% by weight of the dried composition, or (ii) present in an amount of least 50 mg.

Further provided herein are kits comprising a composition provided herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which.

FIG. 1 shows repRNA constructs disclosed herein. Schematic representations of the SARS-CoV-2 spike are shown with the signal peptide (sp), S1 and S2 domains, transmembrane domain (TM), and cytoplasmic domain (CD) indicated. The repRNAs are identified as SEQ ID NO: 1 encoding the A.1 spike, B.1 spike, SEQ ID NO: 2 encoding the A.1. pre-fusion stabilized spike, B.1 pre-fusion stabilized spike, SEQ ID NO: 5 encoding the B.1.1.7 pre-fusion stabilized spike; and SEQ ID NO: 4 encoding the B.1.351 pre-fusion stabilized spike. Mutations are shown relative to the A.1 strain (SEQ ID NO: 1).

FIG. 3A shows an oil-in-water emulsion. FIG. 3B shows a nanostructured lipid carrier (NLC). FIG. 3C shows a nanoparticle having an inorganic nanoparticle in liquid oil.

FIG. 4A shows the first assay. FIG. 4B shows the second assay.

FIG. 5A shows the first assay. FIG. 5B shows the second assay.

FIG. 6A shows the first assay. FIG. 6B shows the second assay.

FIG. 7A shows SEAP levels on day 4 post-injection. FIG. 7B shows SEAP levels on day 6 post-injection. FIG. 7C shows SEAP levels on day 8 post-injection. FIG. 7D shows SEAP levels on day 4 post-injection.

FIG. 7E shows SEAP levels on day 6 post-injection. FIG. 7F shows SEAP levels on day 8 post-injection. X-axis: Condition, Y-axis: Relative light units (RLU).

Figure 2:
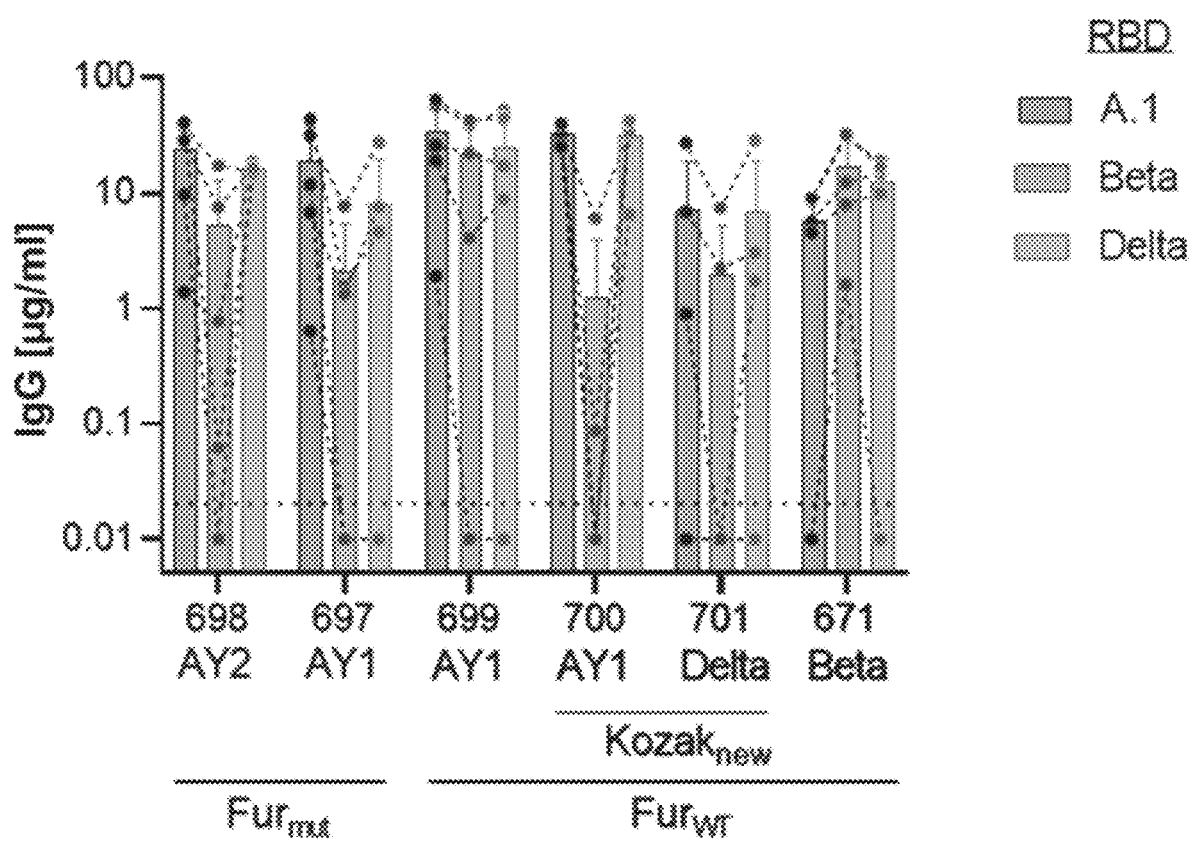
FIG. 2 shows the effect of spike modifications on binding antibody responses in mice. C57BL/6 mice (n=5/group) were immunized with lipid carrier-formulated repRNA encoding the wild-type (WT), the prefusion-stabilized (PreF), the furin cleavage site-deleted ($Fur_{mut}$), or a combination of the PreF and $Fur_{mut}$ modifications of the full-length spike of A.1 lineage SARS-CoV-2. Vaccinations were administered on days 0 and 28, and serum collected on days 14, 28, and 38 assayed for anti-spike binding IgG by enzyme linked immunosorbent assay.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

DETAILED DESCRIPTION OF THE INVENTION

Provided herein are compositions, kits, methods, and uses thereof for inducing an immune response to a coronavirus. Briefly, further described herein are (1) nanoparticle carrier systems; (2) nucleic acids encoding for coronavirus antigens and RNA polymerases; (3) combination compositions; (4) thermally stable, dried, and lyophilized SARS-CoV-2 RNA vaccines; (5) pharmaceutical compositions; (6) dosing; (7) administration; (8) therapeutic applications; and (9) kits.

Definitions

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document. All references disclosed herein, including patent references and non-patent references, are hereby incorporated by reference in their entirety as if each was incorporated individually. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supersede.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein, "optional" or "optionally" means that the subsequently described circumstance may or may not occur, so that the description includes instances where the circumstance occurs and instances where it does not.

As used herein, the term "about" or "approximately" means a range of up to +20%, of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

The term "effective amount" or "therapeutically effective amount" refers to an amount that is sufficient to achieve or at least partially achieve the desired effect.

Nanoparticle Carrier Systems

Provided herein are various compositions comprising a nanoparticle or a plurality of nanoparticles. Nanoparticles also referred to herein as carriers or abbreviated as NPs. Nanoparticles provided herein may be an organic, inorganic, or a combination of inorganic and organic materials that are less than about 1 micrometer (µm) in diameter. In some embodiments, nanoparticles provided herein are used as a delivery system for a bioactive agent provided herein.

Figure 3A:
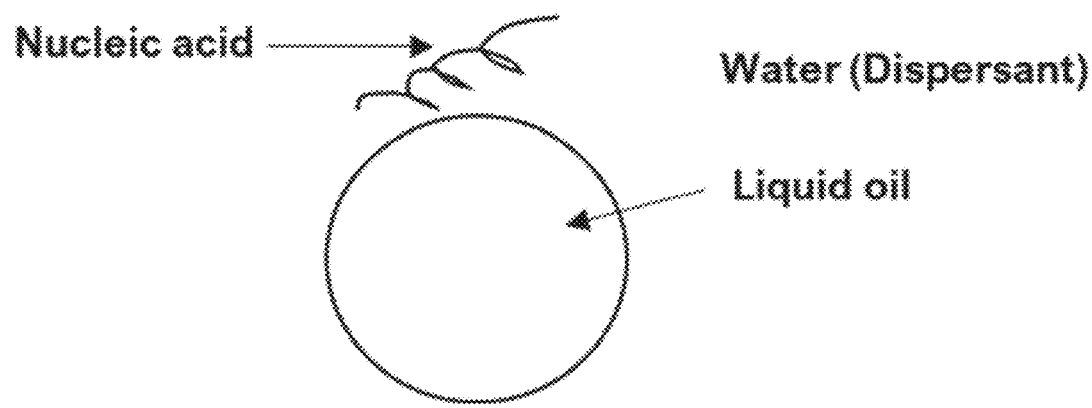
FIGS. 3A-3C show schematic representations of exemplary nanoparticle (NP) carriers.
Figure 3B:
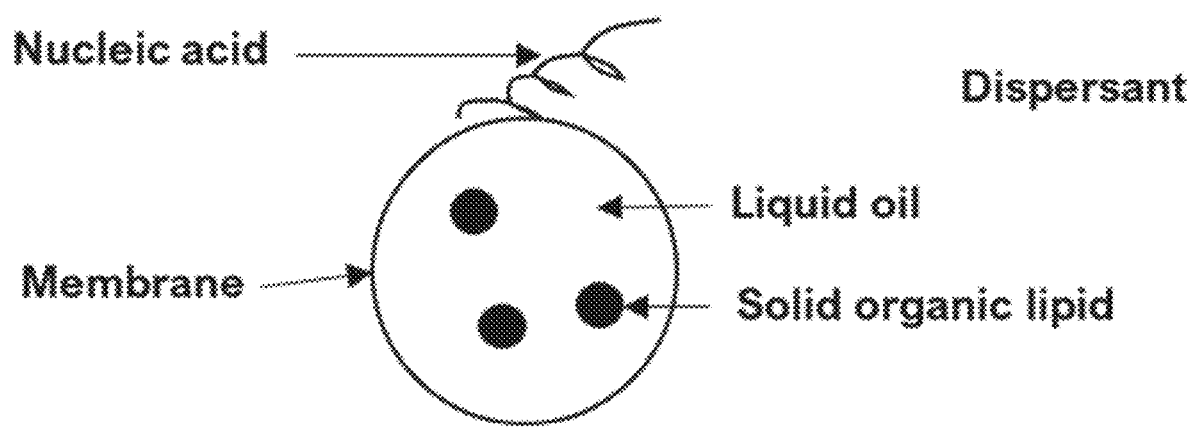
Figure 3C:
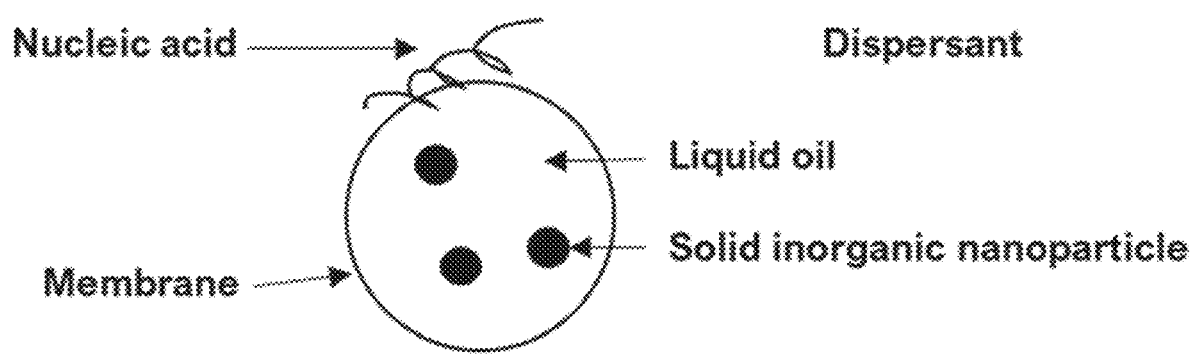

Various nanoparticles and formulations of nanoparticles (i.e., nanoemulsions) are employed. Exemplary nanoparticles are illustrated in FIGS. 3A-3C. Nanoparticles provided herein can include but are not limited to: oil in water emulsions, nanostructured lipid carriers (NLCs), cationic nanoemulsions (CNEs), vesicular phospholipid gels (VPG), polymeric nanoparticles, cationic lipid nanoparticles, liposomes, gold nanoparticles, solid lipid protein nanoparticles, polyethylenimine nanoparticles (LNPs or SLNs), mixed phase core NLCs, ionizable lipid carriers, magnetic carriers, polyethylene glycol (PEG)-functionalized carriers, cholesterol-functionalized carriers, polylactic acid (PLA)-functionalized carriers, and polylactic-co-glycolic acid (PLGA)-functionalized lipid carriers.

Oil in water emulsions, as illustrated in FIG. 3A (not to scale), are stable, immiscible fluids containing an oil droplet dispersed in water or aqueous phase. FIG. 3B (not to scale) illustrates a nanostructured lipid carrier (NLCs) which can comprise a blend of solid organic lipids (e.g., trimyristin) and liquid oil (e.g., squalene). In NLCs, the solid lipid is dispersed in the liquid oil. The entire nanodroplet is dispersed in the aqueous (water) phase. In some embodiments, the nanoparticle comprises inorganic nanoparticles, as illustrated in FIG. 3C (not to scale), as solid inorganic nanoparticles (e.g., iron oxide nanoparticles) dispersed in liquid oil. The entire nanodroplet is then dispersed as a colloid in the aqueous (water) phase. In some embodiments, the nanoparticles provided herein are dispersed in an aqueous solution. Non-limiting examples of aqueous solutions include water (e.g., sterilized, distilled, deionized, ultrapure, RNase-free, etc.), saline solutions (e.g., Kreb's, *Ascaris*, Dent's, Tet's saline), or 1% (w/v) dimethyl sulfoxide (DMSO) in water.

In some embodiments, the nanoparticles provided herein comprise a hydrophilic surface. In some embodiments, the hydrophilic surface comprises a cationic lipid. In some embodiments, the hydrophilic surface comprises an ionizable lipid. In some embodiments, the nanoparticle comprises a membrane. In some embodiments, the membrane comprises a cationic lipid. In some embodiments, the nanoparticles provided herein comprise a cationic lipid. Exemplary cationic lipids for inclusion in the hydrophilic surface include, without limitation: 1,2-dioleoyloxy-3 (trimethylammonium)propane (DOTAP), 3β-[N—(N',N'-dimethylaminoethane) carbamoyl]cholesterol (DC Cholesterol), dimethyldioctadecylammonium (DDA); 1,2-dimyristoyl 3-trimethylammoniumpropane(DMTAP),dipalmitoyl(C16:0)trimethyl ammonium propane (DPTAP), distearoyltrimethylammonium propane (DSTAP), N-[l-(2,3-dioleyloxy) propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis(2-hydroxy-dodecyl)amino)ethyl)(2-hydroxydodecyl)amino)ethyl)piperazin-1-yl)ethyl)azanediyl) bis(dodecan-2-ol) (C12-200), 306Oi10, tetrakis(8-methylnonyl) 3,3',3",3"'-(((methylazanediyl) bis(propane-3,1 diyl))bis (azanetriyl))tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl)azanediyl)bis(hexane-6,1-diyl)bis(2-hexyldecanoate); ALC-0159, 2-[(polyethylene glycol)-2000]-N,N-ditetradecylacetamide; β-sitosterol, (3S,8S,9S,10R,13R, 14S,17R)-17-((2R,5R)-5-ethyl-6-methylheptan-2-yl)-10, 13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R, 13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 3β-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9",9"',9"",9""'-((((benzene-1,3,5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4,1-diyl))bis(azanetriyl))tetrakis(ethane-2, 1-diyl) (9Z,9'Z,9"Z,9"'Z,12Z,12',12"Z,12"'Z)-tetrakis (octadeca-9,12-dienoate); PEG2000-DMG, (R)-2,3-bis (myristoyloxy)propyl-1-(methoxy poly(ethylene glycol) 2000) carbamate; TT3, or N1,N3,N5-tris(3-(didodecylamino)propyl)benzene-1,3,5-tricarboxamide. Other examples for suitable classes of lipids include, but are not limited to, the phosphatidylcholines (PCs), phosphatidylethanolamines (PEs), phosphatidylglycerol (PGs); and PEGylated lipids including PEGylated version of any of the above lipids (e.g., DSPE-PEGs). In some embodiments, the nanoparticle provided herein comprises DOTAP.

In some embodiments, the nanoparticle provided herein comprises an oil. In some embodiments, the oil is in liquid phase. Non-limiting examples of oils that can be used include α-tocopherol, coconut oil, dihydroisosqualene (DHIS), farnesene, grapeseed oil, lauroyl polyoxylglyceride, mineral oil, monoacylglycerol, palmkernal oil, olive oil, paraffin oil, peanut oil, propolis, squalene, squalane, solanesol, soy lecithin, soybean oil, sunflower oil, a triglyceride, or vitamin E. In some embodiments, the nanoparticle provided herein comprises a triglyceride. Exemplary triglycerides include but are not limited to: capric triglycerides, caprylic triglycerides, a caprylic and capric triglycerides, triglyceride esters, and myristic acid triglycerins.

In some embodiments, the nanoparticles provided herein comprise a liquid organic material and a solid inorganic material. In some embodiments, the nanoparticle provided herein comprises an inorganic particle. In some embodiments, the inorganic particle is a solid inorganic particle. In some embodiments, the nanoparticle provided herein comprises the inorganic particle within the hydrophobic core.

In some embodiments, the nanoparticle provided herein comprises a metal. In some embodiments, the nanoparticle provided herein comprises a metal within the hydrophobic core. The metal can be without limitation, a metal salt such as a transition metal salt, a metal oxide such as a transition metal oxide, a metal hydroxide such as a transition metal hydroxide, a metal phosphate such as a transition metal phosphate, or a metalloid (e.g., silicon and silicon-based compounds or alloys). In some embodiments, the nanoparticle provided herein comprises aluminum oxide ($Al_2O_3$), aluminum oxyhydroxide, iron oxide ($Fe_3O_4$, $Fe_2O_3$, FeO, or combinations thereof), titanium dioxide, silicon dioxide ($SiO_2$), aluminum hydroxyphosphate ($Al(OH)_x(PO_4)_y$), calcium phosphate ($Ca_3(PO_4)_2$), calcium hydroxyapatite ($Ca_{10}(PO_4)_6(OH)_2$), iron gluconate, or iron sulfate. The inorganic particles may be formed from one or more same or different metals (any metals including transition metal). In some embodiments, the inorganic particle is a transition metal oxide. In some embodiments, the transition metal is magnetite ($Fe_3O_4$), maghemite (γ-$Fe_2O_3$), wüstite (FeO), or hematite (alpha (α)-$Fe_2O_3$). In some embodiments, the metal is aluminum hydroxide or aluminum oxyhydroxide, and a phosphate-terminated lipid or a surfactant, such as oleic acid, oleylamine, SDS, TOPO or DSPA is used to coat the inorganic solid nanoparticle before it is mixed with the liquid oil to form the hydrophobic core. In some embodiments, the metal can comprise a paramagnetic, a superparamagnetic, a ferrimagnetic or a ferromagnetic compound. In some embodiments, the metal is a superparamagnetic iron oxide ($Fe_3O_4$).

In some embodiments, the nanoparticle provided herein comprises a cationic lipid, an oil, and an inorganic particle. In some embodiments, the nanoparticle provided herein comprises DOTAP; squalene and/or glyceryl trimyristate-dynasan; and iron oxide. In some embodiments, the nanoparticle provided herein further comprises a surfactant. Thus, in some embodiments, the nanoparticles provided herein comprise a cationic lipid, an oil, an inorganic particle, and a surfactant.

Surfactants are compounds that lower the surface tension between two liquids or between a liquid and a solid component of the nanoparticles provided herein. Surfactants can be hydrophobic, hydrophilic, or amphiphilic. In some embodiments, the nanoparticle provided herein comprises a hydrophobic surfactant. Exemplary hydrophobic surfactants that can be employed include but are not limited to: sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), and sorbitan trioleate (SPAN® 85). Suitable hydrophobic surfactants include those having a hydrophilic-lipophilic balance (HLB) value of 10 or less, for instance, 5 or less, from 1 to 5, or from 4 to 5. For instance, the hydrophobic surfactant can be a sorbitan ester having an HLB value from 1 to 5, or from 4 to 5.

In some embodiments, the nanoparticle provided herein comprises a hydrophilic surfactant, also called an emulsifier. In some embodiments, the nanoparticle provided herein comprises polysorbate. Polysorbates are oily liquids derived from ethoxylated sorbitan (a derivative of sorbitol) esterified with fatty acids. Exemplary hydrophilic surfactants that can be employed include but are not limited to: polysorbates such as Tween, Kolliphor, Scattics, Alkest, or Canarcel; polyoxyethylene sorbitan ester (polysorbate); polysorbate 80 (polyoxyethylene sorbitan monooleate, or Tween 80); polysorbate 60 (polyoxyethylene sorbitan monostearate, or Tween 60); polysorbate 40 (polyoxyethylene sorbitan monopalmitate, or Tween 40); and polysorbate 20 (polyoxyethylene sorbitan monolaurate, or Tween 20). In one embodiment, the hydrophilic surfactant is polysorbate 80.

Nanoparticles provided herein comprises a hydrophobic core surrounded by a lipid membrane (e.g., a cationic lipid such as DOTAP). In some embodiments, the hydrophobic core comprises: one or more inorganic particles; a phosphate-terminated lipid; and a surfactant.

Inorganic solid nanoparticles described herein may be surface modified before mixing with the liquid oil. For instance, if the surface of the inorganic solid nanoparticle is hydrophilic, the inorganic solid nanoparticle may be coated with hydrophobic molecules (or surfactants) to facilitate the miscibility of the inorganic solid nanoparticle with the liquid oil in the "oil" phase of the nanoemulsion particle. In some embodiments, the inorganic particle is coated with a capping ligand, the phosphate-terminated lipid, and/or the surfactant. In some embodiments the hydrophobic core comprises a phosphate-terminated lipid. Exemplary phosphate-terminated lipids that can be employed include but are not limited to: trioctylphosphine oxide (TOPO) or distearyl phosphatidic acid (DSPA). In some embodiments, the hydrophobic core comprises a surfactant such as a phosphorous-terminated surfactant, a carboxylate-terminated surfactant, a sulfate-terminated surfactant, or an amine-terminated surfactant. Typical carboxylate-terminated surfactants include oleic acid. Typical amine terminated surfactants include oleylamine. In some embodiments, the surfactant is distearyl phosphatidic acid (DSPA), oleic acid, oleylamine or sodium dodecyl sulfate (SDS). In some embodiments, the inorganic solid nanoparticle is a metal oxide such as an iron oxide, and a surfactant, such as oleic acid, oleylamine, SDS, DSPA, or TOPO, is used to coat the inorganic solid nanoparticle before it is mixed with the liquid oil to form the hydrophobic core.

In some embodiments, the hydrophobic core comprises: one or more inorganic particles containing at least one metal hydroxide or oxyhydroxide particle optionally coated with a phosphate-terminated lipid, a phosphorous-terminated surfactant, a carboxylate-terminated surfactant, a sulfate-terminated surfactant, or an amine-terminated surfactant; and a liquid oil containing naturally occurring or synthetic squalene; a cationic lipid comprising DOTAP; a hydrophobic surfactant comprising a sorbitan ester selected from the group consisting of: sorbitan monostearate, sorbitan monooleate, and sorbitan trioleate; and a hydrophilic surfactant comprising a polysorbate.

In some embodiments, the hydrophobic core comprises: one or more inorganic nanoparticles containing aluminum hydroxide or aluminum oxyhydroxide nanoparticles optionally coated with TOPO, and a liquid oil containing naturally occurring or synthetic squalene; the cationic lipid DOTAP; a hydrophobic surfactant comprising sorbitan monostearate; and a hydrophilic surfactant comprising polysorbate 80.

In some embodiments, the hydrophobic core consists of: one or more inorganic particles containing at least one metal hydroxide or oxyhydroxide particle optionally coated with a phosphate-terminated lipid, a phosphorous-terminated surfactant, a carboxylate-terminated surfactant, a sulfate-terminated surfactant, or an amine-terminated surfactant; and a liquid oil containing naturally occurring or synthetic squalene; a cationic lipid comprising DOTAP; a hydrophobic surfactant comprising a sorbitan ester selected from the group consisting of: sorbitan monostearate, sorbitan monooleate, and sorbitan trioleate; and a hydrophilic surfactant comprising a polysorbate. In some embodiments, the hydrophobic core consists of: one or more inorganic nanoparticles containing aluminum hydroxide or aluminum oxyhydroxide nanoparticles optionally coated with TOPO, and a liquid oil containing naturally occurring or synthetic squalene; the cationic lipid DOTAP; a hydrophobic surfactant comprising sorbitan monostearate; and a hydrophilic surfactant comprising polysorbate 80. In some embodiments, the nanoparticle provided herein can comprise from about 0.2% to about 40% w/v squalene, from about 0.001% to about 10% w/v iron oxide nanoparticles, from about 0.2% to about 10% w/v DOTAP, from about 0.25% to about 5% w/v sorbitan monostearate, and from about 0.5% to about 10% w/v polysorbate 80. In some embodiments the nanoparticle provided herein from about 2% to about 6% w/v squalene, from about 0.01% to about 1% w/v iron oxide nanoparticles, from about 0.2% to about 1% w/v DOTAP, from about 0.25% to about 1% w/v sorbitan monostearate, and from about 0.5%) to about 5% w/v polysorbate 80. In some embodiments, the nanoparticle provided herein can comprise from about 0.2% to about 40% w/v squalene, from about 0.001% to about 10% w/v aluminum hydroxide or aluminum oxyhydroxide nanoparticles, from about 0.2% to about 10% w/v DOTAP, from about 0.25% to about 5% w/v sorbitan monostearate, and from about 0.5% to about 10% w/v polysorbate 80. In some embodiments, the nanoparticle provided herein can comprise from about 2% to about 6% w/v squalene, from about 0.01% to about 1% w/v aluminum hydroxide or aluminum oxyhydroxide nanoparticles, from about 0.2% to about 1% w/v DOTAP, from about 0.25% to about 1% w/v sorbitan monostearate, and from about 0.5%) to about 5% w/v polysorbate 80.

In some embodiments, a composition described herein comprises at least one nanoparticle formulations as described in Table 1. In some embodiments, a composition described herein comprises any one of NP-1 to NP-30. In some embodiments, a composition described herein comprises any one of NP-1 to NP-31. In some embodiments, the nanoparticles provided herein are admixed with a nucleic acid provided herein. In some embodiments, nanoparticles provided herein are made by homogenization and ultrasonication techniques.

TABLE 1

Nanoparticle Formulations.

| Name | Cationic Lipid(s) % (w/v) or mg/ml | Oil(s) % (w/v) or mg/ml | Surfactant(s) % (w/v) or mg/ml | Additional Ingredients % (w/v), mg/ml, or mM |
|---|---|---|---|---|
| NP-1 | 30 mg/ml 1,2-dioleoyl-3-trimethylammonium-propane (DOTAP) chloride | 37.5 mg/ml squalene | 37 mg/ml sorbitan monostearate, (2R)-2-[(2R,3R,4S)-3,4-Dihydroxyoxolan-2-yl]-2-hydroxyethyl octadecenoate, $C_{24}H_{46}O_6$) (SPAN® 60) 37 mg/ml polyoxyethylene (20) sorbitan monooleate, $C_{64}H_{124}O_{26}$ Polysorbate 80 (TWEEN 80®) | 0.2 mg Fe/ml 12 nm oleic acid-coated iron oxide nanoparticles 10 mM sodium citrate dihydrate. |
| NP-2 | 30 mg/ml 1,2-dioleoyl-3-trimethylammonium-propane (DOTAP) chloride | 37.5 mg/ml squalene | 37 mg/ml sorbitan monostearate, (2R)-2-[(2R,3R,4S)-3,4-Dihydroxyoxolan-2-yl]-2-hydroxyethyl octadecenoate $C_{24}H_{46}O_6$ (SPAN® 60) 37 mg/ml polyoxyethylene (20) sorbitan monooleate, $C_{64}H_{124}O_{26}$, Polysorbate 80 (TWEEN 80®) | 1 mg Fe/ml 15 nm oleic acid-coated iron oxide nanoparticles 10 mM sodium citrate dihydrate |
| NP-3 | 30 mg/ml 1,2-dioleoyl-3-trimethylammonium-propane (DOTAP) chloride | 37.5 mg/ml Miglyol 812N (triglyceride ester of saturated coconut/palmkernel oil derived caprylic and capric fatty acids and plant derived glycerol) | 37 mg/ml sorbitan monostearate, (2R)-2-[(2R,3R,4S)-3,4-Dihydroxyoxolan-2-yl]-2-hydroxyethyl octadecenoate $C_{24}H_{46}O_6$ (SPAN® 60) 37 mg/ml polyoxyethylene (20) sorbitan monooleate, $C_{64}H_{124}O_{26}$ Polysorbate 80 (TWEEN 80®) | 0.2 mg Fe/ml 15 nm oleic acid-coated iron oxide nanoparticles 10 mM sodium citrate dihydrate |
| NP-4 | 30 mg/ml 1,2-dioleoyl-3-trimethylammonium-propane (DOTAP) chloride | 37.5 mg/ml Miglyol 812N (triglyceride ester of saturated coconut/palmkernel oil derived caprylic and capric fatty acids and plant derived glycerol) | 37 mg/ml sorbitan monostearate, (2R)-2-[(2R,3R,4S)-3,4-Dihydroxyoxolan-2-yl]-2-hydroxyethyl octadecenoate, $C_{24}H_{46}O_6$) (SPAN® 60) 37 mg/ml polyoxyethylene (20) sorbitan | 1 mg Fe/ml 15 nm oleic acid-coated iron oxide nanoparticles 10 mM sodium citrate dihydrate. |

TABLE 1-continued

Nanoparticle Formulations.

| Name | Cationic Lipid(s) % (w/v) or mg/ml | Oil(s) % (w/v) or mg/ml | Surfactant(s) % (w/v) or mg/ml | Additional Ingredients % (w/v), mg/ml, or mM |
|---|---|---|---|---|
| NP-5 | 30 mg/ml DOTAP chloride | 37.5 mg/ml squalene | monooleate, $C_{64}H_{124}O_{26}$, Polysorbate 80 (TWEEN 80 ®) 37 mg/ml sorbitan monostearate (SPAN ® 60) 37 mg/ml polysorbate 80 (TWEEN ® 80) | 1 mg/ml trioctylphosphine oxide (TOPO)-coated aluminum hydroxide (Alhydrogel ® 2%) particles 10 mM sodium citrate dihydrate |
| NP-6 | 30 mg/ml DOTAP chloride | 37.5 mg/ml Solanesol (Cayman chemicals) | 37 mg/ml sorbitan monostearate (SPAN ® 60) 37 mg/ml polysorbate 80 (TWEEN ® 80) | 0.2 mg Fe/ml oleic acid-coated iron oxide nanoparticles 10 mM sodium citrate |
| NP-7 | 30 mg/ml DOTAP chloride | 37.5 mg/ml squalene 2.4 mg/ml Dynasan 114 | 37 mg/ml sorbitan monostearate (SPAN ® 60) 37 mg/ml polysorbate 80 (TWEEN ® 80 | 10 mM sodium citrate |
| NP-8 | 4 mg/ml DOTAP chloride | 43 mg/ml squalene | 5 mg/ml Span ® 85 5 mg/ml Tween ® 80 | 10 mM sodium citrate |
| NP-9 | 7.5 mg/ml 1,2-dioleoyl-3-trimethylammonium-propane (DOTAP) chloride | 9.4 mg/ml squalene ((6E,10E,14E,18E)-2,6,10,15,19,23-Hexamethyltetracosa-2,6,10,14,18,22-hexaene, $C_{30}H_{50}$) 0.63 mg/ml glyceryl trimyristate-dynasan (DYNASAN 114 ®) | 9.3 mg/ml sorbitan monostearate (2R)-2-[(2R,3R,4S)-3,4-Dihydroxyoxolan-2-yl]-2-hydroxyethyl octadecenoate, $C_{24}H_{46}O_6$) (SPAN ® 60) 9.3 mg/ml polyoxyethylene (20) sorbitan monooleate, $C_{64}H_{124}O_{26}$, Polysorbate 80 (TWEEN 80 ®) | 0.05 mg/ml 15 nanometer superparamagnetic iron oxide ($Fe_3O_4$) 10 mM sodium citrate dihydrate |
| NP-10 | 0.4% DOTAP | 0.25% glyceryl trimyristate-dynasan (DYNASAN 114 ®) 4.75% Squalene | 0.5% sorbitan monostearate (SPAN ® 60) 0.5% polysorbate 80 (TWEEN 80 ®) | |
| NP-11 | 3.0% DOTAP | 0.25% glyceryl trimyristate-dynasan (DYNASAN 114 ®) 3.75% Squalene | 3.7% sorbitan monostearate (SPAN ® 60) 3.7% polysorbate 80 (TWEEN 80 ®) | |
| NP-12 | 0.4% DOTAP | 4.3% Squalene | 0.5% sorbitan trioleate (SPAN ® 85) 0.5% polysorbate 80 (TWEEN ® 80) | |
| NP-13 | 0.4% DOTAP | 0.25% glyceryl trimyristate-dynasan (DYNASAN 114 ®) 4.08% squalene | 2.0% polysorbate 80 (TWEEN ® 80) | |
| NP-14 | 0.4% DOTAP | 0.25% glyceryl trimyristate-dynasan (DYNASAN 114 ®) 4.08% squalene | 0.5% sorbitan trioleate (SPAN ® 85) 2.0% polysorbate 80 (TWEEN ® 80) | |

TABLE 1-continued

Nanoparticle Formulations.

| Name | Cationic Lipid(s) % (w/v) or mg/ml | Oil(s) % (w/v) or mg/ml | Surfactant(s) % (w/v) or mg/ml | Additional Ingredients % (w/v), mg/ml, or mM |
|---|---|---|---|---|
| NP-15 | 0.4% DOTAP | 0.25% glyceryl trimyristate-dynasan (DYNASAN 114 ®) 4.08% squalene | 0.25% sorbitan trioleate (SPAN ® 85) 2.0% polysorbate 80 (TWEEN ® 80) | |
| NP-16 | 0.4% DOTAP | 5% squalene | 0.5% sorbitan trioleate (SPAN ® 85) 2.0% polysorbate 80 (TWEEN ® 80) | |
| NP-17 | 0.4% DOTAP | 5% squalene | 0.5% sorbitan monostearate (SPAN ® 60) 2% polysorbate 80 (TWEEN ® 80) | |
| NP-18 | 0.4% DOTAP | 0.25% glyceryl trimyristate-dynasan (DYNASAN 114 ®) 4.08% squalene | 2% sorbitan trioleate (SPAN ® 85) 2% polysorbate 80 (TWEEN ® 80) | |
| NP-19 | 0.4% DOTAP | 0.25% glyceryl trimyristate-dynasan (DYNASAN 114 ®) 4.75% Squalene | 0.5% sorbitan monostearate (SPAN ® 60) 0.5% polysorbate 80 (TWEEN 80 ®) | 1% aluminum hydroxide |
| NP-20 | 3.0% DOTAP | 0.25% glyceryl trimyristate-dynasan (DYNASAN 114 ®) 3.75% Squalene | 3.7% sorbitan monostearate (SPAN ® 60) 3.7% polysorbate 80 (TWEEN ® 80) | 1% aluminum hydroxide |
| NP-21 | 0.4% DOTAP | 4.3% Squalene | 0.5% sorbitan trioleate (SPAN ® 85) 0.5% polysorbate 80 (TWEEN ® 80 | 1% aluminum hydroxide |
| NP-22 | 0.4% DOTAP | 0.25% glyceryl trimyristate-dynasan (DYNASAN 114 ®) 4.08% squalene | 2.0% polysorbate 80 (TWEEN ® 80) | 1% aluminum hydroxide |
| NP-23 | 0.4% DOTAP | 0.25% glyceryl trimyristate-dynasan (DYNASAN 114 ®) 4.08% squalene | 0.5% sorbitan trioleate (SPAN ® 85) 2.0% polysorbate 80 (TWEEN ® 80 | 1% aluminum hydroxide |
| NP-24 | 0.4% DOTAP | 0.25% glyceryl trimyristate-dynasan (DYNASAN 114 ®) 4.08% squalene | 0.25% sorbitan trioleate (SPAN ® 85) 2.0% polysorbate 80 (TWEEN ® 80 | 1% aluminum hydroxide |
| NP-25 | 0.4% DOTAP | 5% squalene | 0.5% sorbitan trioleate (SPAN ® 85) 2.0% polysorbate 80 (TWEEN ® 80 | 1% aluminum hydroxide |
| NP-26 | 0.4% DOTAP | 5% squalene | 0.5% sorbitan monostearate (SPAN ® 60) 2% polysorbate 80 (TWEEN ® 80) | 1% aluminum hydroxide |
| NP-27 | 0.4% DOTAP | 0.25% glyceryl trimyristate-dynasan (DYNASAN 114 ®) 4.08% squalene | 2% sorbitan trioleate (SPAN ® 85) 2% polysorbate 80 (TWEEN ® 80) | 1% aluminum hydroxide |
| NP-28 | 0.5-5.0 mg/ml DOTAP | 0.2-10% (v/v) squalene | 0.01-2.5% (v/v) polysorbate 80 (TWEEN ® 80) | |
| NP-29 | 0.4% (w/w) DOTAP | 4.3% (w/w) squalene | 0.5% (w/w) sorbitan trioleate (SPAN ® 85) 0.5% (w/w) polysorbate 80 (TWEEN ® 80) | |

TABLE 1-continued

Nanoparticle Formulations.

| Name | Cationic Lipid(s) % (w/v) or mg/ml | Oil(s) % (w/v) or mg/ml | Surfactant(s) % (w/v) or mg/ml | Additional Ingredients % (w/v), mg/ml, or mM |
|---|---|---|---|---|
| NP-30 | 30 mg/ml DOTAP chloride | 37.5 mg/ml squalene | 37 mg/ml sorbitan monostearate (SPAN ® 60) 37 mg/ml polysorbate 80 (TWEEN ® 80) | 10 mM sodium citrate |
| NP-31 | 30 mg/ml DOTAP chloride | 37.5 mg/ml squalene | 37 mg/ml sorbitan monostearate (SPAN ® 60) 37 mg/ml polysorbate 80 (TWEEN ® 80) | 0.4 mg Fe/ml 5 nm oleic acid-coated iron oxide nanoparticles 10 mM sodium citrate dihydrate |

In some embodiments, nanoparticles provided herein comprise: sorbitan monostearate (e.g., SPAN-60), polysorbate 80 (e.g., TWEEN-80), DOTAP, squalene, and no solid particles. In some embodiments, nanoparticles provided herein comprise: sorbitan monostearate (e.g., SPAN-60), polysorbate 80 (e.g., TWEEN-80), DOTAP, squalene, and iron oxide particles. In some embodiments, nanoparticles provided herein comprise an immune stimulant. In some embodiments, the immune stimulant is squalene. In some embodiments, the immune stimulant is Miglyol 810 or Miglyol 812. In some embodiments, the immune stimulant can decrease the total amount of protein produced, but can increase the immune response to a composition provided herein (e.g., when delivered as a vaccine). In some embodiments, the immune stimulant can increase the total amount of protein produced, but can decrease the immune response to a composition provided herein.

Nanoparticles provided herein can be of various average diameters in size. In some embodiments, nanoparticles provided herein have an average diameter (z-average hydrodynamic diameter, measured by dynamic light scattering) ranging from about 20 nm to about 200 nm. In some embodiments, the z-average diameter of the nanoparticle ranges from about 20 nm to about 150 nm, from about 20 nm to about 100 nm, from about 20 nm to about 80 nm, from about 20 nm to about 60 nm. In some embodiments, the z-average diameter of the nanoparticle) ranges from about 40 nm to about 200 nm, from about 40 nm to about 150 nm, from about 40 nm to about 100 nm, from about 40 nm to about 90 nm, from about 40 nm to about 80 nm, or from about 40 nm to about 60 nm. In one embodiment, the z-average diameter of the nanoparticle is from about 40 nm to about 80 nm. In some embodiments, the z-average diameter of the nanoparticle is from about 40 nm to about 60 nm. In some embodiments, the nanoparticle is up to 100 nm in diameter. In some embodiments, the nanoparticle is 50 to 70 nm in diameter. In some embodiments, the nanoparticle is 40 to 80 nm in diameter. In some embodiments, the inorganic particle (e.g., iron oxide) within the hydrophobic core of the nanoparticle can be an average diameter (number weighted average diameter) ranging from about 3 nm to about 50 nm. For instance, the inorganic particle can have an average diameter of about 5 nm, about 10 nm, about 15 nm, about 20 nm, about 25 nm, about 30 nm, about 35 nm, about 40 nm, about 45 nm, or about 50 nm. In some embodiments, the ratio of esters and lipids yield a particle size between 30 nm and 200 nm. In some embodiments, the ratio of esters and lipids yield a particle size between 40 nm and 70 nm.

Nanoparticles provided herein may be characterized by the polydispersity index (PDI), which is an indication of their quality with respect to size distribution. In some embodiments, average polydispersity index (PDI) of the nanoparticles provided herein ranges from about 0.1 to about 0.5. In some embodiments, the average PDI of the nanoparticles can range from about 0.2 to about 0.5, from about 0.1 to about 0.4, from about 0.2 to about 0.4, from about 0.2 to about 0.3, or from about 0.1 to about 0.3.

In some embodiments, the nanoparticles provided herein comprise an oil-to-surfactant molar ratio ranging from about 0.1:1 to about 20:1, from about 0.5:1 to about 12:1, from about 0.5:1 to about 9:1, from about 0.5:1 to about 5:1, from about 0.5:1 to about 3:1, or from about 0.5:1 to about 1:1. In some embodiments, the nanoparticles provided herein comprise a hydrophilic surfactant-to-lipid ratio ranging from about 0.1:1 to about 2:1, from about 0.2:1 to about 1.5:1, from about 0.3:1 to about 1:1, from about 0.5:1 to about 1:1, or from about 0.6:1 to about 1:1. In some embodiments, the nanoparticles provided herein comprise a hydrophobic surfactant-to-lipid ratio ranging from about 0.1:1 to about 5:1, from about 0.2:1 to about 3:1, from about 0.3:1 to about 2:1, from about 0.5:1 to about 2:1, or from about 1:1 to about 2:1.

In some embodiments, the nanoparticles provided herein comprise from about 0.2% to about 40% w/v liquid oil, from about 0.001% to about 10% w/v inorganic solid nanoparticle, from about 0.2% to about 10% w/v lipid, from about 0.25% to about 5% w/v hydrophobic surfactant, and from about 0.5% to about 10% w/v hydrophilic surfactant. In some embodiments, the lipid comprises a cationic lipid, and the oil comprises squalene, and/or the hydrophobic surfactant comprises sorbitan ester.

In some embodiments, nanoparticles provided herein comprise a ratio of the esters that yields a hydrophilic-lipophilic balance between 8 and 11.

In some embodiments, nucleic acids provided herein are incorporated, associated with, or complexed a lipid carrier provided herein to form a lipid carrier-nucleic acid complex. The lipid carrier-nucleic acid complex is formed via non-covalent interactions or via reversible covalent interactions.

Nucleic Acids

Provided herein is a composition comprising a nucleic acid. In some embodiments, the nucleic acid is in complex with the nanoparticle. In some embodiments, the nucleic acid is in complex with the membrane of the nanoparticle. In some embodiments, the nucleic acid is in complex with the hydrophilic surface of the nanoparticle. In some embodiments, the nucleic acid is within the nanoparticle. In some embodiments, the nucleic acid is within the hydrophobic core.

In some embodiments, the nucleic acid is deoxyribonucleic acid (DNA) or ribonucleic acid (RNA). The nucleic acid may be linear or include a secondary structure (e.g., a hair pin). In some embodiments, the nucleic acid is a polynucleotide comprising modified nucleotides or bases, and/or their analogs. A polynucleotide may comprise modified nucleotides, such as methylated nucleotides and their analogs. If present, modification to the nucleotide structure may be imparted before or after assembly of compositions provided herein. Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A (N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-($C_1$-$C_6$)-alkyluracil, 5-methyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-methylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-O-methyl-U. Any one or any combination of these modified nucleobases may be included in the self-replicating RNA of the invention. Many of these modified nucleobases and their corresponding ribonucleosides are available from commercial suppliers. If desired, the nucleic acid can contain phosphoramidate, phosphorothioate, and/or methylphosphonate linkages. The RNA sequence can be modified with respect to its codon usage, for example, to increase translation efficacy and half-life of the RNA. A poly A tail (e.g., of about 30 adenosine residues or more) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methyltransferase, which catalyzes the construction of N7-monomethylated cap 0 structures). Cap structure can provide stability and translational efficacy to the RNA molecule. The 5' cap of the RNA molecule may be further modified by a 2'-O-Methyltransferase which results in the generation of a cap 1 structure (m7Gppp [m2'-O]N), which may further increase translation efficacy. A cap 1 structure may also increase in vivo potency.

In some embodiments, compositions provided herein comprise one or more nucleic acids. In some embodiments, compositions provided herein comprise two or more nucleic acids. In some embodiments, compositions provided herein comprise at least one DNA. In some embodiments, compositions provided herein comprise at least one RNA. In some embodiments, compositions provided herein comprise at least one DNA and at least one RNA. In some embodiments, nucleic acids provided herein are present in an amount of above 5 ng to about 1 mg. In some embodiments, nucleic acids provided herein are present in an amount of up to about 25, 50, 75, 100, 150, 175 ng. In some embodiments, nucleic acids provided herein are present in an amount of up to about 1 mg. In some embodiments, nucleic acids provided herein are present in an amount of about 0.05 µg, 0.1 µg, 0.2 µg, 0.5 µg, 1 µg, 5 µg, 10 µg, 12.5 µg, 15 µg, 25 µg, 40 µg, 50 µg, 100 µg, 200 µg, 300 µg, 400 µg, 500 µg, 600 µg, 700 µg, 800 µg, 900 µg, 1 mg. In some embodiments, nucleic acids provided herein are present in an amount of 0.05 µg, 0.1 µg, 0.2 µg, 0.5 µg, 1 µg, 5 µg, 10 µg, 12.5 µg, 15 µg, 25 µg, 40 µg, 50 µg, 100 µg, 200 µg, 300 µg, 400 µg, 500 µg, 600 µg, 700 µg, 800 µg, 900 µg, 1 mg. In some embodiments, the nucleic acid is at least about 200, 250, 500, 750, 1000, 2000, 3000, 4000, 5000, 6000, 7000, 8000, 9000, 10,000, 11,000, 12,000, 13,000, 14,000, 15,000, 16,000, 17,000, 18,000, 19,000, or 20,000 nucleotides in length. In some embodiments, the nucleic acid is up to about 7000, 8000, 9000, 10,000, 11,000, 12,000, 13,000, 14,000, 15,000, 16,000, 17,000, 18,000, 19,000, or 20,000 nucleotides in length. In some embodiments, the nucleic acid is about 7500, 10,000, 15,000, or 20,000 nucleotides in length.

In some embodiments, compositions provided herein comprise at least one nucleic acid sequence comprising a sequence which encodes a viral antigen. In some embodiments, the viral antigen is a surface protein or a transmembrane protein. In some embodiments, the viral antigen is a spike protein, a glycoprotein, or an envelope protein. In some embodiments, the viral antigen is a coronavirus antigen or a fragment thereof. In some embodiments, the antigen is a SARS-CoV antigen, a SARS-CoV-2 antigen, a Middle East Respiratory Syndrome (MERS) coronavirus antigen, a fragment or a variant thereof.

SARS-CoV-2 Spike Protein Antigens

Severe acute respiratory syndrome coronavirus 2 (SARS-CoV-2) is a virus that causes the infectious disease called COVID-19 (coronavirus disease 2019). Variants of the SARS-CoV-2 virus include the alpha, beta, delta, mu, and omicron variants. The Alpha (B.1.1.7), Beta (B.1.351, B.1.351.2, B.1.351.3), Delta (B.1.617.2, AY.1, AY.2, AY.3), Omicron (B.1.1.529), and Gamma (P.1, P.1.1, P.1.2) variants circulating in the United States are classified as variants of concern. SARS-CoV-2 structure, its components, along with variants and their various features are described below.

Coronaviruses are single-stranded RNA-enveloped viruses that have four structural proteins, known as the S (spike), E (envelope), M (membrane), and N (nucleocapsid) proteins. The N protein holds the RNA genome, and the S, E, and M proteins together create the viral envelope. In SARS-CoV-2, the spike (S) protein facilitates viral attachment and fusion with the membrane of a host cell via the host cell receptor, angiotensin-converting enzyme 2 (ACE2). The S protein mediates viral cell entry into the host cell. The total length of SARS-CoV-2 spike is generally 1273 amino acids and includes a signal peptide (amino acids 1-13) located at the N-terminus, the S1 subunit (residues 14-685), and the S2 subunit (residues 686-1273); the last two regions are responsible for receptor binding and membrane fusion, respectively. In the S1 subunit, there is an N-terminal domain (14-305 residues) and a receptor-binding domain (RBD, 319-541 residues). The fusion peptide (FP) (788-806 residues), heptapeptide repeat sequence 1 (HR1) (912-984 residues), HR2 (1163-1213 residues), TM domain (1213-1237 residues), and cytoplasm domain (1237-1273 residues) comprise the S2 subunit. Specifically, the HR1 and HR2 are composed of a repetitive heptapeptide: HPPHCPC, where H is a hydrophobic or traditionally bulky residue, P is a polar or hydrophilic residue, and C is another charged residue. HR1 and HR2 form a six-helical bundle (6-HB) referred to as the "stem helix" domain of the S2 protein. When the RBD binds to ACE2 on a host cell membrane, S2 changes conformation by inserting FP into the target cell membrane, exposing the pre-hairpin coiled-coil of the HR1 domain and triggering interaction between the HR2 domain and HR1 trimer to form the stem helix (6-HB), thus bringing the viral envelope and cell membrane into proximity for viral fusion and entry. The wild-type spike protein amino acid sequence is provided in SEQ ID NO: 17. The amino acid sequence corresponding to the stem helix is provided in SEQ ID NO: 18.

Coronaviruses regularly undergo antigenic drift, a type of genetic variation in viruses, arising from the accumulation of mutations in viral genes that encode for virus-surface proteins that host antibodies recognize. Several SARS-CoV-2 variants have been identified by public health agencies and are provided in Table 2 below.

TABLE 2

SARS-CoV-2 Variants.

| WHO label | Pango lineage* | GISAID clade | Nextstrain clade | Additional spike amino acid changes monitored ° | Earliest documented samples | Date of designation |
|---|---|---|---|---|---|---|
| Alpha | B.1.1.7 # | GRY | 20I (V1) | N501Y<br>A570D<br>P681H<br>T716I<br>S982A<br>D1118H | United Kingdom, September 2020 | 18 Dec. 2020 |
| Beta | B.1.351 | GH/501Y.V2 | 20H (V2) | D80A<br>D215G<br>K417N<br>A701V<br>N501Y<br>E484K | South Africa, May 2020 | 18 Dec. 2020 |
| Gamma | P.1 | GR/501Y.V3 | 20J (V3) | L18F<br>T20N<br>P26S<br>D138Y<br>R190S<br>K417T<br>E484K<br>N501Y<br>H655Y<br>T1027I | Brazil, November 2020 | 11 Jan. 2021 |

TABLE 2-continued

SARS-CoV-2 Variants.

| WHO label | Pango lineage* | GISAID clade | Nextstrain clade | Additional spike amino acid changes monitored ° | Earliest documented samples | Date of designation |
|---|---|---|---|---|---|---|
| Delta | B.1.617.2§ | G/478K.V1 | 21A | T19R, L452R, T478K, P681R, D950N | India, October 2020 | VOI: 4 Apr. 2021 VOC: 11 May 2021 |
| Eta | B.1.525 | G/484K.V3 | 21D | | Multiple countries, December 2020 | 17 Mar. 2021 |
| Iota | B.1.526 | GH/253G.V1 | 21F | | United States of America, November 2020 | 24 Mar. 2021 |
| Kappa | B.1.617.1 | G/452R.V3 | 21B | | India, October 2020 | 4 Apr. 2021 |
| Lambda | C.37 | GR/452Q.V1 | 21G | | Peru, December 2020 | 14 Jun. 2021 |
| Mu | B.1.621 | GH | 21H | | Colombia, January 2021 | 30 Aug. 2021 |
| Omicron | B.1.1.529 | GR/484A | 21K | A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F | November 2021 South Africa, Hong Kong, Belgium, Israel | VOC: 26 Nov. 2021 |

*includes all descendent lineages. The full list of Pango lineages can be found here: Error! Hyperlink reference not valid.cov-lineages.org/lineage_list.html; for FAQ, visit: pango.network/faqs/

In some embodiments, the antigen is derived from a SARS-CoV-2 variant of concern (VOC). A variant of concern is a variant for which there is evidence of an increase in transmissibility, more severe disease (e.g., increased hospitalizations or deaths), significant reduction in neutralization by antibodies generated during previous infection or vaccination, reduced effectiveness of treatments or vaccines, or diagnostic detection failures. Possible attributes of a variant of concern include, in addition to the possible attributes of a variant of interest, (i) evidence of impact on diagnostics, treatments, or vaccines, (ii) widespread interference with diagnostic test targets, (iii) evidence of substantially decreased susceptibility to one or more class of therapies, (iv) evidence of significant decreased neutralization by antibodies generated during previous infection or vaccination, (v) evidence of reduced vaccine-induced protection from severe disease, (vi) evidence of increased transmissibility, and (vii) evidence of increased disease severity.

In some embodiments, the antigen is derived from a SARS-CoV-2 variant of interest (VOI). A variant of interest is a variant with specific genetic markers that have been associated with changes to receptor binding, reduced neutralization by antibodies generated against previous infection or vaccination, reduced efficacy of treatments, potential diagnostic impact, or predicted increase in transmissibility or disease severity. Possible attributes of a variant of interest include (i) specific genetic markers that are predicted to affect transmission, diagnostics, therapeutics, or immune escape, (ii) evidence that it is the cause of an increased proportion of cases or unique outbreak clusters, and (iii) limited prevalence or expansion in the US or in other countries.

In some embodiments, nucleic acids provided herein encodes for an antigen listed in Table 3 or a fragment thereof. In some embodiments, the nucleic acid comprises at least 80%, 85%, 90%, 95%, 96%, 97%, 98%, or 99% sequence identity to a sequence which specifically binds an antigen listed in Table 3. In some embodiments, the nucleic acid provided herein comprises at least 80%, 85%, 90%, 95%, 96%, 97%, 98%, or 99% sequence similarity to an RNA sequence listed in Table 3. Percent (%) sequence identity for a given sequence relative to a reference sequence is defined as the percentage of identical residues identified after aligning the two sequences and introducing gaps if necessary, to achieve the maximum percent sequence identity. Percent identity can be calculated using alignment methods known in the art, for instance alignment of the sequences can be conducted using publicly available software such as BLAST, Align, ClustalW2. Those skilled in the art can determine the appropriate parameters for alignment, but the default parameters for BLAST are specifically contemplated. Exemplary nucleic acid sequences encoding for exemplary SARS-CoV-2 antigens are listed in Table 3.

TABLE 3

SARS CoV-2 Spike Protein Nucleic Acid and Amino Acid Sequences.

| SEQ ID NOS | Name | Variant |
|---|---|---|
| SEQ ID NO: 1 | Delta V5 RNA Sequence | A.1 |
| SEQ ID NO: 2 | K995P-V996P RNA Sequence | A.1-preF |
| SEQ ID NO: 3 | D614G RNA Sequence | B.1 |
| SEQ ID NO: 4 | B.1.351-PP-D614G RNA Sequence | Beta-preF |
| SEQ ID NO: 5 | B.1.1.7-PP-D614G RNA Sequence | Alpha-preF |
| SEQ ID NO: 6 | Delta.AY1-S2P-wtFur RNA Sequence | Delta-preF |
| SEQ ID NO: 7 | Delta.AY1-S2P-wtFur-newKozak RNA Sequence | Delta-preF-kozak |
| SEQ ID NO: 8 | Omicron-B.1.1.529 RNA Sequence | Omicron |
| SEQ ID NO: 9 | Delta V5 Amino Acid Sequence | A.1 |
| SEQ ID NO: 10 | K995P-V996P Amino Acid Sequence | A.1-preF |
| SEQ ID NO: 11 | D614G Amino Acid Sequence | B.1 |
| SEQ ID NO: 12 | B.1.351-PP-D614G Amino Acid Sequence | Beta-preF |
| SEQ ID NO: 13 | B.1.1.7-PP-D614G Amino Acid Sequence | Alpha-preF |
| SEQ ID NO: 14 | Delta.AY1-S2P-wtFur Amino Acid Sequence | Delta-preF |
| SEQ ID NO: 15 | Delta.AY1-S2P-wtFur-newKozak | Delta-preF-kozak |
| SEQ ID NO: 16 | Omicron-B.1.1.529 Amino Acid Sequence | Omicron |
| SEQ ID NO: 17 | Wuhan-Hu-1-Full-Length Wild-Type Spike Protein Amino Acid Sequence | Wild-type (WT) Spike |
| SEQ ID NO: 18 | Wuhan-Hu-1-Wild-Type Spike Protein-Stem Helix Amino Acid Sequence [residues 913 to 1213] | Wild-type (WT) Spike |
| SEQ ID NO: 19 | Omicron-B.1.1.529 Amino Acid Sequence of the Stem Helix (HR1 and HR2) | Omicron |

*Pre-F is stabilized pre-fusion spike protein

In some embodiments, compositions provided herein comprise a SARS-CoV-2 spike protein or a fragment thereof, wherein the SARS-CoV-2 spike protein amino acid sequence is encoded by any nucleic acid sequence disclosed herein. In some embodiments, compositions provided herein comprise an RNA sequence set forth in any one of SEQ ID NOS: 1 to 8. In some embodiments, the spike protein has an amino acid sequence corresponding to any of the sequences set forth in any one of SEQ ID NOS: 9 to 19.

In some embodiments, compositions provided herein comprise a nucleic acid sequence comprising (i) any vector backbone, and (ii) any of the antigen sequences set forth in SEQ ID NOS: 24-31, or any nucleic acid sequence which is at least 80%, or at least 85%, or at least 90%, or at least 93%, or at least 95%, or at least 97% identical to any of the antigen sequences set forth in SEQ ID NOS: 24-31.

In some embodiments, compositions provided herein comprise a nucleic acid sequence comprising (i) a vector backbone as set forth in one of SEQ ID NOS: 32-38, and (ii) any sequence encoding an amino acid sequence defining any SARS-CoV-2 spike protein, or any sequence encoding an amino acid sequence which is at least 80%, or at least 85%, or at least 90%, or at least 93%, or at least 95%, or at least 97% identical to the sequence defining any SARS-CoV-2 spike protein.

In some embodiments, compositions provided herein comprise a nucleic acid sequence comprising (i) a vector backbone as set forth in one of SEQ ID NOS: 32-38, or any sequence which is at least 80%, or at least 85%, or at least 90%, or at least 93%, or at least 95%, or at least 97% identical to a sequence as set forth in one of SEQ ID NOS: 32-38, and (ii) any sequence encoding an amino acid sequence defining any SARS-CoV-2 spike protein, or any sequence encoding an amino acid sequence which is at least 80%, or at least 85%, or at least 90%, or at least 93%, or at least 95%, or at least 97% identical to the sequence defining any SARS-CoV-2 spike protein.

Self-Replicating Nucleic Acids

Provided herein are compositions comprising a self-replicating nucleic acid. The SARS-CoV-2 spike antigen provided herein or fragment thereof can be encoded as part of a self-replicating nucleic acid construct. In some embodiments, the self-replicating nucleic acid molecule comprises at least one or more genes selected from the group consisting of viral replicases, viral proteases, viral helicases and other nonstructural viral proteins, and also comprises 5'- and 3'-end cis-active replication sequences, and an antigenic sequence encoding a SARS-CoV-2 spike protein. A subgenomic promoter that directs expression of the heterologous sequence(s) can be included in the self-replicating nucleotide sequence. If desired, a heterologous sequence may be fused in frame to other coding regions in the self-replicating RNA and/or may be under the control of an internal ribosome entry site (IRES).

In some embodiments, the self-replicating nucleotide sequence is a self-replicating RNA molecule. Self-replicating RNA molecules are designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alphavirus, such as Sindbis virus (SIN), Semliki forest virus and Venezuelan equine encephalitis virus (VEE), one or more genes encoding viral structural proteins, such as capsid and/or envelope glycoproteins, can be omitted. If desired, self-replicating RNA molecules of the invention can be designed to induce production of infectious viral particles that are attenuated or virulent, or to produce viral particles that are capable of a single round of subsequent infection.

A self-replicating RNA molecule can, when delivered to an animal cell even without any proteins, lead to the production of multiple daughter RNAs by transcription from itself (or from an antisense copy of itself). The self-replicating RNA can be directly translated after delivery to a cell, and this translation provides an RNA-dependent RNA polymerase which then produces transcripts from the delivered RNA. Thus, the delivered RNA leads to the production of multiple daughter RNAs. These transcripts are antisense relative to the delivered RNA and may be translated themselves to provide in situ expression of encoded SARS-CoV-2 spike protein, or may be transcribed to provide further transcripts with the same sense as the delivered RNA which are translated to provide in situ expression of the encoded SARS-CoV-2 spike protein (s).

The self-replicating RNA molecules provided herein can contain one or more modified nucleotides and therefore have improved stability and be resistant to degradation and clearance in vivo, and other advantages. In some embodiments, self-replicating RNA molecules that contain modified nucleotides avoid or reduce stimulation of endosomal and cytoplasmic immune receptors when the self-replicating RNA is delivered into a cell. This permits self-replication, amplification and expression of protein to occur. This also reduces safety concerns relative to self-replicating RNA that does not contain modified nucleotides, because the self-replicating RNA that contains modified nucleotides reduce activation of the innate immune system and subsequent undesired consequences (e.g., inflammation at injection site, irritation at injection site, pain, and the like). RNA molecules produced as a result of self-replication are recognized as foreign nucleic acids by the cytoplasmic immune receptors. Thus, self-replicating RNA molecules that contain modified nucleotides provide for efficient amplification of the RNA in a host cell and expression of SARS-CoV-2 spike proteins, as well as adjuvant effects.

In some embodiments, self-replicating RNA molecules provided herein contain at least one modified nucleotide. Modified nucleotides that are not part of the 5' cap (e.g., in addition to the modification that are part of the 5" cap) can be used. Accordingly, the self-replicating RNA molecule can contain a modified nucleotide at a single position, can contain a particular modified nucleotide (e.g., pseudouridine, N6-methyladenosine, 5-methylcytidine, 5-methyluridine) at two or more positions, or can contain two, three, four, five, six, seven, eight, nine, ten or more modified nucleotides (e.g., each at one or more positions). Preferably, the self-replicating RNA molecules comprise modified nucleotides that contain a modification on or in the nitrogenous base, but do not contain modified sugar or phosphate moieties. In some examples, between 0.001% and 99% or 100% of the nucleotides in a self-replicating RNA molecule are modified nucleotides. For example, 0.001%-25%, 0.01%-25%, 0.1%-25%, or 1%-25% of the nucleotides in a self-replicating RNA molecule are modified nucleotides. In other examples, between 0.001% and 99% or 100% of a particular unmodified nucleotide in a self-replicating RNA molecule is replaced with a modified nucleotide. For example, about 1% of the nucleotides in the self-replicating RNA molecule that contain uridine can be modified, such as by replacement of uridine with pseudouridine. In other examples, the desired amount (percentage) of two, three, or four particular nucleotides (nucleotides that contain uridine, cytidine, guanosine, or adenine) in a self-replicating RNA molecule are modified nucleotides. For example, 0.001%-25%, 0.01%-25%, 0.1%-25%, or 1%-25% of a particular nucleotide in a self-replicating RNA molecule are modified nucleotides. In other examples, 0.001%-20%, 0.001%-15%, 0.001%-10%, 0.01%-20%, 0.01%-15%, 0.1%-25, 0.01%-10%, 1%-20%, 1%-15%, 1%-10%, or about 5%, about 10%, about 15%, about 20% of a particular nucleotide in a self-replicating RNA molecule are modified nucleotides. It is preferred that less than 100% of the nucleotides in a self-replicating RNA molecule are modified nucleotides. It is also preferred that less than 100% of a particular nucleotide in a self-replicating RNA molecule are modified nucleotides. Thus, preferred self-replicating RNA molecules comprise at least some unmodified nucleotides.

Self-replicating RNA molecules that comprise at least one modified nucleotide can be prepared using any suitable method. Several suitable methods are known in the art for producing RNA molecules that contain modified nucleotides. For example, a self-replicating RNA molecule that contains modified nucleotides can be prepared by transcribing (e.g., in vitro transcription) a DNA that encodes the self-replicating RNA molecule using a suitable DNA-dependent RNA polymerase, such as T7 phage RNA polymerase, SP6 phage RNA polymerase, T3 phage RNA polymerase, and the like, or mutants of these polymerases which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of nucleotide analogs into a self-replicating RNA may be engineered, for example, to alter the stability of such RNA molecules, to increase resistance against RNases, to establish replication after introduction into appropriate host cells ("infectivity" of the RNA), and/or to induce or reduce innate and adaptive immune responses. Suitable synthetic methods can be used alone, or in combination with one or more other methods (e.g., recombinant DNA or RNA technology), to produce a self-replicating RNA molecule that contain one or more modified nucleotides.

Nucleic acid synthesis can also be performed using suitable recombinant methods that are well-known and conventional in the art, including cloning, processing, and/or expression of polynucleotides and gene products encoded by such polynucleotides. DNA shuffling by random fragmentation and PCR reassembly of gene fragments and synthetic polynucleotides are examples of known techniques that can be used to design and engineer polynucleotide sequences. Site-directed mutagenesis can be used to alter nucleic acids and the encoded proteins, for example, to insert new restriction sites, alter glycosylation patterns, change codon preference, produce splice variants, introduce mutations and the like.

In some embodiments, nucleic acids provided herein encode for an RNA polymerase. In some embodiments, nucleic acids provided herein encode for a viral RNA polymerase. In some embodiments, nucleic acids provided herein encode for: (1) a viral RNA polymerase; and (2) a protein or functional fragment thereof. In some embodiments, compositions provided herein comprise a first nucleic acid encoding for a viral RNA polymerase; and a second nucleic acid encoding for a protein or functional fragment thereof.

Provided herein are compositions comprising a self-replicating RNA. A self-replicating RNA (also called a replicon) includes any genetic element, for example, a plasmid, cosmid, bacmid, phage or virus that is capable of replication largely under its own control. Self-replication provides a system for self-amplification of the nucleic acids provided herein in mammalian cells. In some embodiments, the self-replicating RNA is single stranded. In some embodiments, the self-replicating RNA is double stranded.

An RNA polymerase provided herein can include but is not limited to: an alphavirus RNA polymerase, an Eastern equine encephalitis virus (EEEV) RNA polymerase, a Western equine encephalitis virus (WEEV), Venezuelan equine encephalitis virus (VEEV), Also, Chikungunya virus (CHIKV), Semliki Forest virus (SFV), or Sindbis virus (SINV). In some embodiments, the RNA polymerase is a VEEV RNA polymerase. In some embodiments, the nucleic acid encoding for the RNA polymerase comprises at least 85% identity to the nucleic acid sequence of SEQ ID NO: 20. In some embodiments, the nucleic acid encoding for the RNA polymerase comprises at least 90% identity to the nucleic acid sequence of SEQ ID NO: 20. In some embodiments, the nucleic acid encoding for the RNA polymerase comprises at least 95% identity to the nucleic acid sequence of SEQ ID NO: 20. In some embodiments, the nucleic acid encoding for the RNA polymerase comprises at least 99% identity to the nucleic acid sequence of SEQ ID NO: 20. In some embodiments, the nucleic acid encoding for the RNA polymerase is SEQ ID NO: 20.

In some embodiments, the amino acid sequence for VEEV RNA polymerase comprises at least 85% identity to RELPVLDSAAFNVECFKKYACNNEYWETFKENPIRLTEEN VVNYITKLKGP (SEQ ID NO: 21), TQM-RELPVLDSAAFNVECFKKYACNNEYWE TFKENPIRLTE (SEQ ID NO: 22), or SEQ ID NO: 23. In some embodiments, the amino acid sequence for VEEV RNA polymerase comprises at least 90% identity to SEQ ID NO:

21, SEQ ID NO: 22, or SEQ ID NO: 23. In some embodiments, the amino acid sequence for VEEV RNA polymerase comprises at least 95% identity to SEQ ID NO: 21, SEQ ID NO: 22, or SEQ ID NO: 23. In some embodiments, the amino acid sequence for VEEV RNA polymerase comprises at least 99% identity to SEQ ID NO: 21, SEQ ID NO: 22, or SEQ ID NO: 23. In some embodiments, the amino acid sequence for VEEV RNA polymerase is SEQ ID NO: 21, SEQ ID NO: 22, or SEQ ID NO: 23.

Provided herein are compositions and methods comprising replicon RNA (repRNA) encoding one or more structural proteins from a non-enveloped virus. In some embodiments, the repRNA encodes a protease. In some embodiments, the repRNA encodes the 3CD protease. In some embodiments, the structural protein and the protease are co-expressed. In further embodiments, the repRNA comprises one or more open reading frames. In some embodiments, the open reading frames are separated by an internal ribosomal entry site (IRES). In some embodiments, the open reading frames are separated by a ribosomal skipping peptide sequence. In some embodiments the ribosomal skipping peptide sequence is from Thosea asigna virus (T2A).

Combination Compositions

Provided herein are compositions comprising a nanoparticle described herein and a nucleic acid encoding for a coronavirus antigen. Further provided herein is a nanoemulsion comprising a plurality of nanoparticles provided herein. In some embodiments, the nucleic acid further encodes for an RNA polymerase. In some embodiments the RNA polymerase is a viral RNA polymerase. In some embodiments, the nucleic acid encoding the RNA polymerase is on the same nucleic acid strand as the nucleic acid sequence encoding the protein (e.g., cis). In some embodiments, the nucleic acid encoding the RNA polymerase is on a different nucleic acid strand as the nucleic acid sequence encoding the protein (e.g., trans). In some embodiments, the nucleic acid encoding the RNA polymerase is a DNA molecule. In some embodiments, nucleic acid sequences encoding an antigen provided herein are DNA or RNA molecules. In some embodiments, antigens provided herein are encoded by DNA. Nanoparticles for inclusion include, without limitation, any one of NP-1 to NP-30, or any one of NP-1 to NP-31. Nucleic acids for inclusion include, without limitation, comprise a region comprising any one of, or a plurality of, SEQ ID NOS: 1 to 8 and/or SEQ ID NOS: 24 to 31. In some instances, the nucleic acids further comprise a region encoding for an RNA polymerase, e.g., a region comprising a sequence of SEQ ID NO: 20.

Compositions provided herein can be characterized by an nitrogen:phosphate (N:P) molar ratio. The N:P ratio is determined by the amount of cationic lipid in the nanoparticle which contain nitrogen and the amount of nucleic acid used in the composition which contain negatively charged phosphates. A molar ratio of the lipid carrier to the nucleic acid can be chosen to increase the delivery efficiency of the nucleic acid, increase the ability of the nucleic acid-carrying nanoemulsion composition to elicit an immune response to the antigen, increase the ability of the nucleic acid-carrying nanoemulsion composition to elicit the production of antibody titers to the antigen in a subject. In some embodiments, compositions provided herein have a molar ratio of the lipid carrier to the nucleic acid can be characterized by the nitrogen-to-phosphate molar ratio, which can range from about 0.01:1 to about 1000:1, for instance, from about 0.2:1 to about 500:1, from about 0.5:1 to about 150:1, from about 1:1 to about 150:1, from about 1:1 to about 125:1, from about 1:1 to about 100:1, from about 1:1 to about 50:1, from about 1:1 to about 50:1, from about 5:1 to about 50:1, from about 5:1 to about 25:1, or from about 10:1 to about 20:1. In certain embodiments, the molar ratio of the lipid carrier to the nucleic acid, characterized by the nitrogen-to-phosphate (N:P) molar ratio, ranges from about 1:1 to about 150:1, from about 5:1 to about 25:1, or from about 10:1 to about 20:1. In one embodiment, the N:P molar ratio of the nanoemulsion composition is about 15:1. In some embodiments, the nanoparticle comprises a nucleic acid provided herein covalently attached to the membrane.

Compositions provided herein can be characterized by an oil-to-surfactant molar ratio. In some embodiments, the oil-to-surfactant ratio is the molar ratio of squalene:DOTAP, hydrophobic surfactant, and hydrophilic surfactant. In some embodiments, the oil-to-surfactant ratio is the molar ratio of squalene:DOTAP, sorbitan monostearate, and polysorbate 80. In some embodiments, the oil-to surfactant molar ratio ranges from about 0.1:1 to about 20:1, from about 0.5:1 to about 12:1, from about 0.5:1 to about 9:1, from about 0.5:1 to about 5:1, from about 0.5:1 to about 3:1, or from about 0.5:1 to about 1:1. In some embodiments, the oil-to-surfactant molar ratio is at least about 0.1:1, at least about 0.2:1, at least about 0.3:1, at least about 0.4:1, at least about 0.5:1, at least about 0.6:1, at least about 0.7:1. In some embodiments, the oil-to surfactant molar ratio is at least about 0.4:1 up to 1:1.

Compositions provided herein can be characterized by hydrophilic surfactant-to-lipid (e.g., cationic lipid) ratio. In some embodiments, the hydrophilic surfactant-to-lipid ratio ranges from about 0.1:1 to about 2:1, from about 0.2:1 to about 1.5:1, from about 0.3:1 to about 1:1, from about 0.5:1 to about 1:1, or from about 0.6:1 to about 1:1. Compositions provided herein can be characterized by hydrophobic surfactant-to-lipid (e.g., cationic lipid) ratio ranging. In some embodiments, the hydrophobic surfactant-to-lipid ratio ranges from about 0.1:1 to about 5:1, from about 0.2:1 to about 3:1, from about 0.3:1 to about 2:1, from about 0.5:1 to about 2:1, or from about 1:1 to about 2:1.

Provided herein is a dried composition comprising a sorbitan fatty acid ester, an ethoxylated sorbitan ester, a cationic lipid, an immune stimulant, and an RNA. Further provided herein are dried compositions, wherein the dried composition comprises sorbitan monostearate (e.g., SPAN-60), polysorbate 80 (e.g., TWEEN-80), DOTAP, an immune stimulant, and an RNA.

Thermally Stable, Dried, and Lyophilized SARS-CoV-2 RNA Vaccines

Provided herein are dried or lyophilized compositions and vaccines. Further provided herein are pharmaceutical compositions comprising a dried or lyophilized composition provided herein that is reconstituted in a suitable diluent and a pharmaceutically acceptable carrier. In some embodiments, the diluent is aqueous. In some embodiments, the diluent is water.

A lyophilized composition is generated by a low temperature dehydration process involving the freezing of the composition, followed by a lowering of pressure, and removal of ice by sublimation. In certain cases, lyophilisation also involves the removal of bound water molecules through a desorption process. In some embodiments, compositions and vaccines provided herein are spray-dried. Spray drying is a process by which a solution is fed through an atomizer to create a spray, which is thereafter exposed to a heated gas stream to promote rapid evaporation. When sufficient liquid mass has evaporated, the remaining solid material in the droplet forms particles which are then separated from the gas stream (e.g., using a filter or a cyclone). Drying aids in the storage of the compositions and vaccines provided herein at higher temperatures (e.g., greater than 4° C.) as compared to the sub-zero temperatures needed for the storage of existing mRNA vaccines. In some embodiments, dried compositions and lyophilized compositions provided herein comprise (a) a lipid carrier, wherein the lipid carrier is a nanoemulsion comprising: (i) a hydrophobic core; (ii) one or more inorganic nanoparticles; (iii) and one or more lipids; (b) one or more nucleic acids; and (c) at least one cryoprotectant. In some embodiments, the cryoprotectant is selected from the group consisting of: sucrose, maltose, trehalose, mannitol, glucose, and any combinations thereof. Additional examples of cryoprotectants include but are not limited to: dimethyl sulfoxide (DMSO), glycerol, propylene glycol, ethylene glycol, 3-O-methyl-D-glucopyranose (3-OMG), olyethylene glycol (PEG), 1,2-propanediol, acetamide, trehalose, formamide, sugars, proteins, and carbohydrates.

In some embodiments, compositions and methods provided herein comprise at least one cryoprotectant. Exemplary cryoprotectants for inclusion are, but not limited to, sucrose, maltose, trehalose, mannitol, or glucose, and any combinations thereof. In some embodiments, additional or alternative cryoprotectant for inclusion is sorbitol, ribitol, erthritol, threitol, ethylene glycol, or fructose. In some embodiments, additional or alternative cryoprotectant for inclusion is dimethyl sulfoxide (DMSO), glycerol, propylene glycol, ethylene glycol, 3-O-methyl-D-glucopyranose (3-OMG), polyethylene glycol (PEG), 1,2-propanediol, acetamide, trehalose, formamide, sugars, proteins, and carbohydrates. In some embodiments, the cryoprotectant is present at about 1% w/v to at about 20% w/v, preferably about 10% w/v to at about 20% w/v, and more preferably at about 10% w/v. In certain aspects of the disclosure, the cryoprotectant is sucrose. In some aspects of the disclosure, the cryoprotectant is maltose. In some aspects of the disclosure, the cryoprotectant is trehalose. In some aspects of the disclosure, the cryoprotectant is mannitol. In some aspects of the disclosure, the cryoprotectant is glucose. In some embodiments, the cryoprotectant is present in an amount of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 325, 350, 375, 400, 450, 500 or more mg. In some embodiments, the cryoprotectant is present in an amount of about 50 to about 500 mg. In some embodiments, the cryoprotectant is present in an amount of about 200 to about 300 mg. In some embodiments, the cryoprotectant is present in an amount of about 250 mg. In some embodiments, the cryoprotectant is present in amount of a lyophilized composition by weight of at least about 50, 55, 60, 65, 70, 75, 80, 85, 90, 95 or more percent. In some embodiments, the cryoprotectant is present in amount of a lyophilized composition by weight of about 95%. In some embodiments, the cryoprotectant is present in amount of a lyophilized composition by weight of 80 to 98%, 85 to 98%, 90 to 98%, or 94 to 96%. In some embodiments, the cryoprotectant is a sugar. In some embodiments, the sugar is sucrose, maltose, trehalose, mannitol, or glucose. In some embodiments, the sugar is sucrose. In some embodiments, the sucrose is present in an amount of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 325, 350, 375, 400, 450, 500 or more mg. In some embodiments, the sucrose is present in an amount of about 50 to about 500 mg. In some embodiments, the sucrose is present in an amount of about 200 to about 300 mg. In some embodiments, the sucrose is present in an amount of about 250 mg. In some embodiments, the sucrose is present in amount of a lyophilized composition by weight of at least about 50, 55, 60, 65, 70, 75, 80, 85, 90, 95 or more percent. In some embodiments, the sucrose is present in amount of a lyophilized composition by weight of about 95%. In some embodiments, the sucrose is present in amount of a lyophilized composition by weight of 80 to 98%, 85 to 98%, 90 to 98%, or 94 to 96%.

In some embodiments, the cryoprotectant is sucrose. In some embodiments, the cryoprotectant is at a concentration of at least about 0.1% w/v. In some embodiments, the cryoprotectant is at a concentration of about 1% w/v to at about 20% w/v. In some embodiments, the cryoprotectant is at a concentration of about 10% w/v to at about 20% w/v. In some embodiments, the cryoprotectant is at a concentration of about 10% w/v.

In some embodiments, compositions and vaccines provided herein are thermally stable. A composition is considered thermally stable when the composition resists the action of heat or cold and maintains its properties, such as the ability to protect a nucleic acid molecule from degradation at given temperature. In some embodiments, compositions and vaccines provided herein are thermally stable at about 25° C. or standard room temperature. In some embodiments, compositions and vaccines provided herein are thermally stable at about 45° C. In some embodiments, compositions and vaccines provided herein are thermally stable at about 20° C. In some embodiments, compositions and vaccines provided herein are thermally stable at about 2° C. to about 8° C. In some embodiments, compositions and vaccines provided herein are thermally stable at a temperature of at least about −80° C., at least about −20° C., at least about 0° C., at least about 2° C., at least about 4° C., at least about 6° C., at least about 8° C., at least about 10° C., at least about 20° C., at least about 25° C., at least about 30° C., at least about 37° C., up to 45° C. In some embodiments, compositions and vaccines provided herein are thermally stable for at least about 5 day, at least about 1 week, at least about 2 weeks, at least about 1 month, up to 3 months. In some embodiments, compositions and vaccines provided herein are stored at a temperature of at least about 4° C. up to 37° C. for at least about 5 day, at least about 1 week, at least about 2 weeks, at least about 1 month, up to 3 months. In some embodiments, compositions and vaccines provided herein are stored at a temperature of at least about 20° C. up to 25° C. for at least about 5 day, at least about 1 week, at least about 2 weeks, at least about 1 month, up to 3 months.

Also provided herein are methods for preparing a lyophilized composition comprising obtaining a lipid carrier, wherein the lipid carrier is a nanoemulsion comprising a hydrophobic core, one or more inorganic nanoparticles and one or more lipids; incorporating one or more nucleic acid into the lipid carrier to form a lipid carrier-nucleic acid complex; adding at least one cryoprotectant to the lipid carrier-nucleic acid complex to form a formulation; and lyophilizing the formulation to form a lyophilized composition.

Further provided herein are methods for preparing a spray-dried composition comprising obtaining a lipid carrier, wherein the lipid carrier is a nanoemulsion comprising a hydrophobic core, one or more inorganic nanoparticles and one or more lipids; incorporating one or more nucleic acid into the lipid carrier to form a lipid carrier-nucleic acid complex; adding at least one cryoprotectant to the lipid carrier-nucleic acid complex to form a formulation; and spray drying the formulation to form a spray-dried composition.

Further provided herein are methods for reconstituting a lyophilized composition comprising: obtaining a lipid carrier, wherein the lipid carrier is a nanoemulsion comprising a hydrophobic core, one or more inorganic nanoparticles, and one or more lipids; incorporating one or more nucleic acid into the said lipid carrier to form a lipid carrier-nucleic acid complex; adding at least one cryoprotectant to the lipid carrier-nucleic acid complex to form a formulation; lyophilizing the formulation to form a lyophilized composition; and reconstituting the lyophilized composition in a suitable diluent.

Further provided herein are methods for reconstituting a spray-dried composition comprising: obtaining a lipid carrier, wherein the lipid carrier is a nanoemulsion comprising a hydrophobic core, one or more inorganic nanoparticles, and one or more lipids, incorporating one or more nucleic acid into the said lipid carrier to form a lipid carrier-nucleic acid complex; adding at least one cryoprotectant to the lipid carrier-nucleic acid complex to form a formulation; spray drying the formulation to form a spray-dried composition; and reconstituting the spray-dried composition in a suitable diluent.

Pharmaceutical Compositions

Provided herein is a suspension comprising a composition provided herein. In some embodiments, suspensions provided herein comprise a plurality of nanoparticles or compositions provided herein. In some embodiments, compositions provided herein are in a suspension, optionally a homogeneous suspension. In some embodiments, compositions provided herein are in an emulsion form.

Also provided herein is a pharmaceutical composition comprising a composition provided herein. In some embodiments, compositions provided herein are combined with pharmaceutically acceptable salts, excipients, and/or carriers to form a pharmaceutical composition. Pharmaceutical salts, excipients, and carriers may be chosen based on the route of administration, the location of the target issue, and the time course of delivery of the drug. A pharmaceutically acceptable carrier or excipient may include solvents, dispersion media, coatings, antibacterial and antifungal agents, isotonic and absorption delaying agents, etc., compatible with pharmaceutical administration.

In some embodiments, the pharmaceutical composition is in the form of a solid, semi-solid, liquid or gas (aerosol). Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent. Among the acceptable vehicles and solvents that may be employed are water, Ringer's solution, U.S.P., and isotonic sodium chloride solution. In addition, sterile, fixed oils are employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Dosing

Compositions provided herein may be formulated in dosage unit form for ease of administration and uniformity of dosage. A dosage unit form is a physically discrete unit of a composition provided herein appropriate for a subject to be treated. It will be understood, however, that the total usage of compositions provided herein will be decided by the attending physician within the scope of sound medical judgment. For any composition provided herein the therapeutically effective dose can be estimated initially either in cell culture assays or in animal models, such as mice, rabbits, dogs, pigs, or non-human primates. The animal model is also used to achieve a desirable concentration range and route of administration. Such information can then be used to determine useful doses and routes for administration in humans. Therapeutic efficacy and toxicity of compositions provided herein can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies may be used in formulating a range of dosage for human use.

Administration

Provided herein are compositions and pharmaceutical compositions for administering to a subject in need thereof. In some embodiments, pharmaceutical compositions provided here are in a form which allows for compositions provided herein to be administered to a subject.

In some embodiments, the administering is local administration or systemic administration. In some embodiments, a composition described herein is formulated for administration/for use in administration via a subcutaneous, intradermal, intramuscular, inhalation, intravenous, intraperitoneal, intracranial, or intrathecal route. In some embodiments, the administering is every 1, 2, 4, 6, 8, 12, 24, 36, or 48 hours. In some embodiments, the administering is daily, weekly, or monthly. In some embodiments, the administering is repeated at least about every 28 days or 56 days.

In some embodiments, a single dose of a composition provided herein is administered to a subject. In some embodiments, a composition or pharmaceutical composition provided herein is administered to the subject by two doses. In some embodiments, a second dose of a composition or pharmaceutical composition provided herein is administered about 28 days or 56 days after the first dose. In some embodiments, a first dose is administered, and a second dose is administered about 14 days later, or about 21 days later, or about 28 days later, or about 35 days later, or about 42 days later, or about 49 days later, or about 56 days later, or about 63 days later, or about 70 days later, or about 77 days later, or about 84 days later. In some embodiments, the second dose is administered about 10-90 days following administration of the first dose, or about 15-85 days following administration of the first dose, or about 20-80 days following administration of the first dose, or about 25-75 days following administration of the first dose, or about 30-70 days following administration of the first dose, or about 35-65 days following administration of the first dose, or about 40-60 days following administration of the first dose.

In some embodiments, a third dose of a composition or pharmaceutical composition provided herein is administered to a subject. In some embodiments, the third dose is administered about 1 month following administration of the second dose, about 2 months following administration of the second dose, about 3 months following administration of the second dose, about 4 months following administration of the second dose, about 5 months following administration of the second dose, about 6 months following administration of the second dose, about 7 months following administration of the second dose, about 8 months following administration of the second dose, about 9 months following administration of the second dose, about 10 months following administration of the second dose, about 11 months following administration of the second dose, about 12 months following administration of the second dose, about 13 months following administration of the second dose, about 14 months following administration of the second dose, about 15 months following administration of the second dose, about 16 months following administration of the second dose, about 17 months following administration of the second dose, or about 18 months following administration of the second dose.

Therapeutic Applications

Provided herein are methods of treating or preventing a disease in a subject. In some embodiments, compositions described herein are used for the treatment of an infection. In some embodiments, compositions described herein are used for the treatment of a respiratory infection. In some embodiments, the infection is a viral infection. In some embodiments, the viral infection is from a Coronavirus. In some embodiments, the coronavirus is SARS-CoV-2. In some embodiments, the Coronavirus is MERS or SARS. In some embodiments, the Coronavirus is a SARS-CoV-2 variant.

Further provided herein are methods for immunoprotecting the subject. In some embodiments, the method reduces the severity of a SARS-CoV-2 infection. In some embodiments, the method prevents a SARS-CoV-2 infection in a subject. In some embodiments, compositions described herein are used for enhancing the immune response of a subject to a viral antigen provided herein or a variant thereof. In some embodiments, compositions described herein are used for immunizing a subject. In some embodiments, compositions described herein are used for the reduction of severity of an infection in a subject. In some embodiments, compositions described herein provide for reduction of severity or duration of symptoms associated with an infection in a subject.

In some embodiments, the subject is a mammal. In some embodiments, the subject is a human. In some embodiments, the subject has or is suspected of having a viral infection. In some embodiments, the subject has or is suspected of having a coronavirus infection. In some embodiments, the subject has or is suspected of having COVID-19 caused by the SARS-CoV-2 virus or a variant thereof. In some embodiments, the subject has COVID-19 caused by the delta variant of SARS-CoV-2. In some embodiments, the subject has COVID-19 caused by the omicron variant of SARS-CoV-2. In some embodiments, the subject is administered a composition provided herein that comprises a nucleic acid encoding a stem helix region of the SARS-CoV-2 spike protein. In some embodiments, the subject is immunocompromised. In some embodiments, the subject is immunosuppressed prior to administration (e.g., by an immunosuppressive agent). In some embodiments, the subject has received at least one dose of a SARS-CoV-2 vaccine prior to administration of a composition provided herein. In some embodiments, the subject had previously exhibited at least one symptom of an upper respiratory infection.

Kits

Provided herein is a kit comprising a composition provided herein, a pharmaceutical composition provided herein; and optionally, a delivery system for administration to a subject.

In some embodiments, the kit further comprises one or more surfactants. In some embodiments, a formulation of a composition described herein is prepared in a single container for administration. In some embodiments, a formulation of a composition described herein is prepared two containers for administration, separating the nucleic acid from the nanoparticle carrier. As used herein, "container" includes vessel, vial, ampule, tube, cup, box, bottle, flask, jar, dish, well of a single-well or multi-well apparatus, reservoir, tank, or the like, or other device in which the herein disclosed compositions may be placed, stored and/or transported, and accessed to remove the contents. Examples of such containers include glass and/or plastic sealed or re-sealable tubes and ampules, including those having a rubber septum or other sealing means that is compatible with withdrawal of the contents using a needle and syringe. In some implementations, the containers are RNase free.

In some embodiments, the kit comprises: (a) a lipid carrier, wherein the lipid carrier is a nanoemulsion comprising a hydrophobic core, one or more lipids, and one or more surfactants; and (b) at least one nucleic acid sequence, which comprises a sequence which encodes a sequence capable of expressing an antigen, wherein the antigen is a SARS-CoV-2 spike protein.

Exemplary Embodiments

Provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the at least one nucleic acid comprises a sequence at least 85% identical to SEQ ID NOS: 1-8. Further provided herein, the nucleic acid is at least 85% identical to the sequence SEQ ID NO: 4. Further provided herein, the nucleic acid is at least 85% identical to the sequence SEQ ID NO: 8. Further provided herein, the nucleic acid is identical to SEQ ID NO: 4. Further provided herein, the nucleic acid is identical to SEQ ID NO: 8. Further provided herein, the nucleic acid is in complex with the lipid carrier. Further provided herein, the nucleic acid further codes for an RNA polymerase. Further provided herein, the RNA polymerase is a Venezuelan equine encephalitis virus (VEEV) RNA polymerase. Further provided herein, the nucleic acid coding the RNA polymerase comprises the nucleic acid sequence of SEQ ID NO: 20. Further provided herein, the liquid oil is α-tocopherol, coconut oil, grapeseed oil, lauroyl polyoxylglyceride, mineral oil, monoacylglycerol, palmkemal oil, olive oil, paraffin oil, peanut oil, propolis, squalene, squalane, solanesol, soy lecithin, soybean oil, sunflower oil, a triglyceride, or vitamin E. Further provided herein, the triglyceride is capric triglyceride, caprylic triglyceride, a caprylic and capric triglyceride, a triglyceride ester, or myristic acid triglycerin. Further provided herein, the cationic lipid is 1,2-dioleoyloxy-3 (trimethylammonium)propane (DOTAP), 3β-[N—(N',N'-dimethylaminoethane) carbamoyl]cholesterol (DC Cholesterol), dimethyldioctadecylammonium (DDA); 1,2-dimyristoyl 3-trimethylammoniumpropane(DMTAP),dipalmitoyl(C16:0)trimethyl ammonium propane (DPTAP), distearoyltrimethylammonium propane (DSTAP), N-[l-(2,3-dioleyloxy)propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis(2-hydroxydodecyl)amino)ethyl)(2-hydroxydodecyl)amino)ethyl)piperazin-1-yl)ethyl)azanediyl) bis(dodecan-2-ol) (C12-200), 306Oi10, tetrakis(8-methylnonyl) 3,3',3",3'"-(((methylazanediyl) bis(propane-3,1 diyl))bis (azanetriyl))tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl)azanediyl)bis(hexane-6,1-diyl)bis(2-hexyldecanoate); ALC-0159, 2-[(polyethylene glycol)-2000]-N,N-ditetradecylacetamide; (3-sitosterol, (3S,8S,9S,10R,13R,14S,17R)-17-((2R,5R)-5-ethyl-6-methylheptan-2-yl)-10,13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 30-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9",9"',9"",9""'-((((benzene-1,3,5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4,1-diyl))bis(azanetriyl))tetrakis(ethane-2,1-diyl) (9Z,9'Z,9"Z,9"'Z,12Z,12',12"Z,12"'Z)-tetrakis (octadeca-9,12-dienoate); PEG2000-DMG, (R)-2,3-bis (myristoyloxy)propyl-1-(methoxy poly(ethylene glycol) 2000) carbamate; TT3, or N1,N3,N5-tris(3-(didodecylamino)propyl)benzene-1,3,5-tricarboxamide.

Provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the nucleic acid comprises a sequence coding a SARS-CoV-2 omicron variant spike protein antigen or functional variant thereof. Further provided herein, the SARS-CoV-2 omicron variant spike protein antigen or functional variant thereof comprises the stem helix of the SARS-CoV-2 omicron variant spike protein antigen. Further provided herein, the stem helix of the SARS-CoV-2 omicron variant spike protein antigen comprises an amino acid sequence of SEQ ID NO: 19. Further provided herein, the nucleic acid coding the SARS-CoV-2 omicron variant spike protein antigen comprises a polynucleotide sequence of SEQ ID NO: 8. Further provided herein, the SARS-CoV-2 omicron variant spike protein comprises the amino acid sequence of SEQ ID NO: 16. Further provided herein, the nucleic acid is in complex with the lipid carrier. Further provided herein, the nucleic acid further codes for an RNA polymerase. Further provided herein, the RNA polymerase is a Venezuelan equine encephalitis virus (VEEV) RNA polymerase. Further provided herein, the nucleic acid encoding for the RNA polymerase comprises the nucleic acid sequence of SEQ ID NO: 20. Further provided herein, the liquid oil is α-tocopherol, coconut oil, grapeseed oil, lauroyl polyoxylglyceride, mineral oil, monoacylglycerol, palmkemal oil, olive oil, paraffin oil, peanut oil, propolis, squalene, squalane, solanesol, soy lecithin, soybean oil, sunflower oil, a triglyceride, or vitamin E. Further provided herein, the triglyceride is capric triglyceride, caprylic triglyceride, a caprylic and capric triglyceride, a triglyceride ester, or myristic acid triglycerin. Further provided herein, the cationic lipid is 1,2-dioleoyloxy-3 (trimethylammonium)propane (DOTAP), 3β-[N—(N',N'-dimethylaminoethane) carbamoyl]cholesterol (DC Cholesterol), dimethyldioctadecylammonium (DDA); 1,2-dimyristoyl 3-trimethylammoniumpropane(DMTAP),dipalmitoyl(C16:0)trimethyl ammonium propane (DPTAP), distearoyltrimethylammonium propane (DSTAP), N-[l-(2,3-dioleyloxy)propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis(2-hydroxydodecyl)amino)ethyl)(2-hydroxydodecyl)amino)ethyl)piperazin-1-yl)ethyl)azanediyl) bis(dodecan-2-ol) (C12-200), 306Oi10, tetrakis(8-methylnonyl) 3,3',3",3'"-(((methylazanediyl) bis(propane-3,1 diyl))bis (azanetriyl))tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl)azanediyl)bis(hexane-6,1-diyl)bis(2-hexyldecanoate); ALC-0159, 2-[(polyethylene glycol)-2000]-N,N-ditetradecylacetamide; (3-sitosterol, (3S,8S,9S,10R,13R,14S,17R)-17-((2R,5R)-5-ethyl-6-methylheptan-2-yl)-10,13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide;

cKK-E12, 3,6-bis(4-(bis(2-hydroxydodecyl)amino)butyl) piperazine-2,5-dione; DC-Cholesterol, 3β-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9",9''',9"",9"'''-((((benzene-1,3, 5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4,1-diyl))bis(azanetriyl))tetrakis(ethane-2, 1-diyl) (9Z,9'Z,9"Z,9'''Z,12Z,12',12"Z,12'''Z)-tetrakis (octadeca-9,12-dienoate); PEG2000-DMG, (R)-2,3-bis (myristoyloxy)propyl-1-(methoxy poly(ethylene glycol) 2000) carbamate; TT3, or N1,N3,N5-tris(3-(didodecylamino)propyl)benzene-1,3,5-tricarboxamide.

Provided herein are compositions, wherein the compositions comprise: a lipid carrier, wherein the lipid carrier comprises: liquid oil; and surfactants, wherein the surfactants comprise: a cationic lipid; a hydrophilic surfactant; and a hydrophobic surfactant; and at least one nucleic acid, wherein the nucleic acid comprises a sequence coding a stem helix of SARS-CoV-2 spike protein antigen or functional variant thereof. Further provided herein, the SARS-CoV-2 spike protein antigen is derived from an alpha variant of SARS-CoV-2, a beta variant of SARS-CoV-2, a delta variant of SARS-CoV-2, a gamma variant of SARS-CoV-2, a mu variant of SARS-CoV-2, or an omicron variant of SARS-CoV-2. Further provided herein, the stem helix of the SARS-CoV-2 spike protein antigen comprises an amino acid sequence of SEQ ID NO: 18 or SEQ ID NO: 19. Further provided herein, the nucleic acid is in complex with the lipid carrier. Further provided herein, the nucleic acid further codes for an RNA polymerase. Further provided herein, the RNA polymerase is a Venezuelan equine encephalitis virus (VEEV) RNA polymerase. Further provided herein, the nucleic acid coding the RNA polymerase comprises the nucleic acid sequence of SEQ ID NO: 20. Further provided herein, the liquid oil is α-tocopherol, coconut oil, grapeseed oil, lauroyl polyoxylglyceride, mineral oil, monoacylglycerol, palmkernal oil, olive oil, paraffin oil, peanut oil, propolis, squalene, squalane, solanesol, soy lecithin, soybean oil, sunflower oil, a triglyceride, or vitamin E. Further provided herein, the triglyceride is capric triglyceride, caprylic triglyceride, a caprylic and capric triglyceride, a triglyceride ester, or myristic acid triglycerin. Further provided herein, the cationic lipid is 1,2-dioleoyloxy-3 (trimethylammonium)propane (DOTAP), 3β-[N—(N',N'-dimethylaminoethane) carbamoyl]cholesterol (DC Cholesterol), dimethyldioctadecylammonium (DDA); 1,2-dimyristoyl 3-trimethylammoniumpropane(DMTAP),dipalmitoyl(C16: 0)trimethyl ammonium propane (DPTAP), distearoyltrimethylammonium propane (DSTAP), N-[l-(2,3-dioleyloxy) propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1, 1'-((2-(4-(2-((2-(bis(2-hydroxydodecyl)amino)ethyl)(2-hydroxydodecyl)amino)ethyl)piperazin-1-yl)ethyl)azanediyl) bis(dodecan-2-ol) (C12-200), 306Oi10, tetrakis(8-methylnonyl) 3,3',3",3'''-(((methylazanediyl) bis(propane-3,1 diyl))bis (azanetriyl))tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl)azanediyl)bis(hexane-6,1-diyl)bis(2-hexyldecanoate); ALC-0159, 2-[(polyethylene glycol)-2000]-N, N-ditetradecylacetamide; (3-sitosterol, (3S,8S,9S,10R,13R, 14S,17R)-17-((2R,5R)-5-ethyl-6-methylheptan-2-yl)-10, 13-dimethyl-2,3,4,7,8,9,10,11,12,13,14,15,16,17-tetradecahydro-TH-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R, 13R,14S,17R)-10,13-dimethyl-17-((R)-6-methylheptan-2-yl)-2,3,4,7,8,9,10,11,12,13,14,15,16,17-tetradecahydro-TH-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 3β-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9",9''',9"",9"'''-((((benzene-1,3, 5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4,1-diyl))bis(azanetriyl))tetrakis(ethane-2, 1-diyl) (9Z,9'Z,9"Z,9'''Z,12Z,12',12"Z,12'''Z)-tetrakis (octadeca-9,12-dienoate); PEG2000-DMG, (R)-2,3-bis (myristoyloxy)propyl-1-(methoxy poly(ethylene glycol) 2000) carbamate; TT3, or N1,N3,N5-tris(3-(didodecylamino)propyl)benzene-1,3,5-tricarboxamide.

Provided herein are compositions, wherein the compositions comprise: a lipid carrier, wherein the lipid carrier comprises: liquid oil; an inorganic nanoparticle, wherein the inorganic nanoparticle comprises iron oxide present in an amount of about 0.2 mg/ml 12 nm iron oxide; and surfactants, wherein the surfactants comprise a cationic lipid; and at least one nucleic acid, wherein the nucleic acid comprises a sequence coding a SARS-CoV-2 spike protein antigen sequence or functional variant thereof. Further provided herein are compositions comprising: a nucleic acid present in an amount of up to about 200 ug; a cationic lipid present in a concentration of up to about 1.5 mg/ml; iron oxide present in a concentration of up to about 0.01 mg/ml; squalene present in a concentration of up to about 1.88 mg/ml; sorbitan monostearate present in a concentration of up to about 1.86 mg/ml; polysorbate 80 present in a concentration of up to about 1.86 mg/ml; sucrose present in a concentration of up to about 50 mg/ml; and optionally, citric acid monohydrate present in a concentration of up to about 2.1 mg/ml. Further provided herein are compositions wherein the nucleic acid is RNA or DNA. Further provided herein are compositions wherein the nucleic acid is RNA and present in an amount of up to about 50 ug. Further provided herein, the liquid oil is α-tocopherol, coconut oil, grapeseed oil, lauroyl polyoxylglyceride, mineral oil, monoacylglycerol, palmkemal oil, olive oil, paraffin oil, peanut oil, propolis, squalene, squalane, solanesol, soy lecithin, soybean oil, sunflower oil, a triglyceride, or vitamin E. Further provided herein, the triglyceride is capric triglyceride, caprylic triglyceride, a caprylic and capric triglyceride, a triglyceride ester, or myristic acid triglycerin. Further provided herein, the cationic lipid is 1,2-dioleoyloxy-3-(trimethylammonium)propane (DOTAP), 3β-[N—(N',N'-dimethylaminoethane) carbamoyl]cholesterol (DC Cholesterol), dimethyldioctadecylammonium (DDA); 1,2-dimyristoyl 3-trimethylammoniumpropane(DMTAP),dipalmitoyl (C16:0)trimethyl ammonium propane (DPTAP), distearoyltrimethylammonium propane (DSTAP), N-[1-(2,3-dioleyloxy)propyl]N,N,Ntrimethylammonium, chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), and 1,2-dilinoleyloxy-3-dimethylaminopropane (DLinDMA),1,1'-((2-(4-(2-((2-(bis(2-hydroxydodecyl)amino)ethyl)(2-hydroxydodecyl)amino)ethyl)piperazin-1-yl)ethyl)azanediyl)bis(dodecan-2-ol) (C12-200), 306Oi10, tetrakis(8-methylnonyl) 3,3',3",3"'-(((methylazanediyl) bis(propane-3,1 diyl))bis (azanetriyl)) tetrapropionate, 9A1P9, decyl (2-(dioctylammonio)ethyl) phosphate; A2-Iso5-2DC18, ethyl 5,5-di((Z)-heptadec-8-en-1-yl)-1-(3-(pyrrolidin-1-yl)propyl)-2,5-dihydro-1H-imidazole-2-carboxylate; ALC-0315, ((4-hydroxybutyl) azanediyl)bis(hexane-6,1-diyl)bis(2-hexyldecanoate); ALC-0159, 2-[(polyethylene glycol)-2000]-N,N-ditetradecylacetamide; (3-sitosterol, (3S,8S,9S,10R,13R,14S,17R)-17-((2R,5R)-5-ethyl-6-methylheptan-2-yl)-10, 13-dimethyl-2,3,4,7,8,9,10,11,12,13,14,15,16,17-tetradecahydro-1H-cyclopenta[a]phenanthren-3-ol; BAME-O16B, bis(2-(dodecyldisulfanyl)ethyl) 3,3'-((3-methyl-9-oxo-10-oxa-13,14-dithia-3,6-diazahexacosyl)azanediyl) dipropionate; BHEM-Cholesterol, 2-(((((3S,8S,9S,10R, 13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide; cKK-E12, 3,6-bis(4-(bis(2-hydroxydodecyl)amino)butyl) piperazine-2,5-dione; DC-Cholesterol, 30-[N—(N',N'-dimethylaminoethane)-carbamoyl]cholesterol; DLin-MC3-DMA, (6Z,9Z,28Z,31Z)-heptatriaconta-6,9,28,31-tetraen-19-yl 4-(dimethylamino) butanoate; DOPE, 1,2-dioleoyl-sn-glycero-3-phosphoethanolamine; DOSPA, 2,3-dioleyloxy-N-[2-(sperminecarboxamido)ethyl]-N,N-dimethyl-1-propanaminium trifluoroacetate; DSPC, 1,2-distearoyl-sn-glycero-3-phosphocholine; ePC, ethylphosphatidylcholine; FTT5, hexa(octan-3-yl) 9,9',9",9"',9"",9""'-((((benzene-1,3, 5-tricarbonyl)yris(azanediyl)) tris (propane-3,1-diyl)) tris(azanetriyl))hexanonanoate; Lipid H (SM-102), heptadecan-9-yl 8-((2-hydroxyethyl)(6-oxo-6-(undecyloxy)hexyl) amino) octanoate; OF-Deg-Lin, (((3,6-dioxopiperazine-2,5-diyl)bis(butane-4,1-diyl))bis(azanetriyl))tetrakis(ethane-2, 1-diyl) (9Z,9'Z,9"Z,9"'Z,12Z,12',12"Z,12"'Z)-tetrakis (octadeca-9,12-dienoate); PEG2000-DMG, (R)-2,3-bis(myristoyloxy)propyl-1-(methoxy poly(ethylene glycol) 2000) carbamate; TT3, or N1,N3,N5-tris(3-(didodecylamino)propyl)benzene-1,3,5-tricarboxamide. Further provided herein, the nucleic acid is in complex with the lipid carrier. Further provided herein, the SARS-CoV-2 spike protein antigen is derived from an alpha variant of SARS-CoV-2, a beta variant of SARS-CoV-2, a delta variant of SARS-CoV-2, a gamma variant of SARS-CoV-2, a mu variant of SARS-CoV-2, or an omicron variant of SARS-CoV-2. Further provided herein, the SARS-CoV-2 spike protein is derived from a variant of SARS-CoV-2 comprising an amino acid substitution of D614G. Further provided herein, the nucleic acid comprises a sequence as set forth in one of SEQ ID NOS: 1-8. Further provided herein, the SARS-CoV-2 spike protein antigen sequence or functional variant thereof has an amino acid sequence as set forth in one of SEQ ID NOS: 9-16. Further provided herein, the nucleic acid further codes for an RNA polymerase. Further provided herein, the RNA polymerase is a Venezuelan equine encephalitis virus (VEEV) RNA polymerase. Further provided herein, the nucleic acid coding the RNA polymerase comprises the nucleic acid sequence of SEQ ID NO: 20.

Provided herein are compositions, wherein the compositions comprise: (a) a lipid carrier, wherein the lipid carrier is a nanoemulsion comprising: about 30 mg/mL DOTAP chloride; about 37.5 mg/mL squalene; about 37 mg/ml sorbitan monostearate; about 37 mg/ml polysorbate 80; about 10 mM sodium citrate; and about 0.2 mg Fe/ml 12 nm oleic acid-coated iron oxide nanoparticles; and (b) at least one nucleic acid, wherein the at least one nucleic acid comprises a sequence coding a SARS-CoV-2 spike protein antigen sequence or functional variant thereof. Further provided herein are compositions comprising: a nucleic acid present in an amount of up to about 200 ug; a cationic lipid present in a concentration of up to about 1.5 mg/ml; iron oxide present in a concentration of up to about 0.01 mg/ml; squalene present in a concentration of up to about 1.88 mg/ml; sorbitan monostearate present in a concentration of up to about 1.86 mg/ml; polysorbate 80 present in a concentration of up to about 1.86 mg/ml; sucrose present in a concentration of up to about 50 mg/ml; and optionally, citric acid monohydrate present in a concentration of up to about 2.1 mg/ml. Further provided herein are compositions wherein the nucleic acid is RNA or DNA. Further provided herein are compositions wherein the nucleic acid is RNA and present in an amount of up to about 50 ug. Further provided herein, the composition further comprises sucrose. Further provided herein, the sucrose is present in an about of about 50 mg. Further provided herein, the nucleic acid is in complex with the lipid carrier. Further provided herein, the SARS-CoV-2 spike protein antigen is derived from an alpha variant of SARS-CoV-2, a beta variant of SARS-CoV-2, a delta variant of SARS-CoV-2, a gamma variant of SARS-CoV-2, a mu variant of SARS-CoV-2, or an omicron variant of SARS-CoV-2. Further provided herein, the SARS-CoV-2 spike protein is derived from a variant of SARS-CoV-2 comprising an amino acid substitution of D614G. Further provided herein, the nucleic acid comprises a sequence as set forth in one of SEQ ID NOS: 1-8. Further provided herein, the SARS-CoV-2 spike protein antigen sequence or functional variant thereof has an amino acid sequence as set forth in one of SEQ ID NOS: 9-17. Further provided herein, the nucleic acid further codes for an RNA polymerase. Further provided herein, the RNA polymerase is a Venezuelan equine encephalitis virus (VEEV) RNA polymerase. Further provided herein, the nucleic acid encoding the RNA polymerase comprises the nucleic acid sequence set forth in SEQ ID NO: 20.

Provided herein are compositions, wherein the compositions comprise: comprising: (a) a lipid carrier, wherein the lipid carrier is a nanoemulsion comprising: DOTAP chloride present in an amount of about 0.75 mg; squalene present in an amount of about 0.94 mg; sorbitan monostearate present in an amount of about 0.93 mg; polysorbate 80 present in an amount of about 0.93 mg; citric acid monohydrate present in an amount of about 1.05 mg; and oleic acid-coated iron oxide nanoparticles present in an amount of about 0.005 mg; and (b) at least one nucleic acid, wherein the at least one nucleic acid comprises a sequence coding a SARS-CoV-2 spike protein antigen sequence or functional variant thereof. Further provided herein, the at least one nucleic acid sequence is present in an amount of up to about 100 micrograms (μg). Further provided herein, the at least one nucleic acid sequence is present in an amount of up to about 25 μg. Further provided herein, the composition further comprises sucrose. Further provided herein the sucrose is present in an about of about 50 milligrams (mg). Further provided herein, the nucleic acid is in complex with the lipid carrier. Further provided herein, the SARS-CoV-2 spike protein antigen is derived from an alpha variant of SARS-CoV-2, a beta variant of SARS-CoV-2, a delta variant of SARS-CoV-2, a gamma variant of SARS-CoV-2, a mu variant of SARS-CoV-2, or an omicron variant of SARS-CoV-2. Further provided herein, the SARS-CoV-2 spike protein is derived from a variant of SARS-CoV-2 comprising an amino acid substitution of D614G. Further provided herein, the nucleic acid comprises a sequence as set forth in one of SEQ ID NOS: 1-8. Further provided herein, the SARS-CoV-2 spike protein antigen sequence or functional variant thereof has an amino acid sequence as set forth in one of SEQ ID NOS: 9-19. Further provided herein, the nucleic acid further codes for an RNA polymerase. Further provided herein, the RNA polymerase is a Venezuelan equine encephalitis virus (VEEV) RNA polymerase. Further provided herein, the nucleic acid coding the RNA polymerase comprises the nucleic acid sequence of SEQ ID NO: 20. Further provided herein, the composition is lyophilized.

Provided herein is a suspension comprising the composition provided herein. Further provided herein is a pharmaceutical composition comprising the composition provided herein and a pharmaceutically acceptable excipient.

Provided herein are compositions, wherein the compositions comprise a) a lipid carrier, wherein the lipid carrier is a nanoemulsion comprising a hydrophobic core, one or more inorganic nanoparticles and one or more lipids; b) at least one nucleic acid sequence, wherein the nucleic acid sequence comprises a sequence capable of expressing an antigen, wherein the antigen is a SARS-CoV-2 spike protein. Further provided herein, the nucleic acid is RNA. Further provided herein, the composition further comprises a nucleic acid polymerase or a further nucleic acid encoding a sequence capable of expressing a nucleic acid polymerase. Further provided herein, compositions further comprise an RNA polymerase or a further nucleic acid encoding a sequence capable of expressing an RNA polymerase. Further provided herein, the nucleic acid comprises a sequence as set forth in one of SEQ ID NOS: 1-8. Further provided herein, the SARS-CoV-2 spike protein has an amino acid sequence as set forth in one of SEQ ID NOS: 9-19. Further provided herein, the nucleic acid comprises a sequence as set forth in SEQ ID NO: 1. Further provided herein, the nucleic acid comprises a sequence as set forth in SEQ ID NO: 2. Further provided herein, the nucleic acid comprises a sequence as set forth in SEQ ID NO: 3. Further provided herein, the nucleic acid comprises a sequence as set forth in SEQ ID NO: 4. Further provided herein, the nucleic acid comprises a sequence as set forth in SEQ ID NO: 5. Further provided herein, the nucleic acid comprises a sequence as set forth in SEQ ID NO: 6. Further provided herein, the nucleic acid comprises a sequence as set forth in SEQ ID NO: 7. Further provided herein, the nucleic acid sequence comprises a sequence as set forth in SEQ ID NO: 8. Further provided herein, the SARS-CoV-2 spike protein is derived from the alpha variant of SARS-CoV-2. Further provided herein, the SARS-CoV-2 spike protein is derived from the beta variant of SARS-CoV-2. Further provided herein, the SARS-CoV-2 spike protein is derived from the delta variant of SARS-CoV-2. Further provided herein, the SARS-CoV-2 spike protein is derived from the gamma variant of SARS-CoV-2. Further provided herein, the SARS-CoV-2 spike protein is derived from the mu variant of SARS-CoV-2. Further provided herein, the SARS-CoV-2 spike protein is derived from a variant of SARS-CoV-2 comprising an amino acid substitution of D614G. Further provided herein, the hydrophobic core comprises an oil. Further provided herein, the oil comprises at least one of α-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, and vitamin E, and a medium chain triglyceride. Further provided herein, the one or more inorganic nanoparticles is selected from the group consisting of metal salts, metal oxides, metal hydroxides, metal phosphates, metalloids and any combinations thereof. Further provided herein, the one or more lipids is selected from the group consisting of cationic lipids, anionic lipids, neutral lipids, and any combinations thereof. Further provided herein, the one or more lipids is a cationic lipid. Further provided herein, the cationic lipid is selected from the group consisting of 1,2-dioleoyloxy-3-(trimethylammonium)propane (DOTAP); 3β-[N—(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0)trimethyl ammonium propane (DPTAP); distearoyltrimethylammonium propane (DSTAP); N-[1-(2,3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLinDMA); 1,1'-((2-(4-(2-((2-(bis(2-hydroxydodecyl)amino)ethyl) (2-hydroxydodecyl)amino)ethyl)piperazin-1-yl)ethyl) azanediyl)bis(dodecan-2-ol) (C12-200), and any combinations thereof. Further provided herein, the lipid carrier optionally comprises one or more surfactants. Further provided herein, the one or more surfactants is selected from the group consisting of hydrophobic surfactant, hydrophilic surfactant, and any combinations thereof. Further provided herein, the hydrophobic surfactant comprises a sorbitan ester selected from the group consisting of sorbitan monostearate, sorbitan monooleate, and sorbitan trioleate; and the hydrophilic surfactant comprises a polysorbate. Further provided herein, the lipid carrier have a z-average hydrodynamic diameter ranging from about 40 nm to about 150 nm, with an average polydispersity index ranging from about 0.1 to about 0.4. Further provided herein are compositions, wherein the one or more nucleic acids is incorporated or complexed with the lipid carrier to form a lipid carrier-nucleic acid complex. Further provided herein, the complex is formed via non-covalent interactions or via reversible covalent interactions. Further provided herein, the molar ratio of the lipid carrier to the one or more nucleic acids, characterized by the nitrogen-to-phosphate (N:P) molar ratio, ranges from about 1:1 to about 150:1. Further provided herein, the composition is stable at 2 to 8 degrees Celsius.

Provided herein are vaccine compositions, wherein the vaccine comprises: (a) a lipid carrier, wherein the lipid carrier is a nanoemulsion comprising a hydrophobic core, one or more inorganic nanoparticles and one or more lipids; (b) at least one nucleic acid sequence, wherein the nucleic acid sequence comprises a sequence capable of expressing an antigen, wherein the antigen is a SARS-CoV-2 spike protein. Further provided herein, the nucleic acid is RNA. Further provided herein, the vaccine compositions further comprise a nucleic acid polymerase or a further nucleic acid encoding a sequence capable of expressing a nucleic acid polymerase. Further provided herein, the vaccine compositions further comprise an RNA polymerase or a further nucleic acid sequence encoding a sequence capable of expressing an RNA polymerase. Further provided herein, the nucleic acid comprises a sequence as set forth in one of SEQ ID NOS: 1-8. Further provided herein, the SARS-CoV-2 spike protein has an amino acid sequence as set forth in one of SEQ ID NOS: 9-17. Further provided herein, the nucleic acid comprises a sequence as set forth in SEQ ID NO: 1. Further provided herein, the nucleic acid comprises a sequence as set forth in SEQ ID NO: 2. Further provided herein, the nucleic acid comprises a sequence as set forth in SEQ ID NO: 3. Further provided herein, the nucleic acid comprises a sequence as set forth in SEQ ID NO: 4. Further provided herein, the nucleic acid comprises a sequence as set forth in SEQ ID NO: 5. Further provided herein, the nucleic acid comprises a sequence as set forth in SEQ ID NO: 6. Further provided herein, the nucleic acid comprises a sequence as set forth in SEQ ID NO: 7. Further provided herein, the nucleic acid sequence comprises a sequence as set forth in SEQ ID NO: 8. Further provided herein, the SARS-CoV-2 spike protein is the alpha variant of SARS-CoV-2. Further provided herein, the SARS-CoV-2 spike protein is the beta variant of SARS-CoV-2. Further provided herein, the SARS-CoV-2 spike protein is the delta variant of SARS-CoV-2. Further provided herein, the SARS-CoV-2 spike protein is the gamma variant of SARS-CoV-2. Further provided herein, the SARS-CoV-2 spike protein is the mu variant of SARS-CoV-2. Further provided herein, the SARS-CoV-2 spike protein is the D614G variant of SARS-CoV-2. Further provided herein, the hydrophobic core comprises an oil. Further provided herein, the oil comprises at least one of α-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, vitamin E, a medium chain triglyceride. Further provided herein, the one or more inorganic nanoparticles is selected from the group consisting of metal salts, metal oxides, metal hydroxides, metal phosphates, metalloids, and any combinations thereof. Further provided herein, the one or more lipids is selected from the group consisting of cationic lipids, anionic lipids, neutral lipids, and any combinations thereof. Further provided herein, the one or more lipids is a cationic lipid. Further provided herein, the cationic lipid is selected from the group consisting of 1,2-dioleoyloxy-3-(trimethylammonium)propane (DOTAP); 3β-[N—(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0) trimethyl ammonium propane (DPTAP); distearoyltrimethylammonium propane (DSTAP); N-[1-(2,3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLinDMA); 1,1'-((2-(4-(2-((2-(bis(2-hydroxydodecyl)amino)ethyl) (2-hydroxydodecyl) amino)ethyl)piperazin-1-yl)ethyl)azanediyl)bis(dodecan-2-ol) (C12-200), and any combinations thereof. Further provided herein, the lipid carrier optionally comprises one or more surfactants. Further provided herein, the one or more surfactants is selected from the group consisting of hydrophobic surfactant, hydrophilic surfactant, and any combinations thereof. Further provided herein, the hydrophobic surfactant comprises a sorbitan ester selected from the group consisting of sorbitan monostearate, sorbitan monooleate, and sorbitan trioleate; and the hydrophilic surfactant comprises a polysorbate. Further provided herein, the lipid carrier have a z-average hydrodynamic diameter ranging from about 40 nm to about 150 nm, with an average polydispersity index ranging from about 0.1 to about 0.4. Further provided herein, the one or more nucleic acids is incorporated or complexed with the lipid carrier to form a lipid carrier-nucleic acid complex. Further provided herein, the complex is formed via non-covalent interactions or via reversible covalent interactions. Further provided herein, the molar ratio of the lipid carrier to the one or more nucleic acids, characterized by the nitrogen-to-phosphate (N:P) molar ratio, ranges from about 1:1 to about 150:1. Further provided herein, the composition is stable at 2 to 8 degrees Celsius.

Provided herein are methods of generating an immune response in a subject, wherein the methods comprise administering to said subject a composition comprising: a) a lipid carrier, wherein the lipid carrier is a nanoemulsion comprising a hydrophobic core, one or more inorganic nanoparticles and one or more lipids; b) at least one nucleic acid sequence, wherein the nucleic acid sequence comprises a sequence capable of expressing an antigen, wherein the antigen is a SARS-CoV-2 spike protein. Further provided herein, the composition is administered to the subject by two doses. Further provided herein, the second dose is administered at about 28 days after the first dose. Further provided herein, the methods further comprise administering a third dose of said composition to said subject. Further provided herein, 5 micrograms of said composition is administered to said subject. Further provided herein, 10 micrograms of said composition is administered to said subject. Further provided herein, 25 micrograms of said composition is administered to said subject. Further provided herein, the subject is a mammal. Further provided herein, the mammal is a human. Further provided herein, the composition is administered intramuscularly.

Provided herein are compositions for immunoprotecting a subject, the compositions comprising: a) a lipid carrier, wherein the lipid carrier is a nanoemulsion comprising a hydrophobic core, one or more inorganic nanoparticles and one or more lipids; b) at least one nucleic acid sequence, wherein the nucleic acid sequence comprises a sequence capable of expressing an antigen, wherein the antigen is a SARS-CoV-2 spike protein.

Provided herein are methods of reducing the severity of a SARS-CoV-2 infection, the methods comprising administering prior to infection a composition comprising: a) a lipid carrier, wherein the lipid carrier is a nanoemulsion comprising a hydrophobic core, one or more inorganic nanoparticles and one or more lipids; b) at least one nucleic acid sequence, wherein the nucleic acid sequence comprises a sequence capable of expressing an antigen, wherein the antigen is a SARS-CoV-2 spike protein. Further provided herein, the composition is administered to the subject by two doses. Further provided herein, the second dose is administered at about 28 days after the first dose. Further provided herein, the methods further comprise administering a third dose of said composition to said subject. Further provided herein, 5 micrograms of said composition is administered to said subject. Further provided herein, 10 micrograms of said composition is administered to said subject. Further provided herein, 25 micrograms of said composition is administered to said subject. Further provided herein, the subject is a mammal. Further provided herein, the mammal is a human. Further provided herein, the composition is administered intramuscularly.

Provided herein are methods of immunoprotecting a subject, the methods comprising: a) a lipid carrier, wherein the lipid carrier is a nanoemulsion comprising a hydrophobic core, one or more inorganic nanoparticles and one or more lipids; b) at least one nucleic acid sequence, wherein the nucleic acid sequence comprises a sequence capable of expressing an antigen, wherein the antigen is a SARS-CoV-2 spike protein. Further provided herein, the composition is administered to the subject by two doses. Further provided herein, the second dose is administered at about 28 days after the first dose. Further provided herein, the methods further comprise administering a third dose of said composition to said subject. Further provided herein, 5 micrograms of said composition is administered to said subject. Further provided herein, 10 micrograms of said composition is administered to said subject. Further provided herein, 25 micrograms of said composition is administered to said subject. Further provided herein, the subject is a mammal. Further provided herein, the mammal is a human. Further provided herein, the composition is administered intramuscularly.

Provided herein are kits, the kits comprising: (a) a lipid carrier, wherein the lipid carrier is a nanoemulsion comprising a hydrophobic core, one or more inorganic nanoparticles and one or more lipids; (b) at least one nucleic acid sequence, wherein the nucleic acid sequence comprises a sequence capable of expressing an antigen, wherein the antigen is a SARS-CoV-2 spike protein. Provided herein are kits, the kits comprising: (a) a lipid carrier, wherein the lipid carrier is a nanoemulsion comprising a hydrophobic core, one or more lipids, and one or more surfactants; (b) at least one nucleic acid sequence, which comprises a sequence which encodes a sequence capable of expressing an antigen, wherein the antigen is a SARS-CoV-2 spike protein. Further provided herein, the kit further comprises one or more surfactants. Further provided herein, the RNA comprises a sequence comprising a vector sequence as set forth in SEQ ID NO: 20. Further provided herein, the RNA comprises a sequence comprising an antigen sequence as set forth in one of SEQ ID NOS: 1-8. Further provided herein, the RNA comprises a sequence comprising a sequence as set forth in one of SEQ ID NOS: 24-31. Further provided herein, the RNA comprises a sequence comprising a vector sequence as set forth in one of SEQ ID NOS: 32-38.

Provided herein are dried compositions comprising: a) a lipid carrier, wherein the lipid carrier is a nanoemulsion comprising a hydrophobic core, one or more inorganic nanoparticles and one or more lipids; b) at least one nucleic acid sequence, which comprises a sequence which encodes a sequence capable of expressing an antigen, wherein the antigen is a SARS-CoV-2 spike protein; and c) at least one cryoprotectant. Further provided herein, the composition is lyophilized. Further provided herein, the composition is spray-dried. Further provided herein, the composition is thermally stable. Further provided herein, the composition is thermally stable at about 25 degrees C. Further provided herein, the composition is thermally stable at about 45 degrees C. Further provided herein, the composition is thermally stable at about −20 degrees C. Further provided herein, the composition is thermally stable at about 2 degrees C. to about 8 degrees C. Further provided herein, the composition is thermally stable for at least 1 week, at least 2 weeks, and/or at least 1 month. Further provided herein, the hydrophobic core comprises an oil. Further provided herein, the oil comprises at least one of α-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, vitamin E, a medium chain triglyceride, dihydroisosqualene (DHIS), famesene and squalane. Further provided herein, the one or more inorganic nanoparticles is selected from the group consisting of metal salts, metal oxides, metal hydroxides, metal phosphates, metalloids, and any combinations thereof. Further provided herein, the one or more lipids is selected from the group consisting of cationic lipids, anionic lipids, neutral lipids, and any combinations thereof. Further provided herein, the one or more lipids is a cationic lipid. Further provided herein, the cationic lipid is selected from the group consisting of 1,2-dioleoyloxy-3-(trimethylammonium)propane (DOTAP); 3β-[N—(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0)trimethyl ammonium propane (DPTAP); distearoyltrimethylammonium propane (DSTAP); N-[1-(2,3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLin-DMA); 1,1'-((2-(4-(2-((2-(bis(2-hydroxydodecyl)amino)ethyl) (2-hydroxydodecyl)amino)ethyl)piperazin-1-yl)ethyl) azanediyl)bis(dodecan-2-ol) (C12-200), 1,2-dioleoyl-sn-glycero-3-phosphoethanolamine (DOPE); N-decyl-N,N-dimethyldecan-1-aminium bromide (DDAB); 2,3-dioleyloxy-N-[2-(sperminecarboxamido)ethyl]-N,N-dimethyl-1-propanaminium trifluoroacetate (DOSPA); ethylphosphatidylcholine (ePC); and any combinations thereof. Further provided herein, the lipid carrier optionally comprises at least one surfactant. Further provided herein, the at least one surfactant is selected from the group consisting of a hydrophobic surfactant, a hydrophilic surfactant, and any combinations thereof. Further provided herein, the hydrophobic surfactant comprises a sorbitan ester selected from the group consisting of Span 20, Span 40, Span 60, Span 65, Span 80 and Span 85; and the hydrophilic surfactant comprises a polysorbate. Further provided herein, the lipid carrier has a z-average hydrodynamic diameter ranging from about 40 nm to about 150 nm, with an average polydispersity index ranging from about 0.1 to about 0.4. Further provided herein, the one or more nucleic acid sequence is an RNA. Further provided herein, the RNA is a self-replicating RNA. Further provided herein, the one or more nucleic acid sequence comprises a sequence which encodes an antigen. Further provided herein, the antigen is derived from a virus. Further provided herein, the virus is selected from the group consisting of: a hepatitis virus, a coronavirus, a mosquito-borne virus, and an HIV virus. Further provided herein, the one or more nucleic acid sequence is incorporated or complexed with the lipid carrier to form a lipid carrier-nucleic acid complex. Further provided herein, the lipid carrier-nucleic acid complex is formed via non-covalent interactions or via reversible covalent interactions. Further provided herein, the molar ratio of the lipid carrier to the one or more nucleic acids, characterized by the nitrogen-to-phosphate (N:P) molar ratio, ranges from about 1:1 to about 150:1. Further provided herein, the at least one cryoprotectant is selected from the group consisting of sucrose, maltose, trehalose, mannitol, glucose, and any combinations thereof. Further provided herein, the at least one cryoprotectant is sucrose. Further provided herein, the at least one cryoprotectant is at about 1% w/v to at about 20% w/v. Further provided herein, the at least one cryoprotectant is at about 10% w/v to at about 20% w/v. Further provided herein, the at least one cryoprotectant is at about 10% w/v.

Provided herein are pharmaceutical compositions, wherein the pharmaceutical compositions comprise: a composition provided herein reconstituted in a suitable diluent and a pharmaceutically acceptable carrier. Further provided herein, the diluent is aqueous. Further provided herein, the diluent is water.

Provided herein are kits comprising the pharmaceutical composition provided herein and a delivery system for administration to a subject.

Provided herein are vaccine delivery systems comprising the pharmaceutical composition provided herein and optionally one or more vaccine adjuvants.

Provided herein are methods for generating an immune response in a subject, the methods comprise administering to a subject a composition or a pharmaceutical composition provided herein, thereby generating an immune response to an antigen. Further provided herein, the composition is administered to the subject by two doses. Further provided herein, the second dose is administered at about 28 days after the first dose. Further provided herein, the method further comprises administering a third dose of the composition to said subject. Further provided herein, 5 μg of the composition is administered to the subject. Further provided herein, 10 μg of the composition is administered to said subject. Further provided herein, 25 μg of the composition is administered to said subject. Further provided herein, the composition is administered intramuscularly or intranasally. Further provided herein, the subject is a human. Further provided herein, the subject has or is suspected of having a viral infection. Further provided herein, the viral infection is a coronavirus infection. Further provided herein the coronavirus infection is caused by a SARS-CoV-2 virus or a variant thereof. Further provided herein, the antigen is a SARS-CoV-2 spike protein or a fragment thereof. Further provided herein, the immune response comprises increasing the amount or titer of neutralizing antibodies to the antigen as compared to a subject that has not been administered the composition. Further provided herein, the immune response comprises increasing the amount of CD4+ and/or CD8+ positive T cells as compared to a subject that has not been administered the composition. Further provided herein, the subject is immunocompromised or immunosuppressed.

Provided herein are methods of augmenting an immune response in a subject, the method comprising: administering to a subject the composition provided herein, thereby augmenting an immune response to an antigen.

Provided herein are methods of treating or preventing a disease in a subject, the methods comprise administering a therapeutically effective amount of the pharmaceutical provided herein to the subject.

Provided herein are methods of imaging and/or tracking delivery of one or more nucleic acids in a subject, the methods comprise administering a therapeutically effective amount of the pharmaceutical composition provided herein to the subject.

Provided herein are methods for preparing a lyophilized composition comprising: a) obtaining a lipid carrier, wherein the lipid carrier is a nanoemulsion comprising a hydrophobic core, one or more inorganic nanoparticles and one or more lipids; b) incorporating at least one nucleic acid into the lipid carrier to form a lipid carrier-nucleic acid complex, wherein the nucleic acid comprises a sequence comprising an antigen sequence which is at least 80% identical to a sequence as set forth in one SEQ ID NOS: 1-8, 24-31; c) adding at least one cryoprotectant to the lipid carrier-nucleic acid complex to form a formulation; and d) lyophilizing the formulation to form a lyophilized composition.

Provided herein are methods for preparing a spray-dried composition comprising: (a) obtaining a lipid carrier, wherein the lipid carrier is a nanoemulsion comprising a hydrophobic core, one or more inorganic nanoparticles and one or more lipids; (b) incorporating at least one nucleic acid into the lipid carrier to form a lipid carrier-nucleic acid complex, wherein the nucleic acid comprises a sequence comprising an antigen sequence which is at least 80% identical to a sequence as set forth in one of SEQ ID NOS: 1-8, 24-31; (c) adding at least one cryoprotectant to the lipid carrier-nucleic acid complex to form a formulation; and (d) spray drying the formulation to form a spray-dried composition.

Provided herein are methods for reconstituting a lyophilized composition comprising: (a) obtaining a lipid carrier, wherein the lipid carrier is a nanoemulsion comprising a hydrophobic core, one or more inorganic nanoparticles, and one or more lipids; (b) incorporating at least one nucleic acid into the said lipid carrier to form a lipid carrier-nucleic acid complex, wherein the nucleic acid comprises a sequence comprising an antigen sequence which is at least 80% identical to a sequence as set forth in one of SEQ ID NOS: 1-8, 24-31; (c) adding at least one cryoprotectant to the lipid carrier-nucleic acid complex to form a formulation; (d) lyophilizing the formulation to form a lyophilized composition; and (e) reconstituting the lyophilized composition in a suitable diluent.

Provided herein are methods for reconstituting a spray-dried composition comprising: (a) obtaining a lipid carrier, wherein the lipid carrier is a nanoemulsion comprising a hydrophobic core, one or more inorganic nanoparticles, and one or more lipids; (b) incorporating at least one nucleic acid into the said lipid carrier to form a lipid carrier-nucleic acid complex, wherein the nucleic acid comprises a sequence comprising an antigen sequence which is at least 80% identical to a sequence as set forth in one of SEQ ID NOS: 1-8, 24-31; (c) adding at least one cryoprotectant to the lipid carrier-nucleic acid complex to form a formulation; (d) spray drying the formulation to form a spray-dried composition; and (e) reconstituting the spray-dried composition in a suitable diluent. Further provided herein, the diluent is aqueous. Further provided herein, the diluent is water. Further provided herein, the lyophilized composition is thermally stable. Further provided herein, the lyophilized composition is thermally stable at temperatures up to about 25° C. Further provided herein, the lyophilized composition is thermally stable at temperatures up to about 45° C. Further provided herein, the lyophilized composition is thermally stable at temperatures down to about −20° C. Further provided herein, the lyophilized composition is thermally stable at temperatures ranging from about 2° C. to about 8° C. Further provided herein, the lyophilized composition is thermally stable for at least 1 week, at least 2 weeks, and/or at least 1 month. Further provided herein, the hydrophobic core comprises an oil. Further provided herein, the oil comprises at least one of α-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, vitamin E, medium chain triglyceride, dihydroisosqualene (DHIS), farnesene and squalane. Further provided herein, the one or more inorganic nanoparticles is selected from the group consisting of metal salts, metal oxides, metal hydroxides, metal phosphates, metalloids and any combinations thereof. Further provided herein, the one or more lipids is selected from the group consisting of cationic lipids, anionic lipids, neutral lipids, and any combinations thereof. Further provided herein, the one or more lipids is a cationic lipid. Further provided herein, the cationic lipid is selected from the group consisting of 1,2-dioleoyloxy-3-(trimethylammonium)propane (DOTAP); 3β-[N—(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0) trimethyl ammonium propane (DPTAP); distearoyltrimethylammonium propane (DSTAP); N-[l-(2,3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLin-DMA); 1,1'-((2-(4-(2-((2-(bis (2-hydroxydodecyl)amino)ethyl) (2-hydroxydodecyl) amino)ethyl)piperazin-1-yl)ethyl)azanediyl)bis(dodecan-2-ol) (C12-200), 1,2-dioleoyl-sn-glycero-3-phosphoethanolamine (DOPE); N-decyl-N,N-dimethyldecan-1-aminium bromide (DDAB); 2,3-dioleyloxy-N-[2-(sperminecarboxamido)ethyl]-N,N-dimethyl-1-propanaminium trifluoroacetate (DOSPA); ethylphosphatidylcholine (ePC); and any combinations thereof. Further provided herein, the lipid carrier optionally comprises one or more surfactant. Further provided herein, the one or more surfactant is selected from the group consisting of hydrophobic surfactant, hydrophilic surfactant, and any combinations thereof. Further provided herein, the hydrophobic surfactant comprises a sorbitan ester selected from the group consisting of Span 20, Span 40, Span 60, Span 65, Span 80 and Span 85; and the hydrophilic surfactant comprises a polysorbate. Further provided herein, the lipid carrier has a z-average hydrodynamic diameter ranging from about 40 nm to about 150 nm, with an average polydispersity index ranging from about 0.1 to about 0.4. Further provided herein, the one or more nucleic acid is an RNA. Further provided herein, the RNA is a self-replicating RNA. Further provided herein, the one or more nucleic acid encodes an antigen, wherein the antigen is derived from a bacterial infection, a bacterial disease, a viral infection, a viral disease, a protozoan infection, a protozoan disease, a non-communicable disease, one or more cancers, or an autoimmune disease. Further provided herein, the antigen is derived from a virus. Further provided herein, the virus is selected from the group consisting of a hepatitis virus, a corona virus, a mosquito-borne virus, and a HIV virus. Further provided herein, the one or more nucleic acid is incorporated or complexed with the lipid carrier to form a lipid carrier-nucleic acid complex. Further provided herein, the lipid carrier-nucleic acid complex is formed via non-covalent interactions or via reversible covalent interactions. Further provided herein, the at least one cryoprotectant is selected from the group consisting of sucrose, maltose, trehalose, mannitol, glucose, and any combinations thereof. Further provided herein, the at least one cryoprotectant is sucrose. Further provided herein, the at least one cryoprotectant is at about 1% w/v to at about 20% w/v. Further provided herein, the at least one cryoprotectant is at about 10% w/v to at about 20% w/v. Further provided herein, the at least one cryoprotectant is at about 10% w/v.

Provided herein are compositions for prophylaxis of SARS-CoV-2, the compositions comprising: a) a sorbitan fatty acid ester; b) an ethoxylated sorbitan ester; c) a cationic lipid; d) an immune stimulant; and e) at least one RNA encoding an antigen sequence or functional fragment thereof. Further provided herein, the sorbitan fatty acid ester is sorbitan monostearate. Further provided herein, the ethoxylated sorbitan ester is TWEEN-80. Further provided herein, the cationic lipid is DOTAP. Further provided herein, the immune stimulant is squalene. Further provided herein, the RNA encodes a SARS-CoV-2 spike protein. Further provided herein, the ratio of the esters yields a Hydrophilic-Lipophilic Balance between 8 and 11. Further provided herein, the ratio of esters and lipids yields a particle size between 30 and 200 nanometers. Further provided herein, the ratio of esters and lipids yields a particle size between 40 and 70 nanometers. Further provided herein, the immune stimulant decreases the total amount of protein produced, but increases the immune response to the vaccine. Further provided herein, the immune stimulant increases the total amount of protein, produced, but decreases the immune response to the vaccine. Further provided herein, the immune stimulant is Miglyol 810 or Miglyol 812. Further provided herein, the compositions further comprise sorbitan monostearate, polysorbate 80, DOTAP, and squalene and no solid particles.

Provided herein are compositions for prophylaxis of SARS-CoV-2. wherein the compositions comprise: (a) sorbitan monostearate; (b) polysorbate 80; (c) DOTAP; (d) an immune stimulant; and (e) at least one RNA encoding an antigen sequence or functional fragment thereof. Further provided herein, the immune stimulant decreases the total amount of protein produced, but increases the immune response to the vaccine. Further provided herein, the immune stimulant increases the total amount of protein, produced, but decreases the immune response to the vaccine. Further provided herein, the immune stimulant is Miglyol 810 or Miglyol 812. Further provided herein, the compositions further comprise squalene and no solid particles. Further provided herein, the ratio of the esters yields a Hydrophilic-Lipophilic Balance between 8 and 11. Further provided herein, the particle size is between 30 and 200 nanometers. Further provided herein, the N to P ratio is between 5 and 35. Further provided herein, the RNA encodes an amino acid sequence as set forth in one of SEQ ID NOS: 9-19. Further provided herein, the RNA comprises a sequence as set forth in one of SEQ ID NOS: 1-8. Further provided herein, the RNA comprises a sequence as set forth in one of SEQ ID NOS: 24-31. Further provided herein, the RNA comprises a sequence comprising a vector sequence as set forth in SEQ ID NO: 20. Further provided herein, the RNA comprises a sequence comprising an sequence as set forth in one of SEQ ID NOS: 1-8, 24-31. Further provided herein, the RNA comprises a sequence comprising a vector sequence as set forth in one of SEQ ID NOS: 32-38. Further provided herein, the compositions comprise a nucleic acid comprising an alphavirus replicon.

Provided here are dried compositions comprising: a lipid carrier, wherein the lipid carrier is a nanoemulsion comprising a hydrophobic core, and one or more lipids; at least one nucleic acid that comprises a sequence which encodes a sequence capable of expressing an antigen, optionally wherein the antigen is a SARS-CoV-2 spike protein or a functional variant thereof; and at least one sugar present in amount of (i) at least about 50% by weight of the dried composition, or (ii) present in an amount of least 50 mg. Further provided herein are compositions wherein the composition is lyophilized. Further provided herein are compositions wherein the composition is thermally stable at about 25 degrees Celsius. Further provided herein are compositions wherein the composition is thermally stable at about 45 degrees Celsius. Further provided herein are compositions wherein the composition is thermally stable at about −20 degrees Celsius. Further provided herein are compositions wherein the composition is thermally stable at about 2 degrees Celsius to about 8 degrees Celsius. Further provided herein are compositions wherein the composition is thermally stable for at least 1 week, at least 2 weeks, and/or at least 1 month. Further provided herein are compositions wherein the hydrophobic core comprises an oil. Further provided herein are compositions wherein the oil comprises at least one of α-tocopherol, lauroyl polyoxylglyceride, monoacylglycerol, propolis, squalene, mineral oil, grape-seed oil, olive oil, paraffin oil, peanut oil, soybean oil, sunflower oil, soy lecithin, triglyceride, vitamin E, a caprylic/capric triglyceride, a triglyceride ester of saturated coconut/palmkernel oil derived caprylic and capric fatty acids and plant derived glycerol, dihydroisosqualene (DHIS), farnesene and squalane. Further provided herein are compositions wherein the one or more lipids is selected from the group consisting of cationic lipids, anionic lipids, neutral lipids, and any combinations thereof. Further provided herein are compositions wherein the one or more lipids comprises a cationic lipid. Further provided herein are compositions wherein the cationic lipid is selected from the group consisting of 1,2-dioleoyloxy-3-(trimethylammonium)propane (DOTAP); 3β-[N—(N',N'-dimethylaminoethane)-carbamoyl]cholesterol (DC Cholesterol); dimethyldioctadecylammonium (DDA); 1,2-dimyristoyl-3-trimethylammoniumpropane (DMTAP), dipalmitoyl(C16:0) trimethyl ammonium propane (DPTAP); distearoyltrimethylammonium propane (DSTAP); N-[1-(2,3-dioleyloxy)propyl]-N,N,Ntrimethylammonium chloride (DOTMA); N,N-dioleoyl-N,N-dimethylammonium chloride (DODAC); 1,2-dioleoyl-sn-glycero-3-ethylphosphocholine (DOEPC); 1,2-dioleoyl-3-dimethylammonium-propane (DODAP); and 1,2-dilinoleyloxy-3-dimethylaminopropane (DLin-DMA); 1,1'-((2-(4-(2-((2-(bis(2-hydroxydodecyl)amino)ethyl) (2-hydroxydodecyl)amino)ethyl)piperazin-1-yl)ethyl)azanediyl)bis(dodecan-2-ol) (C12-200), 1,2-dioleoyl-sn-glycero-3-phosphoethanolamine (DOPE); N-decyl-N,N-dimethyldecan-1-aminium bromide (DDAB); 2,3-dioleyloxy-N-[2-(sperminecarboxamido)ethyl]-N,N-dimethyl-1-propanaminium trifluoroacetate (DOSPA); ethylphosphatidylcholine (ePC); and any combinations thereof. Further provided herein are compositions wherein the lipid carrier comprises at least one surfactant. Further provided herein are compositions wherein the at least one surfactant is selected from the group consisting of a hydrophobic surfactant, a hydrophilic surfactant, and any combinations thereof. Further provided herein are compositions wherein the hydrophobic surfactant comprises a sorbitan ester selected from the group consisting of sorbitan monolaurate, sorbitan monopalmitate, sorbitan monostearate, sorbitan tristearate, sorbitan monooleate, and sorbitan trioleate; and the hydrophilic surfactant comprises a polysorbate. Further provided herein are compositions wherein the lipid carrier has a z-average hydrodynamic diameter ranging from about 40 nm to about 150 nm, with an average polydispersity index ranging from about 0.1 to about 0.4. Further provided herein are compositions wherein the one or more nucleic acid is a DNA. Further provided herein are compositions wherein the one or more nucleic acid is a RNA. Further provided herein are compositions wherein the RNA is a self-replicating RNA. Further provided herein, are compositions wherein the hydrophobic core comprises one or more inorganic nanoparticles. Further provided herein are compositions, wherein the one or more inorganic nanoparticles is selected from the group consisting of a metal salt, metal oxide, metal hydroxide, metal phosphate, and any combinations thereof. Further provided herein are compositions wherein the one or more nucleic acid is incorporated or complexed with the lipid carrier to form a lipid carrier-nucleic acid complex. Further provided herein are compositions wherein the lipid carrier-nucleic acid complex is formed via non-covalent interactions or via reversible covalent interactions. Further provided herein are compositions wherein a molar ratio of the lipid carrier to the one or more nucleic acids, characterized by the nitrogen-to-phosphate (N:P) molar ratio, ranges from about 1:1 to about 150:1. Further provided herein are compositions wherein the at least one sugar is selected from the group consisting of sucrose, maltose, trehalose, mannitol, glucose, and any combinations thereof. Further provided herein are compositions wherein the at least one sugar is present in an amount of at least about 50, 60, 70, 80, 90, 100, 110, 120, 130, 140, 150, 160, 170, 180, 190, 200, 210, 220, 230, 240, 250, 260, 270, 280, 290, 300 or more mg. Further provided herein are compositions wherein the at least one sugar is present in an amount of 50 mg to 250 mg. Further provided herein are compositions wherein the at least one sugar is present in an amount of at least about 250 mg. Further provided herein are compositions wherein the sugar is present in amount of the composition by weight of at least about 50, 55, 60, 65, 70, 75, 80, 85, 90, 95% or more. Further provided herein are compositions wherein the sugar is present in amount of the composition by weight of 80 to 98%, optionally 94 to 96%. Further provided herein are compositions wherein the sugar is present in amount of the composition by weight of about 95%. Further provided herein are compositions wherein the at least one sugar comprises sucrose. Further provided herein are pharmaceutical compositions, comprising a dried composition disclosed herein reconstituted in a suitable diluent and a pharmaceutically acceptable carrier. Further provided herein are pharmaceutical compositions wherein the diluent is aqueous. Further provided herein are pharmaceutical compositions wherein the diluent is water. Further provided herein are kits comprising a pharmaceutical composition described herein and a delivery system for administration to a subject. Further provided are methods for generating an immune response in a subject, comprising administering a therapeutically effective amount of the pharmaceutical composition described herein. Further provided are methods of treating or preventing a disease in a subject, comprising administering a therapeutically effective amount of the pharmaceutical composition described herein. Further provided herein are methods of imaging and/or tracking delivery of one or more nucleic acids in a subject, comprising administering a therapeutically effective amount of the pharmaceutical composition described herein.

EXAMPLES

Example 1: Immune Response in Macrophages

Various formulations comprising lipid carrier and repRNA were prepared and analyzed in order to study the innate immune response of the lipid carrier in macrophages. Protein expression and stimulation of TNF production (e.g., TNF alpha production) in THP-1 macrophages were studied.

Initially, the THP-1 monocytes were differentiated into macrophages using phorbol 12-myristate 13-acetate (PMA). The cells were then transfected with various formulations with Nano Luciferase encoding replicon RNA. The cell culture media was then assessed for NanoLuc and TNF expression.

The formulations and their characteristics such as particle size and PDI that were used in this study are described in Table 4. The concentration of repRNA encoding NanoLuc was 909 ng/ul and maintained at −80° C. Miglyol 812 N (caprylic/capric triglyceride) was used in this study.

at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1-0.25 polydispersity index (PDI). The microfluidized formulation was terminally filtered with a 200 nm pore-size polyethersulfone (PES) filter and stored at 2 to 8 degrees C. Iron concentration was determined by ICP-OES. DOTAP and Squalene concentration were measured by RP-HPLC.

TABLE 4

Formulations for immune response study.

| Formulation | Particle size [diameter, nm] | PDI | Iron [mg Fe/ml] | Aluminum [mg Al/ml] | DOTAP [mg/ml] | Squalene [mg/ml] | Miglyol [mg/ml] | Solanesol [mg/ml] |
|---|---|---|---|---|---|---|---|---|
| NP-1: Fe-lipid carrier | 59.3 | 0.23 | 0.19 | n/a | 27.9 | 39.4 | n/a | n/a |
| NP-2: High Fe-lipid carrier | 57.5 | 0.24 | 0.85 | n/a | 29.1 | 40.5 | n/a | n/a |
| NP-3: Fe-lipid carrier miglyol | 48.7 | 0.2 | 0.18 | n/a | 28.3 | n/a | not measured | n/a |
| NP-4: High Fe-lipid carrier miglyol | 62.6 | 0.28 | 0.94 | n/a | 27.7 | n/a | not measured | n/a |
| NP-5: Alum-lipid carrier | 64.5 | 0.25 | n/a | 0.88 | 27.4 | 41.2 | n/a | n/a |
| NP-6: Fe-lipid carrier solanesol (SLN) | 86.1 | 0.26 | 0.16 | n/a | 26.2 | n/a | n/a | 36 |
| NP-7: NLC | 50 | 0.26 | n/a | n/a | 26.7 | 34.1 | n/a | n/a |
| NP-8: CNE | 105.4 | 0.06 | n/a | n/a | 4.4 | 47.4 | n/a | n/a |
| NP-30: lipid carrier (w/o IO) | 54.2 | 0.22 | n/a | n/a | 19.3 | 32.6 | n/a | n/a |

Fe-lipid carrier formulation—NP-1 (prepared at 100 ml scale): Fe-lipid carrier formulation comprises 37.5 mg/ml squalene (SEPPIC), 37 mg/ml SPAN 60 (Millipore Sigma), 37 mg/ml TWEEN 80 (Fisher Chemical), 30 mg/ml DOTAP chloride (LIPOID), 0.2 mgFe/ml 12 nm oleic acid-coated iron oxide nanoparticles (ImagionBio) and 10 mM sodium citrate dihydrate (Fisher Chemical). 1 ml of 20 mgFe/ml 12 nm diameter oleic acid-coated iron oxide nanoparticles in chloroform (ImagionBio, lot #95-127) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams squalene, 3.7 grams SPAN 60, and 3 grams DOTAP were added to produce the oil phase. The oil phase was sonicated for 45 minutes in a 65 degree C. water bath. Separately, the aqueous phase was prepared by dissolving 19.5 grams TWEEN 80 in 500 ml of 10 mM sodium citrate buffer prepared in nuclease free water. 92 ml of the aqueous phase was transferred to a separate glass bottle and heated to 65 degrees C. for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics)

High Fe-lipid carrier formulation NP-2 (prepared at 100 ml scale): High Fe-lipid carrier formulation comprises 37.5 mg/ml squalene (SEPPIC), 37 mg/ml SPAN 60 (Millipore Sigma), 37 mg/ml TWEEN 80 (Fisher Chemical), 30 mg/ml DOTAP chloride (LIPOID), 1 mgFe/ml 15 nm oleic acid-coated iron oxide nanoparticles (ImagionBio) and 10 mM sodium citrate dihydrate (Fisher Chemical). 5 ml of 20 mgFe/ml 15 nm diameter oleic acid-coated iron oxide nanoparticles in chloroform (ImagionBio, Lot #95-133) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams squalene, 3.7 grams SPAN 60, and 3 grams DOTAP were added to produce the oil phase. The oil phase was sonicated for 45 minutes in a 65 degree C. water bath. Separately, the aqueous phase was prepared by dissolving 19.5 grams TWEEN 80 in 500 ml of 10 mM sodium citrate buffer prepared in nuclease free water. 92 ml of the aqueous phase was transferred to a separate glass bottle and heated to 65 degrees C. for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2 to 8 degrees C. Iron concentration was determined by ICP-OES. DOTAP and Squalene concentration were measured by RP-HPLC.

Example 2: Fe-Lipid Carrier Miglyol Formulation NP-3 (Prepared at 100 ml Scale)

Fe-lipid carrier Miglyol formulation comprises 37.5 mg/ml Miglyol 812 N (IOI Oleo GmbH), 37 mg/ml SPAN 60 (Millipore Sigma), 37 mg/ml TWEEN 80 (Fisher Chemical), 30 mg/ml DOTAP chloride (LIPOID), 0.2 mgFe/ml 15 nm oleic acid-coated iron oxide nanoparticles (ImagionBio) and 10 mM sodium citrate dihydrate (Fisher Chemical). 1 ml of 20 mgFe/ml 15 nm diameter oleic acid-coated iron oxide nanoparticles in chloroform (ImagionBio, Lot #95-127) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams squalene, 3.7 grams SPAN 60, and 3 grams DOTAP were added to produce the oil phase. The oil phase was sonicated for 45 minutes in a 65 degree C. water bath. Separately, the aqueous phase was prepared by dissolving 19.5 grams TWEEN 80 in 500 ml of 10 mM sodium citrate buffer prepared in nuclease free water. 92 ml of the aqueous phase was transferred to a separate glass bottle and heated to 65 degree C. for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2 to 8 degrees C. Iron concentration was determined by ICP-OES. DOTAP concentration was measured by RP-HPLC.

Example 3: High Fe-Lipid Carrier Miglyol Formulation NP-4 (Prepared at 100 ml Scale)

High Fe-lipid carrier Miglyol formulation comprises 37.5 mg/ml Miglyol 812 N (IOI Oleo GmbH), 37 mg/ml SPAN 60 (Millipore Sigma), 37 mg/ml TWEEN 80 (Fisher Chemical), 30 mg/ml DOTAP chloride (LIPOID), 1 mg/ml 15 nm oleic acid-coated iron oxide nanoparticles (ImagionBio) and 10 mM sodium citrate dihydrate (Fisher Chemical). 5 ml of 20 mgFe/ml 15 nm diameter oleic acid-coated iron oxide nanoparticles in chloroform (ImagionBio, Lot #95-127) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams squalene, 3.7 grams SPAN 60, and 3 grams DOTAP were added to produce the oil phase. The oil phase was sonicated for 45 minutes in a 65 degree C. water bath. Separately, the aqueous phase was prepared by dissolving 19.5 grams TWEEN 80 in 500 ml of 10 mM sodium citrate buffer prepared in nuclease free water. 92 ml of the aqueous phase was transferred to a separate glass bottle and heated to 65 degrees C. for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2 to 8 degrees C. Iron concentration was determined by ICP-OES. DOTAP concentration was measured by RP-HPLC.

Example 4: Alum-Lipid Carrier Formulation NP-5 (Prepared at 100 ml Scale)

Alum-lipid carrier formulation comprises 37.5 mg/ml squalene (SEPPIC), 37 mg/ml SPAN 60 (Millipore Sigma), 37 mg/ml TWEEN 80 (Fisher Chemical), 30 mg/ml DOTAP chloride (LIPOID), 1 mg Al/ml TOPO-coated Alhydrogel® (aluminum oxyhydroxide) particles (Croda) and 10 mM sodium citrate. 10 ml of Alhydrogel was washed three times in methanol by centrifuging at 1000 rpm for 20 minutes. After the third wash, Alhydrogel was dispersed in 10 ml methanol and to this dispersion was added 1 ml of 250 mg/ml trioctylphosphine oxide (TOPO) and incubated overnight in a 37° C. orbital shaker. Excess TOPO was removed by additional methanol washes and then dispersed in 11 ml methanol. Methanol was allowed to evaporate overnight in the fume hood leaving behind a dry layer of TOPO-Alhydrogel. To this dry TOPO-Alhydrogel layer, 3.75 grams squalene, 3.7 grams SPAN 60, and 3 grams DOTAP were added to produce the oil phase. The oil phase was sonicated for 45 minutes in a 65 degree C. water bath. Separately, the aqueous phase was prepared by dissolving 19.5 grams TWEEN 80 in 500 ml of 10 mM sodium citrate buffer prepared in nuclease free water. 92 ml of the aqueous phase was transferred to a separate glass bottle and heated to 65 degrees C. for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2 to 8 degrees C. Aluminum concentration was determined by ICP-OES. DOTAP and Squalene concentration were measured by RP-HPLC.

Example 5: Fe-Lipid Carrier Solanesol Formulation NP-6 (Prepared at 100 ml Scale)

Fe-lipid carrier solanesol formulation (NP-6) comprises 37.5 mg/ml Solanesol (Cayman chemicals), 37 mg/ml SPAN 60 (Millipore Sigma), 37 mg/ml TWEEN 80 (Fisher Chemical), 30 mg/ml DOTAP chloride (LIPOID), 0.2 mgFe/ml oleic acid-coated iron oxide nanoparticles (ImagionBio) and 10 mM sodium citrate. 1 ml of 20 mgFe/ml 15 nm diameter oleic acid-coated iron oxide nanoparticles in chloroform (ImagionBio, Lot #95-133) were washed three times by magnetically separating in a 4:1 acetone:chloroform (v/v) solvent mixture. After the third wash, the volatile solvents (acetone and chloroform) were allowed to completely evaporate in a fume hood leaving behind a coating of dried oleic acid iron oxide nanoparticles. To this iron oxide coating, 3.75 grams solanesol, 3.7 grams SPAN 60, and 3 grams DOTAP were added to produce the oil phase. The oil phase was sonicated for 45 minutes in a 65 degree C. water bath. Separately, the aqueous phase was prepared by dissolving 19.5 grams TWEEN 80 in 500 ml of 10 mM sodium citrate buffer prepared in nuclease free water. 92 ml of the aqueous phase was transferred to a separate glass bottle and heated to 65 degrees C. for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 µm diamond interaction chamber and an auxiliary H30Z-200 µm ceramic interaction chamber. The microfluidized formulation was terminally filtered with a 200 nm pore-size polyethersulfone (PES) filter and stored at 2 to 8 degrees C. Iron concentration was determined by ICP-OES. DOTAP and solanesol concentration were measured by RP-HPLC.

Example 6: NP-7 Formulation (Prepared at 100 ml Scale)

NP-7 formulation comprises 37.5 mg/ml squalene (SEPPIC), 37 mg/ml SPAN 60 (Millipore Sigma), 37 mg/ml TWEEN 80 (Fisher Chemical), 30 mg/ml DOTAP chloride (LIPOID), 2.4 mg/ml Dynasan 114 (IOI Oleo GmbH) and 10 mM sodium citrate. To a 200 ml beaker 3.75 grams squalene, 3.7 grams SPAN 60, 0.24 grams Dynasan 114 and 3 grams DOTAP were added to produce the oil phase. The oil phase was sonicated for 45 minutes in a 65 degree C. water bath. Separately, the aqueous phase was prepared by dissolving 19.5 grams TWEEN 80 in 500 ml of 10 mM sodium citrate buffer prepared in nuclease free water. 92 ml of the aqueous phase was transferred to a separate glass bottle and heated to 65 degrees C. for 30 minutes. The oil phase was mixed with the 92 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 µm diamond interaction chamber and an auxiliary H30Z-200 µm ceramic interaction chamber until the z-average hydrodynamic diameter—measured by dynamic light scattering (Malvern Zetasizer Nano S)—reached 40-80 nm with a 0.1-0.3 polydispersity index (PDI). The microfluidized formulation was terminally filtered with a 200 nm pore-size polyethersulfone (PES) filter and stored at 2 to 8 degrees C. DOTAP and Squalene concentration were measured by RP-HPLC.

Example 7: NP-8 Formulation (Prepared at 100 ml Scale)

NP-8 formulation comprises 43 mg/ml squalene (SEPPIC), 5 mg/ml SPAN 85 (Millipore Sigma), 5 mg/ml TWEEN 80 (Fisher Chemical), 4 mg/ml DOTAP chloride (LIPOID) and 10 mM sodium citrate. To a 200 ml beaker 4.3 grams squalene, 0.5 grams SPAN 85, and 0.4 grams DOTAP were added to produce the oil phase. The oil phase was sonicated for 45 minutes in a 65 degree C. water bath. Separately, the aqueous phase was prepared by dissolving 2.6 grams TWEEN 80 in 500 ml of 10 mM sodium citrate buffer prepared in nuclease free water. 95 ml of the aqueous phase was transferred to a separate glass bottle and heated to 65 degrees C. for 30 minutes. The oil phase was mixed with the 95 ml of aqueous phase by adding the warm oil phase to the warm aqueous phase. The mixture was emulsified using a VWR 200 homogenizer (VWR International) and the resulting crude emulsion was processed by passaging through a M110P microfluidizer (Microfluidics) at 30,000 psi equipped with a F12Y 75 µm diamond interaction chamber and an auxiliary H30Z-200 µm ceramic interaction chamber until the z-average hydrodynamic diameter—measured by dynamic light scattering (Malvern Zetasizer Nano S)—reached 100±10 nm with a 0.05-0.1 polydispersity index (PDI). The microfluidized formulation was terminally filtered with a 200 nm pore-size polyethersulfone (PES) filter and stored at 2 to 8 degrees C. DOTAP and Squalene concentration were measured by RP-HPLC.

The treatment groups were prepared. Eight of those groups were NanoLuc repRNA groups, with 600 ng dose per well was prepared using the Fe-lipid carrier, High Fe-lipid carrier, Fe-lipid carrier miglyol, High Fe-lipid carrier miglyol, Alum-lipid carrier, Fe-lipid carrier solanesol (SLN), NLC, and CNE formulations. The untreated group did not have NanoLuc.

The various formulations were prepared by diluting NanoLuc repRNA to 8 ng/µL in 2.2 mL of RNAse-free water. The lipid carrier formulations and RNA master mix was complexed by adding 250 µL of each diluted formulation with 250 µL of diluted RNA, and mixed by pipetting up and down.

Cell transfections were carried out by seeding $7 \times 10^5$ THP-1s per well in a 24 well plate. 80 µM of PMA per well was added and incubated at 37 degrees C. The next day, the PMA-containing media was removed and replaced with cRPMI for an hour before transfection. The samples were then serially diluted in Opti-MEM to make a 10-point 1.5-fold dilution series starting at 0.45 ng/µL. The culture media was then removed from the plates by pipetting. 450 µL of Opti-MEM and 150 µL of the complexed formulation was added to the plate in duplicate. The empty wells were given 450 µL of Opti-MEM only. After four hours, the samples were removed from the plate by pipetting and replaced with 500 µL of growth media. The plate was then incubated overnight at 37° C. The growth media was harvested the next day and stored at −80° C. Downstream assays were conducted.

The luciferase assay was performed by first diluting the Nano-Glo luciferase assay reagent 1:50 in buffer. 25 µL of supernatant was removed and mixed with 25 µL of Nano-Glo reagent in a 96-well plate. This was incubated at room temperature for 3 minutes. The luminescence was read.

ELISA assay was performed to evaluate the TNF-alpha protein level in the media using the Human TNF-alpha DuoSet ELISA by R&D Systems according to the manufacturer's protocol. The 96-well microplate was coated with anti-TNF capture antibody. The plate was blocked and then media samples were added directly without dilution. After addition of the biotinylated detection antibody, SA-HRP, and substrate, the absorbance was read at 450 nm on a Spectramax i3 plate reader. No other major differences between formulations were observed.

All studies in this example were done in duplicates. Results from the duplicates are presented as first experiment and second experiment respectively.

Figure 4A:
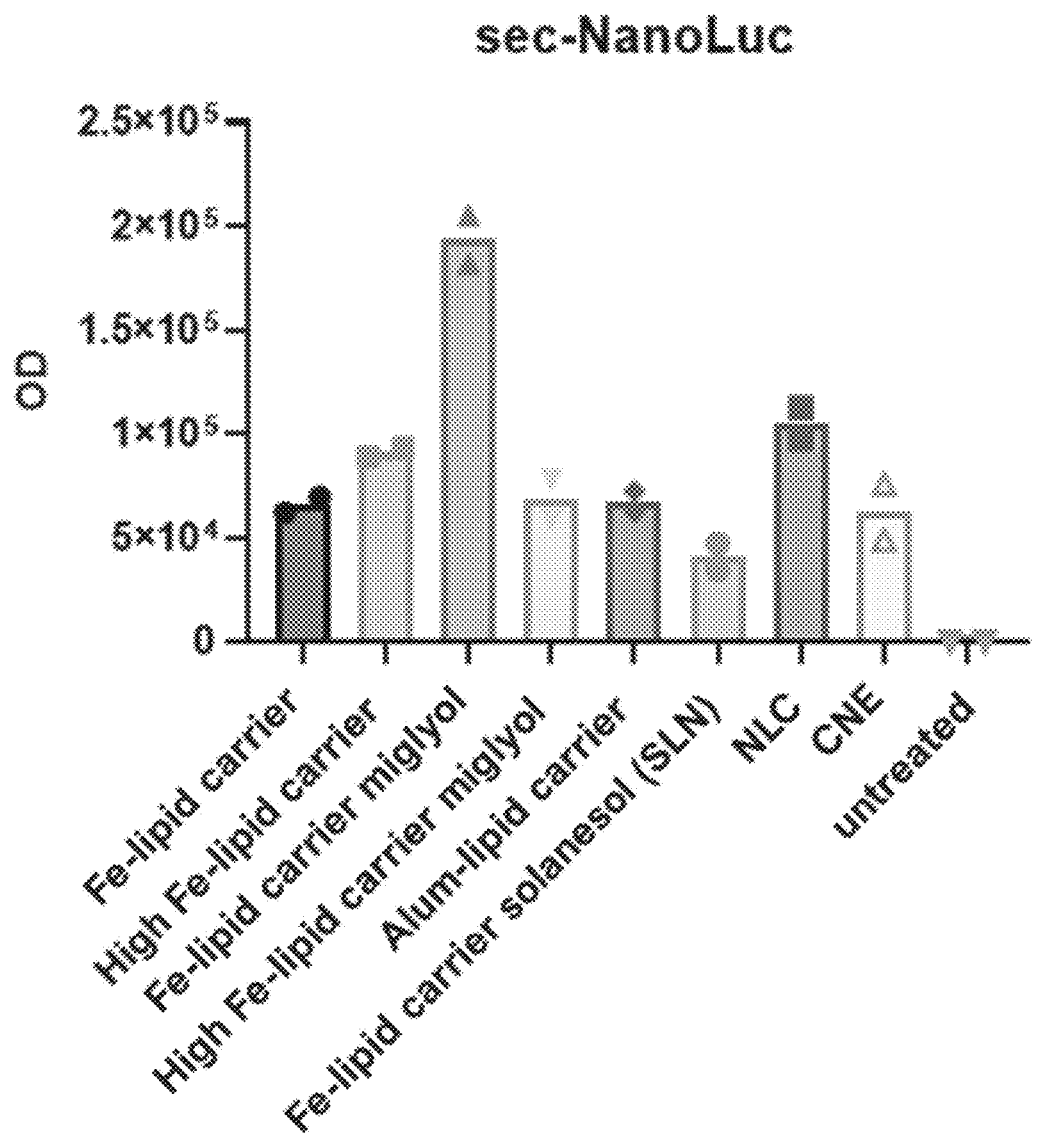
FIGS. 4A-4B show the increased protein production induced by the Miglyol lipid carrier formulation, NP-3.
Figure 4B:
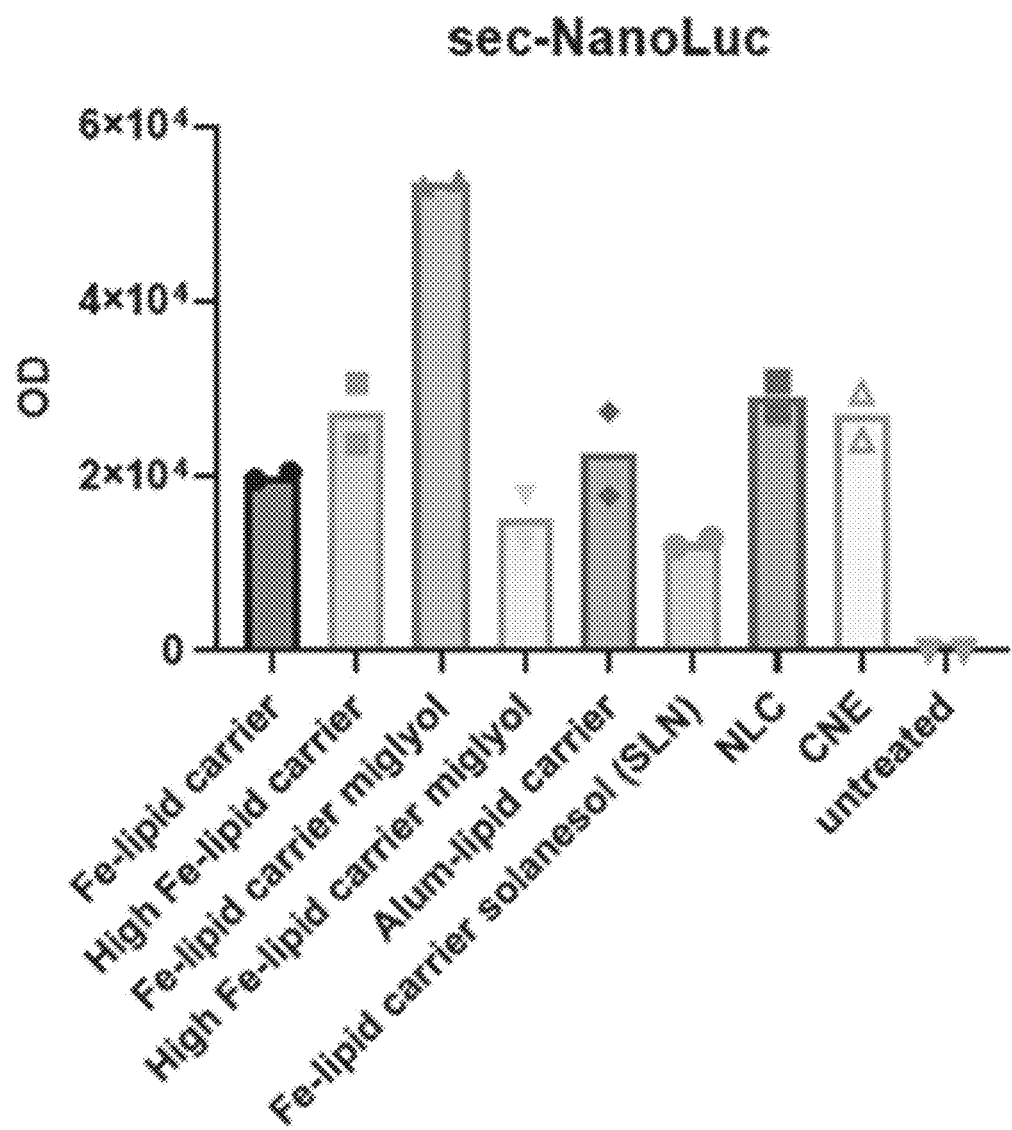
Figure 5A:
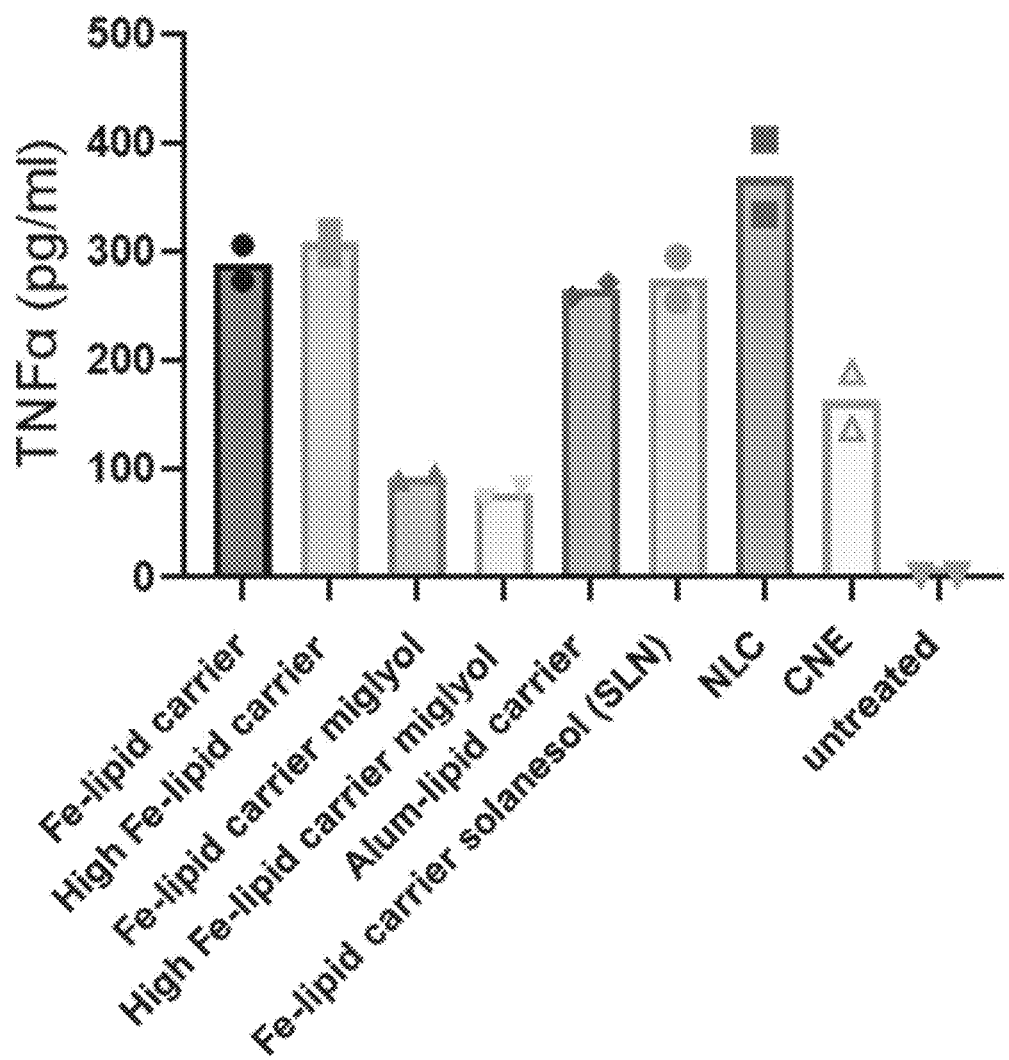
FIGS. 5A-5B show the decreased immune response induced by the Miglyol lipid carrier formulation, NP-3.
Figure 5B:
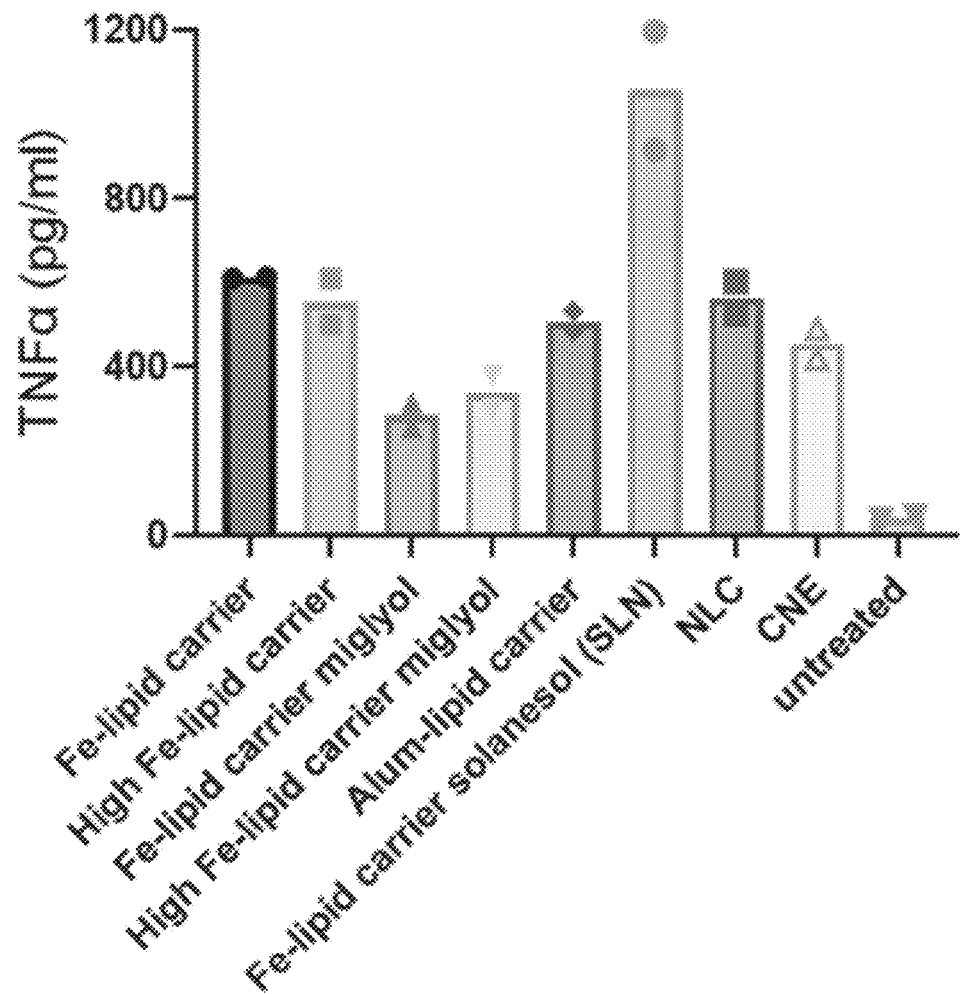

The formulation comprising a lipid carrier and Miglyol induced higher protein production off the replicon, as shown in the first experiment in FIG. 4A and in the second experiment in FIG. 4B. A reduced innate immune response was detected, as measured by TNF-alpha secretion and is shown in the first experiment in FIG. 5A and in the second experiment in FIG. 5B.

Figure 6A:
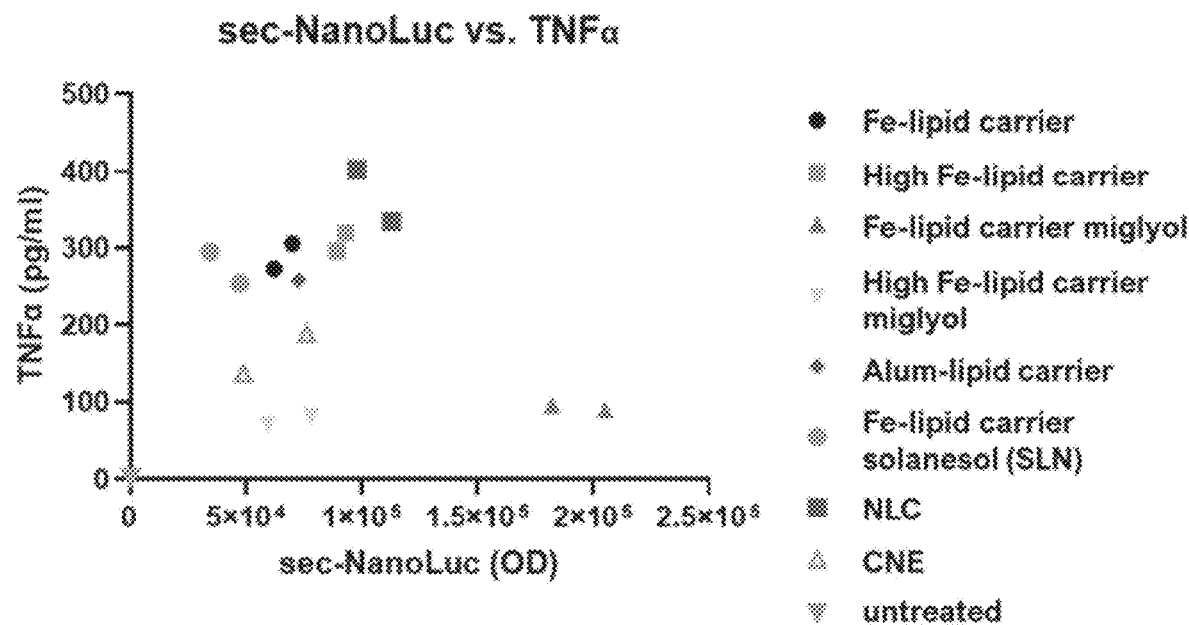
FIGS. 6A-6B show the correlation between enhanced protein production and low TNF (e.g., TNF alpha) stimulation observed with NP-3 as a result of the first and second assays.
Figure 6B:
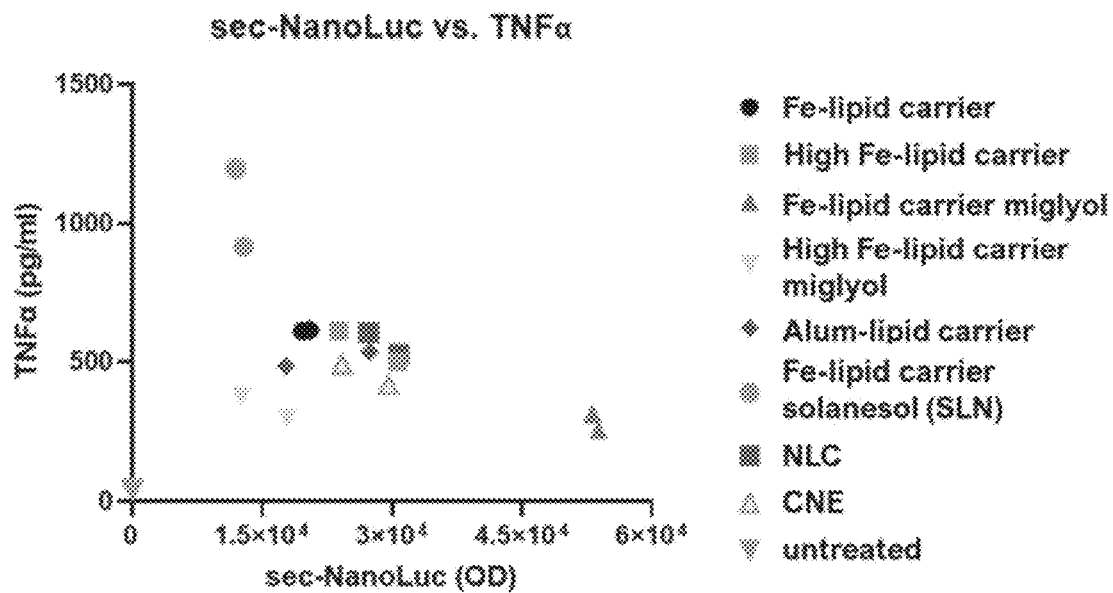
Figure 7A:
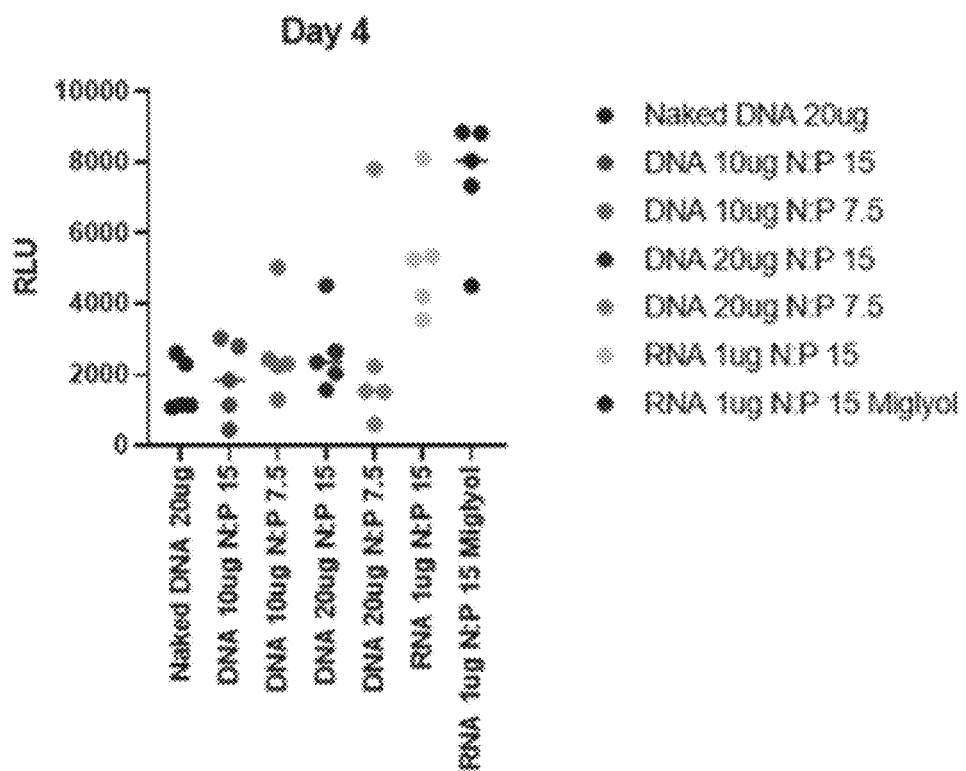
FIGS. 7A-7F show SEAP levels in BALB/c mice injected intramuscularly with various embodiments of lipid carrier formulations described herein.
Figure 7B:
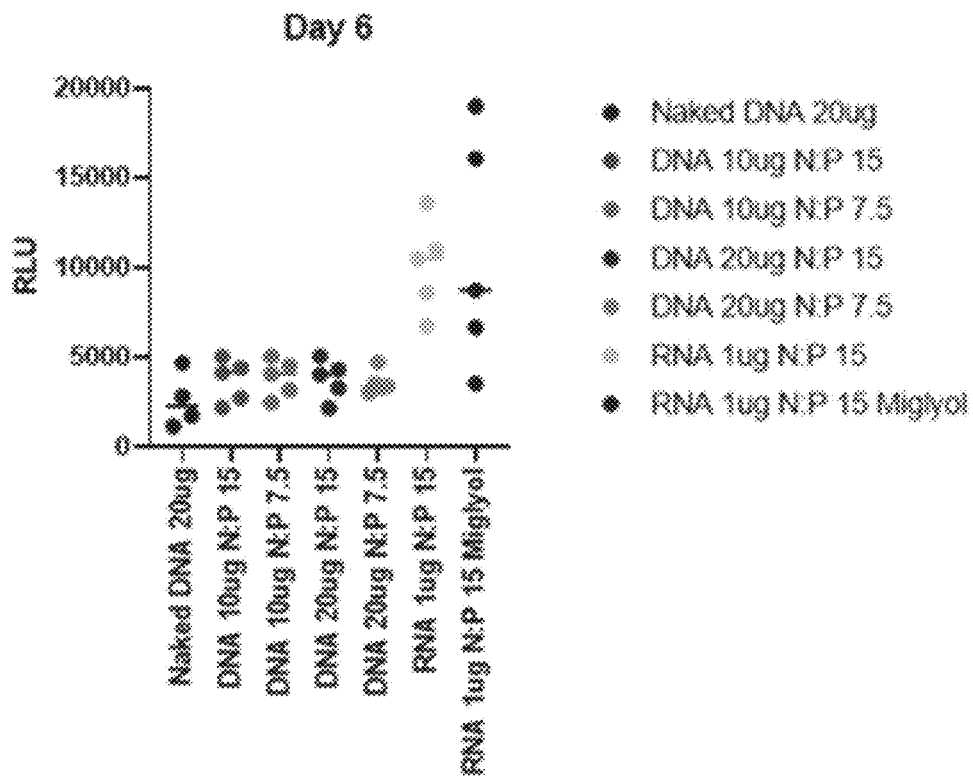
Figure 7C:
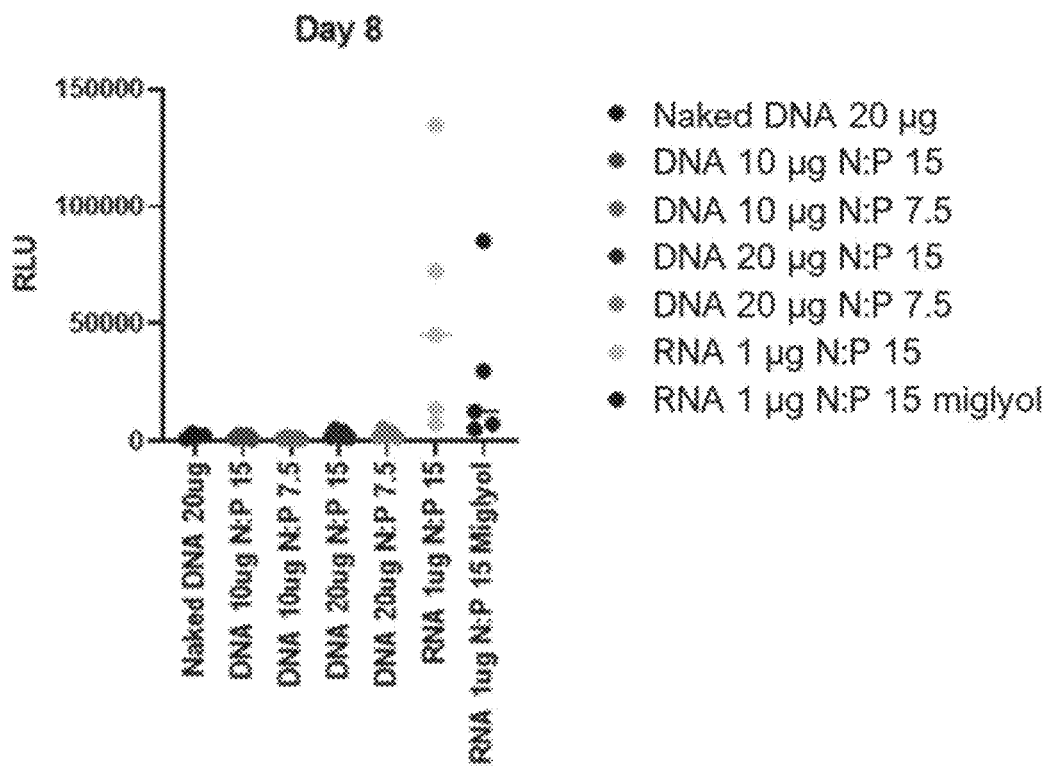
Figure 7D:
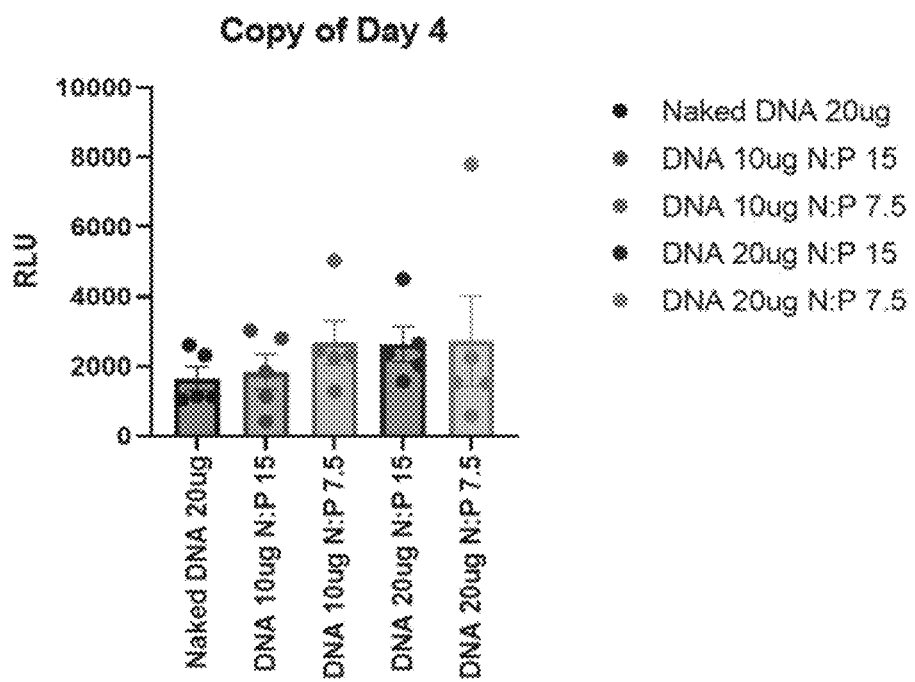
Figure 7E:
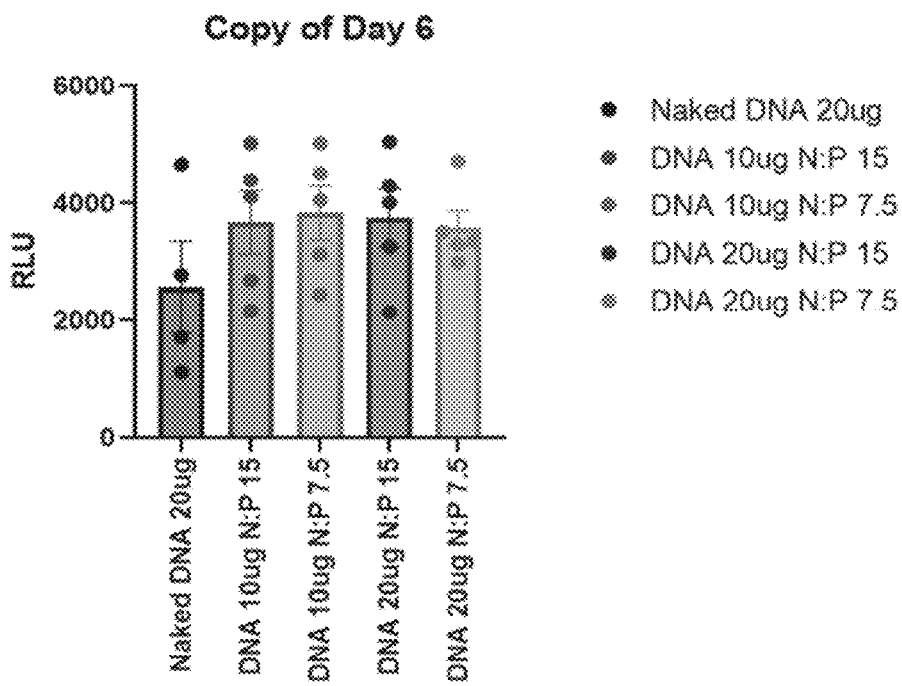
Figure 7F:
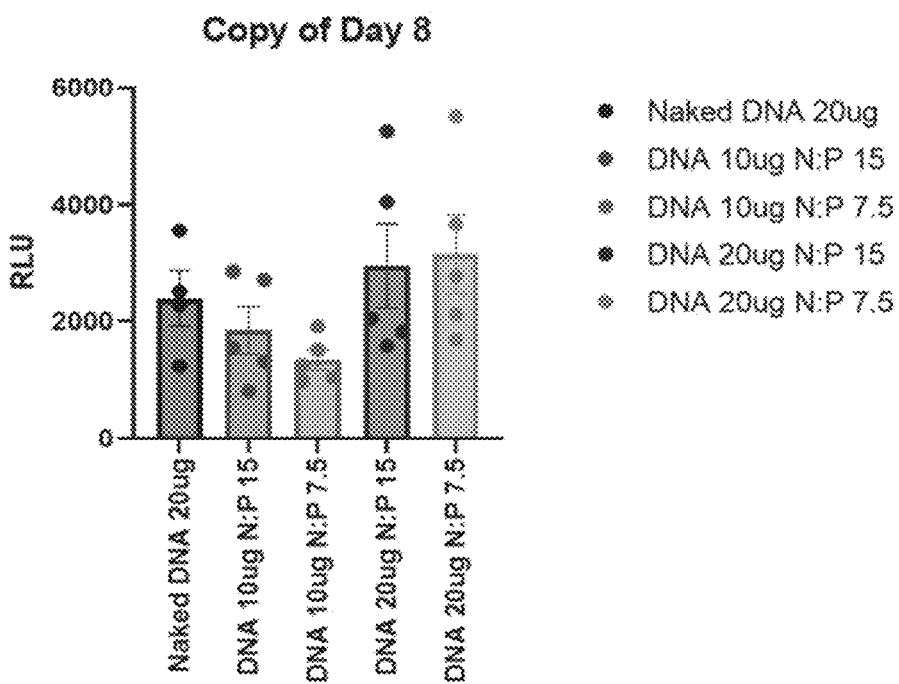

The correlation between enhanced protein production and low TNF-alpha stimulation was observed with Miglyol lipid carrier formulation, as shown in the first experiment in FIG. 6A and in the second experiment in FIG. 6B. The solanesol induced slightly lower protein production, but potentially higher TNF production, shown in the first experiment in FIG. 6A and in the second experiment in FIG. 6B.

Example 8: Techniques and Materials for Production of Lipid Carriers

The following materials were used in the manufacturing of lipid-inorganic nanoparticles (i.e., lipid carriers). The compositions, kits and methods described herein are not limited to the techniques or materials described herein.

Iron oxide nanoparticles at 25 mgFe/ml in chloroform and of various average diameters (5, 10, 15, 20, 25 and 30 nm) were purchased from Ocean Nanotech (San Diego, CA). Squalene and Span® 60 (sorbitan monostearate) were purchased from Millipore Sigma. Tween® 80 (polyethylene glycol sorbitan monooleate) and sodium citrate dihydrate were purchased from Fisher Chemical. The chloride salt of the cationic lipid 1,2-dioleoyl-3-trimethylammoniumpropane (DOTAP chloride) was purchased from Corden Pharma. Ultrapure water (18.2 mega ohm centimeter (MOhm-cm) resistivity) was obtained from a Milli-Q water purification system (Millipore Sigma).

The lipid carrier comprises squalene, sorbitan monostearate (e.g., SPAN-60), polysorbate 80 (e.g., TWEEN-80), DOTAP chloride, iron oxide nanoparticles and sodium citrate dihydrate.

In general, to iron oxide nanoparticles with a number-weighted average diameter of 5 nm, chloroform was added. Chloroform was allowed to evaporate in a fume hood leaving behind a dry coating of iron oxide nanoparticles. To the iron oxide nanoparticles, Span® 60, squalene, and DOTAP chloride were added to prepare the "oil" phase.

The oil phase was sonicated 30 minutes in a water bath pre-heated to 60° C. Separately, in a 1 liter glass bottle, the "aqueous" phase was prepared by adding Tween® 80 to sodium citrate dihydrate solution prepared with Milli-Q water.

The aqueous phase was stirred for 30 minutes to allow complete dissolution of Tween® 80. After complete dissolution of Tween® 80, the aqueous phase was transferred to a beaker and incubated in a water bath pre-heated to 60° C. To the heated oil phase, the pre-heated aqueous phase was added.

The mixture was immediately emulsified using a VWR® 200 homogenizer (VWR International) until a homogenous colloid with a milk-like appearance was produced. The colloid was subsequently processed by passaging the fluid through a Y-type interaction chamber of a LM10 microfluidizer at 20,000 psi.

The fluid was passaged until the z-average hydrodynamic diameter, measured by dynamic light scattering (Malvern Zetasizer Nano S), was 59 nm with a 0.2 polydispersity index.

The microfluidized lipid carrier sample was terminally filtered with a 200 nm pore-size polyethersulfone (PES) syringe filter.

Example 9: Exemplary Techniques and Materials for Producing Lipid Carriers

The following materials were used in the manufacturing of lipid-inorganic nanoparticles (i.e., lipid carriers). The compositions, kits and methods described herein are not limited to the techniques or materials describe herein.

Iron oxide nanoparticles at 25 mgFe/ml in chloroform and of various average diameters (5, 10, 15, 20, 25 and 30 nm) were purchased from Ocean Nanotech (San Diego, CA). Squalene and Span® 60 (sorbitan monostearate) were purchased from Millipore Sigma. Tween® 80 (polyethylene glycol sorbitan monooleate) and sodium citrate dihydrate were purchased from Fisher Chemical. The chloride salt of the cationic lipid 1,2-dioleoyl-3-trimethylammoniumpropane (DOTAP chloride) was purchased from Corden Pharma. Ultrapure water (18.2 MOhm-cm resistivity) was obtained from a Milli-Q water purification system (Millipore Sigma).

Lipid carriers were prepared which comprised 37.5 mg/ml squalene, 37 mg/ml Span® 60, 37 mg/ml Tween® 80, 30 mg/ml DOTAP chloride, 0.1 mg/ml 10 nm iron oxide nanoparticles and 10 mM sodium citrate dihydrate.

The lipid carriers were manufactured using the following procedures. In a 200 ml beaker, 0.4 ml of iron oxide nanoparticles at 25 mgFe/ml in chloroform, with a number-weighted average diameter of 10 nm, were added. Chloroform was allowed to evaporate in a fume hood leaving behind a dry coating of iron oxide nanoparticles. To the iron oxide nanoparticles, 3.7 grams of Span® 60, 3.75 grams of squalene, and 3 grams of DOTAP chloride were added to prepare the "oil" phase.

The oil phase was sonicated 30 minutes in a water bath pre-heated to 60° C. Separately, in a 1 liter glass bottle, the "aqueous" phase was prepared by adding 39 grams of Tween® 80 to 1,000 ml 10 mM sodium citrate dihydrate solution prepared with Milli-Q water.

The aqueous phase was stirred for 30 minutes to allow complete dissolution of Tween® 80. After complete dissolution of Tween® 80, 96 ml of the aqueous phase was transferred to a 200 ml beaker and incubated in a water bath pre-heated to 60° C. To the heated oil phase, 96 ml of the pre-heated aqueous phase was added. The mixture was immediately emulsified using a VWR® 200 homogenizer (VWR International) until a homogenous colloid with a milk-like appearance was produced. The colloid was subsequently processed by passaging the fluid through a Y-type interaction chamber of a LM10 microfluidizer at 20,000 psi. The fluid was passaged until the z-average hydrodynamic diameter, measured by dynamic light scattering (Malvern Zetasizer Nano S), was 54 nm with a 0.2 polydispersity index. The microfluidized lipid carrier sample was terminally filtered with a 200 nm pore-size polyethersulfone (PES) syringe filter.

Example 10: Exemplary Techniques and Materials for Producing Nanoparticles Described Herein Lipid carriers were prepared which comprised 37.5 mg/ml squalene, 37 mg/ml Span® 60, 37 mg/ml Tween® 80, 30 mg/ml DOTAP chloride, 0.2 mg/ml 15 nm iron oxide nanoparticles, and 10 M sodium citrate dihydrate.

The lipid carriers of Example 4 were manufactured using the following procedures.

In a 200 ml beaker, 0.8 ml of iron oxide nanoparticles at 25 mgFe/ml in chloroform, with a number-weighted average diameter of 15 nm, was added. Chloroform was allowed to evaporate in a fume hood leaving behind a dry coating of iron oxide nanoparticles. To the iron oxide nanoparticles, 3.7 grams of Span® 60, 3.75 grams of squalene, and 3 grams of DOTAP chloride were added to prepare the "oil" phase.

The oil phase was sonicated 30 minutes in a water bath pre-heated to 60° C. Separately, in a 1 liter glass bottle, the "aqueous" phase was prepared by adding 39 grams of Tween® 80 to 1,000 ml of 10 mM sodium citrate dihydrate solution prepared with Milli-Q water.

The aqueous phase was stirred for 30 minutes to allow complete dissolution of Tween® 80.

After complete dissolution of Tween® 80, 96 ml of the aqueous phase was transferred to a 200 ml beaker and incubated in a water bath pre-heated to 60° C. To the heated oil phase, 96 ml of the pre-heated aqueous phase was added.

The mixture was immediately emulsified using a VWR® 200 homogenizer (VWR International) until a homogenous colloid with a milk-like appearance was produced. The colloid was subsequently processed by passaging the fluid through a Y-type interaction chamber of a LM10 microfluidizer at 20,000 psi.

The fluid was passaged until the z-average hydrodynamic diameter, measured by dynamic light scattering (Malvern Zetasizer Nano S), was 52 nm with a 0.2 polydispersity index.

The microfluidized lipid carrier sample was terminally filtered with a 200 nm pore-size polyethersulfone (PES) syringe filter.

Example 11: Lipid Carrier without Inorganic Core Formulation (Prepared at 100 mL Scale)

Described herein is a lipid carrier formulation without inorganic core particles comprising: 37.5 mg/ml squalene (SEPPIC), 37 mg/ml Span® 60 (Millipore Sigma), 37 mg/ml Tween® 80 (Fisher Chemical), 30 mg/ml DOTAP chloride (LIPOID) and 10 mM sodium citrate.

This composition was prepared as follows. To a 200 ml beaker 3.75 grams squalene, 3.7 grams span 60, and 3.0 grams DOTAP were added to produce the oil phase. The oil phase was sonicated for 45 minutes in a 65 degree C. water bath. Separately, the aqueous phase was prepared by dissolving 19.5 grams Tween 80 in 500 ml of 10 mM sodium citrate buffer prepared in nuclease free water. 96 ml of the aqueous phase was transferred to a separate glass bottle and heated to 65 degrees C. for 30 minutes. The oil phase was mixed with the 96 ml of aqueous phase by adding the warm oil phase to the warm aqueous phase.

The mixture was then emulsified using a VWR 200® homogenizer (VWR International) and the resulting crude emulsion was processed by passing through a M110P microfluidizer (Microfluidics) at 30,000 psi equipped with a F12Y 75 μm diamond interaction chamber and an auxiliary H30Z-200 μm ceramic interaction chamber until the z-average hydrodynamic diameter—measured by dynamic light scattering (Malvern Zetasizer Nano S)—reached 40-80 nm with a 0.1 to 0.3 polydispersity index (PDI). The microfluidized lipid carrier composition (without inorganic core) formulation was then terminally filtered with a 200 nm pore-size polyethersulfone (PES) filter and stored at 2 to 8 degrees (° C.). DOTAP and squalene concentration were then measured by RP-HPLC.

Example 12: Exemplary Techniques and Materials for Producing Nanoparticles Described Herein In a further murine study, C57BL/6 mice were inoculated as described in Table 6 below, after which secreted embryonic alkaline phosphatase (SEAP) levels were measured in serum. A summary of the materials used in the study is provided in Table 5.

TABLE 5

Materials.

| Description | Concentration | Temperature/Location |
|---|---|---|
| DNA encoding SEAP (DNA sequence as set forth in SEQ ID NO: 39) | 5 mg/mL | −20° C. |
| repRNA encoding SEAP | 2217 μg/mL | −80° C. |
| Lipid carrier formulation | 30 mg DOTAP/mL | 4° C. |

TABLE 6

Treatment Groups.

| Group | n | Formulation | DNA/RNA-SEAP | RNA dose [μg] | DNA dose [μg] | N:P | Injection Volume [μL] |
|---|---|---|---|---|---|---|---|
| 1 | 5 | Naked | DNA-SEAP |  | 20 | n/a | 50 |
| 2 | 5 | Lipid carrier | DNA-SEAP |  | 10 | 15 | 50 |
| 3 | 5 | Lipid carrier | DNA-SEAP |  | 10 | 7.5 |  |
| 4 | 5 | Lipid carrier | DNA-SEAP |  | 20 | 15 |  |
| 5 | 5 | Lipid carrier | DNA-SEAP |  | 20 | 7.5 |  |
| 6 | 5 | Lipid carrier | RNA-SEAP | 1 |  | 15 | 50 |
| 7 | 5 | Miglyol + lipid carrier | RNA-SEAP | 1 |  | 15 | 50 |

Seven different formulations were prepared and administered intramuscularly across the seven treatment groups (Groups 1-7). DNA-SEAP or RNA-SEAP was diluted according to the volumes set forth in Table 7 to prepare the formulations for Groups 1-7.

TABLE 7

Formulation Preparation; Dilution of RNA/DNA

| Group | DNA-or RNA-SEAP | DNA or RNA [μL] | 40% sucrose [μL] | water [μL] | Total [μL] |
|---|---|---|---|---|---|
| 1 | DNA-SEAP | 40.0 | 125.0 | 85.0 | 250.0 |
| 2 | DNA-SEAP | 20.0 | 0.0 | 230.0 | 250.0 |
| 3 | DNA-SEAP | 20.0 | 0.0 | 230.0 | 250.0 |
| 4 | DNA-SEAP | 40.0 | 125.0 | 85.0 | 250.0 |
| 5 | DNA-SEAP | 40.0 | 0.0 | 210.0 | 250.0 |
| 6 | RNA-SEAP | 4.5 | 0.0 | 245.5 | 250.0 |
| 7 | RNA-SEAP | 4.5 | 0.0 | 245.5 | 250.0 |

The concentrations of diluted DNA or RNA prior to complexing with the lipid carrier was as follows (measured by NanoDrop spec): Groups 1, 4 and 5 contains about 820 μg/ml DNA; Groups 2 and 3 contained about 480 μg/ml DNA; and Groups 6 and 7 contained about 43 μg/ml RNA.

Formulations for Groups 1-7 were diluted with 100 mM citrate as set forth in Table 8 below.

TABLE 8

Dilution of lipid carrier formulations.

| Group | Formulation | Lipid Carrier [μl] | 40% sucrose [μl] | 100 mM citrate [μl] | Water [μl] | Total [μl] |
|---|---|---|---|---|---|---|
| 1 | Naked | 0 | 0 | 30 | 270 | 300 |
| 2 | Lipid carrier | 120 | 150 | 30 | 0 | 300 |
| 3 | Lipid carrier | 60 | 150 | 30 | 60 | 300 |
| 4 | Lipid carrier | 240 | 0 | 30 | 30 | 300 |
| 5 | Lipid carrier | 120 | 150 | 30 | 0 | 300 |
| 6 | Lipid carrier | 12 | 150 | 30 | 108 | 300 |
| 7 | Miglyol + lipid carrier | 12 | 150 | 30 | 108 | 300 |

The above formulations were complexed by adding 250 μl diluted lipid carrier to 250 μl diluted DNA or RNA. The resulting complexed formulations were incubated on ice for at least 30 minutes. Table 9 sets forth the experiment schedule for this study.

TABLE 9

Experiment schedule.

| Day | Procedure | Notes on Mice |
|---|---|---|
| 0 | All inoculations | None |
| 4 | Bleed | Group 4 had ruffled fur, one mouse emaciated (died during collection). Hydropaque placed in cage. |
| 6 | Bleed | None |
| 8 | Bleed | None |
| 11 | Bleed | None |
| 14 | Bleed | None |

Mice were bled at regular intervals and serum was prepared immediately and stored at −80 degrees C. until analyses for SEAP activity.

To evaluate SEAP levels in serum, all serum samples were thawed at the same time and SEAP detection was conducted. FIGS. 7A-7F illustrate the SEAP levels in BALB/c mice injected intramuscularly with varying iterations of lipid carrier-formulated DNA SEAP. Mice were bled at regular intervals, serum prepared and stored until analysis by SEAP assay. Data are displayed as mean and SE (n=5 per group).

As can be seen from FIGS. 7A-7F, lipid carrier formulations aid target protein production over delivery of DNA alone, particularly after day 6 following injection. Additionally, the data shows that inclusion of Miglyol enhances protein production from an RNA replicon over lipid carrier formulations lacking Miglyol.

Example 13: Additional Nanoparticle Formulations

Additional nanoparticle formulations are produced according to the following tables (Table 10 and Table 11). The mRNA comprises a sequence encoding the SARS-CoV-2 omicron variant spike protein with a VEEV replicon mRNA backbone (SEQ ID NO: 8).

TABLE 10 mRNA Vaccine Formulation.

| Dosage form: | Solution for Injection for IM route of administration | | |
|---|---|---|---|
| Composition: | Each 0.5 ml Vial Contains: | Quantity | Concentration (mg/ml) |
| | mRNA | 25 mcg | 0.05 |
| | DOTAP | 0.75 mg | 1.5 |
| | Iron Oxide Nanoparticles | 0.005 mg | 0.01 |
| | Squalene | 0.94 mg | 1.88 |
| | Sorbitan Monostearate | 0.93 mg | 1.86 |
| | Polysorbate 80 | 0.93 mg | 1.86 |
| | Sucrose IP | 50 mg | 100 |
| | Citric Acid Monohydrate | 1.05 mg | 2.1 |
| | Water for Injection | q.s. to 0.5 ml | |

TABLE 11

Lyophilized mRNA Vaccine Formulation.

| Dosage form: | Lyophilized powder | | |
|---|---|---|---|
| Composition: | Each 5 dose vial contains: | Quantity | Concentration (mg/ml) | Approximate dry weight % |
| | mRNA | 50 mcg | 0.02 | 0.02 |
| | DOTAP | 1.5 mg | 0.6 | 0.57 |
| | Squalene | 1.88 mg | 0.752 | 0.72 |
| | Sorbitan Monostearate | 1.86 mg | 0.744 | 0.71 |
| | Polysorbate 80 | 1.86 mg | 0.744 | 0.71 |
| | Sucrose IP | 250 mg | 100 | 95.3 |
| | Citric Acid Monohydrate | 5.25 mg | 2.1 | 2 |
| | Water for Injection (for reconstitution) | 2.5 ml | | |

Example 14: Self-Replicating mRNA Construct

A plasmid encoding a T7 promoter followed by the 5' and 3' UTRs and nonstructural genes of Venezuelan equine encephalitis virus (VEEV) strain TC-83 was generated using standard DNA synthesis and cloning methods. The VEEV replicon mRNA backbone is set forth in SEQ ID NO: 20.

Example 15: An Alphavirus-Derived Replicon RNA Vaccine for SARS-CoV-2 Neutralizing Antibody and T Cell Responses in Nonhuman Primates The immunogenicity and safety of NP-1 to NP-31 in combination with repRNA-CoV2 S protein vaccines are assessed in pigtail macaques. To protect the RNA replicons from degradation, NP-1 which consists of inorganic superparamagnetic iron oxide (SPIO) nanoparticles within a hydrophobic squalene core is used to enhance formulation stability. Replicon RNA (SEQ ID NOS: 1 to 8) are complexed with NP formulations. Pigtail macaques are used to test the response to the vaccines. Blood is collected at baseline (week −2 or −1), and at days 10, 14, 28, and 42 post-prime vaccination. Blood is also collected 10 days post-boost (38 days post-prime) in 50 μg vaccinated animals. Serum and plasma are collected and PBMCs are isolated from whole blood. Animals are sedated with an intramuscular injection (10 mg/kg) of ketamine (Ketaset®; Henry Schein) prior to blood collection or vaccination. The 50 μg vaccine is delivered intramuscularly into the quadriceps muscle with one 250 μl injection on weeks 0 and 4. To maintain consistency in the vaccine formulation and concentration, the 250 μg vaccine is delivered intramuscularly by inoculating 250 μl injections into 5 intramuscular injections sites, 2 in the right quadriceps, 1 in the left quadricep, and 1 each in the left and right deltoids on week 0. All injection sites are monitored post-injection for any signs of local reactogenicity. Serum chemistries and complete blood counts are assessed along with antigen-specific antibody responses.

Blood is collected from venipuncture of anesthetized macaques. Antigen-specific IgG, IgG1, IgG2a, and IgG2c responses are detected by enzyme linked immuno-sorbent assay (ELISA) using recombinant SARS-CoV-2 S as the capture antigen. SARS-CoV-2 neutralization assays are also performed to determine whether vaccine compositions can induce antibody responses to SARS-CoV-2 infection. Immune responses in macaques are monitored by IFN-γ ELISpot assay and intracellular cytokine staining. Multiparameter flow cytometry is used to determine T-cell immune responses using peptide stimulated PBMCs. S-specific CD4+ or CD8+ T cells are screened before and after immunization.

Example 16: Evaluation of Lyophilized COVID Vaccines in Mice

The following was performed to assay activity of lyophilized NP-1 with replicon RNA encoded SARS-CoV-2 spike antigen sequence, physicochemical properties of reconstituted vaccines, potency, and immunogenicity. Briefly, materials in Table 12 were used.

TABLE 12

| Name | Stock concentration |
|---|---|
| NP-1 | 30 mg/ml (measuring DOTAP conc.) |
| NP-7 | 30 mg/ml (measuring DOTAP conc.) |
| repRNA-CoV2-spike (wild type) VEE-S-v5 Delta ("WT-S") | 1687 ug/ml |
| repRNA-CoV2-spike (delta) VEE-nCoV19-S-Delta.AY1-S2P-wtFur ("Delta-S") | 783 ug/ml |
| Sucrose (EMD, Millipore) | |
| Na-citrate (Teknova) | 1M |

Preparation of formulation complexes. Compositions of lipid nanoparticle/RNA complexes were prepared in this study as shown below in Table 13. NP-1 or NP-7 and repRNAs were complexed at a N-to-P ratio of 15 and complexed to obtain a final repRNA concentration of 50 mg/ml or 100 mg/ml ("2X" material), and 10% or 20% w/v sucrose content, respectively. Complexed material with 10% sucrose (50 mg/ml repRNA) contained 5 mM sodium citrate while that with 20% sucrose (100 mg/ml repRNA) contained 10 mM citrate. Complexes were filled in 2 ml sterile, depyrogenated and baked vials. Complexes with 10% sucrose were filled at 0.7 ml per vial and 20% sucrose at 0.35 ml per vial. Vials were then either lyophilized and stored or stored as is in liquid form. Storage temperature was 25 degrees C. or 42 degrees C. for 1 week. Quantity of lyophilized and liquid vials per composition is summarized in Table 13.

TABLE 13

| Description | N:P | DOTAP [μg/ml] | RNA [μg/ml] | Volume per vial [ml] | Lyo vials | Liquid vials |
|---|---|---|---|---|---|---|
| NP-1 + WT-S in 10% sucrose | 15 | 1500 | 50 | 0.7 | 8 | 6 |
| NP-1 + Delta-S in 10% sucrose | 15 | 1500 | 50 | 0.7 | 2 | 0 |
| NP-1 + WT-S in 20% sucrose | 15 | 3000 | 100 | 0.35 | 8 | 0 |
| NP-1 + Delta-S in 20% sucrose | 15 | 3000 | 100 | 0.35 | 2 | 0 |
| NP-7 + WT-S in 10% sucrose | 15 | 1500 | 50 | 0.7 | 8 | 6 |

Lyophilization cycle. An SP VirTis Advantage Pro tray and batch lyophilizer with inert gas fill and stoppering capability was used. Summary of the lyophilization cycle is shown in Table 14 below. After end of cycle, vials were backfilled with nitrogen at 48 torr and stoppered, before equilibrating to room pressure.

TABLE 14

| Time [hours] | Temp [° C.] | Pressure [mT] | Notes |
|---|---|---|---|
| 0 | 5 | 760 | Shelf pre-cooled to 5 degrees C. |
| 0.5 | 5 | 760 | Freezing |
| 2 | −50 | 760 | |
| 2.5 | −50 | 50 | Evacuation |
| 3 | −30 | 50 | Primary drying |
| 20.5 | −30 | 50 | |

TABLE 14-continued

| Time [hours] | Temp [° C.] | Pressure [mT] | Notes |
|---|---|---|---|
| 22.5 | 25 | 50 | Secondary drying |
| 24 | 25 | 50 | |

Condition groups. A summary of 14 groups analyzed in this assay is provided in Table 15 below. Groups 1 and 4, as indicated in the storage column, were prepared fresh to serve as positive controls for comparison with standard protocol for vaccine preparation.

TABLE 15

| Group | Formulation | RNA | Sucrose [% w/v] | Form | Storage [temp/time] |
|---|---|---|---|---|---|
| 1 | NP-1 | WT-S | 10 | Liquid | Fresh |
| 2 | NP-1 | WT-S | 10 | Liquid | 25 C./1 wk |
| 3 | NP-1 | WT-S | 10 | Liquid | 42 C./1 wk |
| 4 | NP-7 | WT-S | 10 | Liquid | Fresh |
| 5 | NP-7 | WT-S | 10 | Liquid | 25 C./1 wk |
| 6 | NP-7 | WT-S | 10 | Liquid | 42 C./1 wk |
| 7 | NP-1 | WT-S | 10 | Lyo | 25 C./1 wk |
| 8 | NP-1 | WT-S | 10 | Lyo | 42 C./1 wk |
| 9 | NP-1 | WT-S | 20 | Lyo | 25 C./1 wk |
| 10 | NP-1 | WT-S | 20 | Lyo | 42 C./1 wk |
| 11 | NP-7 | WT-S | 10 | Lyo | 25 C./1 wk |
| 12 | NP-7 | WT-S | 10 | Lyo | 42 C./1 wk |
| 13 | NP-1 | Delta-S | 10 | Lyo | 25 C./1 wk |
| 14 | NP-1 | Delta-S | 20 | Lyo | 25 C./1 wk |

Immunogenicity study. Induction of anti-spike IgG responses were evaluated in 6 to 8 weeks old female C571B1/6 mice. A group size of 5 mice was used. Study schedule is shown in Table 16.

TABLE 16

Immunogenicity study schedule.

| Date | Study Day | Procedure |
|---|---|---|
| Aug. 23, 2021 | −7 | Lyophilization |
| Sep. 1, 2021 | 0 | Immunization by IM route |
| Sep. 15, 2021 | 14 | Bleed |
| Sep. 29, 2021 | 28 | Bleed |
| Oct. 8, 2021 | 37 | Mice sacrificed |

Figure 8:
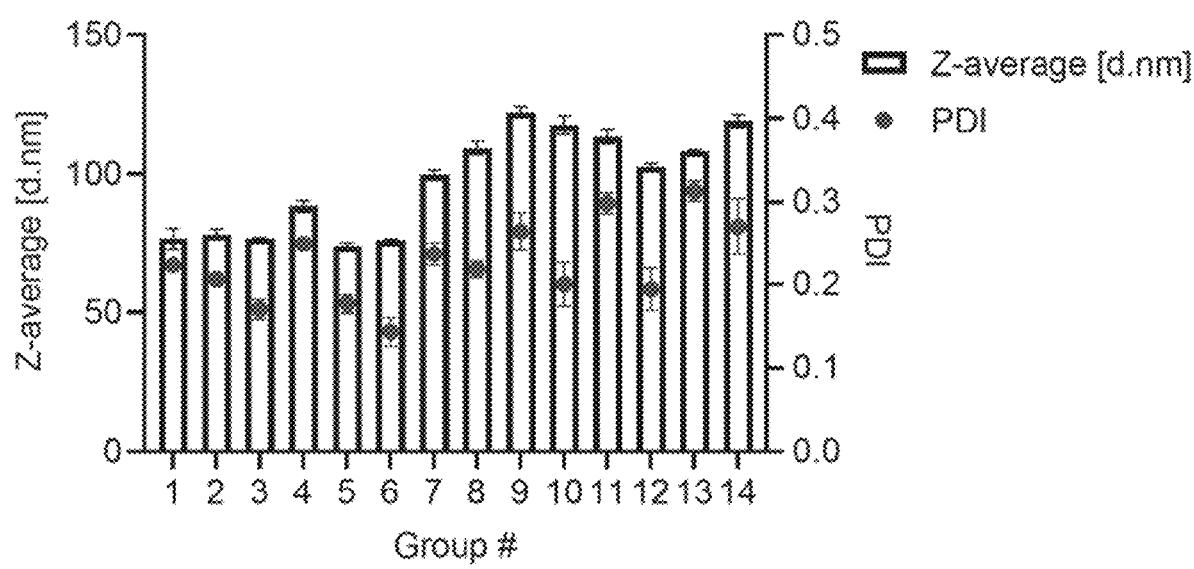
FIG. 8 is a bar chart with measurements of Z-average measurement and polydispersity index (PDI) on the Y-axis and group number on the X-axis for conditions 1 to 14.

After 1 week of storage in 25 degrees C. or 42 degrees C. stability chamber, lyophilized nanoparticle/RNA complexes were reconstituted in 0.7 ml sterile milliQ water and gently swirled until no particles were visible to the naked eye. Particle size (z-average) and size distribution (PDI) of the complexes was measured and is summarized in FIG. 8, with group designations shown in Table 15. Particle size and PDI of freshly prepared NP-1/WT-S complex (group 1) was 76.8 nm and 0.223, respectively. After reconstitution, lyophilized samples (groups 7-14) grew by an average of 45% (+/− 11%). Summary of % change in z-average relative to group 1 is included in Table 17.

TABLE 17

| Group # | 2 | 3 | 4 | 5 | 6 | 7 | 8 | 9 | 10 | 11 | 12 | 13 | 14 |
|---|---|---|---|---|---|---|---|---|---|---|---|---|---|
| % change z-average vs. group 1 | 2% | 0% | 15% | −4% | −1% | 30% | 42% | 59% | 53% | 48% | 33% | 41% | 55% |

Agarose gel electrophoresis of phenol-chloroform extracted repRNA. Liquid formulations of NP-1/repRNA and NP-7+repRNA in 10% sucrose or 20% sucrose, stored for 1 week at NP-1/repRNA and NP-7+repRNA, resulted in partial or full degradation of repRNA product, respectively. (Data not shown.) Lyophilization of NP-1/repRNA and NP-7+repRNA in 10% sucrose or 20% sucrose preserved repRNA integrity after 1 week storage at NP-1/repRNA and NP-7+repRNA. (Data not shown.)

Potency Assay. Lyophilized NP-1/WT-S in 10% sucrose stored for 1 week at 25 degrees C. produced a dose-dependent expression of spike protein in transfected BHK cells. The expression profile was similar to freshly complexed NP-1/WT-S. 1 week storage at 42 degrees C. of lyophilized NP-1/WT-S in 10% sucrose significantly reduced in vitro protein expression. Liquid NP-1/WT-S in 10% sucrose stored for 1 week at 25 degrees C. or 42 degrees C. did not produce spike protein in BHK cells. (Data not shown.)

Figure 9A:
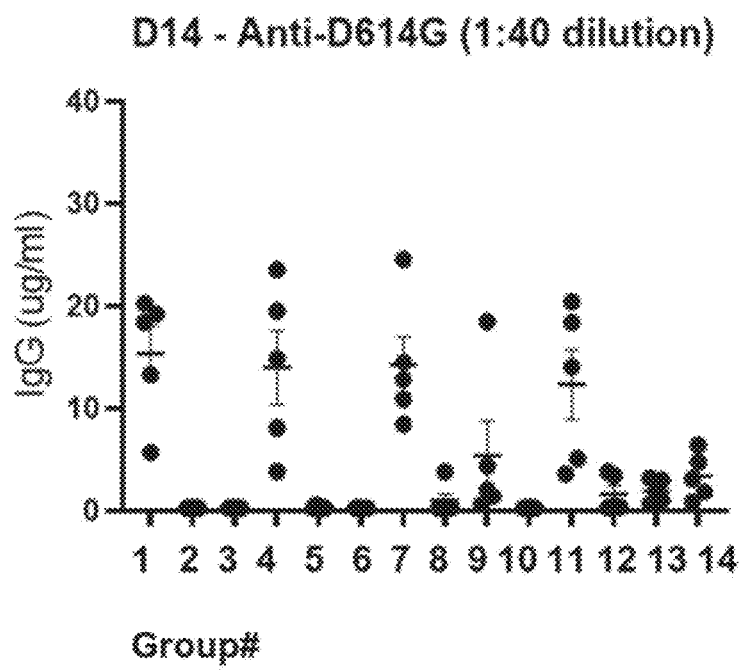
FIGS. 9A-9B are dot charts with IgG (µg/ml) on the Y-axis, group number on the X-axis for conditions 1 to 14, and recordings shown for measurements at day 14 anti-D614G (1:40 dilution) and day 28 anti-D614G (1:200 dilution), respectively.
Figure 9B:
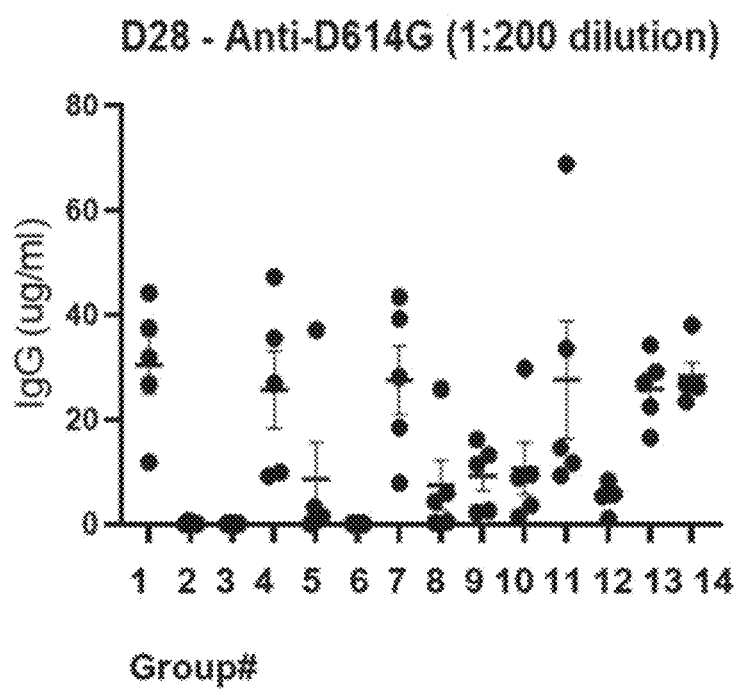

Anti-D614G spike IgG responses by ELISA. Serum anti-D614G spike IgG levels was assessed on days 14 and 28 post-prime shown below in FIGS. 9A and 9B, respectively. Mouse sera were assayed in an anti-D614G spike ELISA at 1:40 (day 14) or 1:200 (day 28) dilution. Serum IgG level in μg/ml was interpolated from a 4PL standard curve generated by a known concentration of mouse IgG standard.

Day 28 post-prime anti-D614G IgG response. After 1 week at 25 degrees C., liquid NP-1/WT-S in 10% sucrose resulted in a statistically significant reduction in anti-spike IgG compared to the freshly prepared NP-1/WT-S positive control. There was no significant difference in mean IgG levels between freshly prepared NP-1/WT-S and lyophilized NP-1/WT-S in 10% sucrose stored for 1 week at 25 degrees C.

After 1 week at 42 degrees C., lyophilized NP-1/WT-S in 10% sucrose induced 100% seroconversion but mean IgG level was significantly reduced compared to freshly prepared NP-1/WT-S. Summary mean +/−standard deviation IgG concentration data from day 28 post-immunization, including p-values determined by ordinary one-way ANOVA comparing against the freshly prepared NP-1/WT-S positive control, shown in Table 18. P<0.05 are considered statistically significant differences.

TABLE 18

| Group | Formulation | RNA | Sucrose [% w/v] | State | Storage temp. and time | D 28 mean IgG at 1:200 serum dilution [μg/ml] | SD [ug/ml] | P-value vs. group 1 |
|---|---|---|---|---|---|---|---|---|
| 1 | NP-1 | WT-S | 10 | Liquid | Fresh | 30.38 | 12.29 | n/a |
| 2 | NP-1 | WT-S | 10 | Liquid | 25 C./1 wk | 0.17 | 0.23 | 0.0014 |
| 3 | NP-1 | WT-S | 10 | Liquid | 42 C./1 wk | 0.02 | 0.02 | 0.0013 |
| 4 | NP-7 | WT-S | 10 | Liquid | Fresh | 25.69 | 16.45 | 0.9990 |
| 5 | NP-7 | WT-S | 10 | Liquid | 25 C./1 wk | 8.47 | 15.99 | 0.0385 |
| 6 | NP-7 | WT-S | 10 | Liquid | 42 C./1 wk | 0.00 | 0.00 | 0.0013 |
| 7 | NP-1 | WT-S | 10 | Lyo | 25 C./1 wk | 27.44 | 14.68 | 0.9994 |
| 8 | NP-1 | WT-S | 10 | Lyo | 42 C./1 wk | 7.34 | 10.63 | 0.0257 |
| 9 | NP-1 | WT-S | 20 | Lyo | 25 C./1 wk | 9.07 | 6.41 | 0.0474 |
| 10 | NP-1 | WT-S | 20 | Lyo | 42 C./1 wk | 10.56 | 11.25 | 0.0777 |
| 11 | NP-7 | WT-S | 10 | Lyo | 25 C./1 wk | 27.53 | 24.96 | 0.9994 |
| 12 | NP-7 | WT-S | 10 | Lyo | 42 C./1 wk | 5.33 | 2.68 | 0.0121 |
| 13 | NP-1 | Delta-S | 10 | Lyo | 25 C./1 wk | 25.83 | 6.66 | 0.9990 |
| 14 | NP-1 | Delta-S | 20 | Lyo | 25 C./1 wk | 28.25 | 5.60 | 0.9996 |

Figure 10:
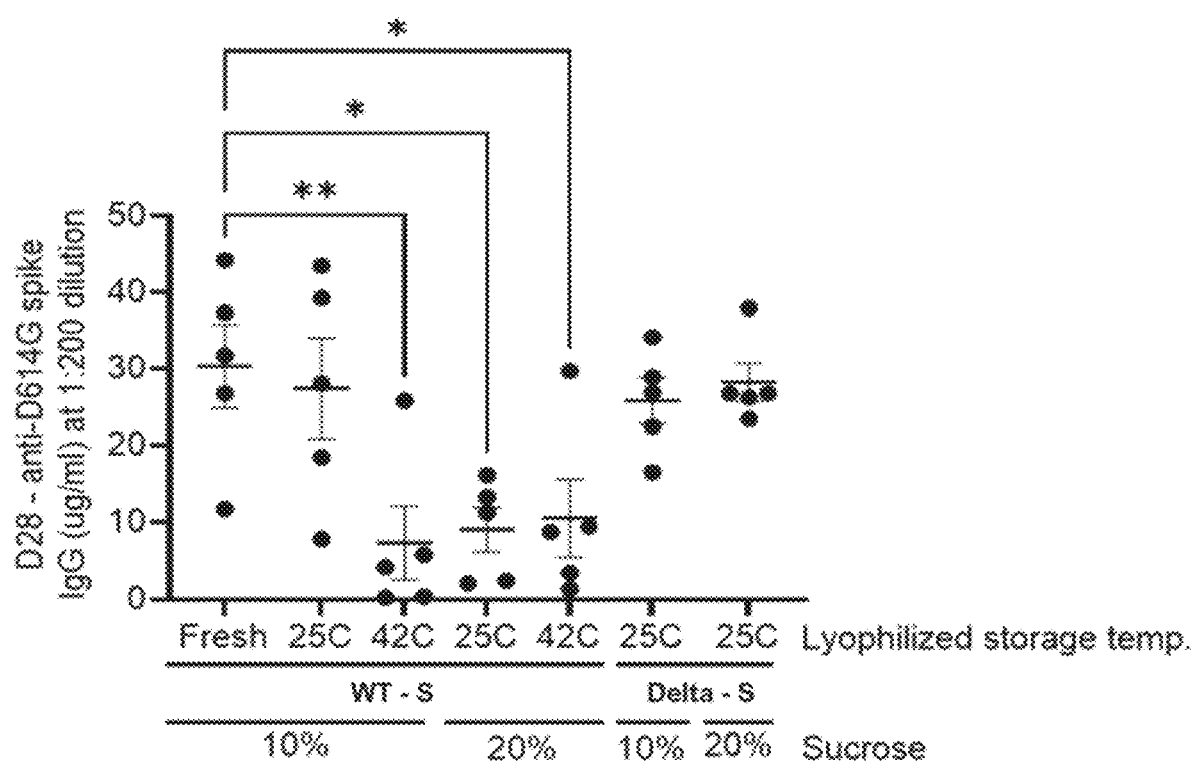
FIG. 10 shows a dot chart at day 28 with anti-D614G (1:200 dilution) IgG (ug/ml) measurements on the Y-axis and indications of storage conditions on the X-axis.

Comparison of fresh versus lyophilized formulations. Day 28 post-prime anti-D614G spike IgG concentration in serum is shown in FIG. 10. Statistical differences between mean IgG values were determined by ordinary one-way ANOVA with Dunnett's multiple comparisons test. All groups compared to freshly prepared NP-1/RNA in 10% sucrose. No significant difference was shown between freshly prepared NP-1/RNA and lyophilized NP-1/RNA in 10% sucrose stored for 7 days at 25 degrees C. At 42 degrees C., lyophilized NP-1/RNA in 10% or 20% sucrose induced significantly lower anti-spike IgG compared to freshly prepared NP-1/RNA. Lyophilized NP-1/RNA in 20% sucrose, and stored at 25 degrees C. or 42 degrees C., induced significantly lower IgG than freshly prepared NP-1/WT-S. Lyophilized NP-1/Delta-S in 10% or 20% sucrose, and stored at 25 degrees C., induced similar mean IgG (statistically not significant) than freshly prepared NP-1/WT-S.

Sequences

```
SEQ ID NO: 1
(Delta V5 Antigen Encoding RNA Sequence)
auguuucugcucacaaccaaacgcacuauguuuguuuuccucgugcugcucccuuugguaaguucucagugugua a accugacaacacgaacccaguugccuccagcuuauaccaacucauuuacucgcggaguauuaucccgauaaggu cuuuagaaguagcguguugcacucuacacaggaucuguucuugcccuucuuuaguaacguuaccugguuucaugca auacaugugagcggaacaaauggaacaaaaagauuugacaauccagugcuuccauuuaaugaugggguuuacuuug ccaguaccgaaaagucaaacauaauccgggguggaucuuuggaaccacuuuggacucuaagacacagucucuccu cauaguaaacaacgccaccaauguugucauaaaaguaugcgaauuucaguuuugcaacgaucccuuucucggggug uauuaccauaagaauaauaaauccuggauggagucugaguuccggguuuauaguagugcuaauaauugcacuuucg aauacguguccCaaccauuccucauggaccuugagggcaaacaggggaauuuuaaaaacuugcgcgaauuugucuu uaagaauaucgacggauacuuuaagaucuauaguaaacacacuccuaucaaccucguucgggaucuuccccaaggc uuuucugcucucgaaccccucguagacuugccaauugggauaaauaucacucgcuuucaaacuuugcuugcccucc acaggagcuaccugacacccggcgacucuucuucugguuggaccgccggcgccgcugccuauuauguugguuaccu ucagccacgaacauucuugcucaaguauaacgagaauggcaccauuaccgacgccgucgauugugcauuggauccc uugucugaaacaaaauguaccuugaaguccuuuaccguagagaaaggcauauaccagacuuccaacuuccgaguuc agccuacagaauccauugugagauuucccaacaucacaaaccucugcccuuucggugaaguauuuaaugcuacacg cuucgcuucagucuaugccuggaauaggaagcgcauaucaaauugcguggccgauuauucaguccucuauaauagc gcauccuucaguacuuucaagugcuacggcguuuccccaccaaacucaaugaucuuugcuucaccaacgucuaug cugacaguuuugucauacgaggcgacgaaguacgccagauugcccccgggcagacagguaaaauugcugauuauaa uuauaaacucccagaugacuuuacuggaugcgucauagccuggaauuccaacaaucuugauuccaagguuggugg g aauuauaauuaccuuuaucgacuguucagaaagaguaacuugaaaccauuugagagagacauauccaccgagauuu accaggcaggcaguacuccuuguaacggcguugagggauuuaacugcuauuuuccuuugcaauccuauggcuuuca
```

-continued accaacaaacggggguuggcuaucaacccuaucgaguggguuguccugagcuuugaacuuuugcacgcucccgccaca
gucugcggaccaaaaagaguacaaaucuugucaagaauaagugcguaaauuucaauuucaauggccuuacaggaa
caggcgugcugacugagucaaacaagaaguuccugccauuucagcaguuuggaggggauauagcagacacaacuga
cgcuguacgcgauccucagacuuuggagaucuuggacaucacucccuguucuuucggaggggguaucugucaucacc
cccggaacuaauacaucaaaucaggucgcugugguguguuguaccaagaugucaacugcacagaaguccccguugcuauac
acgcagaccagcucaccccacauggcggguguacucaacuggcucaaacguauuccagaccagagcugggugcuu
gaucggugcugaacacguaaacaauagcuaugaaugcgauauucccaucggugccgggaucugcgcuagcuaucag
acacagaccaauucccccccggcgagcacgaucuguagcaucccagucuauuauugccuacacuaugucauugggcg
ccgagaauagcgucgcauauucaaauaauucuauugcaauacccaccaacuucacaaucuccguaacuacagaaau
acuuccaguuuccaugacaaagacaucaguggauuguacaaugauauaugcggagauuccacagaaaguguucaaaau
uugcucuugcaguacggcuccuucugcacccagcucaacagggcccuuacagguauugcugucgaacaggacaaga
acacacaagaagucuucgcccaagucaaacagauauacaaaacuccucccauaaaggauuuuggcggcuucaacuu
uagucagauccucccagacccuucaaaaccaucaaacgaucauuuauugaagaucugcuguucaacaaggucacu
cuugccgaugcuggauucauuaagcaauacggugacugccuuggugauauugcugcccgagaucugaucugugccc
agaaauucaacgggcucacuguacuccuccacugcucacagacgaaaugauugcacaguacacaagugcccuguu
ggcaggcacaaucacuagcggcuggaccuuuggcgcaggugcagcacuccaaauaccuuuugccaugcagauggcc
uaucgguuuaaugggauaggcgugacucaaaaaugccucuacgaaaaccaaaaguugauagcuaaccaauucaauu
cagcaaucgggaagauacaggauucacugucuaguacugcuagugcccuugguaagcugcaggacguugucaacca
gaaugcucaagcucugaauacauugguuaagcagcucucucuaguaauuuuggggccaucucuucaguacuuaaugau
auuuugagccgauuggacaaaguggaagcugaaguacagaucgacaggcugauaacaggccggcuccaaucccucc
aaacauacgugacacaacaacucaucgcgcagccgaaauccgagccagcgcuaaccuggcagcuaccaagaugucgu
agaaugcguucugggccagaguaaacgcguagauuucugcgggaaagggguaccaccugauguccuuuccacaaucu
gcaccucacgggucgucuuuuugcauguaacauaugu acccgcacaagagaagaauuuuacuaccgcuccugcca
ucugucaugacgggaaagcucauuuuccucgcgaaggugugguuuguaucuaauugguacacauugguuuugcacaca
gcggaauuucuaugaaccccagaucauuacaacugacaacacuuuuguuccgggaauugugacgguggucauagga
aucguaaauaacacuguauaugaucccccuccaaccagagcuggacucuuuuaagaagaacuggauaaauauuuca
agaaccacacaaguccgacguggaccuuggggacauaaguggguauuaacgcaucugugguuaacauucaaaagga
aaucgacagacucaacgagguggccaaaaaccugaacgaaagcuugauagaucuccaggaguugggcaaguaugaa
caguacauuaaauggccaugguacauauggcuuggcuuuaucgcuggccuuaucgccaucguaauggnuacaauca
ugcugugcugcaugaccuccugcuguucuguuugaaaggggugguguucuugugguaguguguugcaaguuugacga
agaugauuccgaaccuguucuuaaaggggguaaagcuucacuauaca SEQ ID NO: 2
(K995P-V996P Antigen Encoding RNA Sequence)
auguuucugcucacaaccaaacgcacuauguuuguuuccucgugcugcucccuuugguaaguucucagugugugaa
accugacaacacgaaccagugccuccagcuuuauccaacucauuuacucgcggaguauauuauccccgauaaggu
cuuuagaaguagcgguguucacucuacacaggaucuguucuugccucuuuuaguaacguuaccugguuucaugca
auacaugugagcggaacaaauggaacaaaaagauuugacaauccagugcuuccauuuaaugaugggguuuacuuug
ccaguaccgaaaagucaaacauaauccggggguggaucuuuggaaccacuuuggacucuaagacacagucucuccu
cauaguaaacaacgccaccaaugugugcauaaaaguaugcgaauuucaguuuugcaacgaucccuuucucggggug
uauuaccauaagaauaauaaauccuggauggagucugaguuccggguuuauaguagugcuaauaauugcacuuucg
aauacgugucccaaccauuccucauggaccuugagggcaaacaggggaauuaaaaaacuugcgcgaauuugucuu
uaagaauaucgacggauacuuuaagaucuauaguaaaacacacuccuaucaaccucguucgggaucuuccccaaggc -continued uuuucugcucucgaaccccucguagacuugccaauugggauaaauaucacucgcuuucaaacuuugcuugcccucc acaggagcuaccugacacccggcgacucuucuucgguuggaccgccggcgccgcugccuauuauguuguuaccu ucagccacgaacauucuugcucaaguauaacgagaauggcaccauuaccgacgccgucgauugugcauuggaucc uugcugaaacaaaauguaccuugaaguccuuuaccguagagaaaggcauauaccagacuuccaacuuccgaguuc agccuacagaauccauugugagauuucccaacaucacaaaccucugcccuuucggugaaguauuuaaugcuacacg cuucgcuucagucuaugccuggaauaggaagcgcauaucaaauugcguggccgauuauucagucccuauaauagc gcauccuucaguacuuucaagugcuacggcguuccccaccaaacucaaugaucuuugcuucaccaacgucuaug cugacaguuugucauacgaggcgacgaaguacgccagauugccccgggcagacagguaaaauugcugauuauaa uuauaaacucccagaugacuuuacuggaugcgucauagccuggaauuccaacaaucuugauccaagguuggugg aauuauaauuaccuuuaucgacuguucagaaagaguaacuugaaaccauuugagagagacauauccaccgagauuu accaggcaggcaguacuccuuguaacggcguugagggauuuaacugcuauuuccuuugcaauccuauggcuuuca accaacaaacggguuggcuaucaaccccuaucgaguggucgugccugagcuuugaacuuuugcacgcucccgccaca gucugcggaccaaaaagaguacaaaucuugucaagaauaagugcguaaauuucaauucaauggccuuacaggaa caggcgugcugacugagucaaacaagaaguuccugccauuucagcaguuugggcgggauauagcagacacaacuga cgcuguacgcgauccucagacuuuggagaucuuggacaucacucccuguucuuucggaggguaucugucaucacc cccggaacuaauacaucaaaucaggucgcuguguuguaccaagaugucaacugcacagaagucccccguugcuauac acgcagaccagcucaccccacauggcggguguacucaacuggcucaaacguauuccagaccagagcugggugcuu gaucggugcugaacacguaaacaauagcuaugaaugcgauauucccaucggugccgggaucugcgcuagcuaucag acacagaccaauuccccccggcgagcacgaucguguagcauccagucuauuauugccuacacuaugucauugggcg ccgagaauagcgucgcauauucaaauaauucuauugcaauacccaccaacuucacaaucuccguaacuacagaaau acuuccaguuuccaugacaaagacaucaguggauuguacaauguauauaugcggagauuccacagaauguucaaau uugcucuugcaguacggcuccuucugcacccagcucaacaggcccuuacagguauugcugucgaacaggacaaga acacacaagaagucuucgcccaagucaaacagauauacaaaacuccucccauaaaggauuuuggcggcuucaacuu uagucagauccucccagacccuucaaaaccaucuaaacgaucauuuauugaagaucugcuguucaacaaggucacu cuugccgaugcuggauucauuaagcaauacggugacugccuuggugauauugcugcccgagaucugaucugugccc agaaauucaacgggcucacuguacuccuccacugcucacagacgaaaugauugcacaguacacaagugcccuguu ggcaggcacaaucacuagcggcuggaccuuuggcgcaggugcagcacuccaaauaccuuuugccaugcagauggcc uaucgguuuaaugggauaggcgugacucaaaaaugccucuacgaaaaccaaaaguugauagcuaaccaauucaauu cagcaaucgggaagauacaggauucacugucuaguacugcuagugcccuugguaagcugcaggacguugucaacca gaaugcucaagcucugaauacauugguuaagcagcucucuaguaauuuggggccaucucuucaguacuuaaugau auuugagccgauuggacccacccgaagcugaaguacagaucgacaggcugauaacaggccggcuccaaucccucc aaacauacgugacacaacaacucauacgcgcagccgaaauccgagccagcgcuaaccuggcagcuaccaagauguc agaaugcguucugggccagaguaaacgcguagauuucugcgggaaagguaccaccugaugccuuuccacaaucu gcaccucacggggucgucuuuugcauguaacauauguacccgcacaagagaagaauuuuacuaccgcuccugcca ucugucaugacgggaaagcucauuuccucgcgaaggugguguuuguaucuaauggu acacauugguuugucacaca gcggaauuucuaugaaccccagaucauuacaacugacaacacuuuuguuccgggaauugugacguggucauagga aucguaaauaacacuguauaugaucccuccaaccagagcuggacucuuuuaaagaagaacuggauaaauauuuca agaaccacacaagucccgacguggaccuuggggacauaagugguauuaacgcaucguggguuaacauucaaaagga aaucgacagacucaacgaggguggccaaaaaccugaacgaaagcuugauga ucuccaggaguugggcaaguaugaa caguacauuaaauggccauggua cauauggcuuggcuuuaucgcuggccuuaucgccaucguaauggu uacaauca -continued ugcugugcugcaugaccuccugcuguucuuguuugaaagggguguuguucuugugguaguuguugcaaguuugacga agaugauuccgaaccuguucuuaaagggguaaagcuucacuauaca SEQ ID NO: 3
(D614G Antigen Encoding RNA Sequence)
auguuucugcucacaaccaaacgcacuauguuuguuuccucg -continued gaaugcucaagcucugaauacauuggUuaagcagcucucuaguaauuuuggggccaucucuucaguacuuaaugau auuuugagccgauuggacaaagUggaagcugaaguacagaucgacaggcugauaacaggccggcuccaaucccucc aaacauacgugacacaacaacucauacgcgcagccgaaauccgagccagcgcuaaccuggcagcuaccaagauguc agaaugcgUucUgggccagaguaaacgcguagaUuucUgcgggaaagggUaccaccUgaugUccUuccacaaucu gcaccucacggggUcgUcUuUuUgcaUgUaacaUauguacccgcacaagagaagaaUuuUacUaccgcuccUgcca ucugucaugacgggaaagcucauUuuccucgcgaaggUgUgUuugUaucuaaugguacacauugguuugucacaca gcggaauuucUaugaaccccagaucauUacaacugacaacacuuuuguuccgggaauugugacguggucauagga aucguaaauaacacUguauaugaUccccuccaaccagagcuggacucuuuuaaagaagaacuggauaaauauuuca agaaccacacaaguCccgacguggaccuuggggacauaagugguauuaacgcaucugugguuaacauucaaaagga aaucgacagacucaacgaggUggccaaaaaccugaacgaaagcuUgauagaucuccaggaguUgggcaaguaugaa caguacauUaaaUggccaugguacauauggcuuggcuuuaucgcuggccuuaucgccaucguaaugguuacaauca ugcuGucugcaUgaccuccugcUguucuuguuuuGaaagggGugUugUucuGUggUAguuguugcaaguuugaga agaugauuccgaaccuguucuuaaagggguaaagcuucacuauaca SEQ ID NO: 4
(B.1.351-PP-D614G Antigen Encoding RNA Sequence)
auguuucugcucacaaccaaacgcacuauguuuguuuccucgUgcUgcUccccuuugguaaguucucaguguguaa acuucacaacacgaacccaguugccuccagcuuuauaccaaucauuacucgcggaguauauuauccccgauaaggu cuUuagaaguagcgUguugcacUcuacacaggaUcUgUucUugcccUucUuUagUaacgUuaccugguuucaugca auacaUgugagcggaacaaauggaacaaaaagauuUgccaauccagugcUuccauUuaaugauggggUuuacuuug ccaguaccgaaaagucaaacauaauccggggguggaucuuuggaaccacuUuggacucuaagacacagucucuccu cauaguaaacaacgccaccaaUguugUcauaaaagUaUgcgaauuucaguuuugcaacgaucccuuucucggggug uauuaccauaagaauaauaaauccuggauggagucugaguuccggguuuauaguagugcUaauaauugcacuuucg aauacguGucccaaccauuccucauggaccuugagggcaaacaggggaauuuuaaaaacuugcgcgaauuugucuu uaagaauaucgacggauacuuuaagaucuauaguaaaacacacuccuaucaaccucguucggggccuucccccaaggc uuuucugcucucgaaccccucguagacuugccaauugggauaaauaucacucgcuuucaaacuuugcacaucagcu accugacacccggcgacucuucuucugguuggaccgccggcgccgcUgccuauuauguuGguuaccuucagccacg aacauucuugcucaaguauaacgagaauggcaccauuaccgacgccgucgauugugcauuggaucccuugucugaa acaaaaugUaccuUgaaguccuuUaccguagagaaaggcauauaccagacuuccaacUuccgaguucagccuacag aauccauugugagauUuCccaacaucacaaaccucugcccuuucggugaaguauuuaaugcuacacgcUucgcuuc agucuaugccuggaauaggaagcgcauaucaaauugcguggccgauuauucaguccucuauaauagcgcauccuuc aguacuuucaaguGcUacggcgGuuuccccCaccaaacucaaugaucuugcuucaccaacGucuaugcugacaGuu uUgcauacgaggcgacgaaguacgccCagauugccccCgggcagacaggUaacauGcugauuauaauuauaaacu cccagaugacuuuacuggaugcgucauagccuggaauuccaacaaucuugauccaaggUuggugggaauuauaau uaccUuuaucgacuguCagaaagaguaacuugaaaccauuugagagagacauuaccaccgagauuUaccaggcag gcaguacUccuuguaacggcgUuaagggauuuaacugcuauuuuccuuUgcaauccuauggcuuucaaccaacaua cggggUuggcuaUcaacccuaucgaGuggUUguccugagcuUUgaacuUuUgcacgcucccgccacagucugcgga ccaaaaaagaguacaaaucuugucaagaauaagugcguaaauuucaauuucaauggccuuacaggaacaggcugc ugacugagucaaacaagaaguuccugccauuucagcaguuugggcgggauauagcagacacaacugacgcuguacg cgauccucagacuuuggagaucuuggacaucacucccuguUucuucgaggggUaucugucaucacccccggaacu aauacaucaaaucaggucgcuguguuguaccaaggcgucaacugcacagaaguccccguugcuauacacgcagacc agcucaccccacauggcggguguacucaacuggcucaaacguauuccagaccagagcugggugcuugaucgggugc -continued ugaacacguaaacaauagcuaugaaugcgauauucccaucggugccgggaucugcgcuagcuaucagacacagacc aauuccccccggcgagcacgaucuguagcaucccagucuauuauugccuacacuaugucauugggcguggagaaua gcgucgcauauucaaauaauucuauugcaauacccaccaacuucacaaucuccguaacuacagaaauacuuccagu uuccaugacaaagacaucagugggauuguacaauguauauaugcggagauuccacagaauguucaaauuugcucuug caguacggcuccuucugcacccagcucaacagggcccuuacagguauugcugucgaacaggacaagaacacacaag aagucuucgcccaagucaaacagauauacaaaacucucucccauaaaggauuuuggcgguucaacuuuagucagau ccucccagacccuucaaaaccaucuaaacgaucauuuauugaagaucugcuguucaacaaggucacucuugccgau gcuggauucauuaagcaauacggugacugccuuggugauauugcugcccgagaucugaucugugcccagaaauuca acgggcucacguacuccccucacugcucacagacgaaaugauugcacaguacacaagugcccuguuggcaggcac aaucacuagcggcuggaccuuuggcgcaggugcagcacuccaaauaccuuuugccaugcagauggccuaucgguuu aaugggauaggcgugacucaaaauguccucuacgaaaaccaaaaguugauagcuaaccaauucaauucagcaaucg ggaagauacaggauucacugucuaguacugcuagugcccuugguaagcugcaggacguugucaaccagaaugcuca agcucugaauacauugguuaagcagcucucuaguaauuuuggggccaucucuucaguacuuaaugauauuuugagc cgauuggacccaccccgaagcugaaguacagaucgacaggcugauaacaggccggcuccaaucccuccaaacauacg ugacaacaacucaucgcgcagccgaaauccgagccagcgcuaaccuggcagcuaccaagaugucagaaugcgu ucugggccagaguaaacgcguagauuucgcgggaaagguaccaccugauguccuuuccacaaucugcaccucac ggggucgucuuuugcauguaacauaugualucccgcacaagagaagaauuuuacuaccgcuccugccaucugucaug acgggaaagcucauuuccucgcgaagguguguuuguaucuaauggualuacauugguuugucacacagcggaauuuu cuaugaaccccagaucauuacaacugacaacacuuuuguuuccgggaauugugacguggucauaggaaucguaaau aacacuguauaugaucccccuccaaccagagcuggacucuuuuaagaagaacuggauaaauauuucaagaaccaca caagucccgacguggaccuuggggacauaagugguauuaacgcaucugugguuaacauucaaaaggaaaucgacag acucaacgagguggccaaaaaccugaacgaaagcuugauagaucuccaggaguugggcaaguaugaacaguacauu aaauggccauggualcauauggcuuggcuuualucgcuggccuualucgccaucgaaugguuacaaucaugcugugcu gcaugaccuccugcuguucuuguuugaaaggguguuguucuuguggualguuguucaaguuugacgaagaugauuc cgaaccuguucuuaaagggguaaagcuucacuauaca SEQ ID NO: 5
(B.1.1.7-PP-D614G Antigen Encoding RNA Sequence)
auguuucugcucacaaccaaacgcacuauguuuguuuuccucgugcugcucccuuugguaaguucucagugguguaa accugacaacacgaacccaguugccuccagcuuualuccaacucauuuacucgcggaguauauuauccccgauaaggu cuuuagaaguagcguguugcacucuacacaggaucuguucuugcccuucuuuaguaacguuaccugguuucaugca auaagcggaacaaauggaacaaaaagauuugacaauccagugcuuccauuuaaugauggggauuacuuugccagua ccgaaaagucaaacauaauccggggguggaucuuuggaaccacuuuggacucuaagacacagucucuccucauagu aaacaacgccaccaauguugucauaaaaguaugcgaauuucaguuuugcaacgaucccuuucucggggugualcau aagaauauaaaauccuggaulggagucugaulccgggualuaguaguglucuaauaauulgcacuuulcgaalacgugu cccaaccauuccucauggaccuugagggcaaacagggggaauuualaaaaacuugcgcgaauuugucuuuaagaauau cgacggalacuuualagaulcualuaglaaalacacacuccuaulcaaccucgulucggglaucuuccccalaggcuuuucugcu cucgaacccucguagalcuugccaaulgggalualaauualucacucgcuuucaaacuuugcuulgcccuccacaggagcu accugacacccggcgacucuucuucugguuggaccgccggcgccgcugccuauualuguugguualccuulcagccacg aacauucuugcucaaguualacgagaaluggcaccauualccgacgccglucgaulugugcaulggalucccuulgucugaa acaaaaaluguaccuugaaguccuuualccgualagagaaaggcaualuaccagacuuccaacuuccgaguucagccualcag aauccauugugagauuucccaacaucacaaaccucugcccuuucggulgaaguauuualaugcuacacgcuucgcuuc agucuaugccuggaaualaggaagcgcaualucaaaulugcguggccgauualuucagucccucualualauagcgcauccuuc -continued aguacuuucaagugcuacggcguuccccccaccaaacucaaugaucuuugcuucaccaacgucuaugcugacaguu uugucauacgaggcgacgaaguacgccagauugcccccgggcagacagguaaaauugcugauuauaauuauaaacu cccagaugacuuuacuggaugcgucauagccuggaauuccaacaaucuugauuccaagguuggugggaauuauaau uaccuuuaucgacuguucagaaagaguaacuugaaaccauuugagagagacauaccaccgagauuuaccaggcag gcaguacuccuuguaacggcguugagggauuuaacugcuauuuccuuugcaauccuauggcuuucaaccaacaua cgggguuggcuaucaacccuaucgagugguugccugagcuuugaacuuuugcacgcucccgccacagucugcgga ccaaaaaagaguacaaaucuugucaagaauaagugcguaaauuucaauuucaauggccuuacaggaacaggcgugc ugacugagucaaacaagaaguccugccauuucagcaguuugggcgggauauagacgacacaacugacgcuguacg cgauccucagacuuuggagaucuuggacaucacucccuguucuuucggaggguaucugucaucacccccggaacu aauacaucaaaucaggucgcuguguuguaccaaggcgucaacugcacagaaguccccguugcuauacacgcagauc agcucacccccacauggcgggguguacucaacuggcucaaacguauuccagaccagagcugggugcuugaucggugc ugaacacguaaacaauagcuaugaagcgauauucccaucggugccgggaucugcgcuagcuaucagacacagacc aauucccaucggcgagcacgaucuguagcauccagucuauuauugccuacacuaugucauugggcgccgagaaua gcgucgcauauucaaauaauucuauugcaauacccaucaacuucacaaucuccguaacuacagaaauacuuccagu uuccaugacaaagacaucaguggauuguacaauguauauaugcggagauuccacagaauguucaaauuugcucuug caguacggcuccuucugcacccagcucaacagggcccuuacagguauugcugucgaacaggacaagaacacacaag aagucuucgcccaagucaaacagauauacaaaacucuccccauaaaggauuuugggugcuucaacuuuagucagau ccucccagacccuucaaaaccaucuaaacgaucauuuauugaagaucugcuguucaacaaggucacucuugccgau gcuggauucauuaagcaauacggugacugccuuggugauauugcugcccgagaucugaucugugcccagaaauuca acgggcucacuguacucccuccacugcucacagacgaaaugauugcacaguacacaagugcccguugggcaggcac aaucacuagcggcuggaccuuuggcgcaggugcagcacuccaaauaccuuuugccaugcagauggccuaucgguuu aaugggauaggcgugacucaaaaugccucucuacgaaaaccaaaaguugauagcuaaccaauucaauucagcaaucg ggaagauacaggauucacugucuaguacugcuagugcccuugguaagcugcaggacguugucaaccagaaugcuca agcucugaauacauugguuaagcagcucucuaguaauuuuggggccaucucuucaguacuuaaugauauuuuggcc cgauuggacccacccgaagcugaaguacagaucgacaggcugauaacaggccggcuccaaucccuccaaacauacg ugacacaacaacucauacgcgcagccgaaauccgagccagcgcuaaccuggcagcuaccaagaugucagaaugcgu ucugggccagaguaaacgcguagauuucgcgggaaagguaccaccugaugccuuuccacaaucugcaccucac ggggucgucuuuuugcauguaacauaugucccgcacaagagaagaauuuuacuaccgcuccugccaucugucaug acgggaaagcucauuuccucgcgaaggugugguuguaucuaauggacacauugguuugucacacagcggaauuu cuaugaaccccagaucauuacaacucacaacacuuuuguuccgggaauugugacguggucauaggaaucguaaau aacacuguauaugaucccccuccaaccagagcuggacucuuuuaagaagaacuggauaaauauuucaagaaccaca caagucccgacguggaccuuggggacauaaguggguauuaacgcaucuggguuaacauucaaaaggaaaucgacag acucaacgaggugccaaaaaccugaacgaaagcuugauagaucuccaggaguugggcaaguaugaacaguacauu aaauggccaugguacauauggcuuggcuuuaucgcuggccuuaucgccaucgaaugguuacaaucaugcugugcu gcaugaccuccugcuguucuuguuugaaagggugaguguucugugguaguuguugaaguuugagaagaugauuc cgaaccuguucuuaaaggggguaaagcuucacuauaca SEQ ID NO: 6
(Delta.AY1-S2P-wtFur Antigen Encoding RNA Sequence)
auguuucugcucacaaccaaacgcacuaugpuugpuuccucgugcugcucccuuuggpuaaguuucucagpuguaa accugagaacacgaacccaguugccuccagcuuuauaccaacucauuuacucgcggaguauauuauccccgauaaggu cuuuagaaguagcguguugcacucuacacaggaucuguuuugccuuuuuaguaacguuaccuguuucaucaugca -continued auacaugugagcggaacaaauggaacaaaaagauuugacaauccagugcuuccauuuaaugauggggguuuacuuug ccaguaucgaaaagucaaacauaauccggggguggaucuuuggaaccacuuuggacucuaagacacagucucuccu cauaguaaacaacgccaccaauguugucauaaaaguaugcgaauuucaguuuugcaacgaucccuuucucgacgug uauuaccauaagaauaauaaauccuggaugagcucggggguuuauagauagugcuaauaauugcacuuucgaauacg ugucccaaccauuccucauggaccuugagggcaaacaggggaauuuuaaaaacuugcgcgaauuugucuuuaagaa uaucgacggauacuuuaagaucuauaguaaacacacuccuaucaaccucguucgggaucuucccaaggcuuuucu gcucucgaaccccucguagacuugccaauugggauaaauaucacucgcuuucaaacuuugcuugcccuccacagga gcuaccugacacccggcgacucuucuucgguuugaccgccggcgccgcugccuauuauguugguuaccuucagcc acgaacauucuugcucaaguauaacgagaauggcaccauuaccgacgccgucgauugugcauuggaucccuugucu gaaacaaaauguaccuugaaguccuuuaccguagagaaaggcauauaccagacuuccaacuuccgaguucagccua cagaauccaucguacgauuucccaacaucacaaaccucgcccuuucggugaaguauuuaaugcuacacgcuucgc uucagucuaugccuggaauaggaagcgcauaucaaauugcguggccgauuauucagucccucuauaauagcgcaucc uucaguacuuucaagugcuacggcguuuccccccaccaaacucaaugaucuuugCuucaccaacgucuaugcugaca guuuugucauacgaggcgacgaaguacgccagauugcccccgggcagacaggaauauugcugauuauaauuauaa acucccagaugacuuuacuggaugcgucauagccuggaauuccaacaacuagauuccaagguuggugggaauuau aauuaccguuaucgacuguucagaaagaguaacuugaaaccauuugagagagacauauccaccgagauuuaccagg caggcaguaagccuuguaacggcguugagggauuuaacugcuauuuuccuuugcaauccuauggcuuucaaccaac aaacggggguuggcuaucaacccuaucgagugguugccucagcuuugaacuuuugcacgcucccgccacagucugc ggaccaaaaagagaagaauacaaaucuugucaagaauaagugcguaaauuucaauuucaauggccuuacaggaacaggcg ugcugacugagucaaacaagaauuuccugccauuucagcaguuugggCgggauauagcagacacaacugacgcugu acgcgauccucagacuuuggagaucuuggacaucacucccuguuCuuucggaggggguaucugucaucacccccgga acuaauacaucaaaucaggucgcuguguuguaccaaggugucaacugcacagaagucccccguugcuauacacgcag accagcucaccccacauggCggguguacucaacuggcucaaacguauuccagaccagagcgggggugcuugaucgg ugcugaacacgugaacaauagcuaugaaugcgauauucccaucggugccgggaucugcgcuagcuaucagacacag accaauucccgcaggCgggcucgcucuguagcaucccagucuauuauugccuacacuaugucauugggcgccgaga auagcgucgcauauucaaauaauucuauugcaauacccaccaacuucacaaucuccguaacuacagaaauacuucc aguuuccaugacaaagacaucaguggauuguacaauguauauaugcggagauuccacagaauguucaaauuugcuc uugcaguacggcuccuucugcacccagcucaacagggcacuuacagguauugcugucgaacaggacaagaacacac aagaagucuucgcccaagucaaacagauauacaaaacuccuccccauaaaggauuuuggcgcggcuucaacuuuaguca gauccucccagacccuucaaaaccaucuaaacgaucauuuauugaagaucugcuguucaacaaggucacucuugcc gaugcuggauucauuaagcaauacggugacugccuugggugauauugcugcccgagaucugaucugucccagaaau ucaacgggcucacuguacucccuccacugcucacagacgaaaugauugcacaguacacaagugcccguuggcagg cacaaucacuagcggcuggaccuuuggcgcaggugcagcacuccaaauaccuuuugccaugcagauggccuaucgg uuuaaugggauaggcgugacucaaaauguccucuacgaaaaccaaaaguugauagcuaaccaauucaauucagcaa ucgggaagauacaggauucacugucuaguacugcuagugcccuugguaagcugcagaacguugucaaccagaaugc agccgauuggacccaccugaagcugaaguacagaucgacaggcugauaacaggccggcuccaaucccuccaaacau acgugacacaacaacucauacgcgcagccgaaauccgagccagcgcuaaccuggcagcuaccaagaugucagaaug cguucugggccagaguaaacgcguagauuucgcgggaaagguaccaccugaugucccuuuccacaaucugcaccu cacggggucgucuuuugcauguaacauacguacccgcacaagagaagaauuuuacuaccgcuccugccaucuguc augacgggaaagcucauuuccucgcgaagggugugauugucuaauggaucacauugguuugucacacagcggaa uuucuaugaaccccagaucauuacaacugacaacacuuuuguuuccgggaauugugacgugugucauaggaaucgua -continued aauaacacuguauaugauccccuccaaccagagcuggacucuuuuaaagaagaacuggauaaauauuucaagaacc acacaagucccgacguggaccuugggacauaaguguauuaacgcaucuguгguuaacauucaaaaggaaaucga cagacucaacgagguggccaaaaaccugaacgaaagcuugauagaucuccaggaguggggcaaguaugaacaguac auuaaauggccaugguacauauggcuuggcuuuaucgcuggccuuaucgccaucguaaugguuacaaucaugcugu gcugcaugaccuccugcuguucuuguuugaaaggguguuguucuugguguaguuguugcaaguuugacgaagauga uuccgaaccuguucuuaaggggguaaagcuucacauacauga SEQ ID NO: 7
(Delta.AY1-S2P-wtFur-newKozak Antigen Encoding RNA Sequence)
auguuucugcucacaaccaaacgcacuauguuuguuuuccucgugcugcucccuuugguaaguucucaguguguaa accugagaacacgaacccaguugccuccagcuuauaccaacucauuuacucgcggaguauauuaucccgauaaggu auacaugugagcggaacaaauggaacaaaagauuugacaauccagugcuuccauuuaaugaugggguuuacuuug ccaguaucgaaaagucaaacauaauccgggggguggaucuuuggaaccacuuuggacucuaagacacagucucuccu ccaguaucgaaaagucaaacauaauccgggggguggaucuuuggaaccacuuuggacucuaagacacagucucuccu cauaguaaacaacgccaccaauguugucauaaaguaugcgaauuucaguuuugcaacgaucccuuucucgacgug uauuaccauaagaauaauaaauccuggauggagucuggggguuuauaguagugcuaauaauugcacuuucgaauacg ugucccaaccauuccucauggaccuugagggcaaacaggggaauuuuaaaaacuugcgcgaauuugucuuuaagaa uaucgacggauacuuuaagaucuauaguaaacacacuccuaucaaccucguugggaucuuccccaaggcuuuucu gcucucgaaccccucguagacuugccaauugggauaaauaucacgcuuucaaacuuugcuugcccuccacagga gcuaccugacacccggcgacucuucuucggguuugaccgccggcgccgcugccuauuauguugguuaccuucagcc acgaacauucuugcucaaguauaacgagaauggcaccauuaccgacgccgucgauugugcauuggauccuugucu gaaacaaaauguaccuugaagucuuuaccguagagaaaggcauauaccagacuuccaacuuccgaguucagccua cagaauccaucguacgauuucccaacaucacaaaccucugcccuuucggugaaguauuuaaugcuacacgcuucgc uucagucuaugccuggaauaggaagcgcauaucaaauugcguggccgauuauucaguccucuauaauagcgcaucc uucaguacuuucaagugcuacggcguuuccccccaccaaacucaaugaucucuuguucaccaacgucuaugcugaca guuuugucauacgaggcgacgaaguacgccagauugcccccgggcagacagguaauauugcugauuauaauuaaa acucccagaugacuuuacuggaugcgucauagccuggaauuccaacaacuagauuccaagguuuggugggaauuau aauuaccguuaucgacuguucagaaagaguaacuugaaaccauuugagagagacauauccaccgagauuuaccagg caggcaguaagccuuguaacggcguugagggauuuaacugcuauuuuccuuugcaauccuauggcuuucaaccaac aaacgggguuggcuaucaacccuaucgagugguuguccucagcuuugaacuuugcacgcucccgccacagucugc ggaccaaaaaagaguacaaaucuugucaagaauaagugcguaaauucaauuucaauggccuuacaggaacaggcg ugcugacugagucaaacaagaauuccugccauuucagcaguuugggcgggauauagcagacacaacugacgcugu acgcgaucucagacuuuggagaucuuggacaucacucccuguucuuucggagggguaucugucaucacccccgga acuaauacaucaaaucaggucgcuguguuguaccaaggugucaacugcacagaaguccccguugcuauacacgcag accagcucacccccacauggcggguguacucaacuggcucaaacguauuccagaccagagcugggugcuugaucgg ugcugaacacgugaacaauagcuaugaaugcgauauucccaucggugccgggaucugcgcuagcuaucagacacag accaauucccgcaggcgggcucgcucuguagcaucccagucuauuauugccuacacuaugucauugggcgccgaga auagcgucgcauauucaaauaauucuauugcaauacccaccaacuucacaaucuccguaacuacagaaauacuucc aguuccaugacaaagacaucaguggauuguacaauguauauaugcggagauuccacagaauguucaaauuugcuc uugcaguacggcuccuucugcacccagcucaacagggcacuuacagguauugcugucgaacaggacaagaacacac aagaagucuucgcccaagucaaacagauauacaaaacucucccauaaaggauuuuggcggcuucaacuuuaguca gauccucccagacccuucaaaaccaucuaaacgaucauuuauugaagaucugcuguucaacaaggucacucuugcc -continued gaugcuggauucauuaagcaauacggugacugccuuggugauauugcugcccagaaucugaucugugcccagaaau ucaacgggcucacuguacucccuccacugcucacagacgaaaugauugcacaguacacaagugcccguuggcagg cacaaucacuagcggcuggaccuuuggcgcaggugcagcacuccaaauaccuuuugccaugcagauggccuaucgg uuuaaugggauaggcgugacucaaaaugccucuacgaaaaccaaaaguugauagcuaaccaauucaauucagcaa ucgggaagauacaggauucacugucuaguacugcuagugcccugguaagcugcagaacguugucaaccagaaugc ucaagcucugaauacauugguuaagcagcucucuaguaauuuuggggccaucucuucaguacuuaaugauauuug agccgauuggacccaccugaagcugaaguacagaucgacaggcugauaacaggccggcuccaaucccuccaaacau acgugacacaacaacucauacgcgcagccgaaauccgagccagcgcuaaccuggcagcuaccaagaugucagaaug cguucgggccagaguaaacgcguagauuucgcgggaaagggguaccaccugaugccuuuccacaaucugcaccu cacggggucgucuuuugcauguaacauacguacccgcacaagagaagaauuuuacuaccgcuccugccaucuguc augacgggaaagcucauuuccucgcgaaggugugoguuugauacuaauggguacacauugguuugucacacagcggaa uuucuaugaaccccagaucauuacaacugacaacacuuuuguuccgggaauugugacguggucauaggaaucgua aauaacacuguauaugaucccccucaaccagagcuggacucuuuaaagaagaacuggauaaauauuucaagaacc acacaaguccgacguggaccuuggggacauaaguggguauuaacgcaucugugguuaacauucaaaaggaaaucga cagacucaacgagguggccaaaaaccugaacgaaagcuugauagaucuccaggaguugggcaaguauugaacaguac auuaaauggccauggaucauauggcuuggcuuuaucgcuggccuuaucgccaucguaaugguuacaaucaugcugu gcugcaugaccuccugcuguucuuguuugaaagggugugguucuuguggguaguuguugcaaguuugacgaagauga uuccgaaccuguucuuaaggggguaaagcuucacuauacauga SEQ ID NO: 8
(Omicron-B.1.1.529 Antigen Encoding RNA Sequence)
cgccaccauguuucguuugacgaccaagcgaacgauguuc -continued gguguauugacagaaagcaacaagaaguuucugccauuccagcaauuuggagggauauagcggauacaacugaug ccguucgggauccucaaacauuggagaucuuggacaucacaccguguucuuuuggggugucuccguuaucacacc ggguacaaauacgagcaaucagguugcgguccuuuaccaaggcguuaauuguaccgagguuccaguagcaauacac gcggaucaacucacgcccacaugggguuuacaguacaggcaguaauguuuuccaaacgagagcgggaugccuca ucggggcagaauacguaaauaauucuuacgaaugcgacaucccuauuggcgcaggaauuugcgcaaguuaccaaac ccagaccaagucucauaggcgggcgcggucuguugcaagccaaucuauaauagcguacacuauguccccucggcgcg gagaacagugucgcauauuccaacaacucuauugcgauaccuacuaauuucacuauuagcgucacaacugagaucc uucccgucaguaugaccaaaacgucugucgacuguacuaugauauuugcggcgacaguaccgaaugcucuaaucu uuuguugcaguaugguucuuuuugcacgcaacuuaagagagcuugacggggauagcugguggaacaagauaaaaac acacaggagguauuugcacaagugaaacagaucuauaaaacuccaccgaucaaguacuuuggcggcuuuaacuucu cccagaucuugcccgacccgucuaaaccaaguaaacggaguuuuauagaggaccuucucuucaauaagguaacauu ggcagacgccggcuucauuaaacaauacggagauugccuuggagacaucgcugcgcgcgacuugaucugcgcacaa aaauuuaaaggcuugacgguccuccccuccuuugcucacagacgagaugauagcacaauacacuuccgcacugcuug cuggaaccaucaccucugguuggacauucggugcgggagcggcuuugcagauuccguuugcgaugcaaauggcuua ucgguuuaacggcauuggaguaacacagaaugugcucacgagaaucaaaagcuuauugcgaaucaauucaacucu gcgauuggcaaaauucaagauucauugaguagcaccgccagugucucuuggcaagcuucaggaugucguaaaccaca augcacaagcucugaauacacugguuaaacaauugccaguaaauuuggggcaaucucuucagugcugaacgacau uuucucaagauuggauccacccgaagcggagguacagauugaccgccugauaaccgggagguugcaaagccuucag acuuauguuacacaacaguugauccgggcagcagagauaagagccucagcaaaccucgcagcuacgaagaugucag aguguguccuugggcaaucuaagcgggugauuucugcggcaaaggauaucauuugaugagcuuuccccaaucagc cccagaucuugcccgacccgucuaaaccaaguaaacggaguuuuauagaggaccuucucuucaauaagguaacauu ggcagacgccggcuucauuaaacaauacggagauugccuuggagacaucgcugcgcgcgacuugaucugcgcacaa ggaauuucuacgaaccacagaucaucacuaccgacaacacguuugucucuggaaauugugacguugucauagggau agugaacaauacaguauaugauccacuucagccugaacuugacucuuuuaaggaggagcuggacaaauauuucaaa aaucauacaagcccggacgucgaucuuggagauauuucagguaucaacgcaagugcuaaauauucagaaggaga ucgaucgauugaacgagguugcaaaaaaccuuaaugagagccuuauagaucuucaagagcuggggaaguaugaaca auauaucaagugggccuugguacauuuggcucggguucauugcggacuuaugcgauguaaugguacaaucaug augauucugaaccagugcuuaaaggcgugaagcuccacuauaccuga SEQ ID NO: 9
(A.1 Delta V5 Amino Acid Sequence)
MFLLTTKRTMFVFLVLLPLVSSQCVNLRTRTQLPP -continued

FNGIGVTQNVLYENQKLIANQFNSAIGKIQDSLSSTASALGKLQNVVNQNAQALNTLVKQLSSNFGAISSVLNDIL

SRLDPPEAEVQIDRLITGRLQSLQTYVTQQLIRAAEIRASANLAATKMSECVLGQSKRVDFCGKGYHLMSFPQSAP

HGVVFLHVTYVPAQEKNFTTAPAICHDGKAHFPREGVFVSNGTHWFVTQRNFYEPQIITTDNTFVSGNCDVVIGIV

NNTVYDPLQPELDSFKEELDKYFKNHTSPDVDLGDISGINASVVNIQKEIDRLNEVAKNLNESLIDLQELGKYEQY

IKWPWYIWLGFIAGLIAIVMVTIMLCCMTSCCSCLKGCCSCGSCCKFDEDDSEPVLKGVKLHYT

SEQ ID NO: 10
(A.1-preF K995P-V996P Amino Acid Sequence)
MFLLTTKRTMFVFLVLLPLVSSQCVNLRTRTQLPPAYTNSFTRGVYYPDKVFRSSVLHSTQDLFLPFFSNVTWFHA

IHVSGTNGTKRFDNPVLPFNDGVYFASIEKSNIIRGWIFGTTLDSKTQSLLIVNNATNVVIKVCEFQFCNDPFLDV

YYHKNNKSWMESGVYSSANNCTFEYVSQPFLMDLEGKQGNFKNLREFVFKNIDGYFKIYSKHTPINLVRDLPQGFS

ALEPLVDLPIGINITRFQTLLALHRSYLTPGDSSSGLTAGAAAYYVGYLQPRTFLLKYNENGTITDAVDCALDPLS

ETKCTLKSFTVEKGIYQTSNFRVQPTESIVRFPNITNLCPFGEVFNATRFASVYAWNRKRISNCVADYSVLYNSAS

FSTFKCYGVSPTKLNDLCFTNVYADSFVIRGDEVRQIAPGQTGNIADYNYKLPDDFTGCVIAWNSNNLDSKVGGNY

NYRYRLFRKSNLKPFERDISTEIYQAGSKPCNGVEGFNCYFPLQSYGFQPTNGVGYQPYRVVVLSFELLHAPATVC

GPKKSTNLVKNKCVNFNFNGLTGTGVLTESNKNFLPFQQFGRDIADTTDAVRDPQTLEILDITPCSFGGVSVITPG

TNTSNQVAVLYQGVNCTEVPVAIHADQLTPTWRVYSTGSNVFQTRAGCLIGAEHVNNSYECDIPIGAGICASYQTQ

TNSRRRARSVASQSIIAYTMSLGAENSVAYSNNSIAIPTNFTISVTTEILPVSMTKTSVDCTMYICGDSTECSNLL

LQYGSFCTQLNRALTGIAVEQDKNTQEVFAQVKQIYKTPPIKDFGGFNFSQILPDPSKPSKRSFIEDLLFNKVTLA

DAGFIKQYGDCLGDIAARDLICAQKFNGLTVLPPLLTDEMIAQYTSALLAGTITSGWTFGAGAALQIPFAMQMAYR

FNGIGVTQNVLYENQKLIANQFNSAIGKIQDSLSSTASALGKLQNVVNQNAQALNTLVKQLSSNFGAISSVLNDIL

SRLDPPEAEVQIDRLITGRLQSLQTYVTQQLIRAAEIRASANLAATKMSECVLGQSKRVDFCGKGYHLMSFPQSAP

HGVVFLHVTYVPAQEKNFTTAPAICHDGKAHFPREGVFVSNGTHWFVTQRNFYEPQIITTDNTFVSGNCDVVIGIV

NNTVYDPLQPELDSFKEELDKYFKNHTSPDVDLGDISGINASVVNIQKEIDRLNEVAKNLNESLIDLQELGKYEQY

IKWPWYIWLGFIAGLIAIVMVTIMLCCMTSCCSCLKGCCSCGSCCKFDEDDSEPVLKGVKLHYT

SEQ ID NO: 11
(B.1 D614G Amino Acid Sequence)
MFLLTTKRTMFVFLVLLPLVSSQCVNLRTRTQLPPAYTNSFTRGVYYPDKVFRSSVLHSTQDLFLPFFSNVTWFHA

IHVSGTNGTKRFDNPVLPFNDGVYFASIEKSNIIRGWIFGTTLDSKTQSLLIVNNATNVVIKVCEFQFCNDPFLDV

YYHKNNKSWMESGVYSSANNCTFEYVSQPFLMDLEGKQGNFKNLREFVFKNIDGYFKIYSKHTPINLVRDLPQGFS

ALEPLVDLPIGINITRFQTLLALHRSYLTPGDSSSGLTAGAAAYYVGYLQPRTFLLKYNENGTITDAVDCALDPLS

ETKCTLKSFTVEKGIYQTSNFRVQPTESIVRFPNITNLCPFGEVFNATRFASVYAWNRKRISNCVADYSVLYNSAS

FSTFKCYGVSPTKLNDLCFTNVYADSFVIRGDEVRQIAPGQTGNIADYNYKLPDDFTGCVIAWNSNNLDSKVGGNY

NYRYRLFRKSNLKPFERDISTEIYQAGSKPCNGVEGFNCYFPLQSYGFQPTNGVGYQPYRVVVLSFELLHAPATVC

GPKKSTNLVKNKCVNFNFNGLTGTGVLTESNKNFLPFQQFGRDIADTTDAVRDPQTLEILDITPCSFGGVSVITPG

TNTSNQVAVLYQGVNCTEVPVAIHADQLTPTWRVYSTGSNVFQTRAGCLIGAEHVNNSYECDIPIGAGICASYQTQ

TNSRRRARSVASQSIIAYTMSLGAENSVAYSNNSIAIPTNFTISVTTEILPVSMTKTSVDCTMYICGDSTECSNLL

LQYGSFCTQLNRALTGIAVEQDKNTQEVFAQVKQIYKTPPIKDFGGFNFSQILPDPSKPSKRSFIEDLLFNKVTLA

DAGFIKQYGDCLGDIAARDLICAQKFNGLTVLPPLLTDEMIAQYTSALLAGTITSGWTFGAGAALQIPFAMQMAYR

FNGIGVTQNVLYENQKLIANQFNSAIGKIQDSLSSTASALGKLQNVVNQNAQALNTLVKQLSSNFGAISSVLNDIL

SRLDPPEAEVQIDRLITGRLQSLQTYVTQQLIRAAEIRASANLAATKMSECVLGQSKRVDFCGKGYHLMSFPQSAP

HGVVFLHVTYVPAQEKNFTTAPAICHDGKAHFPREGVFVSNGTHWFVTQRNFYEPQIITTDNTFVSGNCDVVIGIV

NNTVYDPLQPELDSFKEELDKYFKNHTSPDVDLGDISGINASVVNIQKEIDRLNEVAKNLNESLIDLQELGKYEQY

IKWPWYIWLGFIAGLIAIVMVTIMLCCMTSCCSCLKGCCSCGSCCKFDEDDSEPVLKGVKLHYT

SEQ ID NO: 12
(Beta-preF B.1.351-PP-D614G Amino Acid Sequence)
MFLLTTKRTMFVFLVLLPLVSSQCVNFTTRTQLPPAYTNSFTRGVYYPDKVFRSSVLHSTQDLFLPFFSNVTWFHA

IHVSGTNGTKRFANPVLPFNDGVYFASTEKSNIIRGWIFGTTLDSKTQSLLIVNNATNVVIKVCEFQFCNDPFLGV

YYHKNNKSWMESEFRVYSSANNCTFEYVSQPFLMDLEGKQGNFKNLREFVFKNIDGYFKIYSKHTPINLVRGLPQG

FSALEPLVDLPIGINITRFQTLHISYLTPGDSSSGWTAGAAAYYVGYLQPRTFLLKYNENGTITDAVDCALDPLSE

TKCTLKSFTVEKGIYQTSNFRVQPTESIVRFPNITNLCPFGEVFNATRFASVYAWNRKRISNCVADYSVLYNSASF

STFKCYGVSPTKLNDLCFTNVYADSFVIRGDEVRQIAPGQTGNIADYNYKLPDDFTGCVIAWNSNNLDSKVGGNYN

YLYRLFRKSNLKPFERDISTEIYQAGSTPCNGVKGFNCYFPLQSYGFQPTYGVGYQPYRVVVLSFELLHAPATVCG

PKKSTNLVKNKCVNFNFNGLTGTGVLTESNKKFLPFQQFGRDIADTTDAVRDPQTLEILDITPCSFGGVSVITPGT

NTSNQVAVLYQGVNCTEVPVAIHADQLTPTWRVYSTGSNVFQTRAGCLIGAEHVNNSYECDIPIGAGICASYQTQT

NSPRRARSVASQSIIAYTMSLGVENSVAYSNNSIAIPTNFTISVTTEILPVSMTKTSVDCTMYICGDSTECSNLLL

QYGSFCTQLNRALTGIAVEQDKNTQEVFAQVKQIYKTPPIKDFGGFNFSQILPDPSKPSKRSFIEDLLFNKVTLAD

AGFIKQYGDCLGDIAARDLICAQKFNGLTVLPPLLTDEMIAQYTSALLAGTITSGWTFGAGAALQIPFAMQMAYRF

NGIGVTQNVLYENQKLIANQFNSAIGKIQDSLSSTASALGKLQDVVNQNAQALNTLVKQLSSNFGAISSVLNDILS

RLDPPEAEVQIDRLITGRLQSLQTYVTQQLIRAAEIRASANLAATKMSECVLGQSKRVDFCGKGYHLMSFPQSAPH

GVVFLHVTYVPAQEKNFTTAPAICHDGKAHFPREGVFVSNGTHWFVTQRNFYEPQIITTDNTFVSGNCDVVIGIVN

NTVYDPLQPELDSFKEELDKYFKNHTSPDVDLGDISGINASVVNIQKEIDRLNEVAKNLNESLIDLQELGKYEQYI

KWPWYIWLGFIAGLIAIVMVTIMLCCMTSCCSCLKGCCSCGSCCKFDEDDSEPVLKGVKLHYT

SEQ ID NO: 13
(Alpha-preF B.1.1.7-PP-D614G Amino Acid Sequence)
MFLLTTKRTMFVFLVLLPLVSSQCVNLTTRTQLPPAYTNSFTRGVYYPDKVFRSSVLHSTQDLFLPFFSNVTWFHA

IHVSGTNGTKRFDNPVLPFNDGVYFASTEKSNIIRGWIFGTTLDSKTQSLLIVNNATNVVIKVCEFQFCNDPFLGV

YYHKNNKSWMESEFRVYSSANNCTFEYVSQPFLMDLEGKQGNFKNLREFVFKNIDGYFKIYSKHTPINLVRDLPQG

FSALEPLVDLPIGINITRFQTLLALHRSYLTPGDSSSGWTAGAAAYYVGYLQPRTFLLKYNENGTITDAVDCALDP

LSETKCTLKSFTVEKGIYQTSNFRVQPTESIVRFPNITNLCPFGEVFNATRFASVYAWNRKRISNCVADYSVLYNS

ASFSTFKCYGVSPTKLNDLCFTNVYADSFVIRGDEVRQIAPGQTGKIADYNYKLPDDFTGCVIAWNSNNLDSKVGG

NYNYLYRLFRKSNLKPFERDISTEIYQAGSTPCNGVEGFNCYFPLQSYGFQPTNGVGYQPYRVVVLSFELLHAPAT

VCGPKKSTNLVKNKCVNFNFNGLTGTGVLTESNKKFLPFQQFGRDIADTTDAVRDPQTLEILDITPCSFGGVSVIT

PGTNTSNQVAVLYQDVNCTEVPVAIHAGQLTPTWRVYSTGSNVFQTRAGCLIGAEHVNNSYECDIPIGAGICASYQ

TQTNSPRRARSVASQSIIAYTMSLGAENSVAYSNNSIAIPTNFTISVTTEILPVSMTKTSVDCTMYICGDSTECSN

LLLQYGSFCTQLNRALTGIAVEQDKNTQEVFAQVKQIYKTPPIKDFGGFNFSQILPDPSKPSKRSFIEDLLFNKVT

LADAGFIKQYGDCLGDIAARDLICAQKFNGLTVLPPLLTDEMIAQYTSALLAGTITSGWTFGAGAALQIPFAMQMA

YRFNGIGVTQNVLYENQKLIANQFNSAIGKIQDSLSSTASALGKLQDVVNQNAQALNTLVKQLSSNFGAISSVLND

ILSRLDKVEAEVQIDRLITGRLQSLQTYVTQQLIRAAEIRASANLAATKMSECVLGQSKRVDFCGKGYHLMSFPQS

APHGVVFLHVTYVPAQEKNFTTAPAICHDGKAHFPREGVFVSNGTHWFVTQRNFYEPQIITTDNTFVSGNCDVVIG

IVNNTVYDPLQPELDSFKEELDKYFKNHTSPDVDLGDISGINASVVNIQKEIDRLNEVAKNLNESLIDLQELGKYE

QYIKWPWYIWLGFIAGLIAIVMVTIMLCCMTSCCSCLKGCCSCGSCCKFDEDDSEPVLKGVKLHYT

SEQ ID NO: 14
(Delta-preF AY1-S2P-wtFur Amino Acid Sequence)
MFLLTTKRTMFVFLVLLPLVSSQCVNLTTRTQLPPAYTNSFTRGVYYPDKVFRSSVLHSTQDLFLPFFSNVTWFHA

IHVSGTNGTKRFDNPVLPFNDGVYFASTEKSNIIRGWIFGTTLDSKTQSLLIVNNATNVVIKVCEFQFCNDPFLGV

-continued

YYHKNNKSWMESEFRVYSSANNCTFEYVSQPFLMDLEGKQGNFKNLREFVFKNIDGYFKIYSKHTPINLVRDLPQG

FSALEPLVDLPIGINITRFQTLLALHRSYLTPGDSSSGWTAGAAAYYVGYLQPRTFLLKYNENGTITDAVDCALDP

LSETKCTLKSFTVEKGIYQTSNFRVQPTESIVRFPNITNLCPFGEVFNATRFASVYAWNRKRISNCVADYSVLYNS

ASFSTFKCYGVSPTKLNDLCFTNVYADSFVIRGDEVRQIAPGQTGKIADYNYKLPDDFTGCVIAWNSNNLDSKVGG

NYNYLYRLFRKSNLKPFERDISTEIYQAGSTPCNGVEGFNCYFPLQSYGFQPTNGVGYQPYRVVVLSFELLHAPAT

VCGPKKSTNLVKNKCVNFNFNGLTGTGVLTESNKKFLPFQQFGRDIADTTDAVRDPQTLEILDITPCSFGGVSVIT

PGTNTSNQVAVLYQDVNCTEVPVAIHADQLTPTWRVYSTGSNVFQTRAGCLIGAEHVNNSYECDIPIGAGICASYQ

TQTNSPRRARSVASQSIIAYTMSLGAENSVAYSNNSIAIPTNFTISVTTEILPVSMTKTSVDCTMYICGDSTECSN

LLLQYGSFCTQLNRALTGIAVEQDKNTQEVFAQVKQIYKTPPIKDFGGFNFSQILPDPSKPSKRSFIEDLLFNKVT

LADAGFIKQYGDCLGDIAARDLICAQKFNGLTVLPPLLTDEMIAQYTSALLAGTITSGWTFGAGAALQIPFAMQMA

YRFNGIGVTQNVLYENQKLIANQFNSAIGKIQDSLSSTASALGKLQDVVNQNAQALNTLVKQLSSNFGAISSVLND

ILSRLDPPEAEVQIDRLITGRLQSLQTYVTQQLIRAAEIRASANLAATKMSECVLGQSKRVDFCGKGYHLMSFPQS

APHGVVFLHVTYVPAQEKNFTTAPAICHDGKAHFPREGVFVSNGTHWFVTQRNFYEPQIITTDNTFVSGNCDVVIG

IVNNTVYDPLQPELDSFKEELDKYFKNHTSPDVDLGDISGINASVVNIQKEIDRLNEVAKNLNESLIDLQELGKYE

QYIKWPWYIWLGFIAGLIAIVMVTIMLCCMTSCCSCLKGCCSCGSCCKFDEDDSEPVLKGVKLHYT

SEQ ID NO: 15
(Delta-preF-AY1-S2P-wtFur-newKozak Amino Acid Sequence)
MFLLTTKRTMFVFLVLLPLVSSQCVNLTTRTQLPPAYTNSFTRGVYYPDKVFRSSVLHSTQDLFLPFFSNVTWFHA

IHVSGTNGTKRFDNPVLPFNDGVYFASTEKSNIIRGWIFGTTLDSKTQSLLIVNNATNVVIKVCEFQFCNDPFLGV

YYHKNNKSWMESEFRVYSSANNCTFEYVSQPFLMDLEGKQGNFKNLREFVFKNIDGYFKIYSKHTPINLVRDLPQG

FSALEPLVDLPIGINITRFQTLLALHRSYLTPGDSSSGWTAGAAAYYVGYLQPRTFLLKYNENGTITDAVDCALDP

LSETKCTLKSFTVEKGIYQTSNFRVQPTESIVRFPNITNLCPFGEVFNATRFASVYAWNRKRISNCVADYSVLYNS

ASFSTFKCYGVSPTKLNDLCFTNVYADSFVIRGDEVRQIAPGQTGKIADYNYKLPDDFTGCVIAWNSNNLDSKVGG

NYNYLYRLFRKSNLKPFERDISTEIYQAGSTPCNGVEGFNCYFPLQSYGFQPTNGVGYQPYRVVVLSFELLHAPAT

VCGPKKSTNLVKNKCVNFNFNGLTGTGVLTESNKKFLPFQQFGRDIADTTDAVRDPQTLEILDITPCSFGGVSVIT

PGTNTSNQVAVLYQDVNCTEVPVAIHADQLTPTWRVYSTGSNVFQTRAGCLIGAEHVNNSYECDIPIGAGICASYQ

TQTNSPRRARSVASQSIIAYTMSLGAENSVAYSNNSIAIPTNFTISVTTEILPVSMTKTSVDCTMYICGDSTECSN

LLLQYGSFCTQLNRALTGIAVEQDKNTQEVFAQVKQIYKTPPIKDFGGFNFSQILPDPSKPSKRSFIEDLLFNKVT

LADAGFIKQYGDCLGDIAARDLICAQKFNGLTVLPPLLTDEMIAQYTSALLAGTITSGWTFGAGAALQIPFAMQMA

YRFNGIGVTQNVLYENQKLIANQFNSAIGKIQDSLSSTASALGKLQDVVNQNAQALNTLVKQLSSNFGAISSVLND

ILSRLDKVEAEVQIDRLITGRLQSLQTYVTQQLIRAAEIRASANLAATKMSECVLGQSKRVDFCGKGYHLMSFPQS

APHGVVFLHVTYVPAQEKNFTTAPAICHDGKAHFPREGVFVSNGTHWFVTQRNFYEPQIITTDNTFVSGNCDVVIG

IVNNTVYDPLQPELDSFKEELDKYFKNHTSPDVDLGDISGINASVVNIQKEIDRLNEVAKNLNESLIDLQELGKYE

QYIKWPWYIWLGFIAGLIAIVMVTIMLCCMTSCCSCLKGCCSCG

SEQ ID NO: 16
(SARS-COV-2-Omicron B.1.1.529 Amino Acid Sequence)
MFLLTTKRTMFVFLVLLPLVSSQCVNLTTRTQLPPAYTNSFTRGVYYPDKVFRSSVLHSTQDLFLPFFSNVTWFHV

ISGTNGTKRFDNPVLPFNDGVYFASIEKSNIIRGWIFGTTLDSKTQSLLIVNNATNVVIKVCEFQFCNDPFFDHKN

NKSWMESEFRVYSSANNCTFEYVSQPFLMDLEGKQGNFKNLREFVFKNIDGYFKIYSKHTPIIVREPEDLPQGFSA

LEPLVDLPIGINITRFQTLLALHRSYLTPGDSSSGWTAGAAAYYVGYLQPRTFLLKYNENGTITDAVDCALDPLSE

TKCTLKSFTVEKGIYQTSNFRVQPTESIVRFPNITNLCPFDEVFNATRFASVYAWNRKRISNCVADYSVLYNLAPF

FTFKCYGVSPTKLNDLCFTNVYADSFVIRGDEVRQIAPGQTGNIADYNYKLPDDFTGCVIAWNSNKLDSKVSGNYN

-continued

YLYRLFRKSNLKPFERDISTEIYQAGNKPCNGVAGFNCYFPLRSYSFRPTYGVGHQPYRVVVLSFELLHAPATVCG

PKKSTNLVKNKCVNFNFNGLKGTGVLTESNKKFLPFQQFGRDIADTTDAVRDPQTLEILDITPCSFGGVSVITPGT

NTSNQVAVLYQGVNCTEVPVAIHADQLTPTWRVYSTGSNVFQTRAGCLIGAEYVNNSYECDIPIGAGICASYQTQT

KSHRRARSVASQSIIAYTMSLGAENSVAYSNNSIAIPTNFTISVTTEILPVSMTKTSVDCTMYICGDSTECSNLLL

QYGSFCTQLKRALTGIAVEQDKNTQEVFAQVKQIYKTPPIKYFGGFNFSQILPDPSKPSKRSFIEDLLFNKVTLAD

AGFIKQYGDCLGDIAARDLICAQKFKGLTVLPPLLTDEMIAQYTSALLAGTITSGWTFGAGAALQIPFAMQMAYRF

NGIGVTQNVLYENQKLIANQFNSAIGKIQDSLSSTASALGKLQDVVNHNAQALNTLVKQLSSKFGAISSVLNDIFS

RLDPPEAEVQIDRLITGRLQSLQTYVTQQLIRAAEIRASANLAATKMSECVLGQSKRVDFCGKGYHLMSFPQSAPH

GVVFLHVTYVPAQEKNFTTAPAICHDGKAHFPREGVFVSNGTHWFVTQRNFYEPQIITTDNTFVSGNCDVVIGIVN

NTVYDPLQPELDSFKEELDKYFKNHTSPDVDLGDISGINASVVNIQKEIDRLNEVAKNLNESLIDLQELGKYEQYI

KWPWYIWLGFIAGLIAIVMVTIMLCCMTSCCSCLKGCCSCGSCCKFDEDDSEPVLKGVKLHYT

SEQ ID NO: 17
(Wuhan-Hu-1-Full-Length Wild-Type Spike
Protein Amino Acid Sequence-NCBI Reference ID: P0DTC2
>YP_009724390.1 surface glycoprotein
[Severe acute respiratory syndrome coronavirus 2]
MFVFLVLLPLVSSQCVNLTTRTQLPPAYTNSFTRGVYYPDKVFRSSVLHSTQDLFLPFFSNVTWFHAIHVSGTNGT

KRFDNPVLPFNDGVYFASTEKSNIIRGWIFGTTLDSKTQSLLIVNNATNVVIKVCEFQFCNDPFLGVYYHKNNKSW

MESEFRVYSSANNCTFEYVSQPFLMDLEGKQGNFKNLREFVFKNIDGYFKIYSKHTPINLVRDLPQGFSALEPLVD

LPIGINITRFQTLLALHRSYLTPGDSSSGWTAGAAAYYVGYLQPRTFLLKYNENGTITDAVDCALDPLSETKCTLK

SFTVEKGIYQTSNFRVQPTESIVRFPNITNLCPFGEVFNATRFASVYAWNRKRISNCVADYSVLYNSASFSTFKCY

GVSPTKLNDLCFTNVYADSFVIRGDEVRQIAPGQTGKIADYNYKLPDDFTGCVIAWNSNNLDSKVGGNYNYLYRLF

RKSNLKPFERDISTEIYQAGSTPCNGVEGFNCYFPLQSYGFQPTNGVGYQPYRVVVLSFELLHAPATVCGPKKSTN

LVKNKCVNFNFNGLTGTGVLTESNKKFLPFQQFGRDIADTTDAVRDPQTLEILDITPCSFGGVSVITPGTNTSNQV

AVLYQDVNCTEVPVAIHADQLTPTWRVYSTGSNVFQTRAGCLIGAEHVNNSYECDIPIGAGICASYQTQTNSPRRA

RSVASQSIIAYTMSLGAENSVAYSNNSIAIPTNFTISVTTEILPVSMTKTSVDCTMYICGDSTECSNLLLQYGSFC

TQLNRALTGIAVEQDKNTQEVFAQVKQIYKTPPIKDFGGFNFSQILPDPSKPSKRSFIEDLLFNKVTLADAGFIKQ

YGDCLGDIAARDLICAQKFNGLTVLPPLLTDEMIAQYTSALLAGTITSGWTFGAGAALQIPFAMQMAYRFNGIGVT

QNVLYENQKLIANQFNSAIGKIQDSLSSTASALGKLQDVVNQNAQALNTLVKQLSSNFGAISSVLNDILSRLDKVE

AEVQIDRLITGRLQSLQTYVTQQLIRAAEIRASANLAATKMSECVLGQSKRVDFCGKGYHLMSFPQSAPHGVVFLH

VTYVPAQEKNFTTAPAICHDGKAHFPREGVFVSNGTHWFVTQRNFYEPQIITTDNTFVSGNCDVVIGIVNNTVYDP

LQPELDSFKEELDKYFKNHTSPDVDLGDISGINASVVNIQKEIDRLNEVAKNLNESLIDLQELGKYEQYIKWPWYI

WLGFIAGLIAIVMVTIMLCCMTSCCSCLKGCCSCGSCCKFDEDDSEPVLKGVKLHYT

SEQ ID NO: 18
(SARS-COV-2 Wuhan-Hu-1-Wild-Type Spike Protein-
Stem Helix Amino Acid Sequence
[residues 913 to 1213])
QNVLYENQKLIANQFNSAIGKIQDSLSSTASALGKLQDVVNQNAQALNTLVKQLSSNFGAISSVLNDILSRLDKVE

AEVQIDRLITGRLQSLQTYVTQQLIRAAEIRASANLAATKMSECVLGQSKRVDFCGKGYHLMSFPQSAPHGVVFLH

VTYVPAQEKNFTTAPAICHDGKAHFPREGVFVSNGTHWFVTQRNFYEPQIITTDNTFVSGNCDVVIGIVNNTVYDP

LQPELDSFKEELDKYFKNHTSPDVDLGDISGINASVVNIQKEIDRLNEVAKNLNESLIDLQELGKYEQYIKWPW

SEQ ID NO: 19
(SARS-COV-2-Omicron Spike Protein Stem Helix Amino Acid Sequence)-
bold indicate stem mutations associated with the omicron variant
QNVLYENQKLIANQFNSAIGKIQDSLSSTASALGKLQDVVNHNAQALNTLVKQLSSKFGAISSVLNDIFSRLDPPE

AEVQIDRLITGRLQSLQTYVTQQLIRAAEIRASANLAATKMSECVLGQSKRVDFCGKGYHLMSFPQSAPHGVVFLH

VTYVPAQEKNFTTAPAICHDGKAHFPREGVFVSNGTHWFVTQRNFYEPQIITTDNTFVSGNCDVVIGIVNNTVYDP

LQPELDSFKEELDKYFKNHTSPDVDLGDISGINASVVNIQKEIDRLNEVAKNLNESLIDLQELGKYEQYIKWPW

SEQ ID NO: 20:
VEEV RNA Sequence
AUAGGCGGCGCAUGAGAGAAGCCCAGACCAAUUACCUACCCAAAAUGGAGAAAGUUCACGUUGACAUCGAGGAAGA

CAGCCCAUUCCUCAGAGCUUUGCAGCGGAGCUUCCCGCAGUUUGAGGUAGAAGCCAAGCAGGUCACUGAUAAUGAC

CAUGCUAAUGCCAGAGCGUUUUCGCAUCUGGCUUCAAAACUGAUCGAAACGGAGGUGGACCCAUCCGACACGAUCC

UUGACAUUGGAAGUGCGCCCGCCCGCAGAAUGUAUUCUAAGCACAAGUAUCAUUGUAUCUGUCCGAUGAGAUGUGC

GGAAGAUCCGGACAGAUUGUAUAAGUAUGCAACUAAGCUGAAGAAAAACUGUAAGGAAAUAACUGAUAAGGAAUUG

GACAAGAAAAUGAAGGAGCUGGCCGCCGUCAUGAGCGACCCUGACCUGGAAACUGAGACUAUGUGCCUCCACGACG

ACGAGUCGUGUCGCUACGAAGGGCAAGUCGCUGUUUACCAGGAUGUAUACGCGGUUGACGGACCGACAAGUCUCUA

UCACCAAGCCAAUAAGGGAGUUAGAGUCGCCUACUGGAUAGGCUUUGACACCACCCCUUUUAUGUUUAAGAACUUG

GCUGGAGCAUAUCCAUCAUACUCUACCAACUGGGCCGACGAAACCGUGUUAACGGCUCGUAACAUAGGCCUAUGCA

GCUCUGACGUUAUGGAGCGGUCACGUAGAGGGAUGUCCAUUCUUAGAAAGAAGUAUUUGAAACCAUCCAACAAUGU

UCUAUUCUCUGUUGGCUCGACCAUCUACCACGAGAAGAGGGACUUACUGAGGAGCUGGCACCUGCCGUCUGUAUUU

CACUUACGUGGCAAGCAAAAUUACACAUGUCGGUGUGAGACUAUAGUUAUUGCGACGGGUACGUCGUUAAAAGAA

UAGCUAUCAGUCCAGGCCUGUAUGGGAAGCCUUCAGGCUAUGCUGCUACGAUGCACCGCGAGGGAUUCUUGUGCUG

CAAAGUGACAGACACAUUGAACGGGGAGAGGGUCUCUUUUCCCGUGUGCACGUAUGUGCCAGCUACAUUGUGUGAC

CAAAUGACUGGCAUACUGGCAACAGAUGUCAGUGCGGACGACGCGCAAAAACUGCUGGUUGGGCUCAACCAGCGUA

UAGUCGUCAACGGUCGCACCCAGAGAAACACCAAUACCAUGAAAAAUUACCUUUUGCCCGUAGUGGCCCAGGCAUU

UGCUAGGUGGGCAAAGGAAUAUAAGGAAGAUCAAGAAGAUGAAAGGCCACUAGGACUACGAGAUAGACAGUUAGUC

AUGGGGUGUUGUUGGGCUUUUAGAAGGCACAAGAUAACAUCUAUUUAUAAGCGCCCGGAUACCCAAACCAUCAUCA

AAGUGAACAGCGAUUUCCACUCAUUCGUGCUGCCCAGGAUAGGCAGUAACACAUUGGAGAUCGGGCUGAGAACAAG

AAUCAGGAAAUGUUAGAGGAGCACAAGGAGCCGUCACCUCUCAUUACCGCCGAGGACGUACAAGAAGCUAAGUGC

GCAGCCGAUGAGGCUAAGGAGGUGCGUGAAGCCGAGGAGUUGCGCGCAGCUCUACCACCUUUGGCAGCUGAUGUUG

AGGAGCCCACUCUGGAGGCAGACGUCGACUUGAUGUUACAAGAGGCUGGGGCCGGCUCAGUGGAGACACCUCGUGG

CUUGAUAAAGGUUACCAGCUACGAUGGCGAGGACAAGAUCGGCUCUUACGCUGUGCUUUCUCCGCAGGCUGUACUC

AAGAGUGAAAAAUUAUCUUGCAUCCACCCUCUCGCUGAACAAGUCAUAGUGAUAACACACUCUGGCCGAAAAGGGC

GUUAUGCCGUGGAACCAUACCAUGGUAAAGUAGUGGUGCCAGAGGGACAUGCAAUACCCGUCCAGGACUUUCAAGC

UCUGAGUGAAAGUGCCACCAUUGUGUACAACGAACGUGAGUUCGUAAACAGGUACCUGCACCAUAUUGCCACACAU

GGAGGAGCGCUGAACACUGAUGAAGAAUAUUACAAAACUGUCAAGCCCAGCGAGCACGACGGCGAAUACCUGUACG

ACAUCGACAGGAAACAGUGCGUCAAGAAAGAACUAGUCACUGGGCUAGGGCUCACAGGCGAGCUGGUGGAUCCUCC

CUUCCAUGAAUUCGCCUACGAGAGUCUGAGAACACGACCAGCCGCUCCUUACCAAGUACCAACCAUAGGGGUGUAU

GGCGUGCCAGGAUCAGGCAAGUCUGGCAUCAUUAAAAGCGCAGUCACCAAAAAAGAUCUAGUGGUGAGCGCAAGA

AAGAAAACUGUGCAGAAAUUAUAAGGGACGUCAAGAAAAUGAAGGGCUGGACGUCAAUGCCAGAACUGUGGACUC

AGUGCUCUUGAAUGGAUGCAAACACCCCGUAGAGACCCGUAUAUUGACGAAGCUUUUGCUUGUCAUGCAGGUACU

CUCAGAGCGCUCAUAGCCAUUAUAAGACCUAAAAAGGCAGUGCUCUGCGGGGAUCCCAAACAGUGCGGUUUUUUA

ACAUGAUGUGCCUGAAAGUGCAUUUUAACCACGAGAUUUGCACACAAGUCUUCCACAAAAGCAUCUCUCGCCGUUG

CACUAAAUCUGUGACUUCGGUCGUCUCAACCUUGUUUUACGACAAAAAAAUGAGAACGACGAAUCCGAAAGAGACU

AAGAUUGUGAUUGACACUACCGGCAGUACCAAACCUAAGCAGGACGAUCUCAUUCUCACUUGUUUCAGAGGGUGGG

UGAAGCAGUUGCAAAUAGAAUUACAAAGGCAACGAAAUAAUGACGGCAGCUGCUCUCAAGGGCUGACCCGUAAAGG

UGUGUAUGCCGUUCGGUACAAGGUGAAUGAAAAUCCUCUGUACGCACCCACCUCAGAACAUGUGAACGUCCUACUG

```
ACCCGCACGGAGGACCGCAUCGUGUGGAAAACACUAGCCGGCGACCCAUGGAUAAAAACACUGACUGCCAAGUACC

CUGGGAAUUUCACUGCCACGAUAGAGGAGUGGCAAGCAGAGCAUGAUGCCAUCAUGAGGCACAUCUUGGAGAGACC

GGACCCUACCGACGUCUUCCAGAAUAAGGCAAACGUGUGUUGGGCCAAGGCUUUAGUGCCGGUGCUGAAGACCGCU

GGCAUAGACAUGACCACUGAACAAUGGAACACUGUGGAUUAUUUUGAAACGGACAAAGCUCACUCAGCAGAGAUAG

UAUUGAACCAACUAUGCGUGAGGUUCUUUGGACUCGAUCUGGACUCCGGUCUAUUUUCUGCACCCACUGUUCCGUU

AUCCAUUAGGAAUAAUCACUGGGAUAACUCCCCGUCGCCUAACAUGUACGGGCUGAAUAAAGAAGUGGUCCGUCAG

CUCUCUCGCAGGUACCCACAACUGCCUCGGGCAGUUGCCACUGGAAGAGUCUAUGACAUGAACACUGGUACACUGC

GCAAUUAUGAUCCGCGCAUAAACCUAGUACCUGUAAACAGAAGACUGCCUCAUGCUUUAGUCCUCCACCAUAAUGA

ACACCCACAGAGUGACUUUCUUCAUUCGUCAGCAAAUUGAAGGGCAGAACUGUCCUGGUGGUCGGGGAAAAGUUG

UCCGUCCCAGGCAAAAUGGUUGACUGGUUGUCAGACCGGCCUGAGGCUACCUUCAGAGCUCGGCUGGAUUUAGGCA

UCCCAGGUGAUGUGCCCAAAUAUGACAUAAUAUUUGUUAAUGUGAGGACCCCAUAUAAAUACCAUCACUAUCAGCA

GUGUGAAGACCAUGCCAUUAAGCUUAGCAUGUUGACCAAGAAAGCUUGUCUGCAUCUGAAUCCCGGCGGAACCUGU

GUCAGCAUAGGUUAUGGUUACGCUGACAGGGCCAGCGAAAGCAUCAUUGGUGCUAUAGCGCGGCAGUUCAAGUUUU

CCCGGGUAUGCAAACCGAAAUCCUCACUUGAAGAGACGGAAGUUCUGUUUGUAUUCAUUGGGUACGAUCGCAAGGC

CCGUACGCACAAUCCUUACAAGCUUUCAUCAACCUUGACCAACAUUUAUACAGGUUCCAGACUCCACGAAGCCGGA

UGUGCACCCUCAUAUCAUGUGGUGCGAGGGGAUAUUGCCACGGCCACCGAAGGAGUGAUUAUAAAUGCUGCUAACA

GCAAAGGACAACCUGGCGGAGGGGUGUGCGGAGCGCUGUAUAAGAAAUUCCCGGAAAGCUUCGAUUUACAGCCGAU

CGAAGUAGGAAAAGCGCGACUGGUCAAAGGUGCAGCUAAACAUAUCAUUCAUGCCGUAGGACCAAACUUCAACAAA

GUUUCGGAGGUUGAAGGUGACAAACAGUUGGCAGAGGCUUAUGAGUCCAUCGCUAAGAUUGUCAACGAUAACAAUU

ACAAGUCAGUAGCGAUUCCACUGUUGUCCACCGGCAUCUUUUCCGGGAACAAAGAUCGACUAACCCAAUCAUUGAA

CCAUUUGCUGACAGCUUUAGACACCACUGAUGCAGAUGUAGCCAUAUACUGCAGGGACAAGAAAUGGGAAAUGACU

CUCAAGGAAGCAGUGGCUAGGAGAGAAGCAGUGGAGGAGAUAUGCAUAUCCGACGACUCUUCAGUGACAGAACCUG

AUGCAGAGCUGGUGAGGGUGCAUCCGAAGAGUUCUUUGGCUGGAAGGAAGGGCUACAGCACAAGCGAUGGCAAAAC

UUUCUCAUAUUUGGAAGGGACCAAGUUUCACCAGGCGGCCAAGGAUAUAGCAGAAAUUAAUGCCAUGUGGCCCGUU

GCAACGGAGGCCAAUGAGCAGGUAUGCAUGUAUAUCCUCGGAGAAAGCAUGAGCAGUAUUAGGUCGAAAUGCCCCG

UCGAAGAGUCGGAAGCCUCCACACCACCUAGCACGCUGCCUUGCUUGUGCAUCCAUGCCAUGACUCCAGAAAGAGU

ACAGCGCCUAAAAGCCUCACGUCCAGAACAAAUUACUGUGUGCUCAUCCUUUCCAUUGCCGAAGUAUAGAAUCACU

GGUGUGCAGAAGAUCCAAUGCUCCCAGCCUAUAUUGUUCUCACCGAAAGUGCCUGCGUAUAUUCAUCCAAGGAAGU

AUCUCGUGGAAACACCACCGGUAGACGAGACUCCGGAGCCAUCGGCAGAGAACCAAUCCACAGAGGGACACCUGA

ACAACCACCACUUAUAACCGAGGAUGAGACCAGGACUAGAACGCCUGAGCCGAUCAUCAUCGAAGAGGAAGAAGAG

GAUAGCAUAAGUUUGCUGUCAGAUGGCCCGACCCACCAGGUGCUGCAAGUCGAGGCAGACAUUCACGGGCCGCCCU

CUGUAUCUAGCUCAUCCUGGUCCAUUCCUCAUGCAUCCGACUUUGAUGUGGACAGUUUAUCCAUACUUGACACCCU

GGAGGGAGCUAGCGUGACCAGCGGGGCAACGUCAGCCGAGACUAACUCUUACUUCGCAAAGAGUAUGGAGUUUCUG

GCGCGACCGGUGCCUGCGCCUCGAACAGUAUUCAGGAACCCUCCACAUCCCGCUCCGCGCACAAGAACACCGUCAC

UUGCACCCAGCAGGGCCUGCUCGAGAACCAGCCUAGUUUCCACCCCGCCAGGCGUGAAUAGGGUGAUCACUAGAGA

GGAGCUCGAGGCGCUUACCCCGUCACGCACUCCUAGCAGGUCGGUCUCGAGAACCAGCCUGGUCUCCAACCCGCCA

GGCGUAAAUAGGGUGAUUCAAGAGAGGAGUUUGAGGCGUUCGUAGCACAACAACAAUGACGGUUUGAUGCGGGUG

CAUACAUCUUUUCCUCCGACACCGGUCAAGGGCAUUUACAACAAAAAUCAGUAAGGCAAACGGUGCUAUCCGAAGU

GGUGUUGGAGAGGACCGAAUUGGAGAUUUCGUAUGCCCCGCGCCUCGACCAAGAAAAAGAAGAAUUACUACGCAAG

AAAUUACAGUUAAAUCCCACACCUGCUAACAGAAGCAGAUACCAGUCCAGGAAGGUGGAGAACAUGAAAGCCAUAA
```

-continued

```
CAGCUAGACGUAUUCUGCAAGGCCUAGGGCAUUAUUUGAAGGCAGAAGGAAAAGUGGAGUGCUACCGAACCCUGCA

UCCUGUUCCUUUGUAUUCAUCUAGUGUGAACCGUGCCUUUUCAAGCCCCAAGGUCGCAGUGGAAGCCUGUAACGCC

AUGUUGAAAGAGAACUUUCCGACUGUGGCUUCUUACUGUAUUAUUCCAGAGUACGAUGCCUAUUUGGACAUGGUUG

ACGGAGCUUCAUGCUGCUUUAGACACUGCCAGUUUUUGCCCUGCAAAGCUGCGCAGCUUUCCAAAGAAACACUCCUA

UUUGGAACCCACAAUACGAUCGGCAGUGCCUUCAGCGAUCCAGAACACGCUCCAGAACGUCCUGGCAGCUGCCACA

AAAAGAAAUUGCAAUGUCACGCAAAUGAGAGAAUUGCCCGUAUUGGAUUCGGCGGCCUUUAAUGUGGAAUGCUUCA

AGAAAUAUGCGUGUAAUAAUGAAUAUUGGGAAACGUUUAAAGAAAACCCCAUCAGGCUUACUGAAGAAAACGUGGU

AAAUUACAUUACCAAAUUAAAAGGACCAAAAGCUGCUGCUCUUUUUGCGAAGACACAUAAUUUGAAUAUGUUGCAG

GACAUACCAAUGGACAGGUUUGUAAUGGACUUAAAGAGAGACGUGAAAGUGACUCCAGGAACAAAACAUACUGAAG

AACGGCCCAAGGUACAGGUGAUCCAGGCUGCCGAUCCGCUAGCAACAGCGUAUCUGUGCGGAAUCCACCGAGAGCU

GGUUAGGAGAUUAAAUGCGGUCCUGCUUCCGAACAUUCAUACACUGUUUGAUAUGUCGGCUGAAGACUUUGACGCU

AUUAUAGCCGAGCACUUCCAGCCUGGGGAUUGUGUUCUGGAAACUGACAUCGCGUCGUUUGAUAAAAGUGAGGACG

ACGCCAUGGCUCUGACCGCGUUAAUGAUUCUGGAAGACUUAGGUGUGGACGCAGAGCUGUUGACGCUGAUUGAGGC

GGCUUUCGGCGAAAUUUCAUCAAUACAUUUGCCCACUAAAACUAAAUUUAAAUUCGGAGCCAUGAUGAAAUCUGGA

AUGUUCCUCACACUGUUUGUGAACACAGUCAUUAACAUUGUAAUCGCAAGCAGAGUGUUGAGAGAACGGCUAACCG

GAUCACCAUGUGCAGCAUUCAUUGGAGAUGACAAUAUCGUGAAAGGAGUCAAAUCGGACAAAUUAAUGGCAGACAG

GUGCGCCACCUGGUUGAAUAUGGAAGUCAAGAUUAUAGAUGCUGUGGUGGGCGAGAAAGCGCCUUAUUUCUGUGGA

GGGUUUAUUUUGUGUGACUCCGUGACCGGCACAGCGUGCCGUGUGGCAGACCCCCUAAAAAGGCUGUUUAAGCUUG

GCAAACCUCUGGCAGCAGACGAUGAACAUGAUGAUGACAGGAGAAGGGCAUUGCAUGAAGAGUCAACACGCUGGAA

CCGAGUGGGUAUUCUUUCAGAGCUGUGCAAGGCAGUAGAAUCAAGGUAUGAAACCGUAGGAACUUCCAUCAUAGUU

AUGGCCAUGACUACUCUAGCUAGCAGUGUUAAAUCAUUCAGCUACCUGAGAGGGCCCCUAUAACUCUCUACGGCU

AACCUGAAUGGACUACGACAUAGUCUAGUCCGCCAAG
```

SEQ ID NO: 21-VEEV RNA polymerase Amino Acid Sequence
(NCBI Accession: AXP98866.1)
RELPVLDSAAFNVECFKKYACNNEYWETFKENPIRLTEENVVNYITKLKGP SEQ ID NO: 22-VEEV RNA polymerase Amino Acid Sequence
(NCBI Accession: AXP98867.1)
TQMRELPVLDSAAFNVECFKKYACNNEYWETFKENPIRLTE SEQ ID NO: 23:
Polyprotein Amino Acid Sequence [Venezuelan equine encephalitis virus]
(GenBank: ALE15116.1)
MKAITARRILQGLGHYLKAEGKVECYRTLHPVPLYSSSVNRAFSSPKVAVEACNAMLKENFPTVASYCIIPEYDAY

LDMIDGASCCLDTASFCPAKLRSFPKKHSYLEPTIRSAVPSAIQNTLQNVLAAATKRNCNVTQMRELPVLDSAAFN

VECFKKYACNNEYWKTFKENPIRLTEENVINYITKLKGPKAAALYAKTHNLNMLQDIPMDRFVMDLKRDVKVTPGT

KHTEERPKVQVIQAADPLATAYLCGIHRELVRRLNAVLLPNIHTLFDMSAEDFDAIIAEHFQPGDCVLETDIASFD

KSEDDAMALTAMMILEDLGVDAELLTLIEAAFGEISSIHLPTKTKFKFGAMMKSGMFLTLFVNTVINIVIASRVLR

ERLTGSPCAAFIGDDNIVKGVKSDKLMADRCATWLNMEVKIIDAVVGEKAPYFCGGFILCDSVTGTACRVADPLKR

LFKLGKPLAADDEHDDDRRRALHEESTRWNRVGILPELCKAVESRYETVGTSVIVMAMATLASSVKSFSYLRGAPI

TLYG

The following sequences (SEQ ID NOS: 24-31) are formatted to signify vector backbone and antigen open reading frames as follows: lower case letter signify the VEEV replicon backbone sequence; UPPER CASE letters signify spike open reading frame; bold signifies start codons; and lowercase-italicized signifies mutated codons relative to the parental Wuhan spike sequence.

SEQ ID NO: 24- Full-length VEEV+ Delta V5 Antigen Encoding RNA Sequence
auaggcggcgcaugagagaagcccagaccaauuaccuacccaaaauggagaaaguucacguugacaucgaggaagacagc ccauuccucagagcuuugcagcggagcuucccgcaguuugagguagaagccaagcaggucacugauaaugaccaugcuaa ugccagagcguuuucgcaucuggcuucaaaacugaucgaaacggagguggacccauccgacacgauccuugacauuggaa gugcgcccgcccgcagaauguauucuaagcacaaguaucauuguaucuguccgaugagaugugcggaagauccggacaga uuguauaaguaugcaacuaagcugaagaaaaacuuaaggaaauaacugauaaggaauuggacaagaaaaugaaggagcu ggccgccgucaugagcgacccugaccuggaaacugagacuaugugccuccacgacgacgagucgugucgcuacgaagggc aagucgcuguuuaccaggauguauacgcgguugacggaccgacaagucucuaucaccaagccaauaagggaguuagaguc gccuacuggauaggcuuugacaccaccccuuuuauguuuaagaacuuggcuggagcauauccaucauacucuaccaacug ggccgacgaaaccuguuaacggcucuaacauaggccuaugcagcucugacguuauggagcggucacguagagggaugu ccauucuuagaaagaaguauuugaaaccauccaacaauguucuauucucuguugcucgaccaucuaccacgagaagagg gacuuacugaggagcuggcaccugccgucuguauuucacuuacgugggcaagcaaaauuacacaugucggugugagacuau aguuaguugcgacgggguacgucguuaaaagaauagcuaucaguccaggccuguauggggaagccuucaggcuaugcugcua cgaugcaccgcgagggauucuugugcugcaaagugacagacacauugaacggggagagggucucuuuucccgugugcacg uaugugccagcuacauugugugaccaaaugacuggcauacuggcaacagaugucagugcggacgacgcgcaaaaacugcu gguugggcucaaccagcguauagucgucaacggucgcacccagagaaacaccaauaccaugaaaaauuaccuuuugcccg uaguggcccaggcauuugcuaggugggcaaaggaauauaaggaagaucaagaagaugaaaggccacuaggacuacgagau agacaguuagucaugggguguguugggcuuuuagaaggcacaagauaacaucuauuuauaagcgcccggauacccaaac caucaucaaagugaacagcgauuuccacucauucgugcugcccaggauaggcaguaacacauuggagaucgggcugagaa caagaaucaggaaaauguuagaggagcacaaggagccgucaccucucauuaccgccgaggacguacaagaagcuaagugc gcagccgaugaggcuaaggaggugcgugaagccgaggaguugcgcgcagcucuaccaccuuuggcagcugauguugagga gcccacucuggaggcagacgucgacuugauguuacaagaggcuggggccggcucaguggagacaccucguggccuugauaa agguuaccagcuacgauggcgaggacaagaucggcucuuacgcgugucuuucccgcaggcuguacucaagagugaaaaa uuaucuugcauccacccucucgcugaacaagucauagugauaacacacucuggccgaaaagggcguuaugccguggaacc auaccaugguaaaguaguggugccagagggacaugcaauacccguccaggacuuucaagcucugagugaaagugccacca uuguguacaacgaacgugaguucuaaaacagguaccugcaccauauugccacacauggaggagcgcugaacacugaugaa gaauauuacaaaacugucaagcccagcgagcacgacggcgaauaccugacgacaucgacaggaaacagugcgucaagaa agaacuagucacugggcuagggcucacaggcgagcuggugggaucccccuuccaugaauucgccuacagagucugagaa cacgaccagccgcuccuuaccaaguaccaaccauaggggguguauggcgugccaggaucaggcaagucuggcaucauuaaa agcgcaguccaccaaaagaucuaguggugagcgccaagaaagaaaacugugcagaaauauaagggacgucaagaaaau gaaagggcuggacgucaaugccagaacugugga cucagugcucuugaauggaugcaaacaccccguagagacccuguaua uugacgaagcuuuugcuugucaugcagguacucucagagcgcucauagccauuauaagaccuaaaaaggcagugcucugc ggggauccaaacagugcgguuuuuuaacaugaugugccugaaagugcauuuuaaccacgagauuugcacacaagucuu ccacaaaagcaucucucgccguugcacuaaaucgugacuucggucgucucaaccuuguuuuacgacaaaaaaaugagaa cgacgaauccgaaagagacuaagauugugauugacacuaccggcaguaccaaaccuaagcaggacgaucucauucucacu uguuucagagggguggguaagcaguugcaaauagauuacaaaggcaacgaaauaaugacggcagcugccucucaagggcu gacccguaaaggugugua ugccguucgguacaaggugaaugaaaauccucuguacgcacccaccucagaacaugugaacg uccuacugaccgcacggaggaccgcaucgugugg aaaacacuagccggcgacccauggauaaaaacacugacugccaag uacccugggaauuucacugccacgauagaggaguggcaagcagagcaugaugccaucaugaggcacaucuuggagagacc ggacccuaccgacgucuuccagaauaaggcaaacguguguuugggccaagcuuuagcgccggucugaagaccgcuggca uagacaugaccacugaacaauggaacacuguggauuauuuugaaacggacaaagcucacucagcagagauaguauugaac -continued caacuaugcgugagguucuuuggacucgaucuggacuccggucuauuuucugcacccacuguuccguuauccauuaggaa uaaucacugggauaacuccccgucgccuaacauguacgggcugaauaaagaaguggccgucagcucucucgcagguacc cacaacugccucgggcaguugccacuggaagagucuaugacaugaacacgguacacugcgcaauuaugauccgcgcaua aaccuaguaccuguaaacagaagacugccucaugcuuuaguccuccaccauaaugaacacccacagagugacuuuucuuc auucgucagcaaauugaagggcagaacugugccugguggucggggaaaaguugugccgucccaggcaaaaugguugacuggu ugucagaccggccugaggcuaccuucagagcucggcuggauuuaggcauccaggugaugugcccaaauaugacauaaua uuuguuaaugugaggaccccauauaaauaccaucacuaucagcagugugaagaccaugccauuaagcuuagcauguugac caagaaagcuugucugcaucugaaucccggcggaaccugugucagcauagguuaugguuacgcugacagggccagcgaaa gcaucauuggugcuauagcgcggcaguucaaguuucccggguaugcaaaccgaaauccucacuugaagagacggaaguu cuguuuguauucauugggacgaucgcaaggcccguacgcacaauccuuacaagcuuucaucaaccuugaccaacauuua uacagguuccagacuccacgaagccggaugugcacccucauaucauguggugcgaggggauauugccacggccaccgaag gagugauuauaaaugcugcuaacagcaaaggacaaccuggcggaggggugugcggagcgcuguauaagaaauucccggaa agcuucgauuuacagccgaucgaaguaggaaaagcgcgacgggucaaaggugcagcuaaacauaucauucaugccguagg accaaacuucaacaaaguuucggagguugaaggugacaaacaguuggcagaggcuuaugagccaucgcuaagauuguca acgauaacaauuacaagucaguagcgauuccacuguugccaccggcaucuuuuccgggaacaaagaucgacuaacccaa ucauugaaccauuugcugacagcuuuagacaccacugaugcagauguagccauauacugcagggacaagaaaugggaaau gacucucaaggaagcaguggcuaggagagaagcaguggaggagauaugcauauccgacgacucuucagugacagaaccug augcagagcuggugagggugcauccgaagaguucuuuggcuggaaggaagggcuacagcacaagcgauggcaaaacuuuc ucauauuuggaagggaccaaguuucaccaggcggccaaggauauagcagaaauuaaugccauguggcccguugcaacgga ggccaaugagcagguaugcauguauauccucggagaaagcaugagcaguauuaggucgaaaugccccgucgaagagucgg aagccuccacaccaccuagcacgcugccuugcuugugcauccaugccaugacuccagaaagaguacagcgccuaaaagcc ucacguccagaacaaauuacuguguguacuauccuuuccauugccgaaguauagaaucacggugugcagaagauccaaug cucccagccuauauuguucuccaccgaaagugccugcguauauucauccaaggaaguaucucguggaaacaccaccgguag acgagacuccggagccaucggcagagaaccaauccacagagggacaccugaacaaccaccacuuauaaccgaggaugag accaggacuagaacgccugagccgaucaucaucgaagaggaagaagaggauagcauaaguuugcugucagauggcccgac ccaccaggugcugcaagucgaggcagacauucacgggccgcccucuguaucuagcucauccugguccauuccucaugcau ccgacuuugaugugacaguuuauccauacuugacacccuggagggagcuagcgugaccagcggggcaacgucagccgag acuaacucuuacuucgcaaagaguauggaguuucggcgcgaccggugccugcgccucgaacaguauucaggaaccccucc acaucccgcuccgcgcacaagaacaccgucacuugcacccagcagggccugcucgagaaccagccuaguuuccaccccgc caggcgugaauagggugaucacuagagaggagcucgaggcgcuuaccccgucacgcacuccuagcaggucggucucgaga accagccuggucuccaacccgccaggcguaaauaggugauuacaagagaggaguuugaggcguucuagcacaacaaca augacgguuugaugcggugcauacaucuuuuccuccgacaccggucaagggcauuuacaacaaaaaucaguaaggcaaa cggugcuauccgaaguggugucuuggagaggaccgaauuggagauuucguaugcccgcgccucgaccaagaaaaagaagaa uuacuacgcaagaaauuacaguuaaaucccacaccugcuaacagaagcagauaccaguccaggaagguggagaacaugaa agccauaacagcuagacguauucgcaaggccuagggcauuauuugaaggcagaaggaaaaguggagugcuaccgaaccc ugcauccuguuccuuuguauucaucuagugugaaccgugccuuuucaagccccaaggucgcaguggaagccuguaacgcc augacgguuugaugcggguacauacaucuuuuccuccgacaccggucaagggcauuuacaacaaaaaucaguaaggcaaa agcuucaugcugcuuagacacugccaguuuugcccugcaaagcugcgcagcuuuccaaagaaacacuccuauuuggaac ccacaauacgaucggcagugccuucagcgauccagaacacgcuccagaacguccuggcagcugccacaaaaagaaauugc aaugucacgcaaaugagagaauugcccguauuggauucggcggccuuuaauguggaaugcuucaagaaauaugcguguaa uaaugaauauugggaaacguuuaagaaaaccccaucaggcuuacugaagaaaacgugguaaauuacauuaccaaauuaa -continued aaggaccaaaagcugcugcucuuuuugcgaagacacauaauuugaauaugu ugcaggacauaccaauggacagguuugua auggacuuaaagagagacgugaaagugacuccaggaacaaaacauacugaagaacggcccaagg uacaggugauccaggc ugccgauccgcuagcaacagcguaucugucggaauccaccgagagcugguuaggagauuaaaugcgguccugcuuccga acauucauacacuguuugauaugucggcugaagacuuugacgcuauuauagccgagcacuuccagccugggg auugug uu cuggaaacugacaucgcgucguuugauaaaag ugaggacgacgccauggcucugaccgcguuaaugauucuggaagacuu aggu guggacgcagagcuguugacgcug au ugaggcggcuuuc -continued

GAAAUACUUCCAGUUUCCAUGACAAAGACAUCAGUGGAUUGUACAAUGUAUAUAUGCGGAGAUUCCACAGAAUGUUCAAA

UUUGCUCUUGCAGUACGGCUCCUUCUGCACCCAGCUCAACAGGGCCCUUACAGGUAUUGCUGUCGAACAGGACAAGAACA

CACAAGAAGUCUUCGCCCAAGUCAAACAGAUAUACAAAACUCCUCCCAUAAAGGAUUUUGGCGGCUUCAACUUUAGUCAG

AUCCUCCCAGACCCUUCAAAACCAUCUAAACGAUCAUUUAUUGAAGAUCUGCUGUUCAACAAGGUCACUCUUGCCGAUGC

UGGAUUCAUUAAGCAAUACGGUGACUGCCUUGGUGAUAUUGCUGCCCGAGAUCUGAUCUGUGCCCAGAAAUUCAACGGGC

UCACUGUACUCCCUCCACUGCUCACAGACGAAAUGAUUGCACAGUACACAAGUGCCCUGUUGGCAGGCACAAUCACUAGC

GGCUGGACCUUUGGCGCAGGUGCAGCACUCCAAAUACCUUUUGCCAUGCAGAUGGCCUAUCGGUUUAAUGGGAUAGGCGU

GACUCAAAAUGUCCUCUACGAAAACCAAAAGUUGAUAGCUAACCAAUUCAAUUCAGCAAUCGGGAAGAUACAGGAUUCAC

UGUCUAGUACUGCUAGUGCCCUUGGUAAGCUGCAGGACGUUGUCAACCAGAAUGCUCAAGCUCUGAAUACAUUGGUUAAG

CAGCUCUCUAGUAAUUUUGGGGCCAUCUCUUCAGUACUUAAUGAUAUUUUGAGCCGAUUGGACAAAGUGGAAGCUGAAGU

ACAGAUCGACAGGCUGAUAACAGGCCGGCUCCAAUCCCUCCAAACAUACGUGACACAACAACUCAUACGCGCAGCCGAAA

UCCGAGCCAGCGCUAACCUGGCAGCUACCAAGAUGUCAGAAUGCGUUCUGGGCCAGAGUAAACGCGUAGAUUUCUGCGGG

AAAGGGUACCACCUGAUGUCCUUUCCACAAUCUGCACCUCACGGGGUCGUCUUUUUGCAUGUAACAUAUGUACCCGCACA

AGAGAAGAAUUUUACUACCGCUCCUGCCAUCUGUCAUGACGGGAAAGCUCAUUUUCCUCGCGAAGGUGUGUUUGUAUCUA

AUGGUACACAUUGGUUUGUCACACAGCGGAAUUUCUAUGAACCCCAGAUCAUUACAACUGACAACACUUUUGUUUCCGGG

AAUUGUGACGUGGUCAUAGGAAUCGUAAAUAACACUGUAUAUGAUCCCCUCCAACCAGAGCUGGACUCUUUUAAGAAGA

ACUGGAUAAAUAUUUCAAGAACCACACAAGUCCCGACGUGGACCUUGGGGACAUAAGUGGUAUUAACGCAUCUGUGGUUA

ACAUUCAAAAGGAAAUCGACAGACUCAACGAGGUGGCCAAAAACCUGAACGAAAGCUUGAUAGAUCUCCAGGAGUUGGGC

AAGUAUGAACAGUACAUUAAAUGGCCAUGGUACAUAUGGCUUGGCUUUAUCGCUGGCCUUAUCGCCAUCGUAAUGGUUAC

AAUCAUGCUGUGCUGCAUGACCUCCUGCUGUUCUUGUUUGAAAGGGUGUUGUUCUUGUGGUAGUUGUUGCAAGUUUGACG

AAGAUGAUUCCGAACCUGUUCUUAAAGGGGUAAAGCUUCACUAUACAugauaaccgcggugucaaaaaccgcguggacgu cugaccaaccagaaacauaauugaauacagcagcaauuggcaagcugcuuacauagaacucgcggcgauuggcaugccgc cuuaaaauuuuauuuuauuuuuucuuucuuuccgaaucggauuuuguuuuuaauauuucaaaaaaaaaaaaaaaaaaaa aaaaaaaaaaaaaaaaaaaaaaaaa SEQ ID NO: 25-
Full-length VEEV+ K995P-V996P RNA Sequence Antigen Encoding RNA Sequence
auaggcggcgcaugagagaagcccagaccaauuaccuacccaaaauggagaaaguucacguugacaucgaggaagacagc ccauuccucagagcuuugcagcggagcuucccgcaguuugagguagaagccaagcaggucacugauaaugaccaugcuaa ugccagagcguuuucgcaucuggcuucaaaacugaucgaaacggagguggacccauccgacacgauccuugacauuggaa gugcgcccgcccgcagaauguauucuaagcacaaguaucauuguaucuguccgaugagaugugcggaagauccggacaga uuguauaaguaugcaacuaagcugaagaaaaacuguaaggaaauaacugauaaggaauuggacaagaaaaugaaggagcu ggccgccgucaugagcgacccugaccuggaaacugagacuaugugccuccacgacgacgagucgugucgcuacgaagggc aagucgcuguuuaccaggauguauacgcgguugacggaccgacaagucucuaucaccaagccaauaagggaguuagaguc gccuacugguauaggcuuugacaccaccccuuuuaugauuuaagaacuuggcuggagcauauccaucauacucuaccaacug ggccgacgaaaccguguuaacggcucuaacauaggccuaugcagcucugacguuauggagcggucacguagagggaugu ccauucuuagaaagaaguauuugaaaccaucaacaauguucuauucucuguuggcucgaccaucuaccacgagaagagg gacuuacugaggagcuggcaccugccgucuguauuucacuuacguggcaagcaaaauuacacaugucggugugagacuau aguuaguugcgacgggacgucguuaaaagaauagcuaucaguccaggccuguaugggaagccuucaggcuaugcugcua cgaugcaccgcgagggauucucugugcugcaaagugacagacacauugaacggggagagggucucuuuuccgugugcacg uaugugccagcuacauugugugaccaaaugacuggcauacuggcaacagauguvcagugcggacgacgcgcaaaaacugcu gguuggucaaccagcguauagucgucaacggucgcacccagagaaacaccaauaccaugaaaaauuaccuuuugcccg uagugggcccaggcauuugcuagguggcaaaggaauauaaggaagaucaagaagaugaaaggccacuaggacuacgagau -continued agacaguuagucaugggguguuggggcuuuuagaaggcacaagauaacaucuauuuauaagcgcccggauacccaaac caucaucaaagugaacagcgauuuccacucauucgugcugcccaggauaggcaguaacacauuggagaucgggcugagaa caagaaucaggaaaauguuagaggagcacaaggagccgucaccucucauuaccgccgaggacguacaagaagcuaagugc gcagccgaugaggcuaaggaggugcgugaagccgaggaguugcgcgcagcucuaccaccuuuggcagcugauguuggagga gcccacucuggaggcagacgucgacuugauguuacaagaggcuggggccggcucaguggagacaccucguggcuugauaa agguuaccagcuacgauggcgaggacaagaucggcucuuacgcgugugcuuuccccgcaggcuguacucaagagugaaaaa uuaucuugcauccacccucucgcugaacaagucauagugauaacacacucuggccgaaaagggcguuaugccguggaacc auaccauguaaaguagugguguggccagagggacaugcaauacccgucccaggacuuucaagcucugagugaaagugccacca uuguguacaacgaacgugaguucguaaacagguaccugcaccauauugccacacauggaggagcgcugaacacugaugaa gaauauuacaaaacugucaagcccagcgagcacgacggcgaauaccguacgacaucgacaggaaacagugcgucaagaa agaacuagucacugggcuagggcucacaggcgagcugguggauccucccuuccaugaauucgccuacgagagucugagaa cacgaccagccgcuccuuaccaaguaccaaccauagggguguauggcgugccaggaucaggcaagucuggcaucauuaaa agcgcagucaccaaaaagaucuaguggugagcgccaagaaagaaaacugugcagaaauuauaagggacgucaagaaaau gaaagggcuggacgucaaugccagaacugguggacucagugucuugaauggaugcaaacaccccguagagacccuguaua uugacgaagcuuuugcuugucaugcagguacucucagagcgcucauagccauuauaagaccuaaaaaggcagugcucugc ggggaucccaaacagugcgguuuuuuaacaugaugugccugaaagugcauuuuaaccacgagauuugcacacaagucuu ccacaaaagcaucucucgccguugcacuaaaucgugacuucggucgucucaaccuuguuuuacgacaaaaaaaugagaa cgacgaauccgaaagagacuaagauugugauugacacuaccggcaguaccaaaccuaagcaggacgaucucauucucacu uguuucagaggguggugaagcaguugcaaauagauuacaaaggcaacgaaauaaugacggcagcugccucucaagggcu gacccguaaaggugugauugccguucgguacaaggugaaugaaaauccucuguacgcacccaccucagaacaugugaacg uccuacugacccgcacggaggaccgcaucgugugaaaacacuagccggcgacccauggauaaaaacacugacugccaag uacccugggaauuucacugccacgauagaggaguggcaagcagagcaugaugccaucaugaggcacaucuuggagagacc ggacccuaccgacgucuuccagaauaaggcaaacgugugugguugggccaaggcuuuagugccggugcugaagaccgcuggca uagacaugaccacugaacaauggaacacaguggauuauuuugaaacggacaaagcucacucagcagagauaguauugaac cacaacugccucgggcaguugccacuggaagagcucuaugacaugaacacugguacacugcgcaauuaugauccgcgcaua uaaucacugggauaacuccccgucgccuaacauguacgggcugaauaaagaaguggccgucagcucucucgcagguacc cacaacugccucgggcaguugccacuggaagagcucuaugacaugaacacugguacacugcgcaauuaugauccgcgcaua aaccuaguaccuguaaacagaagacugccucaugcuuuaguccuccaccauaaugaacacccacagagugacuuuucuuc auucgucagcaaauugaagggcagaacugccuggugggucggggaaaaguugccguccccaggcaaaauggguugacugg ugucagaccggccugaggcuaccuucagagcucggcuggauuuaggcauccaggugaugugcccaaauaugacauaaua uuguuaaugugaggaccccauauaaaauaccaucacuaucagcagugugaagaccaugccauuaagcuuagcauguugac caagaaagcuugucugcaucugaaucccggcggaaccugugucagcauagguuaugguuacgcugacagggccagcgaaa gcaucauuggugcuauagcgcggcaguucaaguuucccggguaugcaaaccgaaauccucacuugaagagacggaaguu cuguuuguauucauugggguacgaucgcaaggcccguacgcacaauccuuacaagcuuucaucaaccuugaccaacauuua uacagguuccagacuccacgaagccggaugugcacccucauaucaugugugugcgagggggauauugccacggccaccgaag gagugauuauaaaugcugcuaacagcaaaggacaaccuggcggagggggugugcggagcgcuguauaagaaauucccggaa agcuucgauuuacagccgaucgaaguaggaaaagcgcgacgguuacaaaggugcagcuaaacauaucauucaugccguagg accaaacuucaacaaaguuucggagguugaaggugacaaacaguuggcagaggcuuaugaguccaucgcuaagauuguca acgauaacaauuacaagucaguagcgauuccacuguugccaccggcaucuuuucccgggaacaaagaucgacuaacccaa ucauugaaccauuugcugacagcuuuagacaccacugaugcagauguaagccauauacugcagggacaagaaauggggaauu -continued gacucucaaggaagcaguggcuaggagagaagcaguggaggagauaugcauauccgacgacucuucagugacagaaccug augcagagcuggugagggugcauccgaagaguucuuuggcuggaaggaagggcuacagcacaagcgaugcaaaacuuuc ucauauuuggaagggaccaaguuucaccaggcggccaaggauauagcagaaauuaaugccaugugggcccguugcaacgga ggccaaugagcagguaugcaugauauccucggagaaagcaugagcaguauuaggucgaaaugcccccgucgaagagucgg aagccuccacaccaccuagcacgcugccuugcuugugcauccaugccaugacuccagaaagaguacagcgccuaaaagcc ucacguccagaacaaauuacugugugcucauccuuuccauugccgaaguauagaaucacggugugcagaagauccaaug cucccagccuauauuguucucaccgaaagugccugcguauauucauccaaggaaguaucucguggaaacaccaccgguag acgagacuccggagccaucggcagagaaccaauccacagaggggacaccugaacaaccaccacuuauaaccgaggaugag accaggacuagaacgccugagccgaucaucaucgaagaggaagaagaggauagcauaaguuugcugucagauggcccgac ccaccaggugcugcaagucgaggcagacauucacgggccgcccucuguaucuagcucauccugguccauuccucaugcau ccgacuuugaugugagacaguuuauccauacuugacacccuggagggagcuagcgugaccagcggggcaacgucagccgag acuaacucuuacuucgcaaagaguauggaguuucuggcgcgaccggugccugcgccucgaacaguauucaggaaccccucc acaucccgcuccgcgcacaagaacaccgucacuugcacccagcagggccugcucgagaaccagccuaguuuccacccccgc caggcgugaauagggugaucacuagagaggagcucgaggcgcuuacccccgucacgcacuccuagcaggucggucucgaga accagccuggucuccaacccgccaggcguaaauaggugugauuacaagagaggaguuugaggcguucuagcacaacaca augacgguuugaugcgggugcauacaucuuuccuccgacaccggucaagggcauuuacaacaaaaaucaguaaggcaaa cggugcuauccgaaguggugguuggagaggaccgaauuggagauuucguaugccccgcgccucgaccaagaaaaagaagaa uuacuacgcaagaaauuacaguuaaauccacaccugcuaacagaagcagauaccaguccaggaaggugagaacaugaa agccauaacagcuagacguauucugcaaggccuagggcauuauuugaaggcagaaggaaaaguggaguagcuaccgaaccc ugcauccuguuccuuuguauucaucuagugugaaccgugccuuuucaagccccaaggucgcaguggaagccuguaacgcc auguugaaagagaacuuuccgacuguggcuucuuacuguauuauuccagaguacgaugccuauuuggacauugguugacgg auguugaaagagaacuuuccgacuguggcuucuuacuguauuauuccagaguacgaugccuauuuggacauugguugacgg ccacaauacgaucggcagugccuucagcgauccagaacacgcuccagaacguccuggcagcugccacaaaagaaauugc aaugucacgcaaaugagagaauugcccguauuggauucggcggccuuuaaugugaaugcuucaagaaauaugcguguaa uaaugaauauugggaaacguuuaaagaaaaccccaucaggcuuacgaagaaaacgugguaaauuacauuaccaaauuaa aaggaccaaaagcugcugcucuuuuugcgaagacacauaauuugaauauguugcaggacauaccaauggacagguuugua auggacuuaaagagagacgugaaagugacuccaggaacaaaacaucugaagaacggcccaaggucacaggugauccaggc ugccgauccgcuagcaacagcguaucugugcggaauccaccgagagcugguuaggagauuaaaugcggccugcuuccga acauucauacacuguuugauaugucggcugaagacuuugacgcuauuauagccgagcacuuccaccugcgggauuguguu cuggaaacugacaucgcgucguuugauaaaagugaggacgacgccauggcucugaccgcguuaaugauucuggaagacuu aggugguggacgcagagcuguugacgcugauugaggcggcuuucggcgaaauuucaucaauacauuugcccacuaaaacua aauuuaaauucggagccaugaugaaaucuggaauguuccucacacuguuugugaacacagucauuaacauuguaaucgca agcagagguguugagagaacggcuaaccggaucaccaugugcagcauucauuggagaugacaauaucgugaaaggagucaa aucggacaaauuaauggcagacaggugcgccaccugguugaauauggaagucaagauuauagaugcuguggugggcgaga aggcuguuuaagcuuggcaaaccucuggcagcagacgaugaacaugaugaugacaggagaagggcauugcaugaagaguc aacacgcuggaaccgaguggguauucuuucagagcugugcaaggcaguagaaucaagguaugaaaccguaggaacuucca ucauaguuuauggccaugacuacucuagcuagcaguguuaaaucauucagcuaccugagaggggcccuauaacucucuac ggcuaaccugaauggacuacgacauagucuaguccgccaag*AUGUUUCUGCUCACAACCAAACGCACAUGUUUGUUUUC
CUCGUGCUGCUCCCUUUGGUAAGUUCUCAGUGUGUAAACCUGACAACACGAACCCAGUUGCCUCCAGCUUAUACCAACUC
AUUUACUCGCGGAGUAUAUUACCCGAUAAGGUCUUUAGAAGUAGCGUGUUGCACUCUACACAGGAUCUGUUCUUGCCCU
UCUUUAGUAACGUUACCUGGUUUCAUGCAAUACAUGUGAGCGGAACAAAUGGAACAAAAAGAUUUGACAAUCCAGUGCUU*

-continued

```
CCAUUUAAUGAUGGGGUUUACUUUGCCAGUACCGAAAAGUCAAACAUAAUCCGGGGGUGGAUCUUUGGAACCACUUUGGA

CUCUAAGACACAGUCUCUCCUCAUAGUAAACAACGCCACCAAUGUUGUCAUAAAAGUAUGCGAAUUUCAGUUUUGCAACG

AUCCCUUUCUCGGGGUGUAUUACCAUAAGAAUAAUAAAUCCUGGAUGGAGUCUGAGUUCCGGGUUUAUAGUAGUGCUAAU

AAUUGCACUUUCGAAUACGUGUCCCAACCAUUCCUCAUGGACCUUGAGGGCAAACAGGGGAAUUUUAAAAACUUGCGCGA

AUUUGUCUUUAAGAAUAUCGACGGAUACUUUAAGAUCUAUAGUAAACACACUCCUAUCAACCUCGUUCGGGAUCUUCCCC

AAGGCUUUUCUGCUCUCGAACCCCUCGUAGACUUGCCAAUUGGGAUAAAUAUCACUCGCUUUCAAACUUUGCUUGCCCUC

CACAGGAGCUACCUGACACCCGGCGACUCUUCUUCUGGUUGGACCGCCGGCGCCGCUGCCUAUUAUGUUGGUUACCUUCA

GCCACGAACAUUCUUGCUCAAGUAUAACGAGAAUGGCACCAUUACCGACGCCGUCGAUUGUGCAUUGGAUCCCUUGUCUG

AAACAAAAUGUACCUUGAAGUCCUUUACCGUAGAGAAAGGCAUAUACCAGACUUCCAACUUCCGAGUUCAGCCUACAGAA

UCCAUUGUGAGAUUUCCCAACAUCACAAACCUCUGCCCUUUCGGUGAAGUAUUUAAUGCUACACGCUUCGCUUCAGUCUA

UGCCUGGAAUAGGAAGCGCAUAUCAAAUUGCGUGGCCGAUUAUUCAGUCCUCUAUAAUAGCGCAUCCUUCAGUACUUUCA

AGUGCUACGGCGUUUCCCCCACCAAACUCAAUGAUCUUUGCUUCACCAACGUCUAUGCUGACAGUUUUGUCAUACGAGGC

GACGAAGUACGCCAGAUUGCCCCCGGGCAGACAGGUAAAAUUGCUGAUUAUAAUUAUAAACUCCCAGAUGACUUUACUGG

AUGCGUCAUAGCCUGGAAUUCCAACAAUCUUGAUUCCAAGGUUGGUGGGAAUUAUAAUUACCUUUAUCGACUGUUCAGAA

AGAGUAACUUGAAACCAUUUGAGAGAGACAUAUCCACCGAGAUUUACCAGGCAGGCAGUACUCCUUGUAACGGCGUUGAG

GGAUUUAACUGCUAUUUUCCUUUGCAAUCCUAUGGCUUUCAACCAACAAACGGGGUUGGCUAUCAACCCUAUCGAGUGGU

UGUCCUGAGCUUUGAACUUUUGCACGCUCCCGCCACAGUCUGCGGACCAAAAAAGAGUACAAAUCUUGUCAAGAAUAAGU

GCGUAAAUUUCAAUUUCAAUGGCCUUACAGGAACAGGCGUGCUGACUGAGUCAAACAAGAAGUUCCUGCCAUUUCAGCAG

UUUGGGCGGGAUAUAGCAGACACAACUGACGCUGUACGCGAUCCUCAGACUUUGGAGAUCUUGGACAUCACUCCCUGUUC

UUUCGGAGGGGUAUCUGUCAUCACCCCCGGAACUAAUACAUCAAAUCAGGUCGCUGUGUUGUACCAAGAUGUCAACUGCA

CAGAAGUCCCCGUUGCUAUACACGCAGACCAGCUCACCCCCACAUGGCGGGUGUACUCAACUGGCUCAAACGUAUUCCAG

ACCAGAGCUGGGUGCUUGAUCGGUGCUGAACACGUAAACAAUAGCUAUGAAUGCGAUAUUCCCAUCGGUGCCGGGAUCUG

CGCUAGCUAUCAGACACAGACCAAUUCCCCCGGCGAGCACGAUCUGUAGCAUCCCAGUCUAUUAUUGCCUACACUAUGU

CAUUGGGCGCCGAGAAUAGCGUCGCAUAUUCAAAUAAUUCUAUUGCAAUACCCACCAACUUCACAAUCUCCGUAACUACA

GAAAUACUUCCAGUUUCCAUGACAAAGACAUCAGUGGAUUGUACAAUGUAUAUAUGCGGAGAUUCCACAGAAUGUUCAAA

UUUGCUCUUGCAGUACGGCUCCUUCUGCACCCAGCUCAACAGGGCCCUUACAGGUAUUGCUGUCGAACAGGACAAGAACA

CACAAGAAGUCUUCGCCCAAGUCAAACAGAUAUACAAAACUCCUCCCAUAAAGGAUUUUGGCGGCUUCAACUUUAGUCAG

AUCCUCCCAGACCCUUCAAAACCAUCUAAACGAUCAUUUAUUGAAGAUCUGCUGUUCAACAAGGUCACUCUUGCCGAUGC

UGGAUUCAUUAAGCAAUACGGUGACUGCCUUGGUGAUAUUGCUGCCCGAGAUCUGAUCUGUGCCCAGAAAUUCAACGGGC

UCACUGUACUCCCUCCACUGCUCACAGACGAAAUGAUUGCACAGUACACAAGUGCCCUGUUGGCAGGCACAAUCACUAGC

GGCUGGACCUUUGGCGCAGGUGCAGCACUCCAAAUACCUUUUGCCAUGCAGAUGGCCUAUCGUUUUAAUGGGAUAGGCGU

GACUCAAAAUGUCCUCUACGAAAACCAAAAGUUGAUAGCUAACCAAUUCAAUUCAGCAAUCGGGAAGAUACAGGAUUCAC

UGUCUAGUACUGCUAGUGCCCUUGGUAAGCUGCAGGACGUUGUCAACCAGAAUGCUCAAGCUCUGAAUACAUUGGUUAAG

CAGCUCUCUAGUAAUUUUGGGGCCAUCUCUUCAGUACUUAAUGAUAUUUUGAGCCGAUUGGACccacccGAAGCUGAAGU

ACAGAUCGACAGGCUGAUAACAGGCCGGCUCCAAUCCCUCCAAACAUACGUGACACAACAACUCAUACGCGCAGCCGAAA

UCCGAGCCAGCGCUAACCUGGCAGCUACCAAGAUGUCAGAAUGCGUUCUGGGCCAGAGUAAACGCGUAGAUUUCUGCGGG

AAAGGGUACCACCUGAUGUCCUUUCCACAAUCUGCACCUCACGGGGUCGUCUUUUUGCAUGUAACAUAUGUACCCGCACA

AGAGAAGAAUUUUACUACCGCUCCUGCCAUCUGUCAUGACGGGAAAGCUCAUUUUCCUCGCGAAGGUGUGUUUGUAUCUA

AUGGUACACAUUGGUUUGUCACACAGCGGAAUUUCUAUGAACCCCAGAUCAUUACAACUGACAACACUUUUGUUUCCGGG

AAUUGUGACGUGGUCAUAGGAAUCGUAAAUAACACUGUAUAUGAUCCCCUCCAACCAGAGCUGGACUCUUUUAAAGAAGA
```

ACUGGAUAAAUAUUUCAAGAACCACACAAGUCCCGACGUGGACCUUGGGGACAUAAGUGGUAUUAACGCAUCUGUGGUUA

ACAUUCAAAAGGAAAUCGACAGACUCAACGAGGUGGCCAAAAACCUGAACGAAAGCUUGAUAGAUCUCCAGGAGUUGGGC

AAGUAUGAACAGUACAUUAAAUGGCCAUGGUACAUAUGGCUUGGCUUUAUCGCUGGCCUUAUCGCCAUCGUAAUGGUUAC

AAUCAUGCUGUGCUGCAUGACCUCCUGCUGUUCUUGUUUGAAAGGGUGUUGUUCUUGUGGUAGUUGUUGCAAGUUUGACG

AAGAUGAUUCCGAACCUGUUCUUAAAGGGGUAAAGCUUCACUAUACAugauaaccgcggugucaaaaaccgcguggacgu cugaccaaccagaaacauaauugaauacagcagcaauuggcaagcugcuuacauagaacucgcggcgauuggcaugccgc cuuaaaauuuuuauuuuauuuuuucuuuucuuuuccgaaucggauuuugunuuuaauauuucaaaaaaaaaaaaaaaaaa aaaaaaaaaaaaaaaaaaaaaaaaaa SEQ ID NO: 26- Full-length VEEV+ D614G Antigen Encoding RNA Sequence
auaggcggcgcaugagagaagcccagaccaauuaccuacccaaaauggagaaaguucacguugacaucgaggaagacagc ccauuccucagagcuuugcagcggagcuucccgcaguuugagguagaagccaagcaggucacugauaaugaccaugcuaa ugccagagcguuuucgcaucuggcuucaaaacugaucgaaacggaggugacccauccgacacgauccuugacauuggaa gugcgcccgcccgcagaauguauucuaagcacaaguaucauuguaucuguccgaugagaugugcggaagauccggacaga uuguauaaguaugcaacuaagcugaagaaaaacuguaaggaaauaacugauaaggaauuggacaagaaaaugaaggagcu ggccgccgucaugagcgacccugaccuggaaacugagacuaugugccuccacgacgacgagucgugucgcuacgaagggc aagucgcuguuuaccaggauguauacgcgguugacggaccgacaagucucuaucaccaagccaauaagggaguuagaguc gccuacuggauaggcuuugacaccacccccuuuuaugunuaagaacuuggcuggagcauauccaucauacucuaccaacug ggccgacgaaaccguguuaacggcucguaacauaggccuaugcagcucugacguuauggagcggucacguagagggaugu ccauucuuagaaagaaguauuugaaaccauccaacaauguucuauucucuguuggcucgaccaucuaccacgagaagagg gacuuacugaggagcuggcaccugccgucuguauuucacuuacgugguaagcaaaauuuacacaugucggugugagacuau aguuaguugcgacgggguacgucguuaaaagaauagcuauacaguccaggccuguaugggaagccuucaggcuaugcugcua cgaugcaccgcgagggauucuugugcugcaaagugacagacacauugaacggggagagggucucuuuucccguuugcacg uaugugccagcuacauugugugaccaaaugacuggcauacuggcaacagaugucagugcggacgacgcgcaaaaacugcu gguugggcucaaccagcguauaguucgucaacggucgcacccagagaaacaccaauaccaugaaaaauuaccuuuugcccg uaguggcccaggcauuugcuaggugggcaaaggaauauaaggaagaucaagaagaugaaaggccacuaggacuacgagau agacaguuagucauggggguguuugggcuuuuagaaggcacaagauaacaucuauuuuauaagcgcccggauacccaaac caucaucaaagugaacagcgauuuccacucauucgugcugcccaggauaggcaguaacacauuggagaucgggcugagaa caagaaucaggaaaauguuagaggagcacaaggagccgucaccucucauuaccgccgaggacguacaagaagcuaagugc gcagccgaugaggcuaaggaggugcgugaagccgaggaguugcgcgcagcucuaccaccuuuggcagcugauguugagga gcccacucuggaggcagacgucgacuugauguuacaagaggcuggggccggcucaguggagacaccucuggccuugauaa agguuaccagcuacgauggcgaggacaagaucggcucuuacgcugugcuuuccgcaggcuguacucaagagugaaaaa uuaucuugcauccacccucucgcugaacaagucauagugauaacacacucuggccgaaaaggggcguuaugccgguggaacc auaccaugguaaaguaguggugccagagggacaugcaauacccguccaggacuuucaagcucugagugaaagugccacca uuguguacaacgaacgugaguucguaaacagguaccugcaccauauugccacacauggaggagcgcugaacacugaugaa gaauauuacaaaacugucaagcccagcgagcacgacggcgaauaccuguacgacaucgacaggaaacagugcgucaagaa agaacuagucacugggcuagggcucacaggcgagcugguggauccucccuuccaugaauucgccuacgagagucugagaa cacgaccagccgcuccuuaccaaguaccaaccauagggguguauggcgugccaggaucaggcaagucuggcaucauuaaa agcgcagucaccaaaaagauacuaguggugagcgccaagaaagaaaacugucagaaauuauaagggacgucaagaaaau gaaagggcuggacgucaaugccagaacugugacucagucucuugaauggaugcaaacaccccguagagacccuauaua uugacgaagcuuuugcuugucaugcagguacucucagagcgcucauagcauuauaagaccuaaaaaggcagugcucugc ggggaucccaaacagugcgguuuuuuuaacaugaugugugccugaaagugcauuuuaaccacgagauuugcacacaagucuu -continued ccacaaaagcaucucucgccguugcacuaaaucugugacuucggucgucucaaccuuguuuuacgacaaaaaaaugagaa cgacgaauccgaaagagacuaagauugugauugacacuacoggcaguaccaaaccuaagcaggacgaucucauucucacu uguuucagagggugggugaagcaguugcaaauagauuacaaaggcaacgaaauaaugacggcagcugccucucaagggcu gacccguaaaggugugugugccguucgguacaaggugaaugaaaauccucguacgcacccaccucagaacaugugaacg uccuacugacccgcacggaggaccgcaucgugugugaaaacacuagccggcgacccauggauaaaaacacugacugccaag uaccugggaauuucacugccacgauagaggaguggcaagcagagcaugaugccaucaugaggcacaucuuggagagacc ggacccuaccgacgucuuccagaauaaggcaaacgugugugugugggccaaggcuuuagugccggugcugaagaccgcuggca uagacaugaccacugaacaauggaacacaguggauuauuuugaaacggacaaagcucacucagcagagauaguauugaac uaaucacugggauaacuccccgucgccuaacaguguacgggcugaauaaagaaguggguccgucagcucucucgcagguacc cacaacugccucgggcaguugccacuggaagagucuaugacaugaacacuggggucacugcgcaauuaugauccgcgcaua aaccuaguaccuguaaacagaagacugccucaugcuuuaguccuccaccauaaugaacacccacagaugugacuuuucuuc auucgucagcaaauugaagggcagaacugucucggguggucgggaaaaguuguccgucccaggcaaaauggugacuggu ugucagaccggccugaggcuaccuucagagcucggcuggauuuaggcaucccaggugaugugcccaaauaugacauaaua uuuguuaaugugaggaccccauauaaauaccaucacuaucagcaguguggaagaccaugccauuaagcuuagcauguugac caagaaagcuugucugcaucugaauccggcggaaccugugucagcauagguaauggguuacgcugacagggccagcgaaa gcaucauuggugcuauagcgcggcaguucaaguuucccggguaugcaaaccgaaauccucacuugaagagacggaaguu cuguuuguauucauugggguacgaucgcaaggcccguacgcacaauccuuacaagcuuucaucaaccuugaccaacauuua uacagguuccagacuccacgaagccggaugugcacccucauaucaugugggugcgagggggauauugccacggccaccgaag gagugauuauaaaugcugcuaacagcaaaggacaaccuggcggaggggugugcggagcgcuguauaagaaauucccggaa agcuucgauuuacagccgaucgaaguaggaaaagcgcgacuggucaaaggugcagcuaaacauaucauucaugccguagg accaaacuucaacaaaguuucggagguugaaggugacaaacaguuggcagaggcuuaugagccaucgcuaagauuguca acgauaacaauuacaagucaguagcgauuccacuguugaccaccggcaucuuuccggaacaaagaucgacuaacccaa ucauugaaccauuugcugacagcuuuagacaccacugaugcagauguagccauauacugcagggacaagaaaugggaaau gacucucaaggaagcaguggcuaggagagaagcaguggaggagauaugcauauccgacgacucuucagugacagaaccug augcagagcuggugagggugcauccgaagaguucuuuggcuggaaggaagggcuacagcacaagcgaugcaaaacuuuc ucauauuuggaagggaccaaguuucaccaggcggccaaggauauagcagaaauuaaugccaugugggcccguugcaacgga ggccaaugagcagguaugcauguauauccucggagaaagcaugagcaguauuaggucgaaaugccccgucgaagagucgg aagccuccacaccaccuagcacgcugccuugcuugugcauccaugccaugacuccagaaagaguacagcgccuaaaagcc ucacguccagaacaaauuacuguguugcucauccuuuccauugccgaaguauagaaucacuggguguagcagaagauccaaug cucccagccuauauuguucuccaccgaaagugccugcguauauucauccaaggaaguaucucguggaaacaccaccgguag acgagacuccggagccaucggcagagaaccaauccacagagggggacaccugaacaaccaccacuuuauaaccgaggaugag accaggacuagaacgccugagccgaucaucaucgaagaggaagaagaggauagcauaaguuugcugucagauggcccgac ccaccaggugcugcaagucgaggcagacauucacgggccgcccucuguaucuagcucauccugguccauuccucaugcau ccgacuuugaugugacaguuuauccauacuugacacccuggagggagcuagcgugaccagcggggcaacgucagccgag acuaacucuuacuucgcaaagaguauggaguuucuggcgcgaccggugccugcgccucgaacaguauucaggaacccucc acaucccgcuccgcgcacaagaacaccgucacuugcacccagcagggccugcucgagaaccagccuaguuuccaccccgc caggcgugaauaggggugaucacuagagaggagcucgaggcgcuuaccccgucacgcacuccuagcaggucggucucgaga accagccuggucuccaacccgccaggcguaaauagggugauuacaagagaggaguuugaggcguucuagcacaacaaca augacgguuugaugcgggugcauacaucuuuuccuccgacaccggucaagggcauuuacaacaaaaaucaguaaggcaaa cggugcuauccgaaguggguguggagaggaccgaauuggagauuucguaugccccgcgccucgaccaagaaaaagaagaa uuacuacgcaagaaauuacaguuaaauccccacaccugcuaacagaagcagauaccaguccaggaaggugagaacaugaa -continued agccauaacagcuagacguauucugcaaggccuagggcauuauuugaaggcagaaggaaaaguggagugcuaccgaaccc ugcauccuguuccuuuguauucaucuagugugaaccgugccuuuucaagccccaaggucgcaguggaagccguaacgcc auguugaaagagaacuuuccgacuguggcuucuuacuguauuauuccagaguacgauguauuuggacaugguuguugagg agcuucaugcugcuuagacacugccaguuuuugcccugcaaagcugcgcagcuuuccaaagaaacacuccuauuuggaac ccacaauacgaucggcagugccuucagcgauccagaacacgcuccagaacguccuggcagcugccacaaaaagaaauugc aaugucacgcaaaugagagaauugcccguauggauucggcggccuuuaauguggaaugcuucaagaaauaugcguguaa uaaugaauauugggaaacguuuaagaaaaccccaucaggcuuacugaagaaaacgugguaaauuacauuaccaaauuaa aaggaccaaaagcugcugcucuuuuugcgaagacacauaauuugaauauguugcaggacauaccaauggacagguuugua auggacuuaagagagacgugaaagugacuccaggaacaaaacauacugaagaacggcccaagguacaggugauccaggc ugccgauccgcuagcaacagcguaucugugcggaauccaccgagagcugguuaggagauuaaaugcgguccugcuuccga acauucauacacuguuugauaugucggcugaagacuuugacgcuauuauagccgagcacuuccagccuggggauugugu u cuggaaacugacaucgcgucguuugauaaaagugaggacgacgccauggcucugaccgcguuaaugauucuggaagacuu aggugug gacgcagagcuguugacgcugauugaggcggcuuucggcgaaauuucaucaauacauuugcccacuaaaacua aauuuaaauucggagccaugaugaaaucuggaauguuccucacacuguuugugaacacaguc auuaacauuguaaucgca agcagaguguugagagaacggcuaaccggaucaccaugugcagcauucauuggagaugacaauaucgugaaaggagucaa aucggacaaauuaauggcagacaggugcgccaccugguugaauauggaagucaagauuauagaugcguguggug ggcgaga aggcuguuuaagcuuggcaaaccucuggcagcagacgaugaacaugaugaugacaggagaagggcauugcaugaagaguc aacacgcuggaaccgaguggguauucuuucagagcugugcaaggcaguagaaucaagguaugaaaccguaggaacuucca ucauaguuauggccaugacuacucuagcuagcaguguuaaaucauucagcuaccugagaggggcccuauaacucucuac ggcuaaccugaauggacuacgacauaguc uagu c cg ccaag*AUGUUUCUGCUCACAACCAAACGCACAUGUUUGUUUUC
CUCGUGCUGCUCCCUUUGGUAAGUUCUCAGUGUGUAAACCUGACAACACGAACCCAGUUGCCUCCAGCUUAUACCAACUC
AUUUACUCGCGGAGUAUAUUAUCCCGAUAAGGUCUUUAGAAGUAGCGUGUUGCACUCUACACAGGAUCUGUUCUUGCCCU
UCUUUAGUAACGUUACCUGGUUUCAUGCAAUACAUGUGAGCGGAACAAAUGGAACAAAAAGAUUUGACAAUCCAGUGCUU
CCAUUUAAUGAUGGGGUUUACUUUGCCAGUACCGAAAAGUCAAACAUAAUCCGGGGGUGGAUCUUUGGAACCACUUUGGA
CUCUAAGACACAGUCUCUCCUCAUAGUAAACAACGCCACCAAUGUUGUCAUAAAAGUAUGCGAAUUUCAGUUUUGCAACG
AUCCCUUUCUCGGGGUGUAUUACCAUAAGAAUAAUAAAUCCUGGAUGGAGUCUGAGUUCCGGGUUUAUAGUAGUGCUAAU
AAUUGCACUUUCGAAUACGUGUCCCAACCAUUCCUCAUGGACCUUGAGGGCAAACAGGGGAAUUUUAAAAACUUGCGCGA
AUUUGUCUUUAAGAAUAUCGACGGAUACUUUAAGAUCUAUAGUAAACACACUCCUAUCAACCUCGUUCGGGAUCUUCCCC
AAGGCUUUUCUGCUCUCGAACCCCUCGUAGACUUGCCAAUUGGGAUAAAUAUCACUCGCUUUCAAACUUUGCUUGCCCUC
CACAGGAGCUACCUGACACCCGGCGACUCUUCUUCUGGUUGGACCGCCGGCGCCGCUGCCUAUUAUGUUGGUUACCUUCA
GCCACGAACAUUCUUGCUCAAGUAUAACGAGAAUGGCACCAUUACCGACGCCGUCGAUUGUGCAUUGGAUCCCUUGUCUG
AAACAAAAUGUACCUUGAAGUCCUUUACCGUAGAGAAAGGCAUAUACCAGACUUCCAACUUCCGAGUUCAGCCUACAGAA
UCCAUUGUGAGAUUUCCCAACAUCACAAACCUCUGCCCUUUCGGUGAAGUAUUUAAUGCUACACGCUUCGCUUCAGUCUA
UGCCUGGAAUAGGAAGCGCAUAUCAAAUUGCGUGGCCGAUUAUUCAGUCCUCUAUAAUAGCGCAUCCUUCAGUACUUUCA
AGUGCUACGGCGUUUCCCCCACCAAACUCAAUGAUCUUUGCUUCACCAACGUCUAUGCUGACAGUUUUGUCAUACGAGGC
GACGAAGUACGCCAGAUUGCCCCCGGGCAGACAGGUAAAAUUGCUGAUUAUAAUUAUAAACUCCCAGAUGACUUUACUGG
AUGCGUCAUAGCCUGGAAUUCCAACAAUCUUGAUUCCAAGGUUGGUGGGAAUUUAUAAUUACCUUUAUCGACUGUUCAGAA
AGAGUAACUUGAAACCAUUUGAGAGAGACAUAUCCACCGAGAUUUACCAGGCAGGCAGUACUCCUUGUAACGGCGUUGAG
GGAUUUAACUGCUAUUUUCCUUUGCAAUCCUAUGGCUUUCAACCAACAAACGGGGUUGGCUAUCAACCCUAUCGAGUGGU
UGUCCUGAGCUUUGAACUUUUGCACGCUCCCGCCACAGUCUGCGGACCAAAAAAGAGUACAAAUCUUGUCAAGAAUAAGU

```
GCGUAAAUUUCAAUUUCAAUGGCCUUACAGGAACAGGCGUGCUGACUGAGUCAAACAAGAAGUUCCUGCCAUUUCAGCAG

UUUGGGCGGGAUAUAGCAGACACAACUGACGCUGUACGCGAUCCUCAGACUUUGGAGAUCUUGGACAUCACUCCCUGUUC

UUUCGGAGGGGUAUCUGUCAUCACCCCCGGAACUAAUACAUCAAAUCAGGUCGCUGUGUUGUACCAAGAUGUCAACUGCA

CAGAAGUCCCCGUUGCUAUACACGCAGGCCAGCUCACCCCCACAUGGCGGGUGUACUCAACUGGCUCAAACGUAUUCCAG

ACCAGAGCUGGGUGCUUGAUCGGUGCUGAACACGUAAACAAUAGCUAUGAAUGCGAUAUUCCCAUCGGUGCCGGGAUCUG

CGCUAGCUAUCAGACACAGACCAAUUCCCCCGGCGAGCACGAUCUGUAGCAUCCCAGUCUAUUAUUGCCUACACUAUGU

CAUUGGGCGCCGAGAAUAGCGUCGCAUAUUCAAAUAAUUCUAUUGCAAUACCCACCAACUUCACAAUCUCCGUAACUACA

GAAAUACUUCCAGUUUCCAUGACAAAGACAUCAGUGGAUUGUACAAUGUAUAUAUGCGGAGAUUCCACAGAAUGUUCAAA

UUUGCUCUUGCAGUACGGCUCCUUCUGCACCCAGCUCAACAGGGCCCUUACAGGUAUUGCUGUCGAACAGGACAAGAACA

CACAAGAAGUCUUCGCCCAAGUCAAACAGAUAUACAAAACUCCUCCCAUAAAGGAUUUUGGCGGCUUCAACUUUAGUCAG

AUCCUCCCAGACCCUUCAAAACCAUCUAAACGAUCAUUUAUUGAAGAUCUGCUGUUCAACAAGGUCACUCUUGCCGAUGC

UGGAUUCAUUAAGCAAUACGGUGACUGCCUUGGUGAUAUUGCUGCCCGAGAUCUGAUCUGUGCCCAGAAAUUCAACGGGC

UCACUGUACUCCCUCCACUGCUCACAGACGAAAUGAUUGCACAGUACACAAGUGCCCUGUUGGCAGGCACAAUCACUAGC

GGCUGGACCUUUGGCGCAGGUGCAGCACUCCAAAUACCUUUUGCCAUGCAGAUGGCCUAUCGGUUUAAUGGGAUAGGCGU

GACUCAAAAUGUCCUCUACGAAAACCAAAAGUUGAUAGCUAACCAAUUCAAUUCAGCAAUCGGGAAGAUACAGGAUUCAC

UGUCUAGUACUGCUAGUGCCCUUGGUAAGCUGCAGGACGUUGUCAACCAGAAUGCUCAAGCUCUGAAUACAUUGGUUAAG

CAGCUCUCUAGUAAUUUUGGGGCCAUCUCUUCAGUACUUAAUGAUAUUUUGAGCCGAUUGGACAAAGUGGAAGCUGAAGU

ACAGAUCGACAGGCUGAUAACAGGCCGGCUCCAAUCCCUCCAAACAUACGUGACACAACAACUCAUACGCGCAGCCGAAA

UCCGAGCCAGCGCUAACCUGGCAGCUACCAAGAUGUCAGAAUGCGUUCUGGGCCAGAGUAAACGCGUAGAUUUCUGCGGG

AAAGGGUACCACCUGAUGUCCUUUCCACAAUCUGCACCUCACGGGGUCGUCUUUUUGCAUGUAACAUAUGUACCCGCACA

AGAGAAGAAUUUUACUACCGCUCCUGCCAUCUGUCAUGACGGGAAAGCUCAUUUUCCUCGCGAAGGUGUGUUUGUAUCUA

AUGGUACACAUUGGUUUGUCACACAGCGGAAUUUCUAUGAACCCCAGAUCAUUACAACUGACAACACUUUUGUUUCCGGG

AAUUGUGACGUGGUCAUAGGAAUCGUAAAUAACACUGUAUAUGAUCCCCUCCAACCAGAGCUGGACUCUUUUAAAGAAGA

ACUGGAUAAAUAUUUCAAGAACCACACAAGUCCCGACGUGGACCUUGGGGACAUAAGUGGUAUUAACGCAUCUGUGGUUA

ACAUUCAAAAGGAAAUCGACAGACUCAACGAGGUGGCCAAAAACCUGAACGAAAGCUUGAUAGAUCUCCAGGAGUUGGGC

AAGUAUGAACAGUACAUUAAAUGGCCAUGGUACAUAUGGCUUGGCUUUAUCGCUGGCCUUAUCGCCAUCGUAAUGGUUAC

AAUCAUGCUGUGCUGCAUGACCUCCUGCUGUUCUUGUUUGAAAGGGUGUUGUUCUUGUGGUAGUUGUUGCAAGUUUGACG

AAGAUGAUUCCGAACCUGUUCUUAAAGGGGUAAAGCUUCACUAUACAuaguaaccgcggugucaaaaaccgcguggacgu cugaccaaccagaaacauaauugaauacagcagcaauuggcaagcugcuuacauagaacucgcggcgauuggcaugccgc cuuaaaauuuauuuuauuuuuucuuuucuuuuccgaaucggauuuuguuuuuaauauuucaaaaaaaaaaaaaaaaaaa aaaaaaaaaaaaaaaaaaaaaaaa
```

SEQ ID NO: 27- Full-length VEEV+ B.1.351-PP-D614G Antigen Encoding RNA Sequence
```
auaggcggcgcaugagagaagcccagaccaauuaccuacccaaaauggagaaaguucacguugacaucgaggaagacagc ccauuccucagagcuuugcagcggagcuucccgcaguuugagguagaagccaagcaggucacugauaaugaccaugcuaa ugccagagcguuuucgcaucuggcuucaaaacugaucgaaacggagguggacccauccgacacgauccuugacauuggaa gugcgcccgcccgcagaauguauucuaagcacaaguaucauuguaucuguccgaugagaugugcggaagauccggacaga uuguauaaguaugcaacuaagcugaagaaaaacuguaaggaaauaacugauaaggaauuggacaagaaaaugaaggagcu ggccgccgucaugagcgacccugaccuggaaacugagacuauguccucacgacgacgagucgugucgcuacgaagggc aagucgcuguuuaccaggauguauacgcgguugacggaccgacaagucucuaucaccaagccaauaagggaguuagaguc gccuacuggauaggcuuugacacaccccuuuuaauguuuaagaacuuggcuggagcauaccaucauacucuaccaacug ggccgacgaaaccuguuuaacggcucguaacauaggccuaugcagcucugacguuauggagcgguucacguagagggaugu
```

-continued ccauucuuagaaagaaguauuugaaaccauccaacaauguucuauucucuguuggcucgaccaucuaccacgagaagagg gacuuacugaggagcuggcaccugccgucuguauuucacuuacguggcaagcaaaauuacacaugucggugugagacuau aguuaguugcgacggguacgucguuaaaagaauagcuaucaguccaggccuguaugggaagccuucaggcuaugcugcua cgaugcaccgcgagggauucuugugcugcaaagugacagacacauugaacggggagagggucucuuuucccgugugcacg uaugugccagcuacauugugugaccaaaugacuggcauacuggcaacagaugucagugcggacgacgcgcaaaaacugcu gguugggcucaaccagcguauagucgucaaccgucgcacccagagaaacaccaauaccaugaaaaauuaccuuuugcccg uaguggcccaggcauuugcuagguggcaaaggaauauaaggaagaucaagaagaugaaaggccacuaggacuacgagau agacaguuagucaugggguguuguuugggcuuuuagaaggcacaagauaacaucuauuuauaagcgcccggauacccaaac caucaucaaagugaacagcgauuuccacucauucgugcugcccaggauaggcaguaacacauuggagaucgggcugagaa caagaaucaggaaaauguuagaggagcacaaggagccgucaccucucauuaccgccgaggacguacaagaagcuaagugc gcagccgaugaggcuaaggaggugcgugaagccgaggaguugcgcgcagcucuaccaccuuuggcagcugauguugagga gcccacucuggaggcagacgucgacuugauguuacaagaggcuggggccggcucagugagacaccucguggcuugauaa agguuaccagcuacgauggcgaggacaagaucggcucuuacgcgugugcuuucccgcaggcuguacucaagagugaaaaa uuaucuugcauccacccucucgcugaacaagucauagugauaacacacucuggccgaaaagggcguuaugccgguggaacc auaccauggugaaaaguaguggugccagagggacaugcaauacccguccaggacuuucaagcucugagugaaagugccacca uuguguacaacgaacgugaguucguaaacagguaccugcaccauauugccacacauggaggagcgcugaacacugaugaa gaauauuacaaaacugucaagcccagcgagcacgacggcgaauaccuguacgacaucgacaggaaacagugcgucaagaa agaacuagucacugggcuagggcucacaggcgagcugguggauccucccuuccaugaauucgccuacgagagucugagaa cacgaccagccgcuccuuaccaaguaccaaccauaggggguguauggcgugccaggaucaggcaagucuggcaucauuaaa agcgcagucaccaaaaaagaucuaguggugagcgccaagaaagaaaacugugcagaaauuauaagggacgucaagaaaau gaaagggcuggacgucaaugccagaacuguggacucagugcucuugaauggaugcaaacaccccguagagacccuguaua uugacgaagcuuuugcuugucaugcagguacucucagagcgcucauagccauuauaagaccuaaaaaggcagugcucugc ggggaucccaaacagugcgguuuuuuuaacaugaugugccugaaagugcauuuuaaccacgagauuugcacacaagucuu ccacaaaagcaucucucgccguugcacuaaaucugugacuucggucgucucaaccuuguuuuacgacaaaaaaaugagaa cgacgaauccgaaagagacuaagauugugauugacacuacoggcaguaccaaaccuaagcaggacgaucucauucucacu uguuucagagggugggugaagcaguugcaaauagauuacaaaggcaacgaaauaaugacggcagcugccucucaagggcu gacccguaaaggugugguaugccguucgguacaaggugaaugaaaauccucuacgcacccaccucagaacaugugaacg uccuacugacccgcacggaggaccgcaucgugugggaaaacacuagccggcgacccauggauaaaaacacugacugccaag uaccugggaauuucacugccacgauagaggaguggcaagcagagcaugaugccaucaugaggcacaucuuggagagacc ggacccuaccgacgucuuccagaauaaggcaaacgugugguugggccaaggcuuuagugccggugcugaagaccgcuggca uagacaugaccacugaacaauggaacacaguggauuauuugaaacggacaaagcucacucagcagagauaguauugaac caacuaugcgugagguucuuuggacucgaucuggacuccggucuauuuucugcacccacuguuccguuauccauuaggaa uaaucacugggauaacucccgucgccuaacauguacgggcugaauaaagaaguggccgucagcucucucgcagguacc cacaacugccucgggcaguugccacuggaagagucuaugacaugaacacuggucacacugcgcaauuaugauccgcgcaua aaccuaguaccuguaaacagaagacugccucaugcuuuaguccuccaccauaaugaacacccacagagugacuuuucuuc auucgucagcaaauugaagggcagaacugucccguggucggggaaaaguugccgucccaggcaaaauggacugcuggu ugucagaccggccugaggcuaccuucagagcucggcuggauuuaggcauccaggugaugugcccaaaaugacauaaua uuuguuaagugaggaccccauauaaauaccaucacuaucagcagugugaagaccaugccauuaagcuuagcauguugac caagaaagcuugucugcaucugaaucccggcggaaccugugucagcauagguuaugguuacgcugacagggccagcgaaa gcaucaauggugcuauagcgcggcaguucaaguuuucccggguaugcaaaccgaaauccucacuugaagagacgaaguu cuguuugauucauuggguacgaucgcaaggcccguacgcacaauccuuacaagcuuucaucaaccuugaccaacauuua -continued uacagguuccagacuccacgaagccggaugugcacccucauacaugugguggcgaggggauauugccacggccaccgaag gagugauuauaaaugcugcuaacagcaaaggacaaccuggcggaggggugugcggagcgcuguauaagaaauucccggaa agcuucgauuuacagccgaucgaaguaggaaaagcgcgacuggucaaaggugcagcuaaacauaucauucaugccguagg accaaacuucaacaaaaguuucggagguugaaggugacaaacaguuggcagaggcuuaugaguccaucgcuaagauuguca acgauaacaauuacaagucaguagcgauccacuguugu ccaccggcaucuuuccgggaacaaagaucgacuaacccaa ucauugaaccauuugcugacagcuuuagacaccacugaugcagaug uagccauauacugcagggacaagaaaugggaaau gacucucaaggaagcaguggcuaggagagaagcaguggaggagauaugcauauccgacgacucuucagugacagaaccug augcagagcuggugagggugcauccgaagaguucuuuggcuggaaggaagggcuacagcacaagcgaug gcaaaacuuuc ucauauuuggaagggaccaaguuucaccaggcggccaaggauauagcagaaauuaaugccauguggcccguugcaacgga ggccaaugagcagguaugcauguauauccucggagaaagcaugagcaguauuaggucgaaaugcccc gucgaagagucgg aagccuccacaccaccuagcacgcugccuugcuugugcauccaugccaugacuccagaaagaguacagcgccuaaaagcc ucacguccagaacaaauuacugugugcucauccuuuccauugccgaaguauagaaucacgguguguagaag auccaaug cucccagccuauauuguucu caccgaaagugccugcguauauucauccaaggaaguaucucguggaaacaccaccgguag acgagacuccggagccaucggcagagaaccaauccacagagggg acaccugaacaaccaccacuuuauaaccgaggaugag accaggacuagaacgccugagccgaucaucaucgaagaggaagaagaggauagcauaaguuugcugucagauggcccgac ccaccaggugcugcaagucgaggcagacauucacgggccgcccucuguaucuagcucauccugguccauuccucaugcau ccgacuuugauguggacaguuuauccauacuugacacccuggagggagcuagcgugaccagcggggcaacgucagccgag acuaacucuuacuucgcaaagaguauggaguuucuggcgcgaccggugccugcgccucgaacaguauucaggaacccucc acaucccgcuccgcgcacaagaacaccgucacuugcacccagcagggccugcucgagaaccagccuaguuuccacccc gc caggcgugaauagggugaucacuagagaggagcucgaggcgcuuaccccgucacgcacuccuagcaggucggucucgaga accagccugguc uccaacccgccaggcguaaauagggugauuacaagagaggaguuugaggcguucguagcacaacaaca augacguuugaugcgggugcauacaucuuuuccuccgacaccggucaagggcauuuacaacaaaaaucaguaaggcaaa cggugcuauccgaaguggu guuggagaggaccgaauuggagauuucguaugccccgcgccucgaccaagaaaaagaagaa uuacuacgcaagaaauuacaguuaaauucccacaccug cuaacagaagcagauaccaguccaggaaggguggagaacaugaa agccauaacagcuagacguauucugcaaggccuagggcauuauuugaaggcagaaggaaaagug gagugcuaccgaaccc ugcauccuguuccuuuguauucaucuagugugaaccgugccuuuucaagccccaaggucgcaguggaagccuguaacgcc auguugaaagagaacuuuccgacuguggcuucuuacuguauuauccagagua cgaugccuauuggacaugguugacgg agcuucaugcugcuuagacacugccaguuuugcccugcaaagcugcgcagcuuuccaaagaaacacuccuauuuggaac ccacaauacgaucggcagugccuucagcgauccagaacacgcuccagaacguccuggcagcugccacaaaaagaaauugc aauguc acgcaaaugagagaauugcccguauuggauucggcggccuuuaaugu ggaaugcuucaagaaauaugcguguaa uaaugaauauuggg aaacguuuaagaaaaccccaucaggcuuacugaagaaaacgugguaaauuacauuaccaaauuaa aaggaccaaaagcugcugcucuuuuugcgaagacacauaauuugaauauguucaggacauaccaauggacagguuugua auggacuuaaagagagacgugaaaugacuccaggaacaaaacauacugaagaacggcccaaggu acaggugauccaggc ugccgauccgcuagcaacagcguaucugugcggaauccaccgagagcugguuaggagauuaaaugcgguccugcuuccga acauucauacacuguuugauaugucggcugaagacuuugacgcuauuauagccgagcacuuccagccuggggauugu guu cuggaaacugacaucgcgucguuugauaaaagugaggacgacgccauggcucugaccgcguuaaugauucuggaagacuu agguguggacgcagagcuguugacgcugauugaggcggcuuucggcgaaauuucaucaauacauuugcccacuaaaacua aauuuaaauucggagccaugaugaaaucggaauguuccucacacuguuugugaacacaguca uuaacauuguaaucgca agcagagu guugagagaacggcuaaccggaucaccaugugcagcauucauuggagaugacaauaucgugaaaggagucaa aucggacaaauu aaugg cagacaggugcgccaccugguugaauauggaagucaagauuauagaugcuguggugggcgaga -continued aagcgccuuauuucugugggaggguuuauuuugugugacuccgugaccggcacagcgugccguguggcagaccccuaaaa aggcuguuuaagcuuggcaaaccucuggcagcagacgaugaacaugaugaugacaggagaagggcauugcaugaagaguc aacacgcuggaaccgaguggguauucuuucagagcugugcaaggcaguagaaucaagguaugaaaccguaggaacuucca ucauaguuauggccaugacuacucuagcuagcaguguuaaaucauucagcuaccugagagggggccccuauaacucucuac ggcuaaccugaauggacuacgacauagucuaguccgccaagAUGUUUCUGCUCACAACCAAACGCACUAUGUUUGUUUUC CUCGUGCUGCUCCCUUUGGUAAGUUCUCAGUGUGUAAAC*uuc*ACAACACGAACCCAGUUGCCUCCAGCUUAUACCAACUC

AUUUACUCGCGGAGUAUAUUAUCCCGAUAAGGUCUUUAGAAGUAGCGUGUUGCACUCUACACAGGAUCUGUUCUUGCCCU

UCUUUAGUAACGUUACCUGGUUUCAUGCAAUACAUGUGAGCGGAACAAAUGGAACAAAAAGAUUU*gcc*AAUCCAGUGCUU

CCAUUUAAUGAUGGGGUUUACUUUGCCAGUACCGAAAAGUCAAACAUAAUCCGGGGGUGGAUCUUUGGAACCACUUUGGA

CUCUAAGACACAGUCUCUCCUCAUAGUAAACAACGCCACCAAUGUUGUCAUAAAAGUAUGCGAAUUUCAGUUUUGCAACG

AUCCCUUUCUCGGGGUGUAUUACCAUAAGAAUAAUAAAUCCUGGAUGGAGUCUGAGUUCCGGGUUUAUAGUAGUGCUAAU

AAUUGCACUUUCGAAUACGUGUCCCAACCAUUCCUCAUGGACCUUGAGGGCAAACAGGGGAAUUUUAAAAACUUGCGCGA

AUUUGUCUUUAAGAAUAUCGACGGAUACUUUAAGAUCUAUAGUAAACACACUCCUAUCAACCUCGUUCGG*ggc*CUUCCCC

AAGGCUUUUCUGCUCUCGAACCCCUCGUAGACUUGCCAAUUGGGAUAAAUAUCACUCGCUUUCAAACUUUGCACAUCAGC

UACCUGACACCCGGCGACUCUUCUUCGGUUGGACCGCCGGCGCCGCUGCCUAUUAUGUUGGUUACCUUCAGCCACGAAC

AUUCUUGCUCAAGUAUAACGAGAAUGGCACCAUUACCGACGCCGUCGAUUGUGCAUUGGAUCCCUUGUCUGAAACAAAAU

GUACCUUGAAGUCCUUUACCGUAGAGAAAGGCAUAUACCAGACUUCCAACUUCCGAGUUCAGCCUACAGAAUCCAUUGUG

AGAUUUCCCAACAUCACAAACCUCUGCCCUUUCGGUGAAGUAUUUAAUGCUACACGCUUCGCUUCAGUCUAUGCCUGGAA

UAGGAAGCGCAUAUCAAAUUGCGUGGCCGAUUAUUCAGUCCUCUAUAAUAGCGCAUCCUUCAGUACUUUCAAGUGCUACG

GCGUUUCCCCCACCAAACUCAAUGAUCUUUGCUUCACCAACGUCUAUGCUGACAGUUUUGUCAUACGAGGCGACGAAGUA

CGCCAGAUUGCCCCCGGGCAGACAGGGUAACAUUGCUGAUUAUAAUUAUAAACUCCCAGAUGACUUUACUGGAUGCGUCAU

AGCCUGGAAUUCCAACAAUCUUGAUUCCAAGGUUGGUGGGAAUUAUAAUUACCUUUAUCGACUGUUCAGAAAGAGUAACU

UGAAACCAUUUGAGAGAGACAUAUCCACCGAGAUUUACCAGGCAGGCAGUACUCCUUGUAACGGCGUU*aag*GGAUUUAAC UGCUAUUUUCCUUUGCAAUCCUAUGGCUUUCAACCAACA*uac*GGGGUUGGCUAUCAACCCUAUCGAGUGGUUGUCCUGAG

CUUUGAACUUUUGCACGCUCCCGCCACAGUCUGCGGACCAAAAAAGAGUACAAAUCUUGUCAAGAAUAAGUGCGUAAAUU

UCAAUUUCAAUGGCCUUACAGGAACAGGCGUGCUGACUGAGUCAAACAAGAAGUUCCUGCCAUUUCAGCAGUUUGGGCGG

GAUAUAGCAGACACAACUGACGCUGUACGCGAUCCUCAGACUUUGGAGAUCUUGGACAUCACUCCCUGUUCUUUCGGAGG

GGUAUCUGUCAUCACCCCCGGAACUAAUACAUCAAAUCAGGUCGCUGUGUUGUACCAA*ggc*GUCAACUGCACAGAAGUCC

CCGUUGCUAUACACGCAGACCAGCUCACCCCCACAUGGCGGGUGUACUCAACUGGCUCAAACGUAUUCCAGACCAGAGCU

GGGUGCUUGAUCGGUGCUGAACACGUAAACAAUAGCUAUGAAUGCGAUAUUCCCAUCGGUGCCGGGAUCUGCGCUAGCUA

UCAGACACAGACCAAUUCCCCCGGCGAGCACGAUCUGUAGCAUCCCAGUCUAUUAUUGCCUACACUAUGUCAUUGGGCG

UGGAGAAUAGCGUCGCAUAUUCAAAUAAUUCUAUUGCAAUACCCACCAACUUCACAAUCUCCGUAACUACAGAAAUACUU

CCAGUUUCCAUGACAAAGACAUCAGUGGAUUGUACAAUGUAUAUAUGCGGAGAUUCCACAGAAUGUUCAAAUUUGCUCUU

GCAGUACGGCUCCUUCUGCACCCAGCUCAACAGGGCCCUUACAGGUAUUGCUGUCGAACAGGACAAGAACACACAAGAAG

UCUUCGCCCAAGUCAAACAGAUAUACAAAACUCCUCCCAUAAAGGAUUUUGGCGGCUUCAACUUUAGUCAGAUCCUCCCA

GACCCUUCAAAACCAUCUAAACGAUCAUUUAUUGAAGAUCUGCUGUUCAACAAGGUCACUCUUGCCGAUGCUGGAUUCAU

UAAGCAAUACGGUGACUGCCUUGGUGAUAUUGCUGCCCGAGAUCUGAUCUGUGCCCAGAAAUUCAACGGGCUCACUGUAC

UCCCUCCACUGCUCACAGACGAAAUGAUUGCACAGUACACAAGUGCCCUGUUGGCAGGCACAAUCACUAGCGGCUGGACC

UUUGGCGCAGGUGCAGCACUCCAAAUACCUUUUGCCAUGCAGAUGGCCUAUCGGUUUAAUGGGAUAGGCGUGACUCAAAA

UGUCCUCUACGAAAACCAAAAGUUGAUAGCUAACCAAUUCAAUUCAGCAAUCGGGAAGAUACAGGAUUCACUGCUAGUA

CUGCUAGUGCCCUUGGUAAGCUGCAGGACGUUGUCAACCAGAAUGCUCAAGCUCUGAAUACAUUGGUUAAGCAGCUCUCU

AGUAAUUUUGGGGCCAUCUCUUCAGUACUUAAUGAUAUUUUGAGCCGAUUGGAC*ccaccc*GAAGCUGAAGUACAGAUCGA
CAGGCUGAUAACAGGCCGGCUCCAAUCCCUCCAAACAUACGUGACACAACAACUCAUACGCGCAGCCGAAAUCCGAGCCA
GCGCUAACCUGGCAGCUACCAAGAUGUCAGAAUGCGUUCUGGGCCAGAGUAAACGCGUAGAUUUCUGCGGGAAAGGGUAC
CACCUGAUGUCCUUUCCACAAUCUGCACCUCACGGGGUCGUCUUUUUGCAUGUAACAUAUGUACCCGCACAAGAGAAGAA
UUUUACUACCGCUCCUGCCAUCUGUCAUGACGGGAAAGCUCAUUUUCCUCGCGAAGGUGUGUUUGUAUCUAAUGGUACAC
AUUGGUUUGUCACACAGCGGAAUUUCUAUGAACCCCAGAUCAUUACAACUGACAACACUUUUGUUUCCGGGAAUUGUGAC
GUGGUCAUAGGAAUCGUAAAUAACACUGUAUAUGAUCCCCUCCAACCAGAGCUGGACUCUUUUAAAGAAGAACUGGAUAA
AUAUUUCAAGAACCACACAAGUCCCGACGUGGACCUUGGGGACAUAAGUGGUAUAACGCAUCUGUGGUUAACAUUCAAA
AGGAAAUCGACAGACUCAACGAGGUGGCCAAAAACCUGAACGAAAGCUUGAUAGAUCUCCAGGAGUUGGGCAAGUAUGAA
CAGUACAUUAAAUGGCCAUGGUACAUAUGGCUUGGCUUUAUCGCUGGCCUUAUCGCCAUCGUAAUGGUUACAAUCAUGCU
GUGCUGCAUGACCUCCUGCUGUUCUUGUUUGAAAGGGUGUUGUUCUUGUGGUAGUUGUUGCAAGUUUGACGAAGAUGAUU
CCGAACCUGUUCUUAAAGGGGUAAAGCUUCACUAUACAugauaaccgcggugucaaaaaccgcguggacgugguuaacau
cccugcugggaggaucagccguaauuauuauaauuggcuuggugcuggcuacuauuguggccauguacgugcugaccaac
cagaaacauaauugaauacagcagcaauuggcaagcugcuuacauagaacucgcggcgauuggcaugccgccuuaaaauu
uuuauuuuauuuuucuuuucuuuccgaaucggauuuuguuuuaauauuucaaaaaaaaaaaaaaaaaaaaaaaaaaaaa
aaaaaaaaaaaaaaaaaaaa SEQ ID NO: 28- Full-length VEEV+ B.1.1.7-PP-D614G Antigen Encoding RNA Sequence
auaggcggcgcaugagagaagcccagaccaauuaccuacccaaaauggagaaaguucacguugacaucgaggaagac
agcccauuccucagagcuuugcagcggagcuucccgcaguuugagguagaagccaagcaggucacugauaaugacca
ugcuaaugccagagcguuuucgcaucuggcuucaaaacugaucgaaacggagguggacccauccgacacgauccuug
acauuggaagugcgcccgcccgcagaauguauucuaagcacaaguaucauuguaucuguccgaugagaugugcggaa
gauccggacagauuguauaaguaugcaacuaagcugaagaaaaacuguaaggaaauaacugauaaggaauuggacaa
gaaaaugaaggagcuggccgccgucaugagcgacccugaccuggaaacugagacuaugugccuccacgacgacgagu
cgugucgcuacgaagggcaagucgcuguuuaccaggauguauacgcgguugacggaccgacaagucucuaucaccaa
gccaauaagggaguuagagucgccuacuggauaggcuuugacaccaccccuuuuauguuuaagaacuuggcuggagc
auauccaucauacucuaccaacugggccgacgaaaccguguuaacggcucguaacauaggccuaugcagcucugacg
uuauggagcggucacguagaggguauguccauucuuagaaagaaguauuugaaaccauccaacaauguucuauucucu
guuggcucgaccaucuaccacgagaagagggacuuacugaggagcuggcaccugccgucuguauuucacuuacgugg
caagcaaaauuacacaugucggugugagacuauaguuaguugcgacgggcuacgucguuaaaagaauagcuaucaguc
caggccuguaugggaagccuucaggcuaugcugcuacgaugcaccgcgagggauucuugugcugcaaagugacagac
acauugaacggggagagggucucuuuucccgugugcacguaugugccagcuacauugugugaccaaaugacuggcau
acuggcaacagaugucagucggacgacgcgcaaaaacugcugguugggcucaaccagcguauagucgucaacgguc
gcacccagagaaacaccaauaccaugaaaaauuaccuuuugcccguaguggcccaggcauuugcuaggugggcaaag
gaauauaaggaagaucaagaagaugaaaggccacuaggacuacgagauagacaguuagucauggggguguuguuggc
uuuuagaaggcacaagauaacaucuauuuauaagcgcccggauacccaaaccaucaucaaagugaacagcgauuucc
acucauucgugcugcccaggauaggcaguaacacauuggagaucgggcugagaacaagaaucaggaaaauguuuagag
gagcacaaggagccgucaccucucauuaccgccgaggacguacaagaagcuaagugcgcagccgaugaggcuaagga
ggugcgugaagccgaggaguugcgcgcagcucuaccaccuuuggcagcugauguugaggagccccacucuggaggcag
acgucgacuugauguuacaagaggcuggggccggcucaguggagacaccucguggcuugauaaagguuaccagcuac
gauggcgaggacaagaucggcucuuacgcuguugcuuucucccgcaggcuguacucaagagugaaaaauuaucuugcau
ccaccccucucgcugaacaagucauagugauaacacacucuggccgaaaagggcguuaugccguggaaccauaccaug -continued guaaaguaguggugccagagggacaugcaauacccguccaggacuuucaagcucugagugaaagugccaccauugug uacaacgaacgugaguucguaaacagguaccugcaccauauugccacacauggaggagcgcugaacacugaugaaga auauuacaaaacugucaagcccagcgagcacgacggcgaauaccuguacgacaucgacaggaaacagugcgucaaga aagaacuagucacuggggcuagggcucacaggcgagcgguggauccucccuuccaugaauucgccuacgagagucug agaacacgaccagccgcuccuuaccaaguaccaaccaugggguguauggcgugccaggaucaggcaagucuggcau cauuaaaagcgcagucaccaaaaaagaucuagugguagagcgccaagaaagaaaacugugcagaaauuauaagggacg ucaagaaaaugaaagggcuggacgucaaugccagaacuguggacucagugucuugaauggaugcaaacaccccgua gagacccuguauauugacgaagcuuuugcuugucaugcagguacucucagagcgcucauagccauuauaagaccuaa aaaggcagugcucugcggggaucccaaacagugcgguuuuuuaacaugaugugccugaaagugcauuuuaaccacg agauuugcacacaagucuuccacaaaagcaucucucgccguugcacuaaaucugugacuucggucgucucaaccuug uuuuacgacaaaaaaaugagaacgacgaauccgaaagagacuaagauuguugauugacacuaccggcaguaccaaacc uaagcaggacgaucucauucucacuuguuucagagggugggugaagcaguugcaaauagauuacaaaggcaacgaaa uaaugacggcagcugccucucaagggcugacccguaaaggugugcuaugccguucgguacaaggugaaugaaaauccu cuguacgcacccaccucagaacaugugaacgucuacugacccgcacggaggaccgcaucgugaagaaaacacuagc cggcgacccauggauaaaaacacugacugccaaguacccugggaauuucacugccacgauagaggaguggcaagcag agcaugaugccaucaugaggcacaucuuggagagaccggacccuaccgacgucuuccagaauaaggcaaacgugugu ugggccaaggcuuuagugccggugcugaagaccgcuggcauagacaugaccacugaacaauggaacacuguggauua uuuugaaacggacaaagcucacucagcagagauaguauugaaccaacuaugcgugagguucuuuggacucgaucugg acuccggucuauuuucugcacccacuguuccguuauccauuaggaauaaucacugggauaacuccccgucgccuaac auguacgggcugaauaaagaaguggucgucagcucucucgcagguacccacaacugccucgggcaguugccacugg aagagucuaugacaugaacacugguacacugcgcaauuaugauccgcgcauaaaccuaguaccuguaaacagaagac ugccucaugcuuuaguccuccaccauaaugaacacccacagagugacuuuucuucauucgucagcaaauugaagggc agaacuguccugguggucggggaaaaguugaaggucccguccaggcaaaaugguugacugguugucagaccggccugaggc uaccuucagagcucggcuggauuuaggcaucccaggugaugugcccaaauaugacaaauauuuguuaaugugagga ccccauauaaauaccaucacuaucagcagugugaagaccaugccauuaagcuuagcauguugaccaagaaagcuugu cugcaucugaaucccggcggaaccugugucagcauagguuaugguuacgcugacagggccagcgaaagcaucauugg ugcuauagcgcggcaguucaaguuuucccggguaugcaaaccgaaauccucacuugaagagacggaaguucuguuug uauucauggguacgaucgcaaggcccguacgcacaauccuuacaagcuuucaucaaccuugaccaacauuuauaca gguuccagacuccacgaagccggaugugcacccucauaucaugugggugcgaggggauauugccacggccaccgaagg agugauuauaaaugcugcuaacagcaaaggacaaccuggcggaggggugugcggagcgcuguauaagaaauucccgg aaagcuucgauuuacagccgaucgaaguaggaaaagcgcgacuggucaaaggugcagcuaaacauaucauucaugcc guaggaccaaacuucaacaaaguuucggagguugaaggugacaaacaguuggcagaggcuuaugaguccaucgcuaa gauugucaacgauaacaauuacaagucaguagcgauccacuguugccaccggcaucuuuuccgggaacaaagauc gacuaacccaaucauugaaccauuugcugacagcuuuagacaccacugaugcagauguagccauauacugcagggac aagaaaugggaaaugacucucaaggaagcagggcuaggagagaagcagguggaggagauaugcauauccgacgacuc uucagugacagaaccugaugcagagcggugagggugcauccgaagaguucuuuggcuggaaggaagggcuacagca caagcgauggcaaaacuuucucauauuuggaagggaccaaguuucaccaggcggccaaggauauagcagaaauuaau gccauguggcccguugcaacggaggccaaugagcagguaugcauguauauccucggagaaagcaugagcaguauuag gucgaaaugccccgucaagagucggaagccuccacaccaccuagcacgcugccuugcuugugcauccaugccauga cuccagaaagaguacagcgccuaaaagccucacguccagaacaaauuacugugugcucauccuuuccauugccgaag -continued uauagaaucacuggugugcagaagauccaaugcucccagccuauauuguucucaccgaaagugccugcguauauuca uccaaggaaguaucucguggaaacaccaccgguagacgagacuccggagccaucggcagagaaccaauccacagagg ggacaccgaacaaccaccacuuauaaccgaggaugagaccaggacuagaacgccugagccgaucaucaucgaagag gaagaagaggauagcauaaguuugcugucagauggcccgacccaccaggugcugcaagucgaggcagacauucacgg gccgcccucuguaucuagcucauccgguccauuccucaugcauccgacuuugauguggacaguuuauccauacuug acacccuggagggagcuagcgugaccagcggggcaacgucagccgagacuaacucuuacuucgaaagaguauggag uuucuggcgcgaccggugccugcgccucgaacaguauucaggaaccuccacauccgcuccgcgcacaagaacacc gucacuugcacccagcagggccugcucgagaaccagccuaguuccaccccgccaggcgugaauagggugaucacua gagaggagcucgaggcgcuuaccccgucacgcacuccuagcaggucggucucgagaaccagccuggucuccaacccg ccaggcguaaauagggugauuacaagagaggaguuugaggcguucguagcacaacaacaaugacgguuugaugcggg ugcauacaucuuuuccuccgacaccggucaagggcauuuacaacaaaaaucaguaaggcaaacggugcuauccgaag ugguguuggagaggaccgaauuggagauuucguaugccccgcgccucgaccaagaaaaagaagaauuacuacgcaag aaauuacaguuaaauuccacaccugcuaacagaagcagauaccaguccaggaagguggagaacaugaaagccauaac agcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaug uugaaagagaacuuuccgacuguggcuucuuacuguauuauuccagaguacgaugccuauuuggacaugguugacgg agcuucaugcugcuuagacacugccaguuuugcccugcaaagcugcgcagcuuccaaagaaacacuccuauuugg aacccacaauacgaucggcagugccuucagcgauccagaacacgcuccagaacguccuggcagcugccacaaaaga aauugcaaugucacgcaaaugagagaauugcccguauuggauucggcggccuuuaaugugaugcuucaagaaaua ugcguguaauaaugaauauugggaaacguuuaagaaaaccccaucaggcuuacugaagaaaacgugguaaauuaca uuaccaaauuaaaaggaccaaaagcugcugcucuuuuugcgaagacacauaauuugaauaauguucaggacauacca auggacagguuuguaauggacuuaagagagacgugaaaugacuccaggaacaaaacauacugaagaacggcccaa ggguacaggugauccaggcugccgauccgcuagcaacagcguaucugugcggaauccaccgagagcugguuaggagau uaaaugcggccugcuuccgaacauucauacacguuugauaugucggcugaagacuuugacgcuauuauagccgag cacuuccagccuggggauuguguucuggaaacugacaucgcgucguuugauaaaagugaggacgacgccauggcucu gaccgcguuaaugauucuggaagacuuaggugguggacgcagagcuguugacgcugauugaggcggcuuucggcgaaa uuucaucaauacauuugcccacuaaaacuaaauuuaaauucggagccaugaugaaaucuggaauguuccucacacug uuugugaacacagucauuaacauuguaaucgcaagcagaguguugagagaacggcuaaccggaucaccaugugcagc auucauuggagaugacaauaucgugaaaggagucaaaucggacaaauuaauggcagacaggugcgccaccugguuga auauggaagucaagauuauagaugcugugguggcgagaaagcgccuuauuucguggagggguuuauuuugugugac uccgugaccggcacagcgugccgugugcagaccccuaaaaagcugcuuuaagcuuggcaaaccucuggcagcaga cgaugaacaugaugaugacaggagaagggcauugcaugaagagucaacacgcuggaaccgaguggguauucuuucag agcugugcaaggcaguagaaucaaggguauguaaaaccguaggaacuuccaucauaguuuauggccaugacuacucuagcu agcagguuaaaucauucagcuaccugagagggccccuauaacucucuacggcuaaccugaauggacuacgacaua gucuagucccgccaagAUGUUUCUGCUCACAACCAAACGCACUAUGUUUGUUUUCCUCGUGCUGCUCCCUUUGGUAAG

UUCUCAGUGUGUAAACCUGACAACACGAACCCAGUUGCCUCCAGCUUAUACCAACUCAUUUACUCGCGGAGUAUAUU

AUCCCGAUAAGGUCUUUAGAAGUAGCGUGUUGCACUCUACACAGGAUCUGUUCUUGCCCUUCUUUAGUAACGUUACC

UGGUUUCAUGCAAUAAGCGGAACAAAUGGAACAAAAAGAUUUGACAAUCCAGUGCUUCCAUUUAAUGAUGGGGUUUA

CUUUGCCAGUACCGAAAAGUCAAACAUAAUCCGGGGUGGAUCUUUGGAACCACUUUGGACUCUAAGACACAGUCUC

UCCUCAUAGUAAACAACGCCACCAAUGUUGUCAUAAAAGUAUGCGAAUUUCAGUUUUGCAACGAUCCCUUUCUCGGG

GUGUACCAUAAGAAUAAUAAAUCCUGGAUGGAGUCUGAGUUCCGGGUUUAUAGUAGUGCUAAUAAUUGCACUUUCGA

-continued

```
AUACGUGUCCCAACCAUUCCUCAUGGACCUUGAGGGCAAACAGGGGAAUUUAAAAACUUGCGCGAAUUUGUCUUUA
AGAAUAUCGACGGAUACUUUAAGAUCUAUAGUAAACACACUCCUAUCAACCUCGUUCGGGAUCUUCCCCAAGGCUUU
UCUGCUCUCGAACCCCUCGUAGACUUGCCAAUUGGGAUAAAUAUCACUCGCUUUCAAACUUUGCUUGCCCUCCACAG
GAGCUACCUGACACCCGGCGACUCUUCUUCUGGUUGGACCGCCGGCGCCGCUGCCUAUUAUGUUGGUUACCUUCAGC
CACGAACAUUCUUGCUCAAGUAUAACGAGAAUGGCACCAUUACCGACGCCGUCGAUUGUGCAUUGGAUCCCUUGUCU
GAAACAAAAUGUACCUUGAAGUCCUUUACCGUAGAGAAAGGCAUAUACCAGACUUCCAACUUCCGAGUUCAGCCUAC
AGAAUCCAUUGUGAGAUUUCCCAACAUCACAAACCUCUGCCCUUUCGGUGAAGUAUUUAAUGCUACACGCUUCGCUU
CAGUCUAUGCCUGGAAUAGGAAGCGCAUAUCAAAUUGCGUGGCCGAUUAUUCAGUCCUCUAUAAUAGCGCAUCCUUC
AGUACUUUCAAGUGCUACGGCGUUUCCCCCACCAAACUCAAUGAUCUUUGCUUCACCAACGUCUAUGCUGACAGUUU
UGUCAUACGAGGCGACGAAGUACGCCAGAUUGCCCCCGGGCAGACAGGUAAAAUUGCUGAUUAUAAUUAUAAACUCC
CAGAUGACUUUACUGGAUGCGUCAUAGCCUGGAAUUCCAACAAUCUUGAUUCCAAGGUUGGUGGGAAUUAUAAUUAC
CUUUAUCGACUGUUCAGAAAGAGUAACUUGAAACCAUUUGAGAGAGACAUAUCCACCGAGAUUUACCAGGCAGGCAG
UACUCCUUGUAACGGCGUUGAGGGAUUUAACUGCUAUUUUCCUUUGCAAUCCUAUGGCUUUCAACCAACAuacGGGG
UUGGCUAUCAACCCUAUCGAGUGGUUGUCCUGAGCUUUGAACUUUUGCACGCUCCCGCCACAGUCUGCGGACCAAAA
AAGAGUACAAAUCUUGUCAAGAAUAAGUGCGUAAAUUUCAAUUUCAAUGGCCUUACAGGAACAGGCGUGCUGACUGA
GUCAAACAAGAAGUUCCUGCCAUUUCAGCAGUUUGGGCGGGAUAUAgacGACACAACUGACGCUGUACGCGAUCCUC
AGACUUUGGAGAUCUUGGACAUCACUCCCUGUUCUUUCGGAGGGGUAUCUGUCAUCACCCCCGGAACUAAUACAUCA
AAUCAGGUCGCUGUGUUGUACCAAggcGUCAACUGCACAGAAGUCCCCGUUGCUAUACACGCAGAUCAGCUCACCCC
CACAUGGCGGGUGUACUCAACUGGCUCAAACGUAUUCCAGACCAGAGCUGGGUGCUUGAUCGGUGCUGAACACGUAA
ACAAUAGCUAUGAAUGCGAUAUUCCCAUCGGUGCCGGGAUCUGCGCUAGCUAUCAGACACAGACCAAUUCCcauCGG
CGAGCACGAUCUGUAGCAUCCCAGUCUAUUAUUGCCUACACUAUGUCAUUGGGCGCCGAGAAUAGCGUCGCAUAUUC
AAAUAAUUCUAUUGCAAUACCCaucAACUUCACAAUCUCCGUAACUACAGAAAUACUUCCAGUUUCCAUGACAAAGA
CAUCAGUGGAUUGUACAAUGUAUAUAUGCGGAGAUUCCACAGAAUGUUCAAAUUUGCUCUUGCAGUACGGCUCCUUC
UGCACCCAGCUCAACAGGGCCCUUACAGGUAUUGCUGUCGAACAGGACAAGAACACACAAGAAGUCUUCGCCCAAGU
CAAACAGAUAUACAAAACUCCUCCCAUAAAGGAUUUUGGCGGCUUCAACUUUAGUCAGAUCCUCCCAGACCCUUCAA
AACCAUCUAAACGAUCAUUUAUUGAAGAUCUGCUGUUCAACAAGGUCACUCUUGCCGAUGCUGGAUUCAUUAAGCAA
UACGGUGACUGCCUUGGUGAUAUUGCUGCCCGAGAUCUGAUCUGUGCCCAGAAAUUCAACGGGCUCACUGUACUCCC
UCCACUGCUCACAGACGAAAUGAUUGCACAGUACACAAGUGCCCUGUUGGCAGGCACAAUCACUAGCGGCUGGACCU
UUGGCGCAGGUGCAGCACUCCAAAUACCUUUUGCCAUGCAGAUGGCCUAUCGGUUUAAUGGGAUAGGCGUGACUCAA
AAUGUCCUCUACGAAAACCAAAAGUUGAUAGCUAACCAAUUCAAUUCAGCAAUCGGGAAGAUACAGGAUUCACUGUC
UAGUACUGCUAGUGCCCUUGGUAAGCUGCAGGACGUUGUCAACCAGAAUGCUCAAGCUCUGAAUACAUUGGUUAAGC
AGCUCUCUAGUAAUUUUGGGGCCAUCUCUUCAGUACUUAAUGAUAUUUUGgccCGAUUGGACccacccGAAGCUGAA
GUACAGAUCGACAGGCUGAUAACAGGCCGGCUCCAAUCCCUCCAAACAUACGUGACACAACAACUCAUACGCGCAGC
CGAAAUCCGAGCCAGCGCUAACCUGGCAGCUACCAAGAUGUCAGAAUGCGUUCUGGGCCAGAGUAAACGCGUAGAUU
UCUGCGGGAAAGGGUACCACCUGAUGUCCUUUCCACAAUCUGCACCUCACGGGGUCGUCUUUUUGCAUGUAACAUAU
GUACCCGCACAAGAGAAGAAUUUUACUACCGCUCCUGCCAUCUGUCAUGACGGGAAAGCUCAUUUUCCUCGCGAAGG
UGUGUUUGUAUCUAAUGGUACACAUUGGUUUGUCACACAGCGGAAUUUCUAUGAACCCCAGAUCAUUACAACUcacA
ACACUUUUGUUUCCGGGAAUUGUGACGUGGUCAUAGGAAUCGUAAAUAACACUGUAUAUGAUCCCCUCCAACCAGAG
CUGGACUCUUUUAAAGAAGAACUGGAUAAAUAUUUCAAGAACCACACAAGUCCCGACGUGGACCUUGGGGACAUAAG
UGGUAUUAACGCAUCUGUGGUUAACAUUCAAAAGGAAAUCGACAGACUCAACGAGGUGGCCAAAAACCUGAACGAAA
```

GCUUGAUAGAUCUCCAGGAGUUGGGCAAGUAUGAACAGUACAUUAAAUGGCCAUGGUACAUAUGGCUUGGCUUUAUC

GCUGGCCUUAUCGCCAUCGUAAUGGUUACAAUCAUGCUGUGCUGCAUGACCUCCUGCUGUUCUUGUUUGAAAGGGUG

UUGUUCUUGUGGUAGUUGUUGCAAGUUUGACGAAGAUGAUUCCGAACCUGUUCUUAAAGGGGUAAAGCUUCACUAUA

CAugauaaccgcggugucaaaaaccgcguggacgugguuaacaucccugcugggaggaucagccguaauuauuauaa uuggcuuggugcuggcuacuauugguggccauguacgugcugaccaaccagaaacauaauugaauacagcagcaauug gaaucggauuuuguuuuaauauuucaaaaaaaaaaaaaaaaaaaaaaaaaaaaaaaaaaaaaaaaaaaaaaa SEQ ID NO: 29- Full-length VEEV+ Delta.AY1-S2P-wtFur Antigen Encoding RNA Sequence
auaggcggcgcaugagagaagcccagaccaauuaccuacccaaaauggagaaaguucacguugacaucgaggaagac agcccauuccucagagcuuugcagcggagcuucccgcaguuugagguagaagccaagcaggucacugauaaugacca ugcuaaugccagagcguuucgcaucuggcuucaaaacugaucgaaacggagguggacccauccgacacgauccuug acauuggaagugcgcccgcccgcagaauguauucuaagcacaaguucauugugucuguccgaugagaugugcggaa gauccggacagauuguauaaguaugcaacuaagcugaagaaaaacuguaaggaaauaacugauaaggaauuggacaa gaaaaugaaggagcuggccgccgucaugagcgacccugaccuggaaacugagacuaugugccuccacgacgacgagu cgugucgcuacgaagggcaagucgcuguuuaccaggauguauacgcgguugacggaccgacaagucucuaucaccaa gccaauaagggaguuagagucgccuacuggauaggcuuugacaccaccccuuuuauguguuaagaacuuggcuggagc auauccaucauacucuaccaacuggggccgacgaaaccguguuaacggcucguaacauaggccuaugcagcucugacg uuauggagcggucacguagaggggauguccauucuuagaaagaaguauuuugaaaccauccaacaauguucuauucucu guuggcucgaccaucuaccacgagaagagggacuuacugaggagcuggcaccugccgucuguauuucacuuacgugg caagcaaaauuacacaugucggugugagacuauaguuaguugcgacgggacgucguuaaaagaauagcuaucaguc caggccuguaugggaagccuucaggcuaugcugcuacgaugcaccgcgagggauucuugugcugcaaagugacagac acauugaacggggagagggucucuuuucccgugugcacguaugugccagcuacauugugugaccaaaugacuggcau acuggcaacagaugucagugcggacgacgcgcaaaaacugcugguugggcucaaccagcguauagucgucaacgguc gcacccagagaaacaccaauaccaugaaaaauuaccuuuugcccguaguggcccaggcauuugcuaggugggcaaag gaauauaaggaagaucaagaagaugaaaggccacuaggacuacgagauagacaguuaguicauggggugu uuuuagaaggcacaagauaacaucuauuuauaagcgcccggauacccaaaccaucaucaaagugaacagcgauuucc acucauucgugcugcccaggauaggcaguaacacauuggagaucgggcugagaacaagaaucaggaaaauguuagag gagcacaaggagccgucaccucucauuaccgccgaggacguacaagaagcuaagugcgcagccgaugaggcuaagga ggugcgugaagccgaggaguugcgcgcagcucuaccaccuuuggcagcugauguugaggagcccacucuggaggcag acgucgacuugauguuacaagaggcuggggccggcucagguggagacaccucguggcuugauaaagguuaccagcuac gauggcgaggacaagaucggcucuuacgcugugcuuuucccgcaggcuguacucaagagugaaaaauuaucuugcau ccaccccucucgcugaacaagucauagugauaacacacucuggccgaaaagggcguuaugccguggaaccauaccaug guaaaguaguggugccagagggacaugcaauacccguccaggacuuucaagcucugaugaaagugccaccauugug uacaacgaacgugaguucguaaacagguaccugcaccauauugccacacauggaggagcgcugaacacugaugaaga auauucaaaacugucaagcccagcgagcacgacggcgaauaccuguacgacaucgacaggaaacagucgcucaaga aagaacuagucacugggcuagggcucacaggcgagcugguggauccucccuuccaugaauucgccuacgagagucug agaacacgaccagccgcuccuuaccaaguaccaaccauaggggguguauggcgugccaggaucaggcaagucuggcau cauuaaaagcgcagucaccaaaaaagaucuaguggugagcgccaagaaagaaaacugugcagaaauuauaagggacg ucaagaaaaugaaaggcuggacgucaaugccagaacugugacucagugucuugaauggaugcaaacacccccgua gagacccuguauauugacgaagcuuuugcuugucaugcagguacucucagagcgcucauagccauuauaagaccaa aaaggcagugcucgcggggauccaaacagugcgguuuuuaacaugaugugccugaaagugcauuuuaaccacg agauuugcacacaagucuuccacaaaagcaucucucgccguugcacuaaaucugugacuucggucgucucaaccuug -continued uuuuacgacaaaaaaaugagaacgacgaauccgaaagagacuaagauugugauugacacuacggcaguaccaaacc uaagcaggacgaucucauucucacuuguuucagagggugggugaagcaguugcaaauagauuacaaaggcaacgaaa uaaugacggcagcugccucucaagggcugacccguaaaggugugu augccguucgguacaaggugaaugaaaauccu cuguacgcacccaccucagaacaugugaacgucc uacugacccgcacggaggaccgcaucgugugga aaacacuagc cggcgacccauggauaaaaacacugacugccaaguacccugggaauuucacugccacgauagaggaguggcaagcag agcaugaugccaucaugaggcacaucuuggagagaccggacccuaccgacgucuuccagaauaaggcaaacgugugu ugggccaaggcuuuagugccggugcugaagaccgcuggcauagacaugaccacugaacaauggaacacuguggauua uuuugaaacggacaaagcucacucagcagagauaguauugaaccaacuaugcgugagguucuuuggacucgaucugg acuccggucuauuuucugcacccacuguuccguuauccauuaggaauaaucacugggauaacuccccgucgccuaac auguacgggcugaauaaagaaguggucc gucagcucucucgcagguacccacaacugccucgggcaguugccacugg aagagucuaugacaugaacacuggu acacugcgcaauuaugauccgcgcauaaaccuaguaccuguaaacagaagac ugccucaugcuuuaguccuccaccauaaugaacacccacagagugacuuuucuucauucgucagcaaauugaagggc agaacuguccuggguggucggggaaaaguuguccgucccaggcaaaauggu ugacugguugucagaccggccugaggc uaccuucagagcucggcuggauuuaggcaucccaggugaugugcccaaauaugacauaauauuuguuaaugugagga ccccauauaaauaccaucacuaucagcagugugaagaccaugccauuaagcuuagcauguugaccaagaaagcuugu cugcaucugaauc ccggcggaaccugugucagcauagguuaugguuacgcugacagggccagcgaaagcaucauugg ugcuauagcgcggcaguucaaguuuucccgggu augcaaaccgaaauccucacuugaagagacggaaguucuguuug uauucauugggu acgaucgcaaggcccgu acgcacaauccuuacaagcuuucaucaaccuugaccaacauuuauaca gguuccagacuccacgaagccggaugugcacccucauaucaugugg ugcgaggggauauugccacggccaccgaagg agugauuauaaaugcugcuaacagcaaaggacaaccuggcggagggguguguggcgagcgcuguauaagaaauucccgg aaagcuucgauuuacagccgaucgaaguaggaaaagcgcgacuggucaaaggugcagcuaaacauaucauucaugcc guaggaccaaacuucaacaaaguuucggagguugaaggugacaaacaguuggcagaggcuuaugaguccaucgcuaa gauugucaacgauaacaauuacaagucaguagcgauccacuguuguccaccggcaucuuuuccgggaacaaagauc gacuaacccaaucauugaaccauuugcugacagcuuuagacaccacugaugcagauguagccauauacugcagggac aagaaaugggaaaugacucucaaggaagcagu gg -continued uggguguuggagaggaccgaauuggagauuucguaugccccgcgccucgaccaagaaaaagaagaauuacuacgcaag aaauuacaguuaaauccccacaccugcuaacagaagcagauaccaguccaggaaggguggagaacaugaaagccauaac agcuagacguauucugcaaggccuagggcauuauuugaaggcagaaggaaaaguggagugcuaccgaacccugcauc cuguuccuuuguauucaucuagugugaaccgugccuuuucaagccccaaggucgcaguggaagccuguaacgccaug uugaaagagaacuuuccgacuguggcuucuuacuguauuauuccagaguacgaugccuauuuggacaugguugacgg agcuucaugcugcuuagacacugccaguuuuugcccugcaaagcugcgcagcuuccaaagaaacacuccuauuugg aacccacaauacgaucggcagugccuucagcgauccagaacacgcuccagaacguccuggcagcugccacaaaaga aauugcaaugucacgcaaaugagagaauugcccguauuggauucggcggccuuuaaugugggaaugcuucaagaaaua ugcguguaauaaugaauauugggaaacguuuaagaaaaccccaucaggcuuacugaagaaaacgugguaaauuaca uuaccaaauuaaaaggaccaaaagcugcugcucuuuuugcgaagacacauaauuugaauauguugcaggacauacca auggacagguuuguaauggacuuaaagagagacgugaaagugacuccaggaacaaaacauacugaagaacggcccaa gguacaggugauccaggcugccgauccgcuagcaacagcguaucugugcggaauccaccgagagcugguuaggagau uaaaugcgguccugcuuccgaacauucauacacuguuugauaugucggcugaagacuuugacgcuauuauagccgag cacuuccagccuggggauuguguucuggaaacugacaucgcgucguuugauaaaagugaggacgacgccauggcucu gaccgcguuaaugauucuggaagacuuaggguguggacgcagagcuguugacgcugauugaggcggcuuucggcgaaa uuucaucaauacauuugcccacuaaaacuaaauuuaaauucggagccaugaugaaaucuggaauguuccucacacug uuugugaacacagucauuaacauuguaaucgcaagcagaguguugagagaacggcuaaccggaucaccaugugcagc auucauuggagaugacaauaucgugaaaggagucaaaucggacaaauuaauggcagacaggugcgccaccugguuga uccgugaccggcacagcgugccguguggcagaccccaaaaaggcuguuuaagcuuggcaaaccucuggcagcaga cgaugaacaugaugaugacaggagaagggcauugcaugaagagucaacacgcuggaaccgaguggguauucuuucag agcugugcaaggcaguagaaucaagguaugaaaccguaggaacuuccaucauaguuauggccaugacuacucuagcu agcagaguuaaaucauucagcuaccugagaggggccccuauaacucucuacggcuaaccugaauggacuacgacaua gucuaguccgccaagAUGUUUCUGCUCACAACCAAACGCACUAUGUUUGUUUUCCUCGUGCUGCUCCCUUUGGUAAG UUCUCAGUGUGUAAACCUGagaACACGAACCCAGUUGCCUCCAGCUUAUACCAACUCAUUUACUCGCGGAGUAUAUU

AUCCCGAUAAGGUCUUUAGAAGUAGCGUGUUGCACUCUACACAGGAUCUGUUCUUGCCCUUCUUUAGUAACGUUACC

UGGUUUCAUGCAAUACAUGUGAGCGGAACAAAUGGAACAAAAAGAUUUGACAAUCCAGUGCUUCCAUUUAAUGAUGG

GGUUUACUUUGCCAGUaucGAAAAGUCAAACAUAAUCCGGGGGUGGAUCUUUGGAACCACUUUGGACUCUAAGACAC

AGUCUCUCCUCAUAGUAAACAACGCCACCAAUGUUGUCAUAAAAGUAUGCGAAUUUCAGUUUUGCAACGAUCCCUUU

CUCgacGUGUAUUACCAUAAGAAUAAUAAAUCCUGGAUGGAGUCUgggGUUUAUAGUAGUGCUAAUAAUUGCACUUU

CGAAUACGUGUCCCAACCAUUCCUCAUGGACCUUGAGGGCAAACAGGGGAAUUUUAAAAACUUGCGCGAAUUUGUCU

UUAAGAAUAUCGACGGAUACUUUAAGAUCUAUAGUAAACACACUCCUAUCAACCUCGUUCGGGAUCUUCCCCAAGGC

UUUUCUGCUCUCGAACCCCUCGUAGACUUGCCAAUUGGGAUAAAUAUCACUCGCUUUCAAACUUUGCUUGCCCUCCA

CAGGAGCUACCUGACACCCGGCGACUCUUCUUUCUGGUuugACCGCCGGCGCCGCUGCCUAUUAUGUUGGUUACCUUC

AGCCACGAACAUUCUUGCUCAAGUAUAACGAGAAUGGCACCAUUACCGACGCCGUCGAUUGUGCAUUGGAUCCCUUG

UCUGAAACAAAAUGUACCUUGAAGUCCUUUACCGUAGAGAAAGGCAUAUACCAGACUUCCAACUUCCGAGUUCAGCC

UACAGAAUCCAUCGUACGAUUUCCCAACAUCACAAACCUCUGCCCUUUCGGUGAAGUAUUUAAUGCUACACGCUUCG

CUUCAGUCUAUGCCUGGAAUAGGAAGCGCAUAUCAAAUUGCUGGGCCGAUUAUUCAGUCCUCUAUAAUAGCGCAUCC

UUCAGUACUUUCAAGUGCUACGGCGUUUCCCCCACCAAACUCAAUGAUCUUUGCUUCACCAACGUCUAUGCUGACAG

UUUUGUCAUACGAGGCGACGAAGUACGCCAGAUUGCCCCGGGCAGACAGGUaauAUUGCUGAUUAUAAUUAUAAAC

UCCCAGAUGACUUUACUGGAUGCGUCAUAGCCUGGAAUUCCAACAAUCUAGAUUCCAAGGUUGGUGGGAAUUAUAAU

-continued

UAC*cgu*UAUCGACUGUUCAGAAAGAGUAACUUGAAACCAUUUGAGAGAGACAUAUCCACCGAGAUUUACCAGGCAGG

CAGU*aag*CCUUGUAACGGCGUUGAGGGAUUUAACUGCUAUUUUCCUUUGCAAUCCUAUGGCUUUCAACCAACAAACG

GGGUUGGCUAUCAACCCUAUCGAGUGGUUGUCCUCAGCUUUGAACUUUUGCACGCUCCCGCCACAGUCUGCGGACCA

AAAAGAGUACAAAUCUUGUCAAGAAUAAGUGCGUAAAUUUCAAUUUCAAUGGCCUUACAGGAACAGGCGUGCUGAC

UGAGUCAAACAAG*aau*UUCCUGCCAUUUCAGCAGUUUGGGCGGGAUAUAGCAGACACAACUGACGCUGUACGCGAUC

CUCAGACUUUGGAGAUCUUGGACAUCACUCCCUGUUCUUUCGGAGGGGUAUCUGUCAUCACCCCCGGAACUAAUACA

UCAAAUCAGGUCGCUGUGUUGUACCAA*ggu*GUCAACUGCACAGAAGUCCCCGUUGCUAUACACGCAGACCAGCUCAC

CCCCACAUGGCGGGUGUACUCAACUGGCUCAAACGUAUUCCAGACCAGAGCUGGGGUGCUUGAUCGGUGCUGAACACG

UGAACAAUAGCUAUGAAUGCGAUAUUCCCAUCGGUGCCGGGAUCUGCGCUAGCUAUCAGACACAGACCAAUUCC*cgc*

AGGCGGGCUCGCUCUGUAGCAUCCCAGUCUAUUAUUGCCUACACUAUGUCAUUGGGCGCCGAGAAUAGCGUCGCAUA

UUCAAAUAAUUCUAUUGCAAUACCCACCAACUUCACAAUCUCCGUAACUACAGAAAUACUUCCAGUUUCCAUGACAA

AGACAUCAGUGGAUUGUACAAUGUAUAUAUGCGGAGAUUCCACAGAAUGUUCAAAUUUGCUCUUGCAGUACGGCUCC

UUCUGCACCCAGCUCAACAGGGCACUUACAGGUAUUGCUGUCGAACAGGACAAGAACACACAAGAAGUCUUCGCCCA

AGUCAAACAGAUAUACAAAACUCCUCCCAUAAAGGAUUUUGGCGGCUUCAACUUUAGUCAGAUCCUCCCAGACCCUU

CAAAACCAUCUAAACGAUCAUUUAUUGAAGAUCUGCUGUUCAACAAGGUCACUCUUGCCGAUGCUGGAUUCAUUAAG

CAAUACGGUGACUGCCUUGGUGAUAUUGCUGCCCGAGAUCUGAUCUGUGCCCAGAAAUUCAACGGGCUCACUGUACU

CCCCUCCACUGCUCACAGACGAAAUGAUUGCACAGUACACAAGUGCCCUGUUGGCAGGCACAAUCACUAGCGGCUGGA

CCUUUGGCGCAGGUGCAGCACUCCAAAUACCUUUUGCCAUGCAGAUGGCCUAUCGGUUUAAUGGGAUAGGCGUGACU

CAAAAUGUCCUCUACGAAAACCAAAAGUUGAUAGCUAACCAAUUCAAUUCAGCAAUCGGGAAGAUACAGGAUUCACU

GUCUAGUACUGCUAGUGCCCUUGGUAAGCUGCAG*aac*GUUGUCAACCAGAAUGCUCAAGCUCUGAAUACAUUGGUUA

AGCAGCUCUCUAGUAAUUUUGGGGCCAUCUCUUCAGUACUUAAUGAUAUUUUGAGCCGAUUGGAC*ccaccu*GAAGCU

GAAGUACAGAUCGACAGGCUGAUAACAGGCCGGCUCCAAUCCCUCCAAACAUACGUGACACAACAACUCAUACGCGC

AGCCGAAAUCCGAGCCAGCGCUAACCUGGCAGCUACCAAGAUGUCAGAAUGCGUUCUGGGCCAGAGUAAACGCGUAG

AUUUCUGCGGGAAAGGGUACCACCUGAUGUCCUUUCCACAAUCUGCACCUCACGGGUCGUCUUUUUGCAUGUAACA

UACGUACCCGCACAAGAGAAGAAUUUUACUACCGCUCCUGCCAUCUGUCAUGACGGGAAAGCUCAUUUUCCUCGCGA

AGGUGUGUUUGUAUCUAAUGGUACACAUUGGUUUGUCACACAGCGGAAUUUCUAUGAACCCCAGAUCAUUACAACUG

ACAACACUUUUGUUUCCGGGAAUUGUGACGUGGUCAUAGGAAUCGUAAAUAACACUGUAUAUGAUCCCCUCCAACCA

GAGCUGGACUCUUUUAAAGAAGAACUGGAUAAAUAUUUCAAGAACCACACAAGUCCCGACGUGGACCUUGGGGACAU

AAGUGGUAUUAACGCAUCUGUGGUUAACAUUCAAAAGGAAAUCGACAGACUCAACGAGGUGGCCAAAAACCUGAACG

AAAGCUUGAUAGAUCUCCAGGAGUUGGGCAAGUAUGAACAGUACAUUAAAUGGCCAUGGUACAUAUGGCUUGGCUUU

AUCGCUGGCCUUAUCGCCAUCGUAAUGGUUACAAUCAUGCUGUGCUGCAUGACCUCCUGCUGUUCUUGUUUGAAAGG

GUGUUGUUCUUGUGGUAGUUGUUGCAAGUUUGACGAAGAUGAUUCCGAACCUGUUCUUAAGGGGGUAAAGCUUCACU

AUACAUGA*uaaccgcggugucaaaaaccgcguggacuggguuaacaucccugcugggaggaucagccguaauuauua*

*uaauuggcuuggugcuggcuacuauuguggccaugacgugcugaccaaccagaaacauaauugaauacagcagcaa*

*uuggcaagcugcuuacauagaacucgcggcgauuggcaugccgccuuaaaauuuuauuuuauuuuuucuuuucuuu*

*uccgaaucggauuuguguuuuaauauuucaaaaaaaaaaaaaaaaaaaaaaaaaaaaaaaaaaaaaaaaaaaaaaaa*

SEQ ID NO: 30-
Full-length VEEV+ AY1-S2P-wtFur-newKozak Antigen Encoding RNA Sequence
auaggcggcgcaugagagaagcccagaccaauuaccuacccaaaauggagaaaguucacguugacaucgaggaagacagc ccauuccucagagcuuugcagcggagcuucccgcaguuugagguagaagccaagcaggucacugauaaugaccaugcuaa ugccagagcguuuucgcaucuggcuucaaaacugaucgaaacggaggugacccauccgacacgauccuugacauuggaa gugcgcccgcccgcagaaugauauucuaagcacaaguaucauuguaucuguccgaugagaugugcggaagauccggacaga -continued uuguauaaguaugcaacuaagcugaagaaaaacuguaaggaaauaacugauaaggaauuggacaagaaaaugaaggagcu ggccgccgucaugagcgacccugaccuggaaacugagacuaugugccuccacgacgacgagucgugucgcuacgaagggc aagucgcuguuuaccaggaugauacgcgguugacggaccgacaagucucuaucaccaagccaauaagggaguuagagruc gccuacuggauaggcuuugacaccaccccuuuuauguuuaagaacuuggcuggagcauauccaucauacucuaccaacug ggccgacgaaaccguguuaacggcucguaacauaggccuaugcagcucugacguuauggagcggucacguagagggaugu ccauucuuagaaagaaguauuugaaaccauccaacaauguucuauucucuguugcucgaccaucuaccacgagaagagg gacuuacugaggagcuggcaccugccgucuguauuucacuuacguggcaagcaaaauuacacaugucggugugagacuau aguuaguugcgacgggucgucguuaaaagaauagcuaucaguccaggccuguagggaagccuucaggcuaugcugcua cgaugcaccgcgagggauucuugugcugcaaagugacagacacauugaacggggagagggucucuuucccgugugcacg uaugugccagcuacauugugugaccaaaugacuggcauacuggcaacagaugucagugcggacgacgcgcaaaaacugcu gguugggcucaaccagcguauagucgucaacggucgcacccagagaaacaccaauaccaugaaaaauuaccuuuugcccg uagugcccaggcauuugcuagguggggcaaaggaauauaaggaagaucaagaagaugaaaggccacuaggacuacgagau agacaguuagucaugggguguuguuggcuuuuagaaggcacaagauaacaucuauuuauaagcgcccggauacccaaac caucaucaaagugaacagcgauuuccacucauucgugcugcccaggauaggcaguaacacauuggagaucgggcugagaa caagaaucaggaaaauguuagaggagcacaaggagccgucaccucucauuaccgccgaggacguacaagaagcuaagugc gcagccgaugaggcuaaggaggugcgugaagccgaggaguugcgcgcagcucuaccaccuuuggcagcugauguugagga gcccacucuggaggcagacgucgacuugauguuacaagaggcuggggccggcucaguggagacaccucguggcuugauaa agguuaccagcuacgauggcgaggacaagaucggcucuuacgcgugugcuuucuccgcaggcuguacucaagagugaaaaa uuaucuugcauccaccccucucgcugaacaagucauagugauaacacacucuggccgaaaagggcguuaugccguggaacc auaccauggauaaaguguguggccagaggggacaugcaauacccguccaggacuuucaagcucugagugaaagugccacca uuguguacaacgaacgugaguucguaaacagguaccugcaccauauugccacacauggaggagcgcugaacacugaugaa gaauauuacaaaacugucaagcccagcgagcacgacggcgaauaccuguacgacaucgacaggaaacagucgucaagaa agaacuagucacugggcuagggcucacaggcgagcuggugauccucccuuccaugaauucgccuacgagagucugagaa cacgaccagccgcuccuuaccaaguaccaaccauaggggguguauggcgugccaggaucaggcaagucuggcaucauuaaa agcgcagucaccaaaaaagaucuaguggugagcgccaagaaagaaaacgugcagaaauuauaagggacgucaagaaaau gaaagggcuggacgucaaugccagaacuguggacucagugcucuugaauggaugcaaacaccccguagagacccuguaua uugacgaagcuuuugcuugucaugcagguacucucagagcgcucauagccauuauaagaccuaaaaaggcagugcucugc ggggaucccaaacagugcgguuuuuuuaacaugaugugccugaaagugcauuuuaaccacgagauuugcacacaagucuu ccacaaaagcaucucucgccguugcacuaaaucugugacuucggucgucucaaccuuguuuuacgacaaaaaaaugagaa cgacgaauccgaaagagacuaagauugugauugacacuacggcaguaccaaaccuaagcaggacgaucucauucucacu uguuucagagggugggugaagcaguugcaaauagauuacaaaggcaacgaaauaaugacggcagcugccucucaagggcu gacccguaaaggugguguaugccguucgguacaaggugaaugaaaauccucuguacgcacccaccucagaacaugugaacg uccuacugacccgcacggaggaccgcaucgugugggaaaacacuagccggcgacccauggauaaaaacacugacugccaag uacccugggaauuucacugccacgauagaggagugggcaagcagagcaugaugccaucaugaggcacaucuuggagagacc ggaccccuaccgacgucuuccagaauaaggcaaacuguguguugggccaaggcuuuagugccggugcugaagaccgcuggca uagacaugaccacugaacaauggaacacguggauuauuuugaaacggacaaagcucacucagcagagauaguauugaac caacuaugcgugagguucuuuggacucgaucggacuccggucuauuuucugcacccacuguuccguuauccauuaggaa uaaucacugggauaacuccccgucgccuaacauguacgggcugaauaaagaaguggucgucagcucucucgcagguacc cacaacugccucgggcaguugccacuggaagagucuaugacaugaacacugguacacugcgcaauuaugauccgcgcaua aaccuaguaccuguaaacagaagacugccucaugcuuuaguccuccaccauaaugaacacccacagagugacuuuucuuc -continued auucgucagcaaauugaagggcagaacuguccuggugguᴄggggaaaaguuguccgucccaggcaaaaugguugacuggu ugucagaccggccugaggcuaccuucagagcucggcuggauuuaggcauccaggugaugugcccaaauaugacauaaua uuuguuaaugugaggaccccauauaaauaccaucacuaucagcagugugaagaccaugccauuaagcuuagcauguugac caagaaagcuugucugcaucugaaucccggcggaaccugugucagcauagguuaugguuacgcugacagggccagcgaaa gcaucauuggugcuauagcgcggcaguucaaguuuucccggguaugcaaaccgaaauccucacuugaagagacggaaguu cuguuuguauucauugggacgaucgcaaggcccguacgcacaauccuuacaagcuuucaucaaccuugaccaacauuua uacagguuccagacuccacgaagccggaugugcacccucauaucaugguggcgaggggauauugccacggccaccgaag gagugauuauaaaugcugcuaacagcaaaggacaaccuggcggaggggugugcggagcgcuguauaagaaauucccggaa agcuucgauuuacagccgaucgaaguaggaaaagcgcgacuggucaaaggugcagcuaaacauaucauucaugccguagg accaaacuucaacaaaguuucggagguugaaggugacaaacaguuggcagaggcuuaugaguccaucgcuaagauuguca acgauaacaauuacaagucaguagcgauuccacuguugucᴄaccggcaucuuuᴄcgggaacaaagaucgacuaacccaa ucauugaaccauuugcugacagcuuuagacaccacugaugcagauguagccauauacugcagggacaagaaaugggaaau gacucucaaggaagcaguggcuaggagagaagcaguggaggagauaugcauaccgacgacucuucagugacagaaccug augcagagcuggugagggugcauccgaagaguucuuuggcuggaaggaagggcuacagcacaagcgauggcaaaacuuuc ucauauuuggaagggaccaaguuucaccaggcggccaaggauauagcagaaauuaagcauguggcccguugcaacgga ggccaaugagcagguaugcauguauauccucggagaaagcaugagcaguauuaggucgaaaugccccgucgaagagucgg aagccuccacaccaccuagcacgcugccuugcuugugcauccaugccaugacuccagaaagaguacagcgccuaaaagcc ucacguccagaacaaauuacugugugcucauccuuuccauugccgaaguauagaaucacuggugugcagaagauccaaug cucccagccauauuguucucaccgaaagugccugcguauauucauccaaggaaguaucucguggaaacaccaccgguag acgagacuccggagccaucggcagagaaccaauccacagaggggacaccugaacaaccaccacuuauaaccgaggaugag accaggacuagaacgccugagccgaucaucaucgaagaggaagaagaggauagcauaaguuugcugucagauggcccgac ccaccaggugcugcaagucgaggcagacauucacgggccgcccucuguaucuagcucauccugguccauuccucaugcau ccgacuuugaugugacaguuuauccauacuugacacccuggagggagcuagcgugaccagcggggcaacgucagccgag acuaacucuuacuucgcaaagaguauggaguuucuggcgcgaccggugccugcgccucgaacaguauucaggaacccucc acaucccgcuccgcgcacaagaacaccgucacuugcacccagcagggccugcucgagaaccagccuaguuuccaccccgc caggcgugaauagggugaucacuagagaggagcucgaggcgcuuaccccgucacgcacuccuagcaggucggucucgaga accagccuggucuccaacccgccaggcguaaauagggugauuacaagagaggaguuugaggcguucuagcacaacaaca augacgguuugaugcgggugcauacaucuuuuccuccgacaccggucaagggcauuuacaacaaaaaucaguaaggcaaa cggugcuauccgaagugguguuggagaggaccgaauuggagauuucguaugcccgcgccucgaccaagaaaaagaagaa uuacuacgcaagaaauuacaguuaaaucccacaccugcuaacagaagcagauaccaguccaggaaggugagaacaugaa agccauaacagcuagacguauucgcaaggccuagggcauuauuugaaggcagaaggaaaaguggagugcuaccgaaccc ugcaucuguccuuuguauucaucuagugugaaccgugccuuuucaagcccaaggucgcaguggaagccuguaacgcca uguugaaagagaacuuccgacuguggcuucuuacuguauuauuccagaguacgaugccuauuuggacauggᴜugacgga gcuucaugcugcuuagacacugccaguuuugccugcaaagcugcgcagcuuuccaagaaacacuccuauuuggaacc cacaauacgaucggcagugccuucagcgauccagaacacgcuccagaacguccuggcagcugccacaaaagaaauugca augucacgcaaaugagagaauugcccguauuggauucggcggccuuuaaugᴜggaaugcuucaagaaauaugcguguaau aaugaauauugggaaacguuuaaagaaaaccccaucaggcuuacugaagaaaacgugguaaaauuacauuaccaaauuaaa aggaccaaaagcugcugcucuuuuugcgaagacacauaauuugaauaugᴜugcaggacuaccaauggacagguuuguaa uggacuuaaagagacgugaaagugacuccaggaacaaaacauacugaagaacggcccaagguacaggugauccaggcu gccgauccgcuagcaacagcguaucugugcggaauccaccgagagcugguuaggagauuaaaugcgguccugcuuccgaa cauucauacacuguuugauaugucggcugaagacuuugacgcuauuauagccgagcacuuccagccugggggauugugᴜuc -continued uggaaacugacaucgcgucguuugauaaaagugaggacgacgccauggcucugaccgcguuaaugauucuggaagacuua ggugugga cgcagagcuguugacgcugauugaggcggcuuucggcgaaauuucaucaauacauuugcccacuaaaacuaa auuuaaauucggagccaugaugaaaucuggaauguuccucacacuguuugugaacacagucauuaacauuguaaucgcaa gcagaguguugagagaacggcuaaccggaucaccaugugcagcauucauggagaugacaauaucgugaaaggagucaaa ucggacaaauuaauggcagacaggugcgccaccugguugaauauggaagucaagauuauagaugcuguggugggcgagaa agcgccuuauuucuguggagggunuauuuugugugacuccgugaccggcacagcgugccguguggcagaccccuaaaaa ggcuguuuaagcuuggcaaaccucuggcagcagacgaugaacaugaugaugacaggagaagggcauugcaugaagaguca acacgcuggaaccgaguggguauucuuucagagcugugcaaggcaguagaaucaagguaugaaaccguaggaacuuccau cauaguuauggccaugacuacucuagcuagcaguguuaaaucauucagcuaccugagaggggccccuauaacucucuacg gcuaaccugaauggacuacgacauagucuaguccgccgccacc*AUGUUUCUGCUCACAACCAAACGCACUAUG**UUUGUUU*

*UCCUCGUGCUGCUCCCUUUGGUAAGUUCU*CAGUGUGUAAACCUGagaACACGAACCCAGUUGCCUCCAGCUUAUACCAAC

UCAUUUACUCGCGGAGUAUAUUAUCCCGAUAAGGUCUUUAGAAGUAGCGUGUUGCACUCUACACAGGAUCUGUUCUUGCC

CUUCUUUAGUAACGUUACCUGGUUUCAUGCAAUACAUGUGAGCGGAACAAAUGGAACAAAAGAUUUGACAAUCCAGUGC

UUCCAUUUAAUGAUGGGGUUUACUUUGCCAGUaucGAAAAGUCAAACAUAAUCCGGGGGUGGAUCUUUUGGAACCACUUUG

GACUCUAAGACACAGUCUCUCCUCAUAGUAAACAACGCCACCAAUGUUGUCAUAAAAGUAUGCGAAUUUCAGUUUUGCAA

CGAUCCCUUUCUCgacGUGUAUUACCAUAAGAAUAAUAAAUCCUGGAUGGAGUCUgggGUUUAUAGUAGUGCUAAUAAUU

GCACUUUCGAAUACGUGUCCCAACCAUUCCUCAUGGACCUUGAGGGCAAACAGGGGAAUUUUAAAAACUUGCGCGAAUUU

GUCUUUAAGAAUAUCGACGGAUACUUUAAGAUCUAUAGUAAACACACUCCUAUCAACCUCGUUCGGGAUCUUCCCCAAGG

CUUUUCUGCUCUCGAACCCCUCGUAGACUUGCCAAUUGGGAUAAAUAUCACUCGCUUUCAAACUUUGCUUGCCCUCCACA

GGAGCUACCUGACACCCGGCGACUCUUCUUCUGGUuugACCGCCGGCGCCGCUGCCUAUUAUGUUGGUUACCUUCAGCCA

CGAACAUUCUUGCUCAAGUAUAACGAGAAUGGCACCAUUACCGACGCCGUCGAUUGUGCAUUGGAUCCCUUGUCUGAAAC

AAAAUGUACCUUGAAGUCCUUUACCGUAGAGAAAGGCAUAUACCAGACUUCCAACUUCCGAGUUCAGCCUACAGAAUCCA

UCGUACGAUUUCCCAACAUCACAAACCUCUGCCCUUUCGGUGAAGUAUUUAAUGCUACACGCUUCGCUUCAGUCUAUGCC

UGGAAUAGGAAGCGCAUAUCAAAUUGCGUGGCCGAUUAUUCAGUCCUCUAUAAUAGCGCAUCCUUCAGUACUUUCAAGUG

CUACGGCGUUUCCCCCACCAAACUCAAUGAUCUUUGCUUCACCAACGUCUAUGCUGACAGUUUUGUCAUACGAGGCGACG

AAGUACGCCAGAUUGCCCCCGGGCAGACAGGUaauAUUGCUGAUUAUAAUUAUAAACUCCCAGAUGACUUUACUGGAUGC GUCAUAGCCUGGAAUUCCAACAAUCUAGAUUCCAAGGUUGGUGGGAAUUAUAAUUACcguUAUCGACUGUUCAGAAAGAG UAACUUGAAACCAUUUGAGAGAGACAUAUCCACCGAGAUUUACCAGGCAGGCAGUaagCCUUGUAACGGCGUUGAGGGAU

UUAACUGCUAUUUUCCUUUGCAAUCCUAUGGCUUUCAACCAACAAACGGGGUUGGCUAUCAACCCUAUCGAGUGGUUGUC

CUCAGCUUUGAACUUUUGCACGCUCCCGCCACAGUCUGCGGACCAAAAAAGAGUACAAAUCUUGUCAAGAAUAAGUGCGU

AAAUUUCAAUUUCAAUGGCCUUACAGGAACAGGCGUGCUGACUGAGUCAAACAAGaauUUCCUGCCAUUUCAGCAGUUUG

GGCGGGAUAUAGCAGACACAACUGACGCUGUACGCGAUCCUCAGACUUUGGAGAUCUUGGACAUCACUCCCUGUUCUUUC

GGAGGGGUAUCUGUCAUCACCCCCGGAACUAAUACAUCAAAUCAGGUCGCUGUGUUGUACCAAgguGUCAACUGCACAGA

AGUCCCCGUUGCUAUACACGCAGACCAGCUCACCCCCACAUGGCGGGUGUACUCAACUGGCUCAAACGUAUUCCAGACCA

GAGCUGGGUGCUUGAUCGGUGCUGAACACGUGAACAAUAGCUAUGAAUGCGAUAUUCCCAUCGGUGCCGGGAUCUGCGCU

AGCUAUCAGACACAGACCAAUUCCcgcAGGCGGGCUCGCUCUGUAGCAUCCCAGUCUAUUAUUGCCUACACUAUGUCAUU

GGGCGCCAGAAUAGCGUCGCAUAUUCAAAUAAUUCUAUUGCAAUACCCACCAACUUCACAAUCUCCGUAACUACAGAAAA

UACUUCCAGUUUCCAUGACAAAGACAUCAGUGGAUUGUACAAUGUAUAUAUGCGGAGAUUCCACAGAAUGUUCAAAUUUG

CUCUUGCAGUACGGCUCCUUCUGCACCCAGCUCAACAGGGCACUACAGGUAUUGCUGUCGAACAGGACAAGAACACACA

AGAAGUCUUCGCCCAAGUCAAACAGAUAUACAAAACUCCUCCCAUAAAGGAUUUUGGCGGCUUCAACUUUAGUCAGAUCC

-continued

UCCCAGACCCUUCAAAACCAUCUAAACGAUCAUUAUUGAAGAUCUGCUGUUCAACAAGGUCACUCUUGCCGAUGCUGGA

UUCAUUAAGCAAUACGGUGACUGCCUUGGUGAUAUUGCUGCCCGAGAUCUGAUCUGUGCCCAGAAAUUCAACGGGCUCAC

UGUACUCCCUCCACUGCUCACAGACGAAAUGAUUGCACAGUACACAAGUGCCCUGUUGGCAGGCACAAUCACUAGCGGCU

GGACCUUUGGCGCAGGUGCAGCACUCCAAAUACCUUUUGCCAUGCAGAUGGCCUAUCGGUUUAAUGGGAUAGGCGUGACU

CAAAAUGUCCUCUACGAAAACCAAAAGUUGAUAGCUAACCAAUUCAAUUCAGCAAUCGGGAAGAUACAGGAUUCACUGUC

UAGUACUGCUAGUGCCCUUGGUAAGCUGCAGaacGUUGUCAACCAGAAUGCUCAAGCUCUGAAUACAUUGGUUAAGCAGC UCUCUAGUAAUUUUGGGGCCAUCUCUUCAGUACUUAAUGAUAUUUUGAGCCGAUUGGACccaccuGAAGCUGAAGUACAG

AUCGACAGGCUGAUAACAGGCCGGCUCCAAUCCCUCCAAACAUACGUGACACAACAACUCUACGCGCAGCCGAAAUCCG

AGCCAGCGCUAACCUGGCAGCUACCAAGAUGUCAGAAUGCGUUCUGGGCCAGAGUAAACGCGUAGAUUUCUGCGGGAAAG

GGUACCACCUGAUGUCCUUUCCACAAUCUGCACCUCACGGGGUCGUCUUUUUGCAUGUAACAUACGUACCCGCACAAGAG

AAGAAUUUUACUACCGCUCCUGCCAUCUGUCAUGACGGGAAAGCUCAUUUUCCUCGCGAAGGUGUGUUUGUAUCUAAUGG

UACACAUGGUUUGUCACACAGCGGAAUUUCUAUGAACCCCAGAUCAUUACAACUGACAACACUUUUGUUUCCGGGAAUU

GUGACGUGGUCAUAGGAAUCGUAAAUAACACUGUAUAUGAUCCCCUCCAACCAGAGCUGGACUCUUUUAAAGAAGAACUG

GAUAAAUAUUUCAAGAACCACACAAGUCCCGACGUGGACCUUGGGGACAUAAGUGGUAUUAACGCAUCUGUGGUUAACAU

UCAAAAGGAAAUCGACAGACUCAACGAGGUGGCCAAAAACCUGAACGAAAGCUUGAUAGAUCUCCAGGAGUUGGGCAAGU

AUGAACAGUACAUUAAAUGGCCAUGGUACAUAUGGCUUGGCUUUAUCGCUGGCCUUAUCGCCAUCGUAAUGGUUACAAUC

AUGCUGUGCUGCAUGACCUCCUGCUGUUCUUGUUUGAAAGGGUGUUGUUCUUGUGGUAGUUGUUGCAAGUUUGACGAAGA

UGAUUCCGAACCUGUUCUUAAGGGGGUAAAGCUUCACUAUACAUGAuaaccgcggugucaaaaaccgcguggacgugguu ccaaccagaaacauaauugaauacagcagcaauuggcaagcugcuuacaugaacucgcggcgauuggcaugccgccuua aaauuuuuauuuuauuuuuucuuuucuuuuccgaaucggauuugguuuuaauauuucaaaaaaaaaaaaaaaaaaaaa aaaaaaaaaaaaaaaaaaaaaa SEQ ID NO: 31- Full-length VEEV+ Omicron-B.1.1.529 Antigen Encoding RNA Sequence
auaggcggcgcaugagagaagcccagaccaauuaccucccaaaauggagaaaguucacguugacaucgaggaaga cagcccauuccucagagcuuugcagcggagcuucccgcaguuugagguagaagccaagcaggucacugauaaugac caugcuaaugccagagcguuuucgcaucuggcuucaaaaacugaucgaaacggagguggacccauccgacacgaucc uugacauuggaagugcgcccgcccgcagaauguauucuaagcacaaguaucauuguaucuguccgaugagaugugc ggaagauccggacagauuguauaaguaugcaacuaagcugaagaaaaacuguaaggaaauaacugauaaggaauug gacaagaaaaugaaggagcuggccgccgucaugagcgacccugaccuggaaacugagacuauguggccuccacgacg acgagucgugucgcuacgaagggcaagucgcuguuuaccaggauguauacgcgguugacggaccgacaagucucua ucaccaagccaauaaggggaguuagagucgccuacuggauaggcuuugacaccaccccuuuuaugguuuaagaacuug gcuggagcauauccaucauacucuaccaacuggggccgacgaaaccguguuaacggcucguaacauaggccuaugca gcucugacguuauggagcggucacguagagggauguccauucuuagaaagaaguauuugaaaccauccaacaaugu ucuauucucuguuggcucgaccaucuaccacgagaagagggacuuacugaggagcuggcaccugccgucuguauuu cacuuacguggcaagcaaaauuacacaugucggugugagacuauaguuaguugcgacggguacgucguuaaaagaa uagcuaucaguccaggccuguauggaagccuucaggcuaugcugcuacgaugcaccgcgagggauucuugugcug caaagugacagacacauugaacggggagagggucucuuuuccccgugugcacguaugugccagcuacauugugugac caaaugacuggcauacuggcaacagaugucagugcggacgacgcgcaaaaacugcugguugggcucaaccagcgua uagucgucaacggucgcacccagagaaacaccaauaccaugaaaaauuaccuuuugcccguaguggcccaggcauu ugcuagguggggcaaaggaauauaaggaagaucaagaagaugaaaggccacuaggacuacgagauagacaguuaguc auggggguguuguugggcuuuuagaaggcacaagauaacaucuauuuauaagcgcccggauacccaaaccaucauca aagugaacagcgauuuccacucauucgugcugcccaggauaggcaguaacacauuggagaucgggcugagaacaag -continued aaucaggaaaauguuagaggagcacaaggagccgucaccucucauuaccgccgaggacguacaagaagcuaagugc gcagccgaugaggcuaaggaggugcgugaagccgaggaguugcgcgcagcucuaccaccuuuggcagcugauguug aggagcccacucuggaggcagacgucgacuugauguuacaagaggcuggggccggcucaguggagacaccucgugg cuugauaaagguuaccagcuacgauggcgaggacaagaucggcucuuacgcugugcuuucuccgcaggcuguacuc aagagugaaaaauuaucuugcauccacccucucgcugaacaagucauagugauaacacacucuggccgaaaagggc guuaugccguggaaccauaccaugguaaaguaguggugccagagggacaugcaauacccguccaggacuuucaagc ucugagugaaagugccaccauuguguacaacgaacgugaguucguaaacagguaccugcaccauauugccacacau ggaggagcgcugaacacugaugaagaauauuacaaaacugucaagcccagcgagcacgacggcgaauaccuguacg acaucgacaggaaacagugcgucaagaagaacuagucacugggcuagggcucacaggcgagcugguggauccucc cuuccaugaauucgccuacgagagucugaaacacgaccagccgcuccuuaccaaguaccaaccauaggggguguau ggcgugccaggaucaggcaagucuggcaucauuaaaagcgcagucaccaaaaaagaucuaguggugagcgccaaga aagaaaacugugcagaaauuauaagggacgucaagaaaaugaaagggcuggacgucaaugccagaacuguggacuc agugcucuugaauggaugcaaacaccccguagagacccguauauugacgaagcuuuugcuugucaugcagguacu cucagagcgcucauagccauuauaagaccuaaaaaggcagugcucugcggggaucccaaacagugcgguuuuuuua acaugaugugccugaaagugcauuuuaaccacgagauuugcacacaagucuuccacaaaagcaucucucgccguug cacuaaaucugugacuucggucgucucaaccuuguuuuacgacaaaaaaugagaacgacgaauccgaaagagacu aagauugugauugacacuacggcaguaccaaaccuaagcaggacgaucucauucucacuuguuucagagggugg ugaagcaguugcaaauagauuacaaaggcaacgaaauaaugacggcagcugccucucaagggcugacccguaaagg uguguaugccguucgguacaaggugaaugaaaauccucuguacgcacccaccucagaacaugugaacguccuacug acccgcacggaggaccgcaucgugugaaaacacuagccggcgacccauggauaaaaacacugacugccaaguacc cugggaauuucacugccacgauagaggaguggcaagcagagcaugaugccaucaugaggcacaucuuggagagacc ggacccuaccgacgucuuccagaauaaggcaaacgugugunuggccaaggcuuuagugccggugcugaagaccgcu ggcauagacaugaccacugaacaauggaacacuguggauuauuuugaaacggacaaagcucacucagcagagauag uauugaaccaacuaugcgugagguucuuggacucgaucuggacuccggucuauuuucugcacccacuguuccguu auccauuaggaauaaucacugggauaacuccccgucgccuaacaugucgggcugaauaaagaaguggucccgucag cucucucgcagguacccacaacugccucgggcaguugccacuggaagagucuaugacaugaacacugguacacugc gcaauuaugauccgcgcauaaaccuaguaccuguaaacagaagacugccucaugcuuuaguccuccaccauaauga acacccacagagugacuuucuucauucgucagcaaauugaagggcagaacuguccugguggucggggaaaaguug uccgucccaggcaaaauguugacugguugucagaccggccugaggcuaccuucagagcucggcuggauuuaggca ucccaggugaugugcccaaauaugacauaauauuuguuaaugugaggaccccauauaaauaccaucacuaucagca gugugaagaccaugccauuaagcuuagcauguugaccaagaaagcuugucugcaucugaaucccggcggaaccugu gucagcauagguuauggulacgcugacagggccagcgaaagcaucauggugcuauagcgcggcaguucaaguuuu cccggguaugcaaaccgaaauccucacuugaagagacggaaguucuguuuguauucauugggguacgaucgcaaggc ccguacgcacaauccuuacaagcuuucaucaaccuugaccaacauuuauacagguucagacuccacgaagccgga ugugcacccucauaucaugguggugcgaggggauauugccacggccaccgaaggagugauuauaaaugcugcuaaca gcaaaggacaaccuggcggaggggugugcggagcgcuguauaagaaauucccggaaagcuucgauuuacagccgau cgaaguaggaaaagcgcgacuggucaaaggugcagcuaaacauaucauucaugccguaggaccaaacuucaacaaa guuucggagguugaaggugacaaacaguuggcagaggcuuaugaguccaucgcuaagauugucaacgauaacaauu acaagucaguagcgauccacuguuguccaccggcaucuuuccgggaacaaagaucgacuaacccaaucauugaa ccauuugcugacagcuuuagacaccacugaugcagaugauagccauauacugcagggacaagaaaugggaaaugacu cucaaggaagcaguggcuaggagagaagcaguggaggagauaugcauauccgacgacucuucagugacagaaccug -continued augcagagcugguganggugcauccgaagaguucuuuggcuggaaggaagggcuacagcacaagcgauggcaaaac uuucucauauuuggaagggaccaaguuucaccaggcggccaaggauauagcagaaauuaaugccauguggcccguu gcaacggaggccaaugagcagguaugcauguauauccucggagaaagcaugagcaguauuaggucgaaaugccccg ucgaagagucggaagccuccacaccaccuagcacgcugccuugcuugugcauccaugccaugacuccagaaagagu acagcgccuaaaagccucacguccagaacaaauuacguguugcucauccuuuccaugccgaaguauagaaucacu gguguugcagaagauccaaugcucccagccuauauuguucucaccgaaagugccugcguauauucauccaaggaagu aucucguggaaacaccaccgguagacgagacuccggagccaucggcagagaaccaauccacagaggggacaccuga acaaccaccuuauaaccgaggaugagaccaggacuagaacgccugagccgaucaucaucgaagaggaagaagag gauagcauaaguuugcugucagauggcccgacccaccaggugcugcaagucgaggcagacauucacgggccgcccu cuguaucuagcucauccuggaucauuccucaugcauccgacuuugaugguggacaguuuauccauacuugacacccu ggagggagcuagcgugaccagcggggcaacgucagccgagacuaacucuuacuucgcaaagaguauggaguuucug gcgcgaccggugccugcgccucgaacaguauucaggaacccuccacaucccgcuccgcgcacaagaacaccgucac uugcacccagcagggccugcucgagaaccagccuaguuuccaccccgccaggcgugaauagggugaucacuagaga ggagcucgaggcgcuuaccccgucacgcacuccuagcaggucggucucgagaaccagccuggucuccaacccgcca ggcguaaauagggugauuacaagagaggaguuugaggcguucguagcacaacaacaaugacgguuugaugcggug cauacaucuuuccuccgacaccggucaagggcauuuacaacaaaaaucaguaaggcaaacggugcuauccgaagu gguguuggagaggaccgaauuggagauuucguaugccccgcgccucgaccaagaaaaagaagaauuacuacgcaag aaauuacaguuaaauccacaccugcuaacagaagcagauaccaguccaggaaggugugagaacaugaaagccauaa cagcuagacguauucugcaaggccuaggggcauuauuugaaggcagaaggaaaaguggagugcuaccgaacccugca uccuguuccuuuguauucaucuagugugaaccgugccuuuucaagccccaaggucgcaguggaagccuguaacgcc auguugaaagagaacuuuccgacugguggcuucuuacuguauuauuccagaguacgaugccuauuuggacaugguug acggagcuucaugcugcuuagacacugccaguuuugcccugcaaagcugcgcagcuuuccaaagaaacacuccua uuuggaacccacaauacgaucggcagugccuucagcgauccagaacacgcuccagaacguccuggcagcugccaca aaaagaaauugcaaugucacgcaaaugagagaauugcccguauuggauucggcggccuuuaauguggaaugcuuca agaaauaugcguguaauaaugaauauugggaaacguuuaaagaaaaccccaucaggcuuacugaagaaaacuggu aaauuacauuaccaaauuaaaaggaccaaaagcugcugcucuuuuugcgaagacacauaauuugaauauguugcag gacauaccaauggacagguuuguaauggacuuaaagagagacgugaaagugacuccaggaacaaaacauacugaag aacggcccaagguacaggugauccaggcugccgauccgcuagcaacagcguaucugugcggaauccaccgagagcu gguuaggagauuaaaugcgguccugcuuccgaacauucauacacuguuugauaugucggcugaagacuuugacgcu auuauagccgagcacuuccagccugggauuguguucuggaaacugacaucgcgucguuugauaaaagugaggacg acgccauggcucugaccgcguuaaugauucuggaagacuuaggugguggacgcagagcuguugacgcugauugaggc ggcuuucggcgaaauuucaucaauacauuugcccacuaaaacuaaauuuaaauucggagccaugaugaaaucgga auguccucacacuguuugugaacacagucauuaacauuguaaucgcaagcagaguguugagagaacggcuaaccg gaucaccaugugcagcauucauuggagaugacaauaucgugaaaggagucaaaucggacaaauuaauggcagacag gugcgccaccgguugaauauggaagucaagauuauagaugcugguggggcgagaaagcgccuuauuucuguugga ggguuauuuugugugacuccgugaccggcacagcgugccgugugggcagaccccuaaaaaggcuguuuaagcuug gcaaaccucuggcagcagacgaugaacaugaugaugacaggagaagggcauugcaugaagagucaacacgcuggaa ccgagugggauucuuucagagcugugcaaggcaguagaaucaagguaugaaaccguaggaacuuccaucauaguu auggccaugacuacucuagcuagcaguguaaaucauucagcuaccugagagggccccuauaacucucuacggcu aaccugaauggacuacgacauagucuaguccgcCGCCACCAUGUUUCUGUUGACGACCAAGCGAACGAUGUUCGUU -continued

UUCUUGGUGCUUUUGCCACUUGUCAGUUCCCAGUGCGUCAAUCUGACGACACGAACACAGCUGCCUCCUGCGUACA

CUAACAGUUUUACGCGAGGAGUGUAUUACCCUGACAAAGUUUUCCGCUCUAGUGUCCUCCAUAGCACACAGGACUU

GUUUCUCCCCUUCUUUUCCAACGUUACGUGGUUCCAUGUGAUUAGUGGAACUAACGGUACUAAAAGAUUCGACAAU

CCAGUAUUGCCUUUCAACGAUGGGGUCUAUUUCGCGUCCAUCGAGAAAUCAAAUAUCAUUCGCGGUUGGAUUUUUG

GAACGACACUCGAUUCAAAGACGCAAUCCCUCCUUAUUGUCAACAACGCCACUAACGUAGUCAUUAAGGUUUGUGA

GUUCCAGUUUUGUAAUGAUCCCUUUUUUGACCACAAGAAUAACAAGAGCUGGAUGGAAAGCGAGUUCAGAGUGUAU

AGCUCUGCAAACAACUGUACUUUUGAAUACGUGAGUCAACCUUUCCUUAUGGACCUUGAAGGUAAACAGGGUAACU

UUAAGAAUUUGCGCGAAUUUGUUUUCAAAAACAUUGAUGGUUACUUUAAAAUCUAUAGUAAGCACACUCCUAUCAU

UGUAAGAGAGCCGGAGGACCUUCCACAGGGUUUUAGUGCGCUCGAGCCCCUCGUUGACCUGCCCAUUGGGAUCAAC

AUAACUCGAUUCCAAACAUUGCUCGCCCUUCAUCGGUCCUAUCUGACUCCCGGUGACUCCUCUAGCGGAUGGACGG

CAGGUGCCGCCGCAUACUACGUGGGGUACCUUCAACCUCGGACAUUUUUGUUGAAAUACAAUGAGAAUGGCACUAU

AACUGACGCGGUUGAUUGCGCGCUCGACCCAUUGUCCGAAACUAAGUGUACUUUGAAGUCAUUUACAGUGGAGAAA

GGAAUAUAUCAGACUAGCAAUUUUCGGGUACAGCCCACGGAGUCUAUCGUACGGUUUCCUAACAUCACGAAUCUGU

GCCCUUUUGAUGAGGUCUUUAAUGCAACACGGUUCGCCUCCGUCUAUGCGUGGAAUAGAAAGCGCAUCUCAAAUUG

UGUAGCUGAUUAUUCCGUACUUUACAACUUGGCCCCGUUCUUCACAUUUAAGUGCUACGGUGUAAGCCCUACUAAA

CUGAACGAUUUGUGUUUCACCAACGUCUAUGCAGAUAGCUUUGUUAUUCGAGGCGAUGAGGUACGCCAGAUUGCGC

CUGGUCAAACGGGUAAUAUCGCCGACUACAAUUAUAAAUUGCCAGACGAUUUUACUGGUUGUGUCAUCGCUUGGAA

UAGUAAUAAGUUGGACAGUAAGGUAUCCGGCAAUUACAACUAUCUCUACCGAUUGUUCCGGAAGUCUAACCUCAAG

CCGUUUGAAAGAGACAUAUCCACUGAGAUAUACCAAGCAGGCAAUAAACCAUGCAACGGAGUUGCUGGUUUCAACU

GCUAUUUCCCGUUGCGGUCUUAUUCCUUCAGACCUACUUACGGAGUCGGACACCAACCCUACAGGGUCGUCGUUUU

GAGUUUUGAAUUGUUGCAUGCUCCAGCAACCGUGUGUGGACCUAAAAAGUCCACGAAUCUCGUGAAGAAUAAGUGC

GUAAACUUCAAUUUCAACGGUCUGAAAGGGACUGGUGUAUUGACAGAAAGCAACAAGAAGUUUCUGCCAUUCCAGC

AAUUUGGUAGGGAUAUAGCGGAUACAACUGAUGCCGUUCGGGAUCCUCAAACAUUGGAGAUCUUGGACAUCACACC

GUGUUCUUUUGGGGGUGUCUCCGUUAUCACACCGGGUACAAAUACGAGCAAUCAGGUUGCGGUCCUUUACCAAGGC

GUUAAUUGUACCGAGGUUCCAGUAGCAAUACACGCGGAUCAACUCACGCCCACAUGGAGGGUUUACAGUACAGGCA

GUAAUGUUUUCCAAACGAGAGCGGGAUGCCUCAUCGGGGCAGAAUACGUAAAUAAUUCUUACGAAUGCGACAUCCC

UAUUGGCGCAGGAAUUUGCGCAAGUUACCAAACCCAGACCAAGUCUCAUAGGCGGGCGCGGUCUGUUGCAAGCCAA

UCUAUAAUAGCGUACACUAUGUCCCUCGGCGCGGAGAACAGUGUCGCAUAUUCCAACAACUCUAUUGCGAUACCUA

CUAAUUUCACUAUUAGCGUCACAACUGAGAUCCUUCCCGUCAGUAUGACCAAAACGUCUGUCGACUGUACUAUGUA

UAUUUGCGGCGACAGUACCGAAUGCUCUAAUCUUUUGUUGCAGUAUGGUUCUUUUUGCACGCAACUUAAGAGAGCU

UUGACGGGGAUAGCUGUGGAACAAGAUAAAAACACACAGGAGGUAUUUGCACAAGUGAAACAGAUCUAUAAAACUC

CACCGAUCAAGUACUUUGGCGGCUUUAACUUCUCCCAGAUCUUGCCCGACCCGUCUAAACCAAGUAAACGGAGUUU

UAUAGAGGACCUUCUCUUCAAUAAGGUAACAUUGGCAGACGCCGGCUUCAUUAAACAAUACGGAGAUUGCCUUGGA

GACAUCGCUGCGCGACUUGAUCUGCGCACAAAAAUUUAAAGGCUUGACGGUCCUCCCUCCUUUGCUCACAGACG

AGAUGAUAGCACAAUACACUUCCGCACUGCUUGCUGGAACCAUCACCUCUGGUUGGACAUUCGGUGCGGGAGCGGC

UUUGCAGAUUCCGUUUGCGAUGCAAAUGGCUUAUCGGUUUAACGGCAUUGGAGUAACACAGAAUGUGCUCUACGAG

AAUCAAAAGCUUAUUGCGAAUCAAUUCAACUCUGCGAUUGGCAAAAUUCAAGAUUCAUUGAGUAGCACCGCCAGUG

CUCUUGGCAAGCUUCAGGAUGUCGUAAACCACAAUGCACAAGCUCUGAAUACACUGGUUAAACAAUUGUCCAGUAA

AUUUGGGGCAAUCUCUUCAGUGCUGAACGACAUUUUCUCAAGAUUGGAUCCACCCGAAGCGGAGGUACAGAUUGAC

CGCCUGAUAACCGGAGGUUGCAAAGCCUUCAGACUUUAUGUUACACAACAGUUGAUUCGGGCAGCAGAGAUAAGAG

CCUCAGCAAACCUCGCAGCUACGAAGAUGUCAGAGUGUGUCCUUGGGCAAUCUAAGCGGGUAGAUUUCUGCGGCAA

```
AGGAUAUCAUUUGAUGAGCUUUCCCCAAUCAGCCCCACAUGGAGUAGUUUUCUUCAUGUCACUUACGUUCCGGCG
CAGGAAAAGAACUUCACCACAGCGCCAGCCAUUUGUCAUGAUGGGAAGGCGCAUUUCCCAAGAGAAGGUGUUUUCG
UGUCUAACGGUACCCACUGGUUCGUUACGCAGCGGAAUUUCUACGAACCACAGAUCAUCACUACCGACAACACGUU
UGUCUCUGGAAAUUGUGACGUUGUCAUAGGGAUAGUGAACAAUACAGUAUAUGAUCCACUUCAGCCUGAACUUGAC
UCUUUUAAGGAGGAGCUGGACAAAUAUUUCAAAAAUCAUACAAGCCCGGACGUCGAUCUUGGAGAUAUUUCAGGUA
UCAACGCAAGUGUCGUAAAUAUUCAGAAGGAGAUCGAUCGAUUGAACGAGGUUGCAAAAAACCUUAAUGAGAGCCU
UAUAGAUCUUCAAGAGCUGGGGAAGUAUGAACAAUAUAUCAAGUGGCCUUGGUACAUUUGGCUCGGGUUCAUUGCC
GGACUUAUCGCGAUCGUAAAUGGUAACAAUCAUGCUCUGCUGUAUGACUUCUUGCUGUUCAUGCCUCAAAGGUUGUU
GCUCCUGUGGGUCUUGCUGUAAAUUUGACGAGGAUGAUUCUGAACCAGUGCUUAAAGGCGUGAAGCUCCACUAUAC
CUGAuaaccgcggugucaaaaaccgcguggacguggUUaacaucccugcugggaggaucagccguaauuauuauaa
uuggcuuggugcuggcuacuauuguggccauguacgugcugaccaaccagaaacauaauugaaaacagcagcaauu
ggcaagcugcuuacauagaacucgcggcgauuggcaugccgccuuaaaauuuuuauuuuauuuuucuuuucuuuu
ccgaaucggauuuuguuuuaauauuucaaaaaaaaaaaaaaaaaaaaaaaaaaaaaaaaaaaaaaaaa SEQ ID NO: 32- Vector Backbone RNA Sequence 1
auaggcggcgcaugagagaagcccagaccaauuaccuacccaaaauggagaaaguucacguugacaucgaggaagacag
cccauuccucagagcuuugcagcggagcuucccgcaguuugagguagaagccaagcaggucacugauaaugaccaugcu
aaugccagagcguuucgcaucuggcuucaaaacugaucgaaacggagguggacccauccgacacgauccuugacauug
gaagugcgcccgcccgcagaauguauucuaagcacaaguaucauuguaucugucccgaugagaugugcggaagauccgga
cagauuguauaaguaugcaacuaagcugaagaaaaacuguaaggaaauaacugauaaggaauuggacaagaaaaugaag
gagcuggccgccgucaugagcgacccugaccuggaaacugagacuaugugccuccacgacgacgagucgugucgcuacg
aagggcaagucgcuguuuaccaggauguauacgcgguugacggaccgacaagucucuaucaccaagccaauaagggagu
uagagucgccuacuggauaggcuuugacaccacccccuuuuauguuuaagaacuuggcuggagcauauccaucauacucu
accaacugggccgacgaaaccguguuaacggcucguaacauaggccuaugcagcucugacguuauggagcggucacgua
gagggauguccauucuuagaaagaaguauuugaaaccauccaacaauguucuauucucuguuggcucgaccaucuacca
cgagaagagggacuuacugaggagcuggcaccugccgucuguauuucacuuacguggcaagcaaaauuacacaugucgg
ugugagacuauaguuaguugcgacggguacgucguuaaaagaauagcuaucaguccaggccuguaugggaagccuucag
gcuaugcugcuacgaugcaccgcgagggauucuugugcugcaaagugacagacacauugaacggggagagggucucuuu
ucccgugugcacguaugugccagcuacauugugugaccaaaugacuggcauacuggcaacagaugucagugcggacgac
gcgcaaaaacugcugguuggcucaaccagcguauagucgucaacgucgcacccagagaaacaccaauaccaugaaaa
auuaccuuugcccguagugggcccaggcauuugcuagguggcaaaggaauauaaggaagaucaagaagaugaaaggcc
acuaggacuacgagauagacaguuagucaugggguguuguuggguuuuagaaggcacaagauaacaucuauuuauaag
cgcccggauacccaaaccaucaucaaagugaacagcgauuuccacucauucgugcugcccaggauaggcaguaacacau
uggagaucgggcugagaacaagaaucaggaaaauguuagaggagcacaaggagccgucaccucucauuaccgccgagga
cguacaagaagcuaagugcgcagccgaugaggcuaaggaggugcgugaagccgaggaguugcgcgcagcucuaccaccu
uuggcagcugauguugaggagcccacucuggaggcagacgucgacuugauguuucaagaggcuggggccggcucagugg
agacaccucguggcuugauaaagguuaccagcuacgauggcgaggacaagaucggcucuuacgcuguguguuucuccgca
ggcuguacucaagagugaaaauuaucuugcauccaccucucgcugaacaagucauagugauaacacacucuggccga
aaagggcguauugccguggaaccauaccauggaaaguaguggugccagagggacaugcaauacccguccaggacuuuc
aagcucugagugaaagugccaccauugugagcaacgaacgugaguucguaaacagguaccugcaccauauugccacaca
uggaggagcgcugaacacgaugaagaauauuacaaaaacugucaagcccagcgagcacgacggcgaauaccuguacgac
aucgacaggaaacaguggggucaagaaagaacuaguagaagcgaugcaaacuaguagaacuaguacaaccgaucucucuucc
``` augaauucgccuacgagagucugagaacacgaccagccgcuccuuaccaaguaccaaccauaggggguguauggcgugcc aggaucaggcaagucuggcaucauuaaaagcgcagucaccaaaaaagaucuaguggugagcgccaagaaagaaaacugu gcagaaauuauaagggacgucaagaaaaugaaagggcuggacgucaaugccagaacuguggacucagugucucuugaaug gaugcaaacaccccguagagacccuguauauugacgaagcuuuugcuugucaugcagguacucucagagcgcucauagc cauuauaagaccuaaaaaggcagugcucugcggggaucccaaacagugcgguuuuuuaacaugaugugccugaaagug cauuuuaaccacgagauuugcacacaagucuuccacaaaagcaucucucgccguugcacuaaaucgugacuucggucg ucucaaccuuguuuacgacaaaaaaaugagaacgacgaauccgaaagagacuaagauugugauugacacuaccggcag uaccaaaccuaagcaggacgaucucauucucacuuguuucagagggugggugaagcaguugcaaauagauuacaaaggc aacgaaauaaugacggcagcugccucucaagggcugacccguaaaggugugauugccguucgguacaaggugaaugaaa auccucuguacgcacccaccucagaacaugugaacguccuacugacccgcacggaggaccgcaucgugugaaaacacu agccggcgacccauggauaaaaacacugacugccaaguacccugggaauuucacugccacgauagaggaguggcaagca gagcaugaugccaucaugaggcacaucuuggagagaccggacccuaccgacgucuuccagaauaaggcaaacgugguu gggccaaggcuuuagugccggugcugaagaccgcuggcauagacaugaccacugaacaauggaacacuguggauuauu ugaaacggacaaagcucacucagcagagauaguauugaaccaacuaugcgugagguucuuuggacucgaucggacucc ggucuauuucugcacccacuguuccguuauccauuaggaauaaucacugggauaaucccccgucgccuaacauguacg ggcugaauaaagaaguggccgucagcucucucgcagguacccacaacugccucgggcaguugccacuggaagagucua ugacaugaacacugguacacugcgcaauuaugauccgcgcauaaaccuaguaccuguaaacagaagacugccucaugcu uuaguccuccaccauaaugaacacccacagagugacuuucuucauucgucagcaaauugaagggcagaacuguccugg uggucggggaaaaguugucgucccaggcaaaauugguugacugguugucagaccggccugaggcuaccuucagagcucg gcuggauuuaggcaucccaggugaugugcccaaauaugacauaauauuuguuaaugugaggaccccauauaaauaccau cacuaucagcagugugaagaccaugccauuaagcuuagcauguugaccaagaaagcuugucugcaucugaaucccggcg gaaccugugucagcauagguuauggguuacgcugacagggccagcgaaagcaucauuggugcuauagcgcggcaguucaa guuucccggguaugcaaaccgaaauccucacuugaagagacggaaguucuguuuguauucauugggguacgaucgcaag gcccguacgcacaauccuuacaagcuuucaucaaccuugaccaacauuuauacagguuccagacuccacgaagccggau gugcacccucauaucaugugguggcgagggggauauugccacggccaccgaaggagugauuauaaaugcugcuaacagcaa aggacaaccuggcggaggggugugcggagcgcuguauaagaaauucccggaaagcuucgauuuacagccgaucgaagua ggaaaagcgcgacuggucaaaggugcagcuaaacauaucauucaugccguaggaccaaacuucaacaaaguuucggagg uugaaggugacaaacaguuggcagaggcuuaugagccaucgcuaagauugucaacgauaacaauuacaagucaguagc gauuccacuguuguccaccggcaucuuuuccgggaacaaagaucgacuacccaaucauugaaccauuugcugacagcu uuagacaccacugaugcagauguagccauauacugcagggacaagaaaugggaaaugacucucaaggaagcaguggcua ggagagaagcaguggaggagauaugcauauccgacgacucuucagugacagaaccugaugcagagcuggugagggugca uccgaagaguucuuuggcuggaaggaagggcuacagcacaagcgauggcaaaacuuucucauauuuggaagggaccaag uuucaccaggcggccaaggauauagcagaaauuaaugccauguggcccguugcaacggaggccaaugagcagguaugca uguauauccucggagaaagcaugagcaguauuaggucgaaaugccccgucgaagagucggaagccuccacaccaccuag cacgcugccuugcuugugcauccaugccaugacuccagaaagaguacagcgccuaaaagccucacguccagaacaaauu acuguguгcucauccuuuccauugccgaaguauagaaucacuggugugcagaagauccaaugcucccagccuauauugu ucucaccgaaagugccugcguauauucauccaaggaaguaucucguggaaacaccaccgguagacgagacuccggagcc aucggcagagaaccaauccacagaggggacaccugaacaaccaccacuuauaaccgaggaugagaccaggacuagaacg ccugagccgaucaucaucgaagaggaagaaggauagcauaaguuugcugucagauggcccgacccaccagguggcugc aagucgaggcagacauucacgggccgccccucuguauвcuagcucauccugguccauuccucaugcauccgacuuugaugu -continued ggacaguuuauccauacuugacacccuggagggagcuagcgugaccagcggggcaacgucagccgagacuaacucuuac uucgcaaagaguauggaguuucuggcgcgaccggugccugcgccucgaacaguauucaggaacccuccacaucccgcuc cgcgcacaagaacaccgucacuugcacccagcagggccugcucgagaaccagccuaguuccaccccgccaggcgugaa uagggugaucacuagagaggagcucgaggcgcuuaccccgucacgcacuccuagcaggucggucucgagaaccagccug gucuccaacccgccaggcguaaauagggugauuacaagagaggaguuugaggcguucguagcacaacaacaaugacggu uugaugcgggugcauacaucuuuuccuccgacaccggucaagggcauuuacaacaaaaaucaguaaggcaaacggugcu auccgaaguggguguuggagaggaccgaauuggagauuucguaugccccgcgccucgaccaagaaaaagaagaauuacua cgcaagaaauuacaguuaaaucccacaccugcuaacagaagcagauaccaguccaggaaggguggagaacaugaaagcca uaacagcuagacguauucugcaaggccuagggcauuauuugaaggcagaaggaaaaguggagugcuaccgaacccugca uccuguuccuuuguauucaucuagugugaaccgugccuuuucaagccccaaggucgcaguggaagccuguaacgccaug uugaaagagaacuuccgacugguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaacc cacaauacgaucggcagugccuucagcgauccagaacacgcuccagaacguccuggcagcugccacaaaaagaaauugc aaugucacgcaaaugagagaauugcccguauuggauucggcggccuuuaaugugguuucaagaaauaugcguga auaaugaauauugggaaacguuuaaagaaaaccccaucaggcuuacugaagaaaacguggucaauuucauuaccauauu aaaaggaccaaaagcugcugcucuuuuugcgaagacacauaauugaauauguugcaggcauaccaauggacagguuu guaauggacuuaaagagagacgugaaagugacuccaggaacaaaacaucugaagaacgcccaaggucacaggugaucc aggcugccgauccgcuagcaacagcguaucugugcggaauccaccgagagcugguuaggagauuaaaugcgguccugcu uccgaacauucauacacuguugauaugucgcugaagacuuugacgcuauuauagccgagcacuuccagccuggggau uguguucuggaaacugacaucgcgucguuugauaaaagugaggacgacgccauggcucugaccgcguuaaugauucugg aagacuuaggugguggacgcagagcuguugacgcugauugaggcggcuuucggcgaaauuucaucaauacauuugcccac uaaaacuaaauuuaaauucggagccaugaugaaaucggaauguuccucacacuguuugugaacacagucauuaacauu guaaucgcaagcagagauguugagagaacggcuaaccggaucaccaugugcagcauucauuggagaugacaauaucguga aaggagucaaaucggacaaauuaauggcagacaggugcgccaccugguugaauauggaagucaagauuauagaugcugu gguggcgagaaagcgccuuauuucguggagggguuuauuuugugugacuccgugaccggcacagcgugccguguggca gacccccuaaaaaggcuguuuaagcuuggcaaaccucuggcagcagacgaugaacaugaugaugacaggagaagggcau ugcaugaagagucaacacgcuggaaccgaguggguauucuuucagagcugugcaaggcaguagaaucaagguaugaaac cguaggaacuuccaucauaguuauggccaugacuacucuagcuagcaguguuaaaucauucagcuaccugagaggggcc ccuauaacucucuacgcuaaccugaauggacuacgacauagucuagccgccaagnugauaaccgcggugucaaaaac gccauguacgugcugaccaaccagaaacauaauugaauacagcagcaauuggcaagcugcuuacauagaacucgcggcg auuggcaugccgccuuaaaauuuuauuuuauuuuucuuuucuuuuccgaaucggauuuuguuuuuaauauuucaaaa aaaaaaaaaaaaaaaaaaaaaaaaaaaaaaaaaa SEQ ID NO: 33- Vector Backbone RNA Sequence 2
auaggcggcgcaugagagaagcccagaccaauuaccuacccaaaauggagaaaguucacguugacaucgaggaagacag cccauuccucagagcuuugcagcggagcuucccgcaguuugaggu agaagccaagcaggucacugauaaugaccaugcu aaugccagagcguuuucgcaucuggcuucaaaacugaucgaaacggagguggacccauccgacacgauccuugacauug gaagugcgcccgcccgcagaauguauucuaagcacaaguaucauuguaucuguccgaugagaugugcggaagauccgga cagauuguauaaguaugcaacuaagcugaagaaaaacuguaaggaaauaacugauaaggaauuggacaagaaaaugaag gagcuggccgccgucaugagcgacccugaccuggaaacugagacuaugugccuccacgacgacgagucgugucgcuacg aagggcaagucgcuguuuaccaggauguauacgcgguugacggaccgacaagucucuauaccaagccaauaagggagu uagagucgccuacuggauaggcuuugacaccaccccuuuuauguuuaagaacuuggcuggagcauauccaucauacucu -continued accaacugggccgacgaaaccguguuaacggcucguaacauaggccuaugcagcucugacguuauggagcggucacgua gagggauguccauucuuagaaagaaguauuugaaaccauccaacaauguucuauucucuguuggcucgaccaucuacca cgagaagagggacuuacugaggagcuggcaccugccgucuguauuucacuuacguggcaagcaaaauuacacaugucgg ugugagacuauaguuaguugcgacgggua cgucguuaaaagaauagcuaucaguccaggccuguaugggaagccuucag gcuaugcugcuacgaugcaccgcgagggauucuugugcugcaaagugacagacauugaacggggagagggucucuuu ucccgugugcacguaugugccagcuacauugugugaccaaaugacuggcauacuggcaacagaugucagugcggacgac gcgcaaaaacugcugguugggcucaaccagcguauagucgucaacggucgcacccagagaaacaccaauaccaugaaaa auuaccuuuugcccguaguggcccaggcauuugcuaggugggcaaaggaauauaaggaagaucaagaagaugaaaggcc acuaggacuacgagauagacaguuagucauggggguguuguuugggcuuuuagaaggcacaagauaacaucuauuuauaag cgcccggauacccaaaccaucaucaaagugaacagcgauuuccacucauucgugcugcccaggauaggcaguaacacau uggagaucgggcugagaacaagaaucaggaaaauguuagaggagcacaaggagccgucaccucucauuaccgccgagga cguacaagaagcuaagugcgcagccgaugaggcuaaggaggugcgugaagccgaggaguugcgcgcagcucuaccaccu uuggcagcugauguugaggagcccacucuggaggcagacgucgacuugauguuacaagaggcuggggccggcucagugg agacaccucguggcuugauaaagguuaccagcuacgauggcgaggacaagaucggcucuuacgcugugcuuucuccgca ggcuguacucaagaugaaaaauuaucuugcauccacccucucgcugaacaagcauagugauaacacacucuggccga aaagggcguuaugccguggaaccauaccaugguaaaguagugguugccagagggacaugcaauacccguccaggacuuuc aagcucugagugaaagugccaccauugugua caacgaacgugaguucguaaacagguaccugcaccauauugccacaca uggaggagcgcugaacacugaugaagaauauuacaaaacugucaagcccagcgagcacgacggcgaauaccuguacgac aucgacaggaaacagucgucaagaagaacuagucacugggcuagggcucacaggcgagcggugaauccucccuucc augaauucgccuacgagagucugagaacacgaccagccgcuccuuaccaaguaccaaccauaggggguguauggcgugcc aggaucaggcaagucuggcaucauuaaaagcgcagucaccaaaaaagaucuaguggugagcgccaagaagaaaacugu gcagaaauuauaagggacgucaagaaaaugaaagggcuggacgucaaugccagaacuguggacucagugcucuugaaug gaugcaaacaccccguagagacccuguauauugacgaagcuuuugcuugucaugcagguacucucagagcgcucauagc cauuauaagaccaaaaaggcagugcucugcggggaucccaaacagugcgguuuuuuaacaugaugugccugaaagug cauuuuaaccacgagauuugcacacaagucuuccacaaaagcaucucucgccguugcacuaaaucugugacuucggucg ucucaaccuuguuuacgacaaaaaaaugagaacgacgaauccgaaagagacuaagauugugauugacacuaccggcag uaccaaaccuaagcaggacgaucucauucucacuuguuucagagggugggugaagcaguugcaaauagauuacaaaggc aacgaaauaaugacggcagcugccucucaagggcugacccguaaaggugguguaugccguucgguacaaggugaaugaaa auccucuguacgcacccaccucagaacaugugaacguccuacugacccgcacggaggaccgcaucgugugga aaacacu agccggcgacccauggauaaaaacacugacugccaaguacccuggaauuucacugccacgauagaggaguggcaagca gagcaugaugccaucaugaggcacaucuuggagagaccggacccuaccgacgucuuccagaauaaggcaaacgugu guu gggccaaggcuuuagugccggugcugaagaccgcuggcauagacaugaccacugaacaauggaacacuguggauuauuu ugaaacggacaaagcucacucagcagagauaguauugaaccaacuaugcgugagguucuuuggacucgaucggacucc ggucuauuucugcacccacuguuccguuauccauuaggaauaaucacugggauaacuccccgucgccuaacauguacg ggcugaauaaagaaguggucagcucucucgcagguacccacaacugccucgggcaguugccacuggaagagucua ugacaugaacacugguacacugcgcaauuaugauccgcgcauaaaccuaguaccuguaaacagaagacugccucaugcu uuaguccuccaccauaaugaacacccacagagugacuuucuucauucgucagcaaauugaagggcagaacugaguccugg uggucggggaaaaguugaccguccccaggcaaaauggaugacgguugucagaccaggccugaggcuaccuucagagcucg gcuggauuuaggcaucccaggaugaugugcccaaaaugacauaauauuuguuaaugugaggaccccauauaaaauaccau cacuaucagcagugugaagaccaugccauuaagcuuagcauguugaccaagaaagcuuguucugcaucugaauccccgcg gaaccugugucagcauagguuaugguuacgcugacagggccagcgaaagcaucauuggugcuauagcgcggcaguucaa -continued guuuucccggguaugcaaaccgaaauccucacuugaagagacggaaguucuguuuguauucauugggguacgaucgcaag gcccguacgcacaauccuuacaagcuuucaucaaccuugaccaacauuuauacagguuccagacuccacgaagccggau gugcacccucauaucauguggugcgaggggauauugccacggccaccgaaggagugauuauaaaugcugcuaacagcaa aggacaaccuggcggaggggugugcggagcgcuguauaagaaauucccggaaagcuucgauuuacagccgaucgaagua ggaaaagcgcgacuggucaaaggugcagcuaaacauaucauucaugccguaggaccaaacuucaacaaaguuucggagg uugaaggugacaaacaguuggcagaggcuuaugaguccaucgcuaagauugucaacgauaacaauuacaagucaguagc gauuccacuguuguccaccggcaucuuuccgggaacaaagaucgacuaacccaaucauugaaccauuugcugacagcu uuagacaccacugaugcagauguagccauauacugcagggacaagaaaugggaaaugacucucaaggaagcagugggcua ggagagaagcaguggaggagauaugcauauccgacgacucuucagugacagaaccugaugcagagcuggugagggugca uccgaagaguucuuuggcuggaaggaagggcuacagcacaagcgauggcaaaacuuucucauauuuggaagggaccaag uuucaccaggcggccaaggauauagcagaaauuaaugccauguggcccguugcaacggaggccaaugagcagguaugca uguauauccucggagaaagcaugagcaguauuaggucgaaaugccccgucgaagagucggaagccuccacaccaccuag cacgcugccuugcuugugcauccaugccaugacuccagaaagaguacagcgccuaaaagccucacguccagaacaaauu acugugugcucauccuuuccauugccgaaguauagaaucacuggugugcagaagauccaaugcucccagccuauauugu ucucaccgaaagugccugcguauauucauccaaggaaguaucucguggaaacaccaccgguagacgagacuccggagcc aucggcagagaaccaauccacagaggggacaccugaacaaccaccacuuauaaccgaggaugagaccaggacuagaacg ccugagccgaucaucaucgaagaggaagaagaggauagcauaaguuugcugucagauggcccgacccaccaggugcugc aagucgaggcagacauuacgggccgcccucuguaucuagcucauccuggccauuccucaugcauccgacuuugaugu ggacaguuuauccauacuugacaccuggagggagcuagcgugaccagcggggcaacgucagccgagacuaacucuuac uucgcaaagaguauggaguuucuggcgcgaccggugccugcgccucgaacaguauucaggaacccuccacauccccgcuc cgcgcacaagaacaccgucacuugcacccagcaggggccugcucgagaaccagccuaguuccacccccgccaggcgugaa uagggugaucacuagagaggagcucgaggcgcuuaccccgucacgcacuccuagcaggucggucucgagaaccagccug gucuccaacccgccaggcguaaauagggugauuacaagagaggaguuugaggcguucguagcacaacaacaaugacggu uugaugcgggugcauacaucuuuuccuccgacaccggucaagggcauuuacaacaaaaaucaguaaggcaaacggugcu auccgaaguggguguuggagaggaccgaaauggagauuucguaugcccccgcgccucgaccaagaaaaagaagaauuacua cgcaagaaauuacaguuaaaucccacaccugcuaacagaagcagauaccaguccaggaaggguggagaacaugaaagcca uaacagcuagacguauucugcaaggccuagggcauuauuugaaggcagaaggaaaaguggagugcuaccgaaccccugca uccuguuccuuuguauucaucuagugugaaccgugccuuuucaagccccaaggucgcaguggaagccuguaacgccaug uugaaagagaacuuccgacuguggcuucuuacuguauuauuccagaguacgaugccuauuuggacaugguugacggag cuucaugcugcuuagacacugccaguuuugcccugcaaagcugcgcagcuuuccaaagaaacacuccuauuuggaacc cacaauacgaucggcagugccuucagcgauccagaacacgcuccagaacguccuggcagcugccacaaaaagaaauugc aaugucacgcaaaugagagaauugcccguauuggauucggcggccuuuaaugugaaugcuucaagaaauaugcguguaa auaaugaauauuggaaacguuuaaagaaaacccccaucaggcuuacugaagaaaacgugguaaauuacauuaccaaauu aaaaggaccaaaagcugcugcucuuuuugcgaagacacauaauuugaauauguucaggacauaccaauggacagguuu guaauggacuuaaagagagacgugaaagugacuccaggaacaaaacauacugaagaacgccaagguacaggugaucc aggcugccgauccgcuagcaacagcguaucugugcggaauccaccgagagcugguuaggagauuaaaugcggccugcu uccgaacauucauacacuguuugauaugucgcugaagacuuugacgcuauuauagccgagcacuuccagccugggggau uguguucuggaaacugacaucgcgucguuugauaaaagugaggacgacgccauggcucugaccgcguuaaugauucugg aagacuuaggugugga cgcagagcuguugacgcugauugaggcggcuuucggcgaaauuucaucaauacauuugcccac uaaaacuaaauuuaaauucggagccaugaugaaaucggaauguccucacacuguuugugaacacagucauuaacauu -continued guaaucgcaagcagagguguugagaacggcuaaccggaucaccaugugcagcauucauuggagaugacaauaucguga
aaggagucaaaucggacaaauuaauggcagacaggugcgccaccugguugaauauggaagucaagauuauagaugcugu
ggugggcgagaaagcgccuuauuucuguggaggguuuauuuugugugacuccgugaccggcacagcgugccgugugca
gaccccuaaaaaggcuguuuaagcuuggcaaaccucuggcagcagacgaugaacaugaugaugacaggagaagggcau
ugcaugaagagucaacacgcuggaaccgaguggguauucuuucagagcugugcaaggcaguagaaucaagguaugaaac
cguaggaacuuccaucauaguuauggccaugacuacucuagcuagcaguguuaaaucauucagcuaccugagaggggcc
ccuauaacucucuacggcuaaccugaauggacuacgacauagucuaguccgccaagnugauaaccgcggugucaaaaac
gccaugacgugcugaccaaccagaaacauaauugaauacagcagcaauuggcaagcugcuuacauagaacucgcggcg
auuggcaugccgccuuaaaauuuuauuuuauuuuucuuuucuuuuccgaaucggauuuuguuuuuaauauuucaaaa
aaaaaaaaaaaaaaaaaaaaaaaaaaaaaaaaaaaaaaaa SEQ ID NO: 34- Vector Backbone RNA Sequence 3
auaggcggcgcaugagagaagcccagaccaauuaccuacccaaaauggagaaaguucacguugacaucgaggaagacag
cccauuccucagagcuuugcagcggagcuucccgcaguuugagguagaagccaagcaggucacugauaaugaccaugcu
aaugccagagcguuucgcaucuggcuucaaaacugaucgaaacggaggugggacccauccgacacgauccuugacauug
gaagugcgcccgcccgcagaauguauucuaagcacaaguaucauugauacugaccgaugagaugugcggaagauccgga
cagauuguauaaguaugcaacuaagcugaagaaaaacuguaaggaaauaacugauaaggaauuggacaagaaaaugaag
gagcuggccgccgucaugagcgacccugaccuggaaacugagacuaugugccuccacgacgacgagucgugucgcuacg
aagggcaagucgcuguuuaccaggauguauacgcgguugacggaccgacaagucucuaucaccaagccaauaagggagu
uagagucgccuacuggauaggcuuugacacaccccuuuuauguuuaagaacuuggcuggagcauauccaucauacucu
accaacugggccgacgaaaccguguuaacggcucguaacauaggccuaugcagcucugacguuauggagcggucacgua
gagggauguccauucuuagaaagaaguauuugaaaccauccaacaauguucuauucucuguuggcucgaccaucuacca
cgagaagagggacuuacugaggagcuggcaccugccgucuguauuucacuuacgugcaagcaaaauuacacaugucgg
ugugagacuauaguuaguugcgacgggacgucguuaaaagaauagcuaucaguccaggccuguaugggaagccuucag
gcgcaaaaacugcugguugggcucaaccagcguauagucgucaacggucgcacccagagaaacaccaauaccaugaaaa
ucccgugugcacguaugugccagcuacauugugugaccaaaugacuggcauacuggcaacagauguucagugcggacgac
gcgcaaaaacugcugguugggcucaaccagcguauagucgucaacggucgcacccagagaaacaccaauaccaugaaaa
auuaccuuugcccguagugggccaggcauuugcuaggugggcaaaggaauauaaggaagaucaagaagaugaaaggcc
auuaccuuugcccguagugggccaggcauuugcuaggugggcaaaggaauauaaggaagaucaagaagaugaaaggcc
cgcccggauacccaaaccaucaucaaagugaacagcgauuuccacucauucgugcugcccaggauaggcaguaacacau
uggagaucgggcugagaacaagaaucaggaaaauguuagaggagcacaaggagccgucaccucucauuaccgccgagga
cguacaagaagcuaagugcgcagccgaugaggcuaaggaggugcgugaagccgaggaguugcgcgcagcucuaccaccu
uuggcagcugauguugaggagcccacucuggaggcagacgucgacuugauguuacaagaggcuggggccggcucagugg
agacaccucguggcuugauaaagguuaccagcuacgauggcgaggacaagaucggcucuuacgcugugcuuucccgca
ggcuguacucaagagugaaaaauuaucuugcauccaccccucucgcugaacaagucauagugauaacacacucuggccga
aaagggcguuaugccguggaaccauaccaugguaaaguaguggugccagagggacaugcaauacccgucaggacuuuc
aagcucugagugaaagugccaccauuguguacaacgaacgugaguucguaaacagguaccugcaccauauugccacaca
uggaggagcgcugaacacugaugaagaauauuacaaaacugucaagcccagcgagcacgacggcgaauaccuguacgac
aucgacaggaaacagugcgucaagaaagaacuagucacgggcuagggcucacaggcgagcuggggauccuccuucc
augaauucgccuacgagagucugagaacacgaccagccgcuccuuaccaaguaccaaccauaggggguguauggcgugcc
aggaucaggcaagucuggcaucauuaaaagcgcagucaccaaaaaagaucuaguggugagcgccaagaaagaaaacugu
gcagaaauuauaagggacguucaagaaaaugaaaggggcuggacgucaaugccagaacuguggacucagugcucuugaaug -continued gaugcaaacaccccguagagacccuguauauugacgaagcuuuugcuugucaugcagguacucucagagcgcucauagc cauuauaagaccuaaaaaggcagugcucugcggggaucccaaacagugcgguuuuuuaacaugaugugccugaaagug cauuuuaaccacgagauuugcacacaagucuuccacaaaagcaucucucgccguugcacuaaaucugugacuucggucg ucucaaccuuguuuacgacaaaaaaaugagaacgacgaauccgaaagagacuaagauugugauugacacuaccggcag uaccaaaccuaagcaggacgaucucauucacuuguuucagaggguggugaagcaguugcaaauagauuacaaaggc aacgaaauaaugacggcagcugccucucaagggcugacccguaaaggugugugauuccguucgguacaaggugaaugaaa auccucuguacgcacccaccucagaacaugugaacguccuacugacccgcacggaggaccgcaucgugggaaaacacu agccggcgacccauggauaaaaacacugacugccaaguacccugggaauuucacugccacgauagaggaguggcaagca gagcaugaugccaucaugaggcacaucuuggagagaccggacccuaccgacgucuuccagaauaaggcaaacgugugu gggccaaggcuuuagugccggugcugaagaccgcuggcauagacaugaccacugaacaauggaacacugugauuauuu ugaaacggacaaagcucacucagcagagauaguauugaaccaacuaugcgugagguucuuuggacucgaucuggacucc ggucuauuuucugcacccacuguuccguuauccauuaggaauaaucacugggauaacuccccgucgccuaacauguacg ggcugaauaagaaguggucgucagcucucucgcagguacccacaacgccucgggcaguugccacuggaagagucua ugacaugaacacugguacacugcgcaauuaugauccgcgcauaaaccuaguaccuguaaacagaagacugccucaugcu uuaguccuccaccauaaugaacacccacagagugacuuuucuucauucgucagcaaauugaagggcagaacuguccugg uggucggggaaaaguugucgucccaggcaaaauggaaugacugguugucagaccggccugaggcuaccuucagagcucg gcuggauuuaggcaucccaggugaugugcccaaaaugacauaauauuuguuaaugugaggaccccauauaaauaccau cacuaucagcagugugaagaccaugccauuaagcuuagcauguugaccaagaaagcuugucugcaucugaaucccggcg gaaccugugucagcauagguuaugguuacgcugacagggccagcgaaagcaucauuggugcuauagcgcggcaguucaa guuucccggguaugcaaaccgaaauccucacuugaagagacggaaguucuguuuguauucauuggguacgaucgcaag gcccguacgcacaauccuuacaagcuuucaucaaccuugaccaacauuuauacagguuccagacuccacgaagccgau gugcacccucauaucaugguggcgaggggauauugccacggccaccgaaggagugauuauaaaugcugcuaacagcaa aggacaaccuggcggagggugugcggagcgcuguauaagaaauuccggaaagcuucgauuuacagccgaucgaagua ggaaaagcgcgacuggucaaaggugcagcuaaacauaucauucaugccguaggaccaaacuucaacaaaguuucggagg uugaaggugacaaacaguuggcagaggcuuaugaguccaucgcuaagauugucaacgauaacaauuacaagucaguagc gauuccacuguuguccaccggcaucuuuuccgggaacaaagaucgacuaacccaaucauugaaccauuugcugacagcu uuagacaccacugaugcagauguagccauauacugcagggacaagaaaugggaaaugacucucaaggaagcaguggcua ggagagaagcagugagaggagauaugcauauccgacgacucuucagugacagaaccugaugcagagcuggugagggugca uccgaagaguucuuuggcuggaaggaagggcuacagcacaagcgauggcaaaacuuucucauauuuggaagggaccaag uuucaccaggcggccaaggauauagcagaaauuaaugccaugugggcccguugcaacggaggccaaugagcagguaugca uguauauccucggagaaagcaugagcaguauuaggucgaaaugccccgucgaagagucgaagccuccacaccaccuag cacgcugccuugcuugugcauccaugccaugacuccagaaagaguacagcgccuaaaagccucacguccagaacaaauu acugugugcucauccuuuccauugccgaaguauagaaucacuggugugcagaagauccaaugcucccagccuauauugu ucucaccgaaagugccugcguauauucauccaaggaaguaucucguggaaacaccaccgguagacgagacuccggagcc aucggcagagaaccaauccacagaggggacaccugaacaaccaccacuuauaaccgaggaugagaccaggacuagaacg ccugagccgaucaucaucgaagaggaagaggauagcauaaguuugcugcagauggcccgacccaccaggugcugc aagucgaggcagacauucacgggccgcccucuguaucuagcucauccugguccauuccucaugcauccgacuuugaugu ggacaguuuauccauacuugacaccguggagggagcuagcgugaccagcggggcaacgucagccgagacuaacucuuac uucgcaaagaguauggaguuucggcgcgaccggugccugcgccucgaacaguauucaggaaccuccacaucccgcuc cgcgcacaagaacaccgucacuugcacccagcagggccugcucgagaaccagccuaguuuccaccccgccaggcgugaa uaggguggaucacuagagaggagcucgaggcgcuuaccccgucacgcacuccuagcaggucggucucgagaaccagccug -continued gucuccaacccgccaggcguaaauagggugauuacaagagaggaguuugaggcguucguagcacaacaacaaugacggu uugaugcgggugcauacaucuuuuccuccgacaccggucaagggcauuuacaacaaaaaucaguaaggcaaacggugcu auccgaaguggguguuggagaggaccgaauuggagauuucguaugccccgcgccucgaccaagaaaaagaagaauuacua cgcaagaaauuacaguuaaauccccacaccugcuaacagaagcagauaccaguccaggaaggugguggagaacaugaaagcca uaacagcuagacguauucugcaaggccuagggcauuauuugaaggcagaaggaaaaguggagugcuaccgaacccugca uccuguuccuuuguauucaucuagugugaaccgugccuuuucaagccccaaggucgcaguggaagccuguaacgccaug uugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaacc cacaauacgaucggcagugccuucagcgauccagaacacgcuccagaacguccuggcagcugccacaaaagaaauugc aaugucacgcaaaugagagaauugcccguauuggauucggccggccuuuaaugugguaaugcuucaagaaauaugcguguua auaaugaauauugggaaacguuuaagaaaaccccaucaggcuuacugaagaaaacgugguaaauuacauuaccaaauu aaaaggaccaaaagcugcugcucuuuuugcgaagacacauaauuugaauaugguugcaggacauaccaauggacagguuu guaauggacuuaaagagagacgugaaagugacuccaggaacaaaacauacugaagaacggcccaagguacaggugaucc aggcugccgauccgcuagcaacagcguaucugugcggaauccaccgagagcugguuaggagauuaaaugcgguccugcu uccgaacauucauacacuguuugauaugucggcugaagacuuugacgcuauuauagccgagcacuuccagccuggggau uguguucuggaaacugacaucgcgucguuugauaaaagugaggacgacgccauggcucugaccgcguuaaugauucugg aagacuuaggugugacgcagagcuguuuggacgcugauugaggcggcuuucggcgaaauuucaucaauacauuugcccac uaaaacuaaauuuaaauucggagccaugaugaaaucuggaauguuccucacacuguuugugaacacagucauuaacauu guaaucgcaagcagagugugagagaacggcuaaccggaucaccaugugcagcauucauuggagaugacaauaucguga aaggagucaaaucggacaaauuaauggcagacaggugcgccaccuugguugaauauggaagucaagauuauagaugcugu ggugggcgagaaagcgccuuauuucuguggagggguuuauuuugugugacuccgugaccggcacagcgugccgugugca gaccccuaaaaagcuguuuaagcuuggcaaaccucuggcagcagacgaugaacaugaugaugacaggagaagggcau ugcaugaagagucaacacgcuggaaccgaguggguauucuuucagagcugugcaaggcaguagaaucaagguaugaaac cguaggaacuuccaucauaguuauggccaugacuacucuagcuagcaguguaaaucauucagcuaccugagaggggcc ccuauaacucucuacggcuaaccugaauggacuacgacauagucuaguccgccaagnuaguaaccgcggugucaaaaac gccaugacugugcugaccaaccagaaacauaauugaauacagcagcaauuggcaagcugcuuacauagaacucgcggcg auuggcaugccgccuuaaaauuuuauuuuauuuuucuuuucuuuuccgaaucggauuuuguuuuuaauauuucaaaa aaaaaaaaaaaaaaaaaaaaaaaaaaaaaaaaaaaaa SEQ ID NO: 35- Vector Backbone RNA Sequence 4
auaggcggcgcaugagagaagcccagaccaauuaccuacccaaaauggagaaaguucacguugacaucgaggaagacag cccauuccucagagcuuugcagcggagcuucccgcaguuugagguagaagccaagcaggucacugauaaugaccaugcu aaugccagagcguuuucgcaucuggcuucaaaacugaucgaaacggagguggaccccauccgacacgauccuugacauug gaagugcgcccgcccgcagaaugauauucuaagcacaaguaucauuguaucuguccgaugagaugugcggaagauccgga cagauuguauaaguaugcaacuaagcugaagaaaaacuguaaggaaauaacugauaaggaauuggacaagaaaaugaag gagcuggccgccgucaugagcgacccugaccuggaaacugagacuaugugccuccacgacgacgagucgugucgcuacg aagggcaagucgcuguuuaccaggauguauacgcggugacggaccgacaagucucuaucaccaagccaauaagggagu uagagcgccuacuggauaggcuuugacaccacccccuuuuaugaauuugcggcuggagcauaccaucauacucu accaacugggccgacgaaaccguguuaacggcucguaacauaggccuaugcagcucgacguuauggagcggucacgua gagggaugucccauucuuagaaagaaguauuugaaaccauccaacaauguucuauucucuguuggcucgaccaucuacca cgagaagagggacuacugaggagcuggcaccugccgucuguauuucacuuacguggcaagcaaaaauuacacaugucgg ugugagacuauaguuaguugcgacgggguacgucguuaaaagaauagcuaucaguccaggccuguauggaagccuucag -continued gcuaugcugcuacgaugcaccgcgagggauucuugugcugcaaagugacagacacauugaacggggagagggucucuuu ucccgugugcacguaugugccagcuacauugugugaccaaaugacuggcauacuggcaacagaugucagugcggacgac gcgcaaaaacugcugguugggcucaaccagcguauagucgucaacggucgcacccagagaaacaccaauaccaugaaaa auuaccuuuugcccguagugggcccaggcauuugcuaggugggcaaaggaauauaaggaagaucaagaagaugaaaggcc acuaggacuacgagauagacaguuagucauggggguguuguugggcuuuagaaggcacaagauaacaucuauuuauaag cgcccggauacccaaaccaucaucaaagugaacagcgauuuccacucauucgugcugcccaggauaggcaguaacacau uggagaucgggcugagaacaagaaucaggaaaauguuagaggagcacaaggagccgucaccucucauuaccgccgagga cguacaagaagcuaagugcgcagccgaugaggcuaaggaggugcgugaagccgaggaguugcgcgcagcucuaccaccu uuggcagcugauguugaggagcccacucuggaggcagacgucgacuugauguuacaagaggcuggggccggcucagugg agacaccucguggcuugauaaagguuaccagcuacgaugcgaggacaagaucggcucuuacgcugugcuuucuccgca ggcuguacucaagagugaaaaauuaucuugcauccacccucucgcugaacaagucauagugauaacacacucuggccga aaagggcguuaugccguggaaccauaccauggugaaaguaguggugccagagggacaugcaauacccguccaggacuuuc aagcucugagugaaagugccaccauugaguacaacgaacgugaguucguaaacagguaccugcaccauauugccacaca uggaggagcgcugaacacugaugaagaauauuacaaaacugucaagcccagcgagcacgacggcgaauaccuguacgac aucgacaggaaacagugcgucaagaaagaacuagucacugggcuagggcucacaggcgagcugguggauccucccuucc augaauucgccuacgagagucugaacacgaccagccgcuccuuaccaaguaccaaccauaggggguguauggcgugcc aggaucaggcaagucuggcaucauuaaaagcgcagucaccaaaaaagaucuaguggugagcgccaagaaagaaaacugu gcagaaauuauaagggacgucaagaaaaugaaagggcuggacgucaaugccagaacugugggacucagugcucuugaaug gaugcaaacaccccguagagacccuguauauugacgaagcuuugcuugcaugcagguacucucagagcgcucauagc cauuauaagaccuaaaaaggcagugcucgcggggaucccaaacagugcgguuuuuuaacaugaugugccugaaagug cauuuuaaccacgagauuugcacacaagucuuccacaaaagcaucucucgccguugcacuaaaaucugugacuucggucg ucucaaccuuguuuuacgacaaaaaaaugagaacgacgaauccgaaagagacuaagauugugauugacacuaccggcag uaccaaaccuaagcaggacgaucucauucucacuuguuucagaggguggugaagcaguugcaaauagauuacaaaggc aacgaaauaaugacggcagcugccucucaagggcugacccguaaaggugugguaugccguucgguacaaggugaaugaaa auccucuguacgcacccaccucagaacaugugaacguccuacugacccgcacggaggaccgcaucgugugaaaacacu agccggcgacccauggauaaaaacacugacugccaaguacccugggaauuucacugccacgauagaggaguggcaagca gagcaugaugccaucaugaggcacaucuuggagagaccggacccuaccgacgucuuccagaauaaggcaaacgugugu gggccaaggcuuuagugccggugcugaagaccgcuggcauagacaugaccacugaacaauggaacacuguggauuauuu ugaaacggacaaagcucacucagcagauaguauugaaccaacuaugcgugagguucuuuggacucgaucuggacucc ggucuauuuucugcacccacuguuccguuauccauuaggaauaaucacugggauaacucccegucgccuaacauguacg ggcugaauaagaaguggaccgucagcucucucgcagguaccacaacugccucgggcaguugccacuggaagagucua ugacaugaacacugguacacugcgcaauuaugauccgcgcauaaaccuaguaccuguaaacagaagacugccucaugcu uuagccuccaccauaaugaacacccacagagugacuuucuucauucgucagcaaauugaagggcagaacuguccugg uggucggggaaaaguugccgucccaggcaaaauggugacugguugucagaccggccugaggcuaccuucagagcucg gcuggauuuaggcaucccaggugaugugcccaaaaugacauaaauuuguuaaugugaggaccccauauaaauaccau cacuaucagcagugugaagaccaugccauuaagcuuagcauguugaccaagaaagcuugucugcaucugaaucccggcg gaaccugugucagcauagguuaugguuacgcugacagggccagcgaaagcaucauuggugcuauagcgcggcaguucaa guuucccgggguaugcaaaccgaaauccucacuugaagagacggaaguucuguuuguauucauugggguacgaucgcaag gcccguacgcacaauccuuacaagcuuucaucaaccuugaccaacauuuauacagguucagacuccacgaagccggau gugcacccucauaucaugugggugcgaggggauauugccacggccaccgaaggagugauuauaaaugcugcuaacagcaa -continued aggacaaccuggcggaggggugugcggagcgcuguauaagaaauucccggaaagcuucgauuuacagccgaucgaagua ggaaaagcgcgacuggucaaaggugcagcuaaacauaucauucaugccguaggaccaaacuucaacaaaguuucggagg uugaaggugacaaacaguuggcagaggcuuaugaguccaucgcuaagauugucaacgauaacaauuacaagucaguagc gauuccacuguuguccaccggcaucuuuuccgggaacaaagaucgacuaacccaaucauugaaccauuugcugacagcu uuagacaccacugaugcagauguagccauauacugcagggacaagaaaugggaaaugacucucaaggaagcagugcua ggagagaagcaguggaggagauaugcauauccgacgacucuucagugacagaaccugaugcagagcuggugagggugca uccgaagaguucuuuggcuggaaggaagggcuacagcacaagcgauggcaaaacuuucucauauuuggaagggaccaag uuucaccaggcggccaaggauauagcagaaauuaaugccauguggcccguugcaacggaggccaaugagcagguaugca uguauauccucggagaaagcaugagcaguauuaggucgaaaugccccgucgaagagucggaagccuccacaccaccuag cacgcugccuugcuugugcauccaugccaugacuccagaaagaguacagcgccuaaaagccucacguccagaacaaauu acugugugcucauccuuuccauugccgaaguauagaaucacuggugugcagaagauccaaugcucccagccuauauugu ucucaccgaaagugccugcguauauucauccaaggaaguaucucguggaaacaccaccgguagacgagacuccggagcc aucggcagagaaccaauccacagaggggacaccgaacaaccaccacuuauaaccgaggaugagaccaggacuagaacg ccugagccgaucaucaagaggaagaagaggauagcauaaguuugcugucagauggcccgacccaccaggugcugc aagucgaggcagacauuacgggccgcccucuguaucuagcucauccugguccauuccucaugcauccgacuuugaugu ggacaguuuauccauacuugacacccuggagggagcuagcgugaccagcggggcaacgucagccgagacuaacucuuac uucgcaaagaguauggaguuucuggcgcgaccggugccugcgccucgaacaguauucaggaacccuccacaucccgcuc cgcgcacaagaacaccgucacuugcacccagcagggccugcucgagaaccagccuaguuuccacccccgccaggcgugaa uagggugaucacuagagaggagcucgaggcgcuuaccccgucacgcacuccuagcaggucggucucgagaaccagccug gucuccaacccgccaggcguaaauagggugauuacaagagaggaguuugaggcguucguagcacaacaacaaugacggu uugaugcgggugcauacaucuuuuccuccgacaccggucaagggcauuuacaacaaaaaucaguaaggcaaacggugcu auccgaaguggguguuggagaggaccgaauuggagauuucguaugccccgcgccucgaccaagaaaaagaagaauuacua cgcaagaaauuacaguuaaaucccacaccugcuaacagaagcagauaccaguccaggaagguggagaacaugaaagcca uaacagcuagacguauucugcaaggccuagggcauuauuugaaggcagaaggaaaaguggagugcuaccgaacccugca uccuguuccuuuguauucaucagugugaaccgugccuuuucaagccccaaggucgcaguggaagccuguaacgccaug uugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaacc cacaauacgaucggcagugccuucagcgauccagaacacgcuccagaacguccuggcagcugccacaaaaagaaauugc aaugucacgcaaaugagagaauugcccguauuggauucggcggccuuuaaugguggaaugcuucaagaaauaugcgugua auaaugaauauugggaaacguuuaagaaaaccccaucaggcuuacugaagaaaacguggaaauuacauuaccaaauu aaaaggaccaaaagcugcugcucuuuuugcgaagacacauaauuugaauaugusucaggacauaccaauggacagguuu guaauggacuuaagagagacgugaaagugacuccaggaacaaaacauacugaagaacggcccaagguacaggugaucc aggcugccgauccgcuagcaacagcguaucugugcggaauccaccgagagcugguuaggagauuaaaugcgguccugcu uccgaacauucauacacuguuugauaugucggcugaagacuuugacgcuauuauagccgagcacuuccagccuggggau uguguucuggaaacugacaucgcgucguuugauaaaagugaggacgacgccauggcucugaccgcguuaaugauucgg aagacuuaggugugacgcagagcuguugacgcugauugaggcggcuuucggcgaaauuucaucaauacauuugcccac uaaaacuaaauuuaaauucggagccaugaugaaaucggaauguuccucacacuguuugugaacacagucauuaacauu guaaucgcaagcagagugugagagaacgcuaaccggaucaccaugugcagcauucauggagaugacaauaucguga aaggagucaaaucggacaaauuaauggcagacaggugcgccaccugguugaauauggaagucaagauuauagaugcugu gaccccuaaaaaggcuguuuaagcuuggcaaaccucuggcagcagacgaugaacaugaugaugacaggagaagggcau ugcaugaagagucaacacgcuggaaccgagugggguauucuuucagagcugugcaaggcaguagaaucaagguaugaaac -continued cguaggaacuuccaucauaguuauggccaugacuacucuagcuagcaguguuaaaucauucagcuaccugagaggggcc ccuauaacucucuacggcuaaccugaauggacuacgacauagucuagccugccaagnugauaaccgcgguguaaaaac gccauguacgugcugaccaaccagaaacauaauugaauacagcagcaauuggcaagcugcuuacauagaacucgcggcg auuggcaugccgccuuaaaauuuuuauuuuauuuuucuuuucuuuuccgaaucggauuuguuuuuaauauuucaaaa aaaaaaaaaaaaaaaaaaaaaaaaaaaaaaaaaaaaaa SEQ ID NO: 36- Vector Backbone RNA Sequence 5
auaggcggcgcaugagagaagcccagaccaauuaccuacccaaaauggagaaaguucacguugacaucgaggaagacag cccauuccucagagcuuugcagcggagcuucccgcaguuugagguagaagccaagcaggucacugauaaugaccaugcu aaugccagagcguuucgcaucuggcuucaaaacugaucgaaacggagguggacccauccgacacgauccuugacauug gaagugcgcccgcccgcagaauguauucuaagcacaaguacauugua cugu ccgaugagaugugcggaagauccgga cagauuguauaaguaugcaacuaagcugaagaaaaacuguaaggaaauaacugauaaggaauuggacaagaaaaugaag gagcuggccgccgucaugagcgacccugaccuggaaacugagacuaugugccuccacgacgacgagucgugucgcuacg aagggcaagucgcuguuuaccaggauguauacgcgguugacggaccgacaagucucuaucaccaagccaauaagggagu uagagucgccuacuggauaggcuuugacaccaccccuuuuauguuuaagaacuuggcuggagcauauccaucauacucu accaacugggccgacgaaaccguguuaacggcucguaacauaggccaugcagcucugacguuauggagcggucacgua gagggauguccauucuuagaaagaaguauuugaaaccauccaacaauguucuauucucuguuggcucgaccaucuacca cgagaagagggacuuacugaggagcuggcaccugccgucuguauuucacuuacguggcaagcaaaauuacacaugucgg ugugagacuauaguuaguugcgacggguacgucguuaaaagaauagcuaucaguccaggccuguaugggaagccuucag gcuaugcugcuacgaugcaccgcgagggauucuugugcugcaaagugacagacacauugaacggggagagggucucuuu ucccgugugcacguaugugccagcuacauugugugaccaaaugacuggcauacuggcaacagaugucagugcggacgac gcgcaaaaacugcugguuugggcucaaccagcguauagucgucaacggucgcacccagagaaacaccaauaccaugaaaa auuaccuuugcccguagugggcccaggcauuugcuagguggcaaaggaauauaaggaagaucaagaagaugaaaggcc acuaggacuacgagauagacaguuagucauggggguguuguugggcuuuuagaaggcacaagauaacaucuauuuauaag cgcccggauacccaaaccaucaucaaagugaacagcgauuuccacucauucgugcugcccaggauaggcaguaacacau uggagaucgggcugagaacaagaaucaggaaaauguuagaggagcacaaggagccgucaccucucauuaccgccgagga cguacaagaagcuaagugcgcagccgaugaggcuaaggaggugcgugaagccgaggaguugcgcgcagcucuaccaccu uuggcagcugauguugaggagcccacucuggaggcagacgucgacuugauguuacaagaggcuggggccggcucagugg agacaccucguggcuugauaaagguuaccagcuacgauggcgaggacaagaucggcucuuacgcugugcuuucccgca ggcuguacucaagagugaaaaauuaucuugcauccacccucucgcugaacaagucauagugauaacacacucuggccga aaagggcguuaugccguggaaccauaccaugguaaaguaguggugccagagggacaugcaauacccguccaggacuuuc aagcucugagugaaagugccaccauuguguacaacgaacgugaguucguaaacagguaccugcaccauauugccacaca uggaggagcgcugaacacugaugaagaauauuacaaaacugucaagcccagcgagcacgacggcgaauaccuguacgac aucgacaggaaacagugcgucaagaaagaacuagucacugggcuagggcucacaggcgagcugguggauccuccuucc augaauucgccuacgagagucugagaacacgaccagccgcuccuuaccaaguaccaaccauaggggguguauggcgugcc aggaucaggcaagucuggcaucauuaaaagcgcagucaccaaaaaagaucuaguggugagcgccaagaaagaaaacugu gcagaaauuauaagggacgucaagaaaaugaaagggcuggacgucaaugccagaacguggacucagugcucuugaaug gaugcaaacaccccguagagacccuguauauugacgaagcuuuugcuugucaugcagguacucucagagcgcucauagc cauuauaagaccuaaaaggcagugucugcggggaucccaaacagugcgguuuuuuaacaugauguugccugaaagug cauuuuaaccacgagauuugcacacaagucuuccacaaaagcaucucucgccguugcacuaaaucugugacuucggucg ucucaaccuuguuuacgacaaaaaaaugagaacgacgaauccgaaagagacuaagauugugauugacacuaccggcag uaccaaaccuaagcaggacgaucucauucucacuuguuucagagggguggugaagcaguugcaaauagauuacaaaggc -continued aacgaaauaaugacggcagcugccucucaagggcugacccguaaaggugguauugccguucgguacaaggugaaugaaa auccucuguacgcacccaccucagaacauguaacguccuacugacccgcacggaggaccgcaucguguggaaaacacu agccggcgacccauggauaaaaacacugacugccaaguacccugggaauuucacugccacgauagaggaguggcaagca gagcaugaugccaucaugaggcacaucuuggagagaccggacccuaccgacgucuuccagaauaaggcaaacguguguu gggccaaggcuuuagugccggugcugaagaccgcuggcauagacaugaccacugaacaauggaacacuguggauuauuu ugaaacggacaaagcucacucagcagagauaguauugaaccaacuaugcgugagguucuuuggacucgaucuggacucc ggucuauuucugcacccacuguuccguuauccauuaggaauaaucacugggauaacuccccgucgccuaacauuacg ggcugaauaaagaaguggucgucagcucucucgcagguacccacaacugccucgggcaguugccacuggaagagucua ugacaugaacacugguacacugcgcaauuaugauccgcgcauaaaccuaguaccuguaaacagaagacugccucaugcu uuaguccuccaccauaaugaacacccacagagugacuuucuucauucgucagcaaauugaagggcagaacuguccugg uggucggggaaaaguugudccgucccaggcaaaaugguugacugguugucagaccggccugaggcuaccuucagagcucg gcuggauuuaggcaucccaggugaugugcccaaauaugcauaauauuuguuaauguggaggaccccauauaaauaccau cacuaucagcagugugaagaccaugccauuaagcuuagcauguugaccaagaaagcuugucugcaucugaaucccggcg gaaccugugucagcauagguuaugguuacgcugacagggccagcgaaagcaucauuggugcuauagcgcggcaguucaa guuuucccggguaugcaaaccgaaauccucacuugaagagacggaaguucuguuguauucauugggguacgaucgcaag gcccgacgcacaauccuuacaagcuuucaucaaccuugaccaacauuuauacagguuccagacuccacgaagccggau gugcacccucauaucaugggugcgagggauauugccacggccaccgaaggagugauuauaaaugcugcuaacagcaa aggacaaccuggcggagggguggugcggagcgcuguauaagaaauucccggaaagcuucgauuuacagccgaucgaagua ggaaaagcgcgacuggucaaaggugcagcuaaacauaucauucaugccguaggaccaaacuucaacaaaguuucggagg uugaaggugacaaacaguuggcagaggcuuaugaguccaucgcuaagauugucaacgauaacaauuacaagucaguagc gauccacuguugnuccaccggcaucuuuuccgggaacaaagaucgacuaacccaaucauugaaccauuugcugacagcu uuagacaccacugaugcagauguagccauauacugcagggacaagaaaugggaaaugacucucaaggaagcaguggcua ggagagaagcaguggaggagauaugcauauccgacgacucuucagugacagaaccugaugcagagcuggugagggugca uccgaagaguucuuuggcuggaaggaagggcuacagcacaagcgauggcaaaacuuucuauauuuggaagggaccaag uuucaccaggcggccaaggauauagcagaaauuaaugccauguggcccguugcaacggaggccaaugagcagguaugca uguauauccucggagaaagcaugagcaguauuaggucgaaaugccccgucgaagagucggaagccuccacaccaccuag cacgcugccuugcuugugcauccaugccaugacuccagaaagaguacagcgccuaaaagccucacguccagaacaaauu acugugugcucauccuuuccauugccgaaguauagaaucacuggugugcagaagauccaaugcucccagccuauauugu ucucaccgaaagugccugcguauauucauccaaggaaguaucucguggaaacaccaccgguagacgagacucccggagcc aucggcagagaaccaauccacagaggggacaccugaacaaccaccacuuauaaccgaggaugagaccaggacuagaacg ccugagccgaucaucaucgaagaggaagaaggagauagcauaaguuugcugucagauggcccgacccaccagguguugc aagucgaggcagacauucacgggccgcccucuguaucuagcucauccuggccauuccucaugcauccgacuuugaugu ggacaguuuauccuacuugacacccuggagggagcuagcgugaccagcggggcaacgucagccgagacuaacucuuac uucgcaaagaguauggaguuucuggcgcgaccggugccugcgccucgaacaguauucaggaaccuccacaucccgcuc cgcgcacaagaacaccgucacuugcacccagcagggccugcucgagaaccagccuaguuccaccccgccaggcgugaa uaggugaucacuagagaggagcucgaggcgcuuaccccgucacgcacuccuagcaggucggucucgagaaccagccug gucuccaaccecgccaggcguaaauaggguugauuacaagagaggagauuugaggcguucguagcacaacaacaaugacggu uugaugcgggugcauacaucuuuccuccgacaccggucaagggcauuuacaacaaaaaucaguaaggcaaacggugcu auccgaaguggguguuggagaggaccgaauuggagauuucguaugcccgcgccucgaccaagaaaaagaagaauuacua cgcaagaaauuacaguuaaaucccacaccugcuaacagaagcagauaccaguccaggaagguggagaacaugaaagcca -continued uaacagcuagacguauucugcaaggccuagggcauuauuugaaggcagaaggaaaaguggagugcuaccgaacccugca uccuguuccuuuguauucaucagugugaaccgugccuuuucaagccccaaggucgcaguggaagccuguaacgccaug uugaaagagaacuuuccgacuguggcuucuuacuguauuauuccagaguacgaugccuauuuggacaugguugacggag cuucaugcugcuuagacacugccaguuuuugcccugcaaagcugcgcagcuuuccaaagaaacacuccuauuuggaacc cacaauacgaucggcagugccuucagcgauccagaacacgcuccagaacguccuggcagcugccacaaaaagaaauugc aaugucacgcaaaugagagaauugcccguauuggauucggcggccuuuaaugugg aaugcuucaagaaauaugcguguaa auaaugaauauugggaaacguuuaaagaaaaccccaucaggcuuacugaagaaaacgugguaaauuacauuaccaaauu aaaaggaccaaaagcugcugcucuuuuugcgaagacacauaauuugaauauguugcaggacauaccaauggacagguuu guaauggacuuaaagagagacgugaaagugacuccaggaacaaaacauacugaagaacggcccaagguacaggugaucc aggcugccgauccgcuagcaacagcguaucgugcggaauccaccgagagcgguuaggagauuaaaugcgguccugcu uccgaacauucauacacuguuugauaugucggcugaagacuuugacgcuauuauagccgagcacuuccagccuggggau uguguucuggaaacugacaucgcgucguuugauaaaagugaggacgacgccauggcucugaccgcguuaaugauucugg aagacuuaggugugg acgcagagcuguuagacgcugauugaggcggcuuucggcgaaauuucaucaauacauuugcccac uaaaacuaaauuuaaauucggagccaugaugaaaucuggaauguuccucacacuguuugugaacacagucauuaacauu guaaucgcaagcagaguguugagagaacggcuaaccggaucaccaugugcagcauucauuggagaugacaauaucguga aaggagucaaaucggacaaauuaauggcagacaggugcgccaccugguugaauaugg aagucaagauuauagaugcugu gguggg cgagaaagcgcccuuauuucguggagggguuuauuuugugugacuccgugaccggcacagcgugccguguggca gaccccc uaaaaag gcuguuuaagcuuggcaaaccucuggcagcagacgaugaacaugaugaugacaggagaagggcau ugcaugaagagucaacacgcuggaaccgagugggguauucuuucagagcugugcaaggcaguagaaucaagguaugaaac cguaggaacuuccaucauaguuauggccaugacuacucuagcuagcaguguuaaaucauucagcuaccugagaggggcc ccuauaacucucuacggcuaaccugaauggacuacgacauaguc uaguccgccaagnugauaaccgcggugucaaaaac gccauguacgugcugaccaaccagaaacauaauugaauacagcagcaauuggcaagcugcuuacauagaacucgcggcg auuggcaugccgccuuaaaauuuuauuuuauuuuucuuuucuuuuccgaaucggauuuuguuuuuaauauuucaaaa aaaaaaaaaaaaaaaaaaaaaaaaaaaaaaaaaaaaaa SEQ ID NO: 37- Vector Backbone RNA Sequence 6
auaggcggcgcaugagagaagcccagaccaauuaccuacccaaaauggagaaaguucacguugacaucgaggaagacag cccauuccucagagcuuugcagcggagcuucccgcaguuugagguagaagccaagcaggucacugauaaugaccaugcu aaugccagagcguuuucgcaucuggcuucaaaacugaucgaaacggagguggacccauccgacacgauccuugacauug gaagugcgcccgcccgcagaauguauucuaagcacaaguaucauuguaucugu ccgaugagaugugcggaagauccgga cagauuguauaagu augcaacuag cugaag aaaaacuguaaggaaauaacugauaaggaauug gacaagaaaaugaag gagcuggccgccgucaugagcgacccugaccuggaaacugagacuaugugccuccacgacgacgagucgugucgcuacg aagggcaagucgcuguuuuaccaggauguauacgcggu ugacggaccgacaagucucuaucaccaagccaauaagggagu uagagucgccuacuggauaggcuuugacacca ccccuuuuaugu uuaag aacuuggcuggagcauaccaucauacucu accaacugggccgacgaaaccguguuaacggcucguaacauagg ccaugcagcucugacguuauggagcggucacgua gagggaugu ccauucuuagaagaaguauuugaaaccauccaacaauguucuauucucuguuggcucgaccaucuacca cgagaagagggacuuacugaggagcuggcaccugccgucuguauuucacuuacguggcaagcaaaauuacacaugucgg ugugagacuauaguuaguugcgacgggu acgucguuaaaagaauagcuaucagu ccaggccuguauggg aagccuucag gcuaugcugcuacgaugcaccgcgagggauucuugugcugcaaagugacagacacauugaacggggagagggucucuuu ucccgugugcacguaugugccagcuacauugugugaccaaaugacuggcauacuggcaacagauguc agugcggacgac gcgcaaaaacugcugguugggcucaaccagcguauagucgucaacgucgcacccagagaaacaccaauaccaugaaaa auuaccuuuugcccguagugggcccaggcauuugcuagguggg caaaggaauauaaggaagaucaagaagaugaaaggcc -continued acuaggacuacgagauagacaguuagucauggggguguuguugggcuuuuagaaggcacaagauaacaucuauuuauaag cgcccggauacccaaaccaucaucaaagugaacagcgauuuccacucauucgugcugcccaggauaggcaguaacacau uggagaucgggcugagaacaagaaucaggaaaauguuagaggagcacaaggagccgucaccucucauuaccgccgagga cguacaagaagcuaagugcgcagccgaugaggcuaaggaggugcgugaagccgaggaguugcgcgcagcucuaccaccu uuggcagcugauguugaggagcccacucuggaggcagacgucgacuugauguuacaagaggcuggggccggcucagugg agacaccucguggcuugauaaagguuaccagcuacgaugscgaggacaagaucggcucuuacgcugugcuuucuccgca ggcuguacucaagagugaaaaauuaucuugcauccaccucucgcugaacaagucauagugauaacacacucuggccga aaagggcguuaugccguggaaccauaccaugguaaaguaguggugccagagggacaugcaauacccguccaggacuuuc aagcucugagugaaagugccaccauugugacaacgaacgugaguucguaaacagguaccugcaccauauugccacaca uggaggagcgcugaacacugaugaagaauauuacaaaacugucaagcccagcgagcacgacggcgaauaccuguacgac aucgacaggaaacagugcgucaagaaagaacuagucacugggcuagggcucacaggcgagcggguggauccuccccuucc augaauucgccuacgagagucugagaacacgaccagccgcuccuuaccaaguaccaaccauagggguguauggcgugcc aggaucaggcaagucggcaucauuaaaagcgcagucaccaaaaaagaucuaguggugagcgccaagaagaaaacugu gcagaaauuauaagggacgucaagaaaaugaaagggcuggacgucaaugccagaacugugggacucagugcucuugaaug gaugcaaacaccccguagagacccuguauauugacgaagcuuugcuugucaugcagguacucucagagcgcucauagc cauuauaagaccuaaaaaggcagugcucugcggggaucccaaacagugcgguuuuuuaacaugaugugccugaaagug cauuuuaaccacgagauuugcacacaagucuuccacaaaagcaucucucgccguugcacuaaaucgugacuucggucg ucucaaccuuguuuuacgacaaaaaaaugagaacgacgaauccgaaagagacuaagauugugauugacacuaccggcag uaccaaaccuaagcaggacgaucucauucuscacuuguuucagaggguggguagaagcaguugcaaauagauuacaaaggc aacgaaauaaugacggcagcugccucucaagggcugacccguaaaggugguguaugccguucgguacaaggugaaugaaa auccucuguacgcacccaccucagaacaugugaacguccuacugacccgcacggaggaccgcaucgugugaaaacacu agccggcgacccauggauaaaaacacugacugccaaguacccugggaauuucacugccacgauagaggaguggcaagca gagcaugaugccaucaugaggcacaucuuggagagaccggacccuaccgacgucuuccagaauaaggcaaacgugaguu gggccaaggcuuuagugccggugcugaagaccgcuggcauagacaugaccacugaacaauggaacacuguggauuauuu ugaaacggacaaagcucacucagcagagauaguauugaaccaacuaugcgugagguucuuuggacucgaucggacucc ggucuauuuucugcacccacuguuccguuauccauuaggaauaaucacugggauaacuccccgucgccuaacauguacg ggcugaauaaagaagguggccgucagcucucucgcagguacccacaacugccucgggcaguugccacuggaagagucua ugacaugaacacugguacacugcgcaauuaugauccgcgcauaaaccuaguaccuguaaacagaagacugccucaugcu uuagccuccaccauaaugaacacccacagagugacuuuucuucauucgucagcaaauugaagggcagaacucuccugg uggucggggaaaaguugccgucccaggcaaaauggusgacugguugucagaccggccugaggcuaccuucagagcucg gcuggauuuaggcaucccaggugaugugcccaaauaugacauaauauuguuaaugugaggaccccauauaaauaccau cacuaucagcagugugaagaccaugccauuaagcuuagcauguugaccaagaaagcuugucugcaucugaaucccggcg gaaccugugucagcauagguuaugguuacgcugacagggccagcgaaagcaucauuggugcuauagcgcggcaguucaa guuucccggguaugcaaaccgaaauccucacuugaagagacggaaguucuguuuguauucauuggguacgaucgcaag gcccguacgcacaauccuuacaagcuuucaucaaccuugaccaacauuuauacagguuccagacuccacgaagccggau gugcacccucauaucaugugggugcgaggggauauugccacggccaccgaaggagugauuauaaaugcugcuaacagcaa aggacaaccuggcggagggggugugcggagcgcuguauaagaaauucccggaaagcuucgauuuacagccgaucgaagua ggaaaagcgcgacugguuuucaaaggugcagcuaaacauaucauucaugccguaggaccaaacuucaacaaaguuucggagg uugaaggugacaaacaguuggcagaggcuuuaugaguccaucgcuaagauugucaacgauaacauuacaagucaguagc gauuccacuguugccaccggcaucuuuuccgggaacaaagaucgacuaacccaaucauugaaccauuugcugacagcu uuagacaccacugaugcagauguagccauauacugcagggacaagaaaugggaaaugacucucaaggaagcaguggcua -continued ggagagaagcaguggaggagagauaugcauauccgacgacucuucagugacagaaccugaugcagagcuggugagggugca uccgaagaguucuuuggcuggaaggaagggcuacagcacaagcgauggcaaaacuuucucauauuuggaagggaccaag uuucaccaggcggccaaggauauagcagaaauuaaugccaugugggcccguugcaacggaggccaaugagcagguaugca uguauauccucggagaaagcaugagcaguauuaggucgaaaugccccgucgaagagucggaagccuccacaccaccuag cacgcugccuugcuugugcauccaugccaugacuccagaaagaguacagcgccuaaaagccucacguccagaacaaauu acugugugcucauccuuuccauugccgaaguauagaaucacggugugcagaagauccaaugcucccagccuauauugu ucucaccgaaagugccugcguauauucauccaaggaaguaucucguggaaacaccaccgguagacgagacuccggagcc aucggcagagaaccaauccacagagggggacaccugaacaaccaccacuuauaaccgaggaugagaccaggacuagaacg ccugagccgaucaucaucgaagaggaagaagaggauagcauaaguuugcugucagauggcccgacccaccaggugcugc aagucgaggcagacauucacgggccgcccucuguaucuagcucauccugguccauuccucaugcauccgacuuugaugu ggacaguuuauccauacuugacacccuggagggagcuagcgugaccagcggggcaacgucagccgagacuaacucuuac uucgcaaagaguauggaguuucuggcgcgaccggugccugcgccucgaacaguauucaggaaccccuccacaucccgcuc cgcgcacaagaacaccgucacuugcacccagcagggccugcucgagaaccagccuaguuuccaccccgccaggcgugaa uagggugaucacuagagaggagcucgaggcgcuuaccccgucacgcacuccuagcaggucggucucgagaaccagccug gucuccaaccccgccaggcguaaauagggugauuacaagagaggaguuugaggcguucguagcacaacaacaaugacggu uugaugcgggugcauacaucuuuuccuccgacaccggucaagggcauuuacaacaaaaaucaguaaggcaaacggugcu auccgaaguggguguuggagaggaccgaauuggagauuucguaugccccgcgccucgaccaagaaaaagaagaauuacua cgcaagaaauuacaguuaaauccccacaccugcuaacagaagcagauaccaguccaggaagguggagaacaugaaagcca uaacagcuagacguauucugcaaggccuagggcauuauuugaaggcagaaggaaaagguggagugcuaccgaacccugca uccuguuccuuuguauucaucuagugugaaccgugccuuuucaagccccaaggucgcaguggaagccuguaacgccaug uugaaagagaacuuccgacugugcuucuuacuguauuauuccagaguacgaugccuauuuggacaugguugacggag cuucaugcugcuuagacacugccaguuuuugcccugcaaagcugcgcagcuuuccaaagaaacacuccuauuuggaacc cacaauacgaucggcagugccuucagcgauccagaacacgcuccagaacguccuggcagcugccacaaaaagaaauugc aaugucacgcaaaugagagaauugcccguauuggauucggcggccuuuaaugugggaaugcuucaagaaauaugcguguaaauaauaauauaugaaaacguuuaaagaaaaaccccaucaggcuuacugaagaaaacgugguaaauuacauuaccaaauuaaaaaggaccaaaagcugcugcucuuuuugcgaagacacauaauuugaauauguugcaggacauaccaauggacagguuuguaauggacuuaaagagagacgugaaaugacuccaggaacaaaacauacugaagaacgg CC CaaggAbsorb cagucagigicucctgcorr uccgaacauucauacacugguugauaugucggcugaagacuuugacgcuauuauagccgagcacuuccagccuggggau uguguucggaaacugacaucgcgucguuugauaaaagugagacgagccauggcucugaccgcguuaaugauucugg aagacuuaggugggacgcagagcguugacgcugauugaggcggcuuucggcgaaauuucaucaauacauuugcccac uaaaacuaaauuuaaauucggagccaugaugaaaucggaauguuccucacacuguuugaacacagucauuaacauu guaaucgcaagcagagucguugagagaacggcuaaccggaucaccaugugcagcauucauuggagaugacaauaucguga aaggagucaaaucggacaaauuaauggcagacaggugcgccaccugguugaauauggaagucaagauuauagaugcugu gguggcgagaaagcgccuuauuucugcugggguuauuuugugugacuccgugaccggcacagcgugccgugugca gaccccuaaaaaggcuguuuaagcuuggcaaaccucuggcagcagacgaugaacaugaugaugacaggagaagggcau ugcaugaagagucaacacgcuggaaccgagugggauuucuucagagcugugcaaggcaguagaaucaagguaugaaac cguaggaacuuccaucauaguuauggccaugacuacucuagcuagcaguguuaaaucauucagcuaccugagaggggcc ccuauaacucucuacggcuaaccgaauggacuacgacauagucuaguccgccaag*AUGUUUCUGCUCACAACCAAACG*

*CACUAUGUUUGUUUCCUCGUGCUGCUCCCUUUGGUAAGUUCUCAGUGUGUAAACCUG*aga*ACACGAACCCAGUUGCCU*

-continued

CCAGCUUAUACCAACUCAUUUACUCGCGGAGUAUAUUAUCCCGAUAAGGUCUUUAGAAGUAGCGUGUUGCACUCUACAC

AGGAUCUGUUCUUGCCCUUCUUUAGUAACGUUACCUGGUUUCAUGCAAUACAUGUGAGCGGAACAAAUGGAACAAAAG

AUUUGACAAUCCAGUGCUUCCAUUUAAUGAUGGGGUUUACUUUGCCAGUaucGAAAAGUCAAACAUAAUCCGGGGUGG

AUCUUUGGAACCACUUUGGACUCUAAGACACAGUCUCUCCUCAUAGUAAACAACGCCACCAAUGUUGUCAUAAAAGUAU

GCGAAUUUCAGUUUUGCAACGAUCCCUUUCUCgacGUGUAUUACCAUAAGAAUAAUAAAUCCUGGAUGGAGUCUgggGU

UUAUAGUAGUGCUAAUAAUUGCACUUUCGAAUACGUGUCCCAACCAUUCCUCAUGGACCUUGAGGGCAAACAGGGGAAU

UUUAAAAACUUGCGCGAAUUUGUCUUUAAGAAUAUCGACGGAUACUUUAAGAUCUAUAGUAAACACACUCCUAUCAACC

UCGUUCGGGAUCUUCCCCAAGGCUUUUCUGCUCUCGAACCCCUCGUAGACUUGCCAAUUGGGAUAAAUAUCACUCGCUU

UCAAACUUUGCUUGCCCUCCACAGGAGCUACCUGACACCCGGCGACUCUUCUUCUGGUuugACCGCCGGCGCCGCUGCC

UAUUAUGUUGGUUACCUUCAGCCACGAACAUUCUUGCUCAAGUAUAACGAGAAUGGCACCAUUACCGACGCCGUCGAUU

GUGCAUUGGAUCCCUUGUCUGAAACAAAAUGUACCUUGAAGUCCUUUACCGUAGAGAAAGGCAUAUACCAGACUUCCAA

CUUCCGAGUUCAGCCUACAGAAUCCAUCGUACGAUUUCCAACAUCACAAACCUCUGCCCUUUCGGUGAAGUAUUUAAU

GCUACACGCUUCGCUUCAGUCUAUGCCUGGAAUAGGAAGCGCAUAUCAAAUUGCGUGGCCGAUUAUUCAGUCCUCUAUA

AUAGCGCAUCCUUCAGUACUUUCAAGUGCUACGGCGUUUCCCCCACCAAACUCAAUGAUCUUUGCUUCACCAACGUCUA

UGCUGACAGUUUUGUCAUACGAGGCGACGAAGUACGCCAGAUUGCCCCCGGGCAGACAGGUaauAUUGCUGAUUAUAAU

UAUAAACUCCCAGAUGACUUUACUGGAUGCGUCAUAGCCUGGAAUUCCAACAAUCUAGAUUCCAAGGUUGGUGGGAAUU

AUAAUUACcguUAUCGACUGUUCAGAAAGAGUAACUUGAAACCAUUUGAGAGAGACAUAUCCACCGAGAUUUACCAGGC

AGGCAGUaagCCUUGUAACGGCGUUGAGGGAUUUAACUGCUAUUUCCUUUGCAAUCCUAUGGCUUUCAACCAACAAAC

GGGGUUGGCUAUCAACCCUAUCGAGUGGUUGUCCUCAGCUUUGAACUUUUGCACGCUCCCGCCACAGUCUGCGGACCAA

AAAAGAGUACAAAUCUUGUCAAGAAUAAGUGCGUAAAUUUCAAUUUCAAUGGCCUUACAGGAACAGGCGUGCUGACUGA

GUCAAACAAGaauUUCCUGCCAUUUCAGCAGUUUGGGCGGGAUAUAGCAGACACAACUGACGCUGUACGCGAUCCUCAG

ACUUUGGAGAUCUUGGACAUCACUCCCUGUUCUUUCGGAGGGGUAUCUGUCAUCACCCCCGGAACUAAUACAUCAAAUC

AGGUCGCUGUGUUGUACCAAgguGUCAACUGCACAGAAGUCCCCGUUGCUAUACACGCAGACCAGCUCACCCCCACAUG

GCGGGUGUACUCAACUGGCUCAAACGUAUUCCAGACCAGAGCUGGGUGCUUGAUCGGUGCUGAACACGUGAACAAUAGC

UAUGAAUGCGAUAUUCCCAUCGGUGCCGGGAUCUGCGCUAGCUAUCAGACACAGACCAAUUCCcgcAGGCGGGCUCGCU

CUGUAGCAUCCCAGUCUAUUAUUGCCUACACUAUGUCAUUGGGCGCCGAGAAUAGCGUCGCAUAUUCAAAUAAUUCUAU

UGCAAUACCCACCAACUUCACAAUCUCCGUAACUACAGAAAUACUUCCAGUUUCCAUGCAAAGACAUCAGUGGAUUGU

ACAAUGUAUAUAUGCGGAGAUUCCACAGAAUGUUCAAAUUUGCUCUUGCAGUACGGCUCCUUCUGCACCCAGCUCAACA

GGGCACUUACAGGUAUUGCUGUCGAACAGGACAAGAACACACAAGAAGUCUUCGCCCAAGUCAAACAGAUAUACAAAAC

UCCUCCCAUAAAGGAUUUUGGCGGCUUCAACUUUAGUCAGAUCCUCCCAGACCCUUCAAAACCAUCUAAACGAUCAUUU

AUUGAAGAUCUGCUGUUCAACAAGGUCACUCUUGCCGAUGCUGGAUUCAUUAAGCAAUACGGUGACUGCCUUGGUGAUA

UUGCUGCCCGAGAUCUGAUCUGUGCCCAGAAAUUCAACGGGCUCACUGUACUCCCUCCACUGCUCACAGACGAAAUGAU

UGCACAGUACACAAGUGCCCUGUUGGCAGGCACAAUCACUAGCGGCUGGACCUUUGGCGCAGGUGCAGCACUCCAAAUA

CCUUUUGCCAUGCAGAUGGCCUAUCGGUUUAAUGGGAUAGGCGUGACUCAAAAUGUCCUCUACGAAAACCAAAAGUUGA

UAGCUAACCAAUUCAAUUCAGCAAUCGGGAAGAUACAGGAUUCACUGUCUAGUACUGCUAGUGCCCUUGGUAAGCUGCA

GaacGUUGUCAACCAGAAUGCUCAAGCUCUGAAUACAUUGGUUAAGCAGCUCUCUAGUAAUUUUGGGGCCAUCUCUUCA

GUACUUAAUGAUAUUUUGAGCCGAUUGGACccaccuGAAGCUGAAGUACAGAUCGACAGGCUGAUAACAGGCCGGCUCC

AAUCCCUCCAAACAUACGUGACACAACAACUCAUACGCGCAGCCGAAAUCCGAGCCAGCGCUAACCUGGCAGCUACCAA

GAUGUCAGAAUGCGUUCUGGGCCAGAGUAAACGCGUAGAUUUCUGCGGGAAAGGGUACCACCUGAUGUCCUUUCCACAA

UCUGCACCUCACGGGGUCGUCUUUUUGCAUGUAACAUACGUACCCGCACAAGAGAAGAAUUUUACUACCGCUCCUGCCA

UCUGUCAUGACGGGAAAGCUCAUUUUCCUCGCGAAGGUGUGUUUGUAUCUAAUGGUACACAUUGGUUUGUCACACAGCG

```
GAAUUUCUAUGAACCCCAGAUCAUUACAACUGACAACACUUUUGUUUCCGGGAAUUGUGACGUGGUCAUAGGAAUCGUA

AAUAACACUGUAUAUGAUCCCCUCCAACCAGAGCUGGACUCUUUUAAAGAAGAACUGGAUAAAUAUUUCAAGAACCACA

CAAGUCCCGACGUGGACCUUGGGGACAUAAGUGGUAUUAACGCAUCUGUGGUUAACAUUCAAAAGGAAAUCGACAGACU

CAACGAGGUGGCCAAAAACCUGAACGAAAGCUUGAUAGAUCUCCAGGAGUUGGGCAAGUAUGAACAGUACAUUAAAUGG

CCAUGGUACAUAUGGCUUGGCUUUAUCGCUGGCCUUAUCGCCAUCGUAAUGGUUACAAUCAUGCUGUGCUGCAUGACCU

CCUGCUGUUCUUGUUUGAAAGGGUGUUGUUCUUGUGGUAGUUGUUGCAAGUUUGACGAAGAUGAUUCCGAACCUGUUCU

UAAGGGGGUAAAGCUUCACUAUACAUGAuaaccgcggugucaaaaaccgcguggacgugguuaacaucccugcugggag gaucagccguaauuauuauaauuggcuuggugcuggcuacuauugugggccauguacgugcugaccaaccagaaacauaa uugaauacagcagcaauuggcaagcugcuuacauagaacucgcggcgauuggcaugccgccuuaaaauuuuuauuuuau uuuucuuuucuuuuccgaaucggauuuuguuuuaauauuucaaaaaaaaaaaaaaaaaaaaaaaaaaaaaaaaaaaaaa aaaaaaaaaaa SEQ ID NO: 38- Vector Backbone RNA Sequence 7
auaggcggcgcaugagagaagcccagaccaauuaccuacccaaaauggagaaaguucacguugacaucgaggaagacagc ccauuccucagagcuuugcagcggagcuucccgcaguuugagguagaagccaagcaggucacugauaaugaccaugcuaa ugccagagcguuuucgcaucuggcuucaaaacugaucgaaacggaggugacccauccgacacgauccuugacauuggaa gugcgcccgccgcagaaugauauucuaagcacaaguaucauuguaucuguccgaugagaugugcggaagauccggacaga uuguauaaguaugcaacuaagcugaagaaaaacguaaggaaauaacugauaaggaauuggacaagaaaaugaaggagcu ggccgccgucaugagcgacccugaccuggaaacugagacuaugugccuccacgacgacgagucgugucgcuacgaagggc aagucgcuguuuaccaggauguauacgcgguugacggaccgacaagucucuaucaccaagccaauaagggagUuagaguc gccuacuggauaggcuuugacaccacccccuuuuauguuuaagaacuuggcuggagcauauccaucauacucuaccaacug ggccgacgaaaccguguuaacggcucguaacauaggccaugcagcucugacguuauggagcggucacguagagggaugu ccauucuuagaaagaaguauuugaaaccauccaacaauguucuauucucguuggcucgaccaucuaccacgagaagagg gacuuacugaggagcuggcaccugccgucuguauuucacuuacguggcaagcaaaauuacacaugucgguguguacuau aguuaguugcgacggguacgucguuaaaagaauagcuaucaguccaggccuguaugggaagccuucaggcuaugcugcua cgaugcaccgcgagggauucuugugcugcaaagugacagacacauugaacggggagagggucucuuuucccgugugcacg uauguğccagcuacauugugugaccaaaugacuggcauacuggcaacagaugucagugcggacgacgcgcaaaaacugcu gguugggcucaaccagcguauagucgucaacggucgcacccagagaaacaccaauaccaugaaaaauuaccuuuugcccg uaguggcccaggcauuugcuagguğggcaaaggaauauaaggaagaucaagaagaugaaaggccacuaggacuacgagau agacaguuagucauggggugugugugggcuuuuagaaggcacaagauaaacaucuauuuauaagcgcccggauacccaaac caucaucaaagugaacagcgauuuccacucauucgugcugcccaggauaggcaguaacacauuggagaucgggcugagaa caagaaucaggaaaauguuagaggagcacaaggagccgucaccucucauuaccgccgaggacguacaagaagcuaagugc gcagccgaugaggcuaaggaggugcgugaagccgaggaguugcgcgcagcucuaccaccuuuggcagcugauguugagga gcccacucuggaggcagacgucgacuugauguuacaagaggcuggggccggcucaguggagacaccucguggcuugauaa agguuaccagcuacgauggcgaggacaagaucggcucuuacgcgugugcuuuccucgcaggcuguacucaagagugaaaaa uuaucuugcauccacccucucgcugaacaagucauagugauaacacacucuggccgaaaagggcguuaugccguggaacc auaccaugguaaaguaguggugccagagggacaugcaauacccguccaggacuuucaagcucugagugaaagugccacca uuguguacaacgaacgugaguucguaaacaggguaccugcaccauauugccacacauggaggagcgcugaacacugaugaa gaauauuacaaaacugucaagcccagcgagcacgacggcgaauaccugacgacaucgacaggaaacagugcgucaagaa agaacuagucacugggcuagggcucacaggcgagcugguggauccucccuuccaugaauucgccuacgagagucugagaa cacgaccagccgcuccuuaccaaguaccaaccauagggguguauggcugccaggaucaggcaagucuggcaucauuaaa agcgcagucaccaaaaaagaucuagugguggagcgccaagaaagaaaaacugugcagaaauuauaagggacgucaagaaaau
```

-continued gaaagggcuggacgucaaugccagaacuguggacucagugcucuugaauggaugcaaacaccccguagagacccuguaua uugacgaagcuuuugcuugucaugcagguacucucagagcgcucauagccauuauaagaccuaaaaaggcagugcucugc ggggaucccaaacagugcgguuuuuuaacaugaugugccugaaagugcauuuuaaccacgagauuugcacacaagucuu ccacaaaagcaucucucgccguugcacuaaaucgugacuucggucgucucaaccuuguuuuacgacaaaaaaaugagaa cgacgaauccgaaagagacuaagauugugauugacacuacggcaguaccaaaccuaagcaggacgaucucauucucacu uguuucagagggugggugaagcaguugcaaauagauuacaaaggcaacgaaauaaugacggcagcugccucucaagggcu gacccguaaaggugugu augccguucgguacaaggugaaugaaaauccucuguacgcacccaccucagaacaugugaacg uccuacugacccgcacggaggaccgcaucgugu ggaaaacacuagccggcgacccauggauaaaaacacugacugccaag uacccugggaauuucacugccacgauagaggaguggcaagcagagcaugaugccaucaugaggcacaucuuggagagacc ggacccuaccgacgucuuccagaauaaggcaaacgugu guuugggccaaggcuuuagugccggugcugaagaccgcuggca uagacaugaccacugaacaauggaacacuguggauuauuuugaaacggacaaagcucacucagcagagauaguauugaac caacuaugcgugaggu ucuuuggacucgaucuggacuccggucuauuuucugcacccacuguuccguuauccauuaggaa uaaucacugggauaacuccccgucgccuaacauguacgggcugaauaaagaaguggu ccgucagcucucucgcagguacc cacaacugccucgggcaguugccacuggaagagucuaugacaugaacacugguacacugcgcaauuaugauccgcgcaua aaccuaguaccuguaaacagaagacugccucaugcuuuaguccuccaccauaaugaacacccacagagugacuuuucuuc auucgucagcaaauugaagggcagaacugu ccgguggucggggaaaaguuguccgucccaggcaaaauggu ugacuggu ugucagaccggccugaggcuaccuucagagcucggcuggauuuaggcaucccaggugaugugcccaaauaugacauaaua uuuguuaaugugaggaccccauauaaauaccaucacuaucagcagugugaagaccaugccauuaagcuuagcauguugac caagaaagcuugucugcaucugaauccggcggaaccugugucagcauagguuaugguuacgcugacagggccagcgaaa gcaucauuggugcuauagcgcggcaguucaaguuucccgggu augcaaaccgaaauccucacuugaagagacggaaguu cuguuuguauucauugggu acgaucgcaaggcccgu acgcacaauccuuacaagcuuucaucaaccuugaccaacauuua uacagguuccagacuccacgaagccggaugu gcacccucauaucaugu ggugcgaggggauauugccacggccaccgaag gagugauuauaaaugcugcuaacagcaaaggacaaccuggcggagggu gugcggagcgcuguauaagaaauucccggaa agcuucgauuuacagccgaucgaaguaggaaaagcgcgacuggucaaaggugcagcuaaacauaucauucaugccguagg accaaacuucaacaaaguuucggagguugaaggugacaaacaguuggcagaggcuuaugagu ccaucgcuaagauugu ca acgauaacaauuacaagucaguagcgauuccacuguuguccaccggcaucuuuccgggaacaaagaucgacuaacccaa ucauugaaccauuugcugacagcuuuagacaccacugaugcagauguagccauauacugcagggacaagaaaugggaaau gacucucaaggaagcaguggcuaggagagaagcaguggaggagauaugcauauccgacgacucuucagugacagaaccug augcagagcggugagggugcauccgaagaguucuuuggcuggaaggaagggcuacagcacaagcgaugcaaaacuuuc ucauauuuggaagggaccaaguuucaccaggcggccaaggauauagcagaaauuaaugccauguggcccguugcaacgga ggccaaugagcagguaugcauguauauccucggagaaagcaugagcaguauuaggucgaaaugccccgucgaagagucgg aagccuccacaccaccuagcacgcugccuugcuugu gcauccaugccaugacuccagaaagaguacagcgccuaaaagcc ucacguccagaacaaauuacuguguguucaaucucuuuccauugccgaaguauagaaucacuggu gugcagaagauccaaug cucccagccuauauugu ucucaccgaaagugccugcguauauucauccaaggaaguaucucguggaaacaccaccgguag acgagacuccggagccaucggcagagaaccaauccacagagggg acaccugaacaaccaccacuuauaaccgaggaugag accaggacuagaacgccugagccgaucaucaucgaagaggaagaagaggauagcauaaguuugcugucagauggcccgac ccaccaggu gcugcaagucgaggcagacauucacgggccgccccucuguaucuagcucauccgguccauuccucaugcau ccgacuuugaugu ggacaguuuauccauacuugacacccuggagggagcuagcgu gaccagcggggcaacgucagccgag acuaacucuuacuucgcaaagaguauggaguuucggcgcgaccggugccugcgccucgaacaguauucaggaaccccucc acaucccgcuccgcgcacaagaacaccgucacuugcacccagcagggccugcucgagaaccagccuaguuuccacccgc -continued caggcgugaauagggugaucacuagagaggagcucgaggcgcuuaccccgucacgcacuccuagcaggucggucucgaga accagccuggucuccaacccgccaggcguaaaugggugauuacaagagaggaguuugaggcguucuagcacaacaaca augacgguuugaugcgggugcauacaucuuuuccuccgacaccggucaagggcauuuacaacaaaaaucaguaaggcaaa cggugcuauccgaaguggguguuggagaggaccgaauuggagauuucguaugccccgcgccucgaccaagaaaaagaagaa uuacuacgcaagaaauuacaguuaaaucccacaccugcuaacagaagcagauaccaguccaggaaggguggagaacaugaa agccauaacagcuagacguauucugcaaggccuagggcauuauuugaaggcagaaggaaaaguggagugcuaccgaaccc ugcauccuguuccuuuguauucaucuagugugaaccgugccuuucaagccccaaggucgcaguggaagccuguaacgcc auguugaaagagaacuuuccgacuguggcuucuuacuguauuauuccagaguacgaugccuauuuggacaugguugacgg agcuucaugcugcuuagacacugccaguuuugcccugcaaagcugcgcagcuuuccaaagaaacacuccuauuuggaac ccacaauacgaucggcagugccuucagcgauccagaacacgcuccagaacguccuggcagcugccacaaaaagaaauugc aaugucacgcaaaugagagaauugcccguauuggaucggcggccuuuaaugguggaaugcuucaagaaauaugcguguaa uaaugaauauugggaaacguuuaaagaaaaccccaucaggcuuacugaagaaaacguggaaauuacauuaccaaauuaa aaggaccaaaagcugcugcucuuuuugcgaagacacauaauuugaauauguugcaggacauaccaauggacagguuugua auggacuuaaagagagacgugaaagugacuccaggaacaaaacauacugaagaacggcccaaggucacaggugauccaggc ugccgauccgcuagcaacagcguaucugugcggaauccaccgagagcugguuaggagauuaaaugcggaccugcuuccga acauucauacacuguuugauaugucggcugaagacuuugacgcuauuauagccgagcacuuccagccuggggauugguguu cuggaaacugacaucgcgucguuugauaaaagugaggacgacgccauggcucugaccgcguuaaugauucuggaagacuu aggugguggacgcagagcuguugacgcugauugaggcggcuuucggcgaaauuucaucaauacauuugcccacuaaaacua aauuuaaauucggagccaugaugaaaucggaauguuccucacacuguuugugaacacagucauuaacauuguaaucgca agcagagguugagagaacggcuaaccggaucaccaugugcagcauucauuggagaugacaauaucgugaaaggagucaa aucggacaaauuaauggcagacaggugcgccaccugguugaauauggaagucaagauuauagaugcgugugguggcgaga aagcgccuuauuucuguggaggguuuauuugugugacuccgugaccggcacagcgugccguguggcagaccccuaaaa aggcuguuuaagcuuggcaaaccucuggcagcagacgaugaacaugaugaugacaggagaagggcauugcaugaagaguc aacacgcuggaaccgagugggguauucuuucagagcugugcaaggcaguagaaucaagguaugaaaccguaggaacuucca ucauaguuauggccaugacuacucuagcuagcaguguuaaaucauucagcuaccugagagggcccccuauaacucucuac ggcuaaccugaauggacuacgacauagucuaguccgccgccaccnuaaccgcggugucaaaaaccgcguggacgugguua caaccagaaacauaauugaauacagcagcaauuggcaagcugcuuacauagaacucgcggcgauuggcaugccgccuuaa aauuuuauuuuauuuuuucuuuucuuuccgaaucgaaucggauuuuguuuuuaauauuucaaaaaaaaaaaaaaaaaaaa aaaaaaaaaaaaaaaaaaaaa SEQ ID NO: 39- DNA Sequence Encoding SEAP
tcgcgcgtttcggtgatgacggtgaaaacctctgacacatgcagctcccggagacggtcacagcttgtctgtaagcggat gccgggagcagacaagcccgtcagggcgcgtcagcgggtgttggcgggtgtcggggctggcttaactatgcggcatcaga gcagattgtactgagagtgcaccatatgcggtgtgaaataccgcacagatgcgtaaggagaaaataccgcatcagattgg ctattggccattgcatacgttgtatccatatcataatatgtacatttatattggctcatgtccaacattaccgccatgtt gacattgattattgactagttattaatagtaatcaattacggggtcattagttcatagcccatatatggagttccgcgtt acataacttacggtaaatggcccgcctggctgaccgcccaacgacccccgcccattgacgtcaataatgacgtatgttcc catagtaacgccaatagggactttccattgacgtcaatgggtggagtatttacggtaaactgcccacttggcagtacatc aagtgtatcatatgccaagtacgccccctattgacgtcaatgacggtaaatggcccgcctggcattatgcccagtacatg acctatgggactttcctacttggcagtacatctacgtattagtcatcgctattaccatggtgatgcggttttggcagta catcaatgggcgtggatagcggtttgactcacggggatttccaagtctccaccccattgacgtcaatgggagtttgtttt ggcaccaaaatcaacgggactttccaaaatgtcgtaacaactccgccccattgacgcaaatgggcggtaggcgtgtacgg -continued

```
tgggaggtctatataagcagagctcgtttagtgaaccgtcagatcgcctggagacgccatccacgctgttttgacctcca tagaagacaccgggaccgatccagcctccgcggccgggaacggtgcattggaacgcggattcccgtgccaagagtgacg taagtaccgcctatagactctataggcacacccctttggctcttatgcatgctatactgtttttggcttggggcctatac accccgcttccttatgctataggtgatggtatagcttagcctataggtgtgggttattgaccattattgaccactcccc tattggtgacgatactttccattactaatccataacatggctcttttgccacaactatctctattggctatatgccaatac tctgtccttcagagactgacacggactctgtatttttacaggatggggtcccatttattatttacaaattcacatataca acaacgccgtccccgtgcccgcagttttattaaacatagcgtgggatctccacgcgaatctcgggtacgtgttccgga catgggctcttctccggtagcggcggagcttccacatccgagccctggtcccatgcctccagcggctcatggtcgctcgg cagctccttgctcctaacagtggaggccagacttaggcacagcacaatgccaccaccagtgtgccgcacaaggccg tggcggtagggtatgtgtctgaaaatgagcgtggagattgggctcgcacggctgacgcagatggaagacttaaggcagcg gcagaagaagatgcaggcagctgagttgttgtattctgataagagtcagaggtaactcccgttgcggtgctgttaacggt ggagggcagtgtagtctgagcagtactcgttgctgccgcgcgcgccaccagacataatagctgacagactaacagactgt tcctttccatgggtctttctgcagtcaccgtcgtcgacaagcttcctgcatgctgctgctgctgctgctgggcctg aggctacagctctccctgggcatcatcccagttgaggaggagaacccggacttctggaaccgcgaggcagccgaggccct gggtgccgccaagaagctgcagcctgcacagacagccgccaagaacctcatcatcttcctgggcgatgggatgggggtgt ctacggtgacagctgccaggatcctaaaagggcagaagaaggacaaactggggcctgagatacccctggccatggaccgc ttcccatatgtggctctgtccaagacatacaatgtagacaaacatgtgccagacagtggagccacagccacggcctacct gtgcggggtcaagggcaacttccagaccattggcttgagtgcagccgcccgctttaaccagtgcaacacgacacgcggca acgaggtcatctccgtgatgaatcgggccaagaaagcagggaagtcagtgggagtggtaaccaccacgagtgcagcac gcctcgccagccggcacctacgcccacacggtgaaccgcaactggtactcggacgccgacgtgcctgcctcggcccgcca ggaggggtgccaggacatcgctacgcagctcatctccaacatggacattgacgtgatcctaggtggaggccgaaagtaca tgtttcgcatgggaaccccagaccctgagtacccagatgactacagccaaggtgggaccaggctggacgggaagaatctg gtgcaggaatggctggcgaagcgccagggtgcccggtatgtgtggaaccgcactgagctcatgcaggcttccctggaccc gtctgtgacccatctcatgggtctcttgagcctggagacatgaaatacgagatccaccgagactccacactggacccct ccctgatggagatgacagaggctgccctgcgcctgctgagcaggaacccccgcggcttcttcctcttcgtgggagggtggt cgcatcgaccatggtcatcatgaaagcagggcttaccgggcactgactgagacgatcatgttcgacgacgccattgagag ggcgggccagctcaccagcgaggaggacacgctgagcctcgtcactgccgaccactcccacgtcttctccttcggaggct accccctgcgagggagctccatcttcgggctggcccctggcaaggcccgggacaggaaggcctacacggtcctcctatac ggaaacggtccaggctatgtgctcaaggacggcgcccggccggatgttaccgagagcgagagcgggagcccgagtatcg gcagcagtcagcagtgcccctggacgaagagacccacgcaggcgaggacgtggcggtgttcgcgcgcggccccgcaggcgc acctggttcacggcgtgcaggagcagaccttcatagcgcacgtcatggccttcgccgcctgcctggagccctacaccgcc tgcgacctggcgcccccgccggcaccaccgacgccgcgcacccgggttaacccgtggtcagatccagatccagatcact tctggctaataaaagatcagagctctagagatctgtgtgttggtttttttgtggatctgctgtgccttctagttgccagcc atctgttgtttgccctcccccgtgccttccttgaccctggaaggtgccactcccactgtccttcctaataaaatgagg aaattgcatcgcattgtctgagtaggtgtcattctattctggggggtggggtggggcagcacagcaaggggaggattgg gaagacaatagcaggcatgctgggatgcggtgggctctatgggtacctctctctctctctctctctctctctctctc tctctctcggtacctctctctctctctctctctctctctctctctctctctcggtaccaggtgctgaagaattgaccc ggttcctcctgggccagaaagaagcaggcacatcccttctctgtgacacacctgtccacgcccctggttcttagttcc agccccactcataggacactcatagctcaggagggctccgccttcaatcccacccgctaaagtacttggagcggtctctc cctccctcatcagcccaccaaaccaaacctagcctccaagagtgggaagaaattaaagcaagataggctattaagtgcag agggagagaaaatgcctccaacatgtgaggaagtaatgagagaaatcatagaatttcttccgcttcctcgctcactgact
```

-continued

```
cgctgcgctcggtcgttcggctgcggcgagcggtatcagctcactcaaaggcggtaatacggttatccacagaatcaggg
gataacgcaggaaagaacatgtgagcaaaaggccagcaaaaggccaggaaccgtaaaaaggccgcgttgctggcgtttttt
ccataggctccgcccccctgacgagcatcacaaaaatcgacgctcaagtcagaggtggcgaaacccgacaggactataaa
gataccaggcgtttccccctggaagctccctcgtgcgctctcctgttccgaccctgccgcttaccggatacctgtccgcc
tttctcccttcgggaagcgtggcgctttctcaatgctcacgctgtaggtatctcagttcggtgtaggtcgttcgctccaa
gctgggctgtgtgcacgaaccccccgttcagcccgaccgctgcgccttatccggtaactatcgtcttgagtccaacccgg
taagacacgacttatcgccactggcagcagccactggtaacaggattagcagagcgaggtatgtaggcggtgctacagag
ttcttgaagtggtggcctaactacggctacactagaaggacagtatttggtatctgcgctctgctgaagccagttacctt
cggaaaaagagttggtagctcttgatccggcaaacaaaccaccgctggtagcggtggttttttttgtttgcaagcagcaga
ttacgcgcagaaaaaaaggatctcaagaagatcctttgatcttttctacggggtctgacgctcagtggaacgaaaactca
cgttaagggattttggtcatgagattatcaaaaaggatcttcacctagatccttttaaattaaaaatgaagttttaaatc
aatctaaagtatatatgagtaaacttggtctgacagttaccaatgcttaatcagtgaggcacctatctcagcgatctgtc
tatttcgttcatccatagttgcctgactccggggggggggggcgctgaggtctgcctcgtgaagaaggtgttgctgactc
ataccaggcctgaatcgccccatcatccagccagaaagtgagggagccacggttgatgagagctttgttgtaggtggacc
agttggtgattttgaacttttgctttgccacggaacggtctgcgttgtcgggaagatgcgtgatctgatccttcaactca
gcaaaagttcgatttattcaacaaagccgccgtcccgtcaagtcagcgtaatgctctgccagtgttacaaccaattaacc
aattctgattagaaaaactcatcgagcatcaaatgaaactgcaatttattcatatcaggattatcaataccatattttg
aaaaagccgtttctgtaatgaaggagaaaactcaccgaggcagttccataggatggcaagatcctggtatcggtctgcga
ttccgactcgtccaacatcaatacaacctattaatttcccctcgtcaaaaataaggttatcaagtgagaaatcaccatga
gtgacgactgaatccggtgagaatggcaaaagcttatgcatttctttccagacttgttcaacaggccagccattacgctc
gtcatcaaaatcactcgcatcaaccaaaccgttattcattcgtgattgcgcctgagcgagacgaaatacgcgatcgctgt
taaaaggacaattacaaacaggaatcgaatgcaaccggcgcaggaacactgccagcgcatcaacaatattttcacctgaa
tcaggatattcttctaatacctggaatgctgttttcccggggatcgcagtggtgagtaaccatgcatcatcaggagtacg
gataaaatgcttgatggtcggaagaggcataaattccgtcagccagtttagtctgaccatctcatctgtaacatcattgg
caacgctacctttgccatgtttcagaaacaactctggcgcatcgggcttcccatacaatcgatagattgtcgcacctgat
tgcccgacattatcgcgagcccatttatacccatataaatcagcatccatgttggaatttaatcgcggcctcgagcaaga
cgtttccgttgaatatggctcataacacccttgtattactgtttatgtaagcagacagttttattgttcatgatgata
tatttttatcttgtgcaatgtaacatcagagattttgagacacaacgtggctttccccccccccccattattgaagcatt
tatcaggttattgtctcatgagcggatacatatttgaatgtatttagaaaaataaacaaatagggttccgcgcacatt
tccccgaaaagtgccacctgacgtctaagaaaccattattatcatgacattaacctataaaaataggcgtatcacgagg
ccctttcgtc
```

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A dried composition comprising:
   a) a lipid carrier, wherein the lipid carrier is a nanoemulsion comprising a hydrophobic core, and one or more lipids;
   b) at least one nucleic acid that comprises a sequence encoding a SARS-CoV-2 spike protein or a functional variant thereof, wherein the at least one nucleic acid comprises a sequence at least 85% identical to any one of SEQ ID NOS: 1-8; and
   c) at least one sugar present in amount of at least about 50% by weight of the dried composition.

2. The dried composition of claim 1, wherein the composition is lyophilized.

3. The dried composition of claim 1, wherein the composition is thermally stable:
   at about −20 degrees Celsius,
   at about 25 degrees Celsius,
   at about 45 degrees Celsius,
   at about 2 degrees Celsius to about 8 degrees Celsius, or a combination thereof.

4. The dried composition of claim 1, wherein the composition is thermally stable for at least 1 week.

5. The dried composition of claim 1, wherein the hydrophobic core comprises an oil.

6. The dried composition of claim 5, wherein the oil comprises at least one of α-tocopherol, lauroyl polyoxylglyceride, monoacylglycerol, propolis, squalene, mineral oil, grapeseed oil, olive oil, paraffin oil, peanut oil, soybean oil, sunflower oil, soy lecithin, triglyceride, vitamin E, a caprylic/capric triglyceride, a triglyceride ester of saturated coconut palm kernal oil derived caprylic and capric fatty acids and plant derived glycerol, dihydroisosqualene (DHIS), farnesene and squalane.

7. The dried composition of claim 1, wherein the one or more lipids is selected from the group consisting of; cationic lipids, anionic lipids, neutral lipids, and any combinations thereof.

8. The dried composition of claim 7, wherein the one or more lipids comprises a cationic lipid.

9. The dried composition of claim 8, wherein the cationic lipid is selected from the group consisting of: 1,2-dioleoyloxy-3-(trimethylammonium) propane, 30-[N-(N',N'-dimethylaminoethane)-carbamoyl]cholesterol, dimethyldioctadecylammonium, 1,2-dimyristoyl-3-trimethylammoniumpropane, dipalmitoyl (C16:0)trimethyl ammonium propane, distearoyltrimethylammonium propane, N-[1-(2,3-dioleyloxy) propyl]-N,N,Ntrimethylammonium chloride, N,N-dioleoyl-N,N-dimethylammonium chloride, 1,2-dioleoyl-sn-glycero-3-ethylphosphocholine, 1,2-dioleoyl-3-dimethylammonium-propane, 1,2-dilinoleyloxy-3-dimethylaminopropane, 1,1'-((2-(4-(2-((2-(bis(2-hydroxydodecyl)amino) ethyl) (2-hydroxydodecyl)amino) ethyl) piperazin-1-yl)ethyl) azanediyl)bis(dodecan-2-ol), 1,2-dioleoyl-sw-glycero-3-phosphoethanolamine, 7V-decyl-7V,7V-dimethyldecan-1-aminium bromide, 2,3-dioleyloxy-7V-[2-(sperminecarboxamido)ethyl]-7V,7V-dimethyl-1-propanaminium trifluoroacetate, ethylphosphatidylcholine, and any combinations thereof.

10. The dried composition of claim 1, wherein the lipid carrier comprises at least one surfactant selected from the group consisting of: a hydrophobic surfactant, a hydrophilic surfactant, and any combinations thereof.

11. The dried composition of claim 10, wherein the hydrophobic surfactant comprises a sorbitan ester selected from the group consisting of: sorbitan monolaurate, sorbitan monopalmitate, sorbitan monostearate, sorbitan tristearate, sorbitan monooleate, and sorbitan trioleate; and the hydrophilic surfactant comprises a polysorbate.

12. The dried composition of claim 1, wherein the lipid carrier has a z-average hydrodynamic diameter ranging from about 40 nm to about 150 nm, with an average poly dispersity index ranging from about 0.1 to about 0.4.

13. The dried composition of claim 1, wherein the at least one nucleic acid comprises a DNA or an RNA.

14. The dried composition of claim 13, wherein the at least one nucleic acid comprises RNA, wherein the RNA is a self-replicating RNA.

15. The dried composition of claim 1, wherein a molar ratio of the lipid carrier to the at least one nucleic acid is characterized by a nitrogen-to-phosphate (N:P) molar ratio that ranges from about 1:1 to about 150:1.

16. The dried composition of claim 1, wherein the at least one sugar is selected from the group consisting of: sucrose, maltose, trehalose, mannitol, glucose, and any combinations thereof.

17. The dried composition of claim 1, wherein the at least one sugar present in an amount of least about 50 mg.

18. A composition comprising:
   (a) a lipid carrier, wherein the lipid carrier comprises:
      liquid oil;
      surfactants, wherein the surfactants comprise a hydrophilic surfactant and a hydrophobic surfactant; and
      a cationic lipid; and
   (b) at least one nucleic acid that comprises a sequence encoding a SARS-CoV-2 spike protein or a functional variant thereof, wherein the at least one nucleic acid comprises a sequence that is at least 85% identical to any one of SEQ ID NOS: 1 to 7.

19. The composition of claim 18, wherein the at least one nucleic acid comprises a sequence encoding for the SARS-CoV-2 spike protein variant, and wherein the at least one nucleic acid comprises a sequence that is at least 85% identical to SEQ ID NO: 4 or SEQ ID NO: 27.

20. The composition of claim 18, wherein the at least one nucleic acid further comprises a sequence that encodes for an RNA polymerase.

21. The composition of claim 20, wherein the RNA polymerase is a Venezuelan equine encephalitis virus (VEEV) RNA polymerase.

22. The composition of claim 21, wherein is the at least one nucleic acid comprises the sequence encoding for the VEEV RNA polymerase, and wherein the at least one nucleic acid comprises SEQ ID NO: 20.

23. The composition of claim 18, wherein the liquid oil is α-tocopherol, coconut oil, grapeseed oil, lauroyl polyoxylglyceride, mineral oil, monoacylglycerol, palm kernal oil, olive oil, paraffin oil, peanut oil, propolis, squalene, squalane, soy lecithin, soybean oil, sunflower oil, a triglyceride, or vitamin E.

24. The composition of claim 23, wherein the triglyceride is capric triglyceride, caprylic triglyceride, a caprylic and capric triglyceride, a triglyceride ester, or myristic acid triglycerin.

25. The composition of claim 18, wherein the cationic lipid is 1,2-dioleoyloxy-3 (trimethylammonium) propane, 3β-[N-(N',N'-dimethylaminoethane) carbamoyl]cholesterol, dimethyldioctadecylammonium, 1,2-dimyristoyl 3-trimethylammoniumpropane, dipalmitoyl (C16:0)trimethyl ammonium propane, distearoyltrimethylammonium propane, N-[1-(2,3-dioleyloxy) propyl]N,N,Ntrimethylammonium chloride, N,N-dioleoyl-N,N-dimethylammonium chloride, 1,2-dioleoyl-sn-glycero-3-ethylphosphocholine, 1,2-dioleoyl-3-dimethylammonium-propane, 1,2-dilinoleyloxy-3- dimethylaminopropane, 1,1'-((2-(4-(2-((2-(bis(2-hydroxydodecyl)amino) ethyl) (2-hydroxydodecyl)amino) ethyl) piperazin-1-yl)ethyl) azanediyl)bis(dodecan-2-ol), 3060$_{i10}$, tetrakis(8-methylnonyl) 3,3',3'',3'''-(((methylazanediyl) bis(propane-3,1 diyl))bis (azanetriyl))tetrapropionate, decyl (2-(dioctylammonio) ethyl) phosphate, ethyl 5,5-di((Z)-heptadec-8-en-1-yl)-1-(3-(pyrrolidin-1-yl) propyl)-2,5-dihydro-1H-imidazole-2-carboxylate, ((4-hydroxybutyl) azanediyl)bis(hexane-6,1-diyl)bis(2-hexyldecanoate), 2-[(polyethylene glycol)-2000]-N,N-ditetradecylacetamide, (3S,8S,9S,10R, 13R, 14S, 17R)-17-((2R,5R)-5-ethyl-6-methylheptan-2-yl)-10,13-dimethyl-2,3, 4, 7,8,9,10,11,12,13,14, 15, 16, 17-tetradecahydro-1H-cyclopenta[a]phenanthren-3-ol, bis(2-(dodecyldisulfanyl) ethyl) 3,3'-((3-methyl-9-oxo-10-oxa-13,14-dithia-3,6-diazahexacosyl) azanediyl)dipropionate, 2-(((((3S,8S,9S,10R,13R,14S,17R)-10,13-dimethyl-17-((R)-6-methylheptan-2-yl)-2,3,4,7,8,9,10,11,12,13,14, 15, 16, 17-tetradecahydro-1H-cyclopenta[a]phenanthren-3-yl)oxy) carbonyl)amino)-N,N-bis(2-hydroxyethyl)-N-methylethan-1-aminium bromide, 3,6-bis(4-(bis(2-hydroxydodecyl) amino) butyl) piperazine-2,5-dione, 3β-[N-(N',N'-dimethylaminoethane)-carbamoyl]cholesterol, (6Z,9Z,28Z,31Z)-heptatriaconta-6,9,28,31-tetraen-19-yl 4-(dimethylamino) butanoate, 1,2-dioleoyl-sn-glycero-3-phosphoethanolamine, 2,3-dioleyloxy-N-[2-(sperminecarboxamido)ethyl]-N,N-dimethyl-1-propanaminium trifluoroacetate, 1,2-distearoyl-sn-glycero-3-phosphocholine, ethylphosphatidylcholine; FTT5, hexa (octan-3-yl) 9,9',9'',9''',9'''',9'''''-((((benzene-1,3,5-tricarbonyl) yris (azanediyl)) tris (propane-3,1-diyl)) tris (azanetriyl)) hexanonanoate, heptadecan-9-yl 8-((2-hydroxyethyl) (6-oxo-6-(undecyloxy) hexyl)amino) octanoate, (((3,6-dioxopiperazine-2,5-diyl)bis(butane-4,1-diyl))bis (azanetriyl))tetrakis(ethane-2,1-diyl) (9Z,9'Z,9''Z,9'''Z,12Z, 12'Z,12''Z,12'''Z)-tetrakis (octadeca-9,12-dienoate) or N1,N3,N5-tris(3-(didodecylamino) propyl)benzene-1,3,5-tricarboxamide.

26. The composition of claim 18, wherein the lipid carrier comprises a hydrophobic core, an inorganic particle, or both.

27. The composition of claim 26, wherein the inorganic particle comprises a metal salt, a metal oxide, a metal hydroxide, or a metal phosphate.

28. The composition of claim 27, wherein the metal oxide comprises aluminum oxide, aluminum oxyhydroxide, iron oxide, titanium dioxide, or silicon dioxide.

29. The composition of claim 18, wherein the hydrophobic surfactant is sorbitan monolaurate, sorbitan monopalmitate, sorbitan monostearate, sorbitan monooleate, or sorbitan trioleate.

30. The composition of claim 18, wherein the hydrophilic surfactant is a polysorbate.

\* \* \* \* \*